US011655460B2

(12) United States Patent
Abeliovich et al.

(10) Patent No.: US 11,655,460 B2
(45) Date of Patent: May 23, 2023

(54) GENE THERAPIES FOR LYSOSOMAL DISORDERS

(71) Applicant: Prevail Therapeutics, Inc., New York, NY (US)

(72) Inventors: Asa Abeliovich, New York, NY (US); Laura Heckman, New York, NY (US); Herve Rhinn, New York, NY (US)

(73) Assignee: Prevail Therapeutics, Inc., New York, NY (US)

( * ) Notice: Subject to any disclaimer, the term of this patent is extended or adjusted under 35 U.S.C. 154(b) by 338 days.

(21) Appl. No.: 16/904,909

(22) Filed: Jun. 18, 2020

(65) Prior Publication Data

US 2020/0308554 A1    Oct. 1, 2020

Related U.S. Application Data

(63) Continuation of application No. 16/690,320, filed on Nov. 21, 2019, now Pat. No. 10,689,625, which is a continuation of application No. PCT/US2018/054227, filed on Oct. 3, 2018.

(60) Provisional application No. 62/567,311, filed on Oct. 3, 2017, provisional application No. 62/567,310, filed on Oct. 3, 2017, provisional application No. 62/567,301, filed on Oct. 3, 2017, provisional application No. 62/567,319, filed on Oct. 3, 2017, provisional application No. 62/567,296, filed on Oct. 3, 2017.

(51) Int. Cl.
| | |
|---|---|
| *C12N 15/85* | (2006.01) |
| *C07H 21/04* | (2006.01) |
| *C12N 7/00* | (2006.01) |
| *C07K 14/47* | (2006.01) |
| *A61P 25/28* | (2006.01) |
| *A61K 9/00* | (2006.01) |
| *A61K 35/76* | (2015.01) |
| *A61K 48/00* | (2006.01) |
| *C07K 14/005* | (2006.01) |
| *C07K 14/61* | (2006.01) |
| *C07K 14/705* | (2006.01) |
| *A61P 25/16* | (2006.01) |
| *C07K 14/435* | (2006.01) |
| *A61K 35/761* | (2015.01) |
| *C12N 15/861* | (2006.01) |
| *C12N 15/86* | (2006.01) |
| *A61K 39/23* | (2006.01) |
| *C12N 15/864* | (2006.01) |

(52) U.S. Cl.
CPC .............. *C12N 7/00* (2013.01); *A61K 9/0019* (2013.01); *A61K 9/0085* (2013.01); *A61K 35/76* (2013.01); *A61K 35/761* (2013.01); *A61K 48/0058* (2013.01); *A61K 48/0075* (2013.01); *A61P 25/16* (2018.01); *A61P 25/28* (2018.01); *C07K 14/005* (2013.01); *C07K 14/435* (2013.01); *C07K 14/47* (2013.01); *C07K 14/61* (2013.01); *C07K 14/70503* (2013.01); *C12N 15/861* (2013.01); *A61K 39/23* (2013.01); *C07H 21/04* (2013.01); *C12N 15/86* (2013.01); *C12N 15/8645* (2013.01); *C12N 2750/14022* (2013.01); *C12N 2750/14043* (2013.01); *C12N 2750/14121* (2013.01); *C12N 2750/14122* (2013.01); *C12N 2750/14143* (2013.01); *C12Y 302/01045* (2013.01)

(58) Field of Classification Search
CPC ........... C12N 7/00; C12N 15/86; C07H 21/04
See application file for complete search history.

(56) References Cited

U.S. PATENT DOCUMENTS

| | | | |
|---|---|---|---|
| 7,452,716 | B2 | 11/2008 | Yew |
| 8,486,635 | B2 | 7/2013 | Hutton et al. |
| 9,034,836 | B2 | 5/2015 | Dodge et al. |
| 9,486,541 | B2 | 11/2016 | Hutton et al. |
| 10,689,625 | B2 | 6/2020 | Abeliovich et al. |
| 2003/0133924 | A1 | 7/2003 | Canfield |
| 2006/0292117 | A1 | 12/2006 | Loiler et al. |
| 2008/0003204 | A1 | 1/2008 | Flotte et al. |
| 2013/0287736 | A1 | 10/2013 | Passini et al. |
| 2015/0284472 | A1 | 8/2015 | Sardi et al. |
| 2017/0246263 | A1 | 8/2017 | Concino et al. |
| 2018/0147300 | A1 | 5/2018 | Park et al. |
| 2019/0282662 | A1 | 9/2019 | Kay et al. |

(Continued)

FOREIGN PATENT DOCUMENTS

| | | |
|---|---|---|
| EP | 2687223 A1 | 1/2014 |
| WO | WO-0183692 A2 | 11/2001 |

(Continued)

OTHER PUBLICATIONS

Anderson, et al. "Humanpathology in NCL." Biochim Biophys Acta. Nov. 2013;1832(11):1807-26. doi: 10.1016/j.bbadis.2012.11.014.

(Continued)

*Primary Examiner* — Shin Lin Chen
(74) *Attorney, Agent, or Firm* — Cooley LLP; Ivor. R. Elrifi

(57) ABSTRACT

The disclosure relates, in some aspects, to compositions and methods for treatment of diseases associated with aberrant lysosomal function, for example Parkinson's disease (PD) and Gaucher disease. In some embodiments, the disclosure provides expression constructs comprising a transgene encoding beta-Glucocerebrosidase (GBA) or a portion thereof alone or in combination with one or more PD-associated genes. In some embodiments, the disclosure provides methods of Parkinson's disease by administering such expression constructs to a subject in need thereof.

14 Claims, 48 Drawing Sheets
Specification includes a Sequence Listing.

(56) References Cited

U.S. PATENT DOCUMENTS

| | | |
|---|---|---|
| 2019/0328906 A1 | 10/2019 | Chen Plotkin et al. |
| 2019/0388507 A1 | 12/2019 | Kay |
| 2020/0231970 A1 | 7/2020 | Abeliovich et al. |
| 2020/0318115 A1 | 10/2020 | Abeliovich et al. |
| 2020/0332265 A1 | 10/2020 | Abeliovich et al. |
| 2020/0338148 A1 | 10/2020 | Abeliovich et al. |
| 2021/0332385 A1 | 10/2021 | Abeliovich et al. |

FOREIGN PATENT DOCUMENTS

| | | |
|---|---|---|
| WO | WO-2009120978 A2 | 10/2009 |
| WO | WO 2014/071282 A1 | 5/2014 |
| WO | WO 2014/186579 A1 | 11/2014 |
| WO | WO 2016/081927 A2 | 3/2016 |
| WO | WO 2017/136202 A1 | 8/2017 |
| WO | WO 2019/070891 A1 | 4/2019 |
| WO | WO 2019/070893 A1 | 4/2019 |
| WO | WO-2019084068 A1 | 5/2019 |
| WO | WO 2020/210615 A1 | 10/2020 |

OTHER PUBLICATIONS

Bond, et al. "Use of model organisms for the study of neuronal ceroid lipofuscinosis." Biochim Biophys Acta. Nov. 2013;1832(11):1842-65, doi: 10.1016/j.bbadis.2013.01.009.

Gotz, et al. "Animal models for Alzheimer's disease and frontotemporal dementia: a perspective." ASN Neuro. Nov. 9, 2009;1(4):e00019. doi: 10.1042/AN20090042.

Xu, et al. "Extracellular progranulin protects cortical neurons from toxic insults by activating survival signaling." Neurobiol Aging, Dec. 2011;32(12):2326.e5-16. doi: 10.1016/j.neurobiolaging.2011.06.017.

Yu, et al. "The spectrum of mutations in progranulin: a collaborative study screening 545 cases of neurodegeneration." Arch Neurol. Feb. 2010;67(2):161-70, doi: 10.1001/archneurol.2009.328.

GenBank Accession No. AAP36904.1 "*Homo sapiens* glucosidase, beta; acid (includes glucosylceramidase), partial [synthetic construct]" Jul. 25, 2016 [online].

GenBank Accession No. BT008212.1 "Synthetic construct *Homo sapiens* glucosidase, beta; acid (includes glucosylceramidase) mRNA, partial cds" Jul. 25, 2016 [online].

GenBank Accession No. NP_000148.2 "lysosomal acid glucosylceramidase isoform 1 precursor [*Homo sapiens*]" Jan. 8, 2020 [online].

GenBank Accession No. NP_005497.1 "lysosome membrane protein 2 isoform 1 precursor [*Homo sapiens*]" Jan. 1, 2020 [online].

GenBank Accession No. NP_002769.1 "prosaposin isoform a preproprotein [*Homo sapiens*]" Sep. 27, 2019 [online].

GenBank Accession No. NP_001191184.1 "lysosome membrane protein 2 isoform 2 precursor [*Homo sapiens*]" Jan. 4, 2020 [online].

GenBank Accession No. AAH01503.1 "Prosaposin [*Homo sapiens*]" Aug. 4, 2008 [online].

GenBank Accession No. AAH07612.1 "Prosaposin [*Homo sapiens*]" Aug. 4, 2008 [online].

GenBank Accession No. AAH04275.1 "Prosaposin [*Homo sapiens*]" Aug. 4, 2008 [online].

GenBank Accession No. AAA60303.1 "Prosaposin [*Homo sapiens*]" Jan. 9, 1995 [online].

GenBank Accession No. NP_001005742.1 "lysosomal acid glucosylceramidase isoform 1 precursor [*Homo sapiens*]" Nov. 11, 2019 [online].

GenBank Accession No. NP_001165282.1 "lysosomal acid glucosylceramidase isoform 2 [*Homo sapiens*]" Nov. 11, 2019 [online].

GenBank Accession No. NP_001165283.1 "lysosomal acid glucosylceramidase isoform 3 [*Homo sapiens*]" Nov. 11, 2019 [online].

GenBank Accession No. NP_065995.1 "non-lysosomal glucosylceramidase isoform 1 [*Homo sapiens*]" Aug. 22, 2019 [online].

GenBank Accession No. NP_000144.2 "galactocerebrosidase isoform a precursor [*Homo sapiens*]" Sep. 26, 2019 [online].

GenBank Accession No. NP_001899.1 "cathepsin B isoform 1 preproprotein [*Homo sapiens*]" Jan. 27, 2020 [online].

GenBank Accession No. NP_000534.3 "sphingomyelin phosphodiesterase isoform 1 precursor [*Homo sapiens*]" Jan. 13, 2020 [online].

GenBank Accession No. NP_003920.1 "ras-related protein Rab-7L1 isoform 1 [*Homo sapiens*]" Dec. 31, 2019 [online].

GenBank Accession No. NP_060676.2 "vacuolar protein sorting-associated protein 35 [*Homo sapiens*]" Oct. 11, 2019 [online].

GenBank Accession No. NP_689669.2 "interleukin-34 isoform 1 precursor [*Homo sapiens*]" Dec. 25, 2019 [online].

GenBank Accession No. NP_061838.1 "triggering receptor expressed on myeloid cells 2 precursor isoform 1 precursor [*Homo sapiens*]" Feb. 2, 2020 [online].

GenBank Accession No. NP_060844.2 "transmembrane protein 106B [*Homo sapiens*]" Jul. 28, 2019 [online].

GenBank Accession No. NP_002078.1 "progranulin precursor [*Homo sapiens*]" Jan. 21, 2020 [online].

GenBank Accession No. NP_001317589.1 "non-lysosomal glucosylceramidase isoform 2 [*Homo sapiens*]" Aug. 7, 2019 [online].

GenBank Accession No. EAW81359.1 "galactosylceramidase, isoform CRA_a [*Homo sapiens*]" Mar. 23, 2015 [online].

GenBank Accession No. EAW81360.1 "galactosylceramidase, isoform CRA_b [*Homo sapiens*]" Mar. 23, 2015 [online].

GenBank Accession No. EAW81362.1 "galactosylceramidase, isoform CRA_c [*Homo sapiens*]" Mar. 23, 2015 [online].

GenBank Accession No. EAW68726.1 "sphingomyelin phosphodiesterase 1, acid lysosomal (acid sphingomyelinase), isoform CRA_a [*Homo sapiens*]" Mar. 23, 2015 [online].

GenBank Accession No. EAW68727.1 "sphingomyelin phosphodiesterase 1, acid lysosomal (acid sphingomyelinase), isoform CRA_b [*Homo sapiens*]" Mar. 23, 2015 [online].

GenBank Accession No. EAW68728.1 "sphingomyelin phosphodiesterase 1, acid lysosomal (acid sphingomyelinase), isoform CRA_c [*Homo sapiens*]" Mar. 23, 2015 [online].

GenBank Accession No. EAW68729.1 "sphingomyelin phosphodiesterase 1, acid lysosomal (acid sphingomyelinase), isoform CRA_d [*Homo sapiens*]" Mar. 23, 2015 [online].

GenBank Accession No. AAC37547.1 "cathepsin B [*Homo sapiens*]" Apr. 7, 1994 [online].

GenBank Accession No. AAH95408.1 "Cathepsin B [*Homo sapiens*]" Jul. 17, 2006 [online].

GenBank Accession No. AAH10240.1 "Cathepsin B [*Homo sapiens*]" Jul. 15, 2006 [online].

GenBank Accession No. AAH02585.1 "RAB7, member RAS oncogene family-like 1 [*Homo sapiens*]" Jul. 15, 2006 [online].

GenBank Accession No. AAH25415.1 "GTP cyclohydrolase 1 [*Homo sapiens*]" Aug. 7, 2008 [online].

GenBank Accession No. AAH29804.1 "Interleukin 34 [*Homo sapiens*]" Jun. 9, 2008 [online].

GenBank Accession No. AAF69824.1 "triggering receptor expressed on myeloid cells 2 [*Homo sapiens*]" May 23, 2000 [online].

GenBank Accession No. NP_002087.1 "general transcription factor IIF, polypeptide 1, 74kDa [*Homo sapiens*]" Jun. 3, 2007 [online].

GenBank Accession No. NP_000152.1 "GTP cyclohydrolase 1 isoform 1 [*Homo sapiens*]" Dec. 30, 2019 [online].

Fath, S. et al. "Multiparameter RNA and Codon Optimization: A Standardized Tool to Assess and Enhance Autologous Mammalian Gene Expression," PLoS ONE, Mar. 3, 2011, 6(3):e17596:1-14.

Arrant, et al. "Progranulin Gene Therapy Improves Lysosomal Dysfunction and Microglial Pathology Associated with Frontotemporal Dementia and Neuronal Ceroid Lipofuscinosis." The Journal of Neuroscience, Feb. 28, 2018, 38(9), 2341-2358.

Ciesielska, et al. "Cerebral infusion of AAV9 vector-encoding non-self proteins can elicit cell-mediated immune responses." Mol Ther., Jan. 2013, 21(1), 158-66.

Database Accession No. Q14108, "Lysosome membrane protein II," Nov. 1, 1997, https://www.uniprot.org/Q14108.txt, 1-10.

Database Accession No. BDA66566, "Adeno-associated virus—2 (AAV2) ITR S-sequence, SEQ ID 3," Jul. 14, 2016, http://ibis.internal.epo.org/exam/dbfetch.jsp?id=GSN:BDA66566, 1 page.

(56) References Cited

OTHER PUBLICATIONS

Renaud-Gabardos, et al., "Internal ribosome entry site-based vectors for combined gene therapy," World Journal of Experimental Medicine, Feb. 20, 2015, 5(1), 11-20.
Rothaug, et al., "LIMP-2 expression is critical for β-glucocerebrosidase activity and α-synuclein clearance," PNAS, Oct. 28, 2014, 111(43), 15573-15578.
Samaranch, et al. "AAV9-mediated expression of a non-self protein in nonhuman primate central nervous system triggers widespread neuroinflammation driven by antigen-presenting cell transduction." Mol Ther., Feb. 2014,;22(2):329-337.
Supplemental European Search Report issued in EP application No. 18864729.1 dated Jul. 2, 2021, 1-12.
Tamargo, et al., "The role of saposin C in Gaucher disease," Molecular Genetics and Metabolism, Apr. 29, 2012, 106, 257-263.
Choi et al., "Optimization of AAV expression cassettes to improve packaging capacity and transgene expression in neurons," Molecular Brain, 2014, 7(17):1-10.
François, A., et al., "The Cellular TATA Binding Protein is Required for Rep-Dependent Replication of a Minimal Adeno-associated Virus Type 2 p5 Element," Journal of Virology, Sep. 2005, 79(17):11082-11094.
G0345, pFBAAVCAGmcsBgHpA Viral Vector Core updated Feb. 22, 2017 [retrieved from the internet on Jun. 10, 2022] URL: https://medicine.uiowa.edu/vectorcore/sites/medicine.uiowa.edu.vectorcore/files/wysiwyg_uploads/Manual_G0345_pFBAAVCAGmcsBgHpA_0.pdf, 7 pages.
Ge, J., et al., "Optimization of eGFP Expression using a Modified Baculovirus Expression System," Journal of biotechnology, 2014, 173:41-6.
Huang, W., et al., "Targeting Visceral Fat by Intraperitoneal Delivery of Novel AAV Serotype Vector Restricting Off-Target Transduction in Liver," Molecular Therapy—Methods & Clinical Development, Sep. 2017, 6:68-78.
Jian, J., et al., "Association Between Progranulin and Gaucher Disease," EBioMedicine, Nov. 2016:127-37.
Sikora, J., et al., "Neurolysosomal pathology in human prosaposin deficiency suggests essential neurotrophic function of prosaposin," Acta Neuropathol., Feb. 2007, 113(2):163-175.
Wang, L., et al., "Enhancing Transgene Expression from Recombinant AAV8 Vectors in Different Tissues Using Woodchuck Hepatitis Virus Post-Transcriptional Regulatory Element," International Journal of medical sciences, 2016, 13:286-291.

PrevailVector_FP12_CMVe_CBA_GBA1_bGH_JetLong_IL34_SV40l_4503nt
11,459 bp

GENE THERAPIES FOR LYSOSOMAL DISORDERS

RELATED APPLICATIONS

This Application is a continuation of U.S. patent application Ser. No. 16/690,320, filed Nov. 21, 2019 and issued as U.S. Pat. No. 10,689,625, which is a continuation of International Patent Application No. PCT/US2018/054227, filed Oct. 3, 2018, which claims the benefit under 35 U.S.C. 119(e) of the filing date of U.S. Provisional Application Ser. No. 62/567,296, filed Oct. 3, 2017, entitled "GENE THERAPIES FOR LYSOSOMAL DISORDERS", 62/567,311, filed Oct. 3, 2017, entitled "GENE THERAPIES FOR LYSOSOMAL DISORDERS", 62/567,319, filed Oct. 3, 2017, entitled "GENE THERAPIES FOR LYSOSOMAL DISORDERS", 62/567,301, filed Oct. 3, 2017, entitled "GENE THERAPIES FOR LYSOSOMAL DISORDERS", and 62/567,310, filed Oct. 3, 2017, entitled "GENE THERAPIES FOR LYSOSOMAL DISORDERS". The disclosure of each of these applications is incorporated herein by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: PRVL_003_06US_SeqList_ST25.txt, date recorded: Jun. 18, 2020, file size ~522,134 bytes).

BACKGROUND

Gaucher disease is a rare inborn error of glycosphingolipid metabolism due to deficiency of lysosomal acid β-glucocerebrosidase (Gcase, "GBA"). Patients suffer from non-CNS symptoms and findings including hepatosplenomegly, bone marrow insufficiency leading to pancytopenia, lung disorders and fibrosis, and bone defects. In addition, a significant number of patients suffer from neurological manifestations, including defective saccadic eye movements and gaze, seizures, cognitive deficits, developmental delay, and movement disorders including Parkinson's disease.

Several therapeutics exist that address the peripheral disease and the principal clinical manifestations in hematopoietic bone marrow and viscera, including enzyme replacement therapies as described below, chaperone-like small molecule drugs that bind to defective Gcase and improve stability, and substrate reduction therapy that block the production of substrate that accumulate in Gaucher disease leading to symptoms and findings. However, other aspects of Gaucher disease (particularly those affecting the skeleton and brain) appear refractory to treatment.

SUMMARY

In addition to Gaucher disease patients (who possess mutations in both chromosomal alleles of GBA1 gene), patients with mutations in only one allele of GBA1 are at highly increased risk of Parkinson's disease (PD). The severity of PD symptoms—which include gait difficulty, a tremor at rest, rigidity, and often depression, sleep difficulties, and cognitive decline—correlate with the degree of enzyme activity reduction. Thus, Gaucher disease patients have the most severe course, whereas patient with a single mild mutation in GBA1 typically have a more benign course. Mutation carriers are also at high risk of other PD-related disorders, including Lewy Body Dementia, characterized by executive dysfunction, psychosis, and a PD-like movement disorder, and multi-system atrophy, with characteristic motor and cognitive impairments. No therapies exist that alter the inexorable course of these disorders.

Deficits in enzymes such as Gcase (e.g., the gene product of GBA1 gene), as well as common variants in many genes implicated in lysosome function or trafficking of macromolecules to the lysosome (e.g., Lysosomal Membrane Protein 1 (LIMP), also referred to as SCARB2), have been associated with increased PD risk. The disclosure is based, in part, on expression constructs (e.g., vectors) encoding one or more PD-associated genes, for example Gcase, GBA2, prosaposin, progranulin, LIMP2, GALC, CTSB, SMPD1, GCH1, RAB7, VPS35, IL-34, TREM2, TMEM106B, or a combination of any of the foregoing (or portions thereof). In some embodiments, combinations of gene products described herein act together (e.g., synergistically) to reduce one or more signs and symptoms of PD when expressed in a subject.

Accordingly, in some aspects, the disclosure provides an isolated nucleic acid comprising an expression construct encoding a Gcase (e.g., the gene product of GBA1 gene). In some embodiments, the isolated nucleic acid comprises a Gcase-encoding sequence that has been codon optimized (e.g., codon optimized for expression in mammalian cells, for example human cells). In some embodiments, the nucleic acid sequence encoding the Gcase encodes a protein comprising an amino acid sequence as set forth in SEQ ID NO: 14 (e.g., as set forth in NCBI Reference Sequence NP_000148.2). In some embodiments, the isolated nucleic acid comprises the sequence set forth in SEQ ID NO: 15. In some embodiments the expression construct comprises adeno-associated virus (AAV) inverted terminal repeats (ITRs), for example AAV ITRs flanking the nucleic acid sequence encoding the Gcase protein.

In some aspects, the disclosure provides an isolated nucleic acid comprising an expression construct encoding Prosaposin (e.g., the gene product of PSAP gene). In some embodiments, the isolated nucleic acid comprises a prosaposin-encoding sequence that has been codon optimized (e.g., codon optimized for expression in mammalian cells, for example human cells). In some embodiments, the nucleic acid sequence encoding the prosaposin encodes a protein comprising an amino acid sequence as set forth in SEQ ID NO: 16 (e.g., as set forth in NCBI Reference Sequence NP_002769.1). In some embodiments, the isolated nucleic acid comprises the sequence set forth in SEQ ID NO: 17. In some embodiments the expression construct comprises adeno-associated virus (AAV) inverted terminal repeats (ITRs), for example AAV ITRs flanking the nucleic acid sequence encoding the prosaposin protein.

In some aspects, the disclosure provides an isolated nucleic acid comprising an expression construct encoding LIMP2/SCARB2 (e.g., the gene product of SCARB2 gene). In some embodiments, the isolated nucleic acid comprises a SCARB2-encoding sequence that has been codon optimized (e.g., codon optimized for expression in mammalian cells, for example human cells). In some embodiments, the nucleic acid sequence encoding the LIMP2/SCARB2 encodes a protein comprising an amino acid sequence as set forth in SEQ ID NO: 18 (e.g., as set forth in NCBI Reference Sequence NP_005497.1). In some embodiments, the isolated nucleic acid comprises the sequence set forth in SEQ ID NO: 29. In some embodiments the expression construct comprises adeno-associated virus (AAV) inverted terminal repeats (ITRs), for example AAV ITRs flanking the nucleic acid sequence encoding the SCARB2 protein.

In some aspects, the disclosure provides an isolated nucleic acid comprising an expression construct encoding GBA2 protein (e.g., the gene product of GBA2 gene). In some embodiments, the isolated nucleic acid comprises a GBA2-encoding sequence that has been codon optimized (e.g., codon optimized for expression in mammalian cells, for example human cells). In some embodiments, the nucleic acid sequence encoding the GBA2 encodes a protein comprising an amino acid sequence as set forth in SEQ ID NO: 30 (e.g., as set forth in NCBI Reference Sequence NP_065995.1). In some embodiments, the isolated nucleic acid comprises the sequence set forth in SEQ ID NO: 31. In some embodiments the expression construct comprises adeno-associated virus (AAV) inverted terminal repeats (ITRs), for example AAV ITRs flanking the nucleic acid sequence encoding the GBA2 protein.

In some aspects, the disclosure provides an isolated nucleic acid comprising an expression construct encoding GALC protein (e.g., the gene product of GALC gene). In some embodiments, the isolated nucleic acid comprises a GALC-encoding sequence that has been codon optimized (e.g., codon optimized for expression in mammalian cells, for example human cells). In some embodiments, the nucleic acid sequence encoding the GALC encodes a protein comprising an amino acid sequence as set forth in SEQ ID NO: 33 (e.g., as set forth in NCBI Reference Sequence NP_000144.2). In some embodiments, the isolated nucleic acid comprises the sequence set forth in SEQ ID NO: 34. In some embodiments the expression construct comprises adeno-associated virus (AAV) inverted terminal repeats (ITRs), for example AAV ITRs flanking the nucleic acid sequence encoding the GALC protein.

In some aspects, the disclosure provides an isolated nucleic acid comprising an expression construct encoding CTSB protein (e.g., the gene product of CTSB gene). In some embodiments, the isolated nucleic acid comprises a CTSB-encoding sequence that has been codon optimized (e.g., codon optimized for expression in mammalian cells, for example human cells). In some embodiments, the nucleic acid sequence encoding the CTSB encodes a protein comprising an amino acid sequence as set forth in SEQ ID NO: 35 (e.g., as set forth in NCBI Reference Sequence NP_001899.1). In some embodiments, the isolated nucleic acid comprises the sequence set forth in SEQ ID NO: 36. In some embodiments the expression construct comprises adeno-associated virus (AAV) inverted terminal repeats (ITRs), for example AAV ITRs flanking the nucleic acid sequence encoding the CTSB protein.

In some aspects, the disclosure provides an isolated nucleic acid comprising an expression construct encoding SMPD1 protein (e.g., the gene product of SMPD1 gene). In some embodiments, the isolated nucleic acid comprises a SMPD1-encoding sequence that has been codon optimized (e.g., codon optimized for expression in mammalian cells, for example human cells). In some embodiments, the nucleic acid sequence encoding the SMPD1 encodes a protein comprising an amino acid sequence as set forth in SEQ ID NO: 37 (e.g., as set forth in NCBI Reference Sequence NP_000534.3). In some embodiments, the isolated nucleic acid comprises the sequence set forth in SEQ ID NO: 38. In some embodiments the expression construct comprises adeno-associated virus (AAV) inverted terminal repeats (ITRs), for example AAV ITRs flanking the nucleic acid sequence encoding the SMPD1 protein.

In some aspects, the disclosure provides an isolated nucleic acid comprising an expression construct encoding GCH1 protein (e.g., the gene product of GCH1 gene). In some embodiments, the isolated nucleic acid comprises a GCH1-encoding sequence that has been codon optimized (e.g., codon optimized for expression in mammalian cells, for example human cells). In some embodiments, the nucleic acid sequence encoding the GCH1 encodes a protein comprising an amino acid sequence as set forth in SEQ ID NO: 45 (e.g., as set forth in NCBI Reference Sequence NP_000534.3). In some embodiments, the isolated nucleic acid comprises the sequence set forth in SEQ ID NO: 46. In some embodiments the expression construct comprises adeno-associated virus (AAV) inverted terminal repeats (ITRs), for example AAV ITRs flanking the nucleic acid sequence encoding the GCH1 protein.

In some aspects, the disclosure provides an isolated nucleic acid comprising an expression construct encoding RAB7L protein (e.g., the gene product of RAB7L gene). In some embodiments, the isolated nucleic acid comprises a RAB7L-encoding sequence that has been codon optimized (e.g., codon optimized for expression in mammalian cells, for example human cells). In some embodiments, the nucleic acid sequence encoding the RAB7L encodes a protein comprising an amino acid sequence as set forth in SEQ ID NO: 47 (e.g., as set forth in NCBI Reference Sequence NP_003920.1). In some embodiments, the isolated nucleic acid comprises the sequence set forth in SEQ ID NO: 48. In some embodiments the expression construct comprises adeno-associated virus (AAV) inverted terminal repeats (ITRs), for example AAV ITRs flanking the nucleic acid sequence encoding the RAB7L protein.

In some aspects, the disclosure provides an isolated nucleic acid comprising an expression construct encoding VPS35 protein (e.g., the gene product of VPS35 gene). In some embodiments, the isolated nucleic acid comprises a VPS35-encoding sequence that has been codon optimized (e.g., codon optimized for expression in mammalian cells, for example human cells). In some embodiments, the nucleic acid sequence encoding the VPS35 encodes a protein comprising an amino acid sequence as set forth in SEQ ID NO: 49 (e.g., as set forth in NCBI Reference Sequence NP_060676.2). In some embodiments, the isolated nucleic acid comprises the sequence set forth in SEQ ID NO: 50. In some embodiments the expression construct comprises adeno-associated virus (AAV) inverted terminal repeats (ITRs), for example AAV ITRs flanking the nucleic acid sequence encoding the VPS35 protein.

In some aspects, the disclosure provides an isolated nucleic acid comprising an expression construct encoding IL-34 protein (e.g., the gene product of IL34 gene). In some embodiments, the isolated nucleic acid comprises a IL-34-encoding sequence that has been codon optimized (e.g., codon optimized for expression in mammalian cells, for example human cells). In some embodiments, the nucleic acid sequence encoding the IL-34 encodes a protein comprising an amino acid sequence as set forth in SEQ ID NO: 55 (e.g., as set forth in NCBI Reference Sequence NP_689669.2). In some embodiments, the isolated nucleic acid comprises the sequence set forth in SEQ ID NO: 56. In some embodiments the expression construct comprises adeno-associated virus (AAV) inverted terminal repeats (ITRs), for example AAV ITRs flanking the nucleic acid sequence encoding the IL_34 protein.

In some aspects, the disclosure provides an isolated nucleic acid comprising an expression construct encoding TREM2 protein (e.g., the gene product of TREM gene). In some embodiments, the isolated nucleic acid comprises a TREM2-encoding sequence that has been codon optimized (e.g., codon optimized for expression in mammalian cells, for example human cells). In some embodiments, the nucleic acid sequence encoding the TREM2 encodes a protein comprising an amino acid sequence as set forth in SEQ ID NO: 57 (e.g., as set forth in NCBI Reference Sequence NP_061838.1). In some embodiments, the isolated nucleic acid comprises the sequence set forth in SEQ ID NO: 58. In some embodiments the expression construct comprises adeno-associated virus (AAV) inverted terminal repeats (ITRs), for example AAV ITRs flanking the nucleic acid sequence encoding the TREM2 protein.

In some aspects, the disclosure provides an isolated nucleic acid comprising an expression construct encoding TMEM106B protein (e.g., the gene product of TMEM106B gene). In some embodiments, the isolated nucleic acid comprises a TMEM106B-encoding sequence that has been codon optimized (e.g., codon optimized for expression in mammalian cells, for example human cells). In some embodiments, the nucleic acid sequence encoding the TMEM106B encodes a protein comprising an amino acid sequence as set forth in SEQ ID NO: 63 (e.g., as set forth in NCBI Reference Sequence NP_060844.2). In some embodiments, the isolated nucleic acid comprises the sequence set forth in SEQ ID NO: 64. In some embodiments the expression construct comprises adeno-associated virus (AAV) inverted terminal repeats (ITRs), for example AAV ITRs flanking the nucleic acid sequence encoding the TMEM106B protein.

In some aspects, the disclosure provides an isolated nucleic acid comprising an expression construct encoding progranulin (e.g., the gene product of PGRN gene). In some embodiments, the isolated nucleic acid comprises a prosaposin-encoding sequence that has been codon optimized (e.g., codon optimized for expression in mammalian cells, for example human cells). In some embodiments, the nucleic acid sequence encoding the progranulin (PRGN) encodes a protein comprising an amino acid sequence as set forth in SEQ ID NO: 67 (e.g., as set forth in NCBI Reference Sequence NP_002078.1). In some embodiments, the isolated nucleic acid comprises the sequence set forth in SEQ ID NO: 68. In some embodiments the expression construct comprises adeno-associated virus (AAV) inverted terminal repeats (ITRs), for example AAV ITRs flanking the nucleic acid sequence encoding the prosaposin protein.

In some aspects, the disclosure provides an isolated nucleic acid comprising an expression construct encoding a first gene product and a second gene product, wherein each gene product independently is selected from the gene products, or portions thereof, set forth in Table 1.

In some embodiments, a first gene product or a second gene product is a Gcase protein, or a portion thereof. In some embodiments, a first gene product is a Gcase protein and a second gene product is selected from GBA2, prosaposin, progranulin, LIMP2, GALC, CTSB, SMPD1, GCH1, RAB7, VPS35, IL-34, TREM2, and TMEM106B.

In some embodiments, an expression construct further encodes an interfering nucleic acid (e.g., shRNA, miRNA, dsRNA, etc.). In some embodiments, an interfering nucleic acid inhibits expression of α-Synuclein (α-Synuclein). In some embodiments, an interfering nucleic acid that targets α-Synuclein comprises a sequence set forth in any one of SEQ ID NOs: 20-25. In some embodiments, an interfering nucleic acid that targets α-Synuclein binds to (e.g., hybridizes with) a sequence set forth in any one of SEQ ID NO: 20-25.

In some embodiments, an interfering nucleic acid inhibits expression of TMEM106B. In some embodiments, an interfering nucleic acid that targets TMEM106B comprises a sequence set forth in SEQ ID NO: 64 or 65. In some embodiments, an interfering nucleic acid that targets TMEM106B binds to (e.g., hybridizes with) a sequence set forth in SEQ ID NO: 64 or 65.

In some embodiments, an expression construct further comprises one or more promoters. In some embodiments, a promoter is a chicken-beta actin (CBA) promoter, a CAG promoter, a CD68 promoter, or a JeT promoter. In some embodiments, a promoter is a RNA pol II promoter (e.g., or an RNA pol III promoter (e.g., U6, etc.).

In some embodiments, an expression construct further comprises an internal ribosomal entry site (IRES). In some embodiments, an IRES is located between a first gene product and a second gene product.

In some embodiments, an expression construct further comprises a self-cleaving peptide coding sequence. In some embodiments, a self-cleaving peptide is a T2A peptide.

In some embodiments, an expression construct comprises two adeno-associated virus (AAV) inverted terminal repeat (ITR) sequences. In some embodiments, ITR sequences flank a first gene product and a second gene product (e.g., are arranged as follows from 5'-end to 3'-end: ITR-first gene product-second gene product-ITR). In some embodiments, one of the ITR sequences of an isolated nucleic acid lacks a functional terminal resolution site (trs). For example, in some embodiments, one of the ITRs is a ΔITR.

The disclosure relates, in some aspects, to rAAV vectors comprising an ITR having a modified "D" region (e.g., a D sequence that is modified relative to wild-type AAV2 ITR, SEQ ID NO: 29). In some embodiments, the ITR having the modified D region is the 5' ITR of the rAAV vector. In some embodiments, a modified "D" region comprises an "S" sequence, for example as set forth in SEQ ID NO: 26. In some embodiments, the ITR having the modified "D" region is the 3' ITR of the rAAV vector. In some embodiments, a modified "D" region comprises a 3'ITR in which the "D" region is positioned at the 3' end of the ITR (e.g., on the outside or terminal end of the ITR relative to the transgene insert of the vector). In some embodiments, a modified "D" region comprises a sequence as set forth in SEQ ID NO: 26 or 27.

In some embodiments, an isolated nucleic acid (e.g., an rAAV vector) comprises a TRY region. In some embodiments, a TRY region comprises the sequence set forth in SEQ ID NO: 28.

In some embodiments, an isolated nucleic acid described by the disclosure comprises or consists of, or encodes a peptide having, the sequence set forth in any one of SEQ ID NOs: 1-78.

In some aspects, the disclosure provides a vector comprising an isolated nucleic acid as described by the disclosure. In some embodiments, a vector is a plasmid, or a viral vector. In some embodiments, a viral vector is a recombinant AAV (rAAV) vector or a Baculovirus vector. In some embodiments, an rAAV vector is single-stranded (e.g., single-stranded DNA).

In some aspects, the disclosure provides a host cell comprising an isolated nucleic acid as described by the disclosure or a vector as described by the disclosure.

In some aspects, the disclosure provides a recombinant adeno-associated virus (rAAV) comprising a capsid protein and an isolated nucleic acid or a vector as described by the disclosure.

In some embodiments, a capsid protein is capable of crossing the blood-brain barrier, for example an AAV9 capsid protein or an AAVrh.10 capsid protein. In some embodiments, an rAAV transduces neuronal cells and non-neuronal cells of the central nervous system (CNS).

In some aspects, the disclosure provides a method for treating a subject having or suspected of having Parkinson's disease, the method comprising administering to the subject a composition (e.g., a composition comprising an isolated nucleic acid or a vector or a rAAV) as described by the disclosure.

In some embodiments, administration comprises direct injection to the CNS of a subject. In some embodiments, direct injection is intracerebral injection, intraparenchymal injection, intrathecal injection, intra-cisterna manga injection, or any combination thereof. In some embodiments, direct injection to the CNS of a subject comprises convection enhanced delivery (CED).

In some embodiments, administration comprises peripheral injection. In some embodiments, peripheral injection is intravenous injection.

BRIEF DESCRIPTION OF THE DRAWINGS

FIG. 36A shows data for overexpression of TREM2. FIG. 36B shows data for overexpression of GBA1 from the same construct.

DETAILED DESCRIPTION

Figure 1:
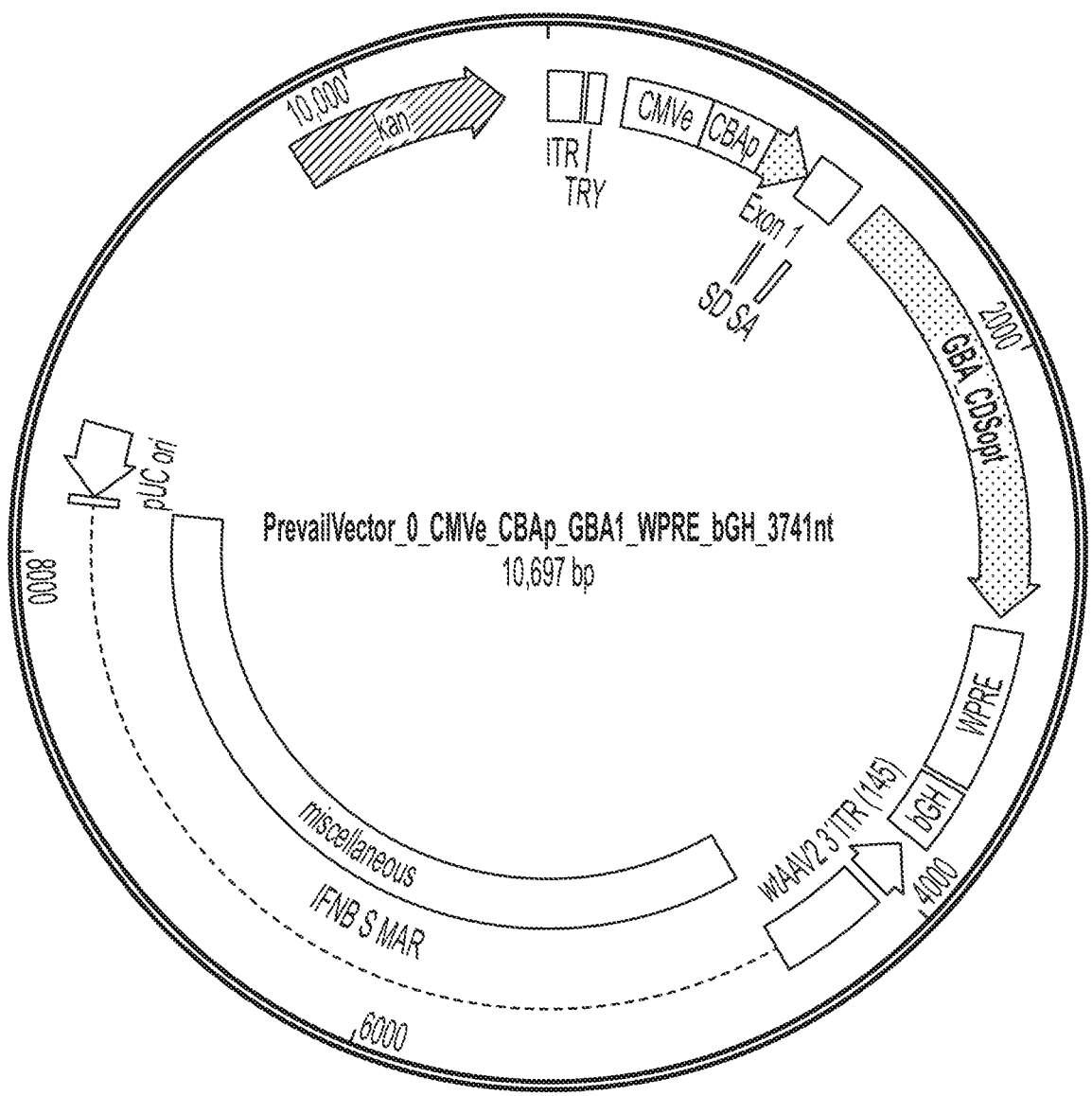
FIG. 1 is a schematic depicting one embodiment of a vector comprising an expression construct encoding Gcase (e.g., GBA1 or a portion thereof).
Figure 2:
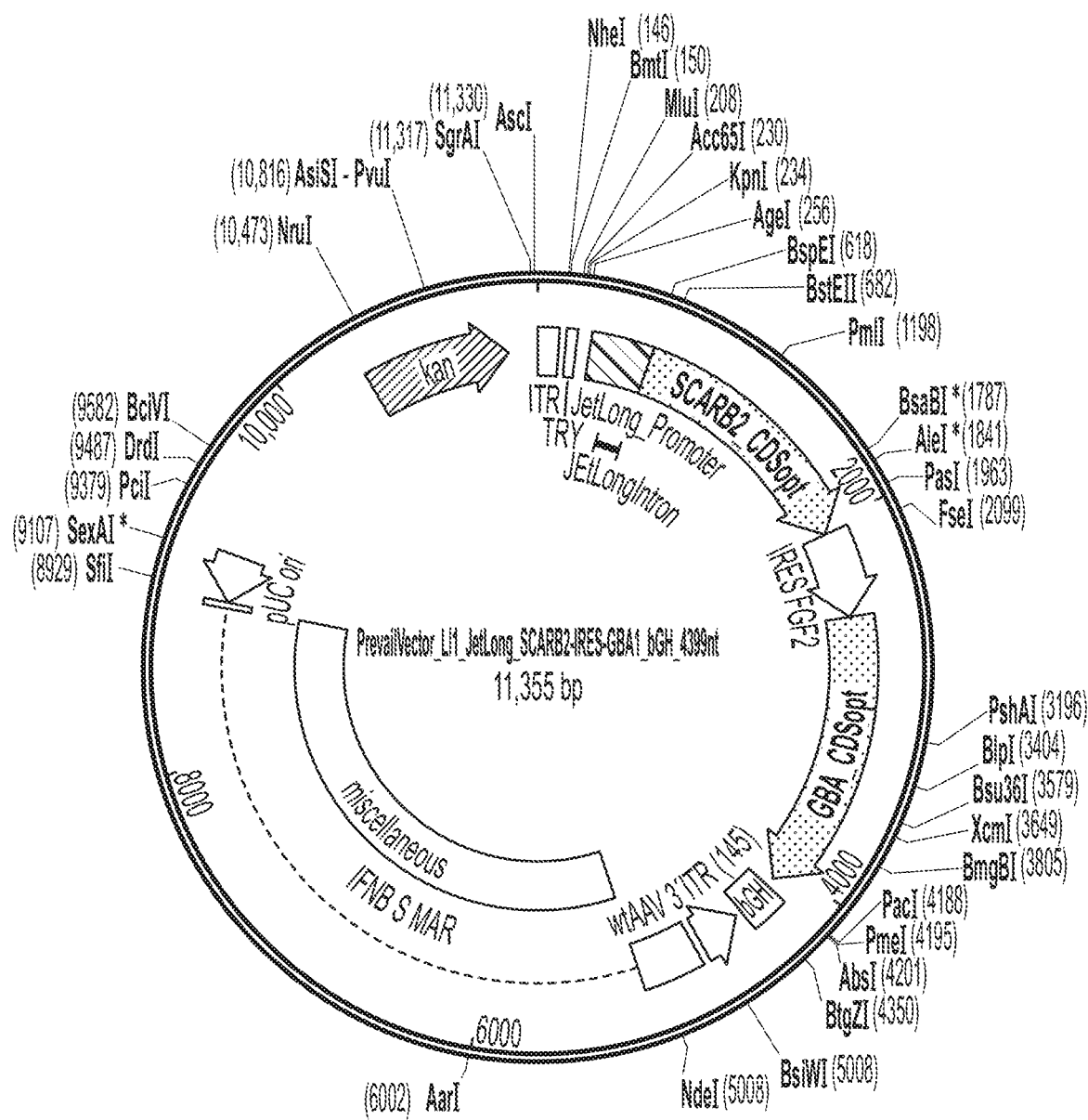
FIG. 2 is a schematic depicting one embodiment of a vector comprising an expression construct encoding Gcase (e.g., GBA1 or a portion thereof) and LIMP2 (SCARB2) or a portion thereof. The coding sequences of Gcase and LIMP2 are separated by an internal ribosomal entry site (IRES).
Figure 3:
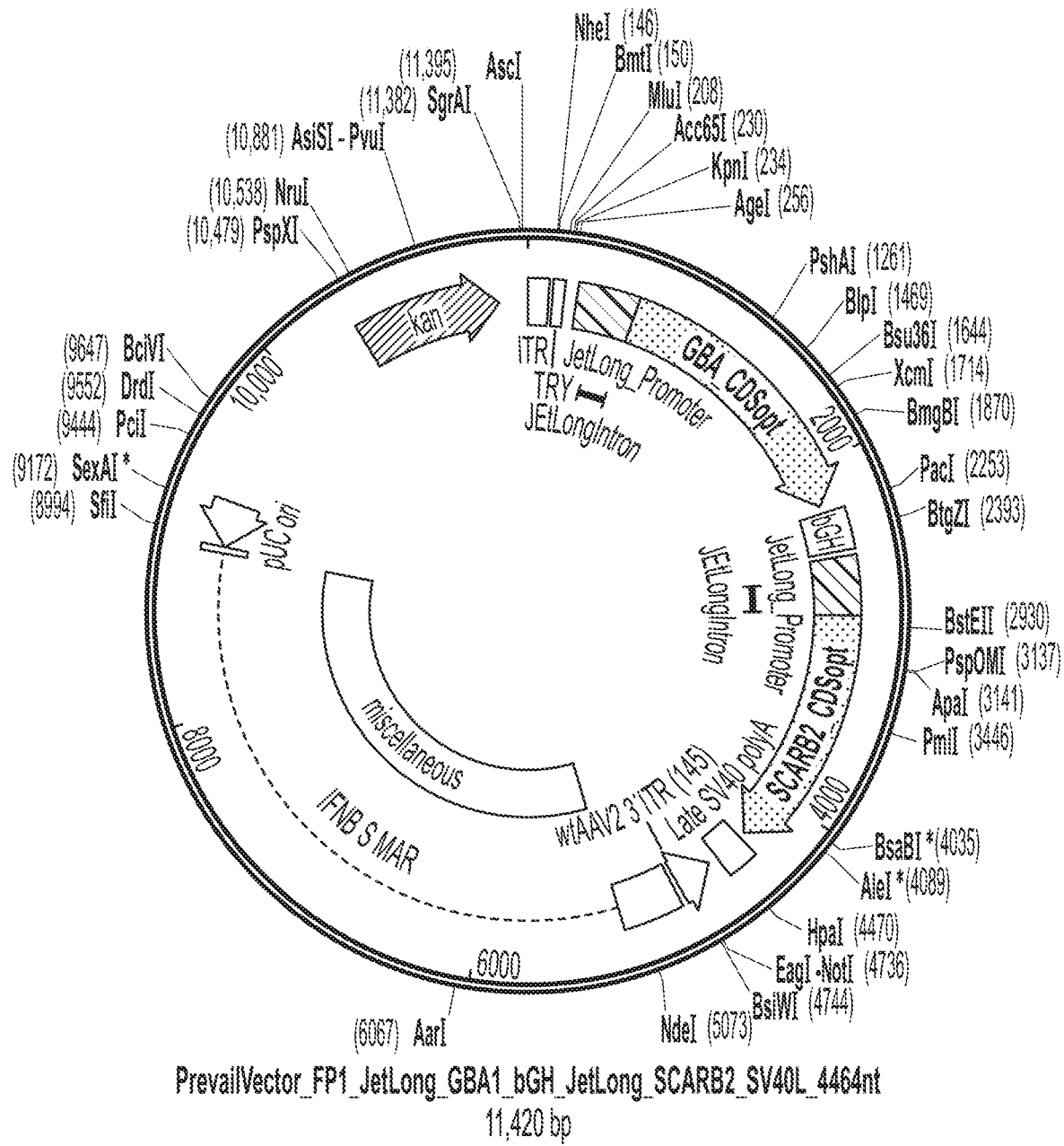
FIG. 3 is a schematic depicting one embodiment of a vector comprising an expression construct encoding Gcase (e.g., GBA1 or a portion thereof) and LIMP2 (SCARB2) or a portion thereof. Expression of the coding sequences of Gcase and LIMP2 are each driven by a separate promoter.
Figure 4:
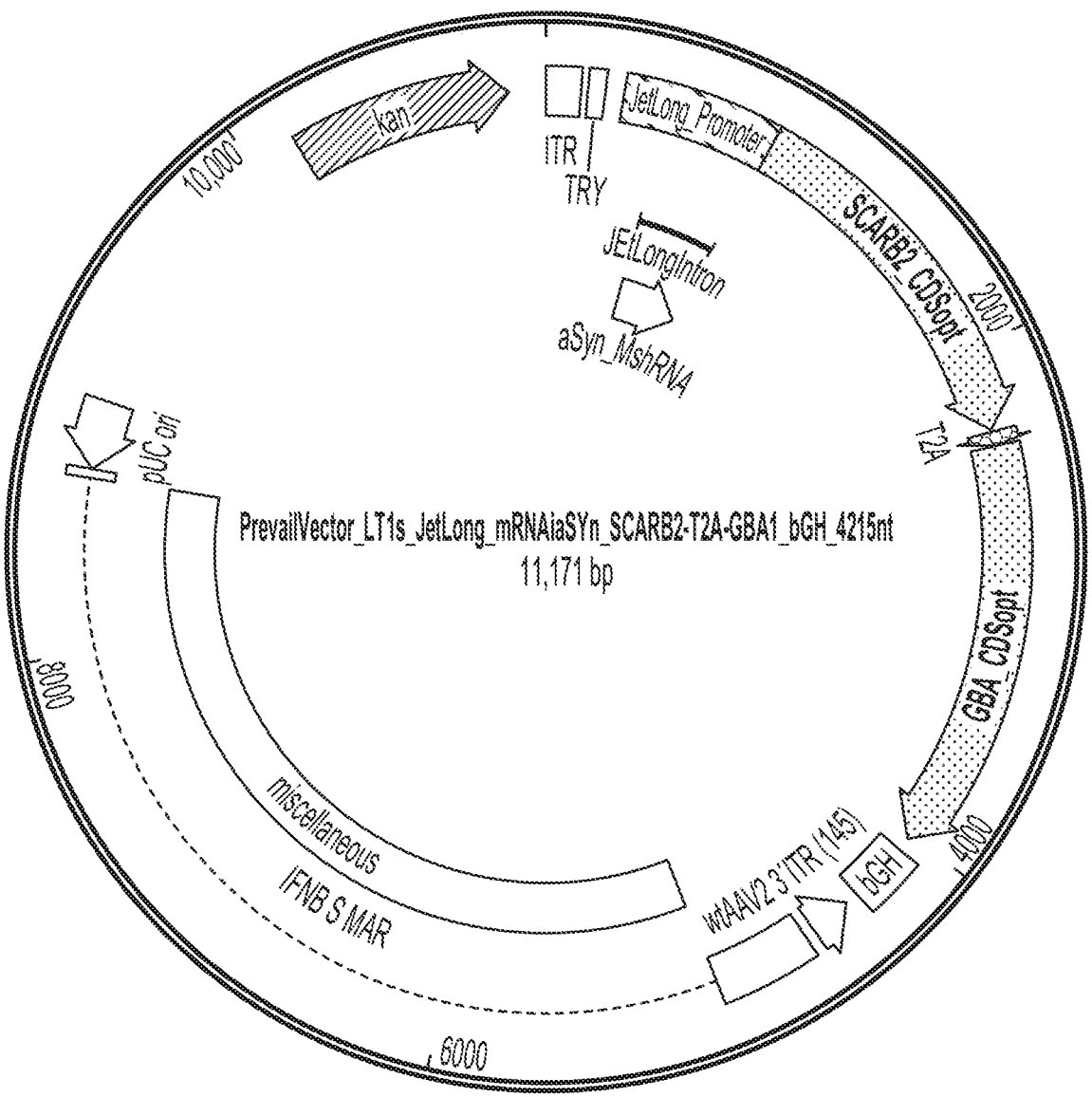
FIG. 4 is a schematic depicting one embodiment of a vector comprising an expression construct encoding Gcase (e.g., GBA1 or a portion thereof), LIMP2 (SCARB2) or a portion thereof, and an interfering RNA for α-Syn.
Figure 5:
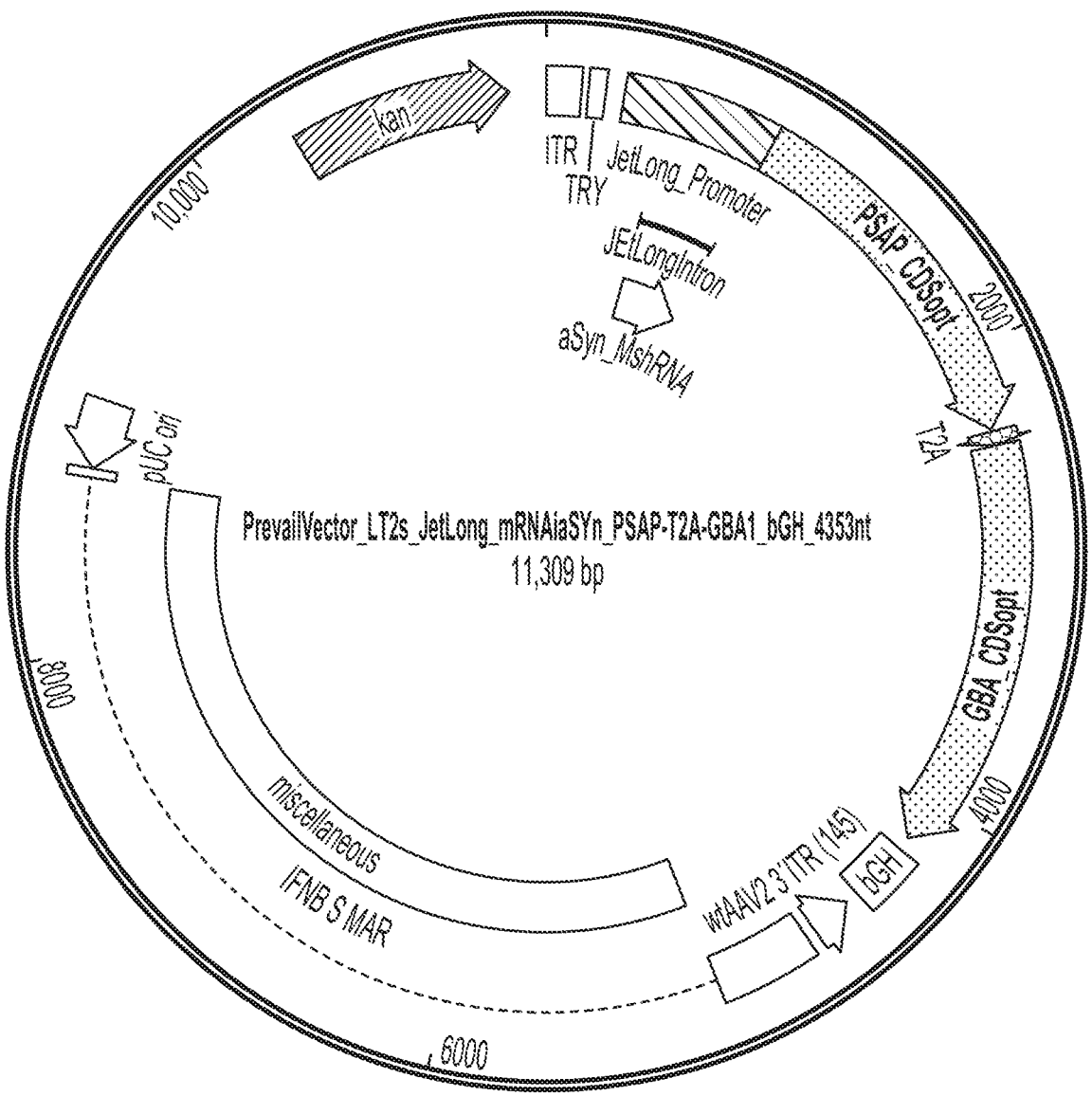
FIG. 5 is a schematic depicting one embodiment of a vector comprising an expression construct encoding Gcase (e.g., GBA1 or a portion thereof), Prosaposin (e.g., PSAP or a portion thereof), and an interfering RNA for α-Syn.
Figure 6:
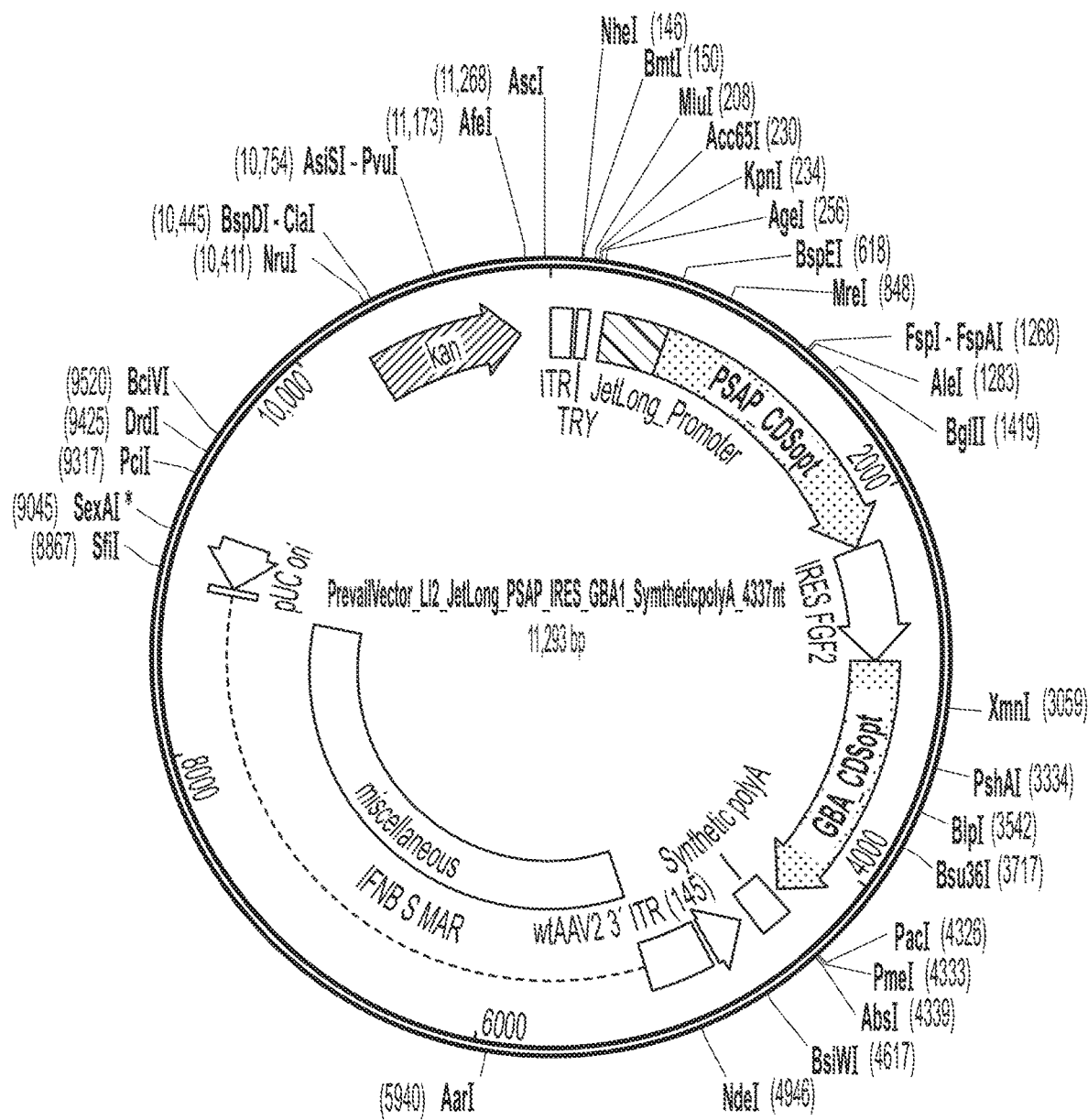
FIG. 6 is a schematic depicting one embodiment of a vector comprising an expression construct encoding Gcase (e.g., GBA1 or a portion thereof) and Prosaposin (e.g., PSAP or a portion thereof). The coding sequences of Gcase and Prosaposin are separated by an internal ribosomal entry site (IRES).

The disclosure is based, in part, on compositions and methods for expression of combinations of PD-associated gene products in a subject. A gene product can be a protein, a fragment (e.g., portion) of a protein, an interfering nucleic acid that inhibits a PD-associated gene, etc. In some embodiments, a gene product is a protein or a protein fragment encoded by a PD-associated gene. In some embodiments, a gene product is an interfering nucleic acid (e.g., shRNA, siRNA, miRNA, amiRNA, etc.) that inhibits a PD-associated gene.

A PD-associated gene refers to a gene encoding a gene product that is genetically, biochemically or functionally associated with PD. For example, individuals having mutations in the GBA1 gene (which encodes the protein Gcase), have been observed to be have an increased risk of developing PD compared to individuals that do not have a mutation in GBA1. In another example, PD is associated with accumulation of protein aggregates comprising α-Synuclein (α-Syn) protein; accordingly, SCNA (which encodes α-Syn) is a PD-associated gene. In some embodiments, an expression cassette described herein encodes a wild-type or non-mutant form of a PD-associated gene (or coding sequence thereof). Examples of PD-associated genes are listed in Table 1.

TABLE 1

Examples of PD-associated genes

| Name | Gene | Function | NCBI Accession No. |
| --- | --- | --- | --- |
| Lysosome membrane protein 2 | SCARB2/ LIMP2 | lysosomal receptor for glucosylceramidase (GBA targeting) | NP_005497.1 (Isoform 1), NP_001191184.1 (Isoform 2) |
| Prosaposin | PSAP | precursor for saposins A, B, C, and D, which localize to the lysosomal compartment and facilitate the catabolism of glycosphingolipids with short oligosaccharide groups | AAH01503.1, AAH07612.1, AAH04275.1, AAA60303.1 |
| beta-Glucocerebrosidase | GBA1 | cleaves the beta-glucosidic linkage of glucocerebroside | NP_001005742.1 (Isoform 1), NP_001165282.1 (Isoform 2), NP_001165283.1 (Isoform 3) |
| Non-lysosomal Glucosyl-ceramidase | GBA2 | catalyzes the conversion of glucosylceramide to free glucose and ceramide | NP_065995.1 (Isoform 1), NP_001317589.1 (Isoform 2) |
| Galactosyl-ceramidase | GALC | removes galactose from ceramide derivatives | EAW81359.1 (Isoform CRA_a), EAW81360.1 (Isoform CRA_b), EAW81362.1 (Isoform CRA_c) |
| Sphingomyelin phosphodi-esterase 1 | SMPD1 | converts sphingomyelin to ceramide | EAW68726.1 (Isoform CRA_a), EAW68727.1 (Isoform CRA_b), EAW68728.1 (Isoform CRA_c), EAW68729.1 (Isoform CRA_d) |
| Cathepsin B | CTSB | thiol protease believed to participate in intracellular degradation and turnover of proteins; also implicated in tumor invasion and metastasis | AAC37547.1, AAH95408.1, AAH10240.1 |
| RAB7, member RAS oncogene family-like 1 | RAB7L1 | regulates vesicular transport | AAH02585.1 |
| Vacuolar protein sorting-associated protein 35 | VPS35 | component of retromer cargo-selective complex | NP_060676.2 |
| GTP cyclohydrolase 1 | GCH1 | responsible for hydrolysis of guanosine triphosphate to form 7,8-dihydroneopterin triphosphate | AAH25415.1 |

TABLE 1-continued

Examples of PD-associated genes

| Name | Gene | Function | NCBI Accession No. |
|---|---|---|---|
| Interleukin 34 | IL34 | increases growth or survival of monocytes; elicits activity by binding the Colony stimulating factor 1 receptor | AAH29804.1 |
| Triggering receptor expressed on myeloid cells 2 | TREM2 | forms a receptor signaling complex with the TYRO protein tyrosine kinase binding protein; functions in immune response and may be involved in chronic inflammation | AAF69824.1 |
| Progranulin | PGRN | plays a role in development, inflammation, cell proliferation and protein homeostasis | NP_002087.1 |

Isolated Nucleic Acids and Vectors

An isolated nucleic acid may be DNA or RNA. The disclosure provides, in some aspects, an isolated nucleic acids (e.g., rAAV vectors) comprising an expression construct encoding one or more PD-associated genes, for example a Gcase (e.g., the gene product of GBA1 gene) or a portion thereof. Gcase, also referred to as β-glucocerebrosidase or GBA, refers to a lysosomal protein that cleaves the beta-glucosidic linkage of the chemical glucocerebroside, an intermediate in glycolipid metabolism. In humans, Gcase is encoded by the GBA1 gene, located on chromosome 1. In some embodiments, GBA1 encodes a peptide that is represented by NCBI Reference Sequence NCBI Reference Sequence NP_000148.2 (SEQ ID NO: 14). In some embodiments, an isolated nucleic acid comprises a Gcase-encoding sequence that has been codon optimized (e.g., codon optimized for expression in mammalian cells, for example human cells), such as the sequence set forth in SEQ ID NO: 15.

In some aspects, the disclosure provides an isolated nucleic acid comprising an expression construct encoding Prosaposin (e.g., the gene product of PSAP gene). Prosaposin is a precursor glycoprotein for sphingolipid activator proteins (saposins) A, B, C, and D, which facilitate the catabolism of glycosphingolipids with short oligosaccharide groups. In humans, the PSAP gene is located on chromosome 10. In some embodiments, PSAP encodes a peptide that is represented by NCBI Reference Sequence NP_002769.1 (e.g., SEQ ID NO: 16). In some embodiments, an isolated nucleic acid comprises a prosaposin-encoding sequence that has been codon optimized (e.g., codon optimized for expression in mammalian cells, for example human cells), such as the sequence set forth in SEQ ID NO: 17.

Aspects of the disclosure relate to an isolated nucleic acid comprising an expression construct encoding LIMP2/SCARB2 (e.g., the gene product of SCARB2 gene). SCARB2 refers to a membrane protein that regulates lysosomal and endosomal transport within a cell. In humans, SCARB2 gene is located on chromosome 4. In some embodiments, the SCARB2 gene encodes a peptide that is represented by NCBI Reference Sequence NP_005497.1 (SEQ ID NO: 18). In some embodiments, an isolated nucleic acid comprises the sequence set forth in SEQ ID NO: 19. In some embodiments the isolated nucleic acid comprises a SCARB2-encoding sequence that has been codon optimized.

Aspects of the disclosure relate to an isolated nucleic acid comprising an expression construct encoding GBA2 protein (e.g., the gene product of GBA2 gene). GBA2 protein refers to non-lysosomal glucosylceramidase. In humans, GBA2 gene is located on chromosome 9. In some embodiments, the GBA2 gene encodes a peptide that is represented by NCBI Reference Sequence NP_065995.1 (SEQ ID NO: 30). In some embodiments, an isolated nucleic acid comprises the sequence set forth in SEQ ID NO: 31. In some embodiments the isolated nucleic acid comprises a GBA2-encoding sequence that has been codon optimized.

Aspects of the disclosure relate to an isolated nucleic acid comprising an expression construct encoding GALC protein (e.g., the gene product of GALC gene). GALC protein refers to galactosylceramidase (or galactocerebrosidase), which is an enzyme that hydrolyzes galactose ester bonds of galactocerebroside, galactosylsphingosine, lactosylceramide, and monogalactosyldiglyceride. In humans, GALC gene is located on chromosome 14. In some embodiments, the GALC gene encodes a peptide that is represented by NCBI Reference Sequence NP_000144.2 (SEQ ID NO: 33). In some embodiments, an isolated nucleic acid comprises the sequence set forth in SEQ ID NO: 34. In some embodiments the isolated nucleic acid comprises a GALC-encoding sequence that has been codon optimized.

Aspects of the disclosure relate to an isolated nucleic acid comprising an expression construct encoding CTSB protein (e.g., the gene product of CTSB gene). CTSB protein refers to cathepsin B, which is a lysosomal cysteine protease that plays an important role in intracellular proteolysis. In humans, CTSB gene is located on chromosome 8. In some embodiments, the CTSB gene encodes a peptide that is represented by NCBI Reference Sequence NP_001899.1 (SEQ ID NO: 35). In some embodiments, an isolated nucleic acid comprises the sequence set forth in SEQ ID NO: 36. In some embodiments the isolated nucleic acid comprises a CTSB-encoding sequence that has been codon optimized.

Aspects of the disclosure relate to an isolated nucleic acid comprising an expression construct encoding SMPD1 protein (e.g., the gene product of SMPD1 gene). SMPD1 protein refers to sphingomyelin phosphodiesterase 1, which is a hydrolase enzyme that is involved in sphingolipid metabolism. In humans, SMPD1 gene is located on chromosome 11. In some embodiments, the SMPD1 gene encodes a peptide that is represented by NCBI Reference Sequence NP_000534.3 (SEQ ID NO: 37). In some embodiments, an isolated nucleic acid comprises the sequence set forth in SEQ ID NO: 38. In some embodiments the isolated nucleic acid comprises a SMPD1-encoding sequence that has been codon optimized.

Aspects of the disclosure relate to an isolated nucleic acid comprising an expression construct encoding GCH1 protein (e.g., the gene product of GCH1 gene). GCH1 protein refers to GTP cyclohydrolase I, which is a hydrolase enzyme that is part of the folate and biopterin biosynthesis pathways. In humans, GCH1 gene is located on chromosome 14. In some embodiments, the GCH1 gene encodes a peptide that is represented by NCBI Reference Sequence NP_000152.1 (SEQ ID NO: 45). In some embodiments, an isolated nucleic acid comprises the sequence set forth in SEQ ID NO: 46. In some embodiments the isolated nucleic acid comprises a GCH1-encoding sequence that has been codon optimized.

Aspects of the disclosure relate to an isolated nucleic acid comprising an expression construct encoding RAB7L protein (e.g., the gene product of RAB7L gene). RAB7L protein refers to RAB7, member RAS oncogene family-like 1, which is a GTP binding protein. In humans, RAB7L gene is located on chromosome 1. In some embodiments, the RAB7L gene encodes a peptide that is represented by NCBI Reference Sequence NP_003920.1 (SEQ ID NO: 47). In some embodiments, an isolated nucleic acid comprises the sequence set forth in SEQ ID NO: 48. In some embodiments the isolated nucleic acid comprises a RAB7L-encoding sequence that has been codon optimized.

Aspects of the disclosure relate to an isolated nucleic acid comprising an expression construct encoding VPS35 protein (e.g., the gene product of VPS35 gene). VPS35 protein refers to vacuolar protein sorting-associated protein 35, which is part of a protein complex involved in retrograde transport of proteins from endosomes to the trans-Golgi network. In humans, VPS35 gene is located on chromosome 16. In some embodiments, the VPS35 gene encodes a peptide that is represented by NCBI Reference Sequence NP_060676.2 (SEQ ID NO: 49). In some embodiments, an isolated nucleic acid comprises the sequence set forth in SEQ ID NO: 50. In some embodiments the isolated nucleic acid comprises a VPS35-encoding sequence that has been codon optimized.

Aspects of the disclosure relate to an isolated nucleic acid comprising an expression construct encoding IL-34 protein (e.g., the gene product of IL34 gene). IL-34 protein refers to interleukin 34, which is a cytokine that increases growth and survival of monocytes. In humans, IL34 gene is located on chromosome 16. In some embodiments, the IL34 gene encodes a peptide that is represented by NCBI Reference Sequence NP_689669.2 (SEQ ID NO: 55). In some embodiments, an isolated nucleic acid comprises the sequence set forth in SEQ ID NO: 56. In some embodiments the isolated nucleic acid comprises a IL-34-encoding sequence that has been codon optimized.

Aspects of the disclosure relate to an isolated nucleic acid comprising an expression construct encoding TREM2 protein (e.g., the gene product of TREM2 gene). TREM2 protein refers to triggering receptor expressed on myeloid cells 2, which is an immunoglobulin superfamily receptor found on myeloid cells. In humans, TREM2 gene is located on chromosome 6. In some embodiments, the TREM2 gene encodes a peptide that is represented by NCBI Reference Sequence NP_061838.1 (SEQ ID NO: 57). In some embodiments, the isolated nucleic acid comprises the sequence set forth in SEQ ID NO: 58. In some embodiments an isolated nucleic acid comprises a TREM2-encoding sequence that has been codon optimized.

Aspects of the disclosure relate to an isolated nucleic acid comprising an expression construct encoding TMEM106B protein (e.g., the gene product of TMEM106B gene). TMEM106B protein refers to transmembrane protein 106B, which is a protein involved in dendrite morphogenesis and regulation of lysosomal trafficking. In humans, TMEM106B gene is located on chromosome 7. In some embodiments, the TMEM106B gene encodes a peptide that is represented by NCBI Reference Sequence NP_060844.2 (SEQ ID NO: 62). In some embodiments, an isolated nucleic acid comprises the sequence set forth in SEQ ID NO: 63. In some embodiments the isolated nucleic acid comprises a TMEM106B-encoding sequence that has been codon optimized.

Aspects of the disclosure relate to an isolated nucleic acid comprising an expression construct encoding progranulin protein (e.g., the gene product of PGRN gene). PGRN protein refers to progranulin, which is a protein involved in development, inflammation, cell proliferation and protein homeostasis. In humans, PGRN gene is located on chromosome 17. In some embodiments, the PGRN gene encodes a peptide that is represented by NCBI Reference Sequence NP_002078.1 (SEQ ID NO: 67). In some embodiments, an isolated nucleic acid comprises the sequence set forth in SEQ ID NO: 68. In some embodiments the isolated nucleic acid comprises a PGRN-encoding sequence that has been codon optimized.

In some aspects, the disclosure provides an isolated nucleic acid comprising an expression construct encoding a first gene product and a second gene product, wherein each gene product independently is selected from the gene products, or portions thereof, set forth in Table 1.

In some embodiments, a gene product is encoded by a coding portion (e.g., a cDNA) of a naturally occurring gene. In some embodiments, a first gene product is a protein (or a fragment thereof) encoded by the GBA1 gene. In some embodiments, a gene product is a protein (or a fragment thereof) encoded by another gene listed in Table 1, for example the SCARB2/LIMP2 gene or the PSAP gene. However, the skilled artisan recognizes that the order of expression of a first gene product (e.g., Gcase) and a second gene product (e.g., LIMP2, etc.) can generally be reversed (e.g., LIMP2 is the first gene product and Gcase is the second gene product). In some embodiments, a gene product is a fragment (e.g., portion) of a gene listed in Table 1. A protein fragment may comprise about 50%, about 60%, about 70%, about 80% about 90% or about 99% of a protein encoded by the genes listed in Table 1. In some embodiments, a protein fragment comprises between 50% and 99.9% (e.g., any value between 50% and 99.9%) of a protein encoded by a gene listed in Table 1.

In some embodiments, an expression construct is monocistronic (e.g., the expression construct encodes a single fusion protein comprising a first gene product and a second gene product). In some embodiments, an expression construct is polycistronic (e.g., the expression construct encodes two distinct gene products, for example two different proteins or protein fragments).

A polycistronic expression vector may comprise a one or more (e.g., 1, 2, 3, 4, 5, or more) promoters. Any suitable promoter can be used, for example, a constitutive promoter, an inducible promoter, an endogenous promoter, a tissue-specific promoter (e.g., a CNS-specific promoter), etc. In some embodiments, a promoter is a chicken beta-actin promoter (CBA promoter), a CAG promoter (for example as described by Alexopoulou et al. (2008) BMC Cell Biol. 9:2; doi: 10.1186/1471-2121-9-2), a CD68 promoter, or a JeT promoter (for example as described by Tornoe et al. (2002) *Gene* 297(1-2):21-32). In some embodiments, a promoter is operably-linked to a nucleic acid sequence encoding a first gene product, a second gene product, or a first gene product and a second gene product. In some embodiments, an expression cassette comprises one or more additional regulatory sequences, including but not limited to transcription factor binding sequences, intron splice sites, poly(A) addition sites, enhancer sequences, repressor binding sites, or any combination of the foregoing.

In some embodiments, a nucleic acid sequence encoding a first gene product and a nucleic acid sequence encoding a second gene product are separated by a nucleic acid sequence encoding an internal ribosomal entry site (IRES). Examples of IRES sites are described, for example, by Mokrejs et al. (2006) *Nucleic Acids Res.* 34(Database issue): D125-30. In some embodiments, a nucleic acid sequence encoding a first gene product and a nucleic acid sequence encoding a second gene product are separated by a nucleic acid sequence encoding a self-cleaving peptide. Examples of self-cleaving peptides include but are not limited to T2A, P2A, E2A, F2A, BmCPV 2A, and BmIFV 2A, and those described by Liu et al. (2017) *Sci Rep.* 7: 2193. In some embodiments, the self-cleaving peptide is a T2A peptide.

Pathologically, disorders such as PD and Gaucher disease are associated with accumulation of protein aggregates composed largely of α-Synuclein (α-Syn) protein. Accordingly, in some embodiments, isolated nucleic acids described herein comprise an inhibitory nucleic acid that reduces or prevents expression of α-Syn protein. A sequence encoding an inhibitory nucleic acid may be placed in an untranslated region (e.g., intron, 5'UTR, 3'UTR, etc.) of the expression vector.

In some embodiments, an inhibitory nucleic acid is positioned in an intron of an expression construct, for example in an intron upstream of the sequence encoding a first gene product. An inhibitory nucleic acid can be a double stranded RNA (dsRNA), siRNA, micro RNA (miRNA), artificial miRNA (amiRNA), or an RNA aptamer. Generally, an inhibitory nucleic acid binds to (e.g., hybridizes with) between about 6 and about 30 (e.g., any integer between 6 and 30, inclusive) contiguous nucleotides of a target RNA (e.g., mRNA). In some embodiments, the inhibitory nucleic acid molecule is an miRNA or an amiRNA, for example an miRNA that targets SNCA (the gene encoding α-Syn protein) or TMEM1106B (e.g., the gene encoding TMEM106B protein). In some embodiments, the miRNA does not comprise any mismatches with the region of SNCA mRNA to which it hybridizes (e.g., the miRNA is "perfected"). In some embodiments, the inhibitory nucleic acid is an shRNA (e.g., an shRNA targeting SNCA or TMEM106B). In some embodiments, an inhibitory nucleic acid is an artificial miRNA (amiRNA) that includes a miR-155 scaffold and a SCNA or TMEM106B targeting sequence.

An isolated nucleic acid as described herein may exist on its own, or as part of a vector. Generally, a vector can be a plasmid, cosmid, phagemid, bacterial artificial chromosome (BAC), or a viral vector (e.g., adenoviral vector, adeno-associated virus (AAV) vector, retroviral vector, baculoviral vector, etc.). In some embodiments, the vector is a plasmid (e.g., a plasmid comprising an isolated nucleic acid as described herein). In some embodiments, an rAAV vector is single-stranded (e.g., single-stranded DNA). In some embodiments, the vector is a recombinant AAV (rAAV) vector. In some embodiments, a vector is a Baculovirus vector (e.g., an *Autographa californica* nuclear polyhedrosis (AcNPV) vector).

Typically an rAAV vector (e.g., rAAV genome) comprises a transgene (e.g., an expression construct comprising one or more of each of the following: promoter, intron, enhancer sequence, protein coding sequence, inhibitory RNA coding sequence, polyA tail sequence, etc.) flanked by two AAV inverted terminal repeat (ITR) sequences. In some embodiments the transgene of an rAAV vector comprises an isolated nucleic acid as described by the disclosure. In some embodiments, each of the two ITR sequences of an rAAV vector is a full-length ITR (e.g., approximately 145 bp in length, and containing functional Rep binding site (RBS) and terminal resolution site (trs)). In some embodiments, one of the ITRs of an rAAV vector is truncated (e.g., shortened or not full-length). In some embodiments, a truncated ITR lacks a functional terminal resolution site (trs) and is used for production of self-complementary AAV vectors (scAAV vectors). In some embodiments, a truncated ITR is a ΔITR, for example as described by McCarty et al. (2003) *Gene Ther.* 10(26):2112-8.

Figure 20:
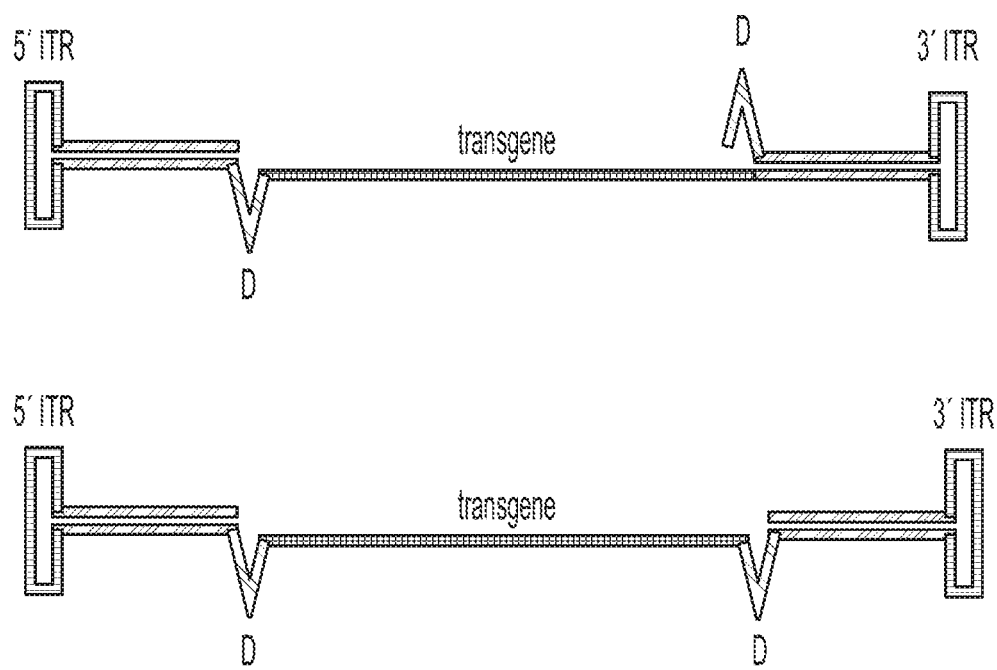
FIG. 20 is a schematic depicting an rAAV vectors comprising a "D" region located on the "outside" of the ITR (e.g., proximal to the terminus of the ITR relative to the transgene insert or expression construct) (top) and a wild-type rAAV vectors having ITRs on the "inside" of the vector (e.g., proximal to the transgene insert of the vector).
Figure 21:
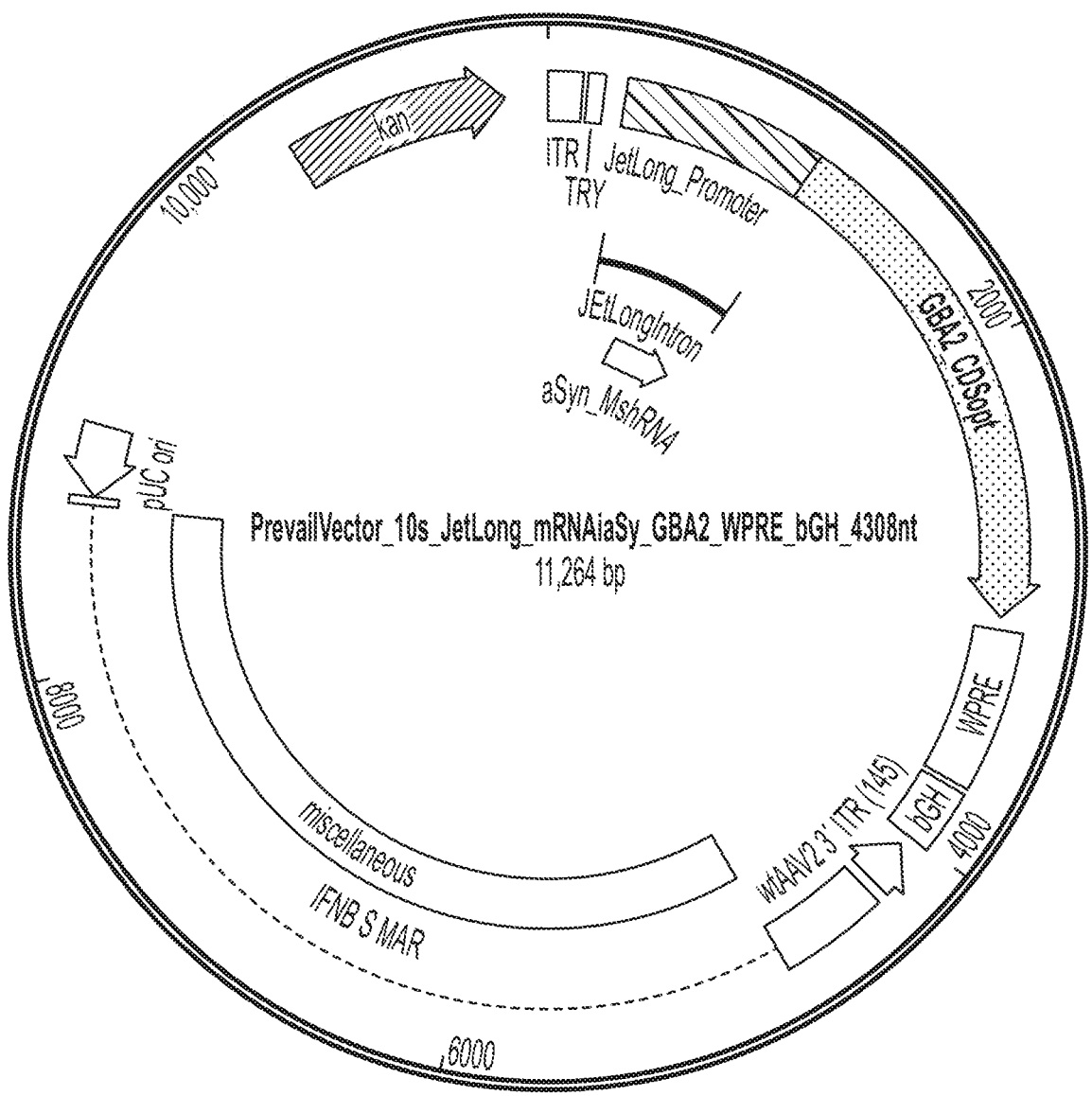
FIG. 21 a schematic depicting one embodiment of a vector comprising an expression construct encoding GBA2 or a portion thereof, and an interfering RNA for α-Syn.
Figure 22:
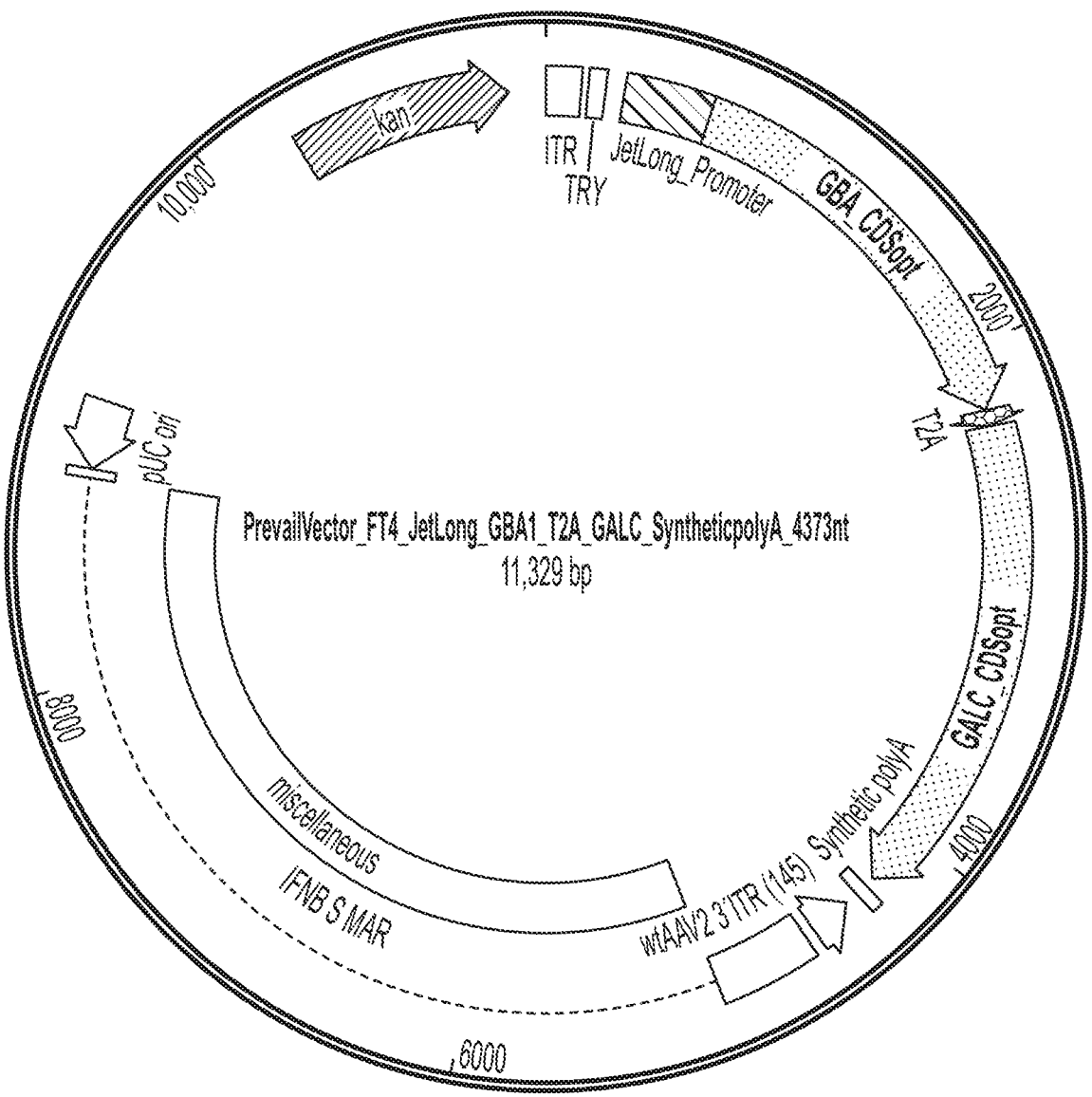
FIG. 22 is a schematic depicting one embodiment of a vector comprising an expression construct encoding Gcase (e.g., GBA1 or a portion thereof) and Galactosylceramidase (e.g., GALC or a portion thereof). Expression of the coding sequences of Gcase and Galactosylceramidase are separated by a T2A self-cleaving peptide sequence.
Figure 23:
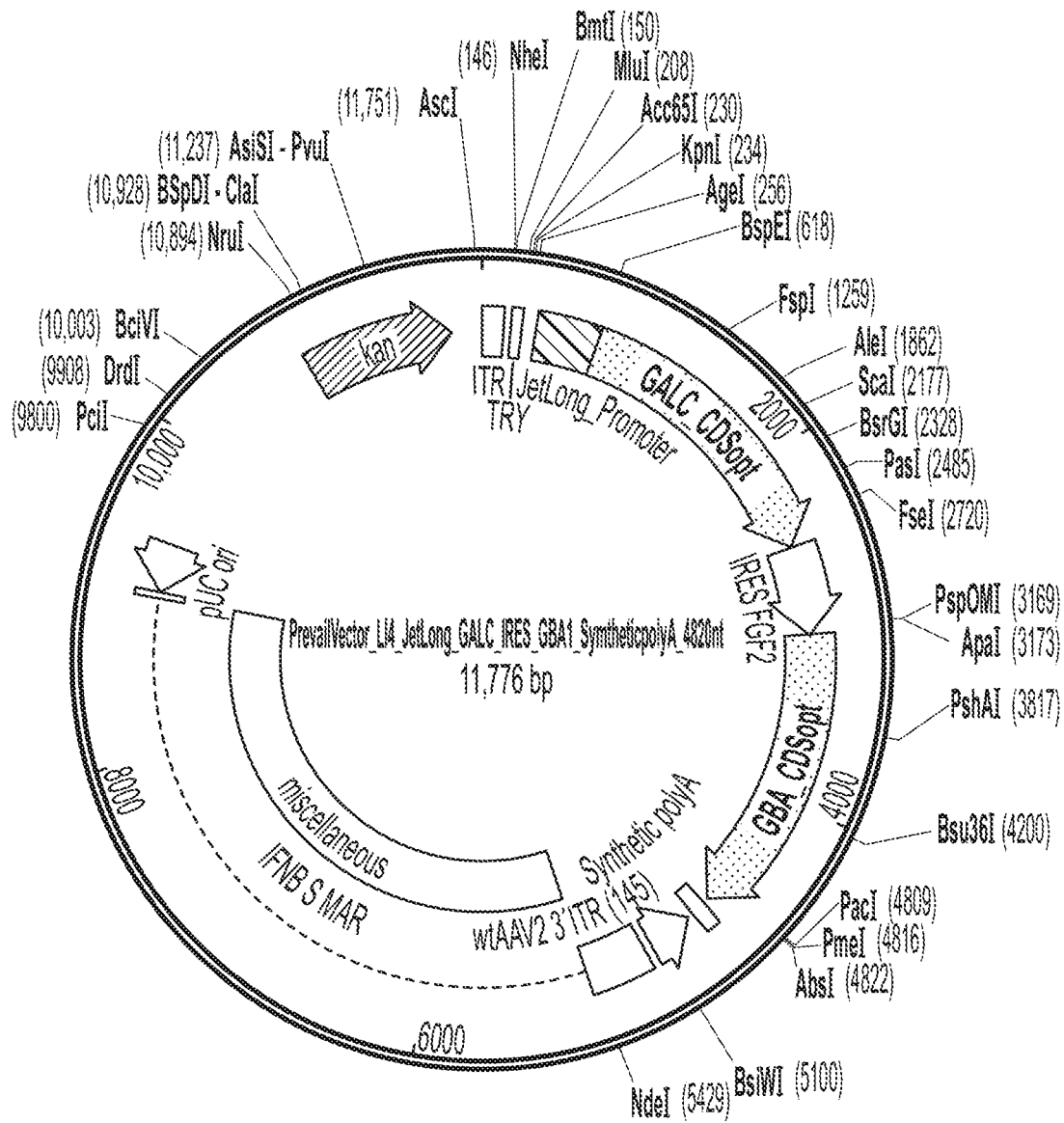
FIG. 23 is a schematic depicting one embodiment of a vector comprising an expression construct encoding Gcase (e.g., GBA1 or a portion thereof) and Galactosylceramidase (e.g., GALC or a portion thereof). Expression of the coding sequences of Gcase and Galactosylceramidase are separated by a T2A self-cleaving peptide sequence.
Figure 24:
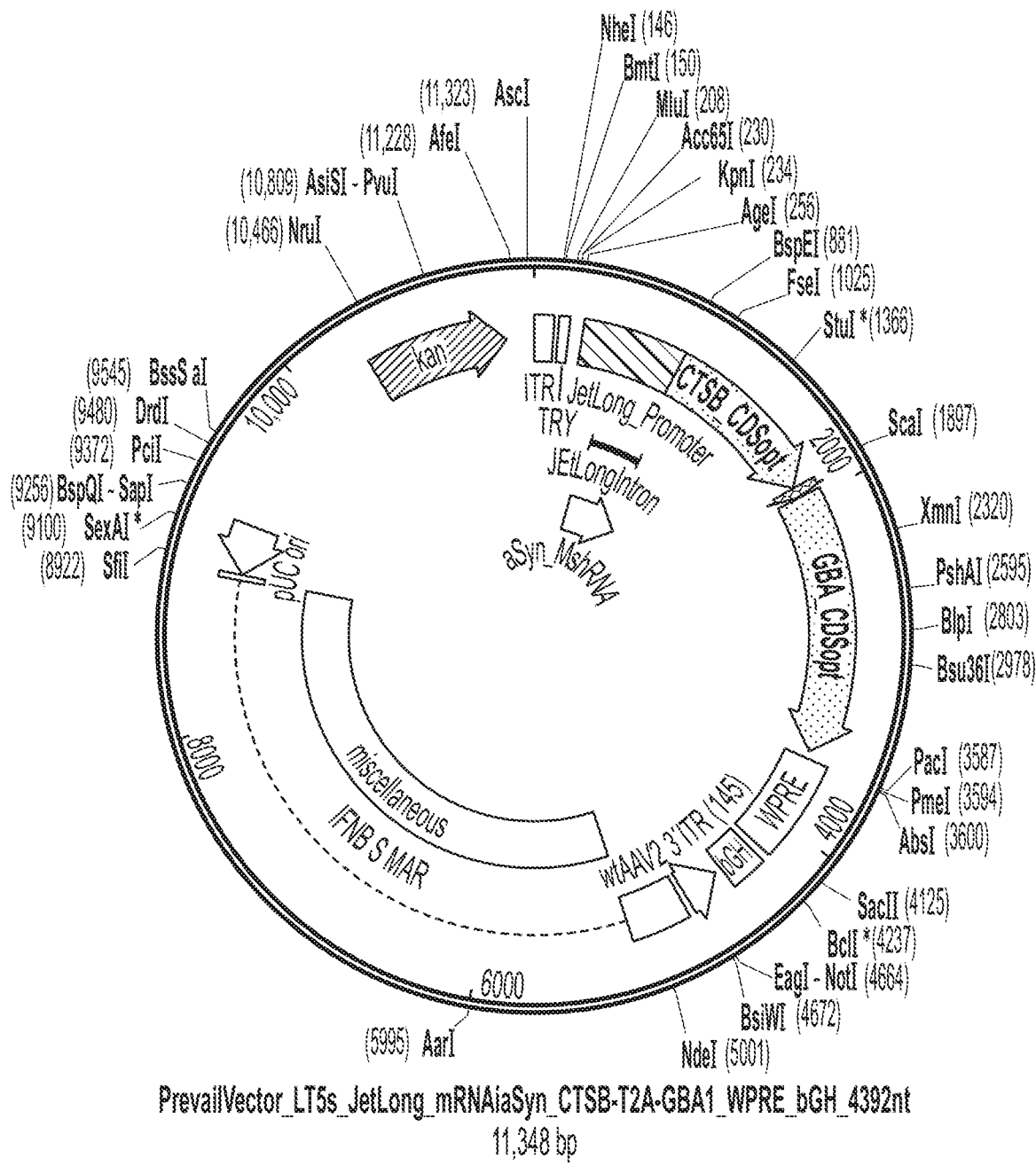
FIG. 24 is a schematic depicting one embodiment of a vector comprising an expression construct encoding Gcase (e.g., GBA1 or a portion thereof), Cathepsin B (e.g., CTSB or a portion thereof), and an interfering RNA for α-Syn. Expression of the coding sequences of Gcase and Cathepsin B are separated by a T2A self-cleaving peptide sequence.
Figure 25:
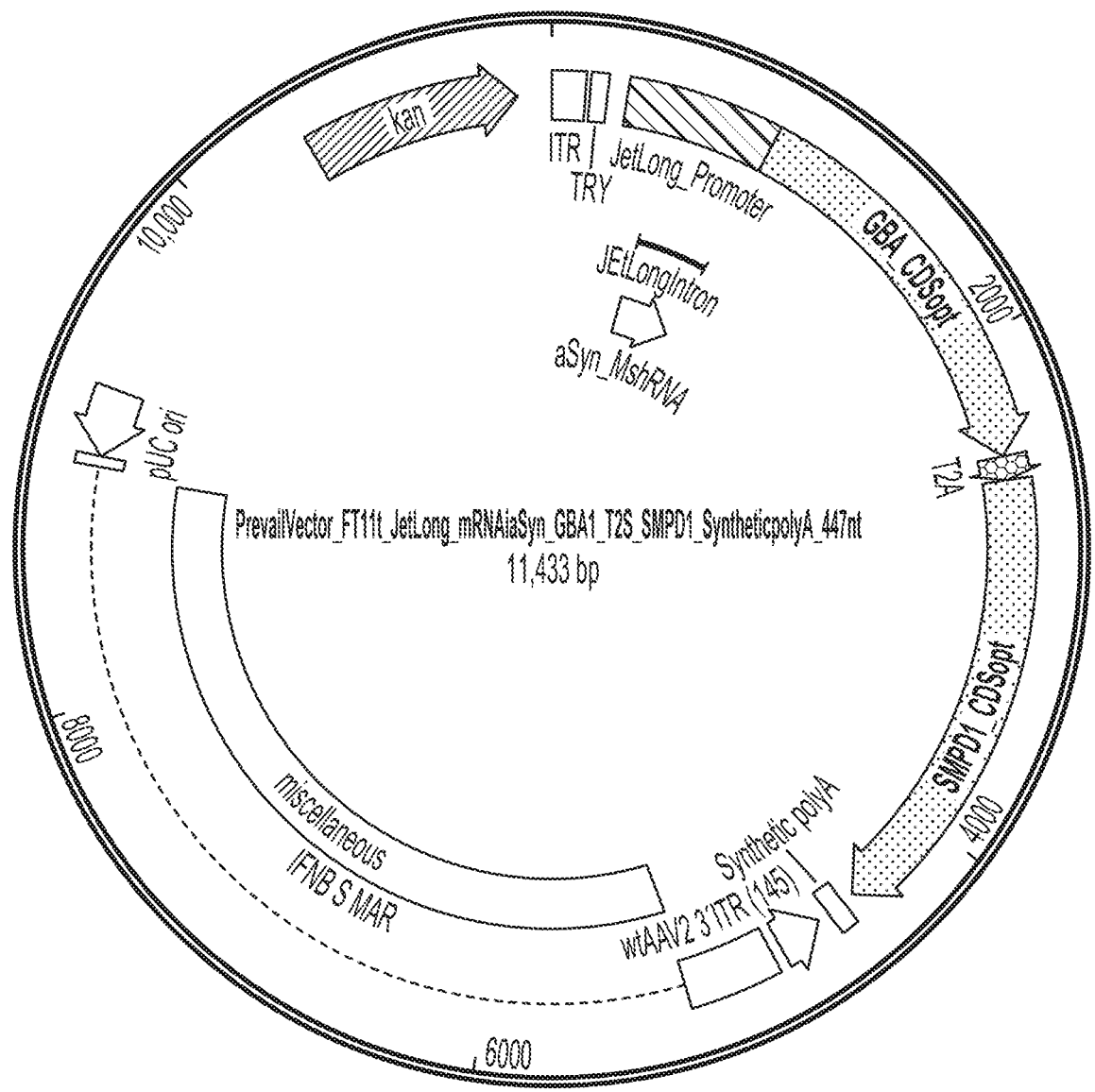
FIG. 25 is a schematic depicting one embodiment of a vector comprising an expression construct encoding Gcase (e.g., GBA1 or a portion thereof), Sphingomyelin phosphodiesterase 1 (e.g., SMPD1 a portion thereof, and an interfering RNA for α-Syn.
Figure 26:
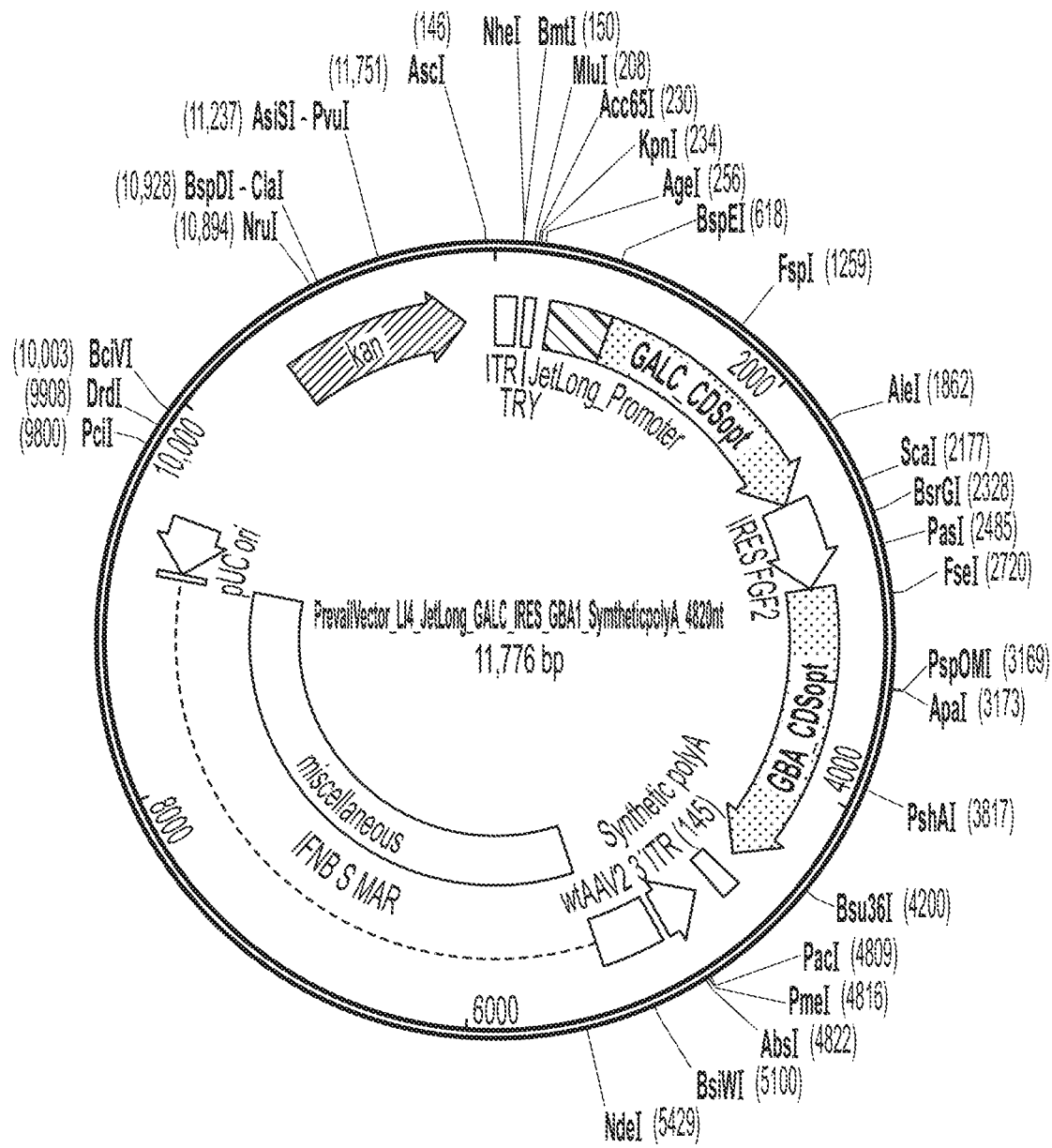
FIG. 26 is a schematic depicting one embodiment of a vector comprising an expression construct encoding Gcase (e.g., GBA1 or a portion thereof) and Galactosylceramidase (e.g., GALC or a portion thereof). The coding sequences of Gcase and Galactosylceramidase are separated by an internal ribosomal entry site (IRES).
Figure 27:
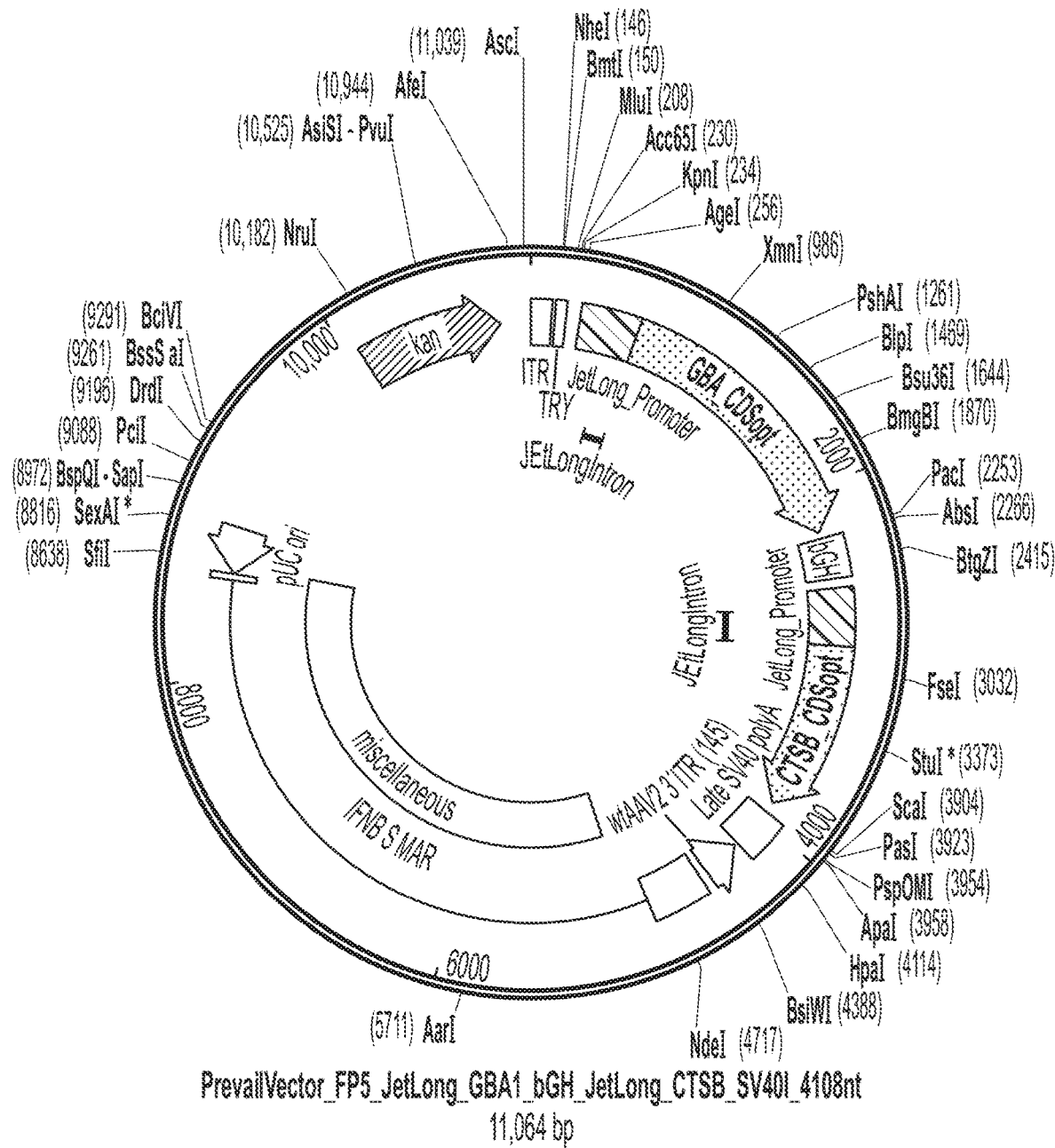
FIG. 27 is a schematic depicting one embodiment of a vector comprising an expression construct encoding Gcase (e.g., GBA1 or a portion thereof) and Cathepsin B (e.g., CTSB or a portion thereof). Expression of the coding sequences of Gcase and Cathepsin B are each driven by a separate promoter.
Figure 28:
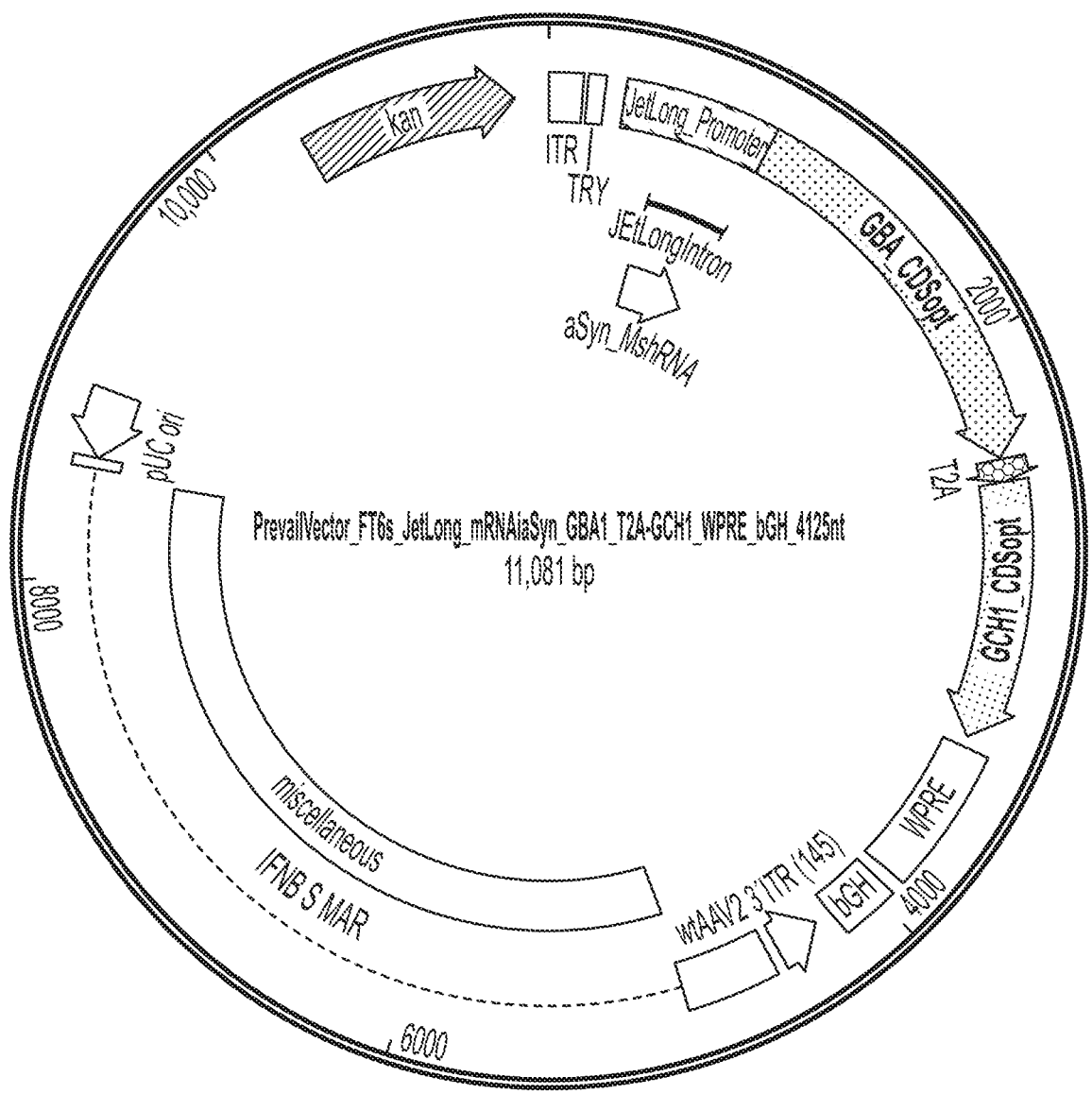
FIG. 28 is a schematic depicting one embodiment of a vector comprising an expression construct encoding Gcase (e.g., GBA1 or a portion thereof), GCH1 (e.g., GCH1 or a portion thereof), and an interfering RNA for α-Syn. The coding sequences of Gcase and GCH1 are separated by an T2A self-cleaving peptide sequence
Figure 29:
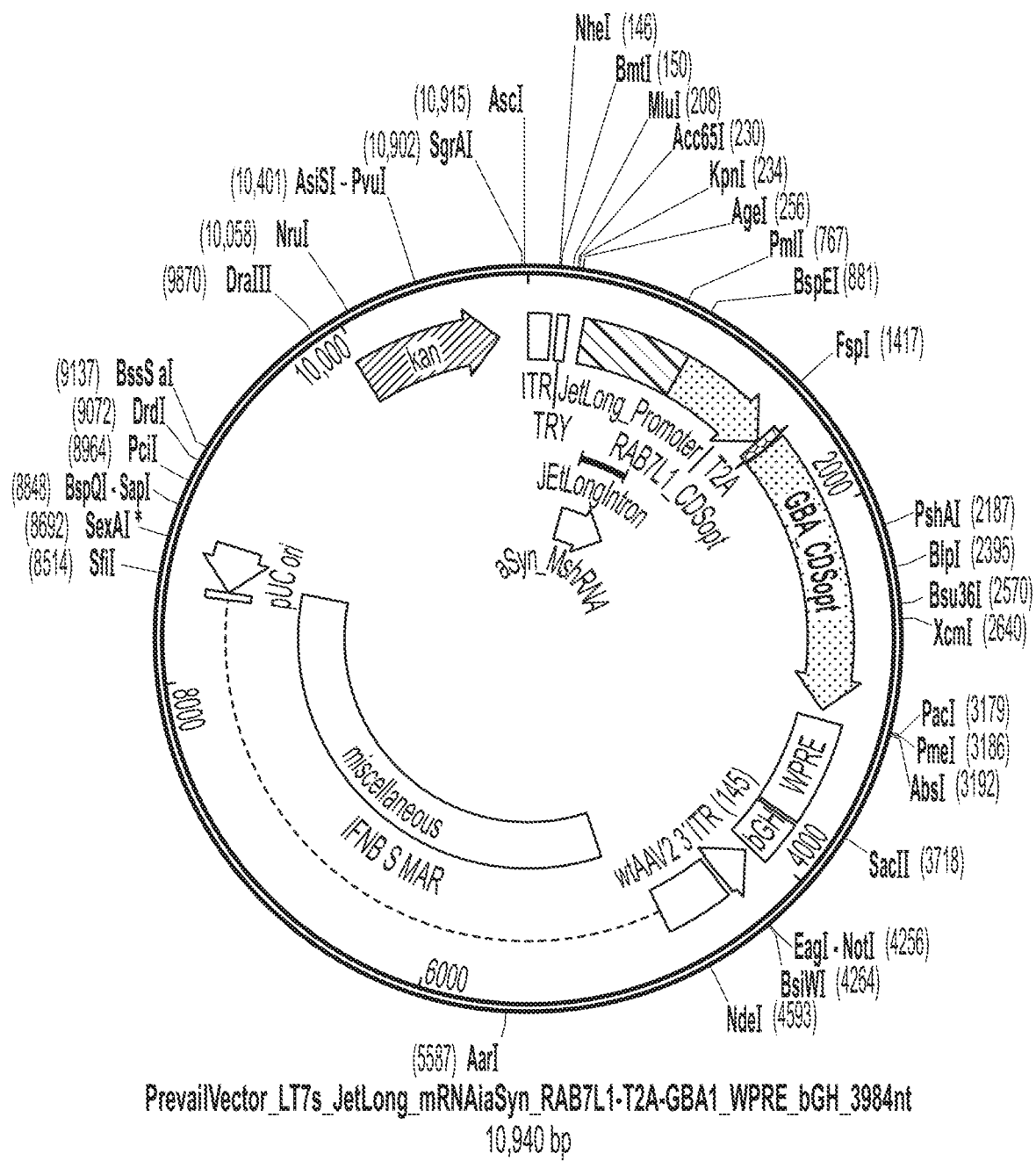
FIG. 29 is a schematic depicting one embodiment of a vector comprising an expression construct encoding Gcase (e.g., GBA1 or a portion thereof), RAB7L1 (e.g., RAB7L1 or a portion thereof), and an interfering RNA for α-Syn. The coding sequences of Gcase and RAB7L1 are separated by an T2A self-cleaving peptide sequence.
Figure 30:
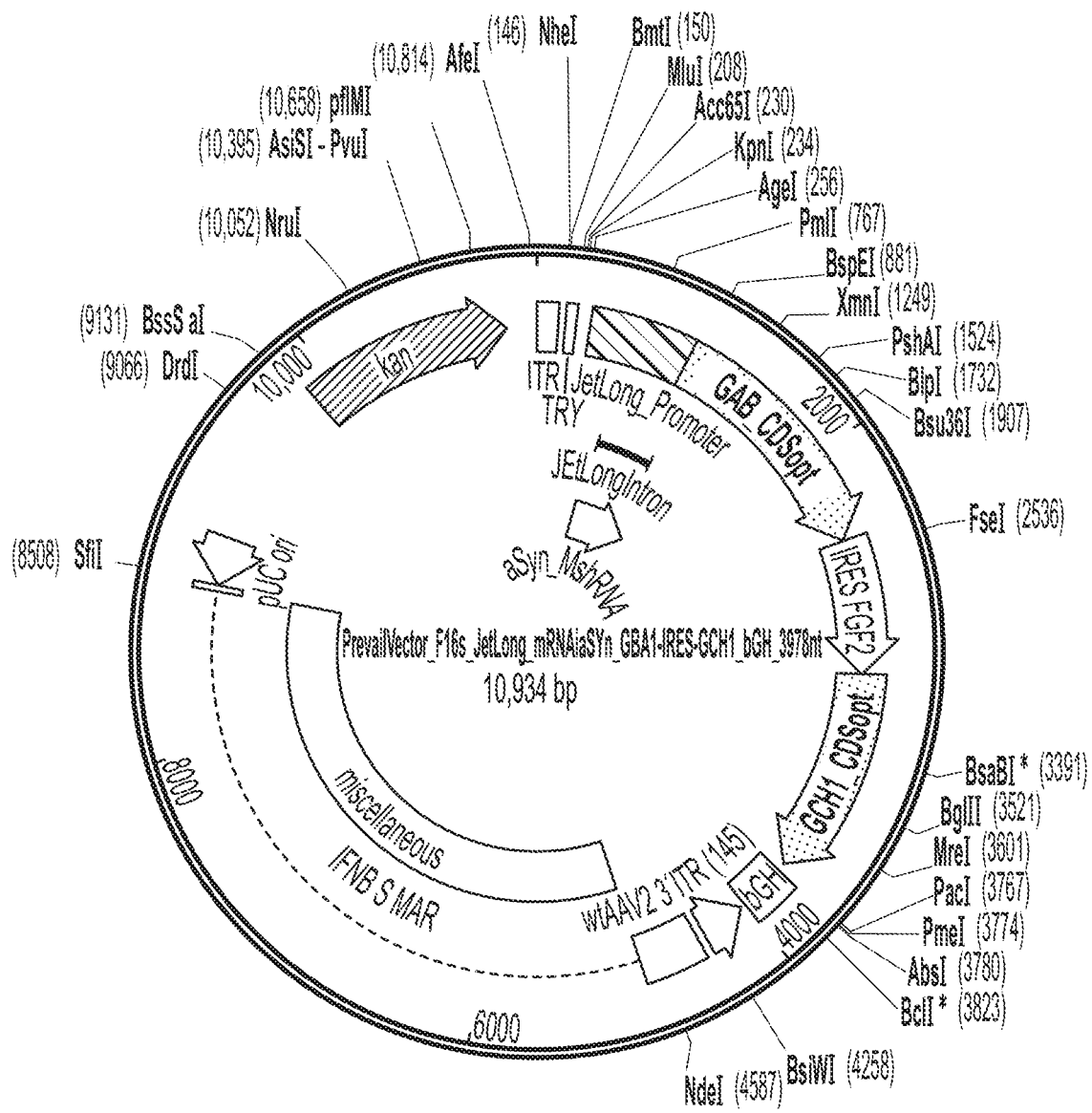
FIG. 30 is a schematic depicting one embodiment of a vector comprising an expression construct encoding Gcase (e.g., GBA1 or a portion thereof), GCH1 (e.g., GCH1 or a portion thereof), and an interfering RNA for α-Syn. Expression of the coding sequences of Gcase and GCH1 are an internal ribosomal entry site (IRES).
Figure 31:
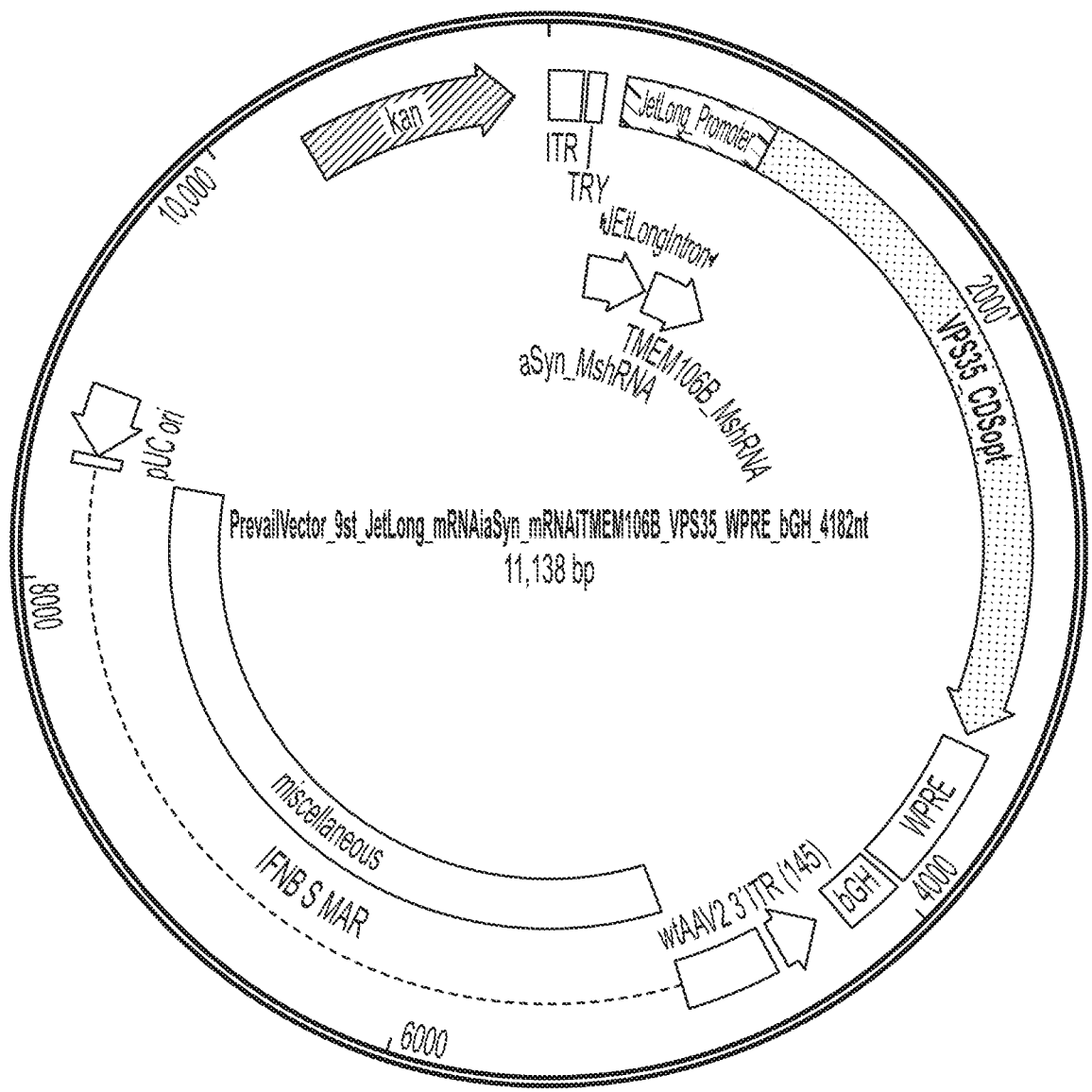
FIG. 31 is a schematic depicting one embodiment of a vector comprising an expression construct encoding VPS35 (e.g., VPS35 or a portion thereof) and interfering RNAs for α-Syn and TMEM106B.
Figure 32:
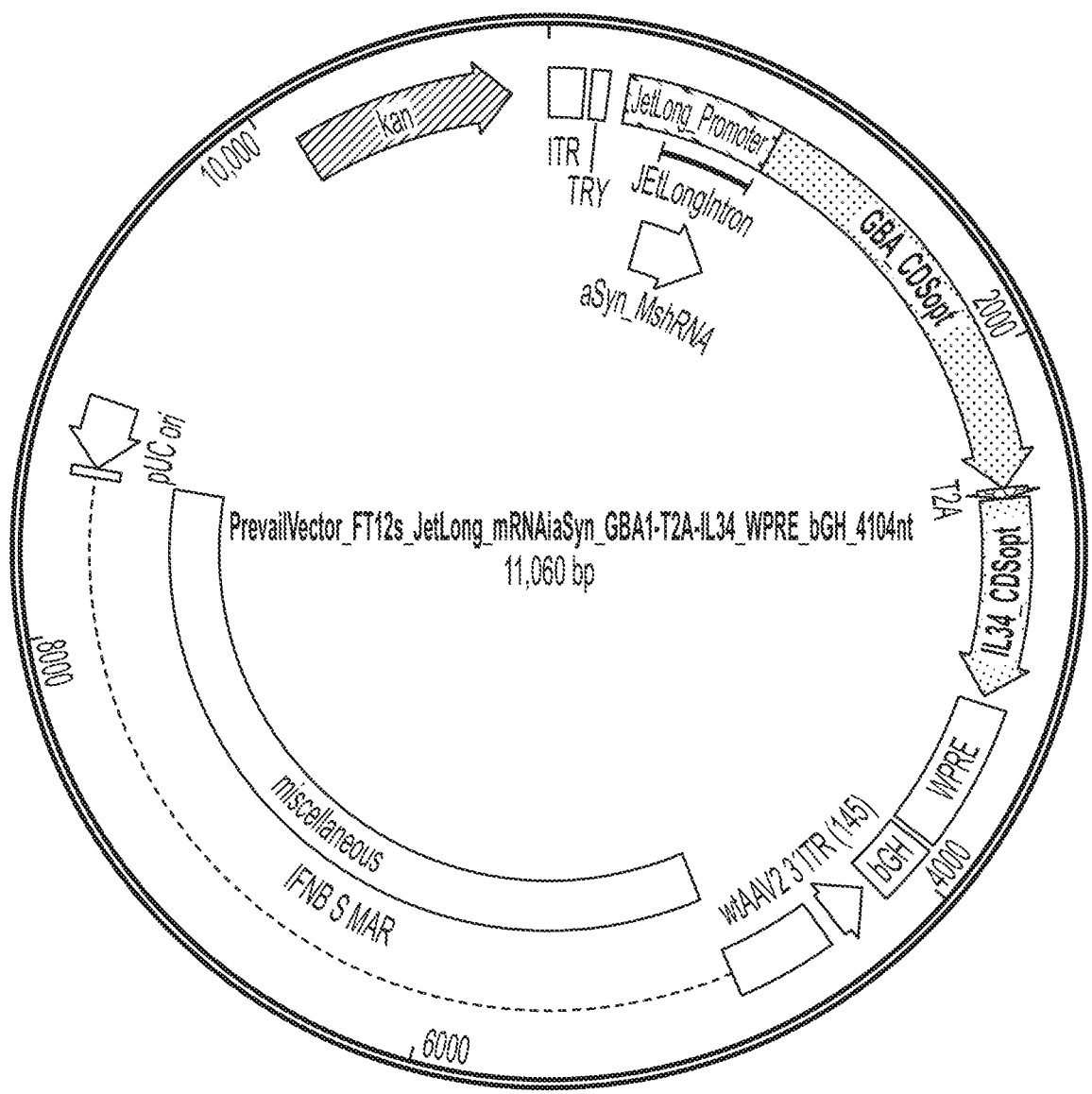
FIG. 32 is a schematic depicting one embodiment of a vector comprising an expression construct encoding Gcase (e.g., GBA1 or a portion thereof), IL-34 (e.g., IL34 or a portion thereof), and an interfering RNA for α-Syn. The coding sequences of Gcase and IL-34 are separated by T2A self-cleaving peptide sequence.
Figure 33:
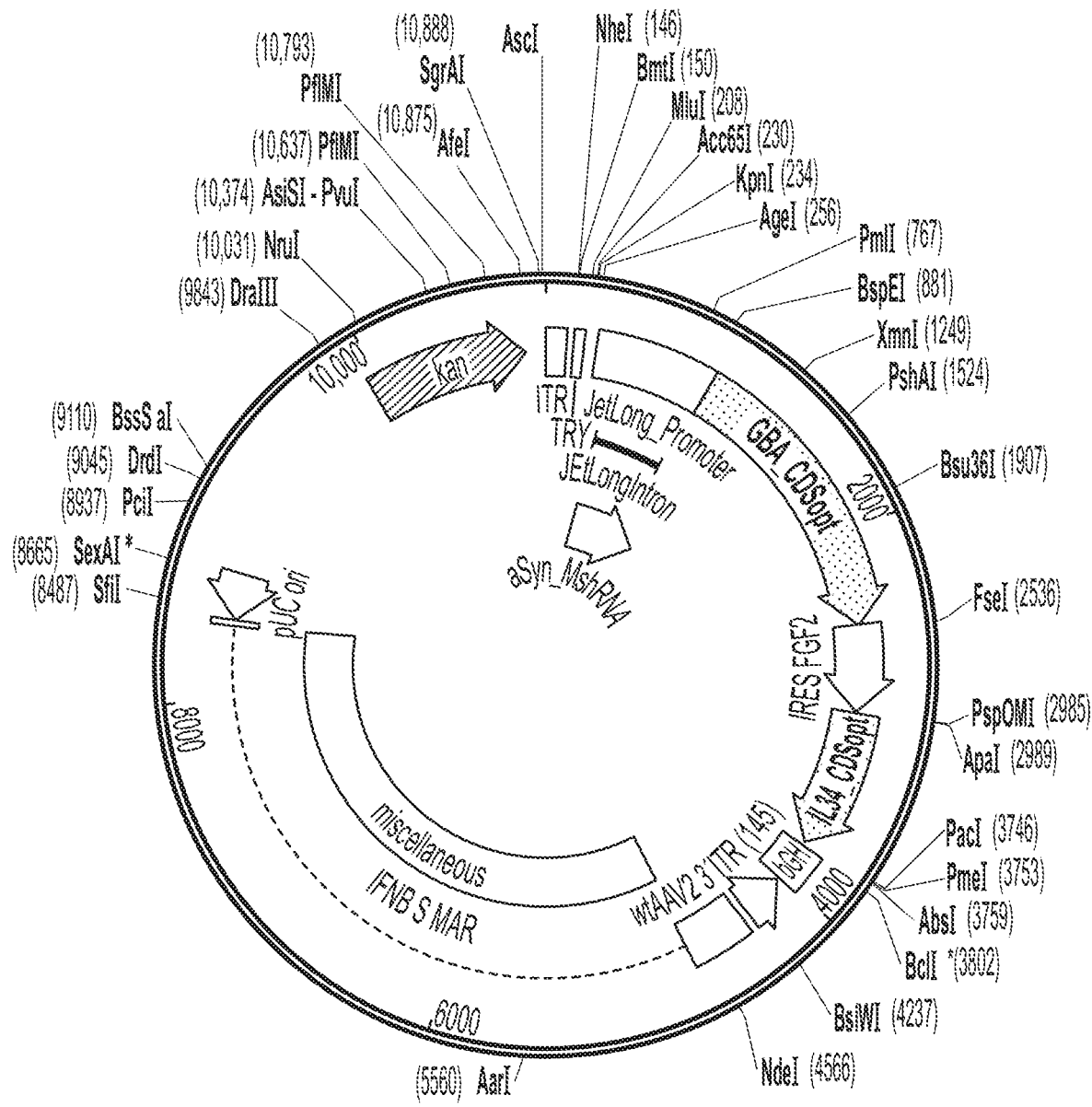
FIG. 33 is a schematic depicting one embodiment of a vector comprising an expression construct encoding Gcase (e.g., GBA1 or a portion thereof) and IL-34 (e.g., IL34 or a portion thereof). The coding sequences of Gcase and IL-34 are separated by an internal ribosomal entry site (IRES).
Figure 34:
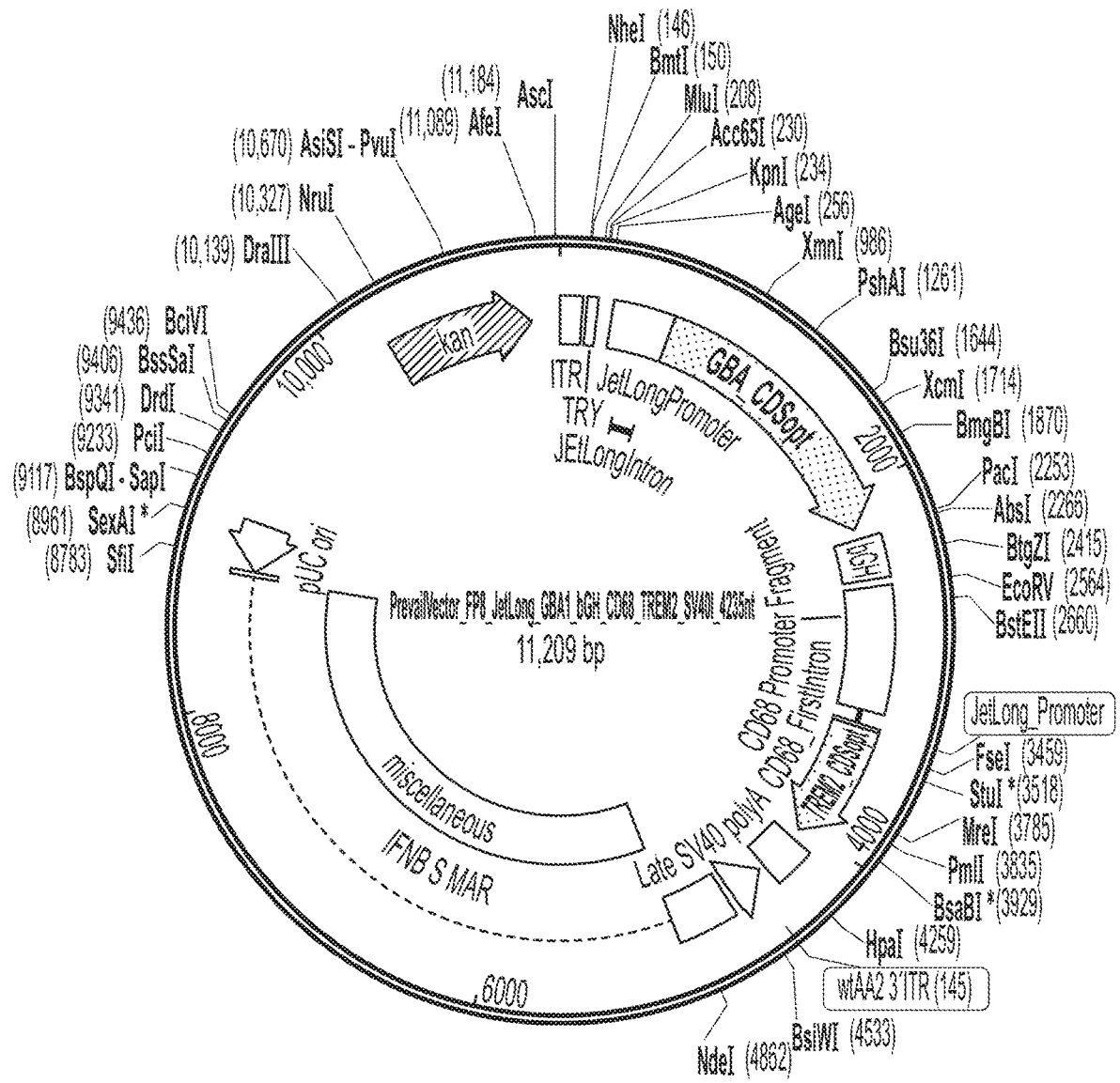
FIG. 34 is a schematic depicting one embodiment of a vector comprising an expression construct encoding Gcase (e.g., GBA1 or a portion thereof) and TREM2 (e.g., TREM2 or a portion thereof). Expression of the coding sequences of Gcase and TREM2 are each driven by a separate promoter.
Figure 35:
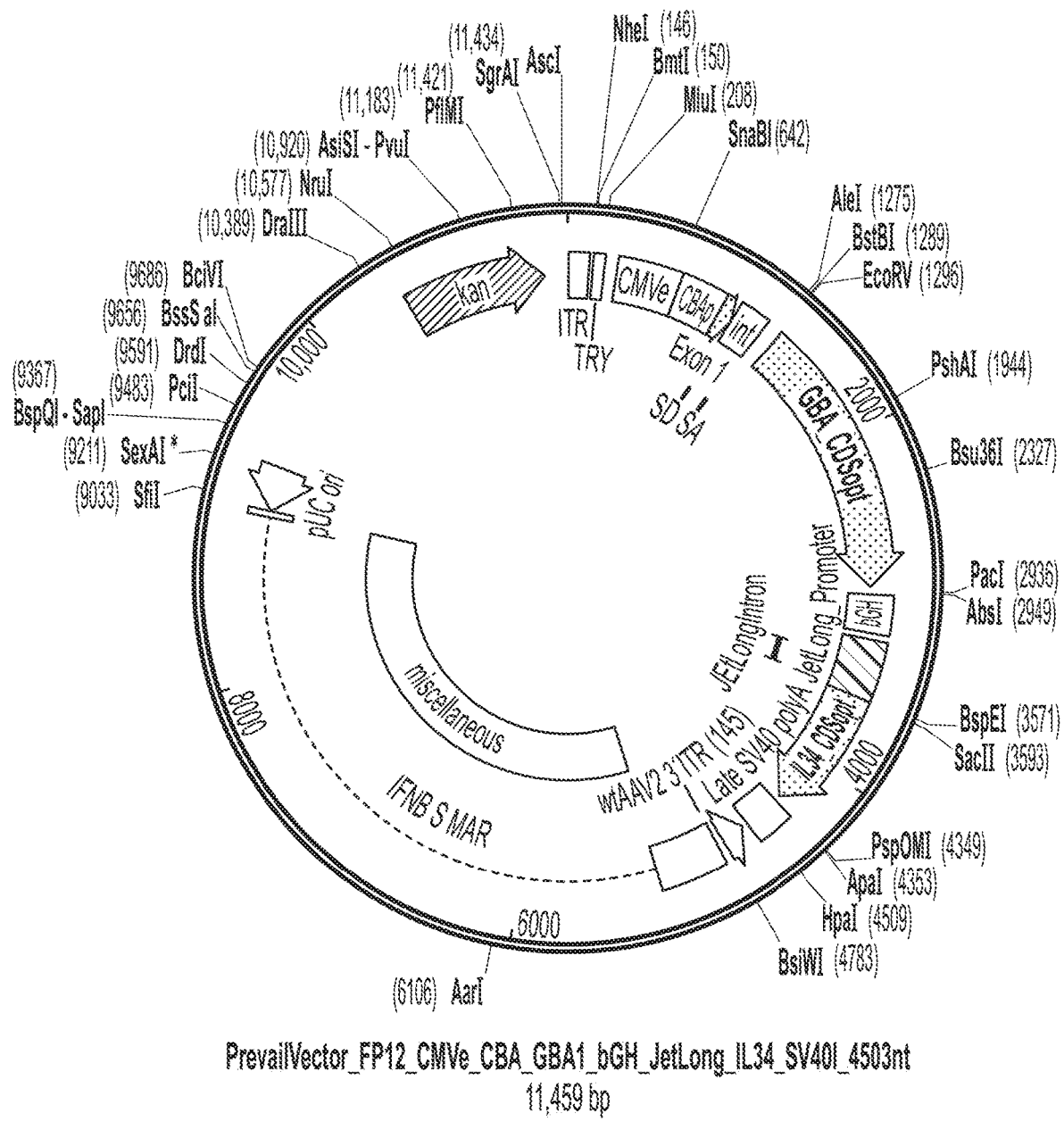
FIG. 35 is a schematic depicting one embodiment of a vector comprising an expression construct encoding Gcase (e.g., GBA1 or a portion thereof) and IL-34 (e.g., IL34 or a portion thereof). Expression of the coding sequences of Gcase and IL-34 are each driven by a separate promoter.

Aspects of the disclosure relate to isolated nucleic acids (e.g., rAAV vectors) comprising an ITR having one or more modifications (e.g., nucleic acid additions, deletions, substitutions, etc.) relative to a wild-type AAV ITR, for example relative to wild-type AAV2 ITR (e.g., SEQ ID NO: 29). The structure of wild-type AAV2 ITR is shown in FIG. 20. Generally, a wild-type ITR comprises a 125 nucleotide region that self-anneals to form a palindromic double-stranded T-shaped, hairpin structure consisting of two cross arms (formed by sequences referred to as B/B' and C/C', respectively), a longer stem region (formed by sequences A/A'), and a single-stranded terminal region referred to as the "D" region (FIG. 20). Generally, the "D" region of an ITR is positioned between the stem region formed by the A/A' sequences and the insert containing the transgene of the rAAV vector (e.g., positioned on the "inside" of the ITR relative to the terminus of the ITR or proximal to the transgene insert or expression construct of the rAAV vector). In some embodiments, a "D" region comprises the sequence set forth in SEQ ID NO: 27. The "D" region has been observed to play an important role in encapsidation of rAAV vectors by capsid proteins, for example as disclosed by Ling et al. (2015) *J Mol Genet Med* 9(3).

The disclosure is based, in part, on the surprising discovery that rAAV vectors comprising a "D" region located on the "outside" of the ITR (e.g., proximal to the terminus of the ITR relative to the transgene insert or expression construct) are efficiently encapsidated by AAV capsid proteins than rAAV vectors having ITRs with unmodified (e.g., wild-type) ITRs In some embodiments, rAAV vectors having a modified "D" sequence (e.g., a "D" sequence in the "outside" position) have reduced toxicity relative to rAAV vectors having wild-type ITR sequences.

In some embodiments, a modified "D" sequence comprises at least one nucleotide substitution relative to a wild-type "D" sequence (e.g., SEQ ID NO: 27). A modified "D" sequence may have at least 1, 2, 3, 4, 5, 6, 7, 8, 9, 10, or more than 10 nucleotide substitutions relative to a wild-type "D" sequence (e.g., SEQ ID NO: 27). In some embodiments, a modified "D" sequence comprises at least 10, 11, 12, 13, 14, 15, 16, 17, 18, or 19 nucleic acid substitutions relative to a wild-type "D" sequence (e.g., SEQ ID NO: 27). In some embodiments, a modified "D" sequence is between about 10% and about 99% (e.g., 10%, 15%, 20%, 25%, 30%, 40%, 45%, 50%, 55%, 60%, 65%, 70%, 75%, 80%, 85%, 90%, 95%, or 99%) identical to a wild-type "D" sequence (e.g., SEQ ID NO: 27). In some embodiments, a modified "D" sequence comprises the sequence set forth in SEQ ID NO: 26, also referred to as an "S" sequence as described in Wang et al. (1995) *J Mol Biol* 250(5):573-80.

An isolated nucleic acid or rAAV vector as described by the disclosure may further comprise a "TRY" sequence, for example as set forth in SEQ ID NO: 28 or as described by Francois, et al. 2005. The Cellular TATA Binding Protein Is Required for Rep-Dependent Replication of a Minimal Adeno-Associated Virus Type 2 p5 Element. J Virol. In some embodiments, a TRY sequence is positioned between an ITR (e.g. a 5' ITR) and an expression construct (e.g. a transgene-encoding insert) of an isolated nucleic acid or rAAV vector.

In some aspects, the disclosure relates to Baculovirus vectors comprising an isolated nucleic acid or rAAV vector as described by the disclosure. In some embodiments, the Baculovirus vector is an *Autographa californica* nuclear polyhedrosis (AcNPV) vector, for example as described by Urabe et al. (2002) *Hum Gene Ther* 13(16):1935-43 and Smith et al. (2009) *Mol Ther* 17(11):1888-1896.

In some aspects, the disclosure provides a host cell comprising an isolated nucleic acid or vector as described herein. A host cell can be a prokaryotic cell or a eukaryotic cell. For example, a host cell can be a mammalian cell, bacterial cell, yeast cell, insect cell, etc. In some embodiments, a host cell is a mammalian cell, for example a HEK293T cell. In some embodiments, a host cell is a bacterial cell, for example an *E. coli* cell.

rAAVs

In some aspects, the disclosure relates to recombinant AAVs (rAAVs) comprising a transgene that encodes a nucleic acid as described herein (e.g., an rAAV vector as described herein). The term "rAAVs" generally refers to viral particles comprising an rAAV vector encapsidated by one or more AAV capsid proteins. An rAAV described by the disclosure may comprise a capsid protein having a serotype selected from AAV1, AAV2, AAV3, AAV4, AAV5, AAV6, AAV7, AAV8, AAV9, and AAV10. In some embodiments, an rAAV comprises a capsid protein from a non-human host, for example a rhesus AAV capsid protein such as AAVrh.10, AAVrh.39, etc. In some embodiments, an rAAV described by the disclosure comprises a capsid protein that is a variant of a wild-type capsid protein, such as a capsid protein variant that includes at least 1, 2, 3, 4, 5, 6, 7, 8, 9, 10, or more than 10 (e.g. 15, 20 25, 50, 100, etc.) amino acid substitutions (e.g., mutations) relative to the wild-type AAV capsid protein from which it is derived.

In some embodiments, rAAVs described by the disclosure readily spread through the CNS, particularly when introduced into the CSF space or directly into the brain parenchyma. Accordingly, in some embodiments, rAAVs described by the disclosure comprise a capsid protein that is capable of crossing the blood-brain barrier (BBB). For example, in some embodiments, an rAAV comprises a capsid protein having an AAV9 or AAVrh.10 serotype. Production of rAAVs is described, for example, by Samulski et al. (1989) *J Virol.* 63(9):3822-8 and Wright (2009) *Hum Gene Ther.* 20(7): 698-706.

In some embodiments, an rAAV as described by the disclosure (e.g., comprising a recombinant rAAV genome encapsidated by AAV capsid proteins to form an rAAV capsid particle) is produced in a Baculovirus vector expression system (BEVS). Production of rAAVs using BEVS are described, for example by Urabe et al. (2002) Hum Gene Ther 13(16):1935-43, Smith et al. (2009) Mol Ther 17(11): 1888-1896, U.S. Pat. Nos. 8,945,918, 9,879,282, and International PCT Publication WO 2017/184879. However, an rAAV can be produced using any suitable method (e.g., using recombinant rep and cap genes).

Pharmaceutical Compositions

In some aspects, the disclosure provides pharmaceutical compositions comprising an isolated nucleic acid or rAAV as described herein and a pharmaceutically acceptable carrier. As used herein, the term "pharmaceutically acceptable" refers to a material, such as a carrier or diluent, which does not abrogate the biological activity or properties of the compound, and is relatively non-toxic, e.g., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

Compositions (e.g., pharmaceutical compositions) provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

Methods

The disclosure is based, in part, on compositions for expression of combinations of PD-associated gene products in a subject that act together (e.g., synergistically) to treat Parkinson's disease. As used herein "treat" or "treating" refers to (a) preventing or delaying onset of Parkinson's disease; (b) reducing severity of Parkinson's disease; (c) reducing or preventing development of symptoms characteristic of Parkinson's disease; (d) and/or preventing worsening of symptoms characteristic of Parkinson's disease. Symptoms of Parkinson's disease include, for example, motor dysfunction (e.g., shaking, rigidity, slowness of movement, difficulty with walking), cognitive dysfunction (e.g., dementia, depression, anxiety), emotional and behavioral dysfunction.

Accordingly, in some aspects, the disclosure provides a method for treating a subject having or suspected of having Parkinson's disease, the method comprising administering to the subject a composition (e.g., a composition comprising an isolated nucleic acid or a vector or a rAAV) as described by the disclosure.

In some embodiments, a composition is administered directly to the CNS of the subject, for example by direct injection into the brain and/or spinal cord of the subject. Examples of CNS-direct administration modalities include but are not limited to intracerebral injection, intraventricular injection, intracisternal injection, intraparenchymal injection, intrathecal injection, and any combination of the foregoing. In some embodiments, direct injection into the CNS of a subject results in transgene expression (e.g., expression of the first gene product, second gene product, and if applicable, third gene product) in the midbrain, striatum and/or cerebral cortex of the subject. In some embodiments, direct injection into the CNS results in transgene expression (e.g., expression of the first gene product, second gene product, and if applicable, third gene product) in the spinal cord and/or CSF of the subject.

In some embodiments, direct injection to the CNS of a subject comprises convection enhanced delivery (CED).

Convection enhanced delivery is a therapeutic strategy that involves surgical exposure of the brain and placement of a small-diameter catheter directly into a target area of the brain, followed by infusion of a therapeutic agent (e.g., a composition or rAAV as described herein) directly to the brain of the subject. CED is described, for example by Debinski et al. (2009) *Expert Rev Neurother.* 9(10):1519-27.

In some embodiments, a composition is administered peripherally to a subject, for example by peripheral injection. Examples of peripheral injection include subcutaneous injection, intravenous injection, intra-arterial injection, intraperitoneal injection, or any combination of the foregoing. In some embodiments, the peripheral injection is intra-arterial injection, for example injection into the carotid artery of a subject.

In some embodiments, a composition (e.g., a composition comprising an isolated nucleic acid or a vector or a rAAV) as described by the disclosure is administered both peripherally and directly to the CNS of a subject. For example, in some embodiments, a subject is administered a composition by intra-arterial injection (e.g., injection into the carotid artery) and by intraparenchymal injection (e.g., intraparenchymal injection by CED). In some embodiments, the direct injection to the CNS and the peripheral injection are simultaneous (e.g., happen at the same time). In some embodiments, the direct injection occurs prior (e.g., between 1 minute and 1 week, or more before) to the peripheral injection. In some embodiments, the direct injection occurs after (e.g., between 1 minute and 1 week, or more after) the peripheral injection.

The amount of composition (e.g., a composition comprising an isolated nucleic acid or a vector or a rAAV) as described by the disclosure administered to a subject will vary depending on the administration method. For example, in some embodiments, a rAAV as described herein is administered to a subject at a titer between about $10^9$ Genome copies (GC)/kg and about $10^{14}$ GC/kg (e.g., about $10^9$ GC/kg, about $10^{10}$ GC/kg, about $10^{11}$ GC/kg, about $10^{12}$ GC/kg, about $10^{12}$ GC/kg, or about $10^{14}$ GC/kg). In some embodiments, a subject is administered a high titer (e.g., $>10^{12}$ Genome Copies GC/kg of an rAAV) by injection to the CSF space, or by intraparenchymal injection.

A composition (e.g., a composition comprising an isolated nucleic acid or a vector or a rAAV) as described by the disclosure can be administered to a subject once or multiple times (e.g., 2, 3, 4, 5, 6, 7, 8, 9, 10, 20, or more) times. In some embodiments, a composition is administered to a subject continuously (e.g., chronically), for example via an infusion pump.

EXAMPLES

Example 1 rAAV Vectors

AAV vectors are generated using cells, such as HEK293 cells for triple-plasmid transfection. The ITR sequences flank an expression construct comprising a promoter/enhancer element for each transgene of interest, a 3' polyA signal, and posttranslational signals such as the WPRE element. Multiple gene products can be expressed simultaneously such as GBA1 and LIMP2 and/or Prosaposin, by fusion of the protein sequences; or using a 2A peptide linker, such as T2A or P2A, which leads 2 peptide fragments with added amino acids due to prevention of the creation of a peptide bond; or using an IRES element; or by expression with 2 separate expression cassettes. The presence of a short intronic sequence that is efficiently spliced, upstream of the expressed gene, can improve expression levels. shRNAs and other regulatory RNAs can potentially be included within these sequences. Examples of expression constructs described by the disclosure are shown in FIGS. 1-8 and 21-35, and in Table 2 below.

TABLE 2

| Name | Promoter 1 | shRNA | CDS1 | PolyA 1 | Bicistronic element | Promoter 2 | CDS2 | PolyA2 | Length between ITRs |
|---|---|---|---|---|---|---|---|---|---|
| CMVe_CBAp_GBA1_WPRE_bGH | CBA | | GBA1 | WPRE-bGH | | | | | 3741 |
| LT1s_JetLong_mRNAiaSYn_SCARB2-T2A-GBA1_bGH | JetLong | aSyn | SCARB2 | bGH | T2A | | GBA1 | | 4215 |
| LI1_JetLong_SCARB2-IRES-GBA1_bGH | JetLong | | SCARB2 | bGH | IRES | | GBA1 | | 4399 |
| FP1_JetLong_GBA1_bGH_JetLong_SCARB2_SV40L | JetLong | | GBA1 | bGH | | JetLong | SCARB2 | SV40L | 4464 |
| PrevailVector_LT2s_JetLong_mRNAiaSYn_PSAP-T2A-GBA1_bGH_4353nt | JetLong | aSyn | PSAP | bGH | T2A | — | GBA1 | — | 4353 |
| PrevailVector_LI2_JetLong_PSAP_IRES_GBA1_SyntheticpolyA_4337nt | JetLong | — | PSAP | Synthetic pA | IRES | — | GBA1 | — | 4337 |
| PrevailVector_10s_JetLong_mRNAiaSy_GBA2_WPRE_bGH_4308nt | JetLong | aSyn | GBA2 | WPRE_bGH | — | — | — | — | 4308 |
| PrevailVector_FT4_JetLong_GBA1_T2A_GALC_SyntheticpolyA_4373nt | JetLong | — | GBA1 | Synthetic pA | T2A | — | GALC | — | 4373 |
| PrevailVector_LT4_JetLong_GALC_T2A_GBA1_SyntheticpolyA_4373nt | JetLong | — | GALC | Synthetic pA | T2A | — | GBA1 | — | 4373 |

TABLE 2-continued

| Name | Promoter 1 | shRNA | CDS1 | PolyA 1 | Bicistronic element | Promoter 2 | CDS2 | PolyA2 | Length between ITRs |
|---|---|---|---|---|---|---|---|---|---|
| PrevailVector_LT5s_JetLong_mRNAiaSyn_CTSB-T2A-GBA1_WPRE_bGH_4392nt | JetLong | aSyn | CTSB | WPRE_bGH | T2A | — | GBA1 | — | 4392 |
| PrevailVector_FT11t_JetLong_mRNAiaSyn GBA1_T2S_SMPD1_SyntheticpolyA_4477nt | JetLong | aSyn | GBA1 | Synthetic pA | T2A | — | SMPD1 | — | 4477 |
| PrevailVector_LI4_JetLong_GALC_IRES_GBA1_SyntheticpolyA_4820nt | JetLong | — | GALC | Synthetic pA | IRES | — | GBA1 | — | 4820 |
| PrevailVector_FP5_JetLong_GBA1_bGH_JetLong_CTSB_5401_4108nt | JetLong | — | GBA1 | bGH | — | JetLong | CTSB | SV40L | 4108 |
| PrevailVector_FT6s_JetLong_mRNAiaSyn_GBA1-T2A-GCH1_WPRE_bGH_4125nt | JetLong | aSyn | GBA1 | WPRE_bGH | T2A | — | GCH1 | — | 4125 |
| PrevailVector_LT7s_JetLong_mRNAiaSyn_RAB7L1-T2A-GBA1_WPRE_bGH_3984nt | JetLong | aSyn | RAB7L1 | WPRE_bGH | T2A | — | GBA1 | — | 3984 |
| PrevailVector_FI6s_JetLong_mRNAiaSYn_GBA1-IRES-GCH1_bGH_3978nt | JetLong | aSyn | GBA1 | bGH | IRES | — | GCH1 | — | 3978 |
| PrevailVector_9st_JetLong_mRNAiaSyn_mRNAiTMEM106B_VPS35_WPRE_bGH_4182nt | JetLong | aSyn & TMEM 106B | VPS35 | WPRE_bGH | — | — | — | — | 4182 |
| PrevailVector FT12s_JetLong_mRNAiaSynGBA1-T2A-IL34_WPRE_bGH_4104nt | JetLong | aSyn | GBA1 | WPRE_bGH | T2A | — | IL34 | — | 4104 |
| PrevailVector_FI12s_JetLong_mRNAiaSYn_GBA1-IRES-IL34_bGH_3957nt | JetLong | aSyn | GBA1 | bGH | IRES | — | IL34 | — | 3957 |
| PrevailVector_FP8_JetLong GBA1_bGH_CD68_TREM2_SV401_4253nt | JetLong | — | GBA1 | bGH | — | CD68 | TREM2 | SV40L | 4253 |
| PrevailVector_FP12_CMVe_CBA_GBA1_bGH_JetLong_IL34_SV401_4503nt | CBA | | GBA1 | bGH | | JetLong | IL34 | SV40L | 4503 |

Example 2

Cell Based Assays of Viral Transduction into GBA-Deficient Cells

Cells deficient in GBA1 are obtained, for example as fibroblasts from GD patients, monocytes, or hES cells, or patient-derived induced pluripotent stem cells (iPSCs). These cells accumulate substrates such as glucosylceramide and glucosylsphingosine (GlcCer and GlcSph). Treatment of wild-type or mutant cultured cell lines with Gcase inhibitors, such as CBE, is also be used to obtain GBA deficient cells.

Using such cell models, lysosomal defects are quantified in terms of accumulation of protein aggregates, such as of α-Synuclein with an antibody for this protein or phospho-αSyn, followed by imaging using fluorescent microscopy. Imaging for lysosomal abnormalities by ICC for protein markers such as LAMP1, LAMP2, LIMP1, LIMP2, or using dyes such as Lysotracker, or by uptake through the endocytic compartment of fluorescent dextran or other markers is also performed. Imaging for autophagy marker accumulation due to defective fusion with the lysosome, such as for LC3, can also be performed. Western blotting and/or ELISA is used to quantify abnormal accumulation of these markers. Also, the accumulation of glycolipid substrates and products of GBA1 is measured using standard approaches.

Therapeutic endpoints (e.g., reduction of PD-associated pathology) are measured in the context of expression of transduction of the AAV vectors, to confirm and quantify activity and function. Gcase can is also quantified using protein ELISA measures, or by standard Gcase activity assays.

Example 3

In Vivo Assays Using Mutant Mice

This example describes in vivo assays of AAV vectors using mutant mice. In vivo studies of AAV vectors as above in mutant mice are performed using assays described, for example, by Liou et al. (2006) *J Biol. Chem.* 281(7): 4242-4253, Sun et al. (2005) *J. Lipid Res.* 46:2102-2113, and Farfel-Becker et al. (2011) *Dis. Model Mech.* 4(6):746-752.

The intrathecal or intraventricular delivery of vehicle control and AAV vectors (e.g., at a dose of $2\times10^{11}$ vg/mouse) are performed using concentrated AAV stocks, for example at an injection volume between 5-10 µL. Intraparenchymal delivery by convection enhanced delivery is performed.

Treatment is initiated either before onset of symptoms, or subsequent to onset. Endpoints measured are the accumulation of substrate in the CNS and CSF, accumulation of Gcase enzyme by ELISA and of enzyme activity, motor and cognitive endpoints, lysosomal dysfunction, and accumulation of α-Synuclein monomers, protofibrils or fibrils.

Example 4

Chemical Models of Disease

This example describes in vivo assays of AAV vectors using a chemically-induced mouse model of Gaucher disease (e.g., the CBE mouse model). In vivo studies of these AAV vectors are performed in a chemically-induced mouse model of Gaucher disease, for example as described by Vardi et al. (2016) *J Pathol.* 239(4):496-509.

Intrathecal or intraventricular delivery of vehicle control and AAV vectors (e.g., at a dose of $2\times10^{11}$ vg/mouse) are performed using concentrated AAV stocks, for example with injection volume between 5-10 µL. Intraparenchymal delivery by convection enhanced delivery is performed. Peripheral delivery is achieved by tail vein injection.

Treatment is initiated either before onset of symptoms, or subsequent to onset. Endpoints measured are the accumulation of substrate in the CNS and CSF, accumulation of Gcase enzyme by ELISA and of enzyme activity, motor and cognitive endpoints, lysosomal dysfunction, and accumulation of α-Synuclein monomers, protofibrils or fibrils.

Example 5

Clinical Trials in PD, LBD, Gaucher Disease Patients

In some embodiments, patients having certain forms of Gaucher disease (e.g., GD1) have an increased risk of developing Parkinson's disease (PD) or Lewy body dementia (LBD). This Example describes clinical trials to assess the safety and efficacy of rAAVs as described by the disclosure, in patients having Gaucher disease, PD and/or LBD.

Clinical trials of such vectors for treatment of Gaucher disease, PD and/or LBD are performed using a study design similar to that described in Grabowski et al. (1995) *Ann. Intern. Med.* 122(1):33-39.

Example 6

Treatment of Peripheral Disease

In some embodiments, patients having certain forms of Gaucher disease exhibit symptoms of peripheral neuropathy, for example as described in Biegstraaten et al. (2010) *Brain* 133(10):2909-2919.

This example describes in vivo assays of AAV vectors as described herein for treatment of peripheral neuropathy associated with Gaucher disease (e.g., Type 1 Gaucher disease). Briefly, Type 1 Gaucher disease patients identified as having signs or symptoms of peripheral neuropathy are administered a rAAV as described by the disclosure. In some embodiments, the peripheral neuropathic signs and symptoms of the subject are monitored, for example using methods described in Biegstraaten et al., after administration of the rAAV.

Levels of transduced gene products as described by the disclosure present in patients (e.g., in serum of a patient, in peripheral tissue (e.g., liver tissue, spleen tissue, etc.)) of a patient are assayed, for example by Western blot analysis, enzymatic functional assays, or imaging studies.

Example 7

Treatment of CNS Forms

This example describes in vivo assays of rAAVs as described herein for treatment of CNS forms of Gaucher disease. Briefly, Gaucher disease patients identified as having a CNS form of Gaucher disease (e.g., Type 2 or Type 3 Gaucher disease) are administered a rAAV as described by the disclosure. Levels of transduced gene products as described by the disclosure present in the CNS of patients (e.g., in serum of the CNS of a patient, in cerebrospinal fluid (CSF) of a patient, or in CNS tissue of a patient) are assayed, for example by Western blot analysis, enzymatic functional assays, or imaging studies.

Example 8

Gene Therapy of Parkinson's Disease in Subjects Having Mutations in GBA1

This example describes administration of a recombinant adeno-associated virus (rAAV) encoding GBA1 to a subject having Parkinson's disease characterized by a mutation in GBA1 gene.

The rAAV-GBA1 vector insert contains the CBA promoter element (CBA), consisting of four parts: the CMV enhancer (CMVe), CBA promoter (CBAp), Exon 1, and intron (int) to constitutively express the codon optimized coding sequence (CDS) of human GBA1 (maroon). The 3' region also contains a Woodchuck hepatitis virus Posttranscriptional Regulatory Element (WPRE) posttranscriptional regulatory element followed by a bovine Growth Hormone polyA signal (bGH polyA) tail. The flanking ITRs allow for the correct packaging of the intervening sequences. Two variants of the 5' ITR sequence (FIG. 7, inset box, bottom sequence) were evaluated; these variants have several nucleotide differences within the 20-nucleotide "D" region of the ITR, which is believed to impact the efficiency of packaging and expression. The rAAV-GBA1 vector product contains the "D" domain nucleotide sequence shown in FIG. 7 (inset box, top sequence). A variant vector harbors a mutant "D" domain (termed an "S" domain herein, with the nucleotide changes shown by shading), performed similarly in preclinical studies. The backbone contains the gene to confer resistance to kanamycin as well as a stuffer sequence to prevent reverse packaging. A schematic depicting a rAAV-GBA1 vector is shown in FIG. 8. The rAAV-GBA1 vector is packaged into an rAAV using AAV9 serotype capsid proteins.

rAAV-GBA1 is administered to a subject as a single dose via a fluoroscopy guided sub-occipital injection into the cisterna magna (intracisternal magna; ICM). One embodiment of a rAAV-GBA1 dosing regimen study is as follows:

A single dose of rAAV-GBA1is administered to patients (N=12) at one of two dose levels (3e13 vg (low dose); 1e14 vg (high dose), etc.) which are determined based on the results of nonclinical pharmacology and toxicology studies.

Initial studies were conducted in a chemical mouse model involving daily delivery of conduritol-b-epoxide (CBE), an inhibitor of GCase to assess the efficacy and safety of the rAAV-GBA1 vector and a rAAV-GBA1 S-variant construct (as described further below). Additionally, initial studies were performed in a genetic mouse model, which carries a homozygous GBA1 mutation and is partially deficient in saposins (4L/PS-NA). Additional dose-ranging studies in mice and nonhuman primates (NHPs) are conducted to further evaluate vector safety and efficacy.

Figure 7:
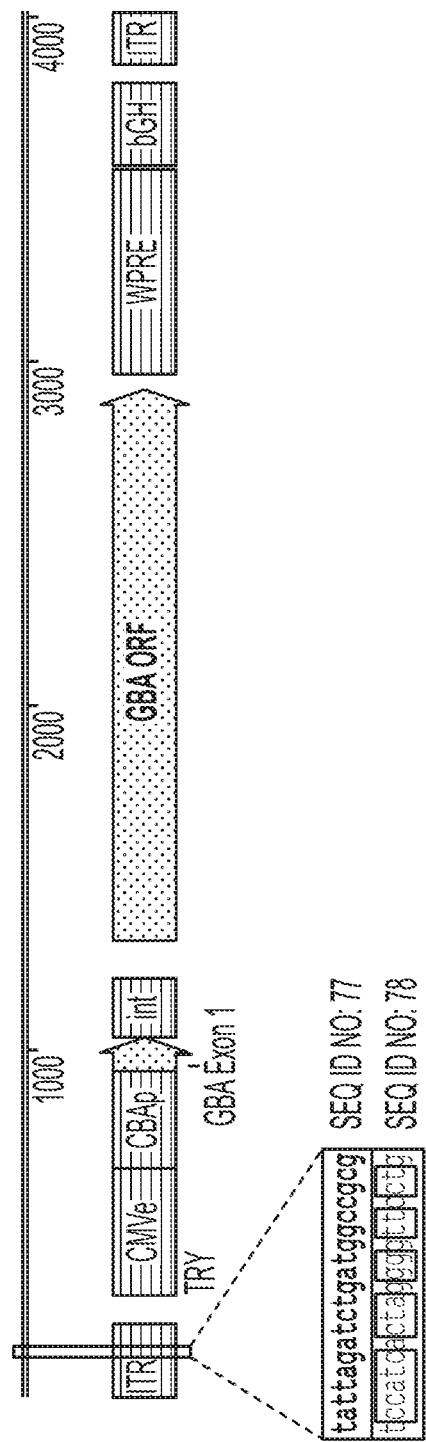
FIG. 7 is a schematic depicting one embodiment of a vector comprising an expression construct encoding a Gcase (e.g., GBA1 or a portion thereof). In this embodiment, the vector comprises a CBA promoter element (CBA), consisting of four parts: the CMV enhancer (CMVe), CBA promoter (CBAp), Exon 1, and intron (int) to constitutively express the codon optimized coding sequence of human GBA1. The 3' region also contains a WPRE regulatory element followed by a bGH polyA tail. Three transcriptional regulatory activation sites are included at the 5' end of the promoter region: TATA, RBS, and YY1. The flanking ITRs allow for the correct packaging of the intervening sequences. Two variants of the 5' ITR sequence (inset box) were evaluated; these have several nucleotide differences within the 20-nucleotide "D" region of wild-type AAV2 ITR. In some embodiments, an rAAV vector contains the "D" domain nucleotide sequence shown on the top line. In some embodiments, a rAAV vector comprises a mutant "D" domain (e.g., an "S" domain, with the nucleotide changes shown on the bottom line).
Figure 8:
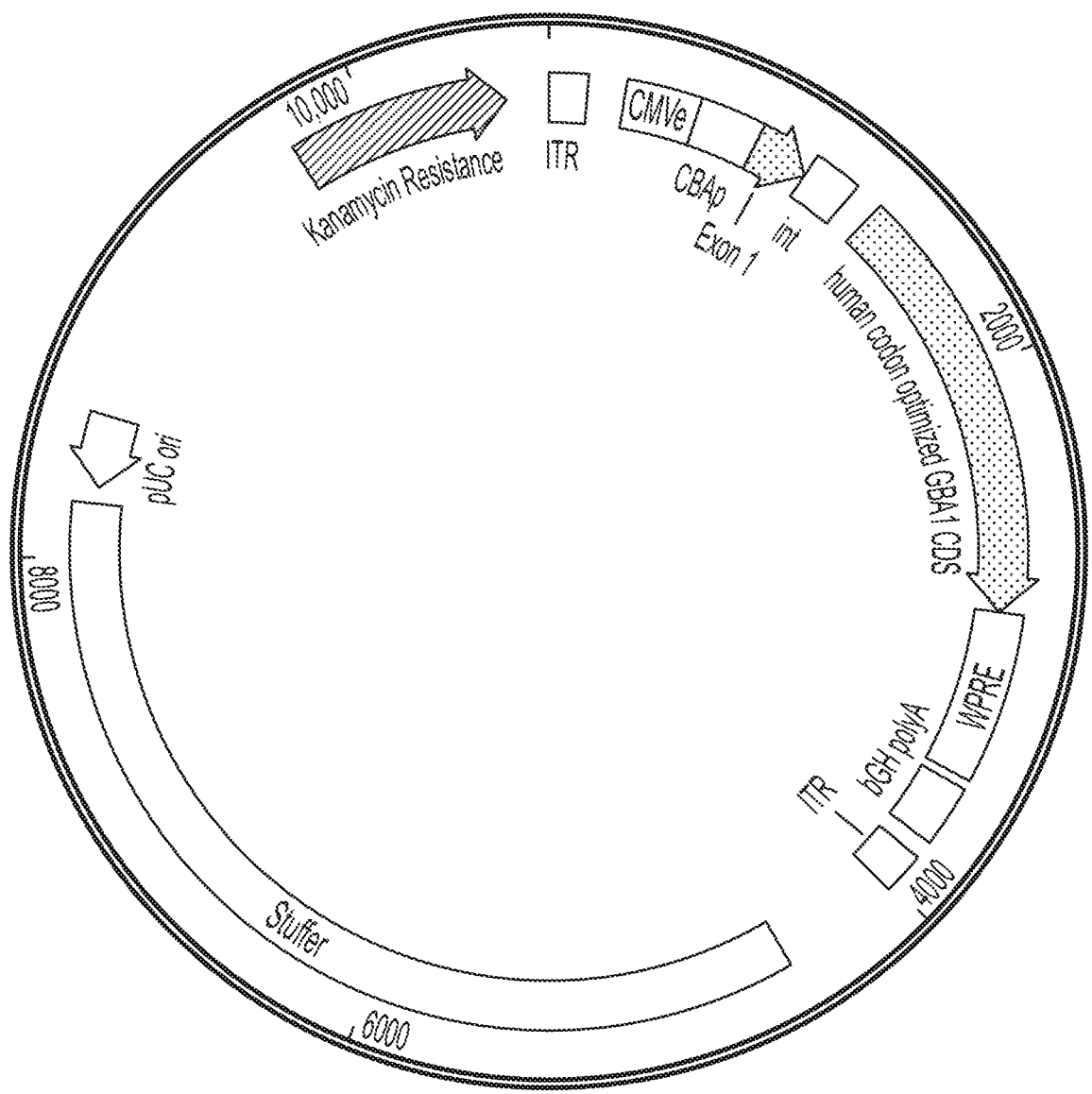
FIG. 8 is a schematic depicting one embodiment of the vector described in FIG. 6

Two slightly different versions of the 5' inverted terminal repeat (ITR) in the AAV backbone were tested to assess manufacturability and transgene expression (FIG. 7). The 20 bp "D" domain within the 145 bp 5' ITR is thought to be necessary for optimal viral vector production, but mutations within the "D" domain have also been reported to increase transgene expression in some cases. Thus, in addition to the viral vector rAAV-GBA1, which harbors an intact "D" domain, a second vector form with a mutant D domain (termed an "S" domain herein) was also evaluated. Both rAAV-GBA1 and the variant express the same transgene. While both vectors produced virus that was efficacious in vivo as detailed below, rAAV-GBA1, which contains a wild-type "D" domain, was selected for further development.

Figure 9:
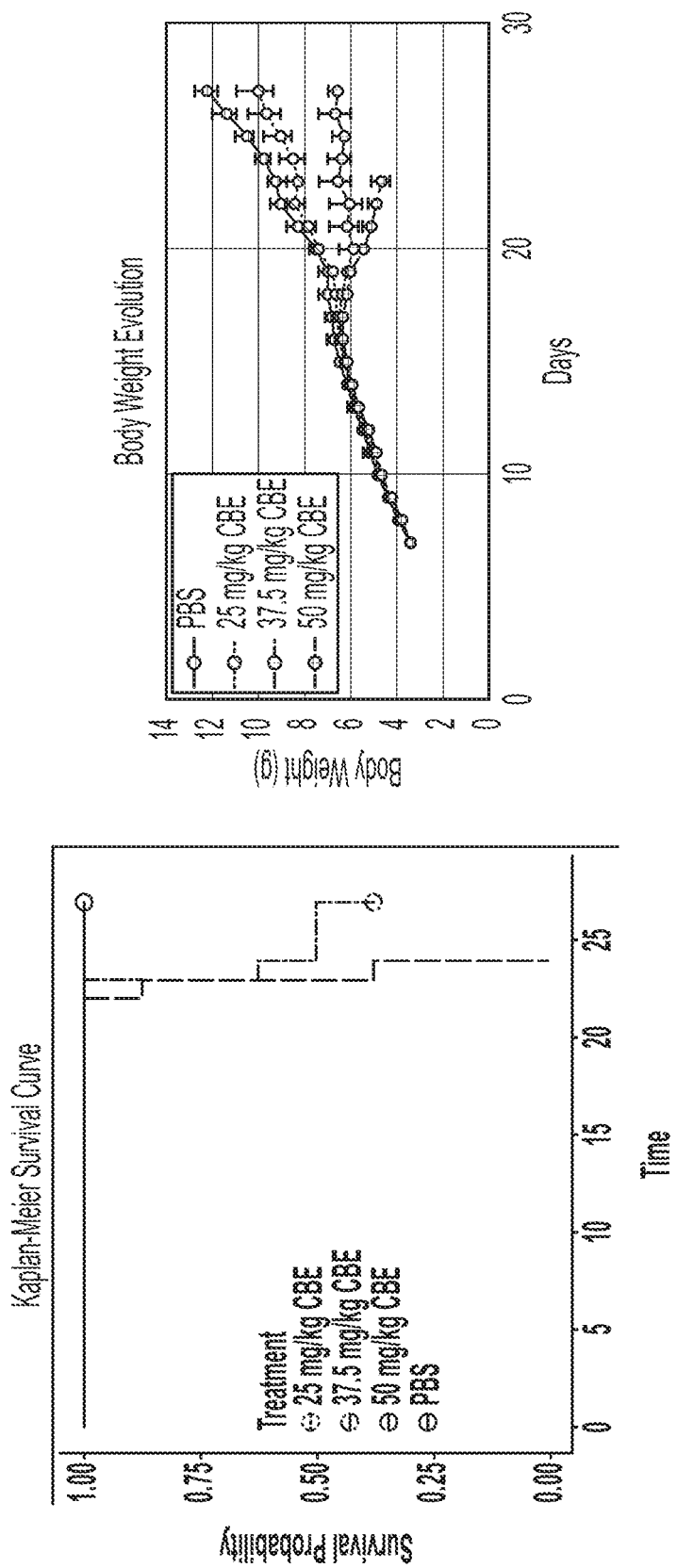
FIG. 9 shows representative data for delivery of an rAAV comprising a transgene encoding a Gcase (e.g., GBA1 or a portion thereof) in a CBE mouse model of Parkinson's disease. Daily IP delivery of PBS vehicle, 25 mg/kg CBE, 37.5 mg/kg CBE, or 50 mg/kg CBE (left to right) initiated at P8. Survival (top left) was checked two times a day and weight (top right) was checked daily. All groups started with n=8. Behavior was assessed by total distance traveled in Open Field (bottom left) at P23 and latency to fall on Rotarod (bottom middle) at P24. Levels of the GCase substrates were analyzed in the cortex of mice in the PBS and 25 mg/kg CBE treatment groups both with (Day 3) and without (Day 1) CBE withdrawal. Aggregate GluSph and GalSph levels (bottom right) are shown as pmol per mg wet weight of the tissue. Means are presented. Error bars are SEM. *$p<0.05$; $p<0.01$; *$p<0.001$, nominal p-values for treatment groups by linear regression.
Figure 9:
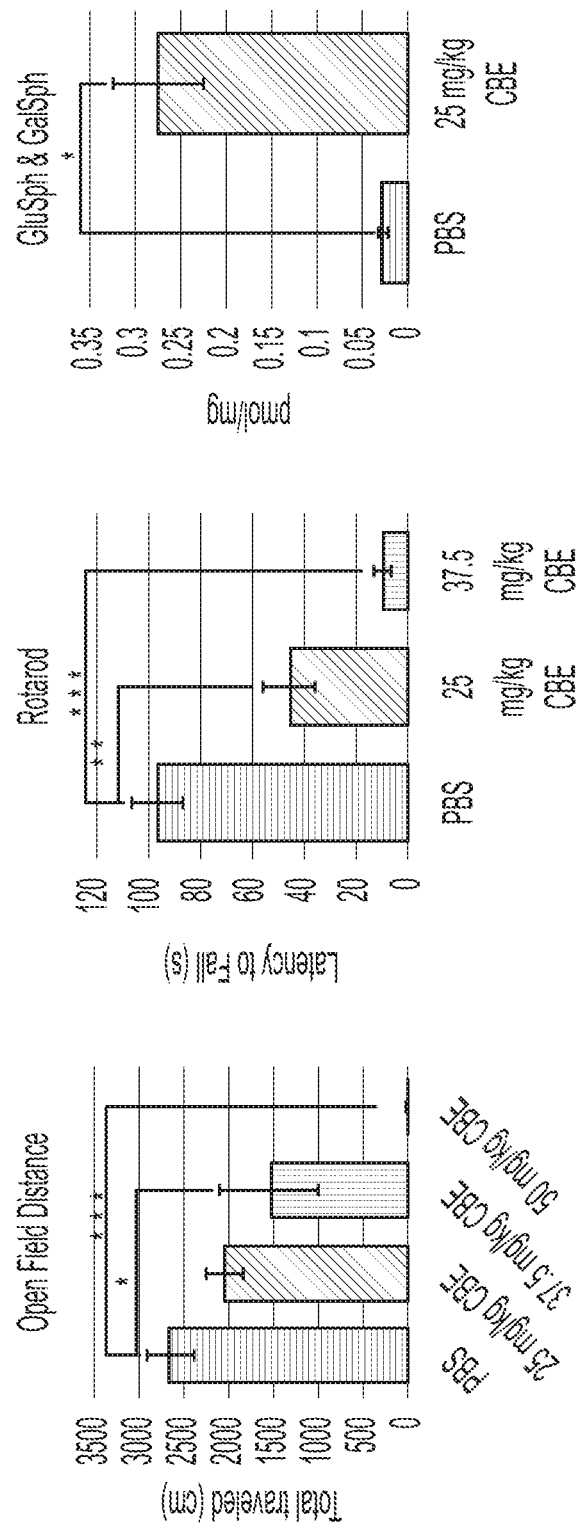

To establish the CBE model of GCase deficiency, juvenile mice were dosed with CBE, a specific inhibitor of GCase. Mice were given CBE by IP injection daily, starting at postnatal day 8 (P8). Three different CBE doses (25 mg/kg, 37.5 mg/kg, 50 mg/kg) and PBS were tested to establish a model that exhibits a behavioral phenotype (FIG. 9). Higher doses of CBE led to lethality in a dose-dependent manner. All mice treated with 50 mg/kg CBE died by P23, and 5 of the 8 mice treated with 37.5 mg/kg CBE died by P27. There was no lethality in mice treated with 25 mg/kg CBE. Whereas CBE-injected mice showed no general motor deficits in the open field assay (traveling the same distance and at the same velocity as mice given PBS), CBE-treated mice exhibited a motor coordination and balance deficit as measured by the rotarod assay.

Mice surviving to the end of the study were sacrificed on the day after their last CBE dose (P27, "Day 1") or after three days of CBE withdrawal (P29, "Day 3"). Lipid analysis was performed on the cortex of mice given 25 mg/kg CBE to evaluate the accumulation of GCase substrates in both the Day 1 and Day 3 cohorts. GluSph and GalSph levels (measured in aggregate in this example) were significantly accumulated in the CBE-treated mice compared to PBS-treated controls, consistent with GCase insufficiency.

Figure 10:
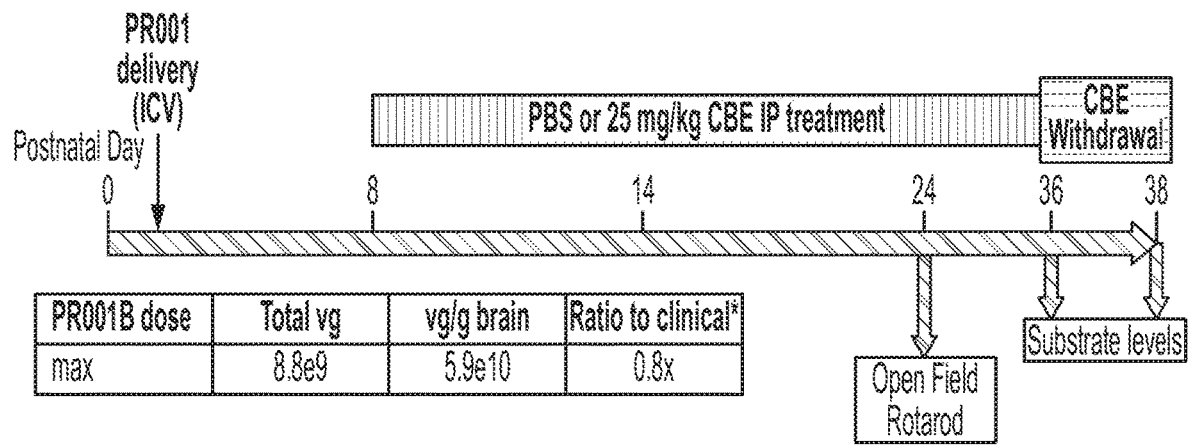
FIG. 10 is a schematic depicting one embodiment of a study design for maximal rAAV dose in a CBE mouse model. Briefly, rAAV was delivered by ICV injection at P3, and daily CBE treatment was initiated at P8. Behavior was assessed in the Open Field and Rotarod assays at P24-25 and substrate levels were measured at P36 and P38.

Based on the study described above, the 25 mg/kg CBE dose was selected since it produced behavioral deficits without impacting survival. To achieve widespread GBA1 distribution throughout the brain and transgene expression during CBE treatment, rAAV-GBA1 or excipient was delivered by intracerebroventricular (ICV) injection at postnatal day 3 (P3) followed by daily IP CBE or PBS treatment initiated at P8 (FIG. 10).

Figure 11:
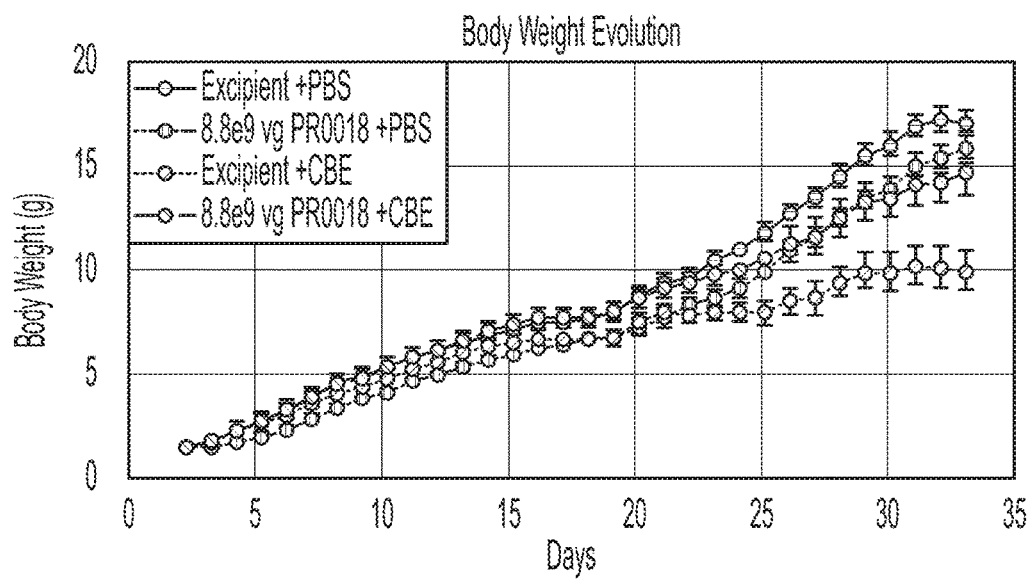
FIG. 11 shows representative data for in-life assessment of maximal rAAV dose in a CBE mouse model. At P3, mice were treated with either excipient or 8.8e9 vg rAAV-GBA1 via ICV delivery. Daily IP delivery of either PBS or 25 mg/kg CBE was initiated at P8. At the end of the study, half the mice were sacrificed one day after their last CBE dose at P36 (Day 1) while the remaining half went through 3 days of CBE withdrawal before sacrifice at P38 (Day3). All treatment groups (excipient+PBS n=8, rAAV-GBA1+PBS n=7, excipient+CBE n=8, and variant+CBE n=9) were weighed daily (top left), and the weight at P36 was analyzed (top right). Behavior was assessed by total distance traveled in Open Field at P23 (bottom left) and latency to fall on Rotarod at P24 (bottom right), evaluated for each animal as the median across 3 trials. Due to lethality, n=7 for the excipient+CBE group for the behavioral assays, while n=8 for all other groups. Means across animals are presented. Error bars are SEM. *$p<0.05$; ***$p<0.001$, nominal p-values for treatment groups by linear regression in the CBE-treated animals.
Figure 11:
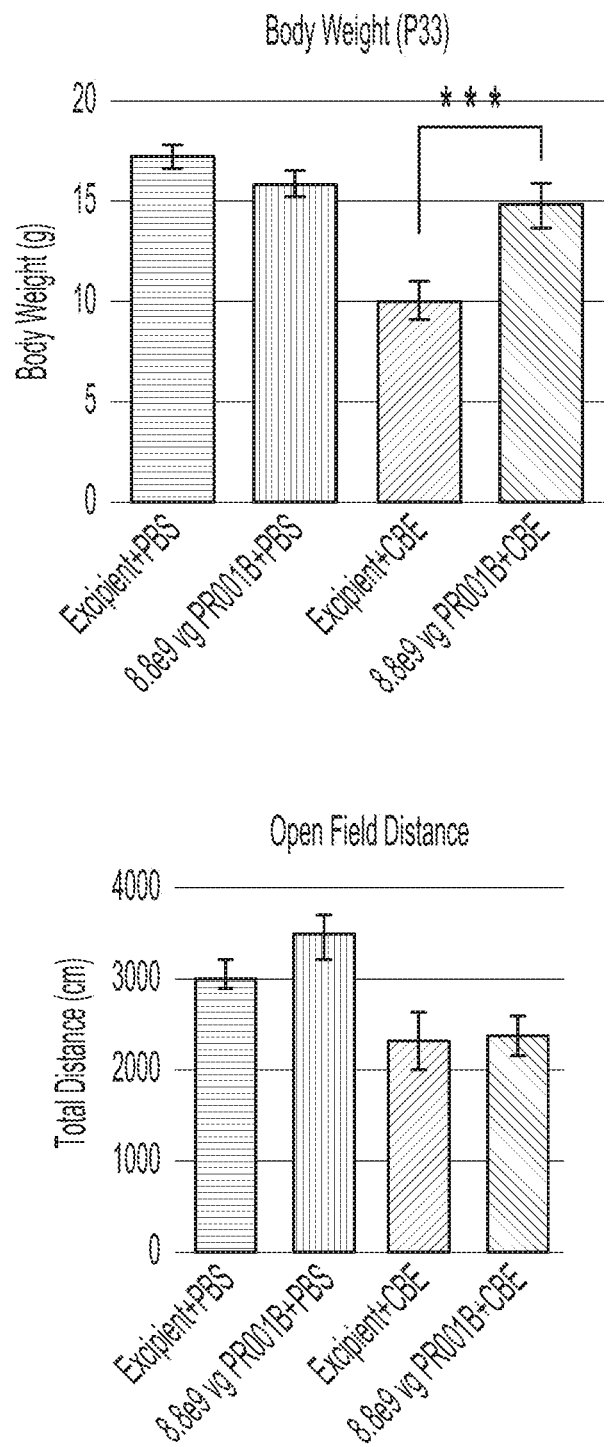
Figure 11:
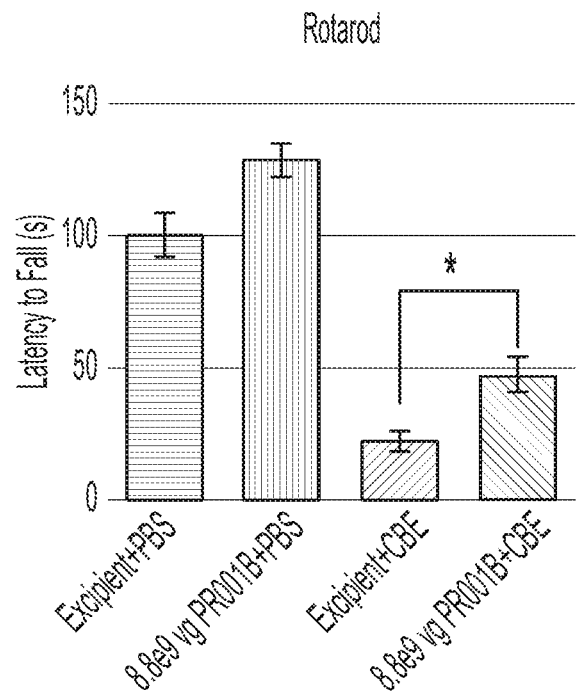

CBE-treated mice that received rAAV-GBA1 performed statistically significantly better on the rotarod than those that received excipient (FIG. 11). Mice in the variant treatment group did not differ from excipient treated mice in terms of other behavioral measures, such as the total distance traveled during testing (FIG. 11).

Figure 12:
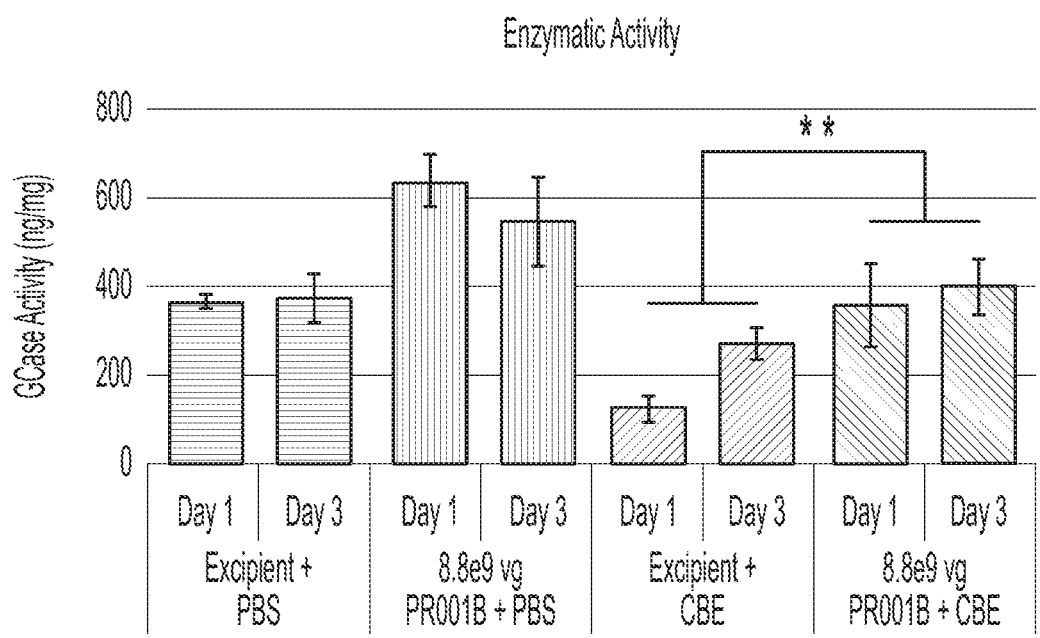
FIG. 12 shows representative data for biochemical assessment of maximal rAAV dose in a CBE mouse model. The cortex of all treatment groups (excipient+PBS n=8, variant+PBS n=7, excipient+CBE n=7, and variant+CBE n=9) was used to measure GCase activity (top left), GluSph levels (top right), GluCer levels (bottom left), and vector genomes (bottom right) in the groups before (Day 1) or after (Day 3) CBE withdrawal. Biodistribution is shown as vector genomes per 1 µg of genomic DNA. Means are presented. Error bars are SEM. (*)$p<0.1$; $p<0.01$; *$p<0.001$, nominal p-values for treatment groups by linear regression in the CBE-treated animals, with collection days and gender corrected for as covariates.
Figure 12:
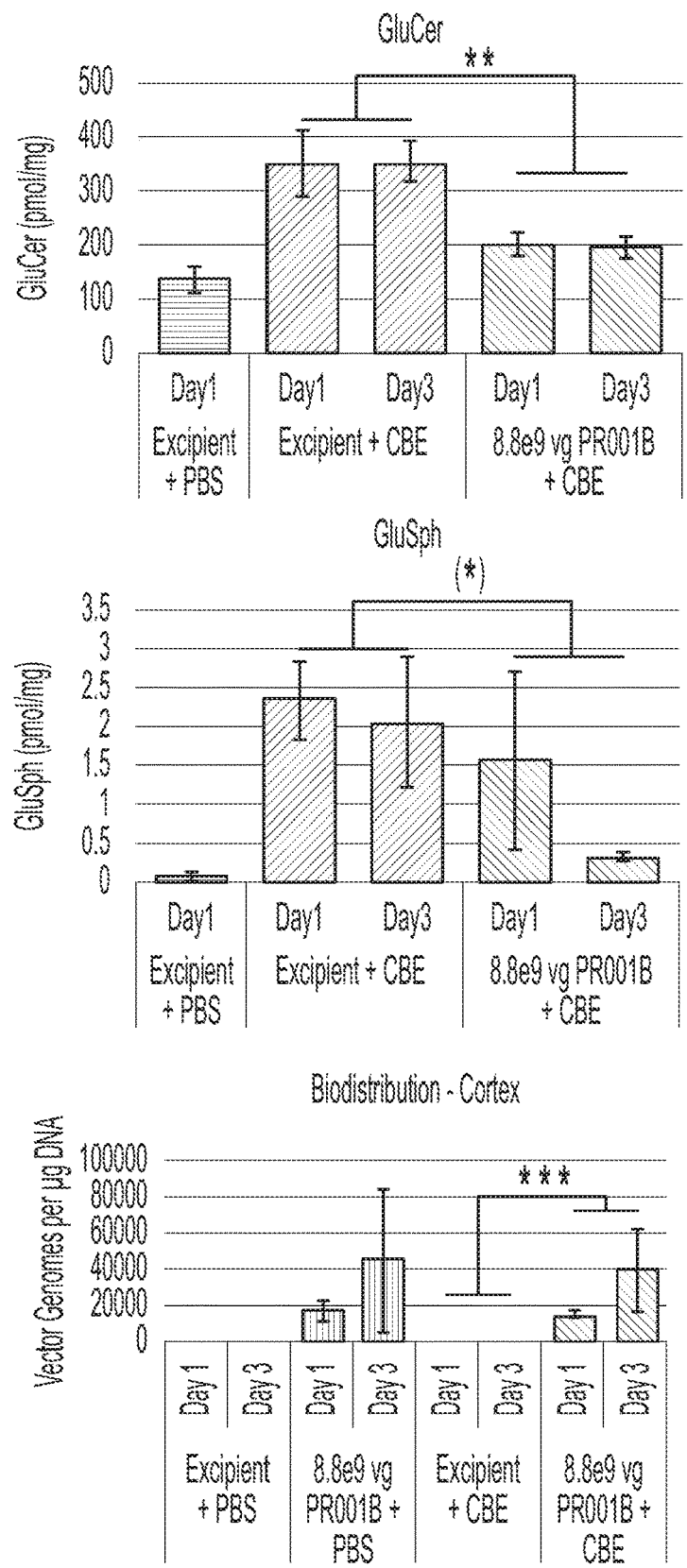

At the completion of the in-life study, half of the mice were sacrificed the day after the last CBE dose (P36, "Day 1") or after three days of CBE withdrawal (P38, "Day 3") for biochemical analysis (FIG. 12). Using a fluorometric enzyme assay performed in biological triplicate, GCase activity was assessed in the cortex. GCase activity was increased in mice that were treated with rAAV-GBA1, while CBE treatment reduced GCase activity. Additionally, mice that received both CBE and rAAV-GBA1 had GCase activity levels that were similar to the PBS-treated group, indicating that delivery of rAAV-GBA1 is able to overcome the inhibition of GCase activity induced by CBE treatment. Lipid analysis was performed on the motor cortex of the mice to examine levels of the substrates GluCer and GluSph. Both lipids accumulated in the brains of mice given CBE, and rAAV-GBA1 treatment significantly reduced substrate accumulation.

Figure 13:
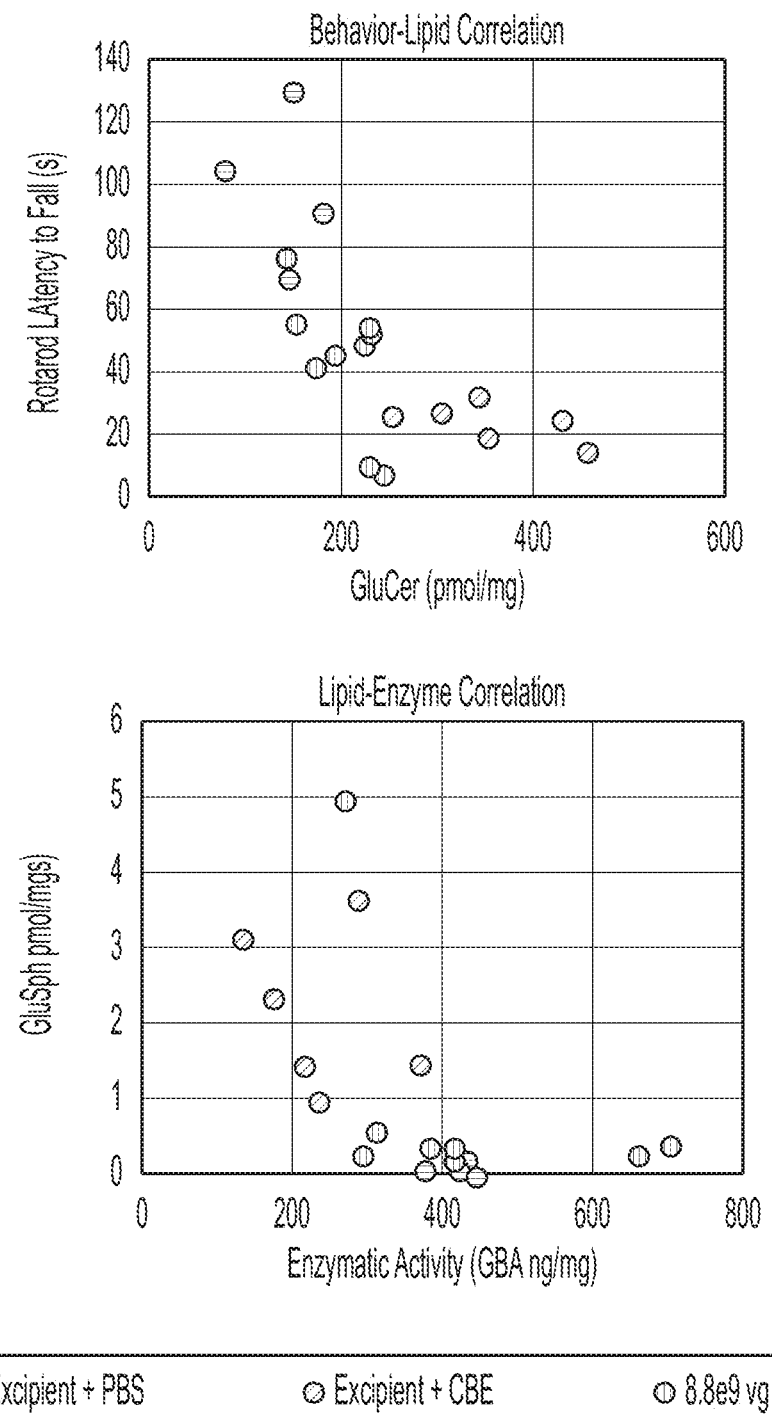
FIG. 13 shows representative data for behavioral and biochemical correlations in a CBE mouse model after administration of excipient+PBS, excipient+CBE, and variant+CBE treatment groups. Across treatment groups, performance on Rotarod was negatively correlated with GluCer accumulation (A, p=0.0012 by linear regression), and GluSph accumulation was negatively correlated with increased GCase activity (B, p=0.0086 by linear regression).
Figure 14:
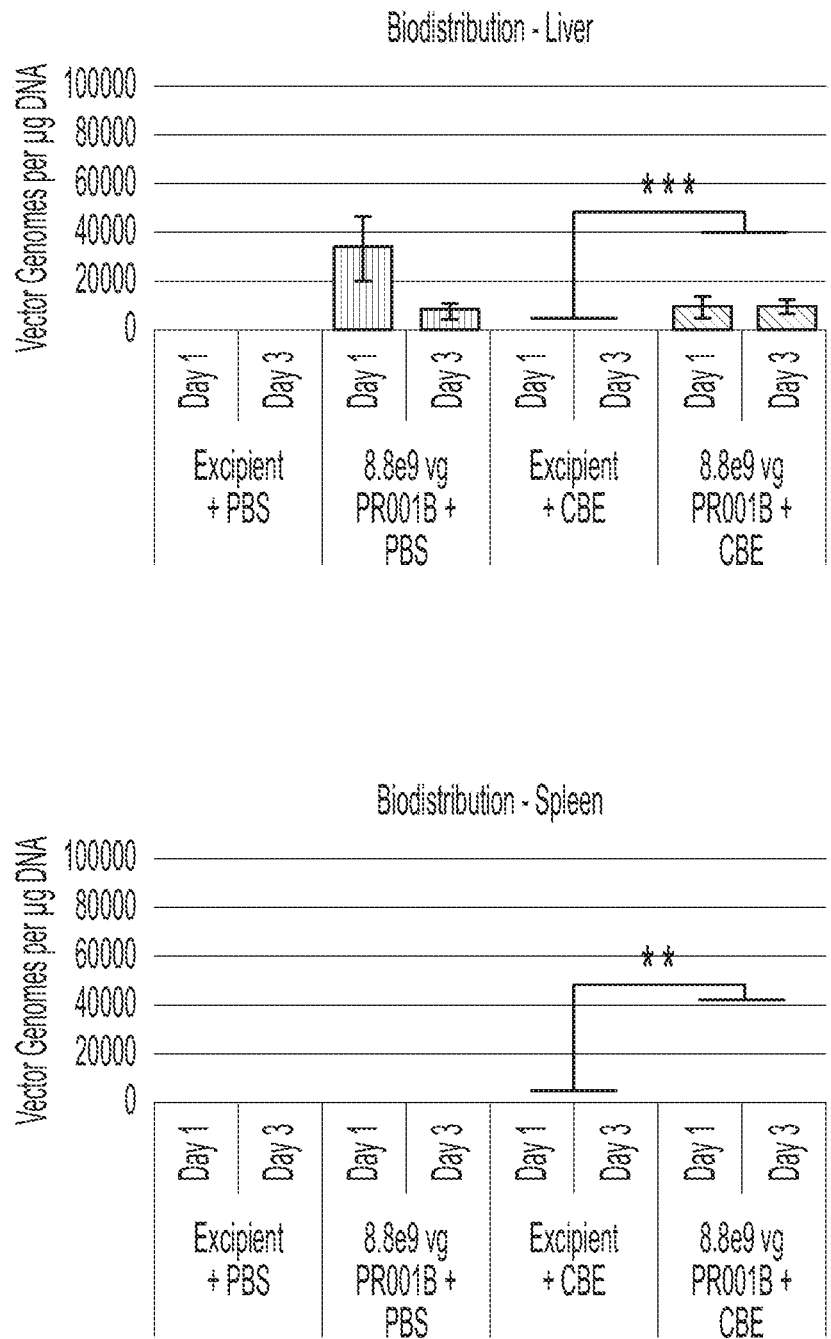
FIG. 14 shows representative data for biodistribution of variant in a CBE mouse model. Presence of vector genomes was assessed in the liver, spleen, kidney, and gonads for all treatment groups (excipient+PBS n=8, variant+PBS n=7, excipient+CBE n=7, and variant+CBE n=9). Biodistribution is shown as vector genomes per 1 µg of genomic DNA. Vector genome presence was quantified by quantitative PCR using a vector reference standard curve; genomic DNA concentration was evaluated by A260 optical density measurement. Means are presented. Error bars are SEM. *p<0.05; p<0.01; *p<0.001, nominal p-values for treatment groups by linear regression in the CBE-treated animals, with collection days and gender corrected for as covariates.
Figure 14:
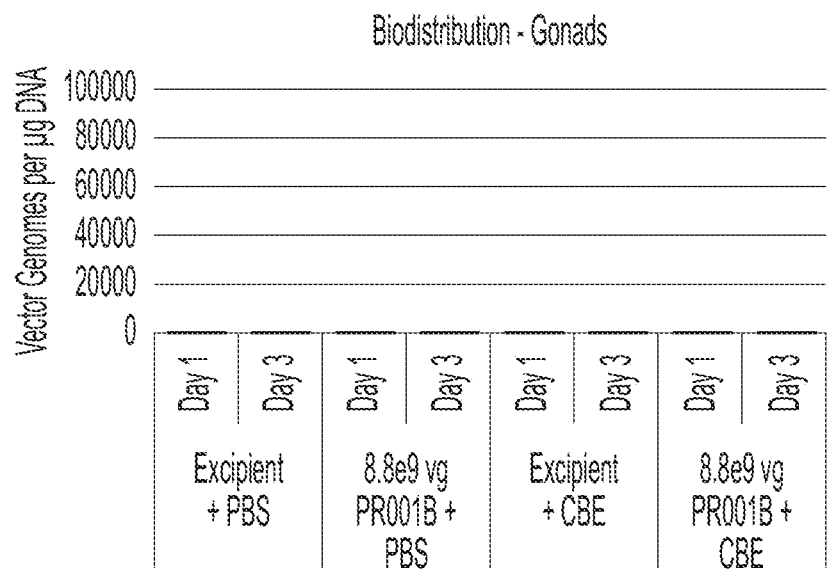
Figure 14:
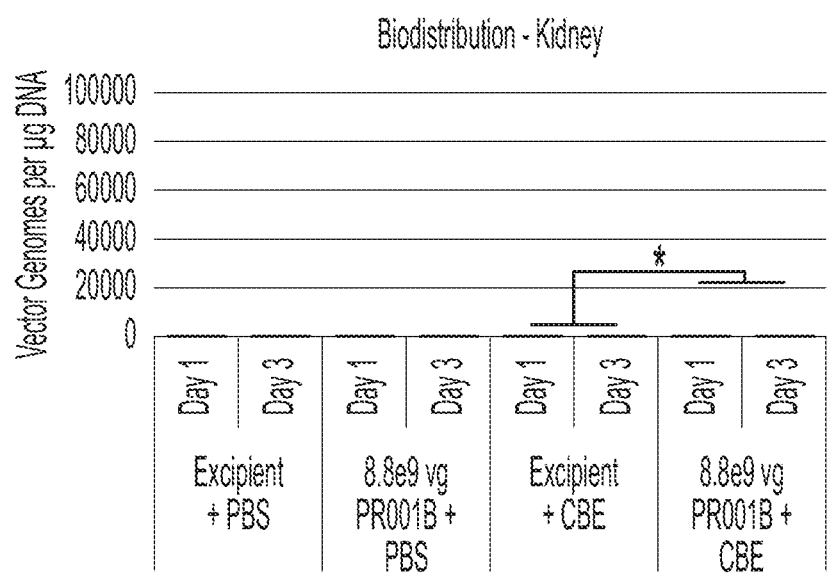

Lipid levels were negatively correlated with both GCase activity and performance on the Rotarod across treatment groups. The increased GCase activity after rAAV-GBA1 administration was associated with substrate reduction and enhanced motor function (FIG. 13). As shown in FIG. 14, preliminary biodistribution was assessed by vector genome presence, as measured by qPCR (with >100 vector genomes per 1 µg genomic DNA defined as positive). Mice that received rAAV-GBA1, both with and without CBE, were positive for rAAV-GBA1 vector genomes in the cortex, indicating that ICV delivery results in rAAV-GBA1 delivery to the cortex. Additionally, vector genomes were detected in the liver, few in spleen, and none in the heart, kidney or gonads. For all measures, there was no statistically significant difference between the Day 1 and Day 3 groups.

A larger study in the CBE model further explored efficacious doses of rAAV-GBA1 in the CBE model. Using the 25 mg/kg CBE dose model, excipient or rAAV-GBA1 was delivered via ICV at P3, and daily IP PBS or CBE treatment initiated at P8. Given the similarity between the groups with and without CBE withdrawal observed in the previous studies, all mice were sacrificed one day after the final CBE dose (P38-40). The effect of three different rAAV-GBA1 doses was assessed, resulting in the following five groups, with 10 mice (5M/5F) per group:

Excipient ICV+PBS IP
Excipient ICV+25 mg/kg CBE IP
3.2e9 vg (2.13e10 vg/g brain) rAAV-GBA1 ICV+25 mg/kg CBE IP
1.0e10 vg (6.67e10 vg/g brain) rAAV-GBA1 ICV+25 mg/kg CBE IP
3.2e10 vg (2.13e11 vg/g brain) rAAV-GBA1 ICV+25 mg/kg CBE IP.

Figure 15:
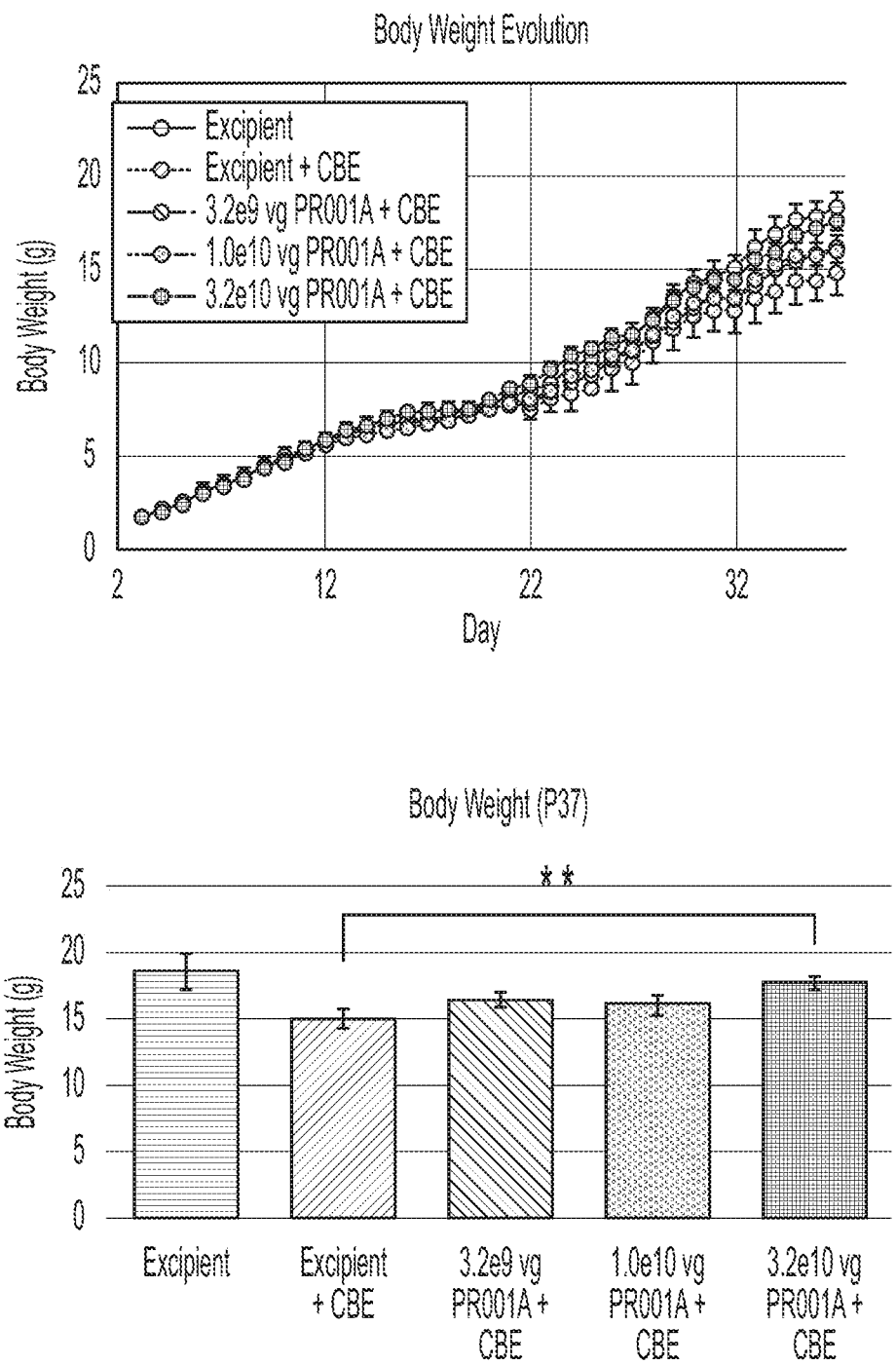
FIG. 15 shows representative data for in-life assessment of rAAV dose ranging in a CBE mouse model. Mice received excipient or one of three different doses of rAAV-GBA1 by ICV delivery at P3: 3.2e9 vg, 1.0e10vg, or 3.2e10 vg. At P8, daily IP treatment of 25 mg/kg CBE was initiated. Mice that received excipient and CBE or excipient and PBS served as controls. All treatment groups started with n=10 (5M/5F) per group. All mice were sacrificed one day after their final CBE dose (P38-P40). All treatment groups were weighed daily, and their weight was analyzed at P36. Motor performance was assessed by latency to fall on Rotarod at P24 and latency to traverse the Tapered Beam at P30. Due to early lethality, the number of mice participating in the behavioral assays was: excipient+PBS n=10, excipient+CBE n=9, and 3.2e9 vg rAAV-GBA1+CBE n=6, 1.0e10 vg rAAV-GBA1+CBE n=10, 3.2e10 vg rAAV-GBA1+CBE n=7. Means are presented. Error bars are SEM; * p<0.05; **p<0.01 for nominal p-values by linear regression in the CBE-treated groups, with gender corrected for as a covariate.
Figure 15:
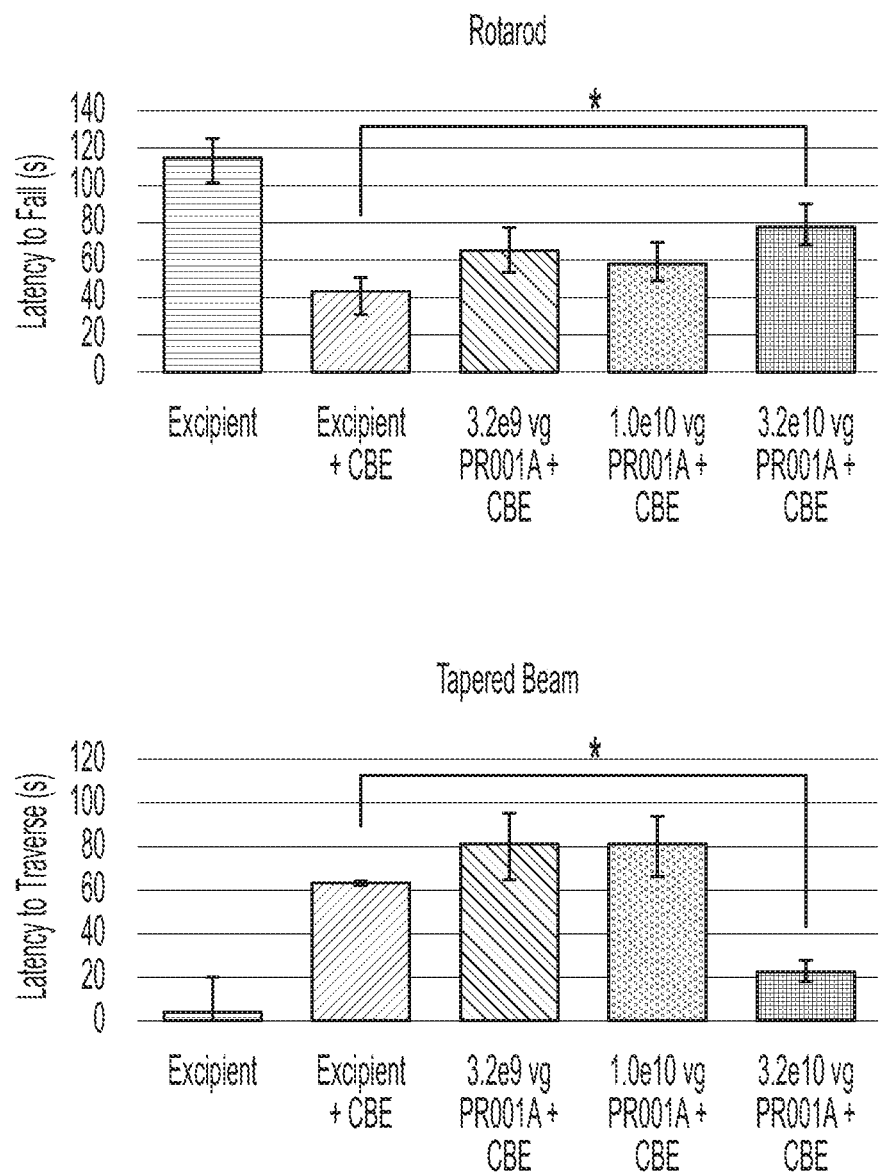

The highest dose of rAAV-GBA1 rescued the CBE treatment-related failure to gain weight at P37. Additionally, this dose resulted in a statistically significant increase in performance on the rotarod and tapered beam compared to the Excipient+CBE treated group (FIG. 15). Lethality was observed in several groups, including both excipient-treated and rAAV-GBA1-treated groups (Excipient+PBS: 0; Excipient+25 mg/kg CBE: 1; 3.2e9 vg rAAV-GBA1+25 mg/kg CBE: 4; 1.0e10 vg rAAV-GBA1+25 mg/kg CBE: 0; 3.2e10 vg rAAV-GBA1+25 mg/kg CBE: 3).

Figure 16:
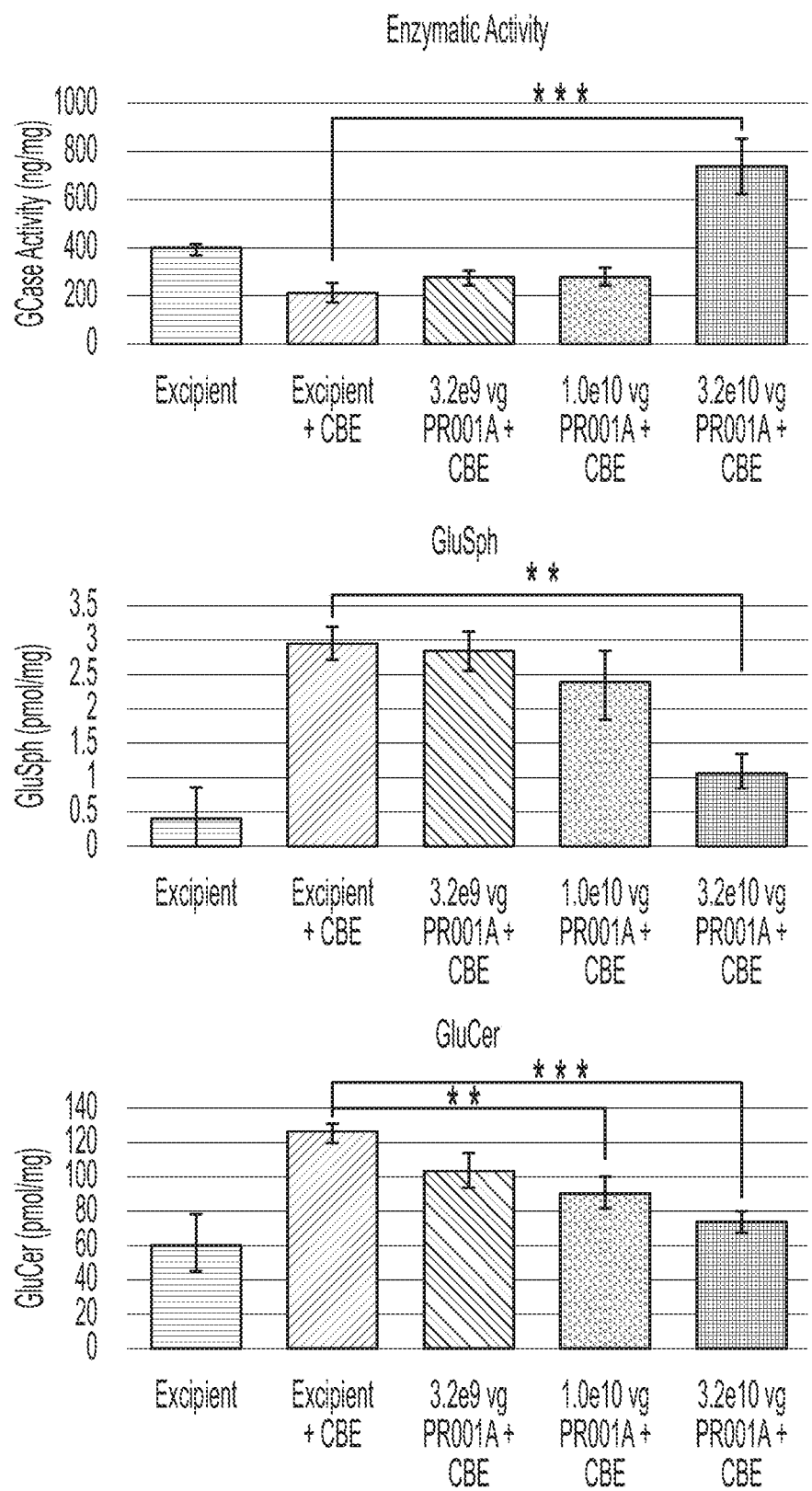
FIG. 16 shows representative data for biochemical assessment of rAAV dose ranging in a CBE mouse model. The cortex of all treatment groups (excipient+PBS n=10, excipient+CBE n=9, and 3.2e9 vg rAAV-GBA1+CBE n=6, 1.0e10 vg rAAV-GBA1+CBE n=10, 3.2e10 vg rAAV-GBA1+CBE n=7) was used to measure GCase activity, GluSph levels, GluCer levels, and vector genomes. GCase activity is shown as ng of GCase per mg of total protein. GluSph and GluCer levels are shown as pmol per mg wet weight of the tissue. Biodistribution is shown as vector genomes per 1 µg of genomic DNA. Vector genome presence was quantified by quantitative PCR using a vector reference standard curve; genomic DNA concentration was evaluated by A260 optical density measurement. Vector genome presence was also measured in the liver (E). Means are presented. Error bars are SEM. p<0.01; *p<0.001 for nominal p-values by linear regression in the CBE-treated groups, with gender corrected for as a covariate.
Figure 16:
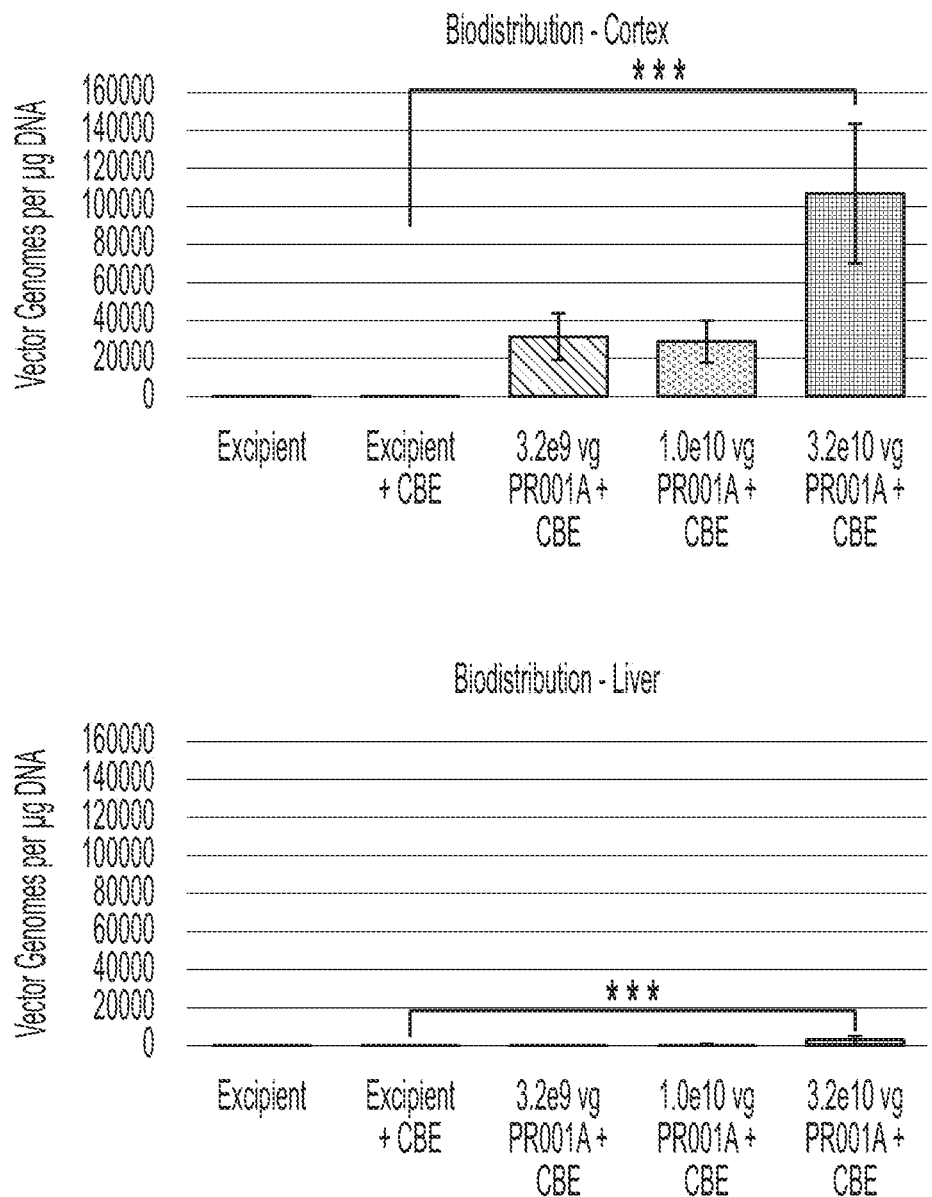

At the completion of the in-life study, mice were sacrificed for biochemical analysis (FIG. 16). GCase activity in the cortex was assessed in biological triplicates by a fluorometric assay. CBE-treated mice showed reduced GCase activity whereas mice that received a high rAAV-GBA1 dose showed a statistically significant increase in GCase activity compared to CBE treatment. CBE-treated mice also had accumulation of GluCer and GluSph, both of which were rescued by administering a high dose of rAAV-GBA1.

Figure 17:
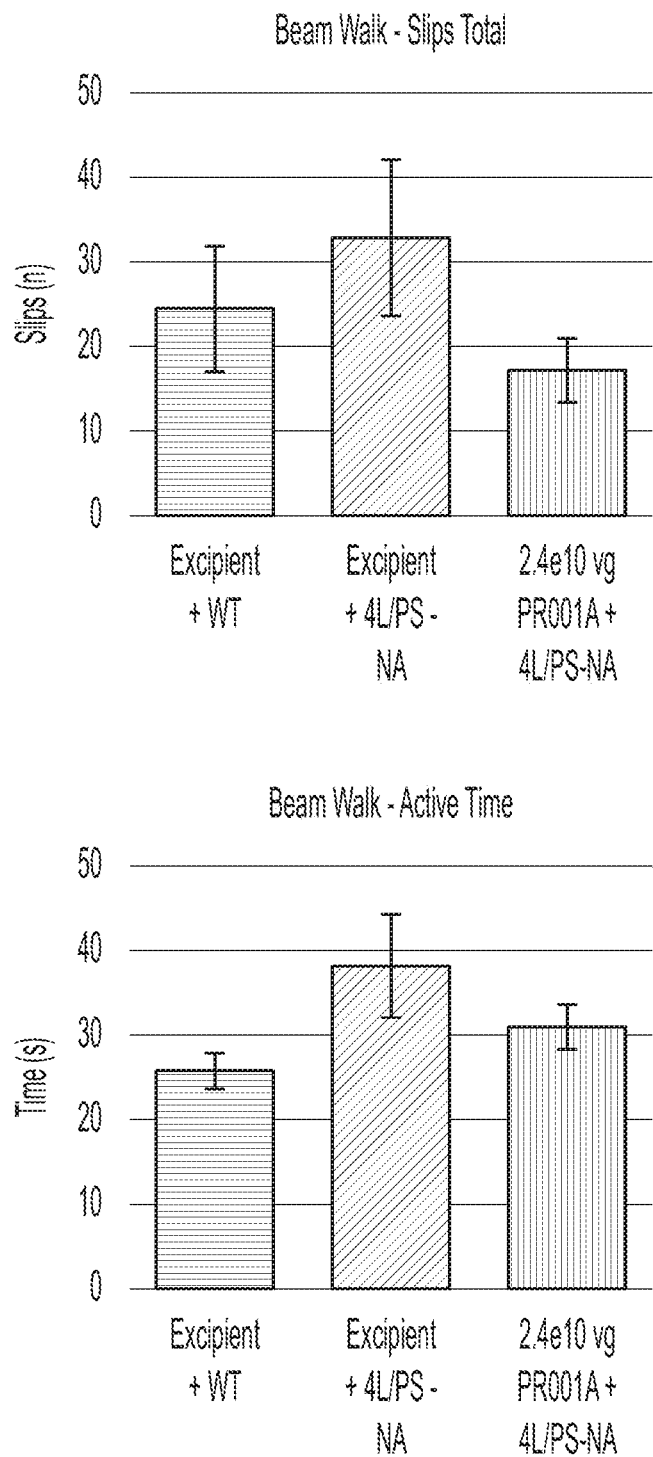
FIG. 17 shows representative data for tapered beam analysis in maximal dose rAAV-GBA1 in a genetic mouse model. Motor performance of the treatment groups (WT+ excipient, n=5), 4L/PS-NA+excipient (n=6), and 4L/PS-NA+rAAV-GBA1 (n=5)) was assayed by Beam Walk 4 weeks post rAAV-GBA1 administration. The total slips and active time are shown as total over 5 trials on different beams. Speed and slips per speed are shown as the average over 5 trials on different beams. Means are presented. Error bars are SEM.
Figure 17:
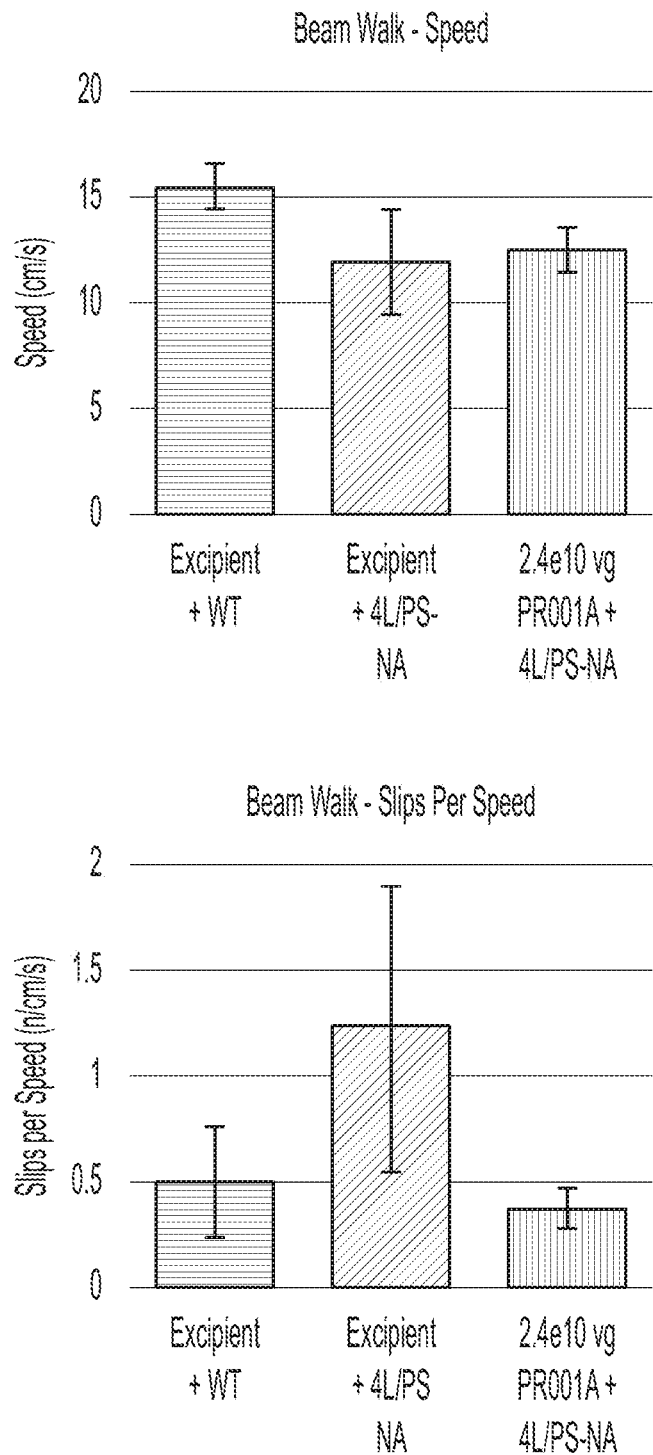

In addition to the established chemical CBE model, rAAV-GBA1 is also evaluated in the 4L/PS-NA genetic model, which is homozygous for the V394L GD mutation in Gba1 and is also partially deficient in saposins, which affect GCase localization and activity. These mice exhibit motor strength, coordination, and balance deficits, as evidenced by their performance in the beam walk, rotarod, and wire hang assays. Typically the lifespan of these mice is less than 22 weeks. In an initial study, 3 µl of maximal titer virus was delivered by ICV at P23, with a final dose of 2.4e10 vg (6.0e10 vg/g brain). With 6 mice per group, the treatment groups were:
  WT+Excipient ICV
  4L/PS-NA+Excipient ICV
  4L/PS-NA+2.4e10 vg (6.0e10 vg/g brain) rAAV-GBA1 ICV Motor performance by the beam walk test was assessed 4 weeks post-rAAV-GBA1 delivery. The group of mutant mice that received rAAV-GBA1 showed a trend towards fewer total slips and fewer slips per speed when compared to mutant mice treated with excipient, restoring motor function to near WT levels (FIG. 17). Since the motor phenotypes become more severe as these mice age, their performance on this and other behavioral tests is assessed at later time points. At the completion of the in-life study, lipid levels, GCase activity, and biodistribution are assessed in these mice.

Additional lower doses of rAAV-GBA1 are currently being tested using the CBE model, corresponding to 0.03×, 0.1×, and 1× the proposed phase 1 high clinical dose. Each group includes 10 mice (5M/5F) per group:

Excipient ICV
  Excipient ICV+25 mg/kg CBE IP
  3.2e8 vg (2.13e9 vg/g brain) rAAV-GBA1 ICV+25 mg/kg CBE IP
  1.0e9 vg (6.67e9 vg/g brain) rAAV-GBA1 ICV+25 mg/kg CBE IP
  1.0e10 vg (6.67e10 vg/g brain) rAAV-GBA1 ICV+25 mg/kg CBE IP.

In addition to motor phenotypes, lipid levels and GCase activity are assessed in the cortex. Time course of treatments and analyses are also performed.

A larger dose ranging study was initiated to evaluate efficacy and safety data. 10 4L/PS-NA mice (5M/5F per group) were injected with 10 µl of rAAV-GBA1. Using an allometric brain weight calculation, the doses correlate to 0.15×, 1.5×, 4.4×, and 14.5× the proposed phase 1 high clinical dose. The injection groups consist of:
  WT+Excipient ICV
  4L/PS-NA+Excipient ICV
  4L/PS-NA+4.3e9 vg (1.1e10 vg/g brain) rAAV-GBA1 ICV
  4L/PS-NA+4.3e10 vg (1.1e11 vg/g/brain) rAAV-GBA1 ICV
  4L/PS-NA+1.3e11 vg (3.2e11 vg/g brain) rAAV-GBA1 ICV
  4L/PS-NA+4.3e11 vg (1.1e12 vg/g brain) rAAV-GBA1 ICV.

A summary of nonclinical studies in the CBE model are shown in Table 3 below.

TABLE 3

Summary of Results in CBE Mouse Model

| Test Material | Study Number | Dose Cohort | Rotarod | Tapered Beam | Open Field | Lipids | Enzyme | BD Brain | BD Liver |
|---|---|---|---|---|---|---|---|---|---|
| rAAV-GBA1 | PRV-2018-005 Dose-ranging rAAV-GBA1 in CBE Model | 3.2e9 vg (2.13e10 vg/g brain) | NS | NS | NS | NS | NS | + | − |
| | | 1.10e10 vg (6.67e10 vg/g brain) | T | NS | NS | T/S | NS | + | + |
| | | 2.3e10vg (2.13e11 vg/g brain) | S | S | NS | S | S | + | + |
| Variant | PRV-2018-005 Dose-ranging Variant in CBE Model | 8.8e9 vg (5.9e10 vg/g brain) | S | N/A | NS | S | S | + | + |

Note that positive biodistribution is defined as >100 vg/1 µg genomic DNA.
Abbreviations: BD = biodistribution; NS = nonsignificant; T = trend; S = significant; N/A = not applicable; + = positive; − = negative.

Example 9

Figure 18:
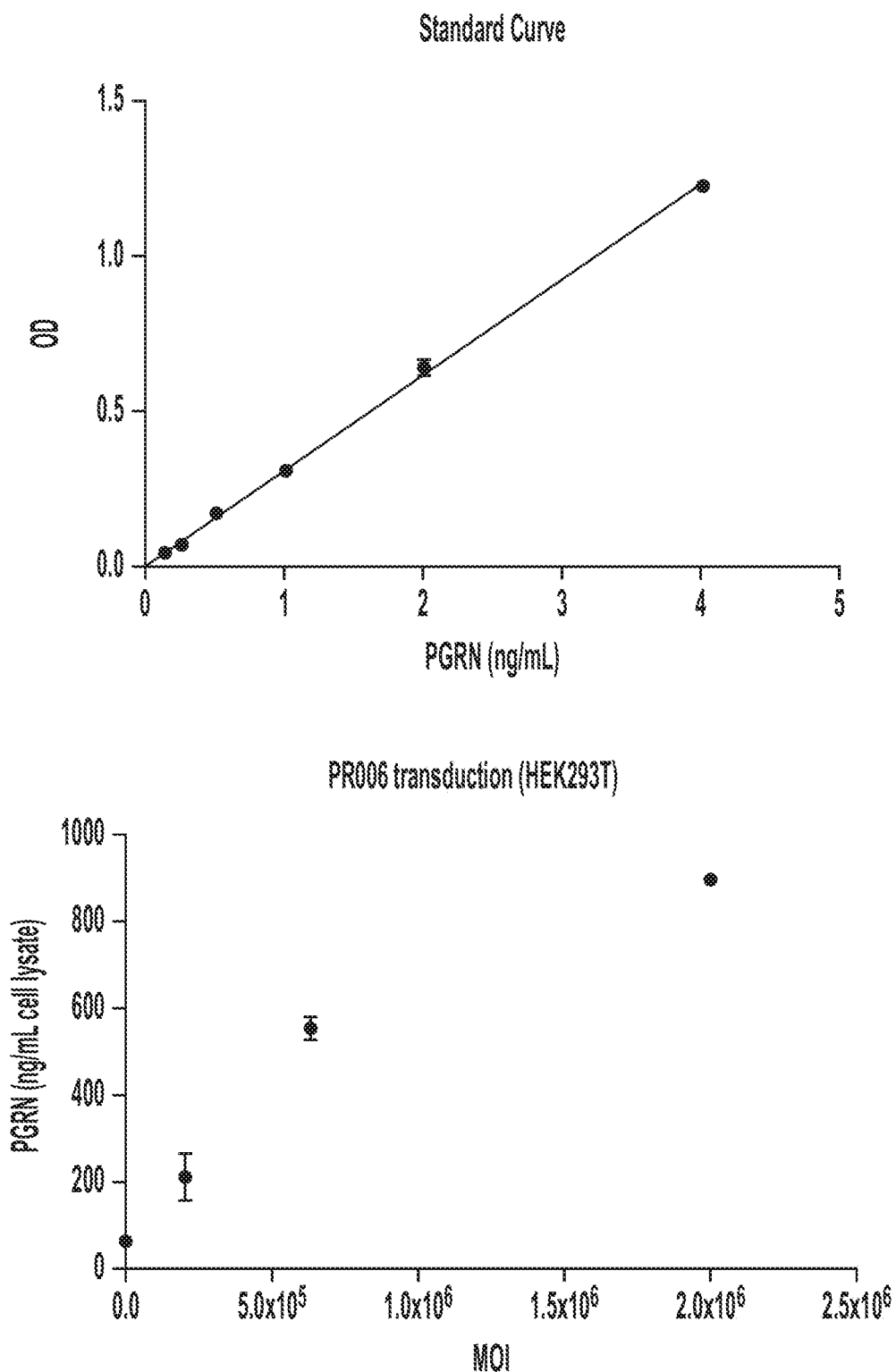
FIG. 18 shows representative data for in vitro expression of rAAV constructs encoding progranulin (PGRN) protein. The left panel shows a standard curve of progranulin (PGRN) ELISA assay. The bottom panel shows a dose-response of PGRN expression measured by ELISA assay in cell lysates of HEK293T cells transduced with rAAV. MOI=multiplicity of infection (vector genomes per cell).

In Vitro Analysis of rAAV Vectors rAAV constructs were tested in vitro and in vivo. FIG. 18 shows representative data for in vitro expression of rAAV constructs encoding progranulin (PGRN) protein. The left panel shows a standard curve of progranulin (PGRN) ELISA assay. The bottom panel shows a dose-response of PGRN expression measured by ELISA assay in cell lysates of HEK293T cells transduced with rAAV. MOI=multiplicity of infection (vector genomes per cell).

Figure 19:
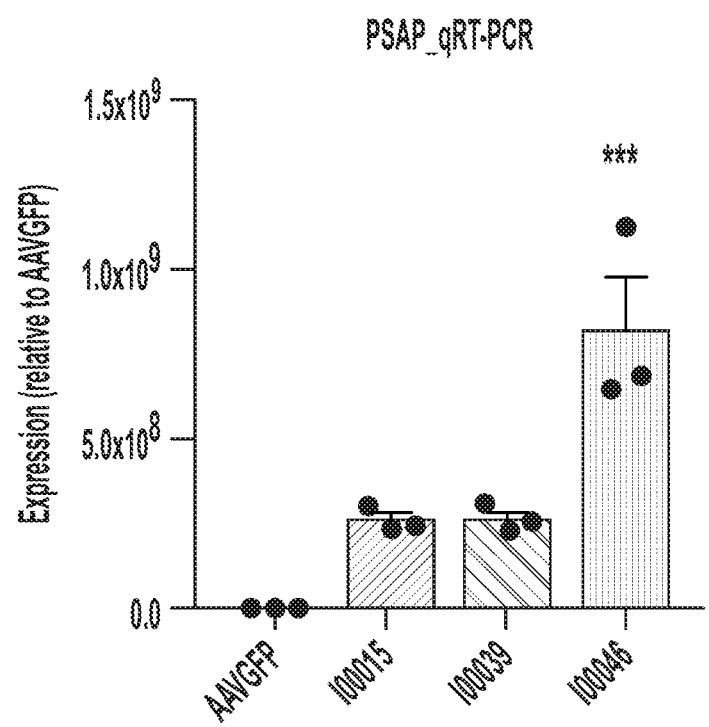
FIG. 19 shows representative data for in vitro expression of rAAV constructs encoding GBA1 in combination with Prosaposin (PSAP), SCARB2, and/or one or more inhibitory nucleic acids. Data indicate transfection of HEK293 cells with each construct resulted in overexpression of the transgenes of interest relative to mock transfected cells.
Figure 19:
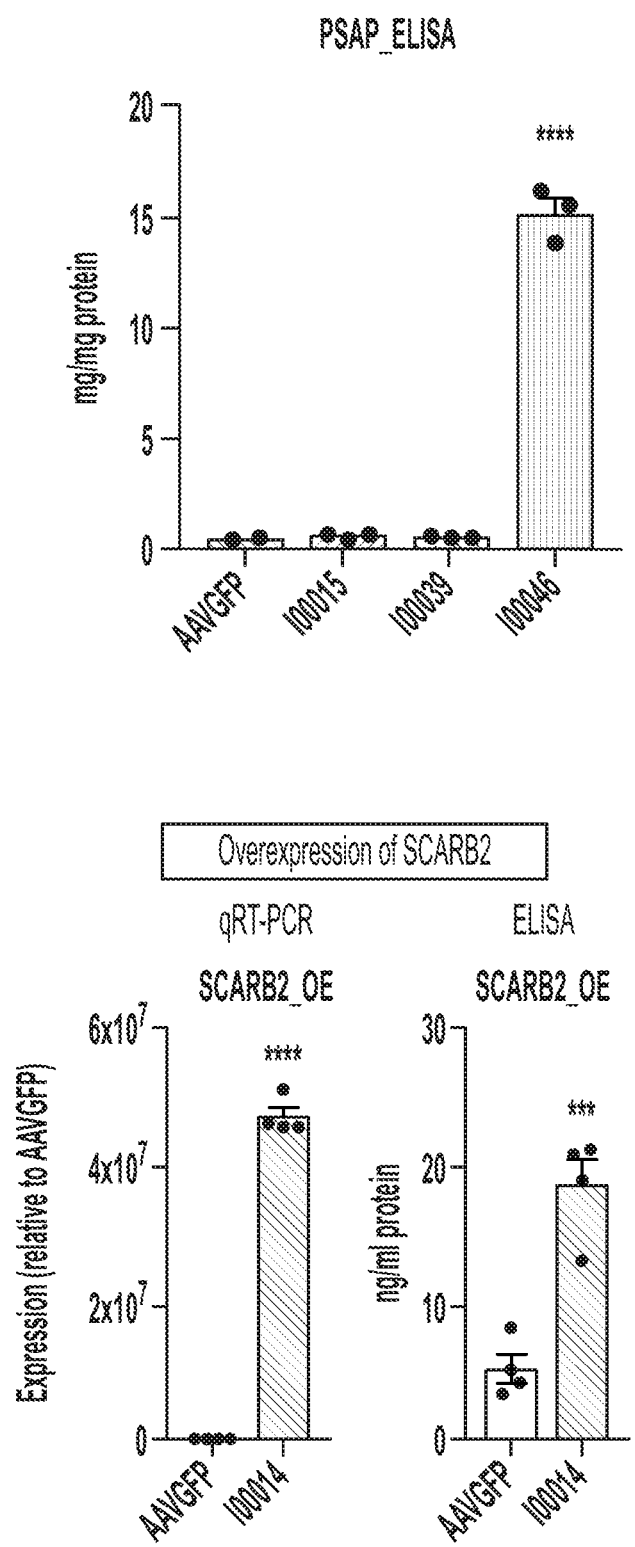
Figure 19:
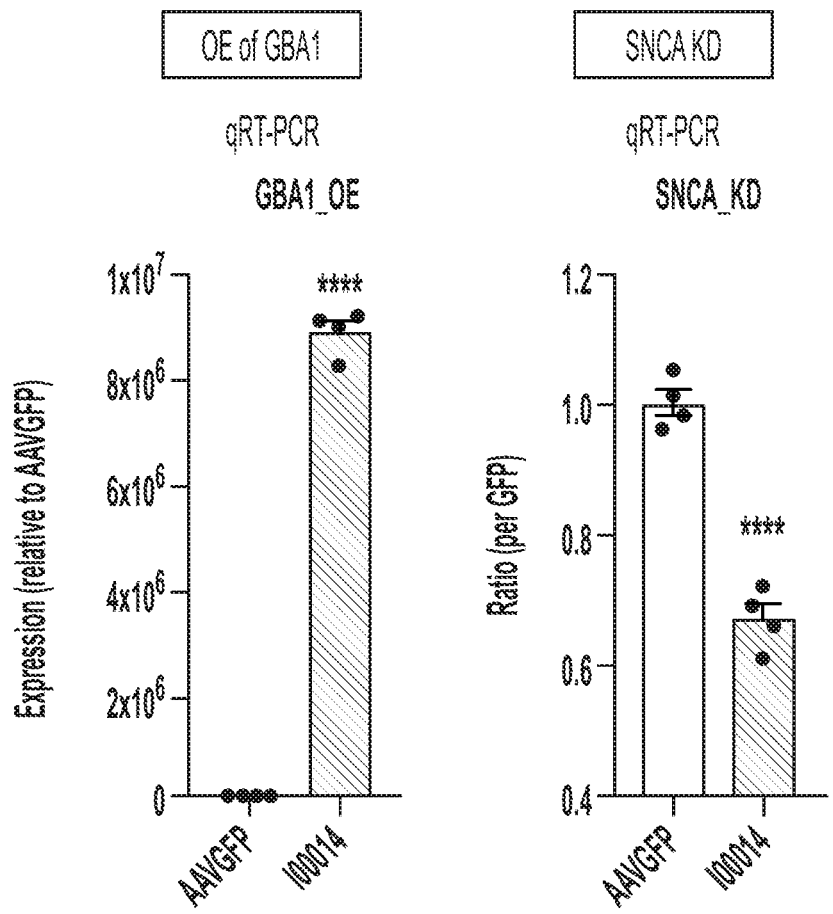

A pilot study was performed to assess in vitro activity of rAAV vectors encoding Prosaposin (PSAP) and SCARB2, alone or in combination with GBA1 and/or one or more inhibitory RNAs. One construct encoding PSAP and progranulin (PGRN) was also tested. Vectors tested include those shown in Table 4. "Opt" refers to a nucleic acid sequence codon optimized for expression in mammalian cells (e.g., human cells). FIG. 19 shows representative data indicating that transfection of HEK293 cells with each of the constructs resulted in overexpression of the corresponding gene product compared to mock transfected cells.

Figure 36A:
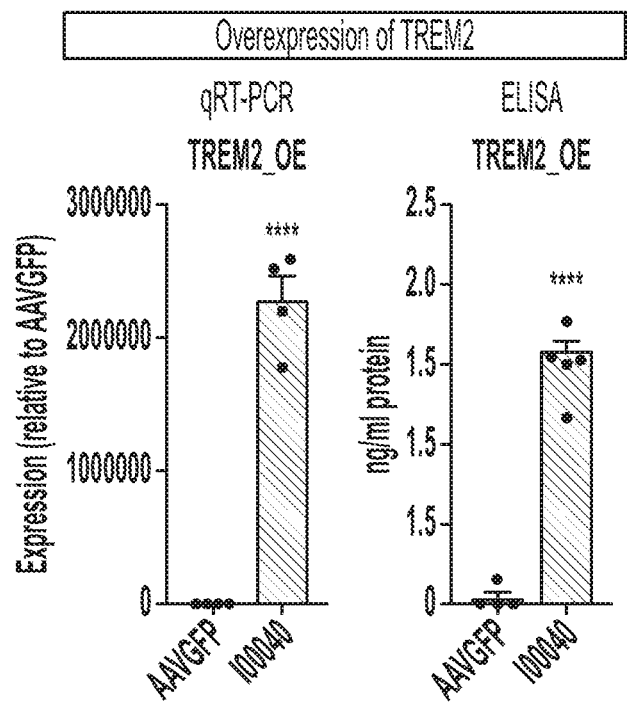
FIGS. 36A-36B show representative data for overexpression of TREM2 and GBA1 in HEK293 cells relative to control transduced cells, as measured by qPCR and ELISA.
Figure 36B:
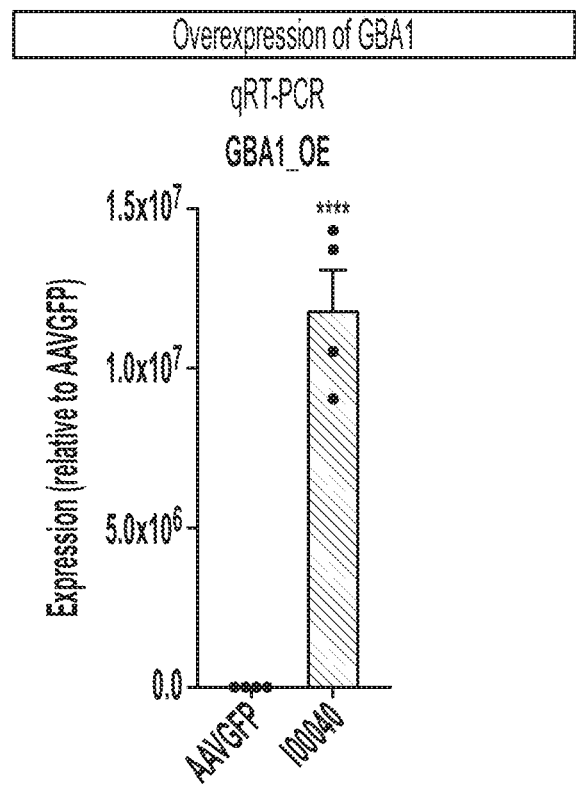

A pilot study was performed to assess in vitro activity of rAAV vectors encoding TREM2, alone or in combination with one or more inhibitory RNAs. Vectors tested include those shown in Table 4. "Opt" refers to a nucleic acid sequence codon optimized for expression in mammalian cells (e.g., human cells). FIGS. 36A-36B show representative data indicating that transfection of HEK293 cells with each of the constructs resulted in overexpression of the corresponding gene product compared to mock transfected cells.

TABLE 4

| ID | Promoter | Inhibitory RNA | Promoter | Transgene |
|---|---|---|---|---|
| I00015 | JL_intronic | SCNA | JetLong | Opt-PSAP_GBA1 |
| I00039 | — | — | JetLong | Opt-PSAP-GRN |
| I00046 | — | — | CBA | Opt-PSAP |
| I00014 | JetLong | SCNA | JetLong | Opt-SCARB2_GBA1 |
| I00040 | | | JL, CD68 | opt-GBA1, TREM2 |

Example 10

Testing of SCNA and TMEM106B shRNA Constructs

HEK293 Cells

Human embryonic kidney 293 cell line (HEK293) were used in this study (#85120602, Sigma-Aldrich). HEK293 cells were maintained in culture media (D-MEM [#11995065, Thermo Fisher Scientific] supplemented with 10% fetal bovine serum [FBS] [#10082147, Thermo Fisher Scientific]) containing 100 units/ml penicillin and 100 µg/ml streptomycin (#15140122, Thermo Fisher Scientific).

Plasmid Transfection

Plasmid transfection was performed using Lipofectamine 2000 transfection reagent (#11668019, Thermo Fisher Scientific) according to the manufacture's instruction. Briefly, HEK293 cells (#12022001, Sigma-Aldrich) were plated at the density of $3\times10^5$ cells/ml in culture media without antibiotics. On the following day, the plasmid and Lipofectamine 2000 reagent were combined in Opti-MEM solution (#31985062, Thermo Fisher Scientific). After 5 minutes, the mixtures were added into the HEK293 culture. After 72 hours, the cells were harvested for RNA or protein extraction, or subjected to the imaging analyses. For imaging analyses, the plates were pre-coated with 0.01% poly-L-Lysine solution (P8920, Sigma-Aldrich) before the plating of cells.

Gene Expression Analysis by Quantitative Real-Time PCR (qRT-PCR)

Relative gene expression levels were determined by quantitative real-time PCR (qRT-PCR) using Power SYBR Green Cells-to-CT Kit (#4402955, Thermo Fisher Scientific) according to the manufacturer's instruction. The candidate plasmids were transiently transfected into HEK293 cells plated on 48-well plates ($7.5\times10^4$ cells/well) using Lipofectamine 2000 transfection reagent (0.5 µg plasmid and 1.5 µl reagent in 50 µl Opti-MEM solution). After 72 hours, RNA was extracted from the cells and used for reverse transcription to synthesize cDNA according to the manufacturer's instruction. For quantitative PCR analysis, 2~5 µl of cDNA products were amplified in duplicates using gene specific primer pairs (250 nM final concentration) with Power SYBR Green PCR Master Mix (#4367659, Thermo Fisher Scientific). The primer sequences for SNCA, TMEM106B, and GAPDH genes were: 5'-AAG AGG GTG TTC TCT ATG TAG GC-3' (SEQ ID NO: 71), 5'-GCT CCT CCA ACA TTT GTC ACT T-3' (SEQ ID NO: 72) for SNCA, 5'-ACA CAG TAC CTA CCG TTA TAG CA-3' (SEQ ID NO: 73), 5'-TGT TGT CAC AGT AAC TTG CAT CA-3' (SEQ ID NO: 74) for TMEM106B, and 5'-CTG GGC TAC ACT GAG CAC C-3' (SEQ ID NO: 75), 5'-AAG TGG TCG TTG AGG GCA ATG-3' (SEQ ID NO: 76) for GAPDH. Quantitative PCR was performed in a QuantStudio 3 Real-Time PCR system (Thermo Fisher Scientific). Expression levels were normalized by the housekeeping gene GAPDH and calculated using the comparative CT method.

Fluorescence Imaging Analysis

EGFP reporter plasmids, which contain 3'-UTR of human SNCA gene at downstream of EGFP coding region, were used for the validation of SNCA and TMEM106B knockdown plasmids. EGFP reporter plasmids and candidate knockdown plasmids were simultaneously transfected into HEK293 cells plated on poly-L-Lysine coated 96-well plates ($3.0\times10^4$ cells/well) using Lipofectamine 2000 transfection reagent (0.04 µg reporter plasmid, 0.06 µg knockdown plasmid and 0.3 µl reagent in 10 µl Opti-MEM solution). After 72 hours, the fluorescent intensities of EGFP signal were measured at excitation 488 nm/emission 512 nm using Varioskan LUX multimode reader (Thermo Fisher Scientific). Cells were fixed with 4% PFA at RT for 10 minutes, and incubated with D-PBS containing 40 µg/ml 7-aminoactinomycin D (7-AAD) for 30 min at RT. After washing with D-PBS, the fluorescent intensities of 7-AAD signal were measured at excitation 546 nm/emission 647 nm using Varioskan reader to quantify cell number. Normalized EGFP signal per 7-AAD signal levels were compared with the control knockdown samples.

Enzyme-Linked Immunosorbent Assay (ELISA)

α-Synuclein reporter plasmids, which contain 3'-UTR of human SNCA gene or TMEM106B gene downstream of SNCA coding region, were used for the validation of knockdown plasmids at the protein level. Levels of α-synuclein protein were determined by ELISA (#KHB0061, Thermo Fisher Scientific) using the lysates extracted from HEK293 cells. The candidate plasmids were transiently transfected into HEK293 cells plated on 48-well plates ($7.5\times10^4$ cells/well) using Lipofectamine 2000 transfection reagent (0.1 µg reporter plasmid, 0.15 µg knockdown plasmid and 0.75 µl reagent in 25 µl Opti-MEM solution). After 72 hours, cells were lysed in radioimmunoprecipitation assay (RIPA) buffer (#89900, Thermo Fisher Scientific) supplemented with protease inhibitor cocktail (#P8340, Sigma-Aldrich), and sonicated for a few seconds. After incubation on ice for 30 min, the lysates were centrifuged at 20,000×g at 4° C. for 15 min, and the supernatant was collected. Protein levels were quantified. Plates were read in a Varioskan plate reader at 450 nm, and concentrations were calculated using SoftMax Pro 5 software. Measured protein concentrations were normalized to total protein concentration determined with a bicinchoninic acid assay (#23225, Thermo Fisher Scientific).

Figure 37:
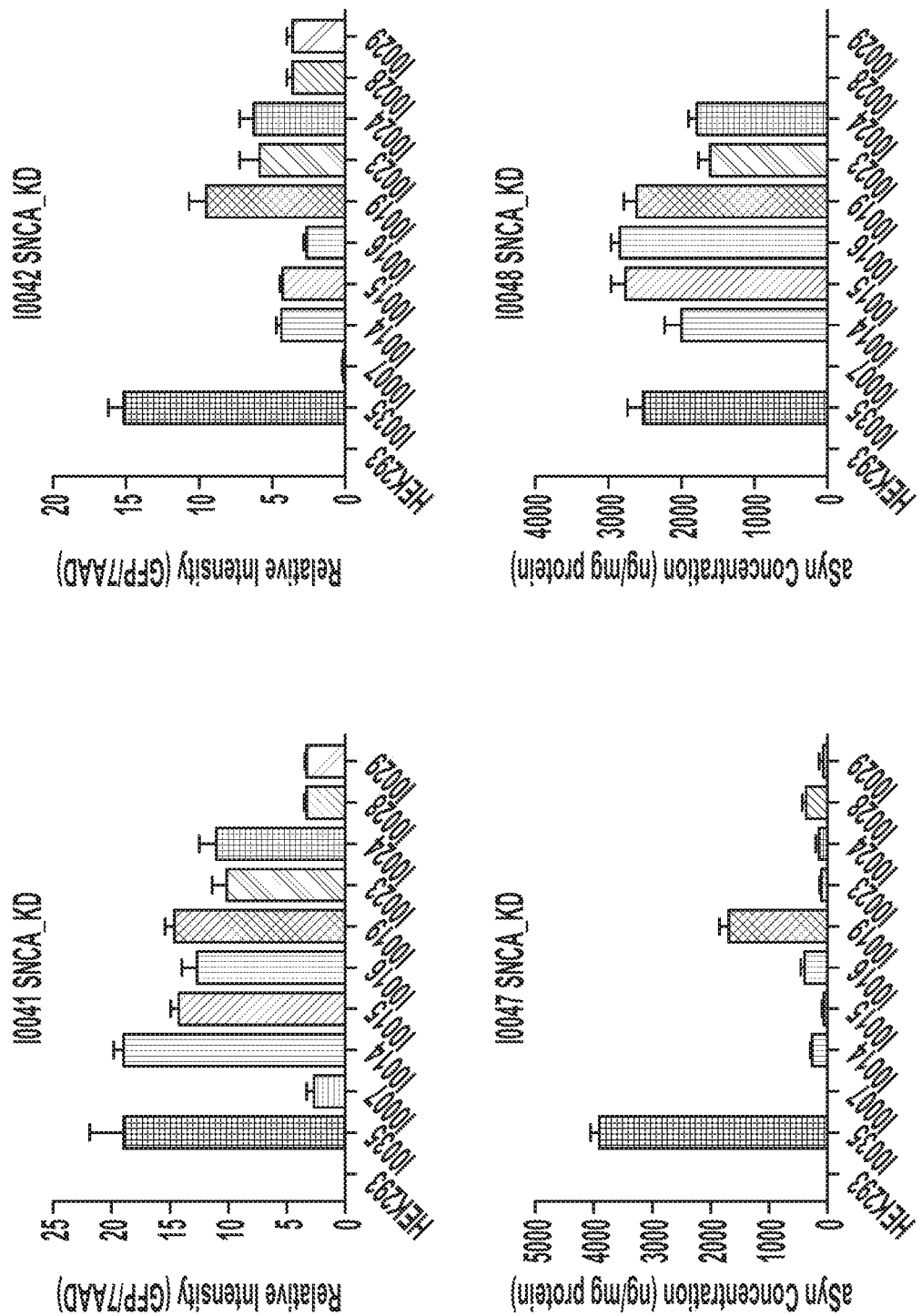
FIG. 37 shows representative data indicating successful silencing of SCNA in vitro by GFP reporter assay (top) and α-Syn assay (bottom).
Figure 38:
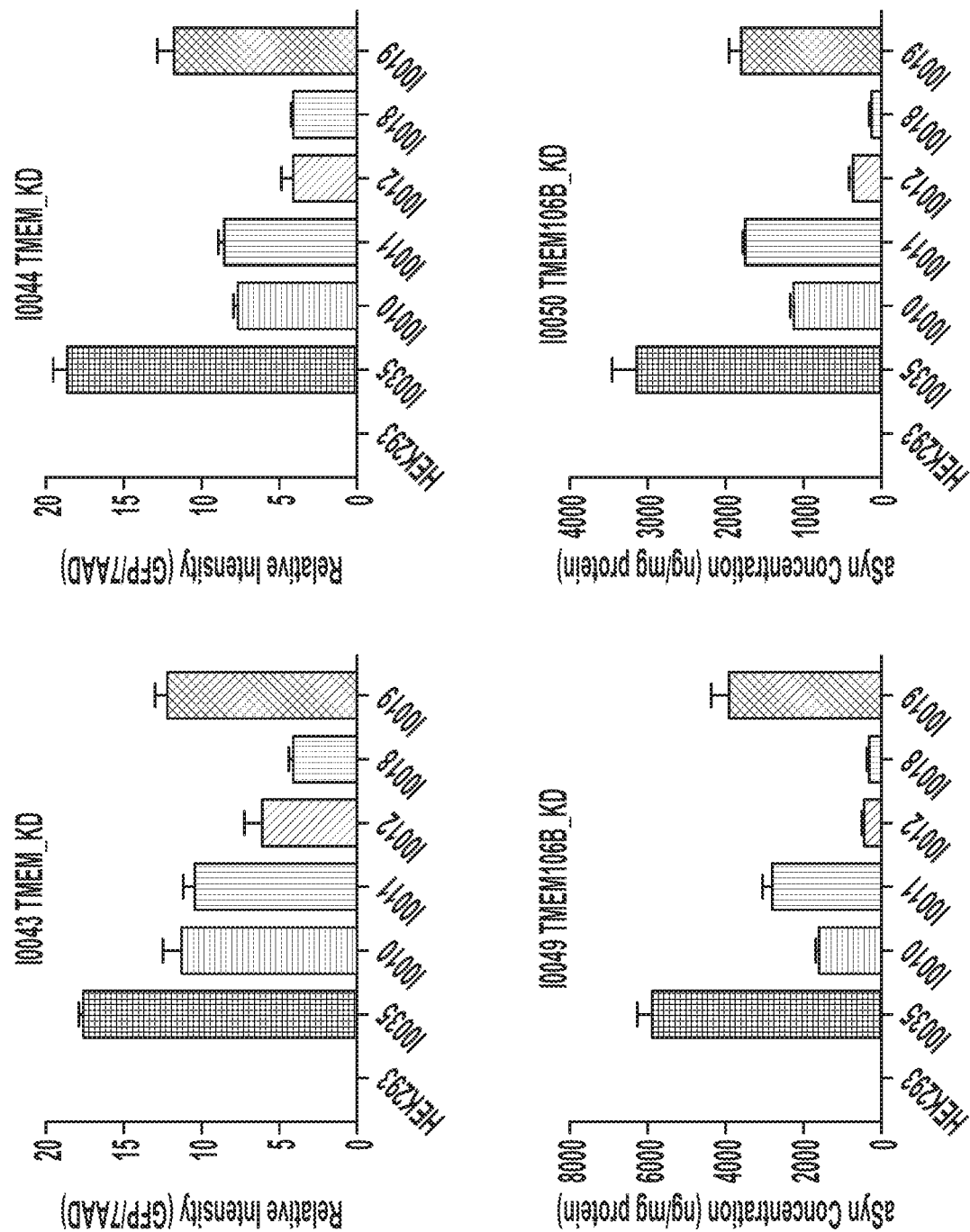
FIG. 38 shows representative data indicating successful silencing of TMEM106B in vitro by GFP reporter assay (top) and α-Syn assay (bottom).

FIG. 37 and Table 5 show representative data indicating successful silencing of SCNA in vitro by GFP reporter assay (top) and α-Syn assay (bottom). FIG. 38 and Table 6 show representative data indicating successful silencing of TMEM106B in vitro by GFP reporter assay (top) and α-Syn assay (bottom).

TABLE 5

| ID | Promoter | Knockdown | Promoter | Overexpress |
|---|---|---|---|---|
| I00007 | CMV_intronic | SNCA_mi | CMV | opt-GBA1 |
| I00008 | H1 | SNCA_sh | CMV | opt-GBA1 |
| I00009 | H1 | SNCA_Pubsh4 | CMV | opt-GBA1 |
| I00014 | JL_intronic | SNCA_mi | JetLong | opt-SCARB2_GBA |
| I00015 | JL_intronic | SNCA_mi | JetLong | opt-PSAP_GBA |
| I00016 | JL_intronic | SNCA_mi | JetLong | opt-CTSB_GBA |
| I00019 | JL_intronic | SNCA_TMEM_mi | JetLong | opt-VPS35 |
| I00023 | JL_intronic | SNCA_mi | JetLong | opt-GBA1_IL34 |
| I00024 | JL_intronic | SNCA_mi | JetLong | opt-GBA2 |
| I00028 | intronic | SNCA_Broadsh | CMV | opt-GBA1 |
| I00029 | intronic | SNCA_Pubsh4 | CMV | opt-GBA1 |

TABLE 6

| ID | Promoter | Knockdown | Promoter | Overexpress |
|---|---|---|---|---|
| I00010 | H1 | TMEM_Pubsh | CMV | opt-GRN |
| I00011 | JL_intronic | TMEM_mi | JetLong | opt-GBA1_GRN |
| I00012 | H1 | TMEM_sh | CMV | opt-GRN |
| I00019 | JL_intronic | SNCA_TMEM_mi | JetLong | opt-VPS35 |

Example 11

ITR "D" Sequence Placement and Cell Transduction

Figure 40:
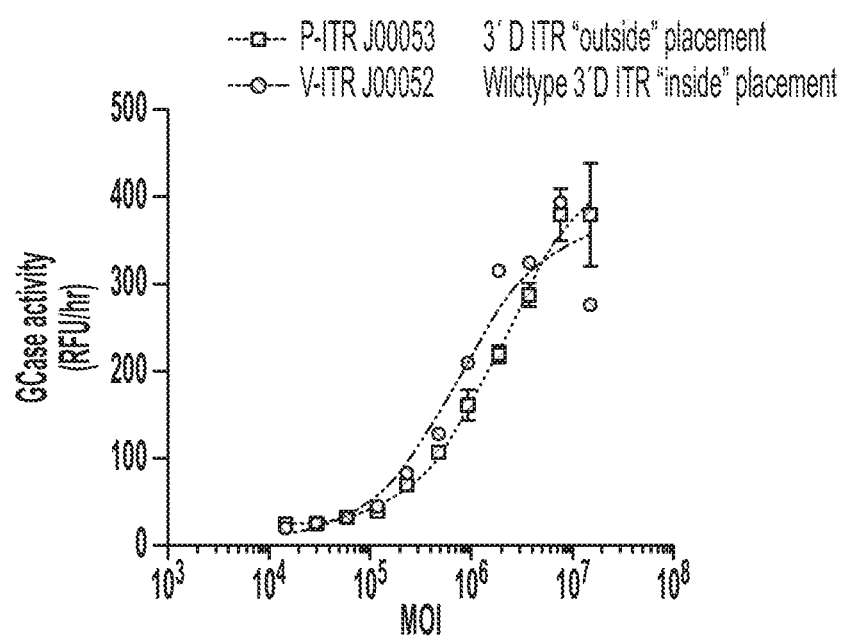
FIG. 40 shows data for transduction of HEK293 cells using rAAVs having ITRs with wild-type (circles) or alternative (e.g., "outside"; squares) placement of the "D" sequence. The rAAVs having ITRs placed on the "outside" were able to transduce cells as efficiently as rAAVs having wild-type ITRs.

The effect of placement of ITR "D" sequence on cell transduction of rAAV vectors was investigated. HEK293 cells were transduced with Gcase-encoding rAAVs having 1) wild-type ITRs (e.g., "D" sequences proximal to the transgene insert and distal to the terminus of the ITR) or 2) ITRs with the "D" sequence located on the "outside" of the vector (e.g., "D" sequence located proximal to the terminus of the ITR and distal to the transgene insert), as shown in FIG. 20. Surprisingly, data indicate that rAAVs having the "D" sequence located in the "outside" position retain the ability to be packaged and transduce cells efficiently (FIG. 40).

Example 12

In Vitro Testing of Progranulin rAAVs

Figure 39:
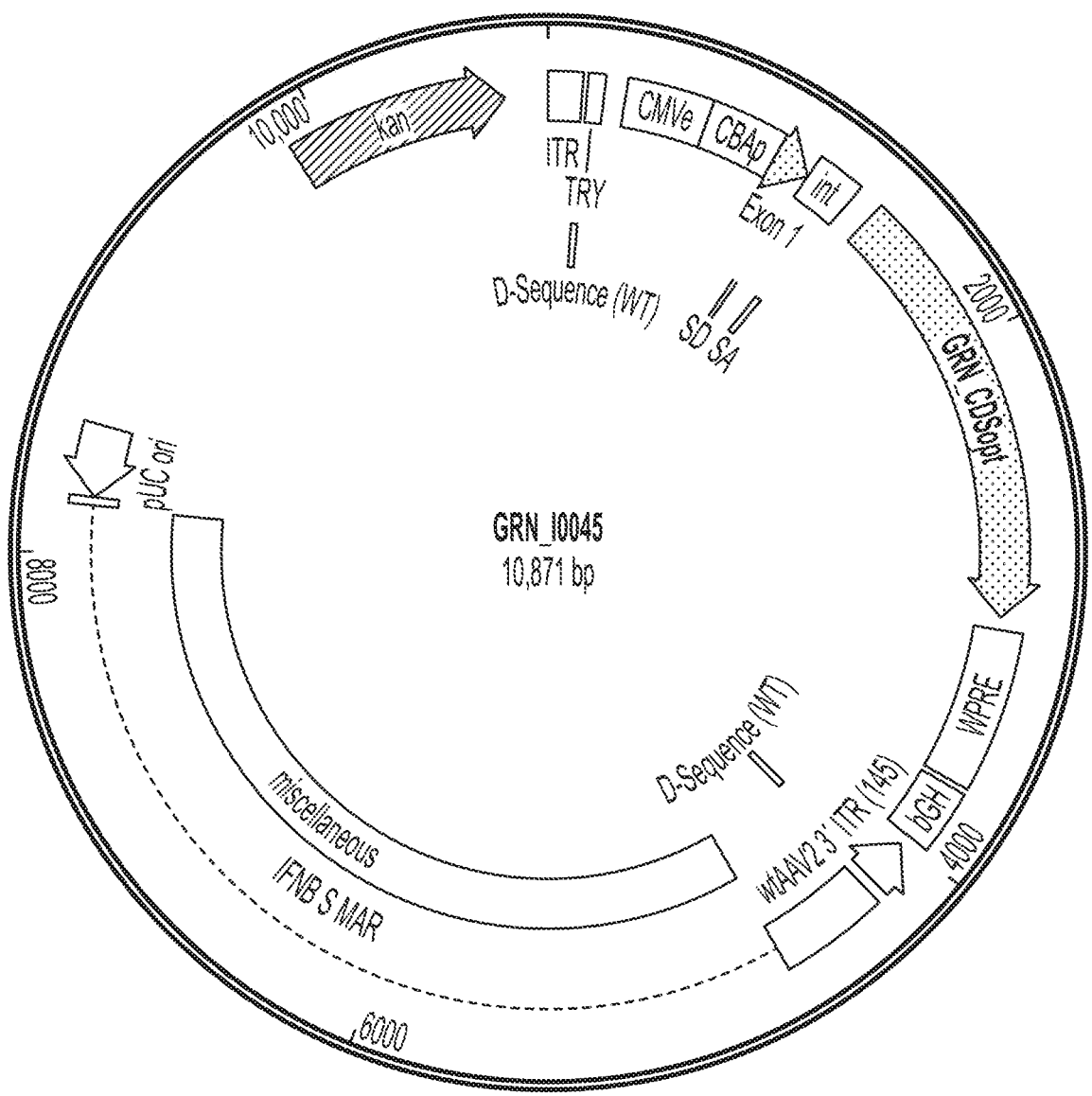
FIG. 39 is a schematic depicting one embodiments of a vector comprising an expression construct encoding PGRN.

FIG. 39 is a schematic depicting one embodiments of a vector comprising an expression construct encoding PGRN. Progranulin is overexpressed in the CNS of rodents deficient in GRN, either heterozygous or homozygous for GRN deletion, by injection of an rAAV vector encoding PGRN (e.g., codon-optimized PGRN), either by intraparenchymal or intrathecal injection such as into the cisterna magna.

Mice are injected at 2 months or 6 months of age, and aged to 6 months or 12 months and analyzed for one or more of the following: expression level of GRN at the RNA and protein levels, behavioral assays (e.g., improved movement), survival assays (e.g., improved survival), microglia and inflammatory markers, gliosis, neuronal loss, Lipofuscinosis, and/or Lysosomal marker accumulation rescue, such as LAMP1. Assays on PGRN-deficient mice are described, for example by Arrant et al. (2017) Brain 140: 1477-1465; Arrant et al. (2018) J. Neuroscience 38(9):2341-2358; and Amado et al. (2018) doi:https://doi.org/10.1101/30869; the entire contents of which are incorporated herein by reference.

EQUIVALENTS

This Application incorporates by reference the contents of the following documents in their entirety: International PCT Application No. PCT/US2018/054225, filed Oct. 3, 2018; International PCT Application No. PCT/US2018/054223, filed Oct. 3, 2018; Provisional Application Ser. Nos. 62/567,296, filed Oct. 3, 2017, entitled "GENE THERAPIES FOR LYSOSOMAL DISORDERS"; 62/567,311, filed Oct. 3, 2017, entitled "GENE THERAPIES FOR LYSOSOMAL DISORDERS"; 62/567,319, filed Oct. 3, 2017, entitled "GENE THERAPIES FOR LYSOSOMAL DISORDERS"; 62/567,301, filed Oct. 3, 2017, entitled "GENE THERAPIES FOR LYSOSOMAL DISORDERS"; 62/567,310, filed Oct. 3, 2017, entitled "GENE THERAPIES FOR LYSOSOMAL DISORDERS"; 62/567,303, filed Oct. 3, 2017, entitled "GENE THERAPIES FOR LYSOSOMAL DISORDERS"; and 62/567,305, filed Oct. 3, 2017, entitled "GENE THERAPIES FOR LYSOSOMAL DISORDERS".

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

SEQUENCES

In some embodiments, an expression cassette encoding one or more gene products (e.g., a first, second and/or third gene product) comprises or consists of (or encodes a peptide having) a sequence set forth in any one of SEQ ID NOs: 1-78. In some embodiments, a gene product is encoded by a portion (e.g., fragment) of any one of SEQ ID NOs: 1-78.

What is claimed is:

1. A Baculovirus vector comprising a nucleic acid comprising an expression construct comprising a promoter operably linked to a transgene insert encoding a Progranulin (PGRN) protein, wherein the transgene insert comprises the nucleotide sequence of SEQ ID NO: 68.

2. The Baculovirus vector of claim 1, wherein the promoter is a chicken beta actin (CBA) promoter.

3. The Baculovirus vector of claim 1, further comprising a cytomegalovirus (CMV) enhancer.

4. The Baculovirus vector of claim 1, further comprising a Woodchuck Hepatitis Virus Posttranscriptional Regulatory Element (WPRE).

5. The Baculovirus vector of claim 1, further comprising a Bovine Growth Hormone polyA signal tail.

6. The Baculovirus vector of claim 1, wherein the nucleic acid comprises two adeno-associated virus inverted terminal repeats (ITR) sequences flanking the expression construct.

7. The Baculovirus vector of claim 6, wherein each ITR sequence is a wild-type AAV2 ITR sequence.

8. The Baculovirus vector of claim 6, wherein each ITR sequence comprises a "D" region (SEQ ID NO: 27) that is proximal to the expression construct.

9. The Baculovirus vector of claim 6, wherein at least one of the ITR sequences comprises a "D" region (SEQ ID NO: 27) positioned on the outside of the ITR sequence relative to the expression construct.

10. The Baculovirus vector of claim 6, wherein the ITR sequence positioned 5' relative to the expression construct comprises a "D" region (SEQ ID NO: 27) that is proximal to the expression construct, and the ITR sequence positioned 3' relative to the expression construct comprises a "D" region (SEQ ID NO: 27) positioned on the outside of the ITR sequence relative to the expression construct.

11. The Baculovirus vector of claim 10, wherein the nucleic acid sequence of the 5' ITR is nucleotides 1-145 of SEQ ID NO: 1 and the nucleic acid sequence of the 3' ITR is nucleic nucleotides 3867-4011 of SEQ ID NO: 1.

12. The Baculovirus vector of claim 10, further comprising a region between the 5' ITR and the expression construct, wherein the region has the sequence set forth in SEQ ID NO: 28.

13. The Baculovirus vector of claim 1, wherein the Baculovirus vector is an *Autographa californica* nuclear polyhedrosis (AcNPV) vector.

14. A Baculovirus vector comprising a nucleic acid comprising, in 5' to 3' order:
(a) a first ITR;
(b) a CMV enhancer;
(c) a CBA promoter;
(d) a transgene insert encoding a PGRN protein, wherein the transgene insert comprises the nucleotide sequence of SEQ ID NO: 68;
(e) a WPRE;
(f) a Bovine Growth Hormone polyA signal tail; and
(g) a second ITR.

* * * * *

SEQUENCE LISTING

```
<160> NUMBER OF SEQ ID NOS: 78

<210> SEQ ID NO 1
<211> LENGTH: 10697
<212> TYPE: DNA
<213> ORGANISM: Artificial sequence
<220> FEATURE:
<223> OTHER INFORMATION: Synthetic polynucleotide

<400> SEQUENCE: 1
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctgctag ctctgggtat ttaagcccga gtgagcacgc     180
```

```
agggtctcca tttgaagcg ggaggttacg cgttcgtcga ctactagtgg gtaccagagc      240
tccctaggtt ctagaaccgg tgacgtctcc catggtgaag cttggatctg aattcggtac    300
cctagttatt aatagtaatc aattacgggg tcattagttc atagcccata tatggagttc    360
cgcgttacat aacttacggt aaatggcccg cctggctgac cgcccaacga cccccgccca    420
ttgacgtcaa taatgacgta tgttcccata gtaacgccaa tagggacttt ccattgacgt    480
caatgggtgg actatttacg gtaaactgcc cacttggcag tacatcaagt gtatcatatg    540
ccaagtacgc cccctattga cgtcaatgac ggtaaatggc ccgcctggca ttatgcccag    600
tacatgacct tatgggactt tcctacttgg cagtacatct acgtattagt catcgctatt    660
accatggtcg aggtgagccc cacgttctgc ttcactctcc ccatctcccc ccctcccca    720 cccccaattt tgtatttatt tattttttaa ttattttgtg cagcgatggg ggcggggggg    780 ggggggggc gcgcgccagg cggggcgggg cgggcgagg ggcggggcgg ggcgaggcgg     840
agaggtgcgg cggcagccaa tcagagcggc gcgctccgaa agtttccttt tatggcgagg    900 cggcggcgg ggcggcccta taaaagcga agcgcgcggc gggcgggagt cgctgcgacg     960
ctgccttcgc cccgtgcccc gctccgccgc cgcctcgcgc cgcccgcccc ggctctgact   1020
gaccgcgtta ctcccacagg tgagcgggcg ggacggcct tctcctccgg gctgtaatta   1080
gcgcttggtt taatgacggc ttgttttctg tggctgcgtg aaagccttga ggggctccgg   1140
gagctagagc ctctgctaac catgttcatg ccttcttctt tttcctacag ctcctgggca   1200
acgtgctggt tattgtgctg tctcatcatt ttggcaaaga attcctcgaa gatccgaagg   1260
gaaagtcttc cacgactgtg ggatccgttc gaagatatca ccggttgagc caccatggaa   1320
ttcagcagcc ccagcagaga ggaatgcccc aagcctctga gccgggtgtc aatcatggcc   1380
ggatctctga caggactgct gctgcttcag gccgtgtctt gggcttctgg cgctagacct   1440
tgcatcccca agagcttcgg ctacagcagc gtcgtgtgcg tgtgcaatgc cacctactgc   1500
gacagcttcg accctcctac ctttcctgct ctgggcacct tcagcagata cgagagcacc   1560
agatccggca gacggatgga actgagcatg ggacccatcc aggccaatca cacaggcact   1620
ggcctgctgc tgacactgca gcctgagcag aaattccaga agtgaaagg cttcggcgga   1680 gccatgacag atgccgccgc tctgaatatc ctggctctgt ctccaccagc tcagaacctg   1740
ctgctcaaga gctacttcag cgaggaaggc atcggctaca acatcatcag agtgcccatg   1800
gccagctgcg acttcagcat caggacctac acctacgccg acacacccga cgatttccag   1860
ctgcacaact tcagcctgcc tgaagaggac accaagctga agatccctct gatccacaga   1920
gccctgcagc tggcacaaag acccgtgtca ctgctggcct ctccatggac atctcccacc   1980
tggctgaaaa caaatggcgc cgtgaatggc aagggcagcc tgaaaggcca acctggcgac   2040
atctaccacc agacctgggc cagatacttc gtgaagttcc tggacgccta tgccgagcac   2100
aagctgcagt ttgggccgt gacagccgag aacgaacctt ctgctggact gctgagcggc    2160
tacccctttc agtgcctggg ctttacaccc gagcaccagc gggactttat cgcccgtgat   2220
ctgggaccca cactggccaa tagcacccac cataatgtgc ggctgctgat gctggacgac   2280
cagagactgc ttctgcccca ctgggctaaa gtggtgctga cagatcctga ggccgccaaa   2340
tacgtgcacg gaatcgccgt gcactggtat ctggactttc tggcccctgc caaggccaca   2400
ctggagagaa cacacagact gttccccaac accatgctgt cgccagcga agcctgtgtg    2460 ggcagcaagt tttgggaaca gagcgtgcgg ctcggcagct gggatagagg catgcagtac   2520
agccacagca tcatcaccaa cctgctgtac cacgtcgtcg gctggaccga ctggaatctg   2580
```

```
gccctgaatc ctgaaggcgg ccctaactgg gtccgaaact tcgtggacag ccccatcatc   2640
gtggacatca ccaaggacac cttctacaag cagcccatgt tctaccacct gggacacttc   2700
agcaagttca tccccgaggg ctctcagcgc gttggactgg tggcttccca gaagaacgat   2760
ctggacgccg tggctctgat gcaccctgat ggatctgctg tggtggtggt cctgaaccgc   2820
agcagcaaag atgtgcccct gaccatcaag gatcccgccg tgggattcct ggaaacaatc   2880
agccctggct actccatcca cacctacctg tggcgtagac agtgacaatt gttaattaag   2940
tttaacccct cgaggccgca agcttatcga taatcaacct ctggattaca aaatttgtga   3000
aagattgact ggtattctta actatgttgc tccttttacg ctatgtggat acgctgcttt   3060
aatgcctttg tatcatgcta ttgcttcccg tatggctttc attttctcct ccttgtataa   3120
atcctggttg ctgtctcttt atgaggagtt gtggcccgtt gtcaggcaac gtggcgtggt   3180
gtgcactgtg tttgctgacg caaccccccac tggttggggc attgccacca cctgtcagct   3240
cctttccggg actttcgctt tccccctccc tattgccacg cggaactcca tcgccgcctg   3300
ccttgcccgc tgctggacag gggctcggct gttgggcact gacaattccg tggtgttgtc   3360
ggggaaatca tcgtccttc cttggctgct cgcctgtgtt gccacctgga ttctgcgcgg   3420
gacgtccttc tgctacgtcc cttcggccct caatccagcg gaccttcctt cccgcggcct   3480
gctgccggct ctgcggcctc ttccgcgtct tcgccttcgc cctcagacga gtcggatctc   3540
cctttgggcc gcctcccgc atcgataccg tcgactagag ctcgctgatc agcctcgact   3600
gtgccttcta gttgccagcc atctgttgtt gcccctccc ccgtgccttc cttgaccctg   3660
gaaggtgcca ctcccactgt cctttcctaa taaaatgagg aaattgcatc gcattgtctg   3720
agtaggtgtc attctattct ggggggtggg gtggggcagg acagcaaggg ggaggattgg   3780
gaagacaata gcaggcatgc tggggagaga tccacgataa caaacagctt ttttggggtg   3840
aacatattga ctgaattccc tgcaggttgg ccactccctc tctgcgcgct cgctcgctca   3900
ctgaggccgc ccgggcaaag cccgggcgtc gggcgacctt tggtcgcccg gcctcagtga   3960
gcgagcgagc gcgcagagag ggagtggcca actccatcac taggggttcc tgcggccgct   4020
cgtacggtct cgaggaattc ctgcaggata acttgccaac tcattctaaa atgtatata    4080 gaagcccaaa agacaataac aaaaatattc ttgtagaaca aaatgggaaa gaatgttcca   4140
ctaaatatca agatttagag caaagcatga gatgtgtggg gatagacagt gaggctgata   4200
aaatagagta gagctcagaa acagacccat tgatatatgt aagtgaccta tgaaaaaaat   4260
atggcatttt acaatgggaa aatgatggtc tttttctttt ttagaaaaac agggaaatat   4320
atttatatgt aaaaaataaa agggaaccca tatgtcatac catacacaca aaaaaattcc   4380
agtgaattat aagtctaaat ggagaaggca aaactttaaa tcttttagaa ataatatag    4440 aagcatgcag accagcctgg ccaacatgat gaaaccctct ctactaataa taaatcagt    4500 agaactactc aggactactt tgagtgggaa gtccttttct atgaagactt ctttggccaa   4560
aattaggctc taaatgcaag gagatagtgc atcatgcctg gctgcactta ctgataaatg   4620
atgttatcac catcttaac caaatgcaca ggaacaagtt atggtactga tgtgctggat    4680
tgagaaggag ctctacttcc ttgacaggac acatttgtat caacttaaaa aagcagattt   4740
ttgccagcag aactattcat tcagaggtag gaaacttaga atagatgatg tcactgatta   4800
gcatggcttc cccatctcca cagctgcttc ccacccaggt tgcccacagt tgagtttgtc   4860
cagtgctcag ggctgcccac tctcagtaag aagccccaca ccagcccctc tccaaatatg   4920
```

```
ttggctgttc cttccattaa agtgacccca ctttagagca gcaagtggat ttctgtttct    4980
tacagttcag gaaggaggag tcagctgtga gaacctggag cctgagatgc ttctaagtcc    5040
cactgctact ggggtcaggg aagccagact ccagcatcag cagtcaggag cactaagccc    5100
ttgccaacat cctgtttctc agagaaactg cttccattat aatggttgtc cttttttaag    5160
ctatcaagcc aaacaaccag tgtctaccat tattctcatc acctgaagcc aagggttcta    5220
gcaaaagtca agctgtcttg taatggttga tgtgcctcca gcttctgtct tcagtcactc    5280
cactcttagc ctgctctgaa tcaactctga ccacagttcc ctggagcccc tgccacctgc    5340
tgcccctgcc accttctcca tctgcagtgc tgtgcagcct tctgcactct tgcagagcta    5400
ataggtggag acttgaagga agaggaggaa agtttctcat aatagccttg ctgcaagctc    5460
aaatgggagg tgggcactgt gcccaggagc cttggagcaa aggctgtgcc caacctctga    5520
ctgcatccag gtttggtctt gacagagata agaagccctg gcttttggag ccaaaatcta    5580
ggtcagactt aggcaggatt ctcaaagttt atcagcagaa catgaggcag aagacccttt    5640
ctgctccagc ttcttcaggc tcaaccttca tcagaataga tagaaagaga ggctgtgagg    5700
gttcttaaaa cagaagcaaa tctgactcag agaataaaca acctcctagt aaactacagc    5760
ttagacagag catctggtgg tgagtgtgct cagtgtccta ctcaactgtc tggtatcagc    5820
cctcatgagg acttctcttc tttccctcat agacctccat ctctgttttc cttagcctgc    5880
agaaatctgg atggctattc acagaatgcc tgtgctttca gagttgcatt ttttctctgg    5940
tattctggtt caagcatttg aaggtaggaa aggttctcca agtgcaagaa agccagccct    6000
gagcctcaac tgcctggcta gtgtggtcag taggatgcaa aggctgttga atgccacaag    6060
gccaaacttt aacctgtgta ccacaagcct agcagcagag gcagctctgc tcactggaac    6120
tctctgtctt ctttctcctg agccttttct tttcctgagt tttctagctc tcctcaacct    6180
tacctctgcc ctacccagga caaacccaag agccactgtt tctgtgatgt cctctccagc    6240
cctaattagg catcatgact tcagcctgac cttccatgct cagaagcagt gctaatccac    6300
ttcagatgag ctgctctatg caacacaggc agagcctaca aacctttgca ccagagccct    6360
ccacatatca gtgtttgttc atactcactt caacagcaaa tgtgactgct gagattaaga    6420
ttttacacaa gatggtctgt aatttcacag ttagttttat cccattaggt atgaaagaat    6480
tagcataatt cccttaaac atgaatgaat cttagatttt ttaataaata gttttggaag    6540
taaagacaga gacatcagga gcacaaggaa tagcctgaga ggacaaacag aacaagaaag    6600
agtctggaaa tacacaggat gttcttggcc tcctcaaagc aagtgcaagc agatagtacc    6660
agcagcccca ggctatcaga gcccagtgaa gagaagtacc atgaaagcca cagctctaac    6720
caccctgttc cagagtgaca gacagtcccc aagacaagcc agcctgagcc agagagagaa    6780
ctgcaagaga aagtttctaa tttaggttct gttagattca gacaagtgca ggtcatcctc    6840
tctccacagc tactcacctc tccagcctaa caaagcctgc agtccacact ccaaccctgg    6900
tgtctcacct cctagcctct cccaacatcc tgctctctga ccatcttctg catctctcat    6960
ctcaccatct cccactgtct acagcctact cttgcaacta ccatctcatt ttctgacatc    7020
ctgtctacat cttctgccat actctgccat ctaccatacc acctcttacc atctaccaca    7080
ccatctttta tctccatccc tctcagaagc ctccaagctg aatcctgctt tatgtgttca    7140
tctcagcccc tgcatggaaa gctgacccca gaggcagaac tattcccaga gagcttggcc    7200
aagaaaaaca aaactaccag cctggccagg ctcaggagta gtaagctgca gtgtctgttg    7260
tgttctagct tcaacagctg caggagttcc actctcaaat gctccacatt tctcacatcc    7320
```

```
tcctgattct ggtcactacc catcttcaaa gaacagaata tctcacatca gcatactgtg   7380
aaggactagt catgggtgca gctgctcaga gctgcaaagt cattctggat ggtggagagc   7440
ttacaaacat tcatgatgc tcccccgct ctgatggctg agcccaatc cctacacaga      7500 ctcctgctgt atgtgttttc ctttcactct gagccacagc cagagggcag gcattcagtc   7560
tcctcttcag gctggggctg gggcactgag aactcaccca acaccttgct ctcactcctt   7620
ctgcaaaaca agaaagagct tgtgctgca gtagccatga agaatgaaag gaaggcttta    7680
actaaaaaat gtcagagatt attttcaacc ccttactgtg gatcaccagc aaggaggaaa   7740
cacaacacag agacatttt tcccctcaaa ttatcaaaag aatcactgca tttgttaaag    7800
agagcaactg aatcaggaag cagagttttg aacatatcag aagttaggaa tctgcatcag   7860
agacaaatgc agtcatggtt gtttgctgca taccagccct aatcattaga agcctcatgg   7920
acttcaaaca tcattccctc tgacaagatg ctctagccta actccatgag ataaaataaa   7980
tctgcctttc agagccaaag aagagtccac cagcttcttc tcagtgtgaa caagagctcc   8040
agtcaggtta gtcagtccag tgcagtagag gagaccagtc tgcatcctct aattttcaaa   8100
ggcaagaaga tttgtttacc ctggacacca ggcacaagtg aggtcacaga gctcttagat   8160
atgcagtcct catgagtgag gagactaaag cgcatgccat caagacttca gtgtagagaa   8220
aacctccaaa aaagcctcct cactacttct ggaatagctc agaggccgag gcggcctcgg   8280
cctctgcata aataaaaaaa attagtcagc catggggcgg agaatgggcg gaactgggcg   8340
gagttagggg cgggatgggc ggagttaggg gcgggactat ggttgctgac taattgagat   8400
gcatgctttg catacttctg cctgctgggg agcctgggga cttttccacac ctggttgctg  8460 actaattgag atgcatgctt tgcatacttc tgcctgctgg ggagcctggg gactttccac   8520
accctaactg acacacattc cacagctgca ttaatgaatc ggccaacgcg cggggagagg   8580
cggtttgcgt attgggcgct cttccgcttc ctcgctcact gactcgctgc gctcggtcgt   8640
tcggctgcgg cgagcggtat cagctcactc aaaggcggta atacggttat ccacagaatc   8700 agggataac gcaggaaaga acatgtgagc aaaaggccag caaaaggcca ggaaccgtaa     8760
aaaggccgcg ttgctggcgt ttttccatag gctccgcccc cctgacgagc atcacaaaaa   8820
tcgacgctca gtcagaggt ggcgaaaccc gacaggacta taaagatacc aggcgtttcc    8880
ccctggaagc tccctcgtgc gctctcctgt tccgaccctg ccgcttaccg gatacctgtc   8940
cgcctttctc ccttcgggaa gcgtggcgct ttctcatagc tcacgctgta ggtatctcag   9000
ttcggtgtag tcgttcgct ccaagctggg ctgtgtgcac gaaccccccg ttcagcccga    9060
ccgctgcgcc ttatccggta actatcgtct tgagtccaac ccggtaagac acgacttatc   9120
gccactggca gcagccactg gtaacaggat tagcagagcg aggtatgtag gcggtgctac   9180
agagttcttg aagtggtggc ctaactacgg ctacactaga agaacagtat tggtatctg    9240 cgctctgctg aagccagtta ccttcggaaa aagagttggt agctcttgat ccggcaaaca   9300
aaccaccgct ggtagcggtg gtttttttgt ttgcaagcag cagattacgc gcagaaaaaa   9360
aggatctcaa gaagatcctt tgatcttttc tacgggtct gacgctcagt ggaacgaaaa    9420
ctcacgttaa gggattttgg tcatgagatt atcaaaagg atcttcacct agatcctttt    9480
aaattaaaaa tgaagtttta aatcaatcta agtatatat gagtaaactt ggtctgacag     9540
ttaccaatgc ttaatcagtg aggcaccat ctcagcgatc tgtctatttc gttcatccat    9600
agttgcctga ctccctgcaaa ccacgttgtg tctcaaaatc tctgatgtta cattgcacaa   9660
```

-continued

| | |
|---|---|
| gataaaaata tatcatcatg aacaataaaa ctgtctgctt acataaacag taatacaagg | 9720 |
| ggtgttatga gccatattca acgggaaacg tcttgctcga ggccgcgatt aaattccaac | 9780 |
| atggatgctg atttatatgg gtataaatgg gctcgcgata atgtcgggca atcaggtgcg | 9840 |
| acaatctatc gattgtatgg gaagcccgat gcgccagagt tgtttctgaa acatggcaaa | 9900 |
| ggtagcgttg ccaatgatgt tacagatgag atggtcagac taaactggct gacggaattt | 9960 |
| atgcctcttc cgaccatcaa gcattttatc cgtactcctg atgatgcatg gttactcacc | 10020 |
| actgcgatcc ccgggaaaac agcattccag gtattagaag aatatcctga ttcaggtgaa | 10080 |
| aatattgttg atgcgctggc agtgttcctg cgccggttgc attcgattcc tgtttgtaat | 10140 |
| tgtcctttta acagcgatcg cgtatttcgt ctcgctcagg cgcaatcacg aatgaataac | 10200 |
| ggtttggttg atgcgagtga ttttgatgac gagcgtaatg gctggcctgt tgaacaagtc | 10260 |
| tggaaagaaa tgcataagct tttgccattc tcaccggatt cagtcgtcac tcatggtgat | 10320 |
| ttctcacttg ataaccttat ttttgacgag gggaaattaa taggttgtat tgatgttgga | 10380 |
| cgagtcggaa tcgcagaccg ataccaggat cttgccatcc tatggaactg cctcggtgag | 10440 |
| ttttctcctt cattacagaa acggcttttt caaaaatatg gtattgataa tcctgatatg | 10500 |
| aataaattgc agtttcattt gatgctcgat gagtttttct aagggcggcc tgccaccata | 10560 |
| cccacgccga aacaagcgct catgagcccg aagtggcgag cccgatcttc cccatcggtg | 10620 |
| atgtcggcga tataggcgcc agcaaccgca cctgtggcgc cggtgatgag ggcgcgccaa | 10680 |
| gtcgacgtcc ggcagtc | 10697 |

<210> SEQ ID NO 2
<211> LENGTH: 11355
<212> TYPE: DNA
<213> ORGANISM: Artificial sequence
<220> FEATURE:
<223> OTHER INFORMATION: Synthetic polynucleotide

<400> SEQUENCE: 2

| | |
|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctgctag ctctgggtat ttaagcccga gtgagcacgc | 180 |
| agggtctcca ttttgaagcg ggaggttacg cgttcgtcga ctactagtgg gtaccagagc | 240 |
| tccctaggtt ctagaaccgg tgacgtctcc catggtgaag cttggatctg agggcggagt | 300 |
| tagggcggag ccaatcagcg tgcgccgttc cgaaagttgc cttttatggc tgggcggaga | 360 |
| atgggcggtg aacgccgatg attatataag gacgcgccgg gtgtggcaca gctagttccg | 420 |
| tcgcagccgg gatttgggtc gcggttcttg tttgtggatc cctgtgatcg tcacttggta | 480 |
| agtcactgac tgtctatgcc tgggaaaggg tgggcaggag atgggcagt gcaggaaaag | 540 |
| tggcactatg aaccctgcag ccctaggaat gcatctagac aattgtacta accttcttct | 600 |
| ctttcctctc ctgacagtcc ggaaagccac catgggccgc tgctgcttct acaccgccgg | 660 |
| caccctgagc ctgctgctgc tggtgaccag cgtgacactg ctggtggccc gcgtgttcca | 720 |
| gaaggccgtg gaccagagca tcgagaagaa gatcgtgctg cgcaacggca ccgaggcctt | 780 |
| cgacagctgg gagaagcccc cctgcccgt gtacacccag ttctacttct tcaacgtgac | 840 |
| caaccccgag gagatcctgc gcggcgagac ccccgcgtg gaggaggtgg gcccctacac | 900 |
| ctaccgcgag ctgcgcaaca aggccaacat ccagttcggc gacaacggca ccaccatcag | 960 |
| cgccgtgagc aacaaggcct acgtgttcga gcgcgaccag agcgtgggcg accccaagat | 1020 |

```
cgacctgatc cgcaccctga acatccccgt gctgaccgtg atcgagtgga gccaggtgca    1080
cttcctgcgc gagatcatcg aggccatgct gaaggcctac cagcagaagc tgttcgtgac    1140
ccacaccgtg gacgagctgc tgtggggcta caaggacgag atcctgagcc tgatccacgt    1200
gttccgcccc gacatcagcc cctacttcgg cctgttctac gagaagaacg caccaacga    1260
cggcgactac gtgttcctga ccggcgagga cagctacctg aacttccacca gatcgtgga    1320
gtggaacggc aagaccagcc tggactggtg gatcaccgac aagtgcaaca tgatcaacgg    1380
caccgacggc gacagcttcc acccctgat caccaaggac gaggtgctgt acgtgttccc     1440
cagcgacttc tgccgcagcg tgtacatcac cttcagcgac tacgagagcg tgcagggcct    1500
gcccgccttc cgctacaagg tgcccgccga gatcctggcc aacaccagcg acaacgccgg    1560
cttctgcatc cccgagggca actgcctggg cagcggcgtg ctgaacgtga gcatctgcaa    1620
gaacggcgcc cccatcatca tgagcttccc ccacttctac caggccgacg agcgcttcgt    1680
gagcgccatc gagggcatgc accccaacca ggaggaccac gagaccttcg tggacatcaa    1740
cccccctgacc ggcatcatcc tgaaggccgc caagcgcttc cagatcaaca tctacgtgaa    1800
gaagctggac gacttcgtgg agaccggcga catccgcacc atggtgttcc ccgtgatgta    1860
cctgaacgag agcgtgcaca tcgacaagga gaccgccagc cgcctgaaga gcatgatcaa    1920
caccaccctg atcatcacca acatcccta catcatcatg gccctgggcg tgttcttcgg    1980
cctggtgttc acctggctgg cctgcaaggg ccagggcagc atggacgagg gcaccgccga    2040
cgagcgcgcc cccctgatcc gcacctgatt gtggccgaac cgccgaactc agaggccggc    2100
cccagaaaac ccgagcgagt aggggcggc gcgcaggagg gaggagaact gggggcgcgg    2160
gaggctggtg ggtgtggggg gtggagatgt agaagatgtg acgccgcggc ccggcgggtg    2220
ccagattagc ggacgcggtg cccgcggttg caacgggatc ccgggcgctg cagcttggga    2280
ggcggctctc cccaggcggc gtccgcggag cacccatcc gtgaaccca ggtcccgggc     2340
cgccggctcg ccgcgcacca ggggccggcg gacagaagag cggccgagcg gctcgaggct    2400
gggggaccgc gggcgcggcc gcgcgctgcc gggcgggagg ctgggggggcc ggggccgggg   2460
ccgtgccccg gagcgggtcg gaggccgggg ccggggccgg gggacggcgg ctccccgcgc    2520
ggctccagcg gctcggggat cccggccggg ccccgcaggg accatgatgg aattcagcag    2580
ccccagcaga gaggaatgcc ccaagcctct gagccgggtg tcaatcatgg ccggatctct    2640
gacaggactg ctgctgcttc aggccgtgtc ttgggcttct ggcgctagac cttgcatccc    2700
caagagcttc ggctacagca gcgtcgtgtg cgtgtgcaat gccacctact gcgacagctt    2760
cgaccctcct accttctcctg ctctgggcac cttcagcaga tacgagagca ccagatccgg    2820
cagacggatg gaactgagca tgggaccat ccaggccaat cacacaggca ctggcctgct     2880
gctgacactg cagcctgagc agaaattcca gaaagtgaaa ggcttcggcg agccatgac    2940
agatgccgcc gctctgaata tcctggctct gtctccacca gctcagaacc tgctgctcaa    3000
gagctacttc agcgaggaag gcatcggcta acatcatc agagtgccca tggccagctg     3060
cgacttcagc atcaggacct acacctacgc cgacacaccc gacgatttcc agctgcacaa    3120
cttcagcctg cctgaagagg acaccaagct gaagatccct ctgatccaca gagccctgca    3180
gctggcacaa agaccgtgt cactgctggc ctctccatgg acatctccca cctggctgaa    3240
aacaaatggc gccgtgaatg gcaagggcag cctgaaaggc caacctggcg acatctacca    3300
ccagacctgg gccagatact tcgtgaagtt cctggacgcc tatgccgagc acaagctgca    3360
```

```
gttttgggcc gtgacagccg agaacgaacc ttctgctgga ctgctgagcg gctacccctt    3420
tcagtgcctg ggctttacac ccgagcacca gcgggacttt atcgcccgtg atctgggacc    3480
cacactggcc aatagcaccc accataatgt gcggctgctg atgctggacg accagagact    3540
gcttctgccc cactgggcta aagtggtgct gacagatcct gaggccgcca atacgtgca     3600
cggaatcgcc gtgcactggt atctggactt tctggcccct gccaaggcca cactgggaga    3660
gacacacaga ctgttcccca acaccatgct gttcgccagc gaagcctgtg tgggcagcaa    3720
gttttgggaa cagagcgtgc ggctcggcag ctgggataga ggcatgcagt acagccacag    3780
catcatcacc aacctgctgt accacgtcgt cggctggacc gactggaatc tggccctgaa    3840
tcctgaaggc ggccctaact gggtccgaaa cttcgtggac agccccatca tcgtggacat    3900
caccaaggac accttctaca agcagcccat gttctaccac ctgggacact tcagcaagtt    3960
catccccgag ggctctcagc gcgttggact ggtggcttcc cagaagaacg atctggacgc    4020
cgtggctctg atgcaccctg atggatctgc tgtggtggtg gtcctgaacc gcagcagcaa    4080
agatgtgccc ctgaccatca aggatcccgc cgtgggattc ctggaaacaa tcagccctgg    4140
ctactccatc cacacctacc tgtggcgtag acagtgacaa ttgttaatta agtttaaacc    4200
ctcgaggccg caagccgcat cgataccgtc gactagagct cgctgatcag cctcgactgt    4260
gccttctagt tgccagccat ctgttgtttg ccccctccccc gtgccttcct gaccctgga    4320
aggtgccact cccactgtcc tttcctaata aatgaggaa attgcatcgc attgtctgag    4380
taggtgtcat tctattctgg ggggtgggt ggggcaggac agcaagggg aggattggga     4440
agacaatagc aggcatgctg gggagagatc cacgataaca aacagctttt ttggggtgaa    4500
catattgact gaattccctg caggttggcc actccctctc tgcgcgctcg ctcgctcact    4560
gaggccgccc gggcaaagcc cgggcgtcgg gcgacctttg gtcgcccggc ctcagtgagc    4620
gagcgagcgc gcagagaggg agtggccaac tccatcacta ggggttcctg cggccgctcg    4680
tacggtctcg aggaattcct gcaggataac ttgccaacct cattctaaaa tgtatataga    4740
agcccaaaag acaataacaa aaatattctt gtagaacaaa atgggaaaga atgttccact    4800
aaatatcaag atttagagca aagcatgaga tgtgtgggga tagacagtga ggctgataaa    4860
atagagtaga gctcagaaac agaccccattg atatatgtaa gtgacctatg aaaaaaatat    4920
ggcattttac aatgggaaaa tgatggtctt tttcttttt agaaaaacag ggaaatatat    4980
ttatatgtaa aaaataaaag ggaacccata tgtcatacca tacacacaaa aaaattccag    5040
tgaattataa gtctaaatgg agaaggcaaa actttaaatc ttttagaaaa taatatagaa    5100
gcatgcagac cagcctggcc aacatgatga aaccctctct actaataata aaatcagtag    5160
aactactcag gactactttg agtgggaagt ccttttctat gaagacttct ttggccaaaa    5220
ttaggctcta aatgcaagga gatagtgcat catgcctggc tgcacttact gataaatgat    5280
gttatcacca tctttaacca aatgcacagg aacaagttat ggtactgatg tgctggattg    5340
agaaggagct ctacttcctt gacaggacac atttgtatca acttaaaaaa gcagattttt    5400
gccagcagaa ctattcattc agaggtagga aacttagaat agatgatgtc actgattagc    5460
atggcttccc catctccaca gctgcttccc acccaggttg cccacagttg agtttgtcca    5520
gtgctcaggg ctgcccactc tcagtaagaa gccccacacc agccctctc caaatatgtt    5580
ggctgttcct tccattaaag tgaccccact ttagagcagc aagtggattt ctgtttctta    5640
cagttcagga aggaggagtc agctgtgaga acctggagcc tgagatgctt ctaagtccca    5700
ctgctactgg ggtcagggaa gccagactcc agcatcagca gtcaggagca ctaagccctt    5760
```

```
gccaacatcc tgtttctcag agaaactgct tccattataa tggttgtcct ttttaagct     5820
atcaagccaa acaaccagtg tctaccatta ttctcatcac ctgaagccaa gggttctagc     5880
aaaagtcaag ctgtcttgta atggttgatg tgcctccagc ttctgtcttc agtcactcca     5940
ctcttagcct gctctgaatc aactctgacc acagttccct ggagcccctg ccacctgctg     6000
cccctgccac cttctccatc tgcagtgctg tgcagccttc tgcactcttg cagagctaat     6060
aggtggagac ttgaaggaag aggaggaaag tttctcataa tagccttgct gcaagctcaa     6120
atgggaggtg ggcactgtgc ccaggagcct ggagcaaag gctgtgccca acctctgact     6180
gcatccaggt ttggtcttga cagagataag aagccctggc ttttggagcc aaaatctagg     6240
tcagacttag gcaggattct caaagtttat cagcagaaca tgaggcagaa gaccctttct     6300
gctccagctt cttcaggctc aaccttcatc agaatagata gaaagagagg ctgtgagggt     6360
tcttaaaaca gaagcaaatc tgactcagag aataaacaac ctcctagtaa actacagctt     6420
agacagagca tctggtggtg agtgtgctca gtgtcctact caactgtctg gtatcagccc     6480
tcatgaggac ttctcttctt tccctcatag acctccatct ctgttttcct tagcctgcag     6540
aaatctggat ggctattcac agaatgcctg tgctttcaga gttgcatttt ttctctggta     6600
ttctggttca agcatttgaa ggtaggaaag gttctccaag tgcaagaaag ccagccctga     6660
gcctcaactg cctggctagt gtggtcagta ggatgcaaag gctgttgaat gccacaaggc     6720
caaactttaa cctgtgtacc acaagcctag cagcagaggc agctctgctc actggaactc     6780
tctgtcttct ttctcctgag cctttctttt cctgagtttt tctagctctc ctcaaccttta    6840
cctctgccct acccaggaca aacccaagag ccactgtttc tgtgatgtcc tctccagccc     6900
taattaggca tcatgacttc agcctgacct tccatgctca gaagcagtgc taatccactt     6960
cagatgagct gctctatgca acacaggcag agcctacaaa cctttgcacc agagccctcc     7020
acatatcagt gtttgttcat actcacttca acagcaaatg tgactgctga gattaagatt     7080
ttacacaaga tggtctgtaa tttcacagtt agttttatcc cattaggtat gaaagaatta     7140
gcataattcc ccttaaacat gaatgaatct tagatttttt aataaatagt tttggaagta     7200
aagacagaga catcaggagc acaaggaata gcctgagagg acaaacagaa caagaaagag     7260
tctggaaata cacaggatgt tcttggcctc ctcaaagcaa gtgcaagcag atagtaccag     7320
cagccccagg ctatcagagc ccagtgaaga gaagtaccat gaaagccaca gctctaacca     7380
ccctgttcca gagtgacaga cagtccccaa gacaagccag cctgagccag agagagaact     7440
gcaagagaaa gtttctaatt taggttctgt tagattcaga caagtgcagg tcatcctctc     7500
tccacagcta ctcacctctc cagcctaaca aagcctgcag tccacactcc aaccctggtg     7560
tctcacctcc tagcctctcc aacatcctg ctctctgacc atcttctgca tctctcatct     7620
caccatctcc cactgtctac agcctactct tgcaactacc atctcatttt ctgacatcct     7680
gtctacatct tctgccatac tctgccatct accataccac ctcttaccat ctaccacacc     7740
atcttttatc tccatccctc tcagaagcct ccaagctgaa tcctgcttta tgtgttcatc     7800
tcagcccctg catggaaagc tgaccccaga ggcagaacta ttcccagaga gcttggccaa     7860
gaaaaacaaa actaccagcc tggccaggct caggagtagt aagctgcagt gtctgttgtg     7920
ttctagcttc aacagctgca ggagttccac tctcaaatgc tccacatttc tcacatcctc     7980
ctgattctgg tcactaccca tcttcaaaga acagaatatc tcacatcagc atactgtgaa     8040
ggactagtca tgggtgcagc tgctcagagc tgcaaagtca ttctggatgg tggagagctt     8100
```

```
acaaacattt catgatgctc cccccgctct gatggctgga gcccaatccc tacacagact    8160
cctgctgtat gtgttttcct ttcactctga gccacagcca gagggcaggc attcagtctc    8220
ctcttcaggc tggggctggg gcactgagaa ctcacccaac accttgctct cactccttct    8280
gcaaaacaag aaagagcttt gtgctgcagt agccatgaag aatgaaagga aggctttaac    8340 taaaaatgt cagagattat tttcaacccc ttactgtgga tcaccagcaa ggaggaaaca     8400
caacacagag acattttttc ccctcaaatt atcaaaagaa tcactgcatt tgttaaagag    8460
agcaactgaa tcaggaagca gagttttgaa catatcagaa gttaggaatc tgcatcagag    8520
acaaatgcag tcatggttgt ttgctgcata ccagccctaa tcattagaag cctcatggac    8580
ttcaaacatc attccctctg acaagatgct ctagcctaac tccatgagat aaaataaatc    8640
tgcctttcag agccaaagaa gagtccacca gcttcttctc agtgtgaaca agagctccag    8700
tcaggttagt cagtccagtg cagtagagga gaccagtctg catcctctaa ttttcaaagg    8760
caagaagatt tgtttaccct ggacaccagg cacaagtgag gtcacagagc tcttagatat    8820
gcagtcctca tgagtgagga gactaaagcg catgccatca agacttcagt gtagagaaaa    8880
cctccaaaaa agcctcctca ctacttctgg aatagctcag aggccgaggc ggcctcggcc    8940
tctgcataaa taaaaaaaat tagtcagcca tggggcggaa atgggcggaa ctgggcggaa    9000
gttaggggcg ggatgggcgg agttaggggc gggactatgg ttgctgacta attgagatgc    9060
atgctttgca tacttctgcc tgctggggag cctggggact ttccacacct ggttgctgac    9120
taattgagat gcatgctttg catacttctg cctgctgggg agcctgggga ctttccacac    9180
cctaactgac acacattcca cagctgcatt aatgaatcgg ccaacgcgcg gggagaggcg    9240
gtttgcgtat tgggcgctct tccgcttcct cgctcactga ctcgctgcgc tcggtcgttc    9300
ggctgcggcg agcggtatca gctcactcaa aggcggtaat acggttatcc acagaatcag    9360
gggataacgc aggaaagaac atgtgagcaa aaggccagca aaaggccagg aaccgtaaaa    9420
aggccgcgtt gctggcgttt ttccataggc tccgcccccc tgacgagcat cacaaaaatc    9480
gacgctcaag tcagaggtgg cgaaacccga caggactata agataccagg cgtttccccc    9540
ctggaagctc cctcgtgcgc tctcctgttc cgaccctgcc gcttaccgga tacctgtccg    9600
cctttctccc ttcgggaagc gtggcgcttt ctcatagctc acgctgtagg tatctcagtt    9660
cggtgtaggt cgttcgctcc aagctgggct gtgtgcacga accccccgtt cagcccgacc    9720
gctgcgcctt atccggtaac tatcgtcttg agtccaaccc ggtaagacac gacttatcgc    9780
cactggcagc agccactggt aacaggatta gcagagcgag gtatgtaggc ggtgctacag    9840
agttcttgaa gtggtggcct aactacggct acactagaag aacagtattt ggtatctgcg    9900
ctctgctgaa gccagttacc ttcggaaaaa gagttggtag ctcttgatcc ggcaaacaaa    9960
ccaccgctgg tagcggtggt ttttttgttt gcaagcagca gattacgcgc agaaaaaaag   10020
gatctcaaga agatcctttg atcttttcta cggggtctga cgctcagtgg aacgaaaact   10080
cacgttaagg gattttggtc atgagattat caaaaaggat cttcacctag atccttttaa   10140
attaaaaatg aagttttaaa tcaatctaaa gtatatatga gtaaacttgg tctgacagtt   10200
accaatgctt aatcagtgag gcacctatct cagcgatctg tctatttcgt tcatccatag   10260
ttgcctgact cctgcaaacc acgttgtgtc tcaaaatctc tgatgttaca ttgcacaaga   10320
taaaaatata tcatcatgaa caataaaact gtctgcttac ataaacagta atacaagggg   10380
tgttatgagc catattcaac gggaaacgtc ttgctcgagg ccgcgattaa attccaacat   10440
ggatgctgat ttatatgggt ataaatgggc tcgcgataat gtcgggcaat caggtgcgac   10500
```

```
aatctatcga ttgtatggga agcccgatgc gccagagttg tttctgaaac atggcaaagg    10560
tagcgttgcc aatgatgtta cagatgagat ggtcagacta aactggctga cggaatttat    10620
gcctcttccg accatcaagc attttatccg tactcctgat gatgcatggt tactcaccac    10680
tgcgatcccc gggaaaacag cattccaggt attagaagaa tatcctgatt caggtgaaaa    10740
tattgttgat gcgctggcag tgttcctgcg ccggttgcat tcgattcctg tttgtaattg    10800
tccttttaac agcgatcgcg tatttcgtct cgctcaggcg caatcacgaa tgaataacgg    10860
tttggttgat gcgagtgatt ttgatgacga gcgtaatggc tggcctgttg aacaagtctg    10920
gaaagaaatg cataagcttt tgccattctc accggattca gtcgtcactc atggtgattt    10980
ctcacttgat aaccttattt ttgacgaggg gaaattaata ggttgtattg atgttggacg    11040
agtcggaatc gcagaccgat accaggatct tgccatccta tggaactgcc tcggtgagtt    11100
ttctccttca ttacagaaac ggcttttttca aaaatatggt attgataatc ctgatatgaa    11160
taaattgcag tttcatttga tgctcgatga gttttctaa gggcggcctg ccaccatacc    11220
cacgccgaaa caagcgctca tgagcccgaa gtggcgagcc cgatcttccc catcggtgat    11280
gtcggcgata taggcgccag caaccgcacc tgtggcgccg gtgatgaggg cgcgccaagt    11340
cgacgtccgg cagtc                                                     11355
```

<210> SEQ ID NO 3
<211> LENGTH: 11420
<212> TYPE: DNA
<213> ORGANISM: Artificial sequence
<220> FEATURE:
<223> OTHER INFORMATION: Synthetic polynucleotide

<400> SEQUENCE: 3

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctgctag ctctgggtat ttaagcccga gtgagcacgc     180
agggtctcca ttttgaagcg ggaggttacg cgttcgtcga ctactagtgg gtaccagagc     240
tccctaggtt ctagaaccgg tgacgtctcc catggtgaag cttggatctg agggcggagt     300
tagggcggag ccaatcagcg tgcgccgttc cgaaagttgc cttttatggc tgggcggaga     360
atgggcggtg aacgccgatg attatataag gacgcgccgg gtgtggcaca gctagttccg     420
tcgcagccgg gatttgggtc gcggttcttg tttgtggatc cctgtgatcg tcacttggta     480
agtcactgac tgtctatgcc tgggaaaggg tgggcaggag atgggcagt gcaggaaaag     540 tggcactatg aaccctgcag ccctaggaat gcatctagac aattgtacta accttcttct     600
ctttcctctc ctgacagtcc ggaaagccac catggaattc agcagcccca gcagagagga     660
atgccccaag cctctgagcc gggtgtcaat catggccgga tctctgacag gactgctgct     720
gcttcaggcc gtgtcttggg cttctggcgc tagaccttgc atcccaaga gcttcggcta     780 cagcagcgtc gtgtgcgtgt gcaatgccac ctactgcgac agcttcgacc tcctaccttt     840
tcctgctctg gcaccttca gcagatacga gagcaccaga tccggcagac ggatggaact     900
gagcatggga cccatccagg ccaatcacac aggcactggc ctgctgctga cactgcagcc     960
tgagcagaaa ttccagaaag tgaaaggctt cggcggagcc atgacagatg ccgccgctct    1020
gaatatcctg gctctgtctc caccagctca gaacctgctg ctcaagagct acttcagcga    1080
ggaaggcatc ggctacaaca tcatcagagt gcccatggcc agctgcgact tcagcatcag    1140
```

-continued

```
gacctacacc tacgccgaca cacccgacga tttccagctg cacaacttca gcctgcctga   1200
agaggacacc aagctgaaga tccctctgat ccacagagcc ctgcagctgg cacaaagacc   1260
cgtgtcactg ctggcctctc catggacatc tcccacctgg ctgaaaacaa atggcgccgt   1320
gaatggcaag ggcagcctga aaggccaacc tggcgacatc taccaccaga cctgggccag   1380
atacttcgtg aagttcctgg acgcctatgc cgagcacaag ctgcagtttt gggccgtgac   1440
agccgagaac gaaccttctg ctggactgct gagcggctac ccctttcagt gcctgggctt   1500
tacacccgag caccagcggg actttatcgc ccgtgatctg ggacccacac tggccaatag   1560
cacccaccat aatgtgcggc tgctgatgct ggacgaccag agactgcttc tgccccactg   1620
ggctaaagtg gtgctgacag atcctgaggc cgccaaatac gtgcacggaa tcgccgtgca   1680
ctggtatctg gactttctgg cccctgccaa ggccacactg ggagagacac acagactgtt   1740
ccccaacacc atgctgttcg ccagcgaagc ctgtgtgggc agcaagtttt gggaacagag   1800
cgtgcggctc ggcagctggg atagaggcat gcagtacagc cacagcatca tcaccaacct   1860
gctgtaccac gtcgtcggct ggaccgactg gaatctggcc ctgaatcctg aaggcggccc   1920
taactgggtc cgaaacttcg tggacagccc catcatcgtg acatcacca aggacacctt   1980 ctacaagcag cccatgttct accacctggg acacttcagc aagttcatcc ccgagggctc   2040
tcagcgcgtt ggactggtgg cttcccagaa gaacgatctg gacgccgtgg ctctgatgca   2100
ccctgatgga tctgctgtgg tggtggtcct gaaccgcagc agcaaagatg tgcccctgac   2160
catcaaggat cccgccgtgg gattcctgga acaatcagcc ctggctactc catccacac   2220 ctacctgtgg cgtagacagt gacaattgtt aattaagttt catcgatacc gtcgactaga   2280
gctcgctgat cagcctcgac tgtgccttct agttgccagc catctgttgt ttgcccctcc   2340
cccgtgcctt ccttgaccct ggaaggtgcc actcccactg tcctttccta ataaaatgag   2400
gaaattgcat cgcattgtct gagtaggtgt cattctattc tggggggtgg ggtggggcag   2460
gacagcaagg gggaggattg gaagacaat agcaggcatg ctgggagag atccacgata   2520 acaaacagct ttttggggg gcggagtta gggcggagcc aatcagcgtg cgccgttccg   2580
aaagttgcct tttatggctg gcggagaat gggcggtgaa cgccgatgat tatataagga   2640
cgcgccgggt gtggcacagc tagttccgtc gcagccggga tttgggtcgc ggttcttgtt   2700
tgtggatccc tgtgatcgtc acttggtaag tcactgactg tctatgcctg ggaaagggtg   2760
ggcaggagat ggggcagtgc aggaaaagtg gcactatgaa ccctgcagcc ctaggaatgc   2820
atctagacaa ttgtactaac cttcttctct ttcctctcct gacagtccgg aaagccacca   2880
tgggccgctg ctgcttctac accgccggca ccctgagcct gctgctgctg gtgaccagcg   2940
tgaccctgct ggtggcccgc gtgttccaga aggccgtgga ccagagcatc gagaagaaga   3000
tcgtgctgcg caacggcacc gaggccttcg acagctggga aagccccccc ctgcccgtgt   3060
acacccagtt ctacttcttc aacgtgacca ccccgagga atcctgcgc ggcgagaccc   3120 cccgcgtgga ggaggtgggc ccctacacct accgcgagct gcgcaacaag gccaacatcc   3180
agttcggcga caacggcacc accatcagcg ccgtgagcaa caaggcctac gtgttcgagc   3240
gcgaccagag cgtgggcgac cccaagatcg acctgatccg caccctgaac atccccgtgc   3300
tgaccgtgat cgagtggagc caggtgcact tcctgcgcga tcatcgag gccatgctga   3360 aggcctacca gcagaagctg ttcgtgaccc acaccgtgga cgagctgctg tggggctaca   3420
aggacgagat cctgagcctg atccacgtgt tccgccccga catcagcccc tacttcggcc   3480
tgttctacga gaagaacggc accaacgacg gcgactacgt gttcctgacc ggcgaggaca   3540
```

```
gctacctgaa cttcaccaag atcgtggagt ggaacggcaa gaccagcctg gactggtgga    3600
tcaccgacaa gtgcaacatg atcaacggca ccgacggcga cagcttccac cccctgatca    3660
ccaaggacga ggtgctgtac gtgttcccca gcgacttctg ccgcagcgtg tacatcacct    3720
tcagcgacta cgagagcgtg cagggcctgc ccgccttccg ctacaaggtg cccgccgaga    3780
tcctggccaa caccagcgac aacgccggct tctgcatccc cgagggcaac tgcctgggca    3840
gcggcgtgct gaacgtgagc atctgcaaga acggcgcccc catcatcatg agcttccccc    3900
acttctacca ggccgacgag cgcttcgtga gcgccatcga gggcatgcac cccaaccagg    3960
aggaccacga gaccttcgtg gacatcaacc ccctgaccgg catcatcctg aaggccgcca    4020
agcgcttcca gatcaacatc tacgtgaaga agctggacga cttcgtggag accggcgaca    4080
tccgcaccat ggtgttcccc gtgatgtacc tgaacgagag cgtgcacatc gacaaggaga    4140
ccgccagccg cctgaagagc atgatcaaca ccaccctgat catcaccaac atcccctaca    4200
tcatcatggc cctgggcgtg ttcttcggcc tggtgttcac ctggctggcc tgcaagggcc    4260
agggcagcat ggacgagggc accgccgacg agcgcgcccc cctgatccgc acctgaccca    4320
ggggactcaa tcagcctcga agacatgata agatacattg atgagtttgg acaaaccaca    4380
acaagaatgc agtgaaaaaa atgctttatt tgtgaaattt gtgatgctat tgctttattt    4440
gtaaccatta taagctgcaa taaacaagtt aacaacaaca attgcattca ttttatgttt    4500
caggttcagg gggagatgtg ggaggttttt taaagcaagt aaaacctcta caaatgtggt    4560
atgaacatat tgactgaatt ccctgcaggt tggccactcc ctctctgcgc gctcgctcgc    4620
tcactgaggc cgcccgggca agcccgggc gtcgggcgac ctttggtcgc ccggcctcag    4680
tgagcgagcg agcgcgcaga gagggagtgg ccaactccat cactagggt tcctgcggcc    4740 gctcgtacgg tctcgaggaa ttcctgcagg ataacttgcc aacctcattc taaaatgtat    4800
atagaagccc aaaagacaat aacaaaaata ttcttgtaga acaaaatggg aaagaatgtt    4860
ccactaaata tcaagattta gagcaaagca tgagatgtgt ggggatagac agtgaggctg    4920
ataaaataga gtagagctca gaaacagacc cattgatata tgtaagtgac ctatgaaaaa    4980
aatatggcat tttacaatgg gaaaatgatg gtctttttct tttttagaaa acagggaaa    5040 tatatttata tgtaaaaaat aaagggaac ccatatgtca taccatacac acaaaaaaat    5100
tccagtgaat tataagtcta aatggagaag gcaaaacttt aaatctttta gaaataata    5160 tagaagcatg cagaccagcc tggccaacat gatgaaaccc tctctactaa taataaaatc    5220
agtagaacta ctcaggacta ctttgagtgg gaagtccttt tctatgaaga cttctttggc    5280
caaaattagg ctctaaatgc aaggagatag tgcatcatgc ctggctgcac ttactgataa    5340
atgatgttat caccatcttt aaccaaatgc acaggaacaa gttatggtac tgatgtgctg    5400
gattgagaag gagctctact tccttgacag gacacatttg tatcaactta aaaaagcaga    5460
tttttgccag cagaactatt cattcagagg taggaaactt agaatagatg atgtcactga    5520
ttagcatggc ttcccccatct ccacagctgc ttcccaccca ggttgcccac agttgagttt    5580
gtccagtgct cagggctgcc cactctcagt aagaagcccc acaccagccc ctctccaaat    5640
atgttggctg ttccttccat taaagtgacc ccactttaga gcagcaagtg gatttctgtt    5700
tcttacagtt caggaaggag gagtcagctg tgagaacctg gagcctgaga tgcttctaag    5760
tcccactgct actggggtca gggaagccag actccagcat cagcagtcag gagcactaag    5820
cccttgccaa catcctgttt ctcagagaaa ctgcttccat tataatggtt gtcctttttt    5880
```

```
aagctatcaa gccaaacaac cagtgtctac cattattctc atcacctgaa gccaagggtt   5940
ctagcaaaag tcaagctgtc ttgtaatggt tgatgtgcct ccagcttctg tcttcagtca   6000
ctccactctt agcctgctct gaatcaactc tgaccacagt tccctggagc ccctgccacc   6060
tgctgcccct gccaccttct ccatctgcag tgctgtgcag ccttctgcac tcttgcagag   6120
ctaataggtg gagacttgaa ggaagaggag gaaagtttct cataatagcc ttgctgcaag   6180
ctcaaatggg aggtgggcac tgtgcccagg agccttggag caaaggctgt gcccaacctc   6240
tgactgcatc caggtttggt cttgacagag ataagaagcc ctggcttttg gagccaaaat   6300
ctaggtcaga cttaggcagg attctcaaag tttatcagca gaacatgagg cagaagaccc   6360
tttctgctcc agcttcttca ggctcaacct tcatcagaat agatagaaag agaggctgtg   6420
agggttctta aaacagaagc aaatctgact cagagaataa acaacctcct agtaaactac   6480
agcttagaca gagcatctgg tggtgagtgt gctcagtgtc ctactcaact gtctggtatc   6540
agccctcatg aggacttctc ttctttccct catagacctc catctctgtt ttccttagcc   6600
tgcagaaatc tggatggcta ttcacagaat gcctgtgctt tcagagttgc attttttctc   6660
tggtattctg gttcaagcat ttgaaggtag gaaaggttct ccaagtgcaa gaaagccagc   6720
cctgagcctc aactgcctgg ctagtgtggt cagtaggatg caaaggctgt tgaatgccac   6780
aaggccaaac tttaacctgt gtaccacaag cctagcagca gaggcagctc tgctcactgg   6840
aactctctgt cttcttcctc ctgagccttt tcttttcctg agttttctag ctctcctcaa   6900
ccttacctct gccctaccca ggacaaaccc aagagccact gtttctgtga tgtcctctcc   6960
agccctaatt aggcatcatg acttcagcct gaccttccat gctcagaagc agtgctaatc   7020
cacttcagat gagctgctct atgcaacaca ggcagagcct acaaaccttt gcaccagagc   7080
cctccacata tcagtgtttg ttcatactca cttcaacagc aaatgtgact gctgagatta   7140
agattttaca caagatggtc tgtaatttca cagttagttt tatcccatta ggtatgaaag   7200
aattagcata attcccctta aacatgaatg aatcttagat ttttttaataa atagttttgg   7260 aagtaaagac agagacatca ggagcacaag gaatagcctg agaggacaaa cagaacaaga   7320
aagagtctgg aaatacacag gatgttcttg gcctcctcaa agcaagtgca agcagatagt   7380
accagcagcc ccaggctatc agagcccagt gaagagaagt accatgaaag ccacagctct   7440
aaccaccctg ttccgagtg acagacagtc cccaagacaa gccagcctga gccagagaga   7500
gaactgcaag agaaagtttc taatttaggt tctgttagat tcagacaagt gcaggtcatc   7560
ctctctccac agctactcac ctctccagcc taacaaagcc tgcagtccac actccaaccc   7620
tggtgtctca cctcctagcc tctcccaaca tcctgctctc tgaccatctt ctgcatctct   7680 catctccacca tctcccactg tctacagcct actcttgcaa ctaccatctc attttctgac   7740
atcctgtcta catcttctgc catactctgc catctaccat accacctctt accatctacc   7800
acaccatctt ttatctccat ccctctcaga agcctccaag ctgaatcctg ctttatgtgt   7860
tcatctcagc ccctgcatgg aaagctgacc ccagaggcag aactattccc agagagcttg   7920
gccaagaaaa acaaaactac cagcctggcc aggctcagga gtagtaagct gcagtgtctg   7980
ttgtgttcta gcttcaacag ctgcaggagt tccactctca aatgctccac atttctcaca   8040
tcctcctgat tctggtcact acccatcttc aaagaacaga atatctcaca tcagcatact   8100
gtgaaggact agtcatgggt gcagctgctc agagctgcaa agtcattctg gatggtggag   8160
agcttacaaa catttcatga tgctcccccc gctctgatgg ctggagccca atccctacac   8220
agactcctgc tgtatgtgtt ttcctttcac tctgagccac agccagaggg caggcattca   8280
```

```
gtctcctctt caggctgggg ctggggcact gagaactcac ccaacacctt gctctcactc    8340
cttctgcaaa acaagaaaga gctttgtgct gcagtagcca tgaagaatga aaggaaggct    8400
ttaactaaaa aatgtcagag attattttca accccttact gtggatcacc agcaaggagg    8460
aaacacaaca cagagacatt ttttcccctc aaattatcaa aagaatcact gcatttgtta    8520
aagagagcaa ctgaatcagg aagcagagtt ttgaacatat cagaagttag gaatctgcat    8580
cagagacaaa tgcagtcatg gttgtttgct gcataccagc cctaatcatt agaagcctca    8640
tggacttcaa acatcattcc ctctgacaag atgctctagc ctaactccat gagataaaat    8700
aaatctgcct ttcagagcca aagaagagtc caccagcttc ttctcagtgt gaacaagagc    8760
tccagtcagg ttagtcagtc cagtgcagta gaggagacca gtctgcatcc tctaattttc    8820
aaaggcaaga agatttgttt accctggaca ccaggcacaa gtgaggtcac agagctctta    8880
gatatgcagt cctcatgagt gaggagacta aagcgcatgc catcaagact tcagtgtaga    8940
gaaaacctcc aaaaaagcct cctcactact tctggaatag ctcagaggcc gaggcggcct    9000
cggcctctgc ataaataaaa aaaattagtc agccatgggg cggagaatgg gcggaactgg    9060
gcggagttag gggcgggatg ggcggagtta ggggcgggac tatggttgct gactaattga    9120
gatgcatgct ttgcatactt ctgcctgctg gggagcctgg ggactttcca cacctggttg    9180
ctgactaatt gagatgcatg cttttgcatac ttctgcctgc tggggagcct ggggactttc    9240
cacaccctaa ctgacacaca ttccacagct gcattaatga atcggccaac gcgcggggag    9300
aggcggtttg cgtattgggc gctcttccgc ttcctcgctc actgactcgc tgcgctcggt    9360
cgttcggctg cggcgagcgg tatcagctca ctcaaaggcg gtaatacggt tatccacaga    9420
atcaggggat aacgcaggaa agaacatgtg agcaaaaggc cagcaaaagg ccaggaaccg    9480
taaaaaggcc gcgttgctgg cgttttttcca taggctccgc cccectgacg agcatcacaa    9540 aaatcgacgc tcaagtcaga ggtggcgaaa cccgacagga ctataaagat accaggcgtt    9600
tccccctgga agctccctcg tgcgctctcc tgttccgacc ctgccgctta ccggatacct    9660
gtccgccttt ctcccttcgg gaagcgtggc gctttctcat agctcacgct gtaggtatct    9720
cagttcggtg taggtcgttc gctccaagct gggctgtgtg cacgaacccc ccgttcagcc    9780
cgaccgctgc gccttatccg gtaactatcg tcttgagtcc aacccggtaa gacacgactt    9840
atcgccactg gcagcagcca ctggtaacag gattagcaga gcgaggtatg taggcggtgc    9900
tacagagttc ttgaagtggt ggcctaacta cggctacact agaagaacag tatttggtat    9960
ctgcgctctg ctgaagccag ttaccttcgg aaaaagagtt ggtagctctt gatccggcaa   10020
acaaaccacc gctggtagcg gtggtttttt tgtttgcaag cagcagatta cgcgcagaaa   10080
aaaaggatct caagaagatc ctttgatctt ttctacgggg tctgacgctc agtggaacga   10140
aaactcacgt taagggattt tggtcatgag attatcaaaa aggatcttca cctagatcct   10200
tttaaattaa aaatgaagtt ttaaatcaat ctaaagtata tatgagtaaa cttggtctga   10260
cagttaccaa tgcttaatca gtgaggcacc tatctcagcg atctgtctat ttcgttcatc   10320
catagttgcc tgactcctgc aaaccacgtt gtgtctcaaa atctctgatg ttacattgca   10380
caagataaaa atatatcatc atgaacaata aaactgtctg cttacataaa cagtaataca   10440
aggggtgtta tgagccatat tcaacgggaa acgtcttgct cgaggccgcg attaaattcc   10500
aacatggatg ctgatttata tgggtataaa tgggctcgcg ataatgtcgg gcaatcaggt   10560
gcgacaatct atcgattgta tgggaagccc gatgcgccag agttgtttct gaaacatggc   10620
```

| | |
|---|---|
| aaaggtagcg ttgccaatga tgttacagat gagatggtca gactaaactg gctgacggaa | 10680 |
| tttatgcctc ttccgaccat caagcatttt atccgtactc ctgatgatgc atggttactc | 10740 |
| accactgcga tccccgggaa aacagcattc caggtattag aagaatatcc tgattcaggt | 10800 |
| gaaaatattg ttgatgcgct ggcagtgttc ctgcgccggt tgcattcgat tcctgttttgt | 10860 |
| aattgtcctt ttaacagcga tcgcgtattt cgtctcgctc aggcgcaatc acgaatgaat | 10920 |
| aacggtttgg ttgatgcgag tgattttgat gacgagcgta atggctggcc tgttgaacaa | 10980 |
| gtctggaaag aaatgcataa gcttttgcca ttctcaccgg attcagtcgt cactcatggt | 11040 |
| gatttctcac ttgataacct tatttttgac gagggaaat taataggttg tattgatgtt | 11100 |
| ggacgagtcg gaatcgcaga ccgataccag gatcttgcca tcctatggaa ctgcctcggt | 11160 |
| gagttttctc cttcattaca gaaacggctt tttcaaaaat atggtattga taatcctgat | 11220 |
| atgaataaat tgcagtttca tttgatgctc gatgagtttt tctaagggcg gcctgccacc | 11280 |
| atacccacgc cgaaacaagc gctcatgagc ccgaagtggc gagcccgatc ttccccatcg | 11340 |
| gtgatgtcgg cgatataggc gccagcaacc gcacctgtgg cgccggtgat gagggcgcgc | 11400 |
| caagtcgacg tccggcagtc | 11420 |

<210> SEQ ID NO 4
<211> LENGTH: 11171
<212> TYPE: DNA
<213> ORGANISM: Artificial sequence
<220> FEATURE:
<223> OTHER INFORMATION: Synthetic polynucleotide

<400> SEQUENCE: 4

| | |
|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctgctag ctctgggtat ttaagcccga gtgagcacgc | 180 |
| agggtctcca ttttgaagcg ggaggttacg cgttcgtcga ctactagtgg gtaccagagc | 240 |
| tccctaggtt ctagaaccgg tgacgtctcc catggtgaag cttggatctg agggcggagt | 300 |
| tagggcggag ccaatcagcg tgcgccgttc cgaaagttgc cttttatggc tgggcggaga | 360 |
| atgggcggtg aacgccgatg attatataag gacgcgccgg gtgtggcaca gctagttccg | 420 |
| tcgcagccgg gatttgggtc gcggttcttg tttgtggatc cctgtgatcg tcacttggta | 480 |
| agtcactgac tgtctatgcc tgggaaaggg tgggcaggag atggggcagt gcaggaaaag | 540 |
| tggcactatg aaccctcctg gtggcgaggg gaggggggtg gtcctcgaac gccttgcaga | 600 |
| actggcctgg atacagagtg gaccggctgg ccccatctgg aagacttcga gatacactgt | 660 |
| tgtcttactg cgctcaacag tgtatctcga agtcttccaa atggtgccag ccatcgcagc | 720 |
| ggggtgcagg aaatggggc agccccccctt tttggctatc cttccacgtg ttcttttttg | 780 |
| tatcttttgt gtttcctaga aaacatctca gtcaccaccg cagccctagg aatgcatcta | 840 |
| gacaattgta ctaaccttct tctctttcct ctcctgacag tccggaaagc caccatgggc | 900 |
| cgctgctgct tctacaccgc cggcaccctg agcctgctgc tgctggtgac cagcgtgacc | 960 |
| ctgctggtgg cccgcgtgtt ccagaaggcc gtggaccaga gcatcgagaa gaagatcgtg | 1020 |
| ctgcgcaacg gcaccgaggc cttcgacagc tgggagaagc ccccctgcc cgtgtacacc | 1080 |
| cagttctact cttcaacgt gaccaacccc gaggagatcc tgcgcggcga cccccccgg | 1140 |
| gtggaggagg tgggccccta cacctaccgc gagctgcgca caaggccaa catccagttc | 1200 |
| ggcgacaacg gcaccaccat cagcgccgtg agcaacaagg cctacgtgtt cgagcgcgac | 1260 |

```
cagagcgtgg gcgacgccaa gatcgacctg atccgcaccc tgaacatccc cgtgctgacc    1320
gtgatcgagt ggagccaggt gcacttcctg cgcgagatca tcgaggccat gctgaaggcc    1380
taccagcaga agctgttcgt gacccacacc gtggacgagc tgctgtgggg ctacaaggac    1440
gagatcctga gcctgatcca cgtgttccgc cccgacatca gccctactt cggcctgttc    1500 tacgagaaga acggcaccaa cgacggcgac tacgtgttcc tgaccggcga ggacagctac    1560
ctgaacttca ccaagatcgt ggagtggaac ggcaagacca gcctggactg gtggatcacc    1620
gacaagtgca acatgatcaa cggcaccgac ggcgacagct ccacccccct gatcaccaag    1680
gacgaggtgc tgtacgtgtt ccccagcgac ttctgccgca gcgtgtacat caccttcagc    1740
gactacgaga gcgtgcaggg cctgcccgcc ttccgctaca aggtgcccgc cgagatcctg    1800
gccaacacca gcgacaacgc cggcttctgc atccccgagg gcaactgcct gggcagcggc    1860
gtgctgaacg tgagcatctg caagaacggc gcccccatca tcatgagctt ccccccactc    1920
taccaggccg acgagcgctt cgtgagcgcc atcgagggca tgcaccccaa ccaggaggac    1980
cacgagacct tcgtggacat caacccccctg accggcatca tcctgaaggc cgccaagcgc    2040
ttccagatca acatctacgt gaagaagctg acgacttcg tggagaccgg cgacatccgc    2100
accatggtgt tccccgtgat gtacctgaac gagagcgtgc acatcgacaa ggagaccgcc    2160
agccgcctga gagcatgat caacaccacc ctgatcatca ccaacatccc ctacatcatc    2220
atggccctgg gcgtgttctt cggcctggtg ttcacctggc tggcctgcaa gggccagggc    2280
agcatggacg agggcaccgc cgacgagcgc gcccccctga tccgcaccga gggcagagga    2340
agtcttctga catgcggaga cgtggaagag aatcccggcc ctatggaatt cagcagcccc    2400
agcagagagg aatgccccaa gcctctgagc cgggtgtcaa tcatggccgg atctctgaca    2460
ggactgctgc tgcttcaggc cgtgtcttgg gcttctggcg ctagaccttg catccccaag    2520
agcttcggct acagcagcgt cgtgtgcgtg tgcaatgcca cctactgcga cagcttcgac    2580
cctcctacct ttcctgctct gggcaccttc agcagatacg agagcaccag atccggcaga    2640
cggatggaac tgagcatggg acccatccag gccaatcaca caggcactgg cctgctgctg    2700
acactgcagc ctgagcagaa attccagaaa gtgaaaggct cggcggagc catgacagat    2760 gccgccgctc tgaatatcct ggctctgtct ccaccagctc agaacctgct gctcaagagc    2820
tacttcagcg aggaaggcat cggctacaac atcatcagag tgcccatggc cagctgcgac    2880
ttcagcatca ggacctacac ctacgccgac acacccgacg atttccagct gcacaacttc    2940
agcctgcctg aagaggacac caagctgaag atccctctga tccacagagc cctgcagctg    3000
gcacaaagac ccgtgtcact gctggcctct ccatggacat ctcccacctg gctgaaaaca    3060 aatgcgccctg taatggcaa gggcagcctg aaaggccaac ctggcgacat ctaccaccag    3120
acctgggcca gatacttcgt gaagttcctg gacgcctatg ccgagcacaa gctgcagttt    3180
tgggccgtga cagccgagaa cgaaccttct gctggactgc tgagcggcta ccccttcag    3240 tgcctgggct ttacacccga gcaccagcgg gactttatcg cccgtgatct ggacccaca    3300 ctggccaata gcacccacca taatgtgcgg ctgctgatgc tggacgacca gagactgctt    3360
ctgccccact gggctaaagt ggtgctgaca gatcctgagg ccgccaaata cgtgcacgga    3420
atcgccgtgc actggtatct ggactttctg gcccctgcca aggccacact gggagagaca    3480
cacagactgt tccccaacac catgctgttc gccagcgaag cctgtgtggg cagcaagttt    3540
tgggaacaga gcgtgcggct cggcagctgg gatagaggca tgcagtacag ccacagcatc    3600
```

```
atcaccaacc tgctgtacca cgtcgtcggc tggaccgact ggaatctggc cctgaatcct    3660
gaaggcggcc ctaactgggt ccgaaacttc gtggacagcc ccatcatcgt ggacatcacc    3720
aaggacacct tctacaagca gcccatgttc taccacctgg acacttcag caagttcatc     3780 cccgagggct ctcagcgcgt tggactggtg gcttcccaga gaacgatct ggacgccgtg     3840 gctctgatgc accctgatgg atctgctgtg gtggtggtcc tgaaccgcag cagcaaagat    3900
gtgcccctga ccatcaagga tcccgccgtg ggattcctgg aaacaatcag ccctggctac    3960
tccatccaca cctacctgtg gcgtagacag tgacaattgt taattaagtt taaaccctcg    4020
aggccgcaag ccgcatcgat accgtcgact agagctcgct gatcagcctc gactgtgcct    4080
tctagttgcc agccatctgt tgtttgcccc tcccccgtgc cttccttgac cctggaaggt    4140
gccactccca ctgtcctttc ctaataaaat gaggaaattg catcgcattg tctgagtagg    4200
tgtcattcta ttctgggggg tggggtgggg caggacagca aggggagga ttgggaagac     4260 aatagcaggc atgctgggga gagatccacg ataacaaaca gcttttttgg ggtgaacata    4320
ttgactgaat tccctgcagg ttggccactc cctctctgcg cgctcgctcg ctcactgagg    4380
ccgcccgggc aaagcccggg cgtcgggcga cctttggtcg cccggcctca gtgagcgagc    4440
gagcgcgcag agagggagtg gccaactcca tcactagggg ttcctgcggc cgctcgtacg    4500
gtctcgagga attcctgcag gataacttgc aacctcatt ctaaaatgta tatagaagcc     4560
caaaagacaa taacaaaaat attcttgtag aacaaaatgg gaaagaatgt tccactaaat    4620
atcaagattt agagcaaagc atgagatgtg tggggataga cagtgaggct gataaaatag    4680
agtagagctc agaaacagac ccattgatat atgtaagtga cctatgaaaa aaatatggca    4740
ttttacaatg ggaaaatgat ggtcttttc ttttttagaa aaacagggaa atatatttat      4800
atgtaaaaaa taaaagggaa cccatatgtc ataccataca cacaaaaaaa ttccagtgaa    4860
ttataagtct aaatggagaa ggcaaaactt taaatctttt agaaataat atagaagcat      4920 gcagaccagc ctggccaaca tgatgaaacc ctctctacta ataataaaat cagtagaact    4980
actcaggact actttgagtg ggaagtcctt ttctatgaag acttctttgg ccaaaattag    5040
gctctaaatg caaggagata gtgcatcatg cctggctgca cttactgata aatgatgtta    5100
tcaccatctt taaccaaatg cacaggaaca agttatggta ctgatgtgct ggattgagaa    5160
ggagctctac ttccttgaca ggacacattt gtatcaactt aaaaaagcag attttttgcca   5220 gcagaactat tcattcagag gtaggaaact tagaatagat gatgtcactg attagcatgg    5280
cttccccatc tccacagctg cttcccaccc aggttgccca cagttgagtt tgtccagtgc    5340
tcagggctgc ccactctcag taagaagccc cacaccagcc cctctccaaa tatgttggct    5400
gttccttcca ttaaagtgac cccactttag agcagcaagt ggatttctgt ttcttacagt    5460
tcaggaagga ggagtcagct gtgagaacct ggagcctgag atgcttctaa gtcccactgc    5520
tactggggtc agggaagcca gactccagca tcagcagtca ggagcactaa gcccttgcca    5580
acatcctgtt tctcagagaa actgcttcca ttataatggt tgtcctttt taagctatca     5640 agccaaacaa ccagtgtcta ccattattct catcacctga agccaagggt tctagcaaaa    5700
gtcaagctgt cttgtaatgg ttgatgtgcc tccagcttct gtcttcagtc actccactct    5760
tagcctgctc tgaatcaact ctgaccacag ttccctggag cccctgccac ctgctgcccc    5820
tgccaccttc tccatctgca gtgctgtgca gccttctgca ctcttgcaga gctaataggt    5880
ggagacttga aggaagagga ggaaagtttc tcataatagc cttgctgcaa gctcaaatgg    5940
gaggtgggca ctgtgcccag gagccttgga gcaaaggctg tgcccaacct ctgactgcat    6000
```

```
ccaggtttgg tcttgacaga gataagaagc cctggctttt ggagccaaaa tctaggtcag    6060
acttaggcag gattctcaaa gtttatcagc agaacatgag gcagaagacc ctttctgctc    6120
cagcttcttc aggctcaacc ttcatcagaa tagatagaaa gagaggctgt gagggttctt    6180
aaaacagaag caaatctgac tcagagaata aacaacctcc tagtaaacta cagcttagac    6240
agagcatctg gtggtgagtg tgctcagtgt cctactcaac tgtctggtat cagccctcat    6300
gaggacttct cttcttccc tcatagacct ccatctctgt tttccttagc ctgcagaaat     6360
ctggatggct attcacagaa tgcctgtgct ttcagagttg cattttttct ctggtattct    6420
ggttcaagca tttgaaggta ggaaaggttc tccaagtgca agaaagccag ccctgagcct    6480
caactgcctg gctagtgtgg tcagtaggat gcaaaggctg ttgaatgcca caaggccaaa    6540 cttaacctg tgtaccacaa gcctagcagc agaggcagct ctgctcactg gaactctctg     6600
tcttctttct cctgagcctt ttcttttcct gagttttcta gctctcctca accttacctc    6660
tgccctaccc aggacaaacc caagagccac tgtttctgtg atgtcctctc cagccctaat    6720
taggcatcat gacttcagcc tgaccttcca tgctcagaag cagtgctaat ccacttcaga    6780
tgagctgctc tatgcaacac aggcagagcc tacaaacctt gcaccagag ccctccacat     6840 atcagtgttt gttcatactc acttcaacag caaatgtgac tgctgagatt aagattttac    6900
acaagatggt ctgtaatttc acagttagtt ttatcccatt aggtatgaaa gaattagcat    6960
aattcccctt aaacatgaat gaatcttaga ttttttaata aatagttttg gaagtaaaga    7020
cagagacatc aggagcacaa ggaatagcct gagaggacaa acagaacaag aaagagtctg    7080
gaaatacaca ggatgttctt ggcctcctca aagcaagtgc aagcagatag taccagcagc    7140
cccaggctat cagagcccag tgaagagaag taccatgaaa gccacagctc taaccaccct    7200
gttccagagt gacagacagt ccccaagaca agccagcctg agcagagag agaactgcaa     7260 gagaaagttt ctaatttagg ttctgttaga ttcagacaag tgcaggtcat cctctctcca    7320
cagctactca cctctccagc ctaacaaagc ctgcagtcca cactccaacc ctggtgtctc    7380
acctcctagc ctctcccaac atcctgctct ctgaccatct tctgcatctc tcatctcacc    7440
atctcccact gtctacagcc tactcttgca actaccatct cattttctga catcctgtct    7500
acatcttctg ccatactctg ccatctacca taccacctct taccatctac cacaccatct    7560
tttatctcca tccctctcag aagcctccaa gctgaatcct gctttatgtg ttcatctcag    7620
cccctgcatg gaaagctgac cccagaggca gaactattcc cagagagctt ggccaagaaa    7680
aacaaaacta ccagcctggc caggctcagg agtagtaagc tgcagtgtct gttgtgttct    7740
agcttcaaca gctgcaggag ttccactctc aaatgctcca catttctcac atcctcctga    7800
ttctggtcac tacccatctt caaagaacag aatatctcac atcagcatac tgtgaaggac    7860
tagtcatggg tgcagctgct cagagctgca aagtcattct ggatggtgga gagcttacaa    7920
acatttcatg atgctccccc cgctctgatg gctggagccc aatccctaca cagactcctg    7980
ctgtatgtgt tttccttca ctctgagcca cagccagagg gcaggcattc agtctcctct     8040
tcaggctggg gctggggcac tgagaactca cccaacacct tgctctcact ccttctgcaa    8100
aacaagaaag agctttgtgc tgcagtagcc atgaagaatg aaaggaaggc tttaactaaa    8160
aaatgtcaga gattattttc aaccccttac tgtggatcac cagcaaggag gaaacacaac    8220
acagagacat ttttttcccct caaattatca aaagaatcac tgcatttgtt aaagagagca    8280
actgaatcag gaagcagagt tttgaacata tcagaagtta ggaatctgca tcagagacaa    8340
```

```
atgcagtcat ggttgtttgc tgcataccag ccctaatcat tagaagcctc atggacttca    8400
aacatcattc cctctgacaa gatgctctag cctaactcca tgagataaaa taaatctgcc    8460
tttcagagcc aaagaagagt ccaccagctt cttctcagtg tgaacaagag ctccagtcag    8520
gttagtcagt ccagtgcagt agaggagacc agtctgcatc ctctaatttt caaaggcaag    8580
aagatttgtt taccctggac accaggcaca agtgaggtca cagagctctt agatatgcag    8640
tcctcatgag tgaggagact aaagcgcatg ccatcaagac ttcagtgtag agaaaacctc    8700 caaaaagcc tcctcactac ttctggaata gctcagaggc cgaggcggcc tcggcctctg    8760
cataaataaa aaaaattagt cagccatggg gcggagaatg gcggaactg gcggagtta    8820 ggggcgggat gggcggagtt aggggcggga ctatggttgc tgactaattg agatgcatgc    8880
tttgcatact tctgcctgct ggggagcctg gggactttcc acacctggtt gctgactaat    8940
tgagatgcat gctttgcata cttctgcctg ctggggagcc tggggacttt ccacacccta    9000
actgacacac attccacagc tgcattaatg aatcggccaa cgcgcgggga gaggcggttt    9060
gcgtattggg cgctcttccg cttcctcgct cactgactcg ctgcgctcgg tcgttcggct    9120
gcggcgagcg gtatcagctc actcaaaggc ggtaatacgg ttatccacag aatcagggga    9180
taacgcagga aagaacatgt gagcaaaagg ccagcaaaag gccaggaacc gtaaaaaggc    9240
cgcgttgctg gcgttttcc ataggctccg ccccctgac gagcatcaca aaaatcgacg    9300
ctcaagtcag aggtggcgaa acccgacagg actataaaga taccaggcgt ttccccctgg    9360
aagctccctc gtgcgctctc ctgttccgac cctgccgctt accggatacc tgtccgcctt    9420
tctcccttcg ggaagcgtgg cgctttctca tagctcacgc tgtaggtatc tcagttcggt    9480
gtaggtcgtt cgctccaagc tgggctgtgt gcacgaaccc cccgttcagc ccgaccgctg    9540
cgccttatcc ggtaactatc gtcttgagtc caacccggta agacacgact tatcgccact    9600
ggcagcagcc actggtaaca ggattagcag agcgaggtat gtaggcggtg ctacagagtt    9660
cttgaagtgg tggcctaact acggctacac tagaagaaca gtatttggta tctgcgctct    9720
gctgaagcca gttaccttcg gaaaaagagt tggtagctct tgatccggca aacaaaccac    9780
cgctggtagc ggtggttttt ttgtttgcaa gcagcagatt acgcgcagaa aaaaaggatc    9840
tcaagaagat cctttgatct ttttctacgg gtctgacgct cagtggaacg aaaactcacg    9900
ttaagggatt ttggtcatga gattatcaaa aaggatcttc acctagatcc ttttaaatta    9960
aaaatgaagt tttaaatcaa tctaaagtat atatgagtaa acttggtctg acagttacca    10020
atgcttaatc agtgaggcac ctatctcagc gatctgtcta tttcgttcat ccatagttgc    10080
ctgactcctg caaaccacgt tgtgtctcaa aatctctgat gttacattgc acaagataaa    10140
aatatatcat catgaacaat aaaactgtct gcttacataa acagtaatac aagggggtgtt    10200 atgagccata ttcaacggga aacgtcttgc tcgaggccgc gattaaattc caacatggat    10260
gctgatttat atgggtataa atgggctcgc gataatgtcg ggcaatcagg tgcgacaatc    10320
tatcgattgt atgggaagcc cgatgcgcca gagttgtttc tgaaacatgg caaaggtagc    10380
gttgccaatg atgttacaga tgagatggtc agactaaact ggctgacgga atttatgcct    10440
cttccgacca tcaagcattt tatccgtact cctgatgatg catggttact caccactgcg    10500
atccccggga aaacagcatt ccaggtatta gaagaatatc ctgattcagg tgaaaatatt    10560
gttgatgcgc tggcagtgtt cctgcgccgg ttgcattcga ttcctgtttg taattgtcct    10620
tttaacagcg atcgcgtatt tcgtctcgct caggcgcaat cacgaatgaa taacggtttg    10680
gttgatgcga gtgattttga tgacgagcgt aatggctggc ctgttgaaca agtctggaaa    10740
```

```
gaaatgcata agcttttgcc attctcaccg gattcagtcg tcactcatgg tgatttctca    10800
cttgataacc ttattttga cgaggggaaa ttaataggtt gtattgatgt tggacgagtc    10860
ggaatcgcag accgatacca ggatcttgcc atcctatgga actgcctcgg tgagttttct    10920
ccttcattac agaaacggct ttttcaaaaa tatggtattg ataatcctga tatgaataaa    10980
ttgcagtttc atttgatgct cgatgagttt ttctaagggc ggcctgccac catacccacg    11040
ccgaaacaag cgctcatgag cccgaagtgg cgagcccgat cttccccatc ggtgatgtcg    11100
gcgatatagg cgccagcaac cgcacctgtg gcgccggtga tgagggcgcg ccaagtcgac    11160
gtccggcagt c                                                        11171

<210> SEQ ID NO 5
<211> LENGTH: 11309
<212> TYPE: DNA
<213> ORGANISM: Artificial sequence
<220> FEATURE:
<223> OTHER INFORMATION: Synthetic polynucleotide

<400> SEQUENCE: 5
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctgctag ctctgggtat ttaagcccga gtgagcacgc     180
agggtctcca ttttgaagcg ggaggttacg cgttcgtcga ctactagtgg gtaccagagc     240
tccctaggtt ctagaaccgg tgacgtctcc catggtgaag cttggatctg agggcggagt     300
tagggcggag ccaatcagcg tgcgccgttc cgaaagttgc cttttatggc tgggcggaga     360
atgggcggtg aacgccgatg attatataag gacgcgccgg gtgtggcaca gctagttccg     420
tcgcagccgg gatttgggtc gcggttcttg tttgtggatc cctgtgatcg tcacttggta     480
agtcactgac tgtctatgcc tgggaaaggg tgggcaggag atgggcagt gcaggaaaag     540 tggcactatg aaccctcctg gtggcgaggg gaggggggtg gtcctcgaac gccttgcaga     600
actggcctgg atacagagtg gaccggctgg ccccatctgg aagacttcga gatacactgt     660
tgtcttactg cgctcaacag tgtatctcga agtcttccaa atggtgccag ccatcgcagc     720
ggggtgcagg aaatggggc agcccccctt tttggctatc cttccacgtg ttctttttg      780 tatcttttgt gtttcctaga aaacatctca gtcaccaccg cagccctagg aatgcatcta     840
gacaattgta ctaaccttct tctctttcct ctcctgacag tccggaaagc caccatgtac     900
gccctgttcc tgctggccag cctgctgggc cgcgcctgg ccggcccgt gctgggcctg     960 aaggagtgca cccgcggcag cgccgtgtgg tgccagaacg tgaagaccgc cagcgactgc    1020
ggcgccgtga agcactgcct gcagaccgtg tggaacaagc ccaccgtgaa gagcctgccc    1080
tgcgacatct gcaaggacgt ggtgaccgcc gccggcgaca tgctgaagga caacgccacc    1140
gaggaggaga tcctggtgta cctggagaag acctgcgact ggctgcccaa gcccaacatg    1200
agcgccagct gcaaggagat cgtggacagc tacctgcccg tgatcctgga catcatcaag    1260
ggcgagatga gccgcccgg cgaggtgtgc agcgccctga acctgtgcga gagcctgcag    1320
aagcacctgg ccgagctgaa ccaccagaag cagctggaga gcaacaagat ccccgagctg    1380
gacatgaccg aggtggtggc cccttcatg gccaacatcc cctgctgct gtaccccag     1440 gacggccccc gcagcaagcc ccagcccaag gacaacggcg acgtgtgcca ggactgcatc    1500
cagatggtga ccgacatcca gaccgccgtg cgcaccaaca gcaccttcgt gcaggcctg     1560
```

-continued

```
gtggagcacg tgaaggagga gtgcgaccgc ctgggccccg gcatggccga catctgcaag    1620
aactacatca gccagtacag cgagatcgcc atccagatga tgatgcacat gcagcccaag    1680
gagatctgcg ccctggtggg cttctgcgac gaggtgaagg agatgcccat gcagaccctg    1740
gtgcccgcca aggtggccag caagaacgtg atccccgccc tggagctggt ggagcccatc    1800
aagaagcacg aggtgcccgc caagagcgac gtgtactgcg aggtgtgcga gttcctggtg    1860
aaggaggtga ccaagctgat cgacaacaac aagaccgaga aggagatcct ggacgccttc    1920
gacaagatgt gcagcaagct gcccaagagc ctgagcgagg agtgccagga ggtggtggac    1980
acctacggca gcagcatcct gagcatcctg ctggaggagg tgagccccga gctggtgtgc    2040
agcatgctgc acctgtgcag cggcacccgc ctgcccgccc tgaccgtgca cgtgacccag    2100
cccaaggacg gcggcttctg cgaggtgtgc aagaagctgg tgggctacct ggaccgcaac    2160
ctggagaaga acagcaccaa gcaggagatc ctggccgccc tggagaaggg ctgcagcttc    2220
ctgcccgacc cctaccagaa gcagtgcgac cagttcgtgg ccgagtacga gcccgtgctg    2280
atcgagatcc tggtggaggt gatggacccc agcttcgtgt gcctgaagat cggcgcctgc    2340
cccagcgccc acaagcccct gctgggcacc gagaagtgca tctggggccc cagctactgg    2400
tgccagaaca ccgagaccgc cgcccagtgc aacgccgtgg agcactgcaa cgccacgtg    2460 tggaacgagg gcagaggaag tcttctgaca tgcggagacg tggaagagaa tcccggccct    2520
atggaattca gcgccccag cagagaggaa tgccccaagc ctctgagccg ggtgtcaatc    2580
atggccggat ctctgacagg actgctgctg cttcaggccg tgtcttgggc ttctggcgct    2640
agaccttgca tccccaagag cttcggctac agcagcgtcg tgtgcgtgtg caatgccacc    2700
tactgcgaca gcttcgaccc tcctacccttt cctgctctgg gcaccttcag cagatacgag    2760
agcaccagat ccggcagacg gatggaactg agcatgggac ccatccaggc caatcacaca    2820
ggcactggcc tgctgctgac actgcagcct gagcagaaat ccagaaagt gaaaggcttc    2880 ggcggagcca tgacagatgc cgccgctctg aatatcctgg ctctgtctcc accagctcag    2940
aacctgctgc tcaagagcta cttcagcgag gaaggcatcg gctacaacat catcagagtg    3000
cccatggcca gctgcgactt cagcatcagg acctacacct acgccgacac acccgacgat    3060
ttccagctgc acaacttcag cctgcctgaa gaggacacca agctgaagat ccctctgatc    3120
cacagagccc tgcagctggc acaaagaccc gtgtcactgc tggcctctcc atggacatct    3180
cccacctggc tgaaaacaaa tggcgccgtg aatggcaagg gcagcctgaa aggccaacct    3240
ggcgacatct accaccagac ctgggccaga tacttcgtga agttcctgga cgcctatgcc    3300
gagcacaagc tgcagttttg ggccgtgaca gccgagaacg aaccttctgc tggactgctg    3360
agcggctacc ccttcagtg cctgggcttt acacccgagc accagcggga ctttatcgcc    3420
cgtgatctgg gacccacact ggccaatagc acccaccata atgtgcggct gctgatgctg    3480
gacgaccaga gactgcttct gcccactgg gctaaagtgg tgctgacaga tcctgaggcc    3540
gccaaatacg tgcacggaat cgccgtgcac tggtatctgg actttctggc ccctgccaag    3600
gccacactgg gagagacaca cagactgttc cccaacacca tgctgttcgc cagcgaagcc    3660
tgtgtgggca gcaagttttg ggaacagagc gtgcggctcg gcagctggga tagaggcatg    3720
cagtacagcc acagcatcat caccaacctg ctgtaccacg tcgtcggctg gaccgactgg    3780
aatctggccc tgaatcctga aggcggccct aactgggtcc gaaacttcgt ggacagcccc    3840
atcatcgtgg acatcaccaa ggacaccttc tacaagcagc ccatgttcta ccacctggga    3900
cacttcagca agttcatccc cgagggctct cagcgcgttg gactggtggc ttcccagaag    3960
```

```
aacgatctgg acgccgtggc tctgatgcac cctgatggat ctgctgtggt ggtggtcctg    4020
aaccgcagca gcaaagatgt gcccctgacc atcaaggatc ccgccgtggg attcctggaa    4080
acaatcagcc ctggctactc catccacacc tacctgtggc gtagacagtg acaattgtta    4140
attaagttta aaccctcgag gccgcaagcc gcatcgatac cgtcgactag agctcgctga    4200
tcagcctcga ctgtgccttc tagttgccag ccatctgttg tttgcccctc cccgtgcct     4260 tccttgaccc tggaaggtgc cactcccact gtcctttcct aataaaatga ggaaattgca    4320
tcgcattgtc tgagtaggtg tcattctatt ctggggggtg gggtgggca ggacagcaag     4380 ggggaggatt gggaagacaa tagcaggcat gctgggggaga gatccacgat aacaaacagc   4440
ttttttgggg tgaacatatt gactgaattc cctgcaggtt ggccactccc tctctgcgcg    4500
ctcgctcgct cactgaggcc gcccgggcaa agcccgggcg tcgggcgacc tttggtcgcc    4560
cggcctcagt gagcgagcga gcgcgcagag agggagtggc caactccatc actagggtt    4620 cctgcggccg ctcgtacggt ctcgaggaat tcctgcagga taacttgcca acctcattct    4680
aaaatgtata tagaagccca aaagacaata acaaaaatat tcttgtagaa caaaatggga    4740
aagaatgttc cactaaatat caagatttag agcaaagcat gagatgtgtg gggatagaca    4800
gtgaggctga taaaatagag tagagctcag aaacagaccc attgatatat gtaagtgacc    4860
tatgaaaaaa atatggcatt ttacaatggg aaaatgatgg tcttttctt tttagaaaa     4920 acagggaaat atatttatat gtaaaaaata aagggaacc catatgtcat accatacaca    4980 caaaaaatt ccagtgaatt ataagtctaa atggagaagg caaaacttta aatcttttag     5040
aaaataatat agaagcatgc agaccagcct ggccaacatg atgaaaccct ctctactaat    5100
aataaaatca gtagaactac tcaggactac tttgagtggg aagtcctttt ctatgaagac    5160
ttctttggcc aaaattaggc tctaaatgca aggagatagt gcatcatgcc tggctgcact    5220
tactgataaa tgatgttatc accatcttta accaaatgca caggaacaag ttatggtact    5280
gatgtgctgg attgagaagg agctctactt ccttgacagg acacatttgt atcaacttaa    5340
aaaagcagat ttttgccagc agaactattc attcagaggt aggaaactta gaatagatga    5400
tgtcactgat tagcatggct tccccatctc cacagctgct tcccacccag gttgcccaca    5460
gttgagtttg tccagtgctc agggctgccc actctcagta agaagcccca caccagcccc    5520
tctccaaata tgttggctgt tccttccatt aaagtgaccc cactttagag cagcaagtgg    5580
atttctgttt cttacagttc aggaaggagg agtcagctgt gagaacctgg agcctgagat    5640
gcttctaagt cccactgcta ctggggtcag ggaagccaga ctccagcatc agcagtcagg    5700
agcactaagc ccttgccaac atcctgtttc tcagagaaac tgcttccatt ataatggttg    5760
tcctttttta agctatcaag ccaaacaacc agtgtctacc attattctca tcacctgaag    5820
ccaagggttc tagcaaaagt caagctgtct tgtaatggtt gatgtgcctc cagcttctgt    5880
cttcagtcac tccactctta gcctgctctg aatcaactct gaccacagtt ccctggagcc    5940
cctgccacct gctgcccctg ccaccttctc catctgcagt gctgtgcagc cttctgcact    6000
cttgcagagc taataggtgg agacttgaag gaagaggagg aaagtttctc ataatagcct    6060
tgctgcaagc tcaaatggga ggtgggcact gtgcccagga gccttggagc aaaggctgtg    6120
cccaacctct gactgcatcc aggtttggtc ttgacagaga taagaagccc tggcttttgg    6180
agccaaaatc taggtcagac ttaggcagga ttctcaaagt ttatcagcag aacatgaggc    6240
agaagaccct ttctgctcca gcttcttcag gctcaaccct catcagaata gatagaaaga    6300
```

```
gaggctgtga gggttcttaa aacagaagca aatctgactc agagaataaa caacctccta    6360
gtaaactaca gcttagacag agcatctggt ggtgagtgtg ctcagtgtcc tactcaactg    6420
tctggtatca gccctcatga ggacttctct tctttccctc atagacctcc atctctgttt    6480
tccttagcct gcagaaatct ggatggctat tcacagaatg cctgtgcttt cagagttgca    6540
ttttttctct ggtattctgg ttcaagcatt tgaaggtagg aaaggttctc caagtgcaag    6600
aaagccagcc ctgagcctca actgcctggc tagtgtggtc agtaggatgc aaaggctgtt    6660
gaatgccaca aggccaaact ttaacctgtg taccacaagc ctagcagcag aggcagctct    6720
gctcactgga actctctgtc ttctttctcc tgagcctttt cttttcctga gttttctagc    6780
tctcctcaac cttacctctg ccctacccag acaaaccca agagccactg tttctgtgat     6840
gtcctctcca gccctaatta ggcatcatga cttcagcctg accttccatg ctcagaagca    6900
gtgctaatcc acttcagatg agctgctcta tgcaacacag gcagagccta caaacctttg    6960
caccagagcc ctccacatat cagtgtttgt tcatactcac ttcaacagca aatgtgactg    7020
ctgagattaa gattttacac aagatggtct gtaatttcac agttagtttt atcccattag    7080
gtatgaaaga attagcataa ttccccttaa acatgaatga atcttagatt ttttaataaa    7140
tagttttgga agtaaagaca gagacatcag gagcacaagg aatagcctga gaggacaaac    7200
agaacaagaa agagtctgga aatacacagg atgttcttgg cctcctcaaa gcaagtgcaa    7260
gcagatagta ccagcagccc caggctatca gagcccagtg aagagaagta ccatgaaagc    7320
cacagctcta accaccctgt tccagagtga cagacagtcc ccaagacaag ccagcctgag    7380
ccagagagag aactgcaaga gaaagtttct aatttaggtt ctgttagatt cagacaagtg    7440
caggtcatcc tctctccaca gctactcacc tcccagcct aacaaagcct gcagtccaca     7500
ctccaaccct ggtgtctcac ctcctagcct ctcccaacat cctgctctct gaccatcttc    7560
tgcatctctc atctcaccat ctcccactgt ctacagccta ctcttgcaac taccatctca    7620
ttttctgaca tcctgtctac atcttctgcc atactctgcc atctaccata ccacctctta    7680
ccatctacca caccatcttt tatctccatc cctctcagaa gcctccaagc tgaatcctgc    7740
tttatgtgtt catctcagcc cctgcatgga aagctgaccc cagaggcaga actattccca    7800
gagagcttgg ccaagaaaaa caaaactacc agcctggcca ggctcaggag tagtaagctg    7860
cagtgtctgt tgtgttctag cttcaacagc tgcaggagtt ccactctcaa atgctccaca    7920
tttctcacat cctcctgatt ctggtcacta cccatcttca aagaacagaa tatctcacat    7980
cagcatactg tgaaggacta gtcatgggtg cagctgctca gagctgcaaa gtcattctgg    8040
atggtggaga gcttacaaac atttcatgat gctcccccg ctctgatggc tggagcccaa     8100
tccctacaca gactcctgct gtatgtgttt tcctttcact ctgagccaca gccagagggc    8160
aggcattcag tctcctcttc aggctggggc tgggcactg agaactcacc caacaccttg     8220
ctctcactcc ttctgcaaaa caagaaagag ctttgtgctg cagtagccat gaagaatgaa    8280
aggaaggctt taactaaaaa atgtcagaga ttattttcaa ccccttactg tggatcacca    8340
gcaaggagga acacaacac agagacattt tttccccctca aattatcaaa agaatcactg    8400
catttgttaa agagagcaac tgaatcagga agcagagttt tgaacatatc agaagttagg    8460
aatctgcatc agagacaaat gcagtcatgg ttgtttgctg cataccagcc ctaatcatta    8520
gaagcctcat ggacttcaaa catcattccc tctgacaaga tgctctagcc taactccatg    8580
agataaaata aatctgcctt tcagagccaa agaaagagtcc accagcttct ctcagtgtgt   8640
aacaagagct ccagtcaggt tagtcagtcc agtgcagtag aggagaccag tctgcatcct    8700
```

```
ctaattttca aaggcaagaa gatttgttta ccctggacac caggcacaag tgaggtcaca   8760
gagctcttag atatgcagtc ctcatgagtg aggagactaa agcgcatgcc atcaagactt   8820
cagtgtagag aaaacctcca aaaaagcctc ctcactactt ctggaatagc tcagaggccg   8880
aggcggcctc ggcctctgca taaataaaaa aaattagtca gccatggggc ggagaatggg   8940
cggaactggg cggagttagg ggcgggatgg gcggagttag gggcgggact atggttgctg   9000
actaattgag atgcatgctt tgcatacttc tgcctgctgg ggagcctggg gacttccac    9060 acctggttgc tgactaattg agatgcatgc tttgcatact tctgcctgct ggggagcctg   9120
gggactttcc acaccctaac tgacacacat tccacagctg cattaatgaa tcggccaacg   9180
cgcggggaga ggcggtttgc gtattgggcg ctcttccgct tcctcgctca ctgactcgct   9240
gcgctcggtc gttcggctgc ggcgagcggt atcagctcac tcaaaggcgg taatacggtt   9300
atccacagaa tcaggggata acgcaggaaa gaacatgtga gcaaaaggcc agcaaaaggc   9360
caggaaccgt aaaaaggccg cgttgctggc gtttttccat aggctccgcc cccctgacga   9420
gcatcacaaa aatcgacgct caagtcagag gtggcgaaac ccgacaggac tataaagata   9480
ccaggcgttt ccccctggaa gctccctcgt gcgctctcct gttccgaccc tgccgcttac   9540
cggatacctg tccgcctttc tcccttcggg aagcgtggcg ctttctcata gctcacgctg   9600
taggtatctc agttcggtgt aggtcgttcg ctccaagctg ggctgtgtgc acgaaccccc   9660
cgttcagccc gaccgctgcg ccttatccgg taactatcgt cttgagtcca acccggtaag   9720
acacgactta tcgccactgg cagcagccac tggtaacagg attagcagag cgaggtatgt   9780
aggcggtgct acagagttct tgaagtggtg gcctaactac ggctacacta agaacagt    9840 atttggtatc tgcgctctgc tgaagccagt taccttcgga aaaagagttg gtagctcttg   9900
atccggcaaa caaaccaccg ctggtagcgg tggtttttt gtttgcaagc agcagattac    9960
gcgcagaaaa aaggatctca agaagatcc tttgatctt tctacggggt ctgacgctca    10020
gtggaacgaa aactcacgtt aagggatttt ggtcatgaga ttatcaaaaa ggatcttcac   10080
ctagatcctt ttaaattaaa aatgaagttt taaatcaatc taaagtatat atgagtaaac   10140
ttggtctgac agttaccaat gcttaatcag tgaggcacct atctcagcga tctgtctatt   10200
tcgttcatcc atagttgcct gactcctgca aaccacgttg tgtctcaaaa tctctgatgt   10260
tacattgcac aagataaaaa tatatcatca tgaacaataa aactgtctgc ttacataaac   10320
agtaatacaa gggtgttat gagccatatt caacgggaaa cgtcttgctc gaggccgcga    10380
ttaaattcca acatggatgc tgatttatat gggtataaat gggctcgcga taatgtcggg   10440
caatcaggtg cgacaatcta tcgattgtat gggaagcccg atgcgccaga gttgtttctg   10500
aaacatggca aaggtagcgt tgccaatgat gttacagatg agatggtcag actaaactgg   10560
ctgacggaat ttatgcctct tccgaccatc aagcatttta tccgtactcc tgatgatgca   10620
tggttactca ccactgcgat ccccgggaaa acagcattcc aggtattaga agaatatcct   10680
gattcaggtg aaaatattgt tgatgcgctg gcagtgttcc tgcgccggtt gcattcgatt   10740
cctgtttgta attgtccttt taacagcgat cgcgtatttc gtctcgctca ggcgcaatca   10800
cgaatgaata acggtttggt tgatgcgagt gattttgatg acgagcgtaa tggctggcct   10860
gttgaacaag tctggaaaga atgcataag cttttgccat tctcaccgga ttcagtcgtc    10920
actcatggtg atttctcact tgataacctt ttttttgacg aggggaaatt aataggttgt   10980
attgatgttg gacgagtcgg aatcgcagac cgataccagg atcttgccat cctatggaac   11040
```

| | |
|---|---:|
| tgcctcggtg agttttctcc ttcattacag aaacggcttt ttcaaaaata tggtattgat | 11100 |
| aatcctgata tgaataaatt gcagtttcat ttgatgctcg atgagttttt ctaagggcgg | 11160 |
| cctgccacca tacccacgcc gaaacaagcg ctcatgagcc cgaagtggcg agcccgatct | 11220 |
| tccccatcgg tgatgtcggc gatataggcg ccagcaaccg cacctgtggc gccggtgatg | 11280 |
| agggcgcgcc aagtcgacgt ccggcagtc | 11309 |

```
<210> SEQ ID NO 6
<211> LENGTH: 11293
<212> TYPE: DNA
<213> ORGANISM: Artificial sequence
<220> FEATURE:
<223> OTHER INFORMATION: Synthetic polynucleotide

<400> SEQUENCE: 6
```

| | |
|---|---:|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctgctag ctctgggtat ttaagcccga gtgagcacgc | 180 |
| agggtctcca ttttgaagcg ggaggttacg cgttcgtcga ctactagtgg gtaccagagc | 240 |
| tccctaggtt ctagaaccgg tgacgtctcc catggtgaag cttggatctg agggcggagt | 300 |
| tagggcggag ccaatcagcg tgcgccgttc cgaaagttgc cttttatggc tgggcggaga | 360 |
| atgggcggtg aacgccgatg attatataag gacgcgccgg gtgtggcaca gctagttccg | 420 |
| tcgcagccgg gatttgggtc gcggttcttg tttgtggatc cctgtgatcg tcacttggta | 480 |
| agtcactgac tgtctatgcc tgggaaaggg tgggcaggag atggggcagt gcaggaaaag | 540 |
| tggcactatg aaccctgcag ccctaggaat gcatctagac aattgtacta accttcttct | 600 |
| ctttcctctc ctgacagtcc ggaaagccac catgtacgcc ctgttcctgc tggccagcct | 660 |
| gctgggcgcc gccctggccg gccccgtgct gggcctgaag gagtgcaccc gcggcagcgc | 720 |
| cgtgtggtgc cagaacgtga agaccgccag cgactgcggc gccgtgaagc actgcctgca | 780 |
| gaccgtgtgg aacaagccca ccgtgaagag cctgccctgc gacatctgca aggacgtggt | 840 |
| gaccgccgcc ggcgacatgc tgaaggacaa cgccaccgag gaggagatcc tggtgtacct | 900 |
| ggagaagacc tgcgactggc tgcccaagcc caacatgagc gccagctgca aggagatcgt | 960 |
| ggacagctac ctgcccgtga tcctggacat catcaagggc gagatgagcc gccccggcga | 1020 |
| ggtgtgcagc gccctgaacc tgtgcgagag cctgcagaag cacctggccg agctgaacca | 1080 |
| ccagaagcag ctggagagca acaagatccc cgagctggac atgaccgagg tggtggcccc | 1140 |
| cttcatggcc aacatccccc tgctgctgta cccccaggac ggccccgca gcaagcccca | 1200 |
| gcccaaggac aacggcgacg tgtgccagga ctgcatccag atggtgaccg acatccagac | 1260 |
| cgccgtgcgc accaacagca ccttcgtgca ggccctggtg gagcacgtga aggaggagtg | 1320 |
| cgaccgcctg ggcccggca tggccgacat ctgcaagaac tacatcagcc agtacgcga | 1380 |
| gatcgccatc cagatgatga tgcacatgca gcccaaggag atctgcgccc tggtgggctt | 1440 |
| ctgcgacgag gtgaaggaga tgcccatgca gaccctggtg cccgccaagg tggccagcaa | 1500 |
| gaacgtgatc cccgccctgg agctggtgga gcccatcaag aagcacgagg tgcccgccaa | 1560 |
| gagcgacgtg tactgcgagg tgtgcgagtt cctggtgaag gaggtgacca agctgatcga | 1620 |
| caacaacaag accagaaagg agatcctgga cgccttcgac aagatgtgca gcaagctgcc | 1680 |
| caagagcctg agcgaggagt gccagggagt ggtggacacc tacggcagca gcatcctgag | 1740 |
| catcctgctg gaggaggtga gccccgagct ggtgtgcagc atgctgcacc tgtgcagcgg | 1800 |

```
cacccgcctg cccgccctga ccgtgcacgt gacccagccc aaggacggcg gcttctgcga   1860
ggtgtgcaag aagctggtgg gctacctgga ccgcaacctg gagaagaaca gcaccaagca   1920
ggagatcctg gccgccctgg agaagggctg cagcttcctg cccgacccct accagaagca   1980
gtgcgaccag ttcgtggccg agtacgagcc cgtgctgatc gagatcctgg tggaggtgat   2040
ggaccccagc ttcgtgtgcc tgaagatcgg cgcctgcccc agcgcccaca gcccctgct   2100 gggcaccgag aagtgcatct ggggcccag ctactggtgc cagaacaccg agaccgccgc   2160
ccagtgcaac gccgtggagc actgcaagcg ccacgtgtgg aactgattgt ggccgaaccg   2220
ccgaactcag aggccggccc cagaaaaccc gagcgagtag ggggcggcgc gcaggaggga   2280
ggagaactgg gggcgcggga ggctggtggg tgtgggggt ggagatgtag aagatgtgac   2340
gccgcggccc ggcgggtgcc agattagcgg acgcggtgcc cgcggttgca acgggatccc   2400
gggcgctgca gcttgggagg cggctctccc caggcggcgt ccgcggagac acccatccgt   2460
gaaccccagg tcccgggccg ccggctcgcc gcgcaccagg ggccggcgga cagaagagcg   2520
gccgagcggc tcgaggctgg gggaccgcgg gcgcggccgc gcgctgccgg cgggaggct   2580 ggggggccgg ggccggggcc gtgccccgga gcgggtcgga ggccggggcc ggggccgggg   2640
gacggcggct ccccgcgcgg ctccagcggc tcggggatcc cggccgggcc ccgcagggac   2700
catgatggaa ttcagcagcc ccagcagaga ggaatgcccc aagcctctga ccgggtgtc   2760 aatcatggcc ggatctctga caggactgct gctgcttcag gccgtgtctt gggcttctgg   2820
cgctagacct tgcatcccca agagcttcgg ctacagcagc gtcgtgtgcg tgtgcaatgc   2880
cacctactgc gacagcttcg accctcctac ctttcctgct ctgggcacct tcagcagata   2940
cgagagcacc agatccggca gacggatgga actgagcatg ggacccatcc aggccaatca   3000
cacaggcact ggcctgctgc tgacactgca gcctgagcag aaattccaga agtgaaagg   3060 cttcggcgga gccatgacag atgccgccgc tctgaatatc ctggctctgt ctccaccagc   3120
tcagaacctg ctgctcaaga gctacttcag cgaggaaggc atcggctaca acatcatcag   3180
agtgcccatg gccagctgcg acttcagcat caggacctac acctacgccg acacacccga   3240
cgatttccag ctgcacaact tcagcctgcc tgaagaggac accaagctga agatccctct   3300
gatccacaga gccctgcagc tggcacaaag accgtgtca ctgctggcct ctccatggac   3360
atctcccacc tggctgaaaa caaatggcgc cgtgaatggc aagggcagcc tgaaaggcca   3420
acctggcgac atctaccacc agacctgggc cagatacttc gtgaagttcc tggacgccta   3480
tgccgagcac aagctgcagt tttgggccgt gacagccgag aacgaaccct tgctggact   3540 gctgagcggc tacccctttc agtgcctggg ctttacaccc gagcaccagc gggactttat   3600
cgcccgtgat ctgggacccca cactggccaa tagcacccac cataatgtgc ggctgctgat   3660
gctggacgac cagagactgc ttctgcccca ctgggctaaa gtggtgctga cagatcctga   3720
ggccgccaaa tacgtgcacg gaatcgccgt gcactggtat ctggactttc tggcccctgc   3780
caaggccaca ctgggagaga cacacagact gttccccaac accatgctgt cgccagcga   3840 agcctgtgtg ggcagcaagt tttgggaaca gagcgtgcgg ctcggcagct gggatagagg   3900
catgcagtac agccacagca tcatcaccaa cctgctgtac cacgtcgtcg gctgaccga   3960 ctggaatctg gccctgaatc ctgaaggcgg ccctaactgg gtccgaaact tcgtggacag   4020
ccccatcatc gtggacatca ccaaggacac cttctacaag cagcccatgt tctaccacct   4080
gggacacttc agcaagttca tccccgaggg ctctcagcgc gttggactgg tggcttccca   4140
```

| | |
|---|---|
| gaagaacgat ctggacgccg tggctctgat gcaccctgat ggatctgctg tggtggtggt | 4200 |
| cctgaaccgc agcagcaaag atgtgcccct gaccatcaag gatcccgccg tgggattcct | 4260 |
| ggaaacaatc agccctggct actccatcca cacctacctg tggcgtagac agtgacaatt | 4320 |
| gttaattaag tttaaaccct cgaggccgca agcaataaaa tatctttatt ttcattacat | 4380 |
| ctgtgtgttg gttttttgtg tggagatcca cgataacaaa cagcttttt ggggtgaaca | 4440 |
| tattgactga attccctgca ggttggccac tccctctctg cgcgctcgct cgctcactga | 4500 |
| ggccgcccgg gcaaagcccg ggcgtcgggc gacctttggt cgcccggcct cagtgagcga | 4560 |
| gcgagcgcgc agagagggag tggccaactc catcactagg ggttcctgcg gccgctcgta | 4620 |
| cggtctcgag gaattcctgc aggataactt gccaacctca ttctaaaatg tatatagaag | 4680 |
| cccaaaagac aataacaaaa atattcttgt agaacaaaat gggaagaat gttccactaa | 4740 |
| atatcaagat ttagagcaaa gcatgagatg tgtggggata gacagtgagg ctgataaaat | 4800 |
| agagtagagc tcagaaacag acccattgat atatgtaagt gacctatgaa aaaaatatgg | 4860 |
| cattttacaa tgggaaaatg atggtctttt tcttttttag aaaaacaggg aaatatattt | 4920 |
| atatgtaaaa aataaagggg aacccatatg tcataccata cacacaaaaa aattccagtg | 4980 |
| aattataagt ctaaatggag aaggcaaaac tttaaatctt ttagaaaata atatagaagc | 5040 |
| atgcagacca gcctggccaa catgatgaaa ccctctctac taataataaa atcagtagaa | 5100 |
| ctactcagga ctactttgag tgggaagtcc ttttctatga agacttcttt ggccaaaatt | 5160 |
| aggctctaaa tgcaaggaga tagtgcatca tgcctggctg cacttactga taaatgatgt | 5220 |
| tatcaccatc tttaaccaaa tgcacaggaa caagttatgg tactgatgtg ctggattgag | 5280 |
| aaggagctct acttccttga caggacacat ttgtatcaac ttaaaaagc agattttgc | 5340 |
| cagcagaact attcattcag aggtaggaaa cttagaatag atgatgtcac tgattagcat | 5400 |
| ggcttcccca tctccacagc tgcttcccac ccaggttgcc cacagttgag tttgtccagt | 5460 |
| gctcagggct gcccactctc agtaagaagc cccacaccag cccctctcca aatatgttgg | 5520 |
| ctgttccttc cattaaagtg accccacttt agagcagcaa gtggatttct gtttcttaca | 5580 |
| gttcaggaag gaggagtcag ctgtgagaac ctggagcctg agatgcttct aagtcccact | 5640 |
| gctactgggg tcagggaagc cagactccag catcagcagt caggagcact aagcccttgc | 5700 |
| caacatcctg tttctcagag aaactgcttc cattataatg gttgtccttt tttaagctat | 5760 |
| caagccaaac aaccagtgtc taccattatt ctcatcacct gaagccaagg gttctagcaa | 5820 |
| aagtcaagct gtcttgtaat ggttgatgtg cctccagctt ctgtcttcag tcactccact | 5880 |
| cttagcctgc tctgaatcaa ctctgaccac agttccctgg agccctgcc acctgctgcc | 5940 |
| cctgccacct tctccatctg cagtgctgtg cagccttctg cactcttgca gagctaatag | 6000 |
| gtggagactt gaaggaagag gaggaaagtt tctcataata gccttgctgc aagctcaaat | 6060 |
| gggaggtggg cactgtgccc aggagccttg agcaaaggc tgtgcccaac ctctgactgc | 6120 |
| atccaggttt ggtcttgaca gagataagaa gccctggctt ttggagccaa aatctaggtc | 6180 |
| agacttaggc aggattctca agtttatca gcagaacatg aggcagaaga ccctttctgc | 6240 |
| tccagcttct tcaggctcaa ccttcatcag aatagataga aagagaggct gtgagggttc | 6300 |
| ttaaaacaga agcaaatctg actcagagaa taaacaacct cctagtaaac tacagcttag | 6360 |
| acagagcatc tggtggtgag tgtgctcagt gtcctactca actgtctggt atcagccctc | 6420 |
| atgaggactt ctcttctttc cctcatagac ctccatctct gttttcctta gcctgcagaa | 6480 |
| atctggatgg ctattcacag aatgcctgtg ctttcagagt tgcatttttt ctctggtatt | 6540 |

```
ctggttcaag catttgaagg taggaaaggt tctccaagtg caagaaagcc agccctgagc    6600
ctcaactgcc tggctagtgt ggtcagtagg atgcaaaggc tgttgaatgc cacaaggcca    6660
aactttaacc tgtgtaccac aagcctagca gcagaggcag ctctgctcac tggaactctc    6720
tgtcttcttt ctcctgagcc ttttcttttc ctgagttttc tagctctcct caaccttacc    6780
tctgccctac ccaggacaaa cccaagagcc actgtttctg tgatgtcctc tccagcccta    6840
attaggcatc atgacttcag cctgaccttc catgctcaga agcagtgcta atccacttca    6900
gatgagctgc tctatgcaac acaggcagag cctacaaacc tttgcaccag agccctccac    6960
atatcagtgt ttgttcatac tcacttcaac agcaaatgtg actgctgaga ttaagatttt    7020
acacaagatg gtctgtaatt tcacagttag ttttatccca ttaggtatga agaattagc     7080
ataattcccc ttaaacatga atgaatctta gattttttaa taaatagttt tggaagtaaa    7140
gacagagaca tcaggagcac aaggaatagc ctgagaggac aaacagaaca agaaagagtc    7200
tggaaataca caggatgttc ttggcctcct caaagcaagt gcaagcagat agtaccagca    7260
gccccaggct atcagagccc agtgaagaga agtaccatga aagccacagc tctaaccacc    7320
ctgttccaga gtgacagaca gtccccaaga caagccagcc tgagccagag agagaactgc    7380
aagagaaagt ttctaattta ggttctgtta gattcagaca agtgcaggtc atcctctctc    7440
cacagctact cacctctcca gcctaacaaa gcctgcagtc cacactccaa ccctggtgtc    7500
tcacctccta gcctctccca acatcctgct ctctgaccat cttctgcatc tctcatctca    7560
ccatctccca ctgtctacag cctactcttg caactaccat ctcatttct gacatcctgt     7620
ctacatcttc tgccatactc tgccatctac cataccacct cttaccatct accacaccat    7680
cttttatctc catccctctc agaagcctcc aagctgaatc ctgctttatg tgttcatctc    7740
agcccctgca tggaaagctg accccagagg cagaactatt cccagagagc ttggccaaga    7800
aaaacaaaac taccagcctg gccaggctca ggagtagtaa gctgcagtgt ctgttgtgtt    7860
ctagcttcaa cagctgcagg agttccactc tcaaatgctc cacatttctc acatcctcct    7920
gattctggtc actacccatc ttcaaagaac agaatatctc acatcagcat actgtgaagg    7980
actagtcatg ggtgcagctg ctcagagctg caaagtcatt ctggatggtg gagagcttac    8040
aaacatttca tgatgctccc cccgctctga tggctggagc ccaatcccta cacagactcc    8100
tgctgtatgt gttttccttt cactctgagc cacagccaga gggcaggcat tcagtctcct    8160
cttcaggctg gggctggggc actgagaact cacccaacac cttgctctca ctccttctgc    8220
aaaacaagaa agagctttgt gctgcagtag ccatgaagaa tgaaaggaag ctttaacta    8280
aaaaatgtca gagattattt tcaaccccctt actgtggatc accagcaagg aggaaacaca    8340
acacagagac attttttccc ctcaaattat caaaagaatc actgcatttg ttaaagagag    8400
caactgaatc aggaagcaga gttttgaaca tatcagaagt taggaatctg catcagagac    8460
aaatgcagtc atggttgttt gctgcatacc agccctaatc attagaagcc tcatggactt    8520
caaacatcat tccctctgac aagatgctct agcctaactc catgagataa aataaatctg    8580
cctttcagag ccaaagaaga gtccaccagc ttcttctcag tgtgaacaag agctccagtc    8640
aggttagtca gtccagtgca gtagaggaga ccagtctgca tcctctaatt ttcaaaggca    8700
agaagatttg tttaccctgg acaccaggca caagtgaggt cacagagctc ttagatatgc    8760
agtcctcatg agtgaggaga ctaaagcgca tgccatcaag acttcagtgt agagaaaacc    8820
tccaaaaaag cctcctcact acttctggaa tagctcagag gccgaggcgg cctcggcctc    8880
```

```
tgcataaata aaaaaatta gtcagccatg gggcggagaa tgggcggaac tgggcggagt    8940
tagggcggg  atgggcggag ttaggggcgg gactatggtt gctgactaat tgagatgcat   9000
gctttgcata cttctgcctg ctggggagcc tggggacttt ccacacctgg ttgctgacta   9060
attgagatgc atgctttgca tacttctgcc tgctggggag cctggggact ttccacaccc   9120
taactgacac acattccaca gctgcattaa tgaatcggcc aacgcgcggg gagaggcggt   9180
ttgcgtattg ggcgctcttc cgcttcctcg ctcactgact cgctgcgctc ggtcgttcgg   9240
ctgcggcgag cggtatcagc tcactcaaag gcggtaatac ggttatccac agaatcaggg   9300
gataacgcag gaaagaacat gtgagcaaaa ggccagcaaa aggccaggaa ccgtaaaaag   9360
gccgcgttgc tggcgttttt ccataggctc cgcccccctg acgagcatca caaaaatcga   9420
cgctcaagtc agaggtggcg aaacccgaca ggactataaa gataccaggc gtttccccct   9480
ggaagctccc tcgtgcgctc tcctgttccg accctgccgc ttaccggata cctgtccgcc   9540
tttctccctt cgggaagcgt ggcgctttct catagctcac gctgtaggta tctcagttcg   9600
gtgtaggtcg ttcgctccaa gctgggctgt gtgcacgaac cccccgttca gcccgaccgc   9660
tgcgccttat ccggtaacta tcgtcttgag tccaacccgg taagacacga cttatcgcca   9720
ctggcagcag ccactggtaa caggattagc agagcgaggt atgtaggcgg tgctacagag   9780
ttcttgaagt ggtggcctaa ctacggctac actagaagaa cagtatttgg tatctgcgct   9840
ctgctgaagc cagttacctt cggaaaaaga gttggtagct cttgatccgg caaacaaacc   9900
accgctggta gcggtggttt ttttgtttgc aagcagcaga ttacgcgcag aaaaaaagga   9960
tctcaagaag atcctttgat cttttctacg gggtctgacg ctcagtggaa cgaaaactca  10020
cgttaaggga ttttggtcat gagattatca aaaaggatct tcacctagat ccttttaaat  10080
taaaaatgaa gttttaaatc aatctaaagt atatatgagt aaacttggtc tgacagttac  10140
caatgcttaa tcagtgaggc acctatctca gcgatctgtc tatttcgttc atccatagtt  10200
gcctgactcc tgcaaaccac gttgtgtctc aaaatctctg atgttacatt gcacaagata  10260
aaaatatatc atcatgaaca ataaaactgt ctgcttacat aaacagtaat acaaggggtg  10320
ttatgagcca tattcaacgg gaaacgtctt gctcgaggcc gcgattaaat tccaacatgg  10380
atgctgattt atatgggtat aaatgggctc gcgataatgt cgggcaatca ggtgcgacaa  10440
tctatcgatt gtatgggaag cccgatgcgc cagagttgtt tctgaaacat ggcaaaggta  10500
gcgttgccaa tgatgttaca gatgagatgg tcagactaaa ctggctgacg gaatttatgc  10560
ctcttccgac catcaagcat tttatccgta ctcctgatga tgcatggtta ctcaccactg  10620
cgatccccgg gaaaacagca ttccaggtat tagaagaata tcctgattca ggtgaaaata  10680
ttgttgatgc gctggcagtg ttcctgcgcc ggttgcattc gattcctgtt tgtaattgtc  10740
cttttaacag cgatcgcgta tttcgtctcg ctcaggcgca atcacgaatg aataacggtt  10800
tggttgatgc gagtgatttt gatgacgagc gtaatggctg gcctgttgaa caagtctgga  10860
aagaaatgca taagcttttg ccattctcac cggattcagt cgtcactcat ggtgatttct  10920
cacttgataa ccttattttt gacgagggga attaatagg ttgtattgat gttggacgag  10980
tcggaatcgc agaccgatac caggatcttg ccatcctatg aactgcctc ggtgagtttt  11040
ctccttcatt acagaaacgg cttttcaaa aatatggtat tgataatcct gatatgaata  11100
aattgcagtt tcatttgatg ctcgatgagt tttctaagg cggcctgcc accataccca  11160
cgccgaaaca agcgctcatg agcccgaagt ggcgagccg atcttcccca tcggtgatgt  11220
cggcgatata ggcgccagca accgcacctg tggcgccggt gatgagggcg cgccaagtcg  11280
```
acgtccggca gtc                                                        11293

<210> SEQ ID NO 7
<211> LENGTH: 10700
<212> TYPE: DNA
<213> ORGANISM: Artificial sequence
<220> FEATURE:
<223> OTHER INFORMATION: Synthetic polynucleotide

<400> SEQUENCE: 7

```
ttggccactc cctctctgcg cgctcgctcg ctcactgagg ccgcccgggc aaagcccggg        60
cgtcgggcga cctttggtcg cccggcctca gtgagcgagc gagcgcgcag agagggagtg       120
gccaactcca tcactagggg ttcctgctag ctctgggtat ttaagcccga gtgagcacgc       180
agggtctcca ttttgaagcg ggaggttacg cgttcgtcga ctactagtgg gtaccagagc       240
tccctaggtt ctagaaccgg tgacgtctcc catggtgaag cttggatctg aattcggtac       300
ctagttatta atagtaatca attacggggt cattagttca tagcccatat atggagttcc       360
gcgttacata acttacggta aatggcccgc ctggctgacc gcccaacgac ccccgcccat       420
tgacgtcaat aatgacgtat gttcccatag taacgccaat agggactttc cattgacgtc       480
aatgggtgga gtatttacgg taaactgccc acttggcagt acatcaagtg tatcatatgc       540
caagtacgcc ccctattgac gtcaatgacg gtaaatggcc cgcctggcat tatgcccagt       600
acatgacctt atgggacttt cctacttggc agtacatcta cgtattagtc atcgctatta       660
ccatggtcga ggtgagcccc acgttctgct tcactctccc catctccccc ccctccccac       720
ccccaattt  gtatttattt  attttttaat tattttgtgc  agcgatgggg  gcggggggg    780
ggggggggcg cgcgccaggc ggggcggggc ggggcgaggg gcgggcgggg gcgaggcgga       840
gaggtgcggc ggcagccaat cagagcggcg cgctccgaaa gtttccttt  atggcgaggc       900
ggcggcggcg gcggccctat aaaaagcgaa gcgcgcggcg ggcgggagtc gctgcgacgc       960
tgccttcgcc ccgtgccccg ctccgccgcc gcctcgcgcc gcccgccccg gctctgactg      1020
accgcgttac tcccacaggt gagcgggcgg gacggcccct tctcctccggg ctgtaattag      1080
cgcttggttt aatgacggct tgtttctttt ctgtggctgc gtgaaagcct tgaggggctc      1140
cgggagctag agcctctgct aaccatgttc atgccttctt ctttttccta cagctcctgg      1200
gcaacgtgct ggttattgtg ctgtctcatc attttggcaa agaattcctc gaagatccga      1260
agggaaagtc ttccacgact gtgggatccg ttcgaagata tcaccggttg agccaccatg      1320
gaattcagca gccccagcag agaggaatgc cccaagcctc tgagccgggt gtcaatcatg      1380
gccggatctc tgacaggact gctgctgctt caggccgtgt cttgggcttc tggcgctaga      1440
ccttgcatcc ccaagagctt cggctacagc agcgtcgtgt cgtgtgcaa  tgccacctac      1500
tgcgacagct tcgaccctcc tacctttcct gctctgggca ccttcagcag atacgagagc      1560
accagatccg gcagacggat ggaactgagc atgggaccca tccaggccaa tcacacaggc      1620
actggcctgc tgctgacact gcagcctgag cagaaattcc agaaagtgaa aggcttcggc      1680
ggagccatga cagatgccgc cgctctgaat atcctggctc tgtctccacc agctcagaac      1740
ctgctgctca gagagctactt cagcgaggaa ggcatcggct acaacatcat cagagtgccc      1800
atgccagct  gcgacttcag catcaggacc tacacctacg ccgacacacc cgacgatttc      1860
cagctgcaca acttcagcct gcctgaagag gacaccaagc tgaagatccc tctgatccac      1920
agccctgc   agctggcaca aagacccgtg tcactgctgg cctctccatg gacatctccc      1980
```

```
acctggctga aaacaaatgg cgccgtgaat ggcaagggca gcctgaaagg ccaacctggc    2040
gacatctacc accagacctg gccagatac ttcgtgaagt tcctggacgc ctatgccgag     2100
cacaagctgc agttttgggc cgtgacagcc gagaacgaac cttctgctgg actgctgagc    2160
ggctacccct tcagtgcct gggctttaca cccgagcacc agcggacttt atcgcccgt      2220
gatctgggac ccacactggc caatagcacc caccataatg tgcggctgct gatgctggac    2280
gaccagagac tgcttctgcc ccactgggct aaagtggtgc tgacagatcc tgaggccgcc    2340
aaatacgtgc acggaatcgc cgtgcactgg tatctggact ttctggcccc tgccaaggcc    2400
acactgggag agacacacag actgttcccc aacaccatgc tgttcgccag cgaagcctgt    2460
gtgggcagca gttttggga acagagcgtg cggctcggca gctgggatag aggcatgcag    2520
tacagccaca gcatcatcac caacctgctg taccacgtcg tcggctggac cgactggaat    2580
ctggccctga atcctgaagg cggccctaac tgggtccgaa acttcgtgga cagccccatc    2640
atcgtggaca tcaccaagga caccttctac aagcagccca tgttctacca cctgggacac    2700
ttcagcaagt tcatccccga gggctctcag cgcgttggac tggtggcttc ccagaagaac    2760
gatctggacg ccgtggctct gatgcaccct gatggatctg ctgtggtggt ggtcctgaac    2820
cgcagcagca aagatgtgcc cctgaccatc aaggatcccg ccgtgggatt cctggaaaca    2880
atcagccctg gctactccat ccacacctac ctgtggcgta cagagtgaca attgttaatt    2940
aagtttaaac cctcgaggcc gcaagcttat cgataatcaa cctctggatt acaaaatttg    3000
tgaaagattg actggtattc ttaactatgt tgctcctttt acgctatgtg gatacgctgc    3060
tttaatgcct ttgtatcatg ctattgcttc ccgtatggct ttcattttct cctccttgta    3120
taaatcctgg ttgctgtctc tttatgagga gttgtggccc gttgtcaggc aacgtggcgt    3180
ggtgtgcact gtgtttgctg acgcaacccc cactggttgg ggcattgcca ccacctgtca    3240
gctcctttcc gggactttcg ctttcccccT cctattgcc acggcggaac tcatcgccgc     3300
ctgccttgcc cgctgctgga caggggctcg gctgttgggc actgacaatt ccgtggtgtt    3360
gtcggggaaa tcatcgtcct tccttggct gctcgcctgt gttgccacct ggattctgcg    3420
cgggacgtcc ttctgctacg tcccttcggc cctcaatcca gcggaccttc cttcccgcgg    3480
cctgctgccg gctctgcggc ctcttccgcg tcttcgcctt cgccctcaga cgagtcggat    3540
ctccctttgg gccgcctccc cgcatcgata ccgtcgacta gagctcgctg atcagcctcg    3600
actgtgcctt ctagttgcca gccatctgtt gtttgcccct cccccgtgcc ttccttgacc    3660
ctggaaggtg ccactcccac tgtccttttc taataaaatg aggaaattgc atcgcattgt    3720
ctgagtaggt gtcattctat tctggggggt ggggtggggc aggacagcaa gggggaggat    3780
tgggaagaca atagcaggca tgctggggag agatccacga taacaaacag ctttttttggg   3840
gtgaacatat tgactgaatt ccctgcaggt tggccactcc ctctctgcgc gctcgctcgc    3900
tcactgaggc cgcccgggca agcccgggc gtcgggcgac cttggtcgc ccggcctcag      3960
tgagcgagcg agcgcgcaga gagggagtgg ccaactccat cactagggt tcctgcggcc     4020
gctcgtacgg tctcgaggaa ttcctgcagg ataacttgcc aacctcattc taaaatgtat    4080
atagaagccc aaaagacaat aacaaaaata ttcttgtaga acaaaatggg aaagaatgtt    4140
ccactaaata tcaagattta gagcaaagca tgagatgtgt ggggatagac agtgaggctg    4200
ataaaataga gtagagctca gaaacagacc cattgatata tgtaagtgac ctatgaaaaa    4260
aatatggcat tttacaatgg gaaaatgatg gtctttttct tttttagaaa acagggaaa    4320
tatattata tgtaaaaaat aaaagggaac ccatatgtca taccatacac acaaaaaaat    4380
```

```
tccagtgaat tataagtcta aatggagaag gcaaaacttt aaatctttta gaaataata    4440 tagaagcatg cagaccagcc tggccaacat gatgaaaccc tctctactaa taataaaatc    4500
agtagaacta ctcaggacta ctttgagtgg gaagtccttt tctatgaaga cttctttggc    4560
caaaattagg ctctaaatgc aaggagatag tgcatcatgc ctggctgcac ttactgataa    4620
atgatgttat caccatcttt aaccaaatgc acaggaacaa gttatggtac tgatgtgctg    4680
gattgagaag gagctctact tccttgacag gacacatttg tatcaactta aaaaagcaga    4740
tttttgccag cagaactatt cattcagagg taggaaactt agaatagatg atgtcactga    4800
ttagcatggc ttccccatct ccacagctgc ttcccaccca ggttgcccac agttgagttt    4860
gtccagtgct cagggctgcc cactctcagt aagaagcccc acaccagccc ctctccaaat    4920
atgttggctg ttccttccat taaagtgacc ccactttaga gcagcaagtg gatttctgtt    4980
tcttacagtt caggaaggag gagtcagctg tgagaacctg gagcctgaga tgcttctaag    5040
tcccactgct actggggtca gggaagccag actccagcat cagcagtcag gagcactaag    5100
cccttgccaa catcctgttt ctcagagaaa ctgcttccat tataatggtt gtcctttttt    5160
aagctatcaa gccaaacaac cagtgtctac cattattctc atcacctgaa gccaagggtt    5220
ctagcaaaag tcaagctgtc ttgtaatggt tgatgtgcct ccagcttctg tcttcagtca    5280
ctccactctt agcctgctct gaatcaactc tgaccacagt tccctggagc ccctgccacc    5340
tgctgcccct gccaccttct ccatctgcag tgctgtgcag ccttctgcac tcttgcagag    5400
ctaataggtg gagacttgaa ggaagaggag gaaagtttct cataatagcc ttgctgcaag    5460
ctcaaatggg aggtgggcac tgtgcccagg agccttggag caaaggctgt gcccaacctc    5520
tgactgcatc caggtttggt cttgacagag ataagaagcc ctggcttttg gagccaaaat    5580
ctaggtcaga cttaggcagg attctcaaag tttatcagca gaacatgagg cagaagaccc    5640
tttctgctcc agcttcttca ggctcaacct tcatcagaat agatagaaag agaggctgtg    5700
agggttctta aaacagaagc aaatctgact cagagaataa acaacctcct agtaaactac    5760
agcttagaca gagcatctgg tggtgagtgt gctcagtgtc ctactcaact gtctggtatc    5820
agccctcatg aggacttctc ttcttccct catagacctc catctctgtt ttccttagcc    5880
tgcagaaatc tggatggcta ttcacagaat gcctgtgctt tcagagttgc attttttctc    5940
tggtattctg gttcaagcat ttgaaggtag gaaaggttct ccaagtgcaa gaaagccagc    6000
cctgagcctc aactgcctgg ctagtgtggt cagtaggatg caaaggctgt tgaatgccac    6060
aaggccaaac tttaacctgt gtaccacaag cctagcagca gaggcagctc tgctcactgg    6120
aactctctgt cttctttctc ctgagccttt tcttttcctg agttttctag ctctcctcaa    6180
ccttacctct gccctaccca ggacaaaccc aagagccact gtttctgtga tgtcctctcc    6240
agccctaatt aggcatcatg acttcagcct gaccttccat gctcagaagc agtgctaatc    6300
cacttcagat gagctgctct atgcaacaca ggcagagcct acaaaccttt gcaccagagc    6360
cctccacata tcagtgtttg ttcatactca cttcaacagc aaatgtgact gctgagatta    6420
agattttaca caagatggtc tgtaatttca cagttagttt tatcccatta ggtatgaaag    6480
aattagcata attcccctta aacatgaatg aatcttagat ttttttaataa atagtttgg    6540 aagtaaagac agagacatca ggagcacaag gaatagcctg agaggacaaa cagaacaaga    6600
aagagtctgg aaatacacag gatgttcttg gcctcctcaa agcaagtgca agcagatagt    6660
accagcagcc ccaggctatc agagcccagt gaagagaagt accatgaaag ccacagctct    6720
```

```
aaccaccctg ttccagagtg acagacagtc cccaagacaa gccagcctga gccagagaga    6780
gaactgcaag agaaagtttc taatttaggt tctgttagat tcagacaagt gcaggtcatc    6840
ctctctccac agctactcac ctctccagcc taacaaagcc tgcagtccac actccaaccc    6900
tggtgtctca cctcctagcc tctcccaaca tcctgctctc tgaccatctt ctgcatctct    6960
catctcacca tctcccactg tctacagcct actcttgcaa ctaccatctc attttctgac    7020
atcctgtcta catcttctgc catactctgc catctaccat accacctctt accatctacc    7080
acaccatctt ttatctccat ccctctcaga agcctccaag ctgaatcctg ctttatgtgt    7140
tcatctcagc ccctgcatgg aaagctgacc ccagaggcag aactattccc agagagcttg    7200
gccaagaaaa acaaaactac cagcctggcc aggctcagga gtagtaagct gcagtgtctg    7260
ttgtgttcta gcttcaacag ctgcaggagt tccactctca aatgctccac atttctcaca    7320
tcctcctgat tctggtcact acccatcttc aaagaacaga atatctcaca tcagcatact    7380
gtgaaggact agtcatgggt gcagctgctc agagctgcaa agtcattctg gatggtggag    7440
agcttacaaa catttcatga tgctcccccc gctctgatgg ctggagccca atccctacac    7500
agactcctgc tgtatgtgtt ttcctttcac tctgagccac agccagaggg caggcattca    7560
gtctcctctt caggctgggg ctggggcact gagaactcac ccaacaccttt gctctcactc    7620 cttctgcaaa acaagaaaga gctttgtgct gcagtagcca tgaagaatga aggaaggct    7680 ttaactaaaa aatgtcagag attatttca accccttact gtggatcacc agcaaggagg    7740
aaacacaaca cagagacatt tttcccctc aaattatcaa agaatcact gcatttgtta    7800 aagagagcaa ctgaatcagg aagcagagtt ttgaacatat cagaagttag gaatctgcat    7860
cagagacaaa tgcagtcatg gttgtttgct gcataccagc cctaatcatt agaagcctca    7920
tggacttcaa acatcattcc ctctgacaag atgctctagc ctaactccat gagataaaat    7980
aaatctgcct ttcagagcca agaagagtc caccagcttc ttctcagtgt gaacaagagc    8040
tccagtcagg ttagtcagtc cagtgcagta gaggagacca gtctgcatcc tctaattttc    8100
aaaggcaaga agatttgttt accctggaca ccaggcacaa gtgaggtcac agagctctta    8160
gatatgcagt cctcatgagt gaggagacta aagcgcatgc catcaagact tcagtgtaga    8220
gaaaacctcc aaaaaagcct cctcactact tctggaatag ctcagaggcc gaggcggcct    8280
cggcctctgc ataaataaaa aaaattagtc agccatgggg cggagaatgg gcggaactgg    8340
gcggagttag gggcgggatg ggcggagtta ggggcgggac tatggttgct gactaattga    8400
gatgcatgct ttgcatactt ctgcctgctg gggagcctgg ggactttcca cacctggttg    8460
ctgactaatt gagatgcatg ctttgcatac ttctgcctgc tggggagcct ggggactttc    8520
cacaccctaa ctgacacaca ttccacagct gcattaatga atcggccaac gcgcggggag    8580
aggcggtttg cgtattgggc gctcttccgc ttcctcgctc actgactcgc tgcgctcggt    8640
cgttcggctg cggcgagcgg tatcagctca ctcaaaggcg gtaatacggt tatccacaga    8700
atcaggggat aacgcaggaa agaacatgtg agcaaaaggc cagcaaaagg ccaggaaccg    8760
taaaaaggcc gcgttgctgg cgtttttcca taggctccgc cccctgacg agcatcacaa    8820 aaatcgacgc tcaagtcaga ggtggcgaaa cccgacagga ctataaagat accaggcgtt    8880
tccccctgga agctccctcg tgcgctctcc tgttccgacc ctgccgctta ccggatacct    8940
gtccgccttt ctcccttcgg gaagcgtggc gctttctcat agctcacgct gtaggtatct    9000
cagttcggtg taggtcgttc gctccaagct gggctgtgtg cacgaacccc ccgttcagcc    9060
cgaccgctgc gccttatccg gtaactatcg tcttgagtcc aacccggtaa gacacgactt    9120
```

| | | |
|---|---|---|
| atcgccactg gcagcagcca ctggtaacag gattagcaga gcgaggtatg taggcggtgc | 9180 |
| tacagagttc ttgaagtggt ggcctaacta cggctacact agaagaacag tatttggtat | 9240 |
| ctgcgctctg ctgaagccag ttaccttcgg aaaaagagtt ggtagctctt gatccggcaa | 9300 |
| acaaaccacc gctggtagcg gtggtttttt tgtttgcaag cagcagatta cgcgcagaaa | 9360 |
| aaaaggatct caagaagatc ctttgatctt ttctacgggg tctgacgctc agtggaacga | 9420 |
| aaactcacgt taagggattt tggtcatgag attatcaaaa aggatcttca cctagatcct | 9480 |
| tttaaattaa aaatgaagtt ttaaatcaat ctaaagtata tatgagtaaa cttggtctga | 9540 |
| cagttaccaa tgcttaatca gtgaggcacc tatctcagcg atctgtctat ttcgttcatc | 9600 |
| catagttgcc tgactcctgc aaaccacgtt gtgtctcaaa atctctgatg ttacattgca | 9660 |
| caagataaaa atatatcatc atgaacaata aaactgtctg cttacataaa cagtaataca | 9720 |
| aggggtgtta tgagccatat tcaacgggaa acgtcttgct cgaggccgcg attaaattcc | 9780 |
| aacatggatg ctgatttata tgggtataaa tgggctcgcg ataatgtcgg gcaatcaggt | 9840 |
| gcgacaatct atcgattgta tgggaagccc gatgcgccag agttgtttct gaaacatggc | 9900 |
| aaaggtagcg ttgccaatga tgttacagat gagatggtca gactaaactg gctgacggaa | 9960 |
| tttatgcctc ttccgaccat caagcatttt atccgtactc ctgatgatgc atggttactc | 10020 |
| accactgcga tccccgggaa aacagcattc caggtattag aagaatatcc tgattcaggt | 10080 |
| gaaaatattg ttgatgcgct ggcagtgttc ctgcgccggt tgcattcgat tcctgtttgt | 10140 |
| aattgtcctt ttaacagcga tcgcgtattt cgtctcgctc aggcgcaatc acgaatgaat | 10200 |
| aacggtttgg ttgatgcgag tgattttgat gacgagcgta atggctggcc tgttgaacaa | 10260 |
| gtctggaaag aaatgcataa gcttttgcca ttctcaccgg attcagtcgt cactcatggt | 10320 |
| gatttctcac ttgataacct tattttgac gaggggaaat taataggttg tattgatgtt | 10380 |
| ggacgagtcg gaatcgcaga ccgataccag gatcttgcca tcctatggaa ctgcctcggt | 10440 |
| gagttttctc cttcattaca gaaacggctt tttcaaaaat atggtattga taatcctgat | 10500 |
| atgaataaat tgcagtttca tttgatgctc gatgagtttt tctaagggcg gcctgccacc | 10560 |
| atacccacgc cgaaacaagc gctcatgagc ccgaagtggc gagcccgatc ttccccatcg | 10620 |
| gtgatgtcgg cgatataggc gccagcaacc gcacctgtgg cgccggtgat gagggcgcgc | 10680 |
| caagtcgacg tccggcagtc | 10700 |

<210> SEQ ID NO 8
<211> LENGTH: 10700
<212> TYPE: DNA
<213> ORGANISM: Artificial sequence
<220> FEATURE:
<223> OTHER INFORMATION: Synthetic polynucleotide

<400> SEQUENCE: 8

| | | |
|---|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactatt agatctgatg gccgcgctag ctctgggtat ttaagcccga gtgagcacgc | 180 |
| agggtctcca ttttgaagcg ggaggttacg cgttcgtcga ctactagtgg gtaccagagc | 240 |
| tccctaggtt ctagaaccgg tgacgtctcc catggtgaag cttggatctg aattcggtac | 300 |
| ctagttatta atagtaatca attacggggt cattagttca tagcccatat atggagttcc | 360 |
| gcgttacata acttacggta aatggcccgc ctggctgacc gcccaacgac ccccgcccat | 420 |

```
tgacgtcaat aatgacgtat gttcccatag taacgccaat agggactttc cattgacgtc    480
aatgggtgga gtatttacgg taaactgccc acttggcagt acatcaagtg tatcatatgc    540
caagtacgcc ccctattgac gtcaatgacg gtaaatggcc cgcctggcat tatgcccagt    600
acatgacctt atgggacttt cctacttggc agtacatcta cgtattagtc atcgctatta    660
ccatggtcga ggtgagcccc acgttctgct tcactctccc catctccccc cctccccac    720 ccccaatttt gtatttattt attttttaat tattttgtgc agcgatgggg gcgggggggg    780
ggggggggcg cgcgccaggc ggggcgggc ggggcgaggg gcggggcggg gcgaggcgga    840
gaggtgcggc ggcagccaat cagagcggcg cgctccgaaa gtttccttt atggcgaggc    900 ggcggcggcg gcggccctat aaaaagcgaa gcgcgcggcg ggcgggagtc gctgcgacgc    960
tgccttcgcc ccgtgcccg ctccgccgcc gcctcgcgcc gcccgcccg gctctgactg   1020 accgcgttac tcccacaggt gagcgggcgg gacggccctt ctcctccggg ctgtaattag   1080
cgcttggttt aatgacggct tgtttctttt ctgtggctgc gtgaaagcct tgagggctc   1140 cgggagctag agcctctgct aaccatgttc atgccttctt cttttcctta cagctcctgg   1200
gcaacgtgct ggttattgtg ctgtctcatc attttggcaa agaattcctc gaagatccga   1260
agggaaagtc ttccacgact gtgggatccg ttcgaagata tcaccggttg agccaccatg   1320
gaattcagca gccccagcag agaggaatgc ccaagcctc tgagccgggt gtcaatcatg   1380
gccggatctc tgacaggact gctgctgctt caggccgtgt cttgggcttc tggcgctaga   1440
ccttgcatcc ccaagagctt cggctacagc agcgtcgtgt gcgtgtgcaa tgccacctac   1500
tgcgacagct tcgaccctcc tacctttcct gctctgggca ccttcagcag atacgagagc   1560
accagatccg gcagacggat ggaactgagc atgggaccca tccaggccaa tcacacaggc   1620
actggcctgc tgctgacact gcagcctgag cagaaattcc agaaagtgaa aggcttcggc   1680
ggagccatga cagatgccgc cgctctgaat atcctggctc tgtctccacc agctcagaac   1740
ctgctgctca agagctactt cagcgaggaa ggcatcggct acaacatcat cagagtgccc   1800
atggccagct gcgacttcag catcaggacc tacacctacg ccgacacacc cgacgatttc   1860
cagctgcaca acttcagcct gcctgaagag gacaccaagc tgaagatccc tctgatccac   1920
agagccctgc agctggcaca aagacccgtg tcactgctgg cctctccatg gacatctccc   1980
acctggctga aaacaaatgg cgccgtgaat ggcaagggca gcctgaaagg ccaacctggc   2040
gacatctacc accagacctg gccagatac ttcgtgaagt tcctggacgc ctatgccgag   2100
cacaagctgc agttttgggc cgtgacagcc gagaacgaac cttctgctgg actgctgagc   2160
ggctacccct ttcagtgcct gggctttaca cccgagcacc agcgggactt tatcgcccgt   2220
gatctgggac ccacactggc caatagcacc accataatg tgcggctgct gatgctggac   2280
gaccagagac tgcttctgcc ccactgggct aaagtggtgc tgacagatcc tgaggccgcc   2340
aaatacgtgc acggaatcgc cgtgcactgg tatctggact ttctggcccc tgccaaggcc   2400
acactgggag agacacacag actgttcccc aacaccatgc tgttcgccag cgaagcctgt   2460
gtgggcagca gttttggga acagagcgtg cggctcggca gctgggatag aggcatgcag   2520
tacagccaca gcatcatcac caacctgctg taccacgtcg tcggctggac cgactggaat   2580
ctggccctga atcctgaagg cggccctaac tgggtccgaa acttcgtgga cagccccatc   2640
atcgtggaca tcaccaagga caccttctac aagcagccca tgttctacca cctgggacac   2700
ttcagcaagt tcatccccga gggctctcag cgcgttggac tggtggcttc ccagaagaac   2760
gatctggacg ccgtggctct gatgcaccct gatggatctg ctgtggtggt ggtcctgaac   2820
```

```
cgcagcagca aagatgtgcc cctgaccatc aaggatcccg ccgtgggatt cctggaaaca   2880
atcagccctg gctactccat ccacacctac ctgtggcgta gacagtgaca attgttaatt   2940
aagtttaaac cctcgaggcc gcaagcttat cgataatcaa cctctggatt acaaaatttg   3000
tgaaagattg actggtattc ttaactatgt tgctcctttt acgctatgtg gatacgctgc   3060
tttaatgcct ttgtatcatg ctattgcttc ccgtatggct ttcattttct cctccttgta   3120
taaatcctgg ttgctgtctc tttatgagga gttgtggccc gttgtcaggc aacgtggcgt   3180
ggtgtgcact gtgtttgctg acgcaacccc cactggttgg ggcattgcca ccacctgtca   3240 gctccttttcc gggactttcg ctttcccct cctattgcc acggcggaac tcatcgccgc   3300
ctgccttgcc cgctgctgga caggggctcg gctgttgggc actgacaatt ccgtggtgtt   3360 gtcgggaaa tcatcgtcct ttccttggct gctcgcctgt gttgccacct ggattctgcg   3420
cgggacgtcc ttctgctacg tcccttcggc cctcaatcca gcggaccttc cttcccgcgg   3480
cctgctgccg gctctgcggc ctcttccgcg tcttcgcctt cgccctcaga cgagtcggat   3540 ctcccctttgg gccgcctccc cgcatcgata ccgtcgacta gagctcgctg atcagcctcg   3600
actgtgcctt ctagttgcca gccatctgtt gtttgcccct ccccgtgcc ttccttgacc   3660 ctggaaggtg ccactcccac tgtcctttcc taataaaatg aggaaattgc atcgcattgt   3720
ctgagtaggt gtcattctat ctggggggt ggggtggggc aggacagcaa gggggaggat   3780
tgggaagaca atagcaggca tgctggggag agatccacga taacaaacag cttttttggg   3840
gtgaacatat tgactgaatt ccctgcaggt tggccactcc ctctctgcgc gctcgctcgc   3900
tcactgaggc cgcccgggca agcccgggc gtcgggcgac ctttggtcgc ccggcctcag   3960
tgagcgagcg agcgcgcaga gagggagtgg ccaactccat cactagggt tcctgcggcc   4020 gctcgtacgg tctcgaggaa ttcctgcagg ataacttgcc aacctcattc taaaatgtat   4080
atagaagccc aaaagacaat aacaaaaata ttcttgtaga acaaaatggg aaagaatgtt   4140
ccactaaata tcaagattta gagcaaagca tgagatgtgt ggggatagac agtgaggctg   4200
ataaaataga gtagagctca gaaacagacc cattgatata tgtaagtgac ctatgaaaaa   4260
aatatggcat tttacaatgg gaaaatgatg gtcttttttct tttttagaaa acagggaaa   4320 tatatttata tgtaaaaaat aaagggaac ccatatgtca taccatacac acaaaaaaat   4380
tccagtgaat tataagtcta aatggagaag gcaaaacttt aaatcttta gaaataata   4440 tagaagcatg cagaccagcc tggccaacat gatgaaaccc tctctactaa taataaaatc   4500
agtagaacta ctcaggacta ctttgagtgg gaagtccttt tctatgaaga cttcttttggc   4560 caaaattagg ctctaaatgc aaggagatag tgcatcatgc ctggctgcac ttactgataa   4620
atgatgttat caccatcttt aaccaaatgc acaggaacaa gttatggtac tgatgtgctg   4680
gattgagaag gagctctact tccttgacag gacacatttg tatcaactta aaaagcaga   4740 tttttgccag cagaactatt cattcagagg taggaaactt agaatagatg atgtcactga   4800
ttagcatggc ttccccatct ccacagctgc ttcccaccca ggttgcccac agttgagttt   4860
gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
cccttgccaa catcctgttt ctcagagaaa ctgcttccat tataatggtt gtcctttttt   5160
```

```
aagctatcaa gccaaacaac cagtgtctac cattattctc atcacctgaa gccaagggtt      5220
ctagcaaaag tcaagctgtc ttgtaatggt tgatgtgcct ccagcttctg tcttcagtca      5280
ctccactctt agcctgctct gaatcaactc tgaccacagt tccctggagc ccctgccacc      5340 tgctgccect gccaccttct ccatctgcag tgctgtgcag ccttctgcac tcttgcagag      5400
ctaataggtg gagacttgaa ggaagaggag gaaagtttct cataatagcc ttgctgcaag      5460
ctcaaatggg aggtgggcac tgtgcccagg agccttggag caaaggctgt gcccaacctc      5520
tgactgcatc caggtttggt cttgacagag ataagaagcc ctggcttttg gagccaaaat      5580
ctaggtcaga cttaggcagg attctcaaag tttatcagca gaacatgagg cagaagaccc      5640
tttctgctcc agcttcttca ggctcaacct tcatcagaat agatagaaag agaggctgtg      5700
agggttctta aaacagaagc aaatctgact cagagaataa acaacctcct agtaaactac      5760
agcttagaca gagcatctgg tggtgagtgt gctcagtgtc ctactcaact gtctggtatc      5820
agccctcatg aggacttctc ttctttccct catagacctc catctctgtt ttccttagcc      5880
tgcagaaatc tggatggcta ttcacagaat gcctgtgctt tcagagttgc atttttctc       5940 tggtattctg gttcaagcat ttgaaggtag gaaaggttct ccaagtgcaa gaaagccagc      6000
cctgagcctc aactgcctgg ctagtgtggt cagtaggatg caaaggctgt tgaatgccac      6060
aaggccaaac tttaacctgt gtaccacaag cctagcagca gaggcagctc tgctcactgg      6120
aactctctgt cttctttctc ctgagccttt tcttttcctg agttttctag ctctcctcaa      6180
ccttacctct gccctaccca ggacaaaccc aagagccact gtttctgtga tgtcctctcc      6240
agccctaatt aggcatcatg acttcagcct gaccttccat gctcagaagc agtgctaatc      6300
cacttcagat gagctgctct atgcaacaca ggcagagcct acaaaccttt gcaccagagc      6360
cctccacata tcagtgtttg ttcatactca cttcaacagc aaatgtgact gctgagatta      6420
agattttaca caagatggtc tgtaatttca cagttagttt tatcccatta ggtatgaaag      6480
aattagcata attccccttta aacatgaatg aatcttagat tttttaataa atagttttgg      6540
aagtaaagac agagacatca ggagcacaag gaatagcctg agaggacaaa cagaacaaga      6600
aagagtctgg aaatacacag gatgttcttg gcctcctcaa agcaagtgca agcagatagt      6660
accagcagcc ccaggctatc agagcccagt gaagagaagt accatgaaag ccacagctct      6720
aaccaccctg ttccagagtg acagacagtc cccaagacaa gccagcctga gccagagaga      6780
gaactgcaag agaaagtttc taatttaggt tctgttagat tcagacaagt gcaggtcatc      6840
ctctctccac agctactcac ctctccagcc taacaaagcc tgcagtccac actccaaccc      6900
tggtgtctca cctcctagcc tctcccaaca tcctgctctc tgaccatctt ctgcatctct      6960
catctcacca tctcccactg tctacagcct actcttgcaa ctaccatctc attttctgac      7020
atcctgtcta catcttctgc catactctgc catctaccat accacctctt accatctacc      7080
acaccatctt ttatctccat ccctctcaga agcctccaag ctgaatcctg ctttatgtgt      7140
tcatctcagc ccctgcatgg aaagctgacc ccagaggcag aactattccc agagagcttg      7200
gccaagaaaa acaaaactac cagcctggcc aggctcagga gtagtaagct gcagtgtctg      7260
ttgtgttcta gcttcaacag ctgcaggagt tccactctca aatgctccac atttctcaca      7320
tcctcctgat tctggtcact acccatcttc aaagaacaga atatctcaca tcagcatact      7380
gtgaaggact agtcatgggt gcagctgctc agagctgcaa agtcattctg gatggtggag      7440
agcttacaaa catttcatga tgctcccccc gctctgatgg ctggagccca atccctacac      7500
agactcctgc tgtatgtgtt ttcctttcac tctgagccac agccagaggg caggcattca      7560
```

```
gtctcctctt caggctgggg ctggggcact gagaactcac ccaacacctt gctctcactc    7620
cttctgcaaa acaagaaaga gctttgtgct gcagtagcca tgaagaatga aaggaaggct    7680
ttaactaaaa aatgtcagag attattttca accccttact gtggatcacc agcaaggagg    7740
aaacacaaca cagagacatt ttttcccctc aaattatcaa aagaatcact gcatttgtta    7800
aagagagcaa ctgaatcagg aagcagagtt ttgaacatat cagaagttag gaatctgcat    7860
cagagacaaa tgcagtcatg gttgtttgct gcataccagc cctaatcatt agaagcctca    7920
tggacttcaa acatcattcc ctctgacaag atgctctagc ctaactccat gagataaaat    7980
aaatctgcct ttcagagcca aagaagagtc caccagcttc ttctcagtgt gaacaagagc    8040
tccagtcagg ttagtcagtc cagtgcagta gaggagacca gtctgcatcc tctaattttc    8100
aaaggcaaga agatttgttt accctggaca ccaggcacaa gtgaggtcac agagctctta    8160
gatatgcagt cctcatgagt gaggagacta aagcgcatgc catcaagact tcagtgtaga    8220
gaaaacctcc aaaaaagcct cctcactact tctggaatag ctcagaggcc gaggcggcct    8280
cggcctctgc ataaataaaa aaaattagtc agccatgggg cggagaatgg gcggaactgg    8340
gcggagttag gggcgggatg ggcggagtta ggggcgggac tatggttgct gactaattga    8400
gatgcatgct ttgcatactt ctgcctgctg gggagcctgg ggactttcca cacctggttg    8460
ctgactaatt gagatgcatg cttttgcatac ttctgcctgc tggggagcct ggggactttc    8520
cacaccctaa ctgacacaca ttccacagct gcattaatga atcggccaac gcgcggggag    8580
aggcggtttg cgtattgggc gctcttccgc ttcctcgctc actgactcgc tgcgctcggt    8640
cgttcggctg cggcgagcgg tatcagctca ctcaaaggcg gtaatacggt tatccacaga    8700
atcaggggat aacgcaggaa agaacatgtg agcaaaaggc cagcaaaagg ccaggaaccg    8760
taaaaaggcc gcgttgctgg cgttttttcca taggctccgc ccccctgacg agcatcacaa    8820
aaatcgacgc tcaagtcaga ggtggcgaaa cccgacagga ctataaagat accaggcgtt    8880
tccccctgga agctccctcg tgcgctctcc tgttccgacc ctgccgctta ccggatacct    8940
gtccgccttt ctcccttcgg gaagcgtggc gctttctcat agctcacgct gtaggtatct    9000
cagttcggtg taggtcgttc gctccaagct gggctgtgtg cacgaacccc ccgttcagcc    9060
cgaccgctgc gccttatccg gtaactatcg tcttgagtcc aacccggtaa gacacgactt    9120
atcgccactg gcagcagcca ctggtaacag gattagcaga gcgaggtatg taggcggtgc    9180
tacagagttc ttgaagtggt ggcctaacta cggctacact agaagaacag tatttggtat    9240
ctgcgctctg ctgaagccag ttaccttcgg aaaaagagtt ggtagctctt gatccggcaa    9300
acaaaccacc gctggtagcg gtggtttttt tgtttgcaag cagcagatta cgcgcagaaa    9360
aaaaggatct caagaagatc ctttgatctt ttctacgggg tctgacgctc agtggaacga    9420
aaactcacgt taagggattt tggtcatgag attatcaaaa aggatcttca cctagatcct    9480
tttaaattaa aaatgaagtt ttaaatcaat ctaaagtata tatgagtaaa cttggtctga    9540
cagttaccaa tgcttaatca gtgaggcacc tatctcagcg atctgtctat ttcgttcatc    9600
catagttgcc tgactcctgc aaaccacgtt gtgtctcaaa atctctgatg ttacattgca    9660
caagataaaa atatatcatc atgaacaata aaactgtctg cttacataaa cagtaataca    9720 agggggtgtta tgagccatat tcaacgggaa acgtcttgct cgaggccgcg attaaattcc    9780
aacatggatg ctgatttata tgggtataaa tgggctcgcg ataatgtcgg gcaatcaggt    9840
gcgacaatct atcgattgta tgggaagccc gatgcgccag agttgtttct gaaacatggc    9900
```

| | |
|---|---:|
| aaaggtagcg ttgccaatga tgttacagat gagatggtca gactaaactg gctgacggaa | 9960 |
| tttatgcctc ttccgaccat caagcatttt atccgtactc ctgatgatgc atggttactc | 10020 |
| accactgcga tccccgggaa aacagcattc caggtattag aagaatatcc tgattcaggt | 10080 |
| gaaaatattg ttgatgcgct ggcagtgttc ctgcgccggt tgcattcgat tcctgtttgt | 10140 |
| aattgtcctt ttaacagcga tcgcgtattt cgtctcgctc aggcgcaatc acgaatgaat | 10200 |
| aacggtttgg ttgatgcgag tgattttgat gacgagcgta atggctggcc tgttgaacaa | 10260 |
| gtctggaaag aaatgcataa gcttttgcca ttctcaccgg attcagtcgt cactcatggt | 10320 |
| gatttctcac ttgataacct tattttttgac gagggggaaat taataggttg tattgatgtt | 10380 |
| ggacgagtcg gaatcgcaga ccgataccag gatcttgcca tcctatggaa ctgcctcggt | 10440 |
| gagttttctc cttcattaca gaaacggctt tttcaaaaat atggtattga taatcctgat | 10500 |
| atgaataaat tgcagtttca tttgatgctc gatgagtttt tctaagggcg gcctgccacc | 10560 |
| atacccacgc cgaaacaagc gctcatgagc ccgaagtggc gagcccgatc ttccccatcg | 10620 |
| gtgatgtcgg cgatataggc gccagcaacc gcacctgtgg cgccggtgat gagggcgcgc | 10680 |
| caagtcgacg tccggcagtc | 10700 |

<210> SEQ ID NO 9
<211> LENGTH: 10700
<212> TYPE: DNA
<213> ORGANISM: Artificial sequence
<220> FEATURE:
<223> OTHER INFORMATION: Synthetic polynucleotide

<400> SEQUENCE: 9

| | |
|---|---:|
| ttggccactc cctctctgcg cgctcgctcg ctcactgagg ccgggcgacc aaaggtcgcc | 60 |
| cgacgcccgg gctttgcccg ggcggcctca gtgagcgagc gagcgcgcag agagggagtg | 120 |
| gccaactcca tcactagggg ttcctgctag ctctgggtat ttaagcccga gtgagcacgc | 180 |
| agggtctcca ttttgaagcg ggaggttacg cgttcgtcga ctactagtgg gtaccagagc | 240 |
| tccctaggtt ctagaaccgg tgacgtctcc catggtgaag cttggatctg aattcggtac | 300 |
| ctagttatta atagtaatca attacggggt cattagttca tagcccatat atggagttcc | 360 |
| gcgttacata acttacggta aatggcccgc ctggctgacc gcccaacgac ccccgcccat | 420 |
| tgacgtcaat aatgacgtat gttcccatag taacgccaat agggactttc cattgacgtc | 480 |
| aatgggtgga gtatttacgg taaactgccc acttggcagt acatcaagtg tatcatatgc | 540 |
| caagtacgcc ccctattgac gtcaatgacg gtaaatggcc cgcctggcat tatgcccagt | 600 |
| acatgacctt atgggacttt cctacttggc agtacatcta cgtattagtc atcgctatta | 660 |
| ccatggtcga ggtgagcccc acgttctgct tcactctccc catctccccc cctccccac | 720 |
| ccccaatttt gtatttattt attttttaat tattttgtgc agcgatgggg gcggggggg | 780 |
| ggggggggcg cgcgccaggc ggggcgggc ggggcgaggg gcgggcggg gcgaggcgga | 840 |
| gaggtgcggc ggcagccaat cagagcggcg cgctccgaaa gtttccttt atggcgaggc | 900 |
| ggcggcggcg gcggccctat aaaaagcgaa gcgcgcggcg gcgggagtc gctgcgacgc | 960 |
| tgccttcgcc ccgtgcccg ctccgccgcc gcctcgcgcc gcccgcccg gctctgactg | 1020 |
| accgcgttac tcccacaggt gagcgggcgg gacggccctt ctcctccggg ctgtaattag | 1080 |
| cgcttggttt aatgacggct tgtttctttt ctgtggctgc gtgaaagcct tgaggggctc | 1140 |
| cgggagctag agcctctgct aaccatgttc atgccttctt ctttttccta cagctcctgg | 1200 |
| gcaacgtgct ggttattgtg ctgtctcatc attttggcaa agaattcctc gaagatccga | 1260 |

```
agggaaagtc ttccacgact gtgggatccg ttcgaagata tcaccggttg agccaccatg    1320
gaattcagca gccccagcag agaggaatgc cccaagcctc tgagccgggt gtcaatcatg    1380
gccggatctc tgacaggact gctgctgctt caggccgtgt cttgggcttc tggcgctaga    1440
ccttgcatcc ccaagagctt cggctacagc agcgtcgtgt gcgtgtgcaa tgccacctac    1500
tgcgacagct tcgaccctcc tacctttcct gctctgggca ccttcagcag atacgagagc    1560
accagatccg gcagacggat ggaactgagc atgggaccca tccaggccaa tcacacaggc    1620
actggcctgc tgctgacact gcagcctgag cagaaattcc agaaagtgaa aggcttcggc    1680
ggagccatga cagatgccgc cgctctgaat atcctggctc tgtctccacc agctcagaac    1740
ctgctgctca agagctactt cagcgaggaa ggcatcggct acaacatcat cagagtgccc    1800
atggccagct gcgacttcag catcaggacc tacacctacg ccgacacacc cgacgatttc    1860
cagctgcaca acttcagcct gcctgaagag gacaccaagc tgaagatccc tctgatccac    1920
agagccctgc agctggcaca agacccgtg tcactgctgg cctctccatg acatctccc    1980 acctggctga aaacaaatgg cgccgtgaat ggcaagggca gcctgaaagg ccaacctggc    2040
gacatctacc accagacctg gccagatac ttcgtgaagt tcctggacgc ctatgccgag    2100
cacaagctgc agttttgggc cgtgacagcc gagaacgaac cttctgctgg actgctgagc    2160
ggctacccct tcagtgcct gggctttaca cccgagcacc agcgggactt tatcgcccgt    2220
gatctgggac ccacactggc caatagcacc caccataatg tgcggctgct gatgctggac    2280
gaccagagac tgcttctgcc ccactgggct aaagtggtgc tgacagatcc tgaggccgcc    2340
aaatacgtgc acggaatcgc cgtgcactgg tatctggact ttctggcccc tgccaaggcc    2400
acactgggag agacacacag actgttcccc aacaccatgc tgttcgccag cgaagcctgt    2460
gtgggcagca gttttggga acagagcgtg cggctcggca gctgggatag aggcatgcag    2520
tacagccaca gcatcatcac caacctgctg taccacgtcg tcggctggac cgactggaat    2580
ctggccctga atcctgaagg cggccctaac tgggtccgaa acttcgtgga cagccccatc    2640
atcgtggaca tcaccaagga cacttctac aagcagccca tgttctacca cctgggacac    2700
ttcagcaagt tcatccccga gggctctcag gcgcttggac tggtggcttc ccagaagaac    2760
gatctggacg ccgtggctct gatgcaccct gatggatctg ctgtggtggt ggtcctgaac    2820
cgcagcagca aagatgtgcc cctgaccatc aaggatcccg ccgtgggatt cctggaaaca    2880
atcagccctg ctactccat ccacacctac ctgtggcgta gacagtgaca attgttaatt    2940
aagtttaaac cctcgaggcc gcaagcttat cgataatcaa cctctggatt acaaaatttg    3000
tgaaagattg actggtattc ttaactatgt tgctcctttt acgctatgtg gatacgctgc    3060
tttaatgcct ttgtatcatg ctattgcttc ccgtatggct ttcattttct cctccttgta    3120
taaatcctgg ttgctgtctc tttatgagga gttgtggccc gttgtcaggc aacgtggcgt    3180
ggtgtgcact gtgtttgctg acgcaacccc cactggttgg gcattgcca ccacctgtca    3240 gctcctttcc gggactttcg ctttccccct ccctattgcc acggcggaac tcatcgccgc    3300
ctgccttgcc cgctgctgga caggggctcg gctgttgggc actgacaatt ccgtggtgtt    3360
gtcggggaaa tcatcgtcct ttccttggct gctcgcctgt gttgccacct ggattctgcg    3420
cgggacgtcc ttctgctacg tcccttcggc cctcaatcca gcggaccttc cttcccgcgg    3480
cctgctgccg gctctgcggc ctcttccgcg tcttcgcctt cgccctcaga cgagtcggat    3540
ctccctttgg gccgcctccc cgcatcgata ccgtcgacta gagctcgctg atcagcctcg    3600
```

```
actgtgcctt ctagttgcca gccatctgtt gtttgcccct cccccgtgcc ttccttgacc   3660
ctggaaggtg ccactcccac tgtcctttcc taataaaatg aggaaattgc atcgcattgt   3720
ctgagtaggt gtcattctat tctgggggt ggggtggggc aggacagcaa gggggaggat    3780
tgggaagaca atagcaggca tgctggggag agatccacga taacaaacag ctttttttggg  3840
gtgaacatat tgactgaatt ccctgcaggt tggccactcc ctctctgcgc gctcgctcgc   3900
tcactgaggc cgcccgggca aagcccgggc gtcgggcgac cttggtcgc ccggcctcag    3960
tgagcgagcg agcgcgcaga gagggagtgg ccaactccat cactaggggt tcctgcggcc   4020
gctcgtacgg tctcgaggaa ttcctgcagg ataacttgcc aacctcattc taaaatgtat   4080
atagaagccc aaaagacaat aacaaaaata ttcttgtaga acaaaatggg aaagaatgtt   4140
ccactaaata tcaagattta gagcaaagca tgagatgtgt ggggatagac agtgaggctg   4200
ataaaataga gtagagctca gaaacagacc cattgatata tgtaagtgac ctatgaaaaa   4260
aatatggcat tttacaatgg gaaaatgatg gtcttttttct tttttagaaa acagggaaa   4320
tatatttata tgtaaaaaat aaaagggaac ccatatgtca taccatacac acaaaaaaat  4380
tccagtgaat tataagtcta aatggagaag gcaaaacttt aaatctttta gaaaataata  4440
tagaagcatg cagaccagcc tggccaacat gatgaaaccc tctctactaa taataaaatc  4500
agtagaacta ctcaggacta ctttgagtgg gaagtccttt tctatgaaga cttctttggc  4560
caaaattagg ctctaaatgc aaggagatag tgcatcatgc ctggctgcac ttactgataa  4620
atgatgttat caccatcttt aaccaaatgc acaggaacaa gttatggtac tgatgtgctg  4680
gattgagaag gagctctact tccttgacag gacacatttg tatcaactta aaaaagcaga  4740
ttttttgccag cagaactatt cattcagagg taggaaactt agaatagatg atgtcactga  4800
ttagcatggc ttccccatct ccacagctgc ttcccaccca ggttgcccac agttgagttt   4860
gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
cccttgccaa catcctgttt ctcagagaaa ctgcttccat tataatggtt gtccttttttt  5160
aagctatcaa gccaaacaac cagtgtctac cattattctc atcacctgaa gccagggtt    5220
ctagcaaaag tcaagctgtc ttgtaatggt tgatgtgcct ccagcttctg tcttcagtca   5280
ctccactctt agcctgctct gaatcaactc tgaccacagt tccctggagc ccctgccacc   5340
tgctgcccct gccaccttct ccatctgcag tgctgtgcag ccttctgcac tcttgcagag   5400
ctaataggtg gagacttgaa ggaagaggag gaaagtttct cataatagcc ttgctgcaag   5460
ctcaaatggg aggtgggcac tgtgcccagg agccttggag caaaggctgt gcccaacctc   5520
tgactgcatc caggttttggt cttgacagag ataagaagcc ctggcttttg gagccaaaat  5580
ctaggtcaga cttaggcagg attctcaaag tttatcagca gaacatgagg cagaagaccc   5640
tttctgctcc agcttcttca ggctcaacct tcatcagaat agatagaaag agaggctgtg   5700
agggttctta aaacagaagc aaatctgact cagagaataa acaacctcct agtaaactac   5760
agcttagaca gagcatctgg tggtgagtgt gctcagtgtc ctactcaact gtctggtatc   5820
agccctcatg aggacttctc ttctttccct catagacctc catctctgtt ttccttagcc   5880
tgcagaaaatc tggatggcta ttcacagaat gcctgtgctt tcagagttgc atttttttctc 5940
tggtattctg gttcaagcat ttgaaggtag gaaaggttct ccaagtgcaa gaaagccagc   6000
```

```
cctgagcctc aactgcctgg ctagtgtggt cagtaggatg caaaggctgt tgaatgccac     6060
aaggccaaac tttaacctgt gtaccacaag cctagcagca gaggcagctc tgctcactgg     6120
aactctctgt cttctttctc ctgagccttt tcttttcctg agttttctag ctctcctcaa     6180
ccttacctct gccctaccca ggacaaaccc aagagccact gtttctgtga tgtcctctcc     6240
agccctaatt aggcatcatg acttcagcct gaccttccat gctcagaagc agtgctaatc     6300
cacttcagat gagctgctct atgcaacaca ggcagagcct acaaaccttt gcaccagagc     6360
cctccacata tcagtgtttg ttcatactca cttcaacagc aaatgtgact gctgagatta     6420
agattttaca caagatggtc tgtaatttca cagttagttt tatcccatta ggtatgaaag     6480
aattagcata attccccta aacatgaatg aatcttagat ttttaataa atagttttgg      6540 aagtaaagac agagacatca ggagcacaag gaatagcctg agaggacaaa cagaacaaga     6600
aagagtctgg aaatacacag gatgttcttg gcctcctcaa agcaagtgca agcagatagt     6660
accagcagcc ccaggctatc agagcccagt gaagagaagt accatgaaag ccacagctct     6720
aaccaccctg ttccagagtg acagacagtc cccaagacaa gccagcctga gccagagaga     6780
gaactgcaag agaaagtttc taatttaggt tctgttagat tcagacaagt gcaggtcatc     6840
ctctctccac agctactcac ctccagcc taacaaagcc tgcagtccac actccaaccc      6900
tggtgtctca cctcctagcc tctcccaaca tcctgctctc tgaccatctt ctgcatctct     6960
catctcacca tctcccactg tctacagcct actcttgcaa ctaccatctc attttctgac     7020
atcctgtcta catcttctgc catactctgc catctaccat accacctctt accatctacc     7080
acaccatctt ttatctccat ccctctcaga agcctccaag ctgaatcctg ctttatgtgt     7140
tcatctcagc ccctgcatgg aaagctgacc cagaggcag aactattccc agagagcttg      7200
gccaagaaaa acaaaactac cagcctggcc aggctcagga gtagtaagct gcagtgtctg     7260
ttgtgttcta gcttcaacag ctgcaggagt tccactctca aatgctccac atttctcaca     7320
tcctcctgat tctggtcact acccatcttc aaagaacaga atatctcaca tcagcatact     7380
gtgaaggact agtcatgggt gcagctgctc agagctgcaa agtcattctg gatggtggag     7440
agcttacaaa catttcatga tgctcccccc gctctgatgg ctggagccca atccctacac     7500
agactcctgc tgtatgtgtt ttcctttcac tctgagccac agccagaggg caggcattca     7560
gtctcctctt caggctgggg ctggggcact gagaactcac ccaacacctt gctctcactc     7620
cttctgcaaa acaagaaaga gctttgtgct gcagtagcca tgaagaatga aaggaaggct     7680
ttaactaaaa aatgtcagag attatttca accccttact gtggatcacc agcaaggagg      7740
aaacacaaca cagagacatt ttttcccctc aaattatcaa agaatcact gcatttgtta      7800 aagagagcaa ctgaatcagg aagcagagtt ttgaacatat cagaagttag gaatctgcat     7860
cagagacaaa tgcagtcatg gttgtttgct gcataccagc cctaatcatt agaagcctca     7920
tggacttcaa acatcattcc ctctgacaag atgctctagc ctaactccat gagataaaat     7980
aaatctgcct ttcagagcca aagaagagtc caccagcttc ttctcagtgt gaacaagagc     8040
tccagtcagg ttagtcagtc cagtgcagta gaggagacca gtctgcatcc tctaattttc     8100
aaaggcaaga agatttgttt accctggaca ccaggcacaa gtgaggtcac agagctctta     8160
gatatgcagt cctcatgagt gaggagacta aagcgcatgc catcaagact tcagtgtaga     8220
gaaaacctcc aaaaaagcct cctcactact tctggaatag ctcagaggcc gaggcggcct     8280
cggcctctgc ataaataaaa aaaattagtc agccatgggg cggagaatgg gcggaactgg     8340
```

```
gcggagttag gggcgggatg ggcggagtta ggggcgggac tatggttgct gactaattga   8400
gatgcatgct ttgcatactt ctgcctgctg gggagcctgg ggactttcca cacctggttg   8460
ctgactaatt gagatgcatg ctttgcatac ttctgcctgc tggggagcct ggggactttc   8520
cacaccctaa ctgacacaca ttccacagct gcattaatga atcggccaac gcgcggggag   8580
aggcggtttg cgtattgggc gctcttccgc ttcctcgctc actgactcgc tgcgctcggt   8640
cgttcggctg cggcgagcgg tatcagctca ctcaaaggcg gtaatacggt tatccacaga   8700
atcaggggat aacgcaggaa agaacatgtg agcaaaaggc cagcaaaagg ccaggaaccg   8760
taaaaaggcc gcgttgctgg cgttttccca taggctccgc cccccgacga gcatcacaa   8820
aaatcgacgc tcaagtcaga ggtggcgaaa cccgacagga ctataaagat accaggcgtt   8880
tccccctgga agctccctcg tgcgctctcc tgttccgacc ctgccgctta ccggatacct   8940
gtccgccttt ctcccttcgg gaagcgtggc gctttctcat agctcacgct gtaggtatct   9000
cagttcggtg taggtcgttc gctccaagct gggctgtgtg cacgaacccc ccgttcagcc   9060
cgaccgctgc gccttatccg gtaactatcg tcttgagtcc aacccggtaa gacacgactt   9120
atcgccactg gcagcagcca ctggtaacag gattagcaga gcgaggtatg taggcggtgc   9180
tacagagttc ttgaagtggt ggcctaacta cggctacact agaagaacag tatttggtat   9240
ctgcgctctg ctgaagccag ttaccttcgg aaaaagagtt ggtagctctt gatccggcaa   9300
acaaaccacc gctggtagcg gtggtttttt tgtttgcaag cagcagatta cgcgcagaaa   9360
aaaaggatct caagaagatc ctttgatctt ttctacgggg tctgacgctc agtggaacga   9420
aaactcacgt taagggattt tggtcatgag attatcaaaa aggatcttca cctagatcct   9480
tttaaattaa aaatgaagtt ttaaatcaat ctaaagtata tatgagtaaa cttggtctga   9540
cagttaccaa tgcttaatca gtgaggcacc tatctcagcg atctgtctat ttcgttcatc   9600
catagttgcc tgactcctgc aaaccacgtt gtgtctcaaa atctctgatg ttacattgca   9660
caagataaaa atatatcatc atgaacaata aaactgtctg cttacataaa cagtaataca   9720
aggggtgtta tgagccatat tcaacgggaa acgtcttgct cgaggccgcg attaaattcc   9780
aacatggatg ctgatttata tgggtataaa tgggctcgcg ataatgtcgg gcaatcaggt   9840
gcgacaatct atcgattgta tgggaagccc gatgcgccag agttgtttct gaaacatggc   9900
aaaggtagcg ttgccaatga tgttacagat gagatggtca gactaaactg gctgacggaa   9960
tttatgcctc ttccgaccat caagcatttt atccgtactc ctgatgatgc atggttactc  10020
accactgcga tccccgggaa aacagcattc caggtattag aagaatatcc tgattcaggt  10080
gaaaatattg ttgatgcgct ggcagtgttc ctgcgccggt tgcattcgat tcctgtttgt  10140
aattgtcctt ttaacagcga tcgcgtattt cgtctcgctc aggcgcaatc acgaatgaat  10200
aacggtttgg ttgatgcgag tgattttgat gacgagcgta atggctggcc tgttgaacaa  10260
gtctggaaag aaatgcataa gcttttgcca ttctcaccgg attcagtcgt cactcatggt  10320
gatttctcac ttgataacct tattttttgac gaggggaaat taataggttg tattgatgtt  10380
ggacgagtcg gaatcgcaga ccgataccag gatcttgcca tcctatggaa ctgcctcggt  10440
gagttttctc cttcattaca gaaacggctt tttcaaaaat atggtattga taatcctgat  10500
atgaataaat tgcagtttca tttgatgctc gatgagtttt tctaagggcg gcctgccacc  10560
atacccacgc cgaaacaagc gctcatgagc ccgaagtggc gagcccgatc ttccccatcg  10620
gtgatgtcgc cgatataggc gccagcaacc gcacctgtgg cgccggtgat gagggcgcgc  10680
caagtcgacg tccggcagtc                                              10700
```

<210> SEQ ID NO 10
<211> LENGTH: 10700
<212> TYPE: DNA
<213> ORGANISM: Artificial sequence
<220> FEATURE:
<223> OTHER INFORMATION: Synthetic polynucleotide

<400> SEQUENCE: 10

| | | | | | |
|---|---|---|---|---|---|
| ttggccactc | cctctctgcg | cgctcgctcg | ctcactgagg | ccgcccgggc | aaagcccggg | 60 |
| cgtcgggcga | cctttggtcg | cccggcctca | gtgagcgagc | gagcgcgcag | agagggagtg | 120 |
| gccaactcca | tcactagggg | ttcctgctag | ctctgggtat | ttaagcccga | gtgagcacgc | 180 |
| agggtctcca | ttttgaagcg | ggaggttacg | cgttcgtcga | ctactagtgg | gtaccagagc | 240 |
| tccctaggtt | ctagaaccgg | tgacgtctcc | catggtgaag | cttggatctg | aattcggtac | 300 |
| ctagttatta | atagtaatca | attacgggt | cattagttca | tagcccatat | atggagttcc | 360 |
| gcgttacata | acttacggta | aatggcccgc | ctggctgacc | gcccaacgac | ccccgcccat | 420 |
| tgacgtcaat | aatgacgtat | gttcccatag | taacgccaat | agggactttc | cattgacgtc | 480 |
| aatgggtgga | gtatttacgg | taaactgccc | acttggcagt | acatcaagtg | tatcatatgc | 540 |
| caagtacgcc | ccctattgac | gtcaatgacg | gtaaatggcc | cgcctggcat | tatgcccagt | 600 |
| acatgacctt | atgggacttt | cctacttggc | agtacatcta | cgtattagtc | atcgctatta | 660 |
| ccatggtcga | ggtgagcccc | acgttctgct | tcactctccc | catctccccc | cctccccac | 720 |
| ccccaatttt | gtatttattt | attttttaat | tattttgtgc | agcgatgggg | gcggggggg | 780 |
| ggggggggcg | cgcgccaggc | ggggcgggc | ggggcgaggg | gcggggcggg | gcgaggcgga | 840 |
| gaggtgcggc | ggcagccaat | cagagcggcg | cgctccgaaa | gtttccttt | atggcgaggc | 900 |
| ggcggcggcg | gcggccctat | aaaaagcgaa | gcgcgcggcg | ggcgggagtc | gctgcgacgc | 960 |
| tgccttcgcc | ccgtgccccg | ctccgccgcc | gcctcgcgcc | gcccgcccg | gctctgactg | 1020 |
| accgcgttac | tcccacaggt | gagcgggcgg | gacggccctt | ctcctccggg | ctgtaattag | 1080 |
| cgcttggttt | aatgacgcct | tgtttctttt | ctgtggctgc | gtgaaagcct | tgaggggctc | 1140 |
| cgggagctag | agcctctgct | aaccatgttc | atgccttctt | ctttttccta | cagctcctgg | 1200 |
| gcaacgtgct | ggttattgtg | ctgtctcatc | attttggcaa | agaattcctc | gaagatccga | 1260 |
| agggaaagtc | ttccacgact | gtgggatccg | ttcgaagata | tcaccggttg | agccaccatg | 1320 |
| gaattcagca | gccccagcag | agaggaatgc | cccaagcctc | tgagccgggt | gtcaatcatg | 1380 |
| gccggatctc | tgacaggact | gctgctgctt | caggccgtgt | cttgggcttc | tggcgctaga | 1440 |
| ccttgcatcc | ccaagagctt | cggctacagc | agcgtcgtgt | gcgtgtgcaa | tgccacctac | 1500 |
| tgcgacagct | tcgaccctcc | tacctttcct | gctctgggca | ccttcagcag | atacgagagc | 1560 |
| accagatccg | gcagacggat | ggaactgagc | atgggaccca | tccaggccaa | tcacacaggc | 1620 |
| actgcctgc | tgctgacact | gcagcctgag | cagaaattcc | agaaagtgaa | aggcttcggc | 1680 |
| ggagccatga | cagatgccgc | cgctctgaat | atcctggctc | tgtctccacc | agctcagaac | 1740 |
| ctgctgctca | agagctactt | cagcgaggaa | ggcatcggct | acaacatcat | cagagtgccc | 1800 |
| atggccagct | gcgacttcag | catcaggacc | tacacctacg | ccgacacacc | cgacgatttc | 1860 |
| cagctgcaca | acttcagcct | gcctgaagag | gacaccaagc | tgaagatccc | tctgatccac | 1920 |
| agagccctgc | agctggcaca | aagacccgtg | tcactgctgg | cctctccatg | gacatctccc | 1980 |
| acctggctga | aaacaaatgg | cgccgtgaat | ggcaagggca | gcctgaaagg | ccaacctggc | 2040 |

```
gacatctacc accagacctg ggccagatac ttcgtgaagt tcctggacgc ctatgccgag    2100
cacaagctgc agttttgggc cgtgacagcc gagaacgaac cttctgctgg actgctgagc    2160
ggctacccct ttcagtgcct gggctttaca cccgagcacc agcgggactt tatcgcccgt    2220
gatctgggac ccacactggc caatagcacc caccataatg tgcggctgct gatgctggac    2280
gaccagagac tgcttctgcc ccactgggct aaagtggtgc tgacagatcc tgaggccgcc    2340
aaatacgtgc acggaatcgc cgtgcactgg tatctggact ttctggcccc tgccaaggcc    2400
acactgggag agacacacag actgttcccc aacaccatgc tgttcgccag cgaagcctgt    2460
gtgggcagca agttttggga acagagcgtg cggctcggca gctgggatag aggcatgcag    2520
tacagccaca gcatcatcac caacctgctg taccacgtcg tcggctggac cgactggaat    2580
ctggccctga tcctgaaggc ggccctaacc tgggtccgaa acttcgtgga cagccccatc    2640
atcgtggaca tcaccaagga caccttctac aagcagccca tgttctacca cctgggacac    2700
ttcagcaagt tcatcccgga gggctctcag cgcgttggac tggtggcttc ccagaagaac    2760
gatctggacg ccgtggctct gatgcaccct gatggatctg ctgtggtggt ggtcctgaac    2820
cgcagcagca agatgtgcc cctgaccatc aaggatcccg ccgtgggatt cctggaaaca    2880
atcagccctg gctactccat ccacacctac ctgtggcgta gacagtgaca attgttaatt    2940
aagtttaaac cctcgaggcc gcaagcttat cgataatcaa cctctggatt acaaatttg    3000 tgaaagattg actggtattc ttaactatgt tgctcctttt acgctatgtg gatacgctgc    3060
tttaatgcct ttgtatcatg ctattgcttc ccgtatggct ttcattttct cctccttgta    3120
taaatcctgg ttgctgtctc tttatgagga gttgtggccc gttgtcaggc aacgtggcgt    3180
ggtgtgcact gtgtttgctg acgcaacccc cactggttgg ggcattgcca ccacctgtca    3240 gctccttttcc gggactttcg ctttcccccct cctattgcc acggcggaac tcatcgccgc    3300
ctgccttgcc cgctgctgga caggggctcg gctgttgggc actgacaatt ccgtggtgtt    3360
gtcggggaaa tcatcgtcct ttccttggct gctcgcctgt gttgccacct ggattctgcg    3420
cgggacgtcc ttctgctacg tcccttcggc cctcaatcca gcggaccttc cttcccgcgg    3480
cctgctgccg gctctgcggc ctcttccgcg tcttcgcctt cgccctcaga cgagtcggat    3540
ctccctttgg gccgcctccc cgcatcgata ccgtcgacta gagctcgctg atcagcctcg    3600
actgtgcctt ctagttgcca gccatctgtt gtttgcccct cccccgtgcc ttccttgacc    3660
ctggaaggtg ccactcccac tgtcctttcc taataaaatg aggaaattgc atcgcattgt    3720
ctgagtaggt gtcattctat tctgggggt ggggtgggc aggacagcaa ggggaggat    3780 tgggaagaca atagcaggca tgctggggag agatccacga taacaaacag ctttttttggg    3840 gtgaacatat tgactgaatt ccctgcagga ggaacccta gtgatggagt tggccactcc    3900
ctctctgcgc gctcgctcgc tcactgaggc cgcccgggca aagcccgggc gtcgggcgac    3960
ctttggtcgc ccggcctcag tgagcgagcg agcgcgcaga gagggagtgg ccaagcggcc    4020
gctcgtacgg tctcgaggaa ttcctgcagg ataacttgcc aacctcattc taaaatgtat    4080
atagaagccc aaaagacaat aacaaaaata ttcttgtaga acaaaatggg aaagaatgtt    4140
ccactaaata tcaagattta gagcaaagca tgagatgtgt ggggatagac agtgaggctg    4200
ataaaataga gtagagctca gaaacagacc cattgatata tgtaagtgac ctatgaaaaa    4260
aatatggcat tttacaatgg gaaaatgatg gtcttttttct tttttagaaa acagggaaa    4320 tatatttata tgtaaaaaat aaagggaac ccatatgtca taccatacac acaaaaaaat    4380
tccagtgaat tataagtcta aatggagaag gcaaaacttt aaatcttttta gaaaataata    4440
```

```
tagaagcatg cagaccagcc tggccaacat gatgaaaccc tctctactaa taataaaatc   4500
agtagaacta ctcaggacta ctttgagtgg gaagtccttt tctatgaaga cttcttggc    4560 caaaattagg ctctaaatgc aaggagatag tgcatcatgc ctggctgcac ttactgataa   4620
atgatgttat caccatcttt aaccaaatgc acaggaacaa gttatggtac tgatgtgctg   4680
gattgagaag gagctctact tccttgacag gacacatttg tatcaactta aaaagcaga    4740 ttttgccag cagaactatt cattcagagg taggaaactt agaatagatg atgtcactga    4800
ttagcatggc ttccccatct ccacagctgc ttcccaccca ggttgcccac agttgagttt    4860
gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
cccttgccaa catcctgttt ctcagagaaa ctgcttccat tataatggtt gtccttttt    5160 aagctatcaa gccaaacaac cagtgtctac cattattctc atcacctgaa gccaagggtt   5220
ctagcaaaag tcaagctgtc ttgtaatggt tgatgtgcct ccagcttctg tcttcagtca   5280
ctccactctt agcctgctct gaatcaactc tgaccacagt tccctggagc ccctgccacc   5340
tgctgcccct gccaccttct ccatctgcag tgctgtgcag ccttctgcac tcttgcagag   5400
ctaataggtg gagacttgaa ggaagaggag gaaagtttct cataatagcc ttgctgcaag   5460
ctcaaatggg aggtgggcac tgtgcccagg agccttggag caaaggctgt gcccaacctc   5520
tgactgcatc caggtttggt cttgacagag ataagaagcc ctggcttttg gagccaaaat   5580
ctaggtcaga cttaggcagg attctcaaag tttatcagca gaacatgagg cagaagaccc    5640
tttctgctcc agcttcttca ggctcaacct tcatcagaat agatagaaag agaggctgtg   5700
agggttctta aaacagaagc aaatctgact cagagaataa acaacctcct agtaaactac   5760
agcttagaca gagcatctgg tggtgagtgt gctcagtgtc ctactcaact gtctggtatc   5820
agccctcatg aggacttctc ttcttttccct catagacctc catctctgtt ttccttagcc   5880
tgcagaaatc tggatggcta ttcacagaat gcctgtgctt tcagagttgc attttttctc   5940
tggtattctg gttcaagcat ttgaaggtag gaaaggttct ccaagtgcaa gaaagccagc   6000
cctgagcctc aactgcctgg ctagtgtggt cagtaggatg caaaggctgt tgaatgccac   6060
aaggccaaac tttaacctgt gtaccacaag cctagcagca gaggcagctc tgctcactgg   6120
aactctctgt cttctttctc ctgagccttt tcttttcctg agttttctag ctctcctcaa   6180
ccttacctct gccctaccca ggacaaaccc aagagccact gtttctgtga tgtcctctcc   6240
agccctaatt aggcatcatg acttcagcct gaccttccat gctcagaagc agtgctaatc   6300
cacttcagat gagctgctct atgcaacaca ggcagagcct acaaaccttt gcaccagagc   6360
cctccacata tcagtgtttg ttcatactca cttcaacagc aaatgtgact gctgagatta   6420
agattttaca caagatggtc tgtaatttca cagttagttt tatcccatta ggtatgaaag   6480
aattagcata attccccta aacatgaatg aatcttagat tttttaataa atagttttgg    6540
aagtaaagac agagacatca ggagcacaag gaatagcctg agaggacaaa cagaacaaga   6600 agagtctgg aaatacacag gatgttcttg gcctcctcaa agcaagtgca agcagatagt     6660
accagcagcc ccaggctatc agagcccagt gaagagaagt accatgaaag ccacagctct    6720
aaccaccctg ttccagagtg acagacagtc cccaagacaa gccagcctga gccagagaga    6780
```

```
gaactgcaag agaaagtttc taatttaggt tctgttagat tcagacaagt gcaggtcatc    6840
ctctctccac agctactcac ctctccagcc taacaaagcc tgcagtccac actccaaccc    6900
tggtgtctca cctcctagcc tctcccaaca tcctgctctc tgaccatctt ctgcatctct    6960
catctcacca tctcccactg tctacagcct actcttgcaa ctaccatctc attttctgac    7020
atcctgtcta catcttctgc catactctgc catctaccat accacctctt accatctacc    7080
acaccatctt ttatctccat ccctctcaga agcctccaag ctgaatcctg ctttatgtgt    7140
tcatctcagc ccctgcatgg aaagctgacc ccagaggcag aactattccc agagagcttg    7200
gccaagaaaa acaaaactac cagcctggcc aggctcagga gtagtaagct gcagtgtctg    7260
ttgtgttcta gcttcaacag ctgcaggagt tccactctca aatgctccac atttctcaca    7320
tcctcctgat tctggtcact acccatcttc aaagaacaga atatctcaca tcagcatact    7380
gtgaaggact agtcatgggt gcagctgctc agagctgcaa agtcattctg gatggtggag    7440
agcttacaaa catttcatga tgctccccc gctctgatgg ctggagccca atccctacac    7500
agactcctgc tgtatgtgtt ttcctttcac tctgagccac agccagaggg caggcattca    7560
gtctcctctt caggctgggg ctggggcact gagaactcac ccaacacctt gctctcactc    7620
cttctgcaaa acaagaaaga gctttgtgct gcagtagcca tgaagaatga aaggaaggct    7680
ttaactaaaa aatgtcagag attattttca accccttact gtggatcacc agcaaggagg    7740
aaacacaaca cagagacatt ttttcccctc aaattatcaa aagaatcact gcatttgtta    7800
aagagagcaa ctgaatcagg aagcagagtt ttgaacatat cagaagttag gaatctgcat    7860
cagagacaaa tgcagtcatg gttgtttgct gcataccagc cctaatcatt agaagcctca    7920
tggacttcaa acatcattcc ctctgacaag atgctctagc ctaactccat gagataaaat    7980
aaatctgcct ttcagagcca aagaagagtc caccagcttc ttctcagtgt gaacaagagc    8040
tccagtcagg ttagtcagtc cagtgcagta gaggagacca gtctgcatcc tctaattttc    8100
aaaggcaaga agatttgttt accctggaca ccaggcacaa gtgaggtcac agagctctta    8160
gatatgcagt cctcatgagt gaggagacta agcgcatgc catcaagact tcagtgtaga    8220
gaaaacctcc aaaaaagcct cctcactact tctggaatag ctcagaggcc gaggcggcct    8280
cggcctctgc ataaataaaa aaattagtc agccatgggg cggagaatgg gcggaactgg    8340
gcggagttag gggcgggatg ggcggagtta ggggcgggac tatggttgct gactaattga    8400
gatgcatgct ttgcatactt ctgcctgctg gggagcctgg ggactttcca cacctggttg    8460
ctgactaatt gagatgcatg cttttgcatac ttctgcctgc tggggagcct ggggactttc    8520
cacaccctaa ctgacacaca ttccacagct gcattaatga atcggccaac gcgcggggag    8580
aggcggtttg cgtattgggc gctcttccgc ttcctcgctc actgactcgc tgcgctcggt    8640
cgttcggctg cggcgagcgg tatcagctca ctcaaaggcg gtaatacggt tatccacaga    8700
atcaggggat aacgcaggaa agaacatgtg agcaaaaggc cagcaaaagg ccaggaaccg    8760
taaaaaggcc gcgttgctgg cgttttttcca taggctccgc cccctgacg agcatcacaa    8820
aaatcgacgc tcaagtcaga ggtggcgaaa cccgacagga ctataaagat accaggcgtt    8880
tccccctgga agctccctcg tgcgctctcc tgttccgacc ctgccgctta ccggatacct    8940
gtccgccttt ctcccttcgg gaagcgtggc gctttctcat agctcacgct gtaggtatct    9000
cagttcggtg taggtcgttc gctccaagct gggctgtgtg cacgaacccc ccgttcagcc    9060
cgaccgctgc gccttatccg gtaactatcg tcttgagtcc aacccggtaa gacacgactt    9120
atcgccactg gcagcagcca ctggtaacag gattagcaga gcgaggtatg taggcggtgc    9180
```

-continued

```
tacagagttc ttgaagtggt ggcctaacta cggctacact agaagaacag tatttggtat    9240
ctgcgctctg ctgaagccag ttaccttcgg aaaaagagtt ggtagctctt gatccggcaa    9300
acaaaccacc gctggtagcg gtggtttttt tgtttgcaag cagcagatta cgcgcagaaa    9360
aaaaggatct caagaagatc ctttgatctt ttctacgggg tctgacgctc agtggaacga    9420
aaactcacgt taagggattt tggtcatgag attatcaaaa aggatcttca cctagatcct    9480
tttaaattaa aaatgaagtt ttaaatcaat ctaaagtata tatgagtaaa cttggtctga    9540
cagttaccaa tgcttaatca gtgaggcacc tatctcagcg atctgtctat ttcgttcatc    9600
catagttgcc tgactcctgc aaaccacgtt gtgtctcaaa atctctgatg ttacattgca    9660
caagataaaa atatatcatc atgaacaata aaactgtctg cttacataaa cagtaataca    9720 agggtgtta tgagccatat tcaacgggaa acgtcttgct cgaggccgcg attaaattcc     9780
aacatggatg ctgatttata tgggtataaa tgggctcgcg ataatgtcgg gcaatcaggt    9840
gcgacaatct atcgattgta tgggaagccc gatgcgccag agttgtttct gaaacatggc    9900
aaaggtagcg ttgccaatga tgttacagat gagatggtca gactaaactg gctgacggaa    9960
tttatgcctc ttccgaccat caagcatttt atccgtactc ctgatgatgc atggttactc   10020
accactgcga tccccgggaa aacagcattc caggtattag aagaatatcc tgattcaggt   10080
gaaaatattg ttgatgcgct ggcagtgttc ctgcgccggt tgcattcgat tcctgttgt    10140 aattgtcctt ttaacagcga tcgcgtattt cgtctcgctc aggcgcaatc acgaatgaat   10200
aacggtttgg ttgatgcgag tgattttgat gacgagcgta atggctggcc tgttgaacaa   10260
gtctggaaag aaatgcataa gcttttgcca ttctcaccgg attcagtcgt cactcatggt   10320
gatttctcac ttgataacct tatttttgac gaggggaaat taataggttg tattgatgtt   10380
ggacgagtcg gaatcgcaga ccgataccag gatcttgcca tcctatggaa ctgcctcggt   10440
gagttttctc cttcattaca gaaacggctt tttcaaaaat atggtattga taatcctgat   10500
atgaataaat tgcagtttca tttgatgctc gatgagtttt tctaagggcg gcctgccacc   10560
atacccacgc cgaaacaagc gctcatgagc ccgaagtggc gagcccgatc ttccccatcg   10620
gtgatgtcgg cgatataggc gccagcaacc gcacctgtgg cgccggtgat gagggcgcgc   10680
caagtcgacg tccggcagtc                                              10700
```

<210> SEQ ID NO 11
<211> LENGTH: 11188
<212> TYPE: DNA
<213> ORGANISM: Artificial sequence
<220> FEATURE:
<223> OTHER INFORMATION: Synthetic polynucleotide

<400> SEQUENCE: 11

```
ttggccactc cctctctgcg cgctcgctcg ctcactgagg ccgggcgacc aaaggtcgcc     60
cgacgcccgg gctttgcccg gcggcctca gtgagcgagc gagcgcgcag agagggagtg    120
gccaactatt agatctgatg gccgcgctag ctctgggtat ttaagcccga gtgagcacgc    180
agggtctcca ttttgaagcg ggaggttacg cgttcgtcga ctactagtgg gtaccagagc    240
gtggtgactg agatgttttc taggaaacac aaaagataca aaaagaaaca cgtggaagga    300
tagccaaaaa gggggggctgc ccccattttcc tgcacccccgc tgcgatggct ggcaccattt    360
ggaagacttc gagatacact gttgagcgca gtaagacaac agtgtatctc gaagtcttcc    420
agatggggcc agccggtcca ctctgtatcc aggccagttc tgcaaggcgt tcgaggacca    480
```

```
cccccctccc ctcgccacca gggtggtctc atacagaact tataagattc ccaaatccaa    540
agacatttca cgtttatggt gatttcccag aacacatagc gacatgcaaa tattgcaggg    600
cgccactccc ctgtccctca cagccatctt cctgccaggg cgcacgcgcg ctgggtgttc    660
ccgcctagtg acactgggcc cgcgattcct tggagcgggt tgatgacgtc agcgtttccc    720
atggtgaatc cctaggttct agaaccggtg acgtctccca tggtgaagct tggatctgaa    780
ttcggtacct agttattaat agtaatcaat tacggggtca ttagttcata gcccatatat    840
ggagttccgc gttacataac ttacggtaaa tggcccgcct ggctgaccgc ccaacgaccc    900
ccgcccattg acgtcaataa tgacgtatgt tcccatagta acgccaatag gactttcca    960
ttgacgtcaa tgggtggagt atttacggta aactgcccac ttggcagtac atcaagtgta   1020
tcatatgcca gtacgcccc ctattgacgt caatgacggt aaatggcccg cctggcatta   1080
tgcccagtac atgaccttat gggactttcc tacttggcag tacatctacg tattagtcat   1140
cgctattacc atggtcgagg tgagcccac gttctgcttc actctcccca tctcccccc    1200
ctccccaccc ccaattttgt atttatttat ttttaatta ttttgtgcag cgatgggggc   1260
gggggggggg gggggcgcg cgccaggcgg ggcggggcgg ggcgagggc ggggcgggc    1320
gaggcggaga ggtgccggcgg cagccaatca gagcggcgcg ctccgaaagt ttccttttat   1380
ggcgaggcgg cggcggcggc ggccctataa aaagcgaagc gcgcggcggg cgggagtcgc   1440
tgcgacgctg ccttcgcccc gtgccccgct ccgccgccgc ctcgccgcc ccgccccggc   1500
tctgactgac cgcgttactc ccacaggtga gcgggcggga cggccccttct cctccgggct   1560
gtaattagcg cttggtttaa tgacggcttg tttcttttct gtggctgcgt gaaagccttg   1620
aggggctccg ggagctagag cctctgctaa ccatgttcat gccttcttct ttttcctaca   1680
gctcctgggca acgtgctgg ttattgtgct gtctcatcat tttggcaaag aattcctcga   1740
agatccgaag ggaaagtctt ccacgactgt gggatccgtt cgaagatatc accggttgag   1800
ccaccatgga attcagcagc cccagcagag aggaatgccc caagcctctg agccgggtgt   1860
caatcatggc cggatctctg acaggactgc tgctgcttca ggccgtgtct tgggcttctg   1920
gcgctagacc ttgcatcccc aagagcttcg gctacagcag cgtcgtgtgc gtgtgcaatg   1980
ccacctactg cgacagcttc gaccctccta cctttcctgc tctgggcacc ttcagcagat   2040
acgagagcac cagatccggc agacggatgg aactgagcat gggacccatc caggccaatc   2100
acacaggcac tggcctgctg ctgacactgc agcctgagca gaaattccag aaagtgaaag   2160
gcttcggcgg agccatgaca gatgccgccg ctctgaatat cctggctctg tctccaccag   2220
ctcagaacct gctgctcaag agctacttca gcgaggaagg catcggctac aacatcatca   2280
gagtgcccat ggccagctgc gacttcagca tcaggaccta cacctacgcc gacacacccg   2340
acgatttcca gctgcacaac ttcagcctgc ctgaagagga caccaagctg aagatccctc   2400
tgatccacag agccctgcag ctggcacaaa gacccgtgtc actgctggcc tctccatgga   2460
catctcccac ctggctgaaa acaaatggcg ccgtgaatgg caagggcagc ctgaaaggcc   2520
aacctggcga catctaccac cagacctggg ccagatactt cgtgaagttc ctggacgcct   2580
atgccgagca caagctgcag ttttgggccg tgacagccga aacgaacct tctgctggac   2640
tgctgagcgg ctacccctt cagtgcctgg gctttacacc cgagcaccag cgggacttta   2700
tcgcccgtga tctgggaccc acactggcca atagcaccca ccataatgtg cggctgctga   2760
tgctggacga ccagagactg cttctgcccc actgggctaa agtggtgctg acagatcctg   2820
aggccgccaa atacgtgcac ggaatcgccg tgcactggta tctggacttt ctggcccctg   2880
```

```
ccaaggccac actgggagag acacacagac tgttccccaa caccatgctg ttcgccagcg    2940
aagcctgtgt gggcagcaag ttttgggaac agagcgtgcg gctcggcagc tgggatagag    3000
gcatgcagta cagccacagc atcatcacca acctgctgta ccacgtcgtc ggctggaccg    3060
actggaatct ggccctgaat cctgaaggcg ccctaactg  gtccgaaac  ttcgtggaca    3120
gccccatcat cgtggacatc accaaggaca ccttctacaa gcagcccatg ttctaccacc    3180
tgggacactt cagcaagttc atccccgagg ctctcagcg  cgttggactg gtggcttccc    3240
agaagaacga tctggacgcc gtggctctga tgcaccctga tggatctgct gtggtggtgg    3300
tcctgaaccg cagcagcaaa gatgtgcccc tgaccatcaa ggatcccgcc gtgggattcc    3360
tggaaacaat cagccctggc tactccatcc acacctacct gtggcgtaga cagtgacaat    3420
tgttaattaa gtttaaaccc tcgaggccgc aagcttatcg ataatcaacc tctgattac     3480
aaaatttgtg aaagattgac tggtattctt aactatgttg ctccttttac gctatgtgga    3540
tacgctgctt taatgccttt gtatcatgct attgcttccc gtatggcttt cattttctcc    3600
tccttgtata atcctggtt  gctgtctctt tatgaggagt tgtggcccgt tgtcaggcaa    3660
cgtggcgtgg tgtgcactgt gtttgctgac gcaaccccca ctggttgggg cattgccacc    3720
acctgtcagc tcctttccgg gactttcgct ttccccctcc ctattgccac ggcggaactc    3780
atcgccgcct gccttgcccg ctgctggaca ggggctcggc tgttgggcac tgacaattcc    3840
gtggtgttgt cggggaaatc atcgtccttt ccttggctgc tcgcctgtgt tgccacctgg    3900
attctgcgcg gacgtccttc tgctacgtc  ccttcggccc tcaatccagc ggaccttcct    3960
tcccgcggcc tgctgccggc tctgcggcct cttccgcgtc ttcgccttcg ccctcagacg    4020
agtcggatct ccctttgggc cgcctcccg  catcgatacc gtcgactaga gctcgctgat    4080
cagcctcgac tgtgccttct agttgccagc catctgttgt ttgcccctcc ccgtgcctt     4140
ccttgaccct ggaaggtgcc actcccactg tcctttccta taaaatgag  gaaattgcat    4200
cgcattgtct gagtaggtgt cattctattc tggggggtgg ggtggggcag gacagcaagg    4260
gggaggattg gaagacaat  agcaggcatg ctggggagag atccacgata acaaacagct    4320
ttttggggt  gaacatattg actgaattcc ctgcaggttg gccactccct ctctgcgcgc    4380
tcgctcgctc actgaggccg cccgggcaaa gcccgggcgt cgggcgacct ttggtcgccc    4440
ggcctcagtg agcgagcgag cgcgcagaga gggagtggcc aactccatca ctaggggttc    4500
ctgcggccgc tcgtacggtc tcgaggaatt cctgcaggat aacttgccaa cctcattcta    4560
aaatgtatat agaagcccaa aagacaataa caaaaatatt cttgtagaac aaaatgggaa    4620
agaatgttcc actaaatatc aagatttaga gcaaagcatg agatgtgtgg ggatagacag    4680
tgaggctgat aaaatagagt agagctcaga aacagaccca ttgatatatg taagtgacct    4740
atgaaaaaaa tatggcattt tacaatggga aaatgatggt cttttctttt tttagaaaaa    4800
cagggaaata tatttatatg taaaaaataa aaggaaccc  atatgtcata ccatacacac    4860
aaaaaaattc cagtgaatta taagtctaaa tggagaaggc aaaactttaa atcttttaga    4920
aaataatata gaagcatgca gaccagcctg gccaacatga tgaaaccctc tctactaata    4980
ataaaatcag tagaactact caggactact ttgagtggga agtcctttc  tatgaagact    5040
tctttggcca aaattaggct ctaaatgcaa ggagatagtg catcatgcct ggctgcactt    5100
actgataaat gatgttatca ccatcttaa  ccaaatgcac aggaacaagt tatggtactg    5160
atgtgctgga ttgagaagga gctctacttc cttgacagga cacatttgta tcaacttaaa    5220
```

```
aaagcagatt tttgccagca gaactattca ttcagaggta ggaaacttag aatagatgat   5280
gtcactgatt agcatggctt ccccatctcc acagctgctt cccacccagg ttgcccacag   5340
ttgagtttgt ccagtgctca gggctgccca ctctcagtaa aagcccccac accagcccct   5400
ctccaaatat gttggctgtt ccttccatta aagtgacccc actttagagc agcaagtgga   5460
tttctgtttc ttacagttca ggaaggagga gtcagctgtg agaacctgga gcctgagatg   5520
cttctaagtc ccactgctac tggggtcagg gaagccagac tccagcatca gcagtcagga   5580
gcactaagcc cttgccaaca tcctgtttct cagagaaact gcttccatta taatggttgt   5640
ccttttttaa gctatcaagc caaacaacca gtgtctacca ttattctcat cacctgaagc   5700
caagggttct agcaaaagtc aagctgtctt gtaatggttg atgtgcctcc agcttctgtc   5760
ttcagtcact ccactcttag cctgctctga atcaactctg accacagttc cctggagccc   5820
ctgccacctg ctgcccctgc caccttctcc atctgcagtg ctgtgcagcc ttctgcactc   5880
ttgcagagct aataggtgga gacttgaagg aagaggagga agtttctca taatagcctt   5940 gctgcaagct caaatgggag gtgggcactg tgcccaggag ccttggagca aaggctgtgc   6000
ccaacctctg actgcatcca ggtttggtct tgacagagat aagaagccct ggcttttgga   6060
gccaaaatct aggtcagact taggcaggat tctcaaagtt tatcagcaga acatgaggca   6120
gaagacccct tctgctccag cttcttcagg ctcaaccttc atcagaatag atagaaagag   6180
aggctgtgag ggttcttaaa acagaagcaa atctgactca gagaataaac aacctcctag   6240
taaactacag cttagacaga gcatctggtg gtgagtgtgc tcagtgtcct actcaactgt   6300
ctggtatcag ccctcatgag gacttctctt ctttccctca tagacctcca tctctgtttt   6360
ccttagcctg cagaaatctg gatggctatt cacagaatgc ctgtgctttc agagttgcat   6420
tttttctctg gtattctggt tcaagcattt gaaggtagga aaggttctcc aagtgcaaga   6480
aagccagccc tgagcctcaa ctgcctggct agtgtggtca gtaggatgca aaggctgttg   6540
aatgccacaa ggccaaactt taacctgtgt accacaagcc tagcagcaga ggcagctctg   6600
ctcactggaa ctctctgtct tctttctcct gagccttttc ttttcctgag ttttctagct   6660
ctcctcaacc ttacctctgc cctacccagg acaaacccaa gagccactgt ttctgtgatg   6720
tcctctccag ccctaattag gcatcatgac ttcagcctga ccttccatgc tcagaagcag   6780
tgctaatcca cttcagatga gctgctctat gcaacacagg cagagcctac aaacctttgc   6840
accagagccc tccacatatc agtgtttgtt catactcact tcaacagcaa atgtgactgc   6900
tgagattaag attttacaca agatggtctg taatttcaca gttagtttta tcccattagg   6960
tatgaaagaa ttagcataat tccccttaaa catgaatgaa tcttagattt tttaataaat   7020
agttttggaa gtaaagacag agacatcagg agcacaagga atagcctgag aggacaaaca   7080
gaacaagaaa gagtctggaa atacacagga tgttcttggc ctcctcaaag caagtgcaag   7140
cagatagtac cagcagcccc aggctatcag agcccagtga agagaagtac catgaaagcc   7200
acagctctaa ccaccctgtt ccagagtgac agacagtccc caagacaagc cagcctgagc   7260
cagagagaga actgcaagag aaagtttcta atttaggttc tgttagattc agacaagtgc   7320
aggtcatcct ctctccacag ctactcacct tccagcccta acaaagcctg cagtccacac   7380
tccaaccctg gtgtctcacc tcctagcctc tcccaacatc ctgctctctg accatcttct   7440
gcatctctca tctcaccatc tcccactgtc tacagcctac tcttgcaact accatctcat   7500
tttctgacat cctgtctaca tcttctgcca tactctgcca tctaccatac cacctcttac   7560
catctaccac accatctttt atctccatcc ctctcagaag cctccaagct gaatcctgct   7620
```

```
ttatgtgttc atctcagccc ctgcatggaa agctgacccc agaggcagaa ctattcccag    7680
agagcttggc caagaaaaac aaaactacca gcctggccag gctcaggagt agtaagctgc    7740
agtgtctgtt gtgttctagc ttcaacagct gcaggagttc cactctcaaa tgctccacat    7800
ttctcacatc ctcctgattc tggtcactac ccatcttcaa agaacagaat atctcacatc    7860
agcatactgt gaaggactag tcatgggtgc agctgctcag agctgcaaag tcattctgga    7920
tggtggagag cttacaaaca tttcatgatg ctcccccgc tctgatggct ggagcccaat     7980
ccctacacag actcctgctg tatgtgtttt cctttcactc tgagccacag ccagagggca    8040
ggcattcagt ctcctcttca ggctggggct ggggcactga gaactcaccc aacaccttgc    8100
tctcactcct tctgcaaaac aagaaagagc tttgtgctgc agtagccatg aagaatgaaa    8160
ggaaggcttt aactaaaaaa tgtcagagat tattttcaac cccttactgt ggatcaccag    8220
caaggaggaa acacaacaca gagacatttt ttccctcaa attatcaaaa gaatcactgc     8280
atttgttaaa gagagcaact gaatcaggaa gcagagtttt gaacatatca gaagttagga    8340
atctgcatca gagacaaatg cagtcatggt tgtttgctgc ataccagccc taatcattag    8400
aagcctcatg gacttcaaac atcattccct ctgacaagat gctctagcct aactccatga    8460
gataaaataa atctgccttt cagagccaaa gaagagtcca ccagcttctt ctcagtgtga    8520
acaagagctc cagtcaggtt agtcagtcca gtgcagtaga ggagaccagt ctgcatcctc    8580
taattttcaa aggcaagaag atttgtttac cctggacacc aggcacaagt gaggtcacag    8640
agctcttaga tatgcagtcc tcatgagtga ggagactaaa gcgcatgcca tcaagacttc    8700
agtgtagaga aaacctccaa aaaagcctcc tcactacttc tggaatagct cagaggccga    8760
ggcggcctcg gcctctgcat aaataaaaaa aattagtcag ccatggggcg gagaatgggc    8820
ggaactgggc ggagttaggg gcgggatggg cggagttagg ggcgggacta tggttgctga    8880
ctaattgaga tgcatgcttt gcatacttct gcctgctggg gagcctgggg actttccaca    8940
cctggttgct gactaattga gatgcatgct ttgcatactt ctgcctgctg gggagcctgg    9000
ggactttcca caccctaact gacacacatt ccacagctgc attaatgaat cggccaacgc    9060
gcggggagag gcggtttgcg tattgggcgc tcttccgctt cctcgctcac tgactcgctg    9120
cgctcggtcg ttcggctgcg gcgagcggta tcagctcact caaaggcggt aatacggtta    9180
tccacagaat caggggataa cgcaggaaag aacatgtgag caaaaggcca gcaaaaggcc    9240
aggaaccgta aaaaggccgc gttgctggcg tttttccata ggctccgccc cctgacgag     9300 catcacaaaa atcgacgctc aagtcagagg tggcgaaacc cgacaggact ataaagatac    9360
caggcgtttc cccctggaag ctccctcgtg cgctctcctg ttccgaccct gccgcttacc    9420
ggatacctgt ccgcctttct cccttcggga agcgtggcgc tttctcatag ctcacgctgt    9480
aggtatctca gttcggtgta ggtcgttcgc tccaagctgg gctgtgtgca cgaaccccc     9540 gttcagcccg accgctgcgc cttatccggt aactatcgtc ttgagtccaa cccggtaaga    9600
cacgacttat cgccactggc agcagccact ggtaacagga ttagcagagc gaggtatgta    9660
ggcggtgcta cagagttctt gaagtggtgg cctaactacg gctacactag aagaacagta    9720
tttggtatct gcgctctgct gaagccagtt accttcggaa aaagagttgg tagctcttga    9780
tccggcaaac aaaccaccgc tggtagcggt ggtttttttg tttgcaagca gcagattacg    9840
cgcagaaaaa aaggatctca agaagatcct ttgatctttt ctacggggtc tgacgctcag    9900
tggaacgaaa actcacgtta agggattttg gtcatgagat tatcaaaaag gatcttcacc    9960
```

```
tagatccttt taaattaaaa atgaagtttt aaatcaatct aaagtatata tgagtaaact     10020
tggtctgaca gttaccaatg cttaatcagt gaggcaccta tctcagcgat ctgtctattt     10080
cgttcatcca tagttgcctg actcctgcaa accacgttgt gtctcaaaat ctctgatgtt     10140
acattgcaca agataaaaat atatcatcat gaacaataaa actgtctgct tacataaaca     10200
gtaatacaag gggtgttatg agccatattc aacgggaaac gtcttgctcg aggccgcgat     10260
taaattccaa catggatgct gatttatatg ggtataaatg ggctcgcgat aatgtcgggc     10320
aatcaggtgc gacaatctat cgattgtatg ggaagcccga tgcgccagag ttgtttctga     10380
aacatggcaa aggtagcgtt gccaatgatg ttacagatga gatggtcaga ctaaactggc     10440
tgacggaatt tatgcctctt ccgaccatca agcattttat ccgtactcct gatgatgcat     10500
ggttactcac cactgcgatc cccgggaaaa cagcattcca ggtattagaa gaatatcctg     10560
attcaggtga aaatattgtt gatgcgctgg cagtgttcct gcgccggttg cattcgattc     10620
ctgtttgtaa ttgtccttt aacagcgatc gcgtatttcg tctcgctcag gcgcaatcac     10680
gaatgaataa cggtttggtt gatgcgagtg attttgatga cgagcgtaat ggctggcctg     10740
ttgaacaagt ctggaaagaa atgcataagc ttttgccatt ctcaccggat tcagtcgtca     10800
ctcatggtga tttctcactt gataaccta ttttttgacga ggggaaatta ataggttgta     10860
ttgatgttgg acgagtcgga atcgcagacc gataccagga tcttgccatc ctatggaact     10920
gcctcggtga gttttctcct tcattacaga acggcttt tcaaaaatat ggtattgata     10980
atcctgatat gaataaattg cagtttcatt tgatgctcga tgagttttc taagggcggc     11040 ctgccaccat acccacgccg aaacaagcgc tcatgagccc gaagtggcga gcccgatctt     11100
ccccatcggt gatgtcggcg atataggcgc cagcaaccgc acctgtggcg ccggtgatga     11160
gggcgcgcca agtcgacgtc cggcagtc                                     11188
```

<210> SEQ ID NO 12
<211> LENGTH: 11187
<212> TYPE: DNA
<213> ORGANISM: Artificial sequence
<220> FEATURE:
<223> OTHER INFORMATION: Synthetic polynucleotide

<400> SEQUENCE: 12

```
ctagaaccgg tgacgtctcc catggtgaag cttggatctg aattcggtac ctagttataa       60
tagtaatcaa ttacggggtc attagttcat agcccatata tggagttccg cgttacataa      120
cttacggtaa atggcccgcc tggctgaccg cccaacgacc cccgcccatt gacgtcaata      180
atgacgtatg ttcccatagt aacgccaata gggactttcc attgacgtca atgggtggag      240
tatttacggt aaactgccca cttggcagta catcaagtgt atcatatgcc aagtacgccc      300
cctattgacg tcaatgacgg taaatggccc gcctggcatt atgcccagta catgacctta      360
tgggactttc ctacttggca gtacatctac gtattagtca tcgctattac catggtcgag      420
gtgagcccca cgttctgctt cactctcccc atctcccccc cctccccacc cccaatttg      480 tatttattta ttttttaatt attttgtgca gcgatggggg cggggggggg ggggggggcgc      540 gcgccaggcg gggcggggcg gggcgagggg cgggcgggg cgaggcggag aggtgcggcg      600
gcagccaatc agagcggcgc gctccgaaag tttccttta tggcgaggcg gcggcggcgg      660
cggccctata aaagcgaag cgcgcggcgg gcgggagtcg ctgcgacgct gccttcgccc      720
cgtgccccgc tccgccgccg cctcgcgccg cccgccccgg ctctgactga ccgcgttact      780
cccacaggtg agcgggcggg acggcccttc tcctccgggc tgtaattagc gcttggttta      840
```

```
atgacggctt gtttcttttc tgtggctgcg tgaaagcctt gaggggctcc gggagctaga    900
gcctctgcta accatgttca tgccttcttc tttttcctac agctcctggg caacgtgctg    960
gttattgtgc tgtctcatca tttttggcaaa gaattcctcg aagatccgaa gggaaagtct   1020
tccacgactg tgggatccgt tcgaagatat caccggttga gccaccatgg aattcagcag   1080
ccccagcaga gaggaatgcc ccaagcctct gagccgggtg tcaatcatgg ccggatctct   1140
gacaggactg ctgctgcttc aggccgtgtc ttgggcttct ggcgctagac cttgcatccc   1200
caagagcttc ggctacagca gcgtcgtgtg cgtgtgcaat gccacctact gcgacagctt   1260
cgaccctcct acctttcctg ctctgggcac cttcagcaga tacgagagca ccagatccgg   1320
cagacggatg gaactgagca tgggacccat ccaggccaat cacacaggca ctggcctgct   1380
gctgacactg cagcctgagc agaaattcca gaaagtgaaa ggcttcggcg agccatgac    1440
agatgccgcc gctctgaata tcctggctct gtctccacca gctcagaacc tgctgctcaa   1500
gagctacttc agcgaggaag catcggcta caacatcatc agagtgccca tggccagctg   1560
cgacttcagc atcaggacct acacctacgc cgacacaccc gacgatttcc agctgcacaa   1620
cttcagcctg cctgaagagg acaccaagct gaagatccct ctgatccaca gagccctgca   1680
gctggcacaa agacccgtgt cactgctggc ctctccatgg acatctccca cctggctgaa   1740
aacaaatggc gccgtgaatg caagggcag cctgaaaggc caacctggcg acatctacca   1800
ccagacctgg gccagatact cgtgaagtt cctggacgcc tatgccgagc acaagctgca   1860
gttttgggcc gtgacagccg agaacgaacc ttctgctgga ctgctgagcg ctacccctt    1920
tcagtgcctg ggctttacac ccgagcacca gcgggacttt atcgcccgtg atctgggacc   1980
cacactggcc aatagcaccc accataatgt gcggctgctg atgctggacg accagagact   2040
gcttctgccc cactgggcta agtggtgct gacagatcct gaggccgcca atacgtgca     2100
cggaatcgcc gtgcactggt atctggactt tctggcccct gccaaggcca cactgggaga   2160
gacacacaga ctgttcccca acaccatgct gttcgccagc gaagcctgtg tgggcagcaa   2220
gttttgggaa cagagcgtgc ggctcggcag ctgggataga ggcatgcagt acagccacag   2280
catcatcacc aacctgctgt accacgtcgt cggctggacc gactggaatc tggccctgaa   2340
tcctgaaggc ggccctaact gggtccgaaa cttcgtggac agccccatca tcgtggacat   2400
caccaaggac accttctaca agcagcccat gttctaccac ctgggacact tcagcaagtt   2460
catccccgag ggctctcagc gcgttggact ggtggcttcc cagaagaacg atctggacgc   2520
cgtggctctg atgcacctg atggatctgc tgtggtggtg gtcctgaacc gcagcagcaa    2580
agatgtgccc ctgaccatca aggatcccgc cgtgggattc ctggaaacaa tcagccctgg   2640
ctactccatc cacacctacc tgtggcgtag acagtgacaa ttgttaatta agtttaaacc   2700
ctcgaggccg caagcttatc gataatcaac ctctggatta caaaatttgt gaaagattga   2760
ctggtattct taactatgtt gctccttta cgctatgtgg atacgctgct ttaatgcctt     2820
tgtatcatgc tattgcttcc cgtatggctt tcattttctc ctccttgtat aaatcctggt   2880
tgctgtctct ttatgaggag ttgtggcccg ttgtcaggca acgtggcgtg gtgtgcactg   2940
tgtttgctga cgcaacccc actggttggg gcattgccac cacctgtcag ctccttccg     3000
ggactttcgc tttcccctc cctattgcca cggcggaact catcgccgcc tgccttgccc   3060
gctgctggac aggggctcgg ctgttggca ctgacaattc cgtggtgttg tcggggaaat    3120
catcgtcctt tccttggctg ctcgcctgtg ttgccacctg gattctgcgc gggacgtcct   3180
```

```
tctgctacgt cccttcggcc ctcaatccag cggaccttcc ttcccgcggc ctgctgccgg    3240
ctctgcggcc tcttccgcgt cttcgccttc gccctcagac gagtcggatc tcccttgggg    3300
ccgcctcccc gcatcgatac cgtcgactag agctcgctga tcagcctcga ctgtgccttc    3360
tagttgccag ccatctgttg tttgcccctc ccccgtgcct tccttgaccc tggaaggtgc    3420
cactcccact gtcctttcct aataaaatga ggaaattgca tcgcattgtc tgagtaggtg    3480
tcattctatt ctgggggtg gggtggggca ggacagcaag ggggaggatt gggaagacaa     3540
tagcaggcat gctggggaga gatccacgat aacaaacagc ttttttgggg tgaacatatt    3600
gactgaattc cctgcaggtt ggccactccc tctctgcgcg ctcgctcgct cactgaggcc    3660
gcccgggcaa agcccgggcg tcgggcgacc tttggtcgcc cggcctcagt gagcgagcga    3720
gcgcgcagag agggagtggc caactccatc actaggggtt cctgcggccg ctcgtacggt    3780
ctcgaggaat tcctgcagga taacttgcca acctcattct aaaatgtata tagaagccca    3840
aaagacaata acaaaaatat tcttgtagaa caaaatggga aagaatgttc cactaaaatat   3900 caagatttag agcaaagcat gagatgtgtg gggatagaca gtgaggctga taaaatagag    3960
tagagctcag aaacagaccc attgatatat gtaagtgacc tatgaaaaaa atatggcatt   4020
ttacaatggg aaaatgatgg tcttttctt tttagaaaaa acagggaaat atatttatat    4080
gtaaaaaata aagggaacc catatgtcat accatacaca caaaaaaatt ccagtgaatt    4140
ataagtctaa atggagaagg caaaacttta aatcttttag aaaataatat agaagcatgc    4200
agaccagcct ggccaacatg atgaaaccct ctctactaat aataaaatca gtagaactac    4260
tcaggactac tttgagtggg aagtcctttt ctatgaagac ttctttggcc aaaattaggc    4320
tctaaatgca aggagatagt gcatcatgcc tggctgcact tactgataaa tgatgttatc    4380
accatcttta accaaatgca caggaacaag ttatggtact gatgtgctgg attgagaagg    4440
agctctactt ccttgacagg acacatttgt atcaacttaa aaaagcagat ttttgccagc    4500
agaactattc attcagaggt aggaaactta gaatagatga tgtcactgat tagcatggct    4560
tccccatctc cacagctgct tcccacccag gttgcccaca gttgagtttg tccagtgctc    4620
agggctgccc actctcagta agaagcccca caccagcccc tctccaaata tgttggctgt    4680
tccttccatt aaagtgaccc cactttagag cagcaagtgg atttctgttt cttacagttc    4740
aggaaggagg agtcagctgt gagaacctgg agcctgagat gcttctaagt cccactgcta    4800
ctggggtcag ggaagccaga ctccagcatc agcagtcagg agcactaagc ccttgccaac    4860
atcctgtttc tcagagaaac tgcttccatt ataatggttg tcctttttta agctatcaag    4920
ccaaacaacc agtgtctacc attattctca tcacctgaag ccaagggttc tagcaaaagt    4980
caagctgtct tgtaatggtt gatgtgcctc cagcttctgt cttcagtcac tccactctta    5040
gcctgctctg aatcaactct gaccacagtt ccctggagcc cctgccacct gctgcccctg    5100
ccaccttctc catctgcagt gctgtgcagc cttctgcact cttgcagagc taataggtgg    5160
agacttgaag gaagaggagg aaagtttctc ataatagcct tgctgcaagc tcaaatggga    5220
ggtgggcact gtgcccagga gccttggagc aaaggctgtg cccaacctct gactgcatcc    5280
aggtttggtc ttgacagaga taagaagccc tggcttttgg agccaaaatc taggtcagac    5340
ttaggcagga ttctcaaagt ttatcagcag aacatgaggc agaagaccct ttctgctcca    5400
gcttcttcag gctcaacctt catcagaata gatagaaaga gaggctgtga gggttcttaa    5460
aacagaagca aatctgactc agagaataaa caacctccta gtaaactaca gcttagacag    5520
agcatctggt ggtgagtgtg ctcagtgtcc tactcaactg tctggtatca gccctcatga    5580
```

```
ggacttctct tctttccctc atagacctcc atctctgttt tccttagcct gcagaaatct    5640
ggatggctat tcacagaatg cctgtgcttt cagagttgca ttttttctct ggtattctgg    5700
ttcaagcatt tgaaggtagg aaaggttctc caagtgcaag aaagccagcc ctgagcctca    5760
actgcctggc tagtgtggtc agtaggatgc aaaggctgtt gaatgccaca aggccaaact    5820
ttaacctgtg taccacaagc ctagcagcag aggcagctct gctcactgga actctctgtc    5880
ttctttctcc tgagccttt  cttttcctga gttttctagc tctcctcaac cttacctctg    5940
ccctacccag gacaaaccca agagccactg tttctgtgat gtcctctcca gccctaatta    6000
ggcatcatga cttcagcctg accttccatg ctcagaagca gtgctaatcc acttcagatg    6060
agctgctcta tgcaacacag gcagagccta caaacctttg caccagagcc ctccacatat    6120
cagtgtttgt tcatactcac ttcaacagca aatgtgactg ctgagattaa gattttacac    6180
aagatggtct gtaatttcac agttagtttt atcccattag gtatgaaaga attagcataa    6240
ttccccttaa acatgaatga atcttagatt ttttaataaa tagttttgga agtaaagaca    6300
gagacatcag gagcacaagg aatagcctga gaggacaaac agaacaagaa agagtctgga    6360
aatacacagg atgttcttgg cctcctcaaa gcaagtgcaa gcagatagta ccagcagccc    6420
caggctatca gagcccagtg aagagaagta ccatgaaagc cacagctcta accaccctgt    6480
tccagagtga cagacagtcc ccaagacaag ccagcctgag ccagagagag aactgcaaga    6540
gaaagtttct aatttaggtt ctgttagatt cagacaagtg caggtcatcc tctctccaca    6600
gctactcacc tctccagcct aacaaagcct gcagtccaca ctccaaccct ggtgtctcac    6660
ctcctagcct ctcccaacat cctgctctct gaccatcttc tgcatctctc atctcaccat    6720
ctcccactgt ctacagccta ctcttgcaac taccatctca ttttctgaca tcctgtctac    6780
atcttctgcc atactctgcc atctaccata ccacctctta ccatctacca caccatcttt    6840
tatctccatc cctctcagaa gcctccaagc tgaatcctgc tttatgtgtt catctcagcc    6900
cctgcatgga aagctgaccc cagaggcaga actattccca gagagcttgg ccaagaaaaa    6960
caaaactacc agcctggcca ggctcaggag tagtaagctg cagtgtctgt tgtgttctag    7020
cttcaacagc tgcaggagtt ccactctcaa atgctccaca tttctcacat cctcctgatt    7080
ctggtcacta cccatcttca agaacagaa  tatctcacat cagcatactg tgaaggacta    7140
gtcatgggtg cagctgctca gagctgcaaa gtcattctgg atggtggaga gcttacaaac    7200
atttcatgat gctcccccg  ctctgatggc tggagcccaa tccctacaca gactcctgct    7260
gtatgtgttt tcctttcact ctgagccaca gccagagggc aggcattcag tctcctcttc    7320
aggctggggc tggggcactg agaactcacc caacaccttg ctctcactcc ttctgcaaaa    7380
caagaaagag ctttgtgctg cagtagccat gaagaatgaa aggaaggctt taactaaaaa    7440
atgtcagaga ttattttcaa ccccttactg tggatcacca gcaaggagga aacacaacac    7500
agagacattt tttcccctca aattatcaaa agaatcactg catttgttaa agagagcaac    7560
tgaatcagga agcagagttt tgaacatatc agaagttagg aatctgcatc agagacaaat    7620
gcagtcatgg ttgtttgctg cataccagcc ctaatcatta gaagcctcat ggacttcaaa    7680
catcattccc tctgacaaga tgctctagcc taactccatg agataaaata aatctgcctt    7740
tcagagccaa agaagagtcc accagcttct tctcagtgtg aacaagagct ccagtcaggt    7800
tagtcagtcc agtgcagtag aggagaccag tctgcatcct ctaattttca aaggcaagaa    7860
gatttgttta ccctggacac caggcacaag tgaggtcaca gagctcttag atatgcagtc    7920
```

```
ctcatgagtg aggagactaa agcgcatgcc atcaagactt cagtgtagag aaaacctcca    7980
aaaaagcctc ctcactactt ctggaatagc tcagaggccg aggcggcctc ggcctctgca    8040
taaataaaaa aaattagtca gccatggggc ggagaatggg cggaactggg cggagttagg    8100
ggcgggatgg gcggagttag gggcgggact atggttgctg actaattgag atgcatgctt    8160
tgcatacttc tgcctgctgg ggagcctggg gactttccac acctggttgc tgactaattg    8220
agatgcatgc tttgcatact tctgcctgct ggggagcctg ggactttcc acaccctaac     8280
tgacacacat tccacagctg cattaatgaa tcggccaacg cgcggggaga ggcggtttgc    8340
gtattgggcg ctcttccgct tcctcgctca ctgactcgct gcgctcggtc gttcggctgc    8400
ggcgagcggt atcagctcac tcaaaggcgg taatacggtt atccacagaa tcaggggata    8460
acgcaggaaa gaacatgtga gcaaaaggcc agcaaaaggc caggaaccgt aaaaaggccg    8520
cgttgctggc gtttttccat aggctccgcc cccctgacga gcatcacaaa aatcgacgct    8580
caagtcagag gtggcgaaac ccgacaggac tataaagata ccaggcgttt ccccctggaa    8640
gctccctcgt gcgctctcct gttccgaccc tgccgcttac cggatacctg tccgcctttc    8700
tcccttcggg aagcgtggcg ctttctcata gctcacgctg taggtatctc agttcggtgt    8760
aggtcgttcg ctccaagctg ggctgtgtgc acgaaccccc cgttcagccc gaccgctgcg    8820
ccttatccgg taactatcgt cttgagtcca acccggtaag acacgactta tcgccactgg    8880
cagcagccac tggtaacagg attagcagag cgaggtatgt aggcggtgct acagagttct    8940
tgaagtggtg gcctaactac ggctacacta agaacagt atttggtatc tgcgctctgc     9000
tgaagccagt taccttcgga aaagagttg gtagctcttg atccggcaaa caaaccaccg     9060
ctggtagcgg tggttttttt gtttgcaagc agcagattac gcgcagaaaa aaggatctc    9120
aagaagatcc tttgatcttt tctacggggt ctgacgctca gtggaacgaa aactcacgtt    9180
aagggatttt ggtcatgaga ttatcaaaaa ggatcttcac ctagatcctt ttaaattaaa    9240
aatgaagttt taaatcaatc taaagtatat atgagtaaac ttggtctgac agttaccaat    9300
gcttaatcag tgaggcacct atctcagcga tctgtctatt tcgttcatcc atagttgcct    9360
gactcctgca aaccacgttg tgtctcaaaa tctctgatgt tacattgcac aagataaaaa    9420
tatatcatca tgaacaataa aactgtctgc ttacataaac agtaatacaa ggggtgttat    9480
gagccatatt caacgggaaa cgtcttgctc gaggccgcga ttaaattcca acatggatgc    9540
tgatttatat gggtataaat gggctcgcga taatgtcggg caatcaggtg cgacaatcta    9600
tcgattgtat gggaagcccg atgcgccaga gttgtttctg aaacatggca aaggtagcgt    9660
tgccaatgat gttacagatg agatggtcag actaaactgg ctgacggaat ttatgcctct    9720
tccgaccatc aagcatttta tccgtactcc tgatgatgca tggttactca ccactgcgat    9780
ccccgggaaa acagcattcc aggtattaga agaatatcct gattcaggtg aaaatattgt    9840
tgatgcgctg gcagtgttcc tgcgccggtt gcattcgatt cctgtttgta attgtccttt    9900
taacagcgat cgcgtatttc gtctcgctca ggcgcaatca cgaatgaata cggtttggt    9960
tgatgcgagt gattttgatg acgagcgtaa tggctggcct gttgaacaag tctggaaaga   10020
aatgcataag cttttgccat tctcaccgga ttcagtcgtc actcatggtg atttctcact   10080
tgataacctt atttttgacg aggggaaatt aataggttgt attgatgttg gacgagtcgg   10140
aatcgcagac cgataccagg atcttgccat cctatggaac tgcctcggtg agttttctcc   10200
ttcattacag aaacggcttt ttcaaaaata tggtattgat aatcctgata tgaataaatt   10260
gcagtttcat ttgatgctcg atgagttttt ctaagggcgg cctgccacca tacccacgcc   10320
```

| | | | | |
|---|---|---|---|---|
| gaaacaagcg | ctcatgagcc | cgaagtggcg | agcccgatct | tccccatcgg tgatgtcggc | 10380 |
| gatataggcg | ccagcaaccg | cacctgtggc | gccggtgatg | agggcgcgcc aagtcgacgt | 10440 |
| ccggcagtct | tggccactcc | ctctctgcgc | gctcgctcgc | tcactgaggc cgggcgacca | 10500 |
| aaggtcgccc | gacgcccggg | ctttgcccgg | gcggcctcag | tgagcgagcg agcgcgcaga | 10560 |
| gagggagtgg | ccaactccat | cactaggggt | tcctgctagc | tctgggtatt taagcccgag | 10620 |
| tgagcacgca | gggtctccat | tttgaagcgg | gaggttacgc | gttcgtcgac tactagtggg | 10680 |
| taccagagcg | tggtgactga | gatgttttct | aggaaacaca | aaagatacaa aaaagaacac | 10740 |
| gtggaaggat | agccaaaaag | gggggctgcc | cccatttcct | gcacccccgct gcgatggctg | 10800 |
| gcaccatttg | gaagacttcg | agatacactg | ttgagcgcag | taagacaaca gtgtatctcg | 10860 |
| aagtcttcca | gatggggcca | gccggtccac | tctgtatcca | ggccagttct gcaaggcgtt | 10920 |
| cgaggaccac | ccccctcccc | tcgccaccag | ggtggtctca | tacagaactt ataagattcc | 10980 |
| caaatccaaa | gacatttcac | gtttatggta | atttcccaga | acacatagcg acatgcaaat | 11040 |
| attgcagggc | gccactcccc | tgtccctcac | agccatcttc | ctgccagggc gcacgcgcgc | 11100 |
| tgggtgttcc | cgcctagtga | cactgggccc | gcgattcctt | ggagcgggtt gatgacgtca | 11160 |
| gcgtttccca | tggtgaatcc | ctaggtt | | | 11187 |

<210> SEQ ID NO 13
<211> LENGTH: 10960
<212> TYPE: DNA
<213> ORGANISM: Artificial sequence
<220> FEATURE:
<223> OTHER INFORMATION: Synthetic polynucleotide

<400> SEQUENCE: 13

| | | | | |
|---|---|---|---|---|
| ttggccactc | cctctctgcg | cgctcgctcg | ctcactgagg | ccgggcgacc aaaggtcgcc | 60 |
| cgacgcccgg | gctttgcccg | gcggcctca | gtgagcgagc | gagcgcgcag agagggagtg | 120 |
| gccaactcca | tcactagggg | ttcctgctag | ctctgggtat | ttaagcccga gtgagcacgc | 180 |
| aggtctcca | ttttgaagcg | ggaggttacg | cgttcgtcga | ctactagtgg gtaccagagc | 240 |
| tccctaggtt | ctagaaccgg | tgacgtctcc | catggtgaag | cttggatctg aattcggtac | 300 |
| cctagttatt | aatagtaatc | aattacgggg | tcattagttc | atagcccata tatggagttc | 360 |
| cgcgttacat | aacttacggt | aaatggcccg | cctggctgac | cgcccaacga ccccgccca | 420 |
| ttgacgtcaa | taatgacgta | tgttcccata | gtaacgccaa tagggacttt | ccattgacgt | 480 |
| caatgggtgg | actatttacg | gtaaactgcc | cacttggcag | tacatcaagt gtatcatatg | 540 |
| ccaagtacgc | cccctattga | cgtcaatgac | ggtaaatggc | ccgcctggca ttatgcccag | 600 |
| tacatgacct | tatgggactt | tcctacttgg | cagtacatct | acgtattagt catcgctatt | 660 |
| accatggtcg | aggtgagccc | cacgttctgc | ttcactctcc | ccatctcccc cccctcccca | 720 |
| ccccaattt | tgtatttatt | tatttttaa | ttattttgtg | cagcgatggg ggcgggggg | 780 |
| gggggggggc | gcgcgccagg | cggggcgggg | cggggcgagg | ggcggggcgg ggcgaggcgg | 840 |
| agaggtgcgg | cggcagccaa | tcagagcggc | gcgctccgaa | agtttccttt tatggcgagg | 900 |
| cggcggcggc | ggcggcccta | taaaaagcga | agcgcgcggc | gggcgggagt cgctgcgacg | 960 |
| ctgccttcgc | cccgtgcccc | gctccgccgc | cgcctcgcgc | cgcccgcccc ggctctgact | 1020 |
| gaccgcgtta | ctcccacagg | tgagcgggcg | ggacggccct | tctcctccgg gctgtaatta | 1080 |
| gcgcttggtt | taatgacggc | ttgtcctggt | ggcgagggga | gggggtggt cctcgaacgc | 1140 |

```
cttgcagaac tggcctggat acagagtgga ccggctggcc ccatctggaa gacttcgaga   1200
tacactgttg tcttactgcg ctcaacagtg tatctcgaag tcttccaaat ggtgccagcc   1260
atcgcagcgg ggtgcaggaa atgggggcag ccccccttttt tggctatcct tccacgtgtt  1320
cttttttgta tcttttgtgt ttcctagaaa acatctcagt caccacctttt ctgtggctgc  1380 gtgaaagcct tgagggctc cgggagctag agcctctgct aaccatgttc atgccttctt    1440 cttttttccta cagctcctgg gcaacgtgct ggttattgtg ctgtctcatc attttggcaa  1500
agaattcctc gaagatccga agggaaagtc ttccacgact gtgggatccg ttcgaagata   1560
tcaccggttg agccaccatg gaattcagca gccccagcag agaggaatgc ccaagcctc    1620 tgagccgggt gtcaatcatg gccggatctc tgacaggact gctgctgctt caggccgtgt   1680
cttgggcttc tggcgctaga ccttgcatcc ccaagagctt cggctacagc agcgtcgtgt   1740
gcgtgtgcaa tgccacctac tgcgacagct tcgaccctcc tacctttcct gctctgggca   1800
ccttcagcag atacgagagc accagatccg gcagacggat ggaactgagc atgggaccca   1860
tccaggccaa tcacacaggc actggcctgc tgctgacact gcagcctgag cagaaattcc   1920
agaaagtgaa aggcttcggc ggagccatga cagatgccgc cgctctgaat atcctggctc   1980
tgtctccacc agctcagaac ctgctgctca agagctactt cagcgaggaa ggcatcggct   2040
acaacatcat cagagtgccc atggccagct gcgacttcag catcaggacc tacacctacg   2100
ccgacacacc cgacgatttc cagctgcaca acttcagcct gcctgaagag gacaccaagc   2160
tgaagatccc tctgatccac agagccctgc agctggcaca agacccgtg tcactgctgg    2220 cctctccatg gacatctccc acctggctga aaacaaatgg cgccgtgaat ggcaagggca   2280
gcctgaaagg ccaacctggc gacatctacc accagacctg gccagatac ttcgtgaagt    2340 tcctggacgc ctatgccgag cacaagctgc agttttgggc cgtgacagcc gagaacgaac   2400
cttctgctgg actgctgagc ggctacccct tcagtgcct gggctttaca cccgagcacc    2460
agcgggactt tatcgcccgt gatctgggac ccacactggc caatagcacc caccataatg   2520
tgcggctgct gatgctggac gaccagagac tgcttctgcc ccactgggct aaagtggtgc   2580
tgacagatcc tgaggccgcc aaatacgtgc acggaatcgc cgtgcactgg tatctggact   2640
ttctggcccc tgccaaggcc acactgggag agacacacag actgttcccc aacaccatgc   2700
tgttcgccag cgaagcctgt gtgggcagca agttttggga acagagcgtg cggctcggca   2760
gctgggatag aggcatgcag tacagccaca gcatcatcac caacctgctg taccacgtcg   2820
tcggctggac cgactggaat ctggccctga atcctgaagg cggccctaac tgggtccgaa   2880
acttcgtgga cagccccatc atcgtggaca tcaccaagga caccttctac aagcagccca   2940
tgttctacca cctgggacac ttcagcaagt tcatccccga gggctctcag cgcgttggac   3000
tggtggcttc ccagaagaac gatctggacg ccgtggctct gatgcaccct gatggatctg   3060
ctgtggtggt ggtcctgaac cgcagcagca agatgtgcc cctgaccatc aaggatcccg    3120
ccgtgggatt cctggaaaca atcagccctg ctactccat ccacacctac ctgtggcgta    3180
gacagtgaca attgttaatt aagtttaaac cctcgaggcc gcaagcttat cgataatcaa   3240
cctctggatt acaaaatttg tgaaagattg actggtattc ttaactatgt tgctcctttt   3300
acgctatgtg gatacgctgc tttaatgcct ttgtatcatg ctattgcttc ccgtatggct   3360
ttcattttct cctccttgta taaatcctgg ttgctgtctc tttatgagga gttgtggccc   3420
gttgtcaggc aacgtggcgt ggtgtgcact gtgtttgctg acgcaacccc cactggttgg   3480
ggcattgcca ccacctgtca gctccttttcc gggactttcg ctttccccct ccctattgcc  3540
```

```
acggcggaac tcatcgccgc ctgccttgcc cgctgctgga caggggctcg gctgttgggc   3600
actgacaatt ccgtggtgtt gtcggggaaa tcatcgtcct ttccttggct gctcgcctgt   3660
gttgccacct ggattctgcg cgggacgtcc ttctgctacg tcccttcggc cctcaatcca   3720
gcggaccttc cttcccgcgg cctgctgccg gctctgcggc ctcttccgcg tcttcgcctt   3780
cgccctcaga cgagtcggat ctccctttgg gccgcctccc cgcatcgata ccgtcgacta   3840
gagctcgctg atcagcctcg actgtgcctt ctagttgcca gccatctgtt gtttgcccct   3900
cccccgtgcc ttccttgacc ctggaaggtg ccactcccac tgtcctttcc taataaaatg   3960
aggaaattgc atcgcattgt ctgagtaggt gtcattctat tctggggggt ggggtggggc   4020
aggacagcaa gggggaggat tgggaagaca atagcaggca tgctggggag agatccacga   4080
taacaaacag cttttttggg gtgaacatat tgactgaatt ccctgcaggt tggccactcc   4140
ctctctgcgc gctcgctcgc tcactgaggc cgcccgggca aagcccgggc gtcgggcgac   4200
ctttggtcgc ccgcctcag tgagcgacg agcgcgcaga gagggagtgg ccaactccat   4260 cactagggggt tcctgcggcc gctcgtacgg tctcgaggaa ttcctgcagg ataacttgcc   4320
aacctcattc taaaatgtat atagaagccc aaaagacaat aacaaaaata ttcttgtaga   4380
acaaaatggg aaagaatgtt ccactaaata tcaagattta gagcaaagca tgagatgtgt   4440
ggggatagac agtgaggctg ataaaataga gtagagctca gaaacagacc cattgatata   4500
tgtaagtgac ctatgaaaaa aatatggcat tttacaatgg gaaaatgatg gtctttttct   4560
tttttagaaa aacagggaaa tatatttata tgtaaaaaat aaaagggaac ccatatgtca   4620
taccatacac acaaaaaaat tccagtgaat tataagtcta aatggagaag gcaaaacttt   4680
aaatctttta gaaataata tagaagcatg cagaccagcc tggccaacat gatgaaaccc   4740
tctctactaa taataaaatc agtagaacta ctcaggacta ctttgagtgg gaagtccttt   4800
tctatgaaga cttctttggc caaaattagg ctctaaatgc aaggagatag tgcatcatgc   4860
ctggctgcac ttactgataa atgatgttat caccatcttt aaccaaatgc acaggaacaa   4920
gttatggtac tgatgtgctg gattgagaag gagctctact tccttgacag gacacatttg   4980
tatcaactta aaaaagcaga tttttgccag cagaactatt cattcagagg taggaaactt   5040
agaatagatg atgtcactga ttagcatggc ttccccatct ccacagctgc ttcccaccca   5100
ggttgcccac agttgagttt gtccagtgct caggctgcc cactctcagt aagaagcccc   5160
acaccagccc ctctccaaat atgttggctg ttccttccat taaagtgacc ccactttaga   5220
gcagcaagtg gatttctgtt tcttacagtt caggaaggag gagtcagctg tgagaacctg   5280
gagcctgaga tgcttctaag tcccactgct actgggttca gggaagccag actccagcat   5340
cagcagtcag gagcactaag cccttgccaa catcctgтттт tcagagaaa ctgcttccat   5400 tataatggtt gtcctttttt aagctatcaa gccaaacaac cagtgtctac cattattctc   5460
atcacctgaa gccaagggtt ctagcaaaag tcagctgtc ttgtaatggt tgatgtgcct   5520
ccagcttctg tcttcagtca ctccactctt agcctgctct gaatcaactc tgaccacagt   5580
tccctggagc cctgccacc tgctgcccct gccaccttct ccatctgcag tgctgtgcag   5640
ccttctgcac tcttgcagag ctaataggtg gagacttgaa ggaagaggag gaaagtttct   5700
cataatagcc ttgctgcaag ctcaaatggg aggtgggcac tgtgcccagg agccttggag   5760
caaaggctgt gccaacctc tgactgcatc caggtttggt cttgacagag ataagaagcc   5820
ctggcttttg gagccaaaat ctaggtcaga cttaggcagg attctcaaag tttatcagca   5880
```

```
gaacatgagg cagaagaccc tttctgctcc agcttcttca ggctcaacct tcatcagaat    5940
agatagaaag agaggctgtg agggttctta aaacagaagc aaatctgact cagagaataa    6000
acaacctcct agtaaactac agcttagaca gagcatctgg tggtgagtgt gctcagtgtc    6060
ctactcaact gtctggtatc agccctcatg aggacttctc ttctttccct catagacctc    6120
catctctgtt ttccttagcc tgcagaaatc tggatggcta ttcacagaat gcctgtgctt    6180
tcagagttgc attttttctc tggtattctg gttcaagcat ttgaaggtag gaaaggttct    6240
ccaagtgcaa gaaagccagc cctgagcctc aactgcctgg ctagtgtggt cagtaggatg    6300
caaaggctgt tgaatgccac aaggccaaac tttaacctgt gtaccacaag cctagcagca    6360
gaggcagctc tgctcactgg aactctctgt cttctttctc ctgagccttt tcttttcctg    6420
agttttctag ctctcctcaa ccttacctct gccctaccca ggacaaaccc aagagccact    6480
gtttctgtga tgtcctctcc agccctaatt aggcatcatg acttcagcct gaccttccat    6540
gctcagaagc agtgctaatc cacttcagat gagctgctct atgcaacaca ggcagagcct    6600
acaaaccttt gcaccagagc cctccacata tcagtgtttg ttcatactca cttcaacagc    6660
aaatgtgact gctgagatta agattttaca caagatggtc tgtaatttca cagttagttt    6720
tatcccatta ggtatgaaag aattagcata attccccttta aacatgaatg aatcttagat    6780
tttttaataa atagttttgg aagtaaagac agagacatca ggagcacaag gaatagcctg    6840
agaggacaaa cagaacaaga aagagtctgg aaatacacag gatgttcttg gcctcctcaa    6900
agcaagtgca agcagatagt accagcagcc ccaggctatc agagcccagt gaagagaagt    6960
accatgaaag ccacagctct aaccaccctg ttcagagtg acagacagtc cccaagacaa    7020
gccagcctga gccagagaga gaactgcaag agaaagtttc taatttaggt tctgttagat    7080
tcagacaagt gcaggtcatc ctctctccac agctactcac ctctccagcc taacaaagcc    7140
tgcagtccac actccaaccc tggtgtctca cctcctagcc tctcccaaca tcctgctctc    7200
tgaccatctt ctgcatctct catctcacca tctcccactg tctacagcct actcttgcaa    7260
ctaccatctc attttctgac atcctgtcta catcttctgc catactctgc catctaccat    7320
accacctctt accatctacc acaccatctt ttatctccat ccctctcaga agcctccaag    7380
ctgaatcctg ctttatgtgt tcatctcagc ccctgcatgg aaagctgacc ccagaggcag    7440
aactattccc agagagcttg gccaagaaaa acaaaactac cagccggcc aggctcagga    7500 gtagtaagct gcagtgtctg ttgtgttcta gcttcaacag ctgcaggagt tccactctca    7560
aatgctccac atttctcaca tcctcctgat tctggtcact acccatcttc aaagaacaga    7620
atatctcaca tcagcatact gtgaaggact agtcatgggt gcagctgctc agagctgcaa    7680
agtcattctg gatggtggag agcttacaaa catttcatga tgctccccc gctctgatgg    7740 ctggagccca atccctacac agactcctgc tgtatgtgtt ttcctttcac tctgagccac    7800
agccagaggg caggcattca gtctcctctt caggctgggg ctgggcact gagaactcac    7860 ccaacacctt gctctcactc cttctgcaaa acaagaaaga gctttgtgct gcagtagcca    7920
tgaagaatga aggaaggct ttaactaaaa aatgtcagag attattttca acccccttact    7980 gtggatcacc agcaaggagg aaacacaaca cagagacatt ttttcccctc aaattatcaa    8040
aagaatcact gcatttgtta agagagcaa ctgaatcagg aagcagagtt ttgaacatat    8100
cagaagttag gaatctgcat cagagacaaa tgcagtcatg gttgtttgct gcataccagc    8160
cctaatcatt agaagcctca tggacttcaa acatcattcc ctctgacaag atgctctagc    8220
ctaactccat gagataaaat aaatctgcct ttcagagcca aagaagagtc caccagcttc    8280
```

```
ttctcagtgt gaacaagagc tccagtcagg ttagtcagtc cagtgcagta gaggagacca   8340
gtctgcatcc tctaattttc aaaggcaaga agatttgttt accctggaca ccaggcacaa   8400
gtgaggtcac agagctctta gatatgcagt cctcatgagt gaggagacta aagcgcatgc   8460
catcaagact tcagtgtaga gaaaacctcc aaaaaagcct cctcactact tctggaatag   8520
ctcagaggcc gaggcggcct cggcctctgc ataaataaaa aaaattagtc agccatgggg   8580
cggagaatgg gcgaactgg gcggagttag gggcgggatg ggcggagtta ggggcgggac    8640
tatggttgct gactaattga gatgcatgct ttgcatactt ctgcctgctg gggagcctgg   8700
ggactttcca cacctggttg ctgactaatt gagatgcatg ctttgcatac ttctgcctgc   8760
tggggagcct ggggactttc cacaccctaa ctgacacaca ttccacagct gcattaatga   8820
atcggccaac gcgcgggag aggcggtttg cgtattgggc gctcttccgc ttcctcgctc    8880
actgactcgc tgcgctcggt cgttcggctg cggcgagcgg tatcagctca ctcaaaggcg   8940
gtaatacggt tatccacaga atcaggggat aacgcaggaa agaacatgtg agcaaaaggc   9000
cagcaaaagg ccaggaaccg taaaaaggcc gcgttgctgg cgtttttcca taggctccgc   9060
ccccctgacg agcatcacaa aaatcgacgc tcaagtcaga ggtggcgaaa cccgacagga   9120
ctataaagat accaggcgtt tcccctgga agctccctcg tgcgctctcc tgttccgacc    9180
ctgccgctta ccggatacct gtccgccttt ctcccttcgg gaagcgtggc gctttctcat   9240
agctcacgct gtaggtatct cagttcggtg taggtcgttc gctccaagct gggctgtgtg   9300
cacgaacccc ccgttcagcc cgaccgctgc gccttatccg gtaactatcg tcttgagtcc   9360
aacccggtaa gacacgactt atcgccactg gcagcagcca ctggtaacag gattagcaga   9420
gcgaggtatg taggcggtgc tacagagttc ttgaagtggt ggcctaacta cggctacact   9480
agaagaacag tatttggtat ctgcgctctg ctgaagccag ttaccttcgg aaaaagagtt   9540
ggtagctctt gatccggcaa acaaaccacc gctggtagcg gtggtttttt tgtttgcaag   9600
cagcagatta cgcgcagaaa aaaaggatct caagaagatc ctttgatctt ttctacgggg   9660
tctgacgctc agtggaacga aaactcacgt taagggattt tggtcatgag attatcaaaa   9720
aggatcttca cctagatcct tttaaattaa aaatgaagtt ttaaatcaat ctaaagtata   9780
tatgagtaaa cttggtctga cagttaccaa tgcttaatca gtgaggcacc tatctcagcg   9840
atctgtctat ttcgttcatc catagttgcc tgactcctgc aaaccacgtt gtgtctcaaa   9900
atctctgatg ttacattgca caagataaaa atatatcatc atgaacaata aaactgtctg   9960
cttacataaa cagtaataca aggggtgtta tgagccatat tcaacgggaa acgtcttgct  10020
cgaggccgcg attaaattcc aacatggatg ctgatttata tgggtataaa tgggctcgcg  10080
ataatgtcgg gcaatcaggt gcgacaatct atcgattgta tgggaagccc gatgcgccag  10140
agttgtttct gaaacatggc aaaggtagcg ttgccaatga tgttacagat gagatggtca  10200
gactaaactg gctgacggaa tttatgcctc ttccgaccat caagcatttt atccgtactc  10260
ctgatgatgc atggttactc accactgcga tccccgggaa aacagcattc caggtattag  10320
aagaatatcc tgattcaggt gaaaatattg ttgatgcgct ggcagtgttc ctgcgccggt  10380
tgcattcgat tcctgtttgt aattgtcctt ttaacagcga tcgcgtattt cgtctcgctc  10440
aggcgcaatc acgaatgaat aacggtttgg ttgatgcgag tgattttgat gacgagcgta  10500
atggctggcc tgttgaacaa gtctggaaag aaatgcataa gcttttgcca ttctcaccgg  10560
attcagtcgt cactcatggt gatttctcac ttgataacct tattttgac gagggggaaat  10620
```

-continued

```
taataggttg tattgatgtt ggacgagtcg gaatcgcaga ccgataccag gatcttgcca    10680
tcctatggaa ctgcctcggt gagttttctc cttcattaca gaaacggctt tttcaaaaat    10740
atggtattga taatcctgat atgaataaat tgcagtttca tttgatgctc gatgagtttt    10800
tctaagggcg gcctgccacc ataccccacgc cgaaacaagc gctcatgagc ccgaagtggc    10860
gagcccgatc ttccccatcg gtgatgtcgg cgatataggc gccagcaacc gcacctgtgg    10920
cgccggtgat gagggcgcgc caagtcgacg tccggcagtc                          10960
```

<210> SEQ ID NO 14
<211> LENGTH: 536
<212> TYPE: PRT
<213> ORGANISM: Homo sapiens

<400> SEQUENCE: 14

```
Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
    290                 295                 300

Pro Thr Leu Ala Asn Ser Thr His His Asn Val Arg Leu Leu Met Leu
305                 310                 315                 320
```

```
Asp Asp Gln Arg Leu Leu Leu Pro His Trp Ala Lys Val Val Leu Thr
            325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
            355                 360                 365

Leu Phe Pro Asn Thr Met Leu Phe Ala Ser Glu Ala Cys Val Gly Ser
        370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
            405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
            435                 440                 445

Thr Phe Tyr Lys Gln Pro Met Phe Tyr His Leu Gly His Phe Ser Lys
        450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
            485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
            515                 520                 525

His Thr Tyr Leu Trp Arg Arg Gln
        530                 535

<210> SEQ ID NO 15
<211> LENGTH: 1608
<212> TYPE: DNA
<213> ORGANISM: Homo sapiens

<400> SEQUENCE: 15
atggaattca gcagcccag cagagaggaa tgccccaagc ctctgagccg ggtgtcaatc      60
atggccggat ctctgacagg actgctgctg cttcaggccg tgtcttgggc ttctggcgct    120
agaccttgca tccccaagag cttcggctac agcagcgtcg tgtgcgtgtg caatgccacc    180
tactgcgaca gcttcgaccc tcctaccttt cctgctctgg gcaccttcag cagatacgag    240
agcaccagat ccggcagacg gatggaactg agcatgggac ccatccaggc caatcacaca    300
ggcactggcc tgctgctgac actgcagcct gagcagaaat ccagaaagt gaaaggcttc    360 ggcggagcca tgacagatgc cgccgctctg aatatcctgg ctctgtctcc accagctcag    420
aacctgctgc tcaagagcta cttcagcgag aaggcatcg ctacaacat catcagagtg    480 cccatggcca gctgcgactt cagcatcagg acctacacct acgccgacac ccccgacgat    540
ttccagctgc acaacttcag cctgcctgaa gaggacacca agctgaagat ccctctgatc    600
cacagagccc tgcagctggc acaaagaccc gtgtcactgc tggcctctcc atggacatct    660
cccacctggc tgaaaacaaa tggcgccgtg aatggcaagg cagcctgaa aggccaacct    720 ggcgacatct accaccagac ctgggccaga tacttcgtga agttcctgga cgcctatgcc    780
gagcacaagc tgcagttttg gcccgtgaca gccgagaacg aaccttctgc tggactgctg    840
```

-continued

```
agcggctacc cctttcagtg cctgggcttt acacccgagc accagcggga ctttatcgcc    900
cgtgatctgg gacccacact ggccaatagc acccaccata atgtgcggct gctgatgctg    960
gacgaccaga gactgcttct gccccactgg gctaaagtgg tgctgacaga tcctgaggcc   1020
gccaaatacg tgcacggaat cgccgtgcac tggtatctgg actttctggc ccctgccaag   1080
gccacactgg agagacaca cagactgttc cccaacacca tgctgttcgc cagcgaagcc   1140
tgtgtgggca gcaagttttg gaacagagc gtgcggctcg gcagctggga tagaggcatg    1200
cagtacagcc acagcatcat caccaacctg ctgtaccacg tcgtcggctg gaccgactgg   1260
aatctggccc tgaatcctga aggcggccct aactgggtcc gaaacttcgt ggacagcccc   1320
atcatcgtgg acatcaccaa ggacaccttc tacaagcagc ccatgttcta ccacctggga   1380
cacttcagca gttcatccc cgagggctct cagcgcgttg gactggtggc ttcccagaag   1440
aacgatctgg acgccgtggc tctgatgcac cctgatggat ctgctgtggt ggtggtcctg   1500
aaccgcagca gcaaagatgt gcccctgacc atcaaggatc cgccgtggg attcctggaa   1560
acaatcagcc ctggctactc catccacacc tacctgtggc gtagacag              1608
```

<210> SEQ ID NO 16
<211> LENGTH: 524
<212> TYPE: PRT
<213> ORGANISM: Homo sapiens

<400> SEQUENCE: 16

```
Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Glu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
        115                 120                 125

Gly Glu Val Cys Ser Ala Leu Asn Leu Cys Glu Ser Leu Gln Lys His
    130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
        195                 200                 205

Gln Thr Ala Val Arg Thr Asn Ser Thr Phe Val Gln Ala Leu Val Glu
    210                 215                 220

His Val Lys Glu Glu Cys Asp Arg Leu Gly Pro Gly Met Ala Asp Ile
225                 230                 235                 240
```

```
Cys Lys Asn Tyr Ile Ser Gln Tyr Ser Glu Ile Ala Ile Gln Met Met
                245                 250                 255

Met His Met Gln Pro Lys Glu Ile Cys Ala Leu Val Gly Phe Cys Asp
        260                 265                 270

Glu Val Lys Glu Met Pro Met Gln Thr Leu Val Pro Ala Lys Val Ala
    275                 280                 285

Ser Lys Asn Val Ile Pro Ala Leu Glu Leu Val Glu Pro Ile Lys Lys
290                 295                 300

His Glu Val Pro Ala Lys Ser Asp Val Tyr Cys Glu Val Cys Glu Phe
305                 310                 315                 320

Leu Val Lys Glu Val Thr Lys Leu Ile Asp Asn Asn Lys Thr Glu Lys
                325                 330                 335

Glu Ile Leu Asp Ala Phe Asp Lys Met Cys Ser Lys Leu Pro Lys Ser
            340                 345                 350

Leu Ser Glu Glu Cys Gln Glu Val Val Asp Thr Tyr Gly Ser Ser Ile
        355                 360                 365

Leu Ser Ile Leu Leu Glu Val Ser Pro Glu Leu Val Cys Ser Met
    370                 375                 380

Leu His Leu Cys Ser Gly Thr Arg Leu Pro Ala Leu Thr Val His Val
385                 390                 395                 400

Thr Gln Pro Lys Asp Gly Gly Phe Cys Glu Val Cys Lys Lys Leu Val
                405                 410                 415

Gly Tyr Leu Asp Arg Asn Leu Glu Lys Asn Ser Thr Lys Gln Glu Ile
            420                 425                 430

Leu Ala Ala Leu Glu Lys Gly Cys Ser Phe Leu Pro Asp Pro Tyr Gln
        435                 440                 445

Lys Gln Cys Asp Gln Phe Val Ala Glu Tyr Glu Pro Val Leu Ile Glu
    450                 455                 460

Ile Leu Val Glu Val Met Asp Pro Ser Phe Val Cys Leu Lys Ile Gly
465                 470                 475                 480

Ala Cys Pro Ser Ala His Lys Pro Leu Leu Gly Thr Glu Lys Cys Ile
                485                 490                 495

Trp Gly Pro Ser Tyr Trp Cys Gln Asn Thr Glu Thr Ala Ala Gln Cys
            500                 505                 510

Asn Ala Val Glu His Cys Lys Arg His Val Trp Asn
        515                 520

<210> SEQ ID NO 17
<211> LENGTH: 1572
<212> TYPE: DNA
<213> ORGANISM: Homo sapiens

<400> SEQUENCE: 17
atgtacgccc tgttcctgct ggccagcctg ctgggcgccg ccctggccgg ccccgtgctg      60
ggcctgaagg agtgcacccg cggcagcgcc gtgtggtgcc agaacgtgaa gaccgccagc     120
gactgcggcg ccgtgaagca ctgcctgcag accgtgtgga caagcccac cgtgaagagc     180 ctgccctgcg acatctgcaa ggacgtggtg accgccgccg cgacatgct gaaggacaac     240 gccaccgagg aggagatcct ggtgtacctg gagaagacct cgactggct gcccaagccc     300 aacatgagcg ccagctgcaa ggagatcgtg gacagctacc tgcccgtgat cctggacatc     360
atcaagggcg agatgagccc ccggcgag tgtgcagcg ccctgaacct gtgcgagagc     420
ctgcagaagc acctggccga gctgaaccac cagaagcagc tggagagcaa caagatcccc     480
gagctggaca tgaccgaggt ggtggccccc ttcatggcca acatcccct gctgctgtac     540
```

-continued

```
cccaggacg gcccccgcag caagccccag cccaaggaca acggcgacgt gtgccaggac    600
tgcatccaga tggtgaccga catccagacc gccgtgcgca ccaacagcac cttcgtgcag    660
gccctggtgg agcacgtgaa ggaggagtgc gaccgcctgg cccccggcat ggccgacatc    720
tgcaagaact acatcagcca gtacagcgag atcgccatcc agatgatgat gcacatgcag    780
cccaaggaga tctgcgccct ggtgggcttc tgcgacgagg tgaaggagat gcccatgcag    840
accctggtgc cgccaaggt ggccagcaag aacgtgatcc ccgccctgga gctggtggag     900
cccatcaaga gcacgaggt gcccgccaag agcgacgtgt actgcgaggt gtgcgagttc     960
ctggtgaagg aggtgaccaa gctgatcgac aacaacaaga ccgagaagga gatcctggac   1020
gccttcgaca gatgtgcag caagctgccc aagagcctga gcgaggagtg ccaggaggtg    1080
gtggacacct acggcagcag catcctgagc atcctgctgg aggaggtgag ccccgagctg   1140
gtgtgcagca tgctgcacct gtgcagcggc acccgcctgc ccgccctgac cgtgcacgtg   1200
acccagccca aggacggcgg cttctgcgag gtgtgcaaga gctggtggg ctacctggac    1260 cgcaacctgg agaagaacag caccaagcag gagatcctgg ccgccctgga agggctgc     1320 agcttcctgc ccgaccccta ccagaagcag tgcgaccagt cgtggccga gtacgagccc    1380 gtgctgatcg agatcctggt ggaggtgatg gaccccagct tcgtgtgcct gaagatcggc   1440
gcctgcccca gcgcccacaa gcccctgctg ggcaccgaga agtgcatctg ggcccccagc   1500
tactggtgcc agaacaccga gaccgccgcc agtgcaacg ccgtggagca ctgcaagcgc    1560
cacgtgtgga ac                                                       1572
```

<210> SEQ ID NO 18
<211> LENGTH: 478
<212> TYPE: PRT
<213> ORGANISM: Homo sapiens

<400> SEQUENCE: 18

```
Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
            20                  25                  30

Val Asp Gln Ser Ile Glu Lys Lys Ile Val Leu Arg Asn Gly Thr Glu
        35                  40                  45

Ala Phe Asp Ser Trp Glu Lys Pro Pro Leu Pro Val Tyr Thr Gln Phe
    50                  55                  60

Tyr Phe Phe Asn Val Thr Asn Pro Glu Glu Ile Leu Arg Gly Glu Thr
65                  70                  75                  80

Pro Arg Val Glu Glu Val Gly Pro Tyr Thr Tyr Arg Glu Leu Arg Asn
                85                  90                  95

Lys Ala Asn Ile Gln Phe Gly Asp Asn Gly Thr Thr Ile Ser Ala Val
            100                 105                 110

Ser Asn Lys Ala Tyr Val Phe Glu Arg Asp Gln Ser Val Gly Asp Pro
        115                 120                 125

Lys Ile Asp Leu Ile Arg Thr Leu Asn Ile Pro Val Leu Thr Val Ile
    130                 135                 140

Glu Trp Ser Gln Val His Phe Leu Arg Glu Ile Ile Glu Ala Met Leu
145                 150                 155                 160

Lys Ala Tyr Gln Gln Lys Leu Phe Val Thr His Thr Val Asp Glu Leu
                165                 170                 175
```

-continued

Leu Trp Gly Tyr Lys Asp Glu Ile Leu Ser Leu Ile His Val Phe Arg
            180                 185                 190

Pro Asp Ile Ser Pro Tyr Phe Gly Leu Phe Tyr Glu Lys Asn Gly Thr
            195                 200                 205

Asn Asp Gly Asp Tyr Val Phe Leu Thr Gly Glu Asp Ser Tyr Leu Asn
    210                 215                 220

Phe Thr Lys Ile Val Glu Trp Asn Gly Lys Thr Ser Leu Asp Trp Trp
225                 230                 235                 240

Ile Thr Asp Lys Cys Asn Met Ile Asn Gly Thr Asp Gly Asp Ser Phe
                245                 250                 255

His Pro Leu Ile Thr Lys Asp Glu Val Leu Tyr Val Phe Pro Ser Asp
            260                 265                 270

Phe Cys Arg Ser Val Tyr Ile Thr Phe Ser Asp Tyr Glu Ser Val Gln
        275                 280                 285

Gly Leu Pro Ala Phe Arg Tyr Lys Val Pro Ala Glu Ile Leu Ala Asn
    290                 295                 300

Thr Ser Asp Asn Ala Gly Phe Cys Ile Pro Glu Gly Asn Cys Leu Gly
305                 310                 315                 320

Ser Gly Val Leu Asn Val Ser Ile Cys Lys Asn Gly Ala Pro Ile Ile
                325                 330                 335

Met Ser Phe Pro His Phe Tyr Gln Ala Asp Glu Arg Phe Val Ser Ala
            340                 345                 350

Ile Glu Gly Met His Pro Asn Gln Glu Asp His Glu Thr Phe Val Asp
        355                 360                 365

Ile Asn Pro Leu Thr Gly Ile Ile Leu Lys Ala Ala Lys Arg Phe Gln
    370                 375                 380

Ile Asn Ile Tyr Val Lys Lys Leu Asp Asp Phe Val Glu Thr Gly Asp
385                 390                 395                 400

Ile Arg Thr Met Val Phe Pro Val Met Tyr Leu Asn Glu Ser Val His
                405                 410                 415

Ile Asp Lys Glu Thr Ala Ser Arg Leu Lys Ser Met Ile Asn Thr Thr
            420                 425                 430

Leu Ile Ile Thr Asn Ile Pro Tyr Ile Ile Met Ala Leu Gly Val Phe
        435                 440                 445

Phe Gly Leu Val Phe Thr Trp Leu Ala Cys Lys Gly Gln Gly Ser Met
    450                 455                 460

Asp Glu Gly Thr Ala Asp Glu Arg Ala Pro Leu Ile Arg Thr
465                 470                 475

<210> SEQ ID NO 19
<211> LENGTH: 1434
<212> TYPE: DNA
<213> ORGANISM: Homo sapiens

<400> SEQUENCE: 19
atgggccgct gctgcttcta caccgccggc accctgagcc tgctgctgct ggtgaccagc      60
gtgaccctgc tggtggcccg cgtgttccag aaggccgtgg accagagcat cgagaagaag     120
atcgtgctgc gcaacggcac cgaggccttc gacagctggg agaagccccc cctgcccgtg     180
tacacccagt tctacttctt caacgtgacc aaccccgagg agatcctgcg cggcgagacc     240
ccccgcgtgg aggaggtggg ccccctacacc taccgcgagc tgcgcaacaa ggccaacatc     300
cagttcggcg acaacggcac caccatcagc gccgtgagca acaaggccta cgtgttcgag     360
cgcgaccaga gcgtgggcga cccccaagatc gacctgatcc gcaccctgaa catccccgtg     420

```
ctgaccgtga tcgagtggag ccaggtgcac ttcctgcgcg agatcatcga ggccatgctg     480
aaggcctacc agcagaagct gttcgtgacc cacaccgtgg acgagctgct gtggggctac     540
aaggacgaga tcctgagcct gatccacgtg ttccgccccg acatcagccc ctacttcggc     600
ctgttctacg agaagaacgg caccaacgac ggcgactacg tgttcctgac cggcgaggac     660
agctacctga acttcaccaa gatcgtggag tggaacggca agaccagcct ggactggtgg     720
atcaccgaca agtgcaacat gatcaacggc accgacggcg acagcttcca ccccctgatc     780
accaaggacg aggtgctgta cgtgttcccc agcgacttct gccgcagcgt gtacatcacc     840
ttcagcgact acgagagcgt gcagggcctg cccgccttcc gctacaaggt gcccgccgag     900
atcctggcca acaccagcga caacgccggc ttctgcatcc ccgagggcaa ctgcctgggc     960
agcggcgtgc tgaacgtgag catctgcaag aacggcgccc ccatcatcat gagcttcccc     1020
cacttctacc aggccgacga gcgcttcgtg agcgccatcg agggcatgca ccccaaccag     1080
gaggaccacg agaccttcgt ggacatcaac cccctgaccg gcatcatcct gaaggccgcc     1140
aagcgcttcc agatcaacat ctacgtgaag aagctggacg acttcgtgga gaccggcgac     1200
atccgcacca tggtgttccc cgtgatgtac ctgaacgaga gcgtgcacat cgacaaggag     1260
accgccagcc gcctgaagag catgatcaac accaccctga tcatcaccaa catcccctac     1320
atcatcatgg ccctgggcgt gttcttcggc ctggtgttca cctggctggc ctgcaagggc     1380
cagggcagca tggacgaggg caccgccgac gagcgcgccc ccctgatccg cacc           1434

<210> SEQ ID NO 20
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 20
tggaagactt cgagatacac tgt                                              23

<210> SEQ ID NO 21
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 21
acagtgtatc tcgaagtctt cca                                              23

<210> SEQ ID NO 22
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 22
tttagaaata agtggtagtc a                                                21

<210> SEQ ID NO 23
<211> LENGTH: 21
<212> TYPE: DNA
<213> ORGANISM: Artificial sequence
<220> FEATURE:
<223> OTHER INFORMATION: Synthetic polynucleotide
```

```
<400> SEQUENCE: 23
tgactaccac ttatttctaa a                                         21

<210> SEQ ID NO 24
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 24
agggtatcaa gactacgaa                                            19

<210> SEQ ID NO 25
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 25
ttcgtagtct tgatacect                                            19

<210> SEQ ID NO 26
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 26
tattagatct gatggccgc                                            19

<210> SEQ ID NO 27
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 27
ctccatcact aggggttcct                                           20

<210> SEQ ID NO 28
<211> LENGTH: 60
<212> TYPE: DNA
<213> ORGANISM: Artificial sequence
<220> FEATURE:
<223> OTHER INFORMATION: Synthetic polynucleotide

<400> SEQUENCE: 28
agctctgggt atttaagccc gagtgagcac gcagggtctc cattttgaag cgggaggtta  60

<210> SEQ ID NO 29
<211> LENGTH: 145
<212> TYPE: DNA
<213> ORGANISM: Unknown
<220> FEATURE:
<223> OTHER INFORMATION: AAV2 ITR

<400> SEQUENCE: 29
aggaacccct agtgatggag ttggccactc cctctctgcg cgctcgctcg ctcactgagg  60
ccgggcgacc aaaggtcgcc cgacgcccgg gctttgcccg gcggcctca gtgagcgagc  120 gagcgcgcag agagggagtg gccaa                                      145
```

```
<210> SEQ ID NO 30
<211> LENGTH: 927
<212> TYPE: PRT
<213> ORGANISM: Homo sapiens

<400> SEQUENCE: 30

Met Gly Thr Gln Asp Pro Gly Asn Met Gly Thr Gly Val Pro Ala Ser
1               5                   10                  15

Glu Gln Ile Ser Cys Ala Lys Glu Asp Pro Gln Val Tyr Cys Pro Glu
            20                  25                  30

Glu Thr Gly Gly Thr Lys Asp Val Gln Val Thr Asp Cys Lys Ser Pro
        35                  40                  45

Glu Asp Ser Arg Pro Pro Lys Glu Thr Asp Cys Cys Asn Pro Glu Asp
50                  55                  60

Ser Gly Gln Leu Met Val Ser Tyr Glu Gly Lys Ala Met Gly Tyr Gln
65                  70                  75                  80

Val Pro Pro Phe Gly Trp Arg Ile Cys Leu Ala His Glu Phe Thr Glu
                85                  90                  95

Lys Arg Lys Pro Phe Gln Ala Asn Asn Val Ser Leu Ser Asn Met Ile
            100                 105                 110

Lys His Ile Gly Met Gly Leu Arg Tyr Leu Gln Trp Trp Tyr Arg Lys
        115                 120                 125

Thr His Val Glu Lys Lys Thr Pro Phe Ile Asp Met Ile Asn Ser Val
130                 135                 140

Pro Leu Arg Gln Ile Tyr Gly Cys Pro Leu Gly Gly Ile Gly Gly Gly
145                 150                 155                 160

Thr Ile Thr Arg Gly Trp Arg Gly Gln Phe Cys Arg Trp Gln Leu Asn
                165                 170                 175

Pro Gly Met Tyr Gln His Arg Thr Val Ile Ala Asp Gln Phe Thr Val
            180                 185                 190

Cys Leu Arg Arg Glu Gly Gln Thr Val Tyr Gln Gln Val Leu Ser Leu
        195                 200                 205

Glu Arg Pro Ser Val Leu Arg Ser Trp Asn Trp Gly Leu Cys Gly Tyr
210                 215                 220

Phe Ala Phe Tyr His Ala Leu Tyr Pro Arg Ala Trp Thr Val Tyr Gln
225                 230                 235                 240

Leu Pro Gly Gln Asn Val Thr Leu Thr Cys Arg Gln Ile Thr Pro Ile
                245                 250                 255

Leu Pro His Asp Tyr Gln Asp Ser Ser Leu Pro Val Gly Val Phe Val
            260                 265                 270

Trp Asp Val Glu Asn Glu Gly Asp Glu Ala Leu Asp Val Ser Ile Met
        275                 280                 285

Phe Ser Met Arg Asn Gly Leu Gly Gly Asp Ala Pro Gly Gly
290                 295                 300

Leu Trp Asn Glu Pro Phe Cys Leu Glu Arg Ser Gly Glu Thr Val Arg
305                 310                 315                 320

Gly Leu Leu Leu His His Pro Thr Leu Pro Asn Pro Tyr Thr Met Ala
                325                 330                 335

Val Ala Ala Arg Val Thr Ala Ala Thr Thr Val Thr His Ile Thr Ala
            340                 345                 350

Phe Asp Pro Asp Ser Thr Gly Gln Gln Val Trp Gln Asp Leu Leu Gln
        355                 360                 365
```

```
Asp Gly Gln Leu Asp Ser Pro Thr Gly Gln Ser Thr Pro Thr Gln Lys
    370                 375                 380

Gly Val Gly Ile Ala Gly Ala Val Cys Val Ser Ser Lys Leu Arg Pro
385                 390                 395                 400

Arg Gly Gln Cys Arg Leu Glu Phe Ser Leu Ala Trp Asp Met Pro Arg
            405                 410                 415

Ile Met Phe Gly Ala Lys Gly Gln Val His Tyr Arg Arg Tyr Thr Arg
                420                 425                 430

Phe Phe Gly Gln Asp Gly Asp Ala Ala Pro Ala Leu Ser His Tyr Ala
        435                 440                 445

Leu Cys Arg Tyr Ala Glu Trp Glu Glu Arg Ile Ser Ala Trp Gln Ser
    450                 455                 460

Pro Val Leu Asp Asp Arg Ser Leu Pro Ala Trp Tyr Lys Ser Ala Leu
465                 470                 475                 480

Phe Asn Glu Leu Tyr Phe Leu Ala Asp Gly Gly Thr Val Trp Leu Glu
            485                 490                 495

Val Leu Glu Asp Ser Leu Pro Glu Glu Leu Gly Arg Asn Met Cys His
                500                 505                 510

Leu Arg Pro Thr Leu Arg Asp Tyr Gly Arg Phe Gly Tyr Leu Glu Gly
        515                 520                 525

Gln Glu Tyr Arg Met Tyr Asn Thr Tyr Asp Val His Phe Tyr Ala Ser
    530                 535                 540

Phe Ala Leu Ile Met Leu Trp Pro Lys Leu Glu Leu Ser Leu Gln Tyr
545                 550                 555                 560

Asp Met Ala Leu Ala Thr Leu Arg Glu Asp Leu Thr Arg Arg Arg Tyr
            565                 570                 575

Leu Met Ser Gly Val Met Ala Pro Val Lys Arg Arg Asn Val Ile Pro
                580                 585                 590

His Asp Ile Gly Asp Pro Asp Glu Pro Trp Leu Arg Val Asn Ala
        595                 600                 605

Tyr Leu Ile His Asp Thr Ala Asp Trp Lys Asp Leu Asn Leu Lys Phe
    610                 615                 620

Val Leu Gln Val Tyr Arg Asp Tyr Tyr Leu Thr Gly Asp Gln Asn Phe
625                 630                 635                 640

Leu Lys Asp Met Trp Pro Val Cys Leu Ala Val Met Glu Ser Glu Met
            645                 650                 655

Lys Phe Asp Lys Asp His Asp Gly Leu Ile Glu Asn Gly Gly Tyr Ala
                660                 665                 670

Asp Gln Thr Tyr Asp Gly Trp Val Thr Thr Gly Pro Ser Ala Tyr Cys
        675                 680                 685

Gly Gly Leu Trp Leu Ala Ala Val Ala Val Met Val Gln Met Ala Ala
    690                 695                 700

Leu Cys Gly Ala Gln Asp Ile Gln Asp Lys Phe Ser Ser Ile Leu Ser
705                 710                 715                 720

Arg Gly Gln Glu Ala Tyr Glu Arg Leu Leu Trp Asn Gly Arg Tyr Tyr
            725                 730                 735

Asn Tyr Asp Ser Ser Ser Arg Pro Gln Ser Arg Ser Val Met Ser Asp
                740                 745                 750

Gln Cys Ala Gly Gln Trp Phe Leu Lys Ala Cys Gly Leu Gly Glu Gly
        755                 760                 765

Asp Thr Glu Val Phe Pro Thr Gln His Val Val Arg Ala Leu Gln Thr
    770                 775                 780
```

```
Ile Phe Glu Leu Asn Val Gln Ala Phe Ala Gly Gly Ala Met Gly Ala
785                 790                 795                 800

Val Asn Gly Met Gln Pro His Gly Val Pro Asp Lys Ser Ser Val Gln
            805                 810                 815

Ser Asp Glu Val Trp Val Gly Val Val Tyr Gly Leu Ala Ala Thr Met
        820                 825                 830

Ile Gln Glu Gly Leu Thr Trp Glu Gly Phe Gln Thr Ala Glu Gly Cys
    835                 840                 845

Tyr Arg Thr Val Trp Glu Arg Leu Gly Leu Ala Phe Gln Thr Pro Glu
850                 855                 860

Ala Tyr Cys Gln Gln Arg Val Phe Arg Ser Leu Ala Tyr Met Arg Pro
865                 870                 875                 880

Leu Ser Ile Trp Ala Met Gln Leu Ala Leu Gln Gln Gln His Lys
            885                 890                 895

Lys Ala Ser Trp Pro Lys Val Lys Gln Gly Thr Gly Leu Arg Thr Gly
            900                 905                 910

Pro Met Phe Gly Pro Lys Glu Ala Met Ala Asn Leu Ser Pro Glu
            915                 920                 925

<210> SEQ ID NO 31
<211> LENGTH: 2781
<212> TYPE: DNA
<213> ORGANISM: Homo sapiens

<400> SEQUENCE: 31
atgggcaccc aggaccccgg caacatgggc accggcgtgc cgccagcga gcagatcagc      60 tgcgccaagg aggaccccca ggtgtactgc cccgaggaga ccggcggcac caaggacgtg     120
caggtgaccg actgcaagag ccccgaggac agccgccccc ccaaggagac cgactgctgc     180
aaccccgagg acagcggcca gctgatggtg agctacgagg gcaaggccat gggctaccag     240 gtgccccct cggctggcg catctgcctg gcccacgagt tcaccgagaa gcgcaagccc       300
ttccaggcca caacgtgag cctgagcaac atgatcaagc acatcggcat gggcctgcgc      360
tacctgcagt ggtggtaccg caagacccac gtggagaaga gaccccctt catcgacatg      420 atcaacagcg tgccctgcg ccagatctac ggctgccccc tgggcggcat cggcggcggc      480
accatcaccc gcggctggcg cggccagttc tgccgctggc agctgaaccc cggcatgtac      540
cagcaccgca ccgtgatcgc cgaccagttc accgtgtgcc tgcgccgcga gggccagacc      600
gtgtaccagc aggtgctgag cctggagcgc cccagcgtgc tgcgcagctg aactgggggc     660
ctgtgcggct acttcgcctt ctaccacgcc ctgtaccccc gcgcctggac cgtgtaccag      720
ctgcccggcc agaacgtgac cctgacctgc cgccagatca cccccatcct gccccacgac      780
taccaggaca gcagcctgcc cgtgggcgtg ttcgtgtggg acgtggagaa cgagggcgac      840
gaggccctgg acgtgagcat catgttcagc atgcgcaacg gcctgggcgg cggcgacgac      900
gcccccggcg gcctgtggaa cgagcccttc gcctggagc agcggcga gaccgtgcgc        960 ggcctgctgc tgcaccaccc cacccctgccc aaccccctaca ccatggccgt ggccgcccgc  1020
gtgaccgccg ccaccaccgt gacccacatc accgccttcg accccgacag caccggccag   1080
caggtgtggg aggacctgct gcaggacggc agctggaca gccccaccgg ccagagcacc    1140
cccacccaga agggcgtggg catcgccggc gccgtgtgcg tgagcagcaa gctgcgcccc    1200
cgcggccagt gccgcctgga gttcagcctg gctgggaca tgccccgcat catgttcggc    1260
gccaagggcc aggtgcacta ccgccgctac acccgcttct tcggccagga cggcgacgcc  1320
```

| | |
|---|---|
| gccccgccc tgagccacta cgccctgtgc cgctacgccg agtgggagga gcgcatcagc | 1380 |
| gcctggcaga gccccgtgct ggacgaccgc agcctgcccg cctggtacaa gagcgccctg | 1440 |
| ttcaacgagc tgtacttcct ggccgacggc ggcaccgtgt ggctggaggt gctggaggac | 1500 |
| agcctgcccg aggagctggg ccgcaacatg tgccacctgc gccccaccct gcgcgactac | 1560 |
| ggccgcttcg gctacctgga gggccaggag taccgcatgt acaacaccta cgacgtgcac | 1620 |
| ttctacgcca gcttcgccct gatcatgctg tgcccaagc tggagctgag cctgcagtac | 1680 |
| gacatggccc tggccaccct gcgcgaggac ctgacccgcc gccgctacct gatgagcggc | 1740 |
| gtgatggccc ccgtgaagcg ccgcaacgtg atccccacg acatcggcga ccccgacgac | 1800 |
| gagccctggc tgcgcgtgaa cgcctacctg atccacgaca ccgccgactg aaggacctg | 1860 |
| aacctgaagt tcgtgctgca ggtgtaccgc gactactacc tgaccggcga ccagaacttc | 1920 |
| ctgaaggaca tgtggcccgt gtgcctggcc gtgatggaga gcgagatgaa gttcgacaag | 1980 |
| gaccacgacg gcctgatcga aacggcggc tacgccgacc agacctacga cggctgggtg | 2040 |
| accaccggcc ccagcgccta ctgcggcggc ctgtggctgg ccgccgtggc cgtgatggtg | 2100 |
| cagatggccg ccctgtgcgg cgcccaggac atccaggaca agttcagcag catcctgagc | 2160 |
| cgcggccagg aggcctacga gcgcctgctg tggaacggcc gctactacaa ctacgacagc | 2220 |
| agcagccgcc cccagagccg cagcgtgatg agcgaccagt gcgccggcca gtggttcctg | 2280 |
| aaggcctgcg gcctgggcga gggcgacacc gaggtgttcc ccacccagca cgtggtgcgc | 2340 |
| gccctgcaga ccatcttcga gctgaacgtg caggccttcg ccggcggcgc catgggcgcc | 2400 |
| gtgaacggca tgcagcccca cggcgtgccc gacaagagca gcgtgcagag cgacgaggtg | 2460 |
| tgggtgggcg tggtgtacgg cctggccgcc accatgatcc aggagggcct gacctgggag | 2520 |
| ggcttccaga ccgccgaggg ctgctaccgc accgtgtggg agcgcctggg cctggccttc | 2580 |
| cagaccccg aggcctactg ccagcagcgc gtgttccgca gcctggccta catgcgcccc | 2640 |
| ctgagcatct gggccatgca gctggccctg cagcagcagc agcacaagaa ggccagctgg | 2700 |
| cccaaggtga gcagggcac cggcctgcgc accggcccca tgttcggccc caaggaggcc | 2760 |
| atggccaacc tgagccccga g | 2781 |

<210> SEQ ID NO 32
<211> LENGTH: 11264
<212> TYPE: DNA
<213> ORGANISM: Artificial sequence
<220> FEATURE:
<223> OTHER INFORMATION: Synthetic polynucleotide

<400> SEQUENCE: 32

| | |
|---|---|
| ttggccactc cctctctgcg cgctcgctcg ctcactgagg ccgggcgacc aaaggtcgcc | 60 |
| cgacgcccgg gctttgcccg gcggccctca gtgagcgagc gagcgcgcag agagggagtg | 120 |
| gccaactcca tcactagggg ttcctgctag ctctgggtat ttaagcccga gtgagcacgc | 180 |
| agggtctcca ttttgaagcg ggaggttacg cgttcgtcga ctactagtgg gtaccagagc | 240 |
| tccctaggtt ctagaaccgg tgacgtctcc catggtgaag cttggatctg agtaagtcac | 300 |
| tgactgtcta tgcctgggaa agggtgggca ggagatgggg cagtgcagga aaagtggcac | 360 |
| tatgaaccct cctggtggcg aggggagggg ggtggtcctc gaacgccttg cagaactggc | 420 |
| ctggatacag agtggaccgg ctggccccat ctggaagact tcgagataca ctgttgtctt | 480 |
| actgcgctca acagtgtatc tcgaagtctt ccaaatggtg ccagccatcg cagcgggtg | 540 |
| caggaaatgg gggcagcccc ccttttttggc tatccttcca cgtgttcttt tttgtatctt | 600 |

-continued

```
ttgtgtttcc tagaaaacat ctcagtcacc accgcagccc taggaatgca tctagacaat      660
tgtactaacc ttcttctctt tcctctcctg acagtccgga aagccaccat gggcacccag      720
gaccccggca acatgggcac cggcgtgccc gccagcgagc agatcagctg cgccaaggag      780
gaccccccagg tgtactgccc cgaggagacc ggcggcacca aggacgtgca ggtgaccgac     840
tgcaagagcc ccgaggacag ccgccccccc aaggagaccg actgctgcaa ccccgaggac      900
agcggccagc tgatggtgag ctacgagggc aaggccatgg gctaccaggt gccccccttc      960
ggctggcgca tctgcctggc ccacgagttc accgagaagc gcaagccctt ccaggccaac     1020
aacgtgagcc tgagcaacat gatcaagcac atcggcatgg gcctgcgcta cctgcagtgg     1080
tggtaccgca agacccacgt ggagaagaag acccccttca tcgacatgat caacagcgtg     1140
cccctgcgcc agatctacgg ctgccccctg ggcggcatcg gcggcggcac catcacccgc     1200
ggctggcgcg ccagttctg ccgctggcag ctgaaccccg gcatgtacca gcaccgcacc      1260
gtgatcgccg accagttcac cgtgtgcctg cgccgcgagg ccagaccgt gtaccagcag      1320
gtgctgagcc tggagcgccc cagcgtgctg cgcagctgga actggggcct gtgcggctac     1380
ttcgccttct accacgccct gtaccccgcg gcctggaccg tgtaccagct gcccggccag     1440
aacgtgaccc tgacctgccg ccagatcacc cccatcctgc cccacgacta ccaggacagc     1500
agcctgcccg tgggcgtgtt cgtgtgggac gtggagaacg agggcgacga ggccctggac     1560
gtgagcatca tgttcagcat gcgcaacggc ctgggcggcg gcgacgacgc ccccggcggc     1620
ctgtggaacg agcccttctg cctggagcgc agcggcgaga ccgtgcgcgg cctgctgctg     1680
caccacccca ccctgcccaa ccctacacc atggccgtgg ccgcccgcgt gaccgccgcc      1740
accaccgtga cccacatcac cgccttcgac cccgacagca ccggccagca ggtgtggcag     1800
gacctgctgc aggacggcca gctggacagc cccaccggcc agagcacccc cacccagaag     1860
ggcgtgggca tcgccggcgc cgtgtgcgtg agcagcaagc tgcgccccg cggccagtgc      1920
cgcctggagt tcagcctggc ctgggacatg ccccgcatca tgttcggcgc caagggccag     1980
gtgcactacc gccgctacac ccgcttcttc ggccaggacg cgacgccgc ccccgccctg      2040
agccactacg ccctgtgccg ctacgccgag tgggaggagc gcatcagcgc ctggcagagc     2100
cccgtgctgg acgaccgcag cctgcccgcc tggtacaaga gcgccctgtt caacgagctg     2160
tacttcctgg ccgacggcgg caccgtgtgg ctggaggtgc tggaggacag cctgcccgag     2220
gagctgggcc gcaacatgtg ccacctgcgc cccaccctgc gcgactacgg ccgcttcggc     2280
tacctggagg ccaggagta ccgcatgtac aacacctacg acgtgcactt ctacgccagc     2340
ttcgccctga tcatgctgtg gcccaagctg gagctgagcc tgcagtacga catggccctg     2400
gccaccctgc gcgaggacct gaccgccgcc gctacctga tgagcggcgt gatggccccc     2460
gtgaagcgcc gcaacgtgat ccccacgac atcggcgacc ccgacgacga gccctggctg     2520
cgcgtgaacg cctacctgat ccacgacacc gccgactgga aggacctgaa cctgaagttc     2580
gtgctgcagg tgtaccgcga ctactacctg accggcgacc agaacttcct gaaggacatg     2640
tggcccgtgt gcctggccgt gatggagagc gagatgaagt cgacaaggga ccacgacggc     2700
ctgatcgaga acgcggcta cgccgaccag acctacgacg ctgggtgac caccggcccc      2760
agcgcctact gcggcggcct gtggctggcc gccgtggccg tgatggtgca gatggccgcc     2820
ctgtgcggcg cccaggacat ccaggacaag ttcagcagca tcctgagccg cggccaggag     2880
gcctacgagc gcctgctgtg gaacggccgc tactacaact acgacagcag cagccgcccc     2940
```

```
cagagccgca gcgtgatgag cgaccagtgc gccggccagt ggttcctgaa ggcctgcggc    3000
ctgggcgagg gcgacaccga ggtgttcccc acccagcacg tggtgcgcgc cctgcagacc    3060
atcttcgagc tgaacgtgca ggccttcgcc ggcggcgcca tgggcgccgt gaacggcatg    3120
cagccccacg gcgtgcccga caagagcagc gtgcagagcg acgaggtgtg ggtgggcgtg    3180
gtgtacggcc tggccgccac catgatccag gagggcctga cctgggaggg cttccagacc    3240
gccgagggct gctaccgcac cgtgtgggag cgcctgggcc tggccttcca gacccccgag    3300
gcctactgcc agcagcgcgt gttccgcagc ctggcctaca tgcgccccct gagcatctgg    3360
gccatgcagc tggccctgca gcagcagcag cacaagaagg ccagctggcc caaggtgaag    3420
cagggcaccg gcctgcgcac cggccccatg ttcggcccca aggaggccat ggccaacctg    3480
agccccgagt gacaattgtt aattaagttt aaaccctcga ggccgcaagc ttatcgataa    3540
tcaacctctg gattacaaaa tttgtgaaag attgactggt attcttaact atgttgctcc    3600
ttttacgcta tgtggatacg ctgctttaat gcctttgtat catgctattg cttcccgtat    3660
ggctttcatt ttctcctcct tgtataaatc ctggttgctg tctctttatg aggagttgtg    3720
gcccgttgtc aggcaacgtg gcgtggtgtg cactgtgttt gctgacgcaa cccccactgg    3780
ttggggcatt gccaccacct gtcagctcct tccgggact ttcgctttcc cctccctat    3840 tgccacggcg gaactcatcg ccgcctgcct tgcccgctgc tggacagggg ctcggctgtt    3900
gggcactgac aattccgtgg tgttgtcggg gaaatcatcg tcctttcctt ggctgctcgc    3960
ctgtgttgcc acctggattc tgcgcgggac gtccttctgc tacgtcccttt cggccctcaa    4020 tccagcggac cttccttccc gcggcctgct gccggctctg cggcctcttc cgcgtcttcg    4080
ccttcgccct cagacgagtc ggatctccct ttgggccgcc tccccgcatc gataccgtcg    4140
actagagctc gctgatcagc ctcgactgtg ccttctagtt gccagccatc tgttgtttgc    4200
ccctcccccg tgccttcctt gaccctggaa ggtgccactc ccactgtcct ttcctaataa    4260
aatgaggaaa ttgcatcgca ttgtctgagt aggtgtcatt ctattctggg gggtggggtg    4320
gggcaggaca gcaaggggga ggattgggaa gacaatagca ggcatgctgg ggagagatcc    4380
acgataacaa acagcttttt tggggtgaac atattgactg aattccctgc aggttggcca    4440
ctccctctct gcgcgctcgc tcgctcactg aggccgcccg ggcaaagccc gggcgtcggg    4500
cgacctttgg tcgcccggcc tcagtgagcg agcgagcgcg cagagaggga gtggccaact    4560
ccatcactag gggttcctgc ggccgctcgt acggtctcga ggaattcctg caggataact    4620
tgccaacctc attctaaaat gtatatagaa gcccaaaaga caataacaaa atattcttg    4680 tagaacaaaa tgggaaagaa tgttccacta aatatcaaga tttagagcaa agcatgagat    4740
gtgtggggat agacagtgag gctgataaaa tagagtagag ctcagaaaca gacccattga    4800
tatatgtaag tgacctatga aaaaaatatg gcattttaca atgggaaaat gatggtcttt    4860 ttcttttta gaaaacagg gaaatatatt tatatgtaaa aaataaaagg gaacccatat    4920
gtcataccat acacacaaaa aaattccagt gaattataag tctaaatgga gaaggcaaaa    4980
ctttaaatct tttagaaaat aatatagaag catgcagacc agcctggcca acatgatgaa    5040
accctctcta ctaataataa aatcagtaga actactcagg actactttga gtgggaagtc    5100
cttttctatg aagacttctt tggccaaaat taggctctaa atgcaaggag atagtgcatc    5160
atgcctggct gcacttactg ataaatgatg ttatcaccat cttttaaccaa atgcacagga    5220 acaagttatg gtactgatgt gctggattga gaaggagctc tacttccttg acaggacaca    5280
tttgtatcaa cttaaaaaag cagatttttg ccagcagaac tattcattca gaggtaggaa    5340
```

-continued

```
acttagaata gatgatgtca ctgattagca tggcttcccc atctccacag ctgcttccca    5400
cccaggttgc ccacagttga gtttgtccag tgctcagggc tgcccactct cagtaagaag    5460
ccccacacca gcccctctcc aaatatgttg gctgttcctt ccattaaagt gaccccactt    5520
tagagcagca agtggatttc tgtttcttac agttcaggaa ggaggagtca gctgtgagaa    5580
cctggagcct gagatgcttc taagtcccac tgctactggg gtcagggaag ccagactcca    5640
gcatcagcag tcaggagcac taagcccttg ccaacatcct gtttctcaga gaaactgctt    5700
ccattataat ggttgtcctt ttttaagcta tcaagccaaa caaccagtgt ctaccattat    5760
tctcatcacc tgaagccaag ggttctagca aaagtcaagc tgtcttgtaa tggttgatgt    5820
gcctccagct tctgtcttca gtcactccac tcttagcctg ctctgaatca actctgacca    5880
cagttccctg gagcccctgc cacctgctgc ccctgccacc ttctccatct gcagtgctgt    5940
gcagccttct gcactcttgc agagctaata ggtggagact tgaaggaaga ggaggaaagt    6000
ttctcataat agccttgctg caagctcaaa tgggaggtgg gcactgtgcc caggagcctt    6060
ggagcaaagg ctgtgcccaa cctctgactg catccaggtt tggtcttgac agagataaga    6120
agccctggct tttggagcca aaatctaggt cagacttagg caggattctc aaagtttatc    6180
agcagaacat gaggcagaag acccttctg ctccagcttc ttcaggctca accttcatca    6240
gaatagatag aaagagaggc tgtgagggtt cttaaaacag aagcaaatct gactcagaga    6300
ataaacaacc tcctagtaaa ctacagctta gacagagcat ctggtggtga gtgtgctcag    6360
tgtcctactc aactgtctgg tatcagccct catgaggact tctcttcttt ccctcataga    6420
cctccatctc tgttttcctt agcctgcaga aatctggatg gctattcaca gaatgcctgt    6480
gctttcagag ttgcatttttt tctctggtat tctggttcaa gcatttgaag gtaggaaagg    6540
ttctccaagt gcaagaaagc cagccctgag cctcaactgc ctggctagtg tggtcagtag    6600
gatgcaaagg ctgttgaatg ccacaaggcc aaactttaac ctgtgtacca caagcctagc    6660
agcagaggca gctctgctca ctggaactct ctgtcttctt tctcctgagc ctttctttt    6720 cctgagtttt ctagctctcc tcaaccttac ctctgcccta cccaggacaa acccaagagc    6780
cactgtttct gtgatgtcct ctccagccct aattaggcat catgacttca gcctgaccct    6840
ccatgctcag aagcagtgct aatccacttc agatgagctg ctctatgcaa cacaggcaga    6900
gcctacaaac ctttgcacca gagccctcca catatcagtg tttgttcata ctcacttcaa    6960
cagcaaatgt gactgctgag attaagattt tacacaagat ggtctgtaat ttcacagtta    7020
gttttatccc attaggtatg aaagaattag cataattccc cttaaacatg aatgaatctt    7080
agatttttta ataaatagtt ttggaagtaa agacagagac atcaggagca caaggaatag    7140
cctgagagga caaacagaac aagaaagagt ctggaaatac acaggatgtt cttggcctcc    7200
tcaaagcaag tgcaagcaga tagtaccagc agcccaggc tatcagagcc cagtgaagag    7260
aagtaccatg aaagccacag ctctaaccac cctgttccag agtgacagac agtcccaag    7320 acaagccagc ctgagccaga gagagaactg caagagaaag tttctaattt aggttctgtt    7380
agattcagac aagtgcaggt catcctctct ccacagctac tcacctctcc agcctaacaa    7440
agcctgcagt ccacactcca accctggtgt ctcacctcct agcctctccc aacatcctgc    7500
tctctgacca tcttctgcat ctctccatctc accatctccc actgtctaca gcctactctt    7560
gcaactacca tctcattttc tgacatcctg tctacatctt ctgccatact ctgccatcta    7620
ccataccacc tcttaccatc taccacacca tcttttatct ccatccctct cagaagcctc    7680
```

-continued

```
caagctgaat cctgctttat gtgttcatct cagcccctgc atggaaagct gaccccagag    7740
gcagaactat tcccagagag cttggccaag aaaaacaaaa ctaccagcct ggccaggctc    7800
aggagtagta agctgcagtg tctgttgtgt tctagcttca acagctgcag gagttccact    7860
ctcaaatgct ccacatttct cacatcctcc tgattctggt cactacccat cttcaaagaa    7920
cagaatatct cacatcagca tactgtgaag gactagtcat gggtgcagct gctcagagct    7980
gcaaagtcat tctggatggt ggagagctta caaacatttc atgatgctcc ccccgctctg    8040
atggctggag cccaatccct acacagactc ctgctgtatg tgttttcctt tcactctgag    8100
ccacagccag agggcaggca ttcagtctcc tcttcaggct ggggctgggg cactgagaac    8160
tcacccaaca ccttgctctc actccttctg caaaacaaga aagagctttg tgctgcagta    8220
gccatgaaga atgaaaggaa ggctttaact aaaaaatgtc agagattatt ttcaacccct    8280
tactgtggat caccagcaag gaggaaacac aacacagaga catttttttcc cctcaaatta    8340
tcaaaagaat cactgcattt gttaaagaga gcaactgaat caggaagcag agttttgaac    8400
atatcagaag ttaggaatct gcatcagaga caaatgcagt catggttgtt tgctgcatac    8460
cagccctaat cattagaagc ctcatggact tcaaacatca ttccctctga caagatgctc    8520
tagcctaact ccatgagata aaataaatct gcctttcaga gccaagaag agtccaccag    8580
cttcttctca gtgtgaacaa gagctccagt caggttagtc agtccagtgc agtagaggag    8640
accagtctgc atcctctaat tttcaaaggc aagaagattt gtttaccctg acaccaggc    8700
acaagtgagg tcacagagct cttagatatg cagtcctcat gagtgaggag actaaagcgc    8760
atgccatcaa gacttcagtg tagagaaaac ctccaaaaaa gcctcctcac tacttctgga    8820
atagctcaga ggccgaggcg gcctcggcct ctgcataaat aaaaaaaatt agtcagccat    8880
ggggcggaga atgggcggaa ctgggcgcag ttaggggcgg gatgggcgga gttaggggcg    8940
ggactatggt tgctgactaa ttgagatgca tgctttgcat acttctgcct gctggggagc    9000
ctggggactt tccacacctg gttgctgact aattgagatg catgctttgc atacttctgc    9060
ctgctgggga gcctggggac tttccacacc ctaactgaca cacattccac agctgcatta    9120
atgaatcggc caacgcgcgg ggagaggcgg tttgcgtatt gggcgctctt ccgcttcctc    9180
gctcactgac tcgctgcgct cggtcgttcg gctgcggcga gcggtatcag ctcactcaaa    9240
ggcggtaata cggttatcca cagaatcagg ggataacgca ggaaagaaca tgtgagcaaa    9300
aggccagcaa aaggccagga accgtaaaaa ggccgcgttg ctggcgtttt tccataggct    9360
ccgcccccct gacgagcatc acaaaaatcg acgctcaagt cagaggtggc gaaacccgac    9420
aggactataa agataccagg cgtttccccc tggaagctcc ctcgtgcgct ctcctgttcc    9480
gaccctgccg cttaccggat acctgtccgc ctttctccct tcgggaagcg tggcgctttc    9540
tcatagctca cgctgtaggt atctcagttc ggtgtaggtc gttcgctcca agctgggctg    9600
tgtgcacgaa ccccccgttc agcccgaccg ctgcgcctta tccggtaact atcgtcttga    9660
gtccaacccg gtaagacacg acttatcgcc actggcagca gccactggta acaggattag    9720
cagagcgagg tatgtaggcg gtgctacaga gttcttgaag tggtggccta actacggcta    9780
cactagaaga acagtatttg gtatctgcgc tctgctgaag ccagttacct tcggaaaaag    9840
agttggtagc tcttgatccg gcaaacaaac caccgctggt agcggtggtt tttttgtttg    9900
caagcagcag attacgcgca gaaaaaaagg atctcaagaa gatcctttga tcttttctac    9960
ggggtctgac gctcagtgga acgaaaactc acgttaaggg attttggtca tgagattatc   10020
aaaaaggatc ttcacctaga tccttttaaa ttaaaaatga agttttaaat caatctaaag   10080
```

-continued

```
tatatatgag taaacttggt ctgacagtta ccaatgctta atcagtgagg cacctatctc    10140
agcgatctgt ctatttcgtt catccatagt tgcctgactc ctgcaaacca cgttgtgtct    10200
caaaatctct gatgttacat tgcacaagat aaaaatatat catcatgaac aataaaactg    10260
tctgcttaca taaacagtaa tacaagggg gttatgagcc atattcaacg ggaaacgtct     10320
tgctcgaggc cgcgattaaa ttccaacatg gatgctgatt tatatgggta taaatgggct    10380
cgcgataatg tcgggcaatc aggtgcgaca atctatcgat tgtatgggaa gcccgatgcg    10440
ccagagttgt ttctgaaaca tggcaaaggt agcgttgcca atgatgttac agatgagatg    10500
gtcagactaa actggctgac ggaatttatg cctcttccga ccatcaagca ttttatccgt    10560
actcctgatg atgcatggtt actcaccact gcgatccccg ggaaaacagc attccaggta    10620
ttagaagaat atcctgattc aggtgaaaat attgttgatg cgctggcagt gttcctgcgc    10680
cggttgcatt cgattcctgt ttgtaattgt ccttttaaca gcgatcgcgt atttcgtctc    10740
gctcaggcgc aatcacgaat gaataacggt ttggttgatg cgagtgattt tgatgacgag    10800
cgtaatggct ggcctgttga acaagtctgg aaagaaatgc ataagctttt gccattctca    10860
ccggattcag tcgtcactca tggtgatttc tcacttgata accttatttt tgacgagggg    10920
aaattaatag gttgtattga tgttggacga gtcggaatcg cagaccgata ccaggatctt    10980
gccatcctat ggaactgcct cggtgagttt tctccttcat tacagaaacg gcttttcaa     11040 aaatatggta ttgataatcc tgatatgaat aaattgcagt tcatttgat gctcgatgag     11100 tttttctaag gcggcctgc caccataccc acgccgaaac aagcgctcat gagcccgaag    11160
tggcgagccc gatcttcccc atcggtgatg tcggcgatat aggcgccagc aaccgcacct    11220
gtggcgccgg tgatgagggc gcgccaagtc gacgtccggc agtc                     11264
```

<210> SEQ ID NO 33
<211> LENGTH: 685
<212> TYPE: PRT
<213> ORGANISM: Artificial sequence
<220> FEATURE:
<223> OTHER INFORMATION: Synthetic polypeptide

<400> SEQUENCE: 33

```
Met Ala Glu Trp Leu Leu Ser Ala Ser Trp Gln Arg Arg Ala Lys Ala
1               5                   10                  15

Met Thr Ala Ala Ala Gly Ser Ala Gly Arg Ala Ala Val Pro Leu Leu
            20                  25                  30

Leu Cys Ala Leu Leu Ala Pro Gly Gly Ala Tyr Val Leu Asp Asp Ser
        35                  40                  45

Asp Gly Leu Gly Arg Glu Phe Asp Gly Ile Gly Ala Val Ser Gly Gly
    50                  55                  60

Gly Ala Thr Ser Arg Leu Leu Val Asn Tyr Pro Glu Pro Tyr Arg Ser
65                  70                  75                  80

Gln Ile Leu Asp Tyr Leu Phe Lys Pro Asn Phe Gly Ala Ser Leu His
                85                  90                  95

Ile Leu Lys Val Glu Ile Gly Gly Asp Gly Gln Thr Thr Asp Gly Thr
            100                 105                 110

Glu Pro Ser His Met His Tyr Ala Leu Asp Glu Asn Tyr Phe Arg Gly
        115                 120                 125

Tyr Glu Trp Trp Leu Met Lys Glu Ala Lys Lys Arg Asn Pro Asn Ile
    130                 135                 140
```

```
Thr Leu Ile Gly Leu Pro Trp Ser Phe Pro Gly Trp Leu Gly Lys Gly
145                 150                 155                 160

Phe Asp Trp Pro Tyr Val Asn Leu Gln Leu Thr Ala Tyr Tyr Val Val
                165                 170                 175

Thr Trp Ile Val Gly Ala Lys Arg Tyr His Asp Leu Asp Ile Asp Tyr
            180                 185                 190

Ile Gly Ile Trp Asn Glu Arg Ser Tyr Asn Ala Asn Tyr Ile Lys Ile
            195                 200                 205

Leu Arg Lys Met Leu Asn Tyr Gln Gly Leu Gln Arg Val Lys Ile Ile
        210                 215                 220

Ala Ser Asp Asn Leu Trp Glu Ser Ile Ser Ala Ser Met Leu Leu Asp
225                 230                 235                 240

Ala Glu Leu Phe Lys Val Val Asp Val Ile Gly Ala His Tyr Pro Gly
                245                 250                 255

Thr His Ser Ala Lys Asp Ala Lys Leu Thr Gly Lys Lys Leu Trp Ser
            260                 265                 270

Ser Glu Asp Phe Ser Thr Leu Asn Ser Asp Met Gly Ala Gly Cys Trp
        275                 280                 285

Gly Arg Ile Leu Asn Gln Asn Tyr Ile Asn Gly Tyr Met Thr Ser Thr
290                 295                 300

Ile Ala Trp Asn Leu Val Ala Ser Tyr Glu Gln Leu Pro Tyr Gly
305                 310                 315                 320

Arg Cys Gly Leu Met Thr Ala Gln Glu Pro Trp Ser Gly His Tyr Val
                325                 330                 335

Val Glu Ser Pro Val Trp Val Ser Ala His Thr Thr Gln Phe Thr Gln
            340                 345                 350

Pro Gly Trp Tyr Tyr Leu Lys Thr Val Gly His Leu Glu Lys Gly Gly
        355                 360                 365

Ser Tyr Val Ala Leu Thr Asp Gly Leu Gly Asn Leu Thr Ile Ile Ile
370                 375                 380

Glu Thr Met Ser His Lys His Ser Lys Cys Ile Arg Pro Phe Leu Pro
385                 390                 395                 400

Tyr Phe Asn Val Ser Gln Gln Phe Ala Thr Phe Val Leu Lys Gly Ser
                405                 410                 415

Phe Ser Glu Ile Pro Glu Leu Gln Val Trp Tyr Thr Lys Leu Gly Lys
            420                 425                 430

Thr Ser Glu Arg Phe Leu Phe Lys Gln Leu Asp Ser Leu Trp Leu Leu
        435                 440                 445

Asp Ser Asp Gly Ser Phe Thr Leu Ser Leu His Glu Asp Glu Leu Phe
450                 455                 460

Thr Leu Thr Thr Leu Thr Thr Gly Arg Lys Gly Ser Tyr Pro Leu Pro
465                 470                 475                 480

Pro Lys Ser Gln Pro Phe Pro Ser Thr Tyr Lys Asp Asp Phe Asn Val
                485                 490                 495

Asp Tyr Pro Phe Phe Ser Glu Ala Pro Asn Phe Ala Asp Gln Thr Gly
            500                 505                 510

Val Phe Glu Tyr Phe Thr Asn Ile Glu Asp Pro Gly Glu His His Phe
        515                 520                 525

Thr Leu Arg Gln Val Leu Asn Gln Arg Pro Ile Thr Trp Ala Ala Asp
530                 535                 540

Ala Ser Asn Thr Ile Ser Ile Ile Gly Asp Tyr Asn Trp Thr Asn Leu
545                 550                 555                 560
```

```
Thr Ile Lys Cys Asp Val Tyr Ile Glu Thr Pro Asp Thr Gly Gly Val
            565                 570                 575

Phe Ile Ala Gly Arg Val Asn Lys Gly Gly Ile Leu Ile Arg Ser Ala
        580                 585                 590

Arg Gly Ile Phe Phe Trp Ile Phe Ala Asn Gly Ser Tyr Arg Val Thr
    595                 600                 605

Gly Asp Leu Ala Gly Trp Ile Ile Tyr Ala Leu Gly Arg Val Glu Val
610                 615                 620

Thr Ala Lys Lys Trp Tyr Thr Leu Thr Leu Thr Ile Lys Gly His Phe
625                 630                 635                 640

Thr Ser Gly Met Leu Asn Asp Lys Ser Leu Trp Thr Asp Ile Pro Val
            645                 650                 655

Asn Phe Pro Lys Asn Gly Trp Ala Ala Ile Gly Thr His Ser Phe Glu
        660                 665                 670

Phe Ala Gln Phe Asp Asn Phe Leu Val Glu Ala Thr Arg
    675                 680                 685

<210> SEQ ID NO 34
<211> LENGTH: 2055
<212> TYPE: DNA
<213> ORGANISM: Artificial sequence
<220> FEATURE:
<223> OTHER INFORMATION: Synthetic polynucleotide

<400> SEQUENCE: 34
atggccgagt ggctgctgag cgccagctgg cagcgccgcg ccaaggccat gaccgccgcc     60
gccggcagcg ccggccgcgc cgccgtgccc ctgctgctgt cgccctgct  ggccccggc    120 ggcgcctacg tgctggacga cagcgacggc ctgggccgcg agttcgacgg catcggcgcc    180
gtgagcggcg cggcgccac cagccgcctg ctggtgaact accccgagcc ctaccgcagc    240
cagatcctgg actacctgtt caagcccaac ttcggcgcca gcctgcacat cctgaaggtg    300
gagatcggcg cgacggcca gaccaccgac ggcaccgagc ccagccacat gcactacgcc    360
ctggacgaga actacttccg cggctacgag tggtggctga tgaaggaggc caagaagcgc    420
aaccccaaca tcaccctgat cggcctgccc tggagcttcc ccggctggct gggcaagggc    480
ttcgactggc cctacgtgaa cctgcagctg accgcctact acgtggtgac ctggatcgtg    540
ggcgccaagc gctaccacga cctggacatc gactacatcg catctggaa cgagcgcagc    600 tacaacgcca actacatcaa gatcctgcgc aagatgctga actaccaggg cctgcagcgc    660
gtgaagatca tcgccagcga caacctgtgg gagagcatca cgccagcat gctgctggac    720 gccgagctgt tcaaggtggt ggacgtgatc ggcgcccact accccggcac ccacagcgcc    780
aaggacgcca agctgaccgg caagaagctg tggagcagcg aggacttcag caccctgaac    840
agcgacatgg gcgccggctg ctgggccgc atcctgaacc agaactacat caacggctac    900
atgaccagca ccatcgcctg gaacctggtg ccagctact acgagcagct gccctacggc    960
cgctgcggcc tgatgaccgc ccaggagccc tggagcggcc actacgtggt ggagagcccc   1020
gtgtgggtga gcgcccacac cacccagttc acccagcccg ctggtactac ctgaagacc   1080 gtgggccacc tggagaaggg cggcagctac gtggccctga ccgacggcct gggcaacctg   1140
accatcatca tcgagaccat gagccacaag cacagcaagt gcatccgccc cttcctgccc   1200
tacttcaacg tgagccagca gttcgccacc ttcgtgctga gggcagctt  cagcgagatc   1260 cccgagctgc aggtgtggta caccaagctg ggcaagacca cgagcgcttc ctgttcaag   1320 cagctggaca gcctgtggct gctggacagc gacggcagct tcaccctgag cctgcacgag   1380
```

```
gacgagctgt tcaccctgac caccctgacc accggccgca agggcagcta ccccctgccc    1440
cccaagagcc agcccttccc cagcacctac aaggacgact tcaacgtgga ctacccttc     1500 ttcagcgagg cccccaactt cgccgaccag accggcgtgt cgagtactt caccaacatc     1560 gaggaccccg gcgagcacca cttcaccctg cgccaggtgc tgaaccagcg ccccatcacc    1620
tgggccgccg acgccagcaa caccatcagc atcatcggcg actacaactg gaccaacctg    1680
accatcaagt gcgacgtgta catcgagacc cccgacaccg gcggcgtgtt catcgccggc    1740
cgcgtgaaca agggcggcat cctgatccgc agcgcccgcg gcatcttctt ctggatcttc    1800
gccaacggca gctaccgcgt gaccggcgac ctggccggct ggatcatcta cgccctgggc    1860
cgcgtggagg tgaccgccaa gaagtggtac accctgaccc tgaccatcaa gggccacttc    1920
accagcggca tgctgaacga caagagcctg tggaccgaca tccccgtgaa cttccccaag    1980
aacggctggg ccgccatcgg cacccacagc ttcgagttcg cccagttcga caacttcctg    2040
gtggaggcca cccgc                                                     2055
```

<210> SEQ ID NO 35
<211> LENGTH: 339
<212> TYPE: PRT
<213> ORGANISM: Artificial sequence
<220> FEATURE:
<223> OTHER INFORMATION: Synthetic polypeptide

<400> SEQUENCE: 35

```
Met Trp Gln Leu Trp Ala Ser Leu Cys Cys Leu Leu Val Leu Ala Asn
1               5                   10                  15

Ala Arg Ser Arg Pro Ser Phe His Pro Leu Ser Asp Glu Leu Val Asn
            20                  25                  30

Tyr Val Asn Lys Arg Asn Thr Thr Trp Gln Ala Gly His Asn Phe Tyr
        35                  40                  45

Asn Val Asp Met Ser Tyr Leu Lys Arg Leu Cys Gly Thr Phe Leu Gly
    50                  55                  60

Gly Pro Lys Pro Pro Gln Arg Val Met Phe Thr Glu Asp Leu Lys Leu
65                  70                  75                  80

Pro Ala Ser Phe Asp Ala Arg Glu Gln Trp Pro Gln Cys Pro Thr Ile
                85                  90                  95

Lys Glu Ile Arg Asp Gln Gly Ser Cys Gly Ser Cys Trp Ala Phe Gly
            100                 105                 110

Ala Val Glu Ala Ile Ser Asp Arg Ile Cys Ile His Thr Asn Ala His
        115                 120                 125

Val Ser Val Glu Val Ser Ala Glu Asp Leu Leu Thr Cys Cys Gly Ser
    130                 135                 140

Met Cys Gly Asp Gly Cys Asn Gly Gly Tyr Pro Ala Glu Ala Trp Asn
145                 150                 155                 160

Phe Trp Thr Arg Lys Gly Leu Val Ser Gly Gly Leu Tyr Glu Ser His
                165                 170                 175

Val Gly Cys Arg Pro Tyr Ser Ile Pro Pro Cys Glu His His Val Asn
            180                 185                 190

Gly Ser Arg Pro Pro Cys Thr Gly Glu Gly Asp Thr Pro Lys Cys Ser
        195                 200                 205

Lys Ile Cys Glu Pro Gly Tyr Ser Pro Thr Tyr Lys Gln Asp Lys His
    210                 215                 220

Tyr Gly Tyr Asn Ser Tyr Ser Val Ser Asn Ser Glu Lys Asp Ile Met
225                 230                 235                 240
```

```
Ala Glu Ile Tyr Lys Asn Gly Pro Val Glu Gly Ala Phe Ser Val Tyr
                245                 250                 255

Ser Asp Phe Leu Leu Tyr Lys Ser Gly Val Tyr Gln His Val Thr Gly
            260                 265                 270

Glu Met Met Gly Gly His Ala Ile Arg Ile Leu Gly Trp Gly Val Glu
        275                 280                 285

Asn Gly Thr Pro Tyr Trp Leu Val Ala Asn Ser Trp Asn Thr Asp Trp
    290                 295                 300

Gly Asp Asn Gly Phe Phe Lys Ile Leu Arg Gly Gln Asp His Cys Gly
305                 310                 315                 320

Ile Glu Ser Glu Val Val Ala Gly Ile Pro Arg Thr Asp Gln Tyr Trp
                325                 330                 335

Glu Lys Ile

<210> SEQ ID NO 36
<211> LENGTH: 1017
<212> TYPE: DNA
<213> ORGANISM: Artificial sequence
<220> FEATURE:
<223> OTHER INFORMATION: Synthetic polynucleotide

<400> SEQUENCE: 36
atgtggcagc tgtgggccag cctgtgctgc ctgctggtgc tggccaacgc ccgcagccgc      60
cccagcttcc accccctgag cgacgagctg gtgaactacg tgaacaagcg caacaccacc     120
tggcaggccg gccacaactt ctacaacgtg gacatgagct acctgaagcg cctgtgcggc     180
accttcctgg gcggccccaa gccccccag cgcgtgatgt tcaccgagga cctgaagctg     240
cccgccagct cgacgcccg cgagcagtgg ccccagtgcc ccaccatcaa ggagatccgc     300
gaccagggca gctgcggcag ctgctgggcc ttcgcgccg tggaggccat cagcgaccgc     360
atctgcatcc acaccaacgc ccacgtgagc gtggaggtga cgccgagga cctgctgacc     420 tgctgcggca gcatgtgcgg cgacggctgc aacggcggct accccgccga ggcctggaac     480
ttctggaccc gcaagggcct ggtgagcggc ggcctgtacg agagccacgt gggctgccgc     540
ccctacagca tcccccctg cgagcaccac gtgaacggca gccgcccccc ctgcaccggc     600
gagggcgaca ccccaagtg cagcaagatc tgcgagcccg gctacagccc cacctacaag     660
caggacaagc actacggcta caacagctac agcgtgagca cagcgagaa ggacatcatg     720 gccgagatct acaagaacgg cccgtggag ggcgccttca gcgtgtacag cgacttcctg     780
ctgtacaaga gcggcgtgta ccagcacgtg accggcgaga tgatgggcgg ccacgccatc     840
cgcatcctgg gctggggcgt ggagaacggc accccctact ggctggtggc caacagctgg     900
aacaccgact ggggcgacaa cggcttcttc aagatcctgc gcggccagga ccactgcggc     960
atcgagagcg aggtggtggc cggcatcccc cgcaccgacc agtactggga agatc        1017

<210> SEQ ID NO 37
<211> LENGTH: 631
<212> TYPE: PRT
<213> ORGANISM: Artificial sequence
<220> FEATURE:
<223> OTHER INFORMATION: Synthetic polypeptide

<400> SEQUENCE: 37

Met Pro Arg Tyr Gly Ala Ser Leu Arg Gln Ser Cys Pro Arg Ser Gly
1               5                   10                  15
```

-continued

```
Arg Glu Gln Gly Gln Asp Gly Thr Ala Gly Ala Pro Gly Leu Leu Trp
         20                  25                  30

Met Gly Leu Val Leu Ala Leu Ala Leu Ala Leu Ala Leu Ala
         35                  40                  45

Leu Ser Asp Ser Arg Val Leu Trp Ala Pro Ala Glu Ala His Pro Leu
 50                  55                  60

Ser Pro Gln Gly His Pro Ala Arg Leu His Arg Ile Val Pro Arg Leu
 65                  70                  75                  80

Arg Asp Val Phe Gly Trp Gly Asn Leu Thr Cys Pro Ile Cys Lys Gly
                 85                  90                  95

Leu Phe Thr Ala Ile Asn Leu Gly Leu Lys Lys Glu Pro Asn Val Ala
                100                 105                 110

Arg Val Gly Ser Val Ala Ile Lys Leu Cys Asn Leu Leu Lys Ile Ala
                115                 120                 125

Pro Pro Ala Val Cys Gln Ser Ile Val His Leu Phe Glu Asp Asp Met
130                 135                 140

Val Glu Val Trp Arg Arg Ser Val Leu Ser Pro Ser Glu Ala Cys Gly
145                 150                 155                 160

Leu Leu Leu Gly Ser Thr Cys Gly His Trp Asp Ile Phe Ser Ser Trp
                165                 170                 175

Asn Ile Ser Leu Pro Thr Val Pro Lys Pro Pro Lys Pro Pro Ser
                180                 185                 190

Pro Pro Ala Pro Gly Ala Pro Val Ser Arg Ile Leu Phe Leu Thr Asp
                195                 200                 205

Leu His Trp Asp His Asp Tyr Leu Glu Gly Thr Asp Pro Asp Cys Ala
                210                 215                 220

Asp Pro Leu Cys Cys Arg Arg Gly Ser Gly Leu Pro Pro Ala Ser Arg
225                 230                 235                 240

Pro Gly Ala Gly Tyr Trp Gly Glu Tyr Ser Lys Cys Asp Leu Pro Leu
                245                 250                 255

Arg Thr Leu Glu Ser Leu Leu Ser Gly Leu Gly Pro Ala Gly Pro Phe
                260                 265                 270

Asp Met Val Tyr Trp Thr Gly Asp Ile Pro Ala His Asp Val Trp His
                275                 280                 285

Gln Thr Arg Gln Asp Gln Leu Arg Ala Leu Thr Thr Val Thr Ala Leu
290                 295                 300

Val Arg Lys Phe Leu Gly Pro Val Pro Val Tyr Pro Ala Val Gly Asn
305                 310                 315                 320

His Glu Ser Thr Pro Val Asn Ser Phe Pro Pro Phe Ile Glu Gly
                325                 330                 335

Asn His Ser Ser Arg Trp Leu Tyr Glu Ala Met Ala Lys Ala Trp Glu
                340                 345                 350

Pro Trp Leu Pro Ala Glu Ala Leu Arg Thr Leu Arg Ile Gly Gly Phe
                355                 360                 365

Tyr Ala Leu Ser Pro Tyr Pro Gly Leu Arg Leu Ile Ser Leu Asn Met
                370                 375                 380

Asn Phe Cys Ser Arg Glu Asn Phe Trp Leu Leu Ile Asn Ser Thr Asp
385                 390                 395                 400

Pro Ala Gly Gln Leu Gln Trp Leu Val Gly Glu Leu Gln Ala Ala Glu
                405                 410                 415

Asp Arg Gly Asp Lys Val His Ile Ile Gly His Ile Pro Pro Gly His
                420                 425                 430
```

Cys Leu Lys Ser Trp Ser Trp Asn Tyr Tyr Arg Ile Val Ala Arg Tyr
            435                 440                 445

Glu Asn Thr Leu Ala Ala Gln Phe Phe Gly His Thr His Val Asp Glu
    450                 455                 460

Phe Glu Val Phe Tyr Asp Glu Glu Thr Leu Ser Arg Pro Leu Ala Val
465                 470                 475                 480

Ala Phe Leu Ala Pro Ser Ala Thr Thr Tyr Ile Gly Leu Asn Pro Gly
                485                 490                 495

Tyr Arg Val Tyr Gln Ile Asp Gly Asn Tyr Ser Gly Ser Ser His Val
            500                 505                 510

Val Leu Asp His Glu Thr Tyr Ile Leu Asn Leu Thr Gln Ala Asn Ile
        515                 520                 525

Pro Gly Ala Ile Pro His Trp Gln Leu Leu Tyr Arg Ala Arg Glu Thr
    530                 535                 540

Tyr Gly Leu Pro Asn Thr Leu Pro Thr Ala Trp His Asn Leu Val Tyr
545                 550                 555                 560

Arg Met Arg Gly Asp Met Gln Leu Phe Gln Thr Phe Trp Phe Leu Tyr
                565                 570                 575

His Lys Gly His Pro Pro Ser Glu Pro Cys Gly Thr Pro Cys Arg Leu
            580                 585                 590

Ala Thr Leu Cys Ala Gln Leu Ser Ala Arg Ala Asp Ser Pro Ala Leu
        595                 600                 605

Cys Arg His Leu Met Pro Asp Gly Ser Leu Pro Glu Ala Gln Ser Leu
    610                 615                 620

Trp Pro Arg Pro Leu Phe Cys
625                 630

<210> SEQ ID NO 38
<211> LENGTH: 1896
<212> TYPE: DNA
<213> ORGANISM: Artificial sequence
<220> FEATURE:
<223> OTHER INFORMATION: Synthetic polynucleotide

<400> SEQUENCE: 38
atgccccgct acggcgccag cctgcgccag agctgccccc gcagcggccg cgagcagggc    60
caggacggca ccgccggcgc ccccggcctg ctgtggatgg gcctggtgct ggccctggcc   120
ctggccctgg ccctggccct ggccctgagc acagccgcg tgctgtgggc ccccgccgag   180
gcccaccccc tgagccccca gggccacccc gcccgcctgc accgcatcgt gccccgcctg   240
cgcgacgtgt tcggctgggg caacctgacc tgccccatct gcaagggcct gttcaccgcc   300
atcaacctgg gcctgaagaa ggagcccaac gtggcccgcg tgggcagcgt ggccatcaag   360
ctgtgcaacc tgctgaagat cgcccccccc gccgtgtgcc agagcatcgt gcacctgttc   420
gaggacgaca tggtggaggt gtggcgccgc agcgtgctga gcccagcga ggcctgcggc   480 ctgctgctgg gcagcacctg cggccactgg gacatcttca gcagctggaa catcagcctg   540
cccaccgtgc ccaagccccc ccccaagccc ccagccccc cgcccccgg cgccccgtg   600 agccgcatcc tgttcctgac cgacctgcac tgggaccacg actacctgga gggcaccgac   660
cccgactgcg ccgaccccct gtgctgccgc gcggcagcg gcctgccccc cgccagccgc   720
cccggcgccg gctactgggg cgagtacagc aagtgcgacc tgcccctgcg cacccgggag   780
agcctgctga cggcctggg ccccgccggc cccttcgaca tggtgtactg gaccggcgac   840
atccccgccc acgacgtgtg caccagacc cgccaggacc agctgcgcgc cctgaccacc   900

```
gtgaccgccc tggtgcgcaa gttcctgggc cccgtgcccg tgtaccccgc cgtgggcaac      960
cacgagagca cccccgtgaa cagcttcccc ccccccttca tcgagggcaa ccacagcagc     1020
cgctggctgt acgaggccat ggccaaggcc tgggagccct ggctgccgc cgaggccctg      1080
cgcaccctgc gcatcggcgg cttctacgcc ctgagcccct accccggcct gcgcctgatc     1140
agcctgaaca tgaacttctg cagccgcgag aacttctggc tgctgatcaa cagcaccgac     1200
cccgccggcc agctgcagtg gctggtgggc gagctgcagg ccgccgagga ccgcggcgac     1260
aaggtgcaca tcatcggcca catccccccc ggccactgcc tgaagagctg gagctggaac     1320
tactaccgca tcgtgcccg ctacgagaac accctggccg cccagttctt cggccacacc      1380
cacgtggacg agttcgaggt gttctacgac gaggagaccc tgagccgccc cctggccgtg     1440
gccttcctgg cccccagcgc caccacctac atcggcctga accccggcta ccgcgtgtac     1500
cagatcgacg gcaactacag cggcagcagc cacgtggtgc tggaccacga gacctacatc     1560
ctgaacctga cccaggccaa catccccggc gccatccccc actggcagct gctgtaccgc     1620
gcccgcgaga cctacggcct gcccaacacc ctgcccaccg cctggcacaa cctggtgtac     1680
cgcatgcgcg cgacatgca gctgttccag accttctggt tcctgtacca caagggccac     1740
cccccagcg agccctgcgg caccccctgc cgcctggcca cctgtgcgc ccagctgagc       1800
gcccgcgccg acagccccgc cctgtgccgc cacctgatgc ccgacggcag cctgcccgag     1860
gcccagagcc tgtggccccg ccccctgttc tgctaa                               1896

<210> SEQ ID NO 39
<211> LENGTH: 11329
<212> TYPE: DNA
<213> ORGANISM: Artificial sequence
<220> FEATURE:
<223> OTHER INFORMATION: Synthetic polynucleotide

<400> SEQUENCE: 39
ttggccactc cctctctgcg cgctcgctcg ctcactgagg ccgggcgacc aaaggtcgcc       60
cgacgcccgg gctttgcccg ggcggcctca gtgagcgagc gagcgcgcag agagggagtg      120
gccaactcca tcactagggg ttcctgctag ctctgggtat ttaagcccga gtgagcacgc      180
agggtctcca ttttgaagcg ggaggttacg cgttcgtcga ctactagtgg gtaccagagc      240
tccctaggtt ctagaaccgg tgacgtctcc catggtgaag cttggatctg agggcggagt      300
tagggcggag ccaatcagcg tgcgccgttc cgaaagttgc ctttatggc tgggcggaga       360
atgggcggtg aacgccgatg attatataag gacgcgccgg gtgtggcaca gctagttccg      420
tcgcagccgg gatttgggtc gcggttcttg tttgtggatc cctgtgatcg tcacttggta      480
agtcactgac tgtctatgcc tgggaaaggg tgggcaggag atgggcagt gcaggaaaag      540
tggcactatg aaccctgcag ccctaggaat gcatctagac aattgtacta accttcttct     600
ctttcctctc ctgacagtcc ggaaagccac catggaattc agcagcccca gcagagagga     660
atgcccaag cctctgagcc gggtgtcaat catggccgga tctctgacag gactgctgct      720
gcttcaggcc gtgtcttggg cttctggcgc tagaccttgc atccccaaga gcttcggcta     780
cagcagcgtc gtgtgcgtgt gcaatgccac ctactgcgac agcttcgacc ctcctacctt     840
tcctgctctg ggcaccttca gcagatacga gagcaccaga tccggcagac ggatggaact     900
gagcatggga cccatccagg ccaatcacac aggcactggc ctgctgctga cactgcagcc     960
tgagcagaaa ttccagaaag tgaaaggctt cggcggagcc atgacagatg ccgccgctct    1020
gaatatcctg gctctgtctc caccagctca gaacctgctg ctcaagagct acttcagcga    1080
```

```
ggaaggcatc ggctacaaca tcatcagagt gcccatggcc agctgcgact tcagcatcag    1140
gacctacacc tacgccgaca caccgacga tttccagctg cacaacttca gcctgcctga    1200
agaggacacc aagctgaaga tccctctgat ccacagagcc ctgcagctgg cacaaagacc    1260
cgtgtcactg ctggcctctc catggacatc tcccacctgg ctgaaaacaa atggcgccgt    1320
gaatggcaag ggcagcctga aaggccaacc tggcgacatc taccaccaga cctgggccag    1380
atacttcgtg aagttcctgg acgcctatgc cgagcacaag ctgcagtttt gggccgtgac    1440
agccgagaac gaaccttctg ctggactgct gagcggctac ccctttcagt gcctgggctt    1500
tacacccgag caccagcggg actttatcgc ccgtgatctg ggacccacac tggccaatag    1560
cacccaccat aatgtgcggc tgctgatgct ggacgaccag agactgcttc tgccccactg    1620
ggctaaagtg gtgctgacag atcctgaggc cgccaaatac gtgcacggaa tcgccgtgca    1680
ctggtatctg gactttctgg cccctgccaa ggccacactg ggagagacac acagactgtt    1740
ccccaacacc atgctgttcg ccagcgaagc tgtgtgggc agcaagtttt gggaacagag    1800
cgtgcggctc ggcagctggg atagaggcat gcagtacagc cacagcatca tcaccaacct    1860
gctgtaccac gtcgtcggct ggaccgactg gaatctggcc ctgaatcctg aaggcggccc    1920
taactgggtc cgaaacttcg tggacagccc catcatcgtg gacatcacca aggacacctt    1980
ctacaagcag cccatgttct accacctggg acacttcagc aagttcatcc ccagggctc    2040 tcagcgcgtt ggactggtgg cttcccagaa gaacgatctg gacgccgtgg ctctgatgca    2100
ccctgatgga tctgctgtgg tggtggtcct gaaccgcagc agcaaagatg tgcccctgac    2160
catcaaggat cccgccgtgg gattcctgga acaatcagc cctggctact ccatccacac    2220
ctacctgtgg cgtagacagg agggcagagg aagtcttctg acatgcggag acgtggaaga    2280
gaatcccggc cctatggccg agtggctgct gagcgccagc tggcagcgcc gcgccaaggc    2340
catgaccgcc gccgccggca cgcgcggccg cgccgccgtg cccctgctgc tgtgcgccct    2400 gctggcccc ggcggcgcct acgtgctgga cgacagcgac ggcctgggcc gcgagttcga    2460
cggcatcggc gccgtgagcg gcggcggcgc caccagccgc ctgctggtga actaccccga    2520
gccctaccgc agccagatcc tggactacct gttcaagccc aacttcggcg ccagcctgca    2580
catcctgaag gtggagatcg gcggcgacgg ccagaccacc gacggcaccg agcccagcca    2640
catgcactac gccctggacg agaactactt ccgcggctac gagtggtggc tgatgaagga    2700
ggccaagaag cgcaacccca acatcaccct gatcggcctg ccctggagct tccccggctg    2760
gctgggcaag ggcttcgact ggccctacgt gaacctgcag ctgaccgcct actacgtggt    2820
gacctggatc gtgggcgcca agcgctacca cgacctggac atcgactaca tcggcatctg    2880
gaacgagcgc agctacaacg ccaactacat caagatcctg cgcaagatgc tgaactacca    2940
gggcctgcag cgcgtgaaga tcatcgccag cgacaacctg tgggagagca tcagcgccag    3000
catgctgctg gacgccgagc tgttcaaggt ggtggacgtg atcggcgccc actacccgg    3060 cacccacagc gccaaggacg ccaagctgac cggcaagaag ctgtggagca gcgaggactt    3120
cagcaccctg aacagcgaca tgggcgccgg ctgctggggc cgcatcctga accagaacta    3180
catcaacggc tacatgacca gcaccatcgc ctggaacctg gtggccagct actacgagca    3240
gctgccctac ggccgctgcg gcctgatgac cgcccaggag ccctggagcg ccactacgt    3300 ggtggagagc cccgtgtggg tgagcgccca caccacccag ttcacccagc ccggctggta    3360
ctacctgaag accgtgggcc acctggagaa gggcggcagc tacgtggccc tgaccgacgg    3420
```

```
cctgggcaac ctgaccatca tcatcgagac catgagccac aagcacagca agtgcatccg    3480 cccccttcctg ccctacttca acgtgagcca gcagttcgcc accttcgtgc tgaagggcag   3540
cttcagcgag atccccgagc tgcaggtgtg gtacaccaag ctgggcaaga ccagcgagcg    3600
cttcctgttc aagcagctgg acagcctgtg gctgctggac agcgacggca gcttcaccct    3660
gagcctgcac gaggacgagc tgttcaccct gaccaccctg accaccggcc gcaagggcag    3720 ctacccctg cccccaaga gccagccctt cccagcacc tacaaggacg acttcaacgt        3780
ggactacccc ttcttcagcg aggccccaa cttcgccgac cagaccggcg tgttcgagta     3840
cttcaccaac atcgaggacc ccggcgagca ccacttcacc ctgcgccagg tgctgaacca    3900 gcgcccatc acctgggccg ccgacgccag caacaccatc agcatcatcg gcgactacaa     3960
ctggaccaac ctgaccatca agtgcgacgt gtacatcgag ccccgaca ccggcggcgt      4020 gttcatcgcc ggccgcgtga acaagggcgg catcctgatc cgcagcgccc gcggcatctt    4080
cttctggatc ttcgccaacg gcagctaccg cgtgaccggc gacctggccg gctggatcat    4140
ctacgccctg ggccgcgtgg aggtgaccgc caagaagtgg tacaccctga ccctgaccat    4200
caagggccac ttcaccagcg gcatgctgaa cgacaagagc ctgtggaccg acatccccgt    4260
gaacttcccc aagaacggct gggccgccat cggcacccac agcttcgagt tcgcccagtt    4320
cgacaacttc ctggtggagg ccacccgctg acaattgtta attaagttta aaccctcgag    4380
gccgcaagca ataaaatatc tttattttca ttacatctgt gtgttggttt tttgtgtgga    4440
gatccacgat aacaaacagc ttttttgggg tgaacatatt gactgaattc cctgcaggtt    4500
ggccactccc tctctgcgcg ctcgctcgct cactgaggcc gcccgggcaa agcccgggcg    4560
tcgggcgacc tttggtcgcc cggcctcagt gagcgagcga gcgcgcagag agggagtggc    4620
caactccatc actaggggtt cctgcggccg ctcgtacggt ctcgaggaat cctgcagga    4680 taacttgcca acctcattct aaaatgtata tagaagccca aaagacaata acaaaaatat    4740
tcttgtagaa caaaatggga aagaatgttc cactaaatat caagatttag agcaaagcat    4800
gagatgtgtg gggatagaca gtgaggctga taaaatagag tagagctcag aaacagaccc    4860
attgatatat gtaagtgacc tatgaaaaaa atatggcatt ttacaatggg aaaatgatgg    4920 tcttttctctt ttttagaaaa acagggaaat atatttatat gtaaaaaata aagggaacc    4980 catatgtcat accatacaca caaaaaaatt ccagtgaatt ataagtctaa atggagaagg    5040
caaaacttta aatcttttag aaaataatat agaagcatgc agaccagcct ggccaacatg    5100
atgaaaccct ctctactaat aataaaatca gtagaactac tcaggactac tttgagtggg    5160
aagtcctttt ctatgaagac ttctttggcc aaaattaggc tctaaatgca aggagatagt    5220
gcatcatgcc tggctgcact tactgataaa tgatgttatc accatcttta accaaatgca    5280
caggaacaag ttatggtact gatgtgctgg attgagaagg agctctactt ccttgacagg    5340
acacatttgt atcaacttaa aaaagcagat ttttgccagc agaactattc attcagaggt    5400
aggaaactta gaatagatga tgtcactgat tagcatggct tccccatctc cacagctgct    5460
tcccacccag gttgcccaca gttgagtttg tccagtgctc agggctgccc actctcagta    5520
agaagcccca caccagcccc tctccaaata tgttggctgt tccttccatt aaagtgaccc    5580
cactttagag cagcaagtgg atttctgttt cttacagttc aggaaggagg agtcagctgt    5640
gagaacctgg agcctgagat gcttctaagt cccactgcta ctggggtcag ggaagccaga    5700
ctccagcatc agcagtcagg agcactaagc ccttgccaac atcctgtttc tcagagaaac    5760
tgcttccatt ataatggttg tccttttta agctatcaag ccaaacaacc agtgtctacc     5820
```

```
attattctca tcacctgaag ccaagggttc tagcaaaagt caagctgtct tgtaatggtt   5880
gatgtgcctc cagcttctgt cttcagtcac tccactctta gcctgctctg aatcaactct   5940
gaccacagtt ccctggagcc cctgccacct gctgccnctg ccaccttctc catctgcagt   6000
gctgtgcagc cttctgcact cttgcagagc taataggtgg agacttgaag gaagaggagg   6060
aaagtttctc ataatagcct tgctgcaagc tcaaatggga ggtgggcact gtgcccagga   6120
gccttggagc aaaggctgtg cccaacctct gactgcatcc aggtttggtc ttgacagaga   6180
taagaagccc tggcttttgg agccaaaatc taggtcagac ttaggcagga ttctcaaagt   6240
ttatcagcag aacatgaggc agaagaccct ttctgctcca gcttcttcag gctcaacctt   6300
catcagaata gatagaaaga gaggctgtga gggttcttaa acagaagca aatctgactc     6360 agagaataaa caacctccta gtaaactaca gcttagacag agcatctggt ggtgagtgtg   6420
ctcagtgtcc tactcaactg tctggtatca gccctcatga ggacttctct tctttccctc   6480
atagacctcc atctctgttt tccttagcct gcagaaatct ggatggctat tcacagaatg   6540
cctgtgcttt cagagttgca ttttttctct ggtattctgg ttcaagcatt tgaaggtagg   6600
aaaggttctc caagtgcaag aaagccagcc ctgagcctca actgcctggc tagtgtggtc   6660
agtaggatgc aaaggctgtt gaatgccaca aggccaaact ttaacctgtg taccacaagc   6720
ctagcagcag aggcagctct gctcactgga actctctgtc ttctttctcc tgagcctttt   6780
cttttcctga gttttctagc tctcctcaac cttacctctg ccctacccag acaaaccca    6840 agagccactg tttctgtgat gtcctctcca gccctaatta ggcatcatga cttcagcctg   6900
accttccatg ctcagaagca gtgctaatcc acttcagatg agctgctcta tgcaacacag   6960
gcagagccta caaaccttg caccagagcc ctccacatat cagtgtttgt tcatactcac     7020
ttcaacagca aatgtgactg ctgagattaa gattttacac aagatggtct gtaatttcac   7080
agttagtttt atcccattag gtatgaaaga attagcataa ttcccettaa acatgaatga   7140 atcttagatt ttttaataaa tagttttgga agtaaagaca gagacatcag gagcacaagg   7200
aatagcctga gaggacaaac agaacaagaa agagtctgga aatacacagg atgttcttgg   7260
cctcctcaaa gcaagtgcaa gcagatagta ccagcagccc caggctatca gagcccagtg   7320
aagagaagta ccatgaaagc cacagctcta accaccctgt tccagagtga cagacagtcc   7380
ccaagacaag ccagcctgag ccagagagag aactgcaaga gaaagtttct aatttaggtt   7440
ctgttagatt cagacaagtg caggtcatcc tctctccaca gctactcacc tctccagcct   7500
aacaaagcct gcagtccaca ctccaaccct ggtgtctcac ctcctagcct ctcccaacat   7560
cctgctctct gaccatcttc tgcatctctc atctcaccat ctcccactgt ctacagccta   7620
ctcttgcaac taccatctca ttttctgaca tcctgtctac atcttctgcc atactctgcc   7680
atctaccata ccacctctta ccatctacca caccatcttt tatctccatc cctctcagaa   7740
gcctccaagc tgaatcctgc tttatgtgtt catctcagcc cctgcatgga aagctgaccc   7800
cagaggcaga actattccca gagagcttgg ccaagaaaaa caaaactacc agcctggcca   7860
ggctcaggag tagtaagctg cagtgtctgt tgtgttctag cttcaacagc tgcaggagtt   7920
ccactctcaa atgctccaca tttctcacat cctcctgatt ctggtcacta cccatcttca   7980
aagaacagaa tatctcacat cagcatactg tgaaggacta gtcatgggtg cagctgctca   8040
gagctgcaaa gtcattctgg atggtggaga gcttacaaac atttcatgat gctcccccg    8100 ctctgatggc tggagcccaa tccctacaca gactcctgct gtatgtgttt tcctttcact   8160
```

-continued

```
ctgagccaca gccagagggc aggcattcag tctcctcttc aggctggggc tggggcactg    8220
agaactcacc caacaccttg ctctcactcc ttctgcaaaa caagaaagag ctttgtgctg    8280
cagtagccat gaagaatgaa aggaaggctt taactaaaaa atgtcagaga ttattttcaa    8340
ccccttactg tggatcacca gcaaggagga aacacaacac agagacattt tttcccctca    8400
aattatcaaa agaatcactg catttgttaa agagagcaac tgaatcagga agcagagttt    8460
tgaacatatc agaagttagg aatctgcatc agagacaaat gcagtcatgg ttgtttgctg    8520
cataccagcc ctaatcatta gaagcctcat ggacttcaaa catcattccc tctgacaaga    8580
tgctctagcc taactccatg agataaaata aatctgcctt tcagagccaa agaagagtcc    8640
accagcttct tctcagtgtg aacaagagct ccagtcaggt tagtcagtcc agtgcagtag    8700
aggagaccag tctgcatcct ctaattttca aaggcaagaa gatttgttta ccctggacac    8760
caggcacaag tgaggtcaca gagctcttag atatgcagtc ctcatgagtg aggagactaa    8820
agcgcatgcc atcaagactt cagtgtagag aaaacctcca aaaaagcctc ctcactactt    8880
ctggaatagc tcagaggccg aggcggcctc ggcctctgca taaataaaaa aaattagtca    8940
gccatggggc ggagaatggg cggaactggg cggagttagg ggcgggatgg gcggagttag    9000
gggcgggact atggttgctg actaattgag atgcatgctt tgcatacttc tgcctgctgg    9060
ggagcctggg gactttccac acctggttgc tgactaattg agatgcatgc tttgcatact    9120
tctgcctgct ggggagcctg gggactttcc acacctaac tgcacacat tccacagctg    9180 cattaatgaa tcggccaacg cgcggggaga ggcggtttgc gtattgggcg ctcttccgct    9240
tcctcgctca ctgactcgct gcgctcggtc gttcggctgc ggcgagcggt atcagctcac    9300
tcaaaggcgg taatacggtt atccacagaa tcagggata acgcaggaaa gaacatgtga    9360
gcaaaaggcc agcaaaaggc caggaaccgt aaaaaggccg cgttgctggc gtttttccat    9420
aggctccgcc ccctgacga gcatcacaaa aatcgacgct caagtcagag gtggcgaaac    9480
ccgacaggac tataaagata ccaggcgttt ccccctggaa gctccctcgt gcgctctcct    9540
gttccgaccc tgccgcttac cggatacctg tccgcctttc tcccttcggg aagcgtggcg    9600
ctttctcata gctcacgctg taggtatctc agttcggtgt aggtcgttcg ctccaagctg    9660
ggctgtgtgc acgaaccccc cgttcagccc gaccgctgcg ccttatccgg taactatcgt    9720
cttgagtcca acccggtaag acacgactta tcgccactgg cagcagccac tggtaacagg    9780
attagcagag cgaggtatgt aggcggtgct acagagttct tgaagtggtg gcctaactac    9840
ggctacacta gaagaacagt atttggtatc tgcgctctgc tgaagccagt taccttcgga    9900
aaaagagttg gtagctcttg atccggcaaa caaaccaccg ctggtagcgg tggtttttt    9960 gtttgcaagc agcagattac gcgcagaaaa aaaggatctc aagaagatcc tttgatcttt    10020
tctacggggt ctgacgctca gtggaacgaa aactcacgtt aagggatttt ggtcatgaga    10080
ttatcaaaaa ggatcttcac ctagatcctt taaattaaaa atgaagtttt aaatcaatc    10140 taaagtatat atgagtaaac ttggtctgac agttaccaat gcttaatcag tgaggcacct    10200
atctcagcga tctgtctatt tcgttcatcc atagttgcct gactcctgca accacgttg    10260 tgtctcaaaa tctctgatgt tacattgcac aagataaaaa tatatcatca tgaacaataa    10320
aactgtctgc ttacataaac agtaatacaa ggggtgttat gagccatatt caacgggaaa    10380
cgtcttgctc gaggccgcga ttaaattcca acatggatgc tgatttatat gggtataaat    10440
gggctcgcga taatgtcggg caatcaggtg cgacaatcta tcgattgtat gggaagcccg    10500
atgcgccaga gttgtttctg aaacatggca aaggtagcgt tgccaatgat gttacagatg    10560
```

```
agatggtcag actaaactgg ctgacggaat ttatgcctct tccgaccatc aagcatttta   10620
tccgtactcc tgatgatgca tggttactca ccactgcgat ccccgggaaa acagcattcc   10680
aggtattaga agaatatcct gattcaggtg aaaatattgt tgatgcgctg gcagtgttcc   10740
tgcgccggtt gcattcgatt cctgtttgta attgtccttt taacagcgat cgcgtatttc   10800
gtctcgctca ggcgcaatca cgaatgaata acggtttggt tgatgcgagt gattttgatg   10860
acgagcgtaa tggctggcct gttgaacaag tctggaaaga aatgcataag cttttgccat   10920
tctcaccgga ttcagtcgtc actcatggtg atttctcact tgataacctt attttgacg    10980 aggggaaatt aataggttgt attgatgttg gacgagtcgg aatcgcagac cgataccagg   11040
atcttgccat cctatggaac tgcctcggtg agttttctcc ttcattacag aaacggcttt   11100
ttcaaaaata tggtattgat aatcctgata tgaataaatt gcagtttcat ttgatgctcg   11160
atgagttttt ctaagggcgg cctgccacca tacccacgcc gaaacaagcg ctcatgagcc   11220
cgaagtggcg agcccgatct tccccatcgg tgatgtcggc gatataggcg ccagcaaccg   11280
cacctgtggc gccggtgatg agggcgcgcc aagtcgacgt ccggcagtc                11329
```

<210> SEQ ID NO 40
<211> LENGTH: 11776
<212> TYPE: DNA
<213> ORGANISM: Artificial sequence
<220> FEATURE:
<223> OTHER INFORMATION: Synthetic polynucleotide

<400> SEQUENCE: 40

```
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg      120
gccaactcca tcactagggg ttcctgctag ctctgggtat ttaagcccga gtgagcacgc     180
agggtctcca ttttgaagcg ggaggttacg cgttcgtcga ctactagtgg gtaccagagc     240
tccctaggtt ctagaaccgg tgacgtctcc catggtgaag cttggatctg agggcggagt     300
tagggcggag ccaatcagcg tgcgccgttc cgaaagttgc cttttatggc tgggcggaga     360
atgggcggtg aacgccgatg attatataag gacgcgccgg gtgtggcaca gctagttccg     420
tcgcagccgg gatttgggtc gcggttcttg tttgtggatc cctgtgatcg tcacttggta     480
agtcactgac tgtctatgcc tgggaaaggg tgggcaggag atggggcagt gcaggaaaag     540
tggcactatg aaccctgcag ccctaggaat gcatctagac aattgtacta accttcttct     600
ctttcctctc ctgacagtcc ggaaagccac catggccgag tggctgctga gcgccagctg     660
gcagcgccgc gccaaggcca tgaccgccgc cgccggcagc gccggccgcg ccgccgtgcc     720
cctgctgctg tgcgccctgc tggccccgg cggcgcctac gtgctggacg acagcgacgg     780
cctgggccgc gagttcgacg gcatcggcgc cgtgagcggc ggcggcgcca ccagccgcct     840
gctggtgaac taccccgagc cctaccgcag ccagatcctg gactacctgt tcaagcccaa     900
cttcggcgcc agcctgcaca tcctgaaggt ggagatcggc ggcgacggcc agaccaccga     960
cggcaccgag cccagccaca tgcactacgc cctggacgag aactacttcc gcggctacga    1020
gtggtggctg atgaaggagg ccaagaagcg caacccccaac atcaccctga tcggcctgcc    1080
ctggagcttc cccggctggc tgggcaaggg cttcgactgg ccctacgtga acctgcagct    1140
gaccgcctac tacgtggtga cctggatcgt gggcgccaag cgctaccacg acctggacat    1200
cgactacatc ggcatctgga acgagcgcag ctacaacgcc aactacatca gatcctgcg    1260
```

```
caagatgctg aactaccagg gcctgcagcg cgtgaagatc atcgccagcg acaacctgtg   1320
ggagagcatc agcgccagca tgctgctgga cgccgagctg ttcaaggtgg tggacgtgat   1380
cggcgcccac taccccggca cccacagcgc caaggacgcc aagctgaccg gcaagaagct   1440
gtggagcagc gaggacttca gcaccctgaa cagcgacatg ggcgccggct gctggggccg   1500
catcctgaac cagaactaca tcaacggcta catgaccagc accatcgcct ggaacctggt   1560
ggccagctac tacgagcagc tgccctacgg ccgctgcggc ctgatgaccg cccaggagcc   1620
ctggagcggc cactacgtgg tggagagccc cgtgtgggtg agcgcccaca ccacccagtt   1680
cacccagccc ggctggtact acctgaagac cgtgggccac ctggagaagg gcggcagcta   1740
cgtggccctg accgacggcc tgggcaacct gaccatcatc atcgagacca tgagccacaa   1800
gcacagcaag tgcatccgcc ccttcctgcc ctacttcaac gtgagccagc agttcgccac   1860
cttcgtgctg aagggcagct tcagcgagat ccccgagctg caggtgtggt acaccaagct   1920
gggcaagacc agcgagcgct tcctgttcaa gcagctggac agcctgtggc tgctggacag   1980
cgacggcagc ttcaccctga gcctgcacga ggacgagctg ttcaccctga ccaccctgac   2040
caccggccgc aagggcagct accccctgcc ccccaagagc cagcccttcc ccagcaccta   2100
caaggacgac ttcaacgtgg actacccctt cttcagcgag gccccaact cgccgacca    2160 gaccggcgtg ttcgagtact tcaccaacat cgaggacccc ggcgagcacc acttcaccct   2220
gcgccaggtg ctgaaccagc gccccatcac ctgggccgcc gacgccagca acaccatcag   2280
catcatcggc gactacaact ggaccaacct gaccatcaag tgcgacgtgt acatcgagac   2340
ccccgacacc ggcggcgtgt catcgccgg ccgcgtgaac aagggcggca tcctgatccg    2400
cagcgcccgc ggcatcttct tctggatctt cgccaacggc agctaccgcg tgaccggcga   2460
cctggccggc tggatcatct acgccctggg ccgcgtggag gtgaccgcca agaagtggta   2520
caccctgacc ctgaccatca agggccactt caccagcggc atgctgaacg caagagcct    2580 gtggaccgac atccccgtga acttccccaa gaacggctgg gccgccatcg cacccacag    2640 cttcgagttc gcccagttcg acaacttcct ggtggaggcc acccgctgat gtggccgaa    2700 ccgccgaact cagaggccgg ccccagaaaa cccgagcgag taggggcgg cgcgcaggag    2760 ggaggagaac tggggcgcg ggaggctggt gggtgtgggg ggtggagatg tagaagatgt    2820
gacgccgcgg cccggcgggt gccagattag cggacgcggt gcccgcggtt gcaacgggat   2880
cccgggcgct gcagcttggg aggcggctct ccccaggcgg cgtccgcgga gacacccatc   2940
cgtgaacccc aggtcccggg ccgccggctc gccgcgcacc aggggccggc ggacagaaga   3000
gcggccgagc ggctcgaggc tggggaccg cgggcgcggc cgcgcgctgc cggcgggag     3060 gctgggggc cggggccggg gccgtgcccc ggagcgggtc ggaggccggg gccggggccg    3120
ggggacggcg gctccccgcg cggctccagc ggctcgggga tcccggccgg gccccgcagg   3180
gaccatgatg gaattcagca gccccagcag agaggaatgc cccaagcctc tgagccgggt   3240
gtcaatcatg gccggatctc tgacaggact gctgctgctt caggccgtgt cttgggcttc   3300
tggcgctaga ccttgcatcc ccaagagctt cggctacagc agcgtcgtgt gcgtgtgcaa   3360
tgccacctac tgcgacagct tcgaccctcc taccttcct gctctgggca ccttcagcag    3420
atacgagagc accagatccg gcagacggat ggaactgagc atgggaccca tccaggccaa   3480
tcacacaggc actggcctgc tgctgacact gcagcctgag cagaaattcc agaaagtgaa   3540
aggcttcggc ggagccatga cagatgccgc cgctctgaat atcctggctc tgtctccacc   3600
agctcagaac ctgctgctca gagagctactt cagcgaggaa ggcatcggct acaacatcat   3660
```

```
cagagtgccc atggccagct gcgacttcag catcaggacc tacacctacg ccgacacacc   3720
cgacgatttc cagctgcaca acttcagcct gcctgaagag acaccaagc tgaagatccc    3780 tctgatccac agagccctgc agctggcaca aagacccgtg tcactgctgg cctctccatg   3840
gacatctccc acctggctga aaacaaatgg cgccgtgaat ggcaagggca gcctgaaagg   3900
ccaacctggc gacatctacc accagacctg ggccagatac ttcgtgaagt tcctggacgc   3960
ctatgccgag cacaagctgc agttttgggc cgtgacagcc gagaacgaac cttctgctgg   4020
actgctgagc ggctacccct ttcagtgcct gggctttaca cccgagcacc agcgggactt   4080
tatcgcccgt gatctgggac ccacactggc caatagcacc caccataatg tgcggctgct   4140
gatgctggac gaccagagac tgcttctgcc ccactgggct aaagtggtgc tgacagatcc   4200
tgaggccgcc aaatacgtgc acggaatcgc cgtgcactgg tatctggact ttctggcccc   4260
tgccaaggcc acactgggag agacacacag actgttcccc aacaccatgc tgttcgccag   4320
cgaagcctgt gtgggcagca gttttggga acagagcgtg cggctcggca gctgggatag   4380
aggcatgcag tacagccaca gcatcatcac caacctgctg taccacgtcg tcggctggac   4440
cgactggaat ctgccctga atcctgaagg cggccctaac tgggtccgaa acttcgtgga   4500 cagcccatc atcgtggaca tcaccaagga caccttctac aagcagccca tgttctacca    4560
cctgggacac ttcagcaagt tcatccccga gggctctcag cgcgttggac tggtggcttc   4620
ccagaagaac gatctggacg ccgtggctct gatgcaccct gatggatctg ctgtggtggt   4680
ggtcctgaac cgcagcagca agatgtgcc cctgaccatc aaggatcccg ccgtgggatt    4740
cctggaaaca atcagccctg ctactccat ccacacctac ctgtggcgta cagtgaca     4800 attgttaatt aagtttaaac cctcgaggcc gcaagcaata aaatatcttt attttcatta   4860
catctgtgtg ttggtttttt gtgtggagat ccacgataac aaacagcttt tttggggtga   4920
acatattgac tgaattccct gcaggttggc cactccctct ctgcgcgctc gctcgctcac   4980
tgaggccgcc cgggcaaagc ccgggcgtcg gcgacctttt ggtcgcccgg cctcagtgag   5040
cgagcgagcg cgcagagagg gagtggccaa ctccatcact aggggttcct gcggccgctc   5100
gtacggtctc gaggaattcc tgcaggataa cttgccaacc tcattctaaa atgtatatag   5160
aagcccaaaa gacaataaca aaatatattct tgtagaacaa aatgggaaag aatgttccac   5220
taaatatcaa gatttagagc aaagcatgag atgtgtgggg atagacagtg aggctgataa   5280
aatagagtag agctcagaaa cagacccatt gatatatgta agtgacctat gaaaaaata    5340 tggcatttta caatgggaaa atgatggtct ttttcttttt tagaaaaaca gggaaatata   5400
tttatatgta aaaataaaa gggaacccat atgtcatacc atacacacaa aaaaattcca   5460
gtgaattata agtctaaatg gagaaggcaa aactttaaat cttttagaaa ataatataga   5520
agcatgcaga ccagcctggc caacatgatg aaaccctctc tactaataat aaaatcagta   5580
gaactactca ggactacttt gagtgggaag tccttttcta tgaagacttc tttggccaaa   5640
attaggctct aaatgcaagg agatagtgca tcatgcctgg ctgcacttac tgataaatga   5700
tgttatcacc atctttaacc aaatgcacag gaacaagtta tggtactgat gtgctggatt   5760
gagaaggagc tctacttcct tgacaggaca catttgtatc aacttaaaaa agcagatttt   5820
tgccagcaga actattcatt cagaggtagg aaacttagaa tagatgatgt cactgattag   5880
catggcttcc ccatctccac agctgcttcc cacccaggtt gcccacagtt gagtttgtcc   5940
agtgctcagg gctgcccact ctcagtaaga agccccacac cagcccctct ccaaatatgt   6000
```

```
tggctgttcc ttccattaaa gtgacccccac tttagagcag caagtggatt tctgtttctt    6060
acagttcagg aaggaggagt cagctgtgag aacctggagc ctgagatgct tctaagtccc    6120
actgctactg gggtcaggga agccagactc cagcatcagc agtcaggagc actaagccct    6180
tgccaacatc ctgtttctca gagaaactgc ttccattata atggttgtcc ttttttaagc    6240
tatcaagcca aacaaccagt gtctaccatt attctcatca cctgaagcca agggttctag    6300
caaaagtcaa gctgtcttgt aatggttgat gtgcctccag cttctgtctt cagtcactcc    6360
actcttagcc tgctctgaat caactctgac cacagttccc tggagcccct gccacctgct    6420 gccctgcca ccttctccat ctgcagtgct gtgcagcctt ctgcactctt gcagagctaa     6480
taggtggaga cttgaaggaa gaggaggaaa gtttctcata atagccttgc tgcaagctca    6540
aatgggaggt gggcactgtg cccaggagcc ttggagcaaa ggctgtgccc aacctctgac    6600
tgcatccagg tttggtcttg acagagataa gaagccctgg cttttggagc caaaatctag    6660
gtcagactta ggcaggattc tcaaagttta tcagcagaac atgaggcaga agacccttc     6720 tgctccagct tcttcaggct caaccttcat cagaatagat agaaagagag gctgtgaggg    6780
ttcttaaaac agaagcaaat ctgactcaga gaataaacaa cctcctagta aactacagct    6840
tagacagagc atctggtggt gagtgtgctc agtgtcctac tcaactgtct ggtatcagcc    6900
ctcatgagga cttctcttct ttccctcata gacctccatc tctgttttcc ttagcctgca    6960
gaaatctgga tggctattca cagaatgcct gtgctttcag agttgcattt tttctctggt    7020
attctggttc aagcatttga aggtaggaaa ggttctccaa gtgcaagaaa gccagccctg    7080
agcctcaact gcctggctag tgtggtcagt aggatgcaaa ggctgttgaa tgccacaagg    7140
ccaaacttta acctgtgtac cacaagccta gcagcagagg cagctctgct cactggaact    7200
ctctgtcttc tttctcctga gccttttctt ttcctgagtt ttctagctct cctcaacctt    7260
acctctgccc tacccaggac aaacccaaga gccactgttt ctgtgatgtc ctctccagcc    7320
ctaattaggc atcatgactt cagcctgacc ttccatgctc agaagcagtg ctaatccact    7380
tcagatgagc tgctctatgc aacacaggca gagcctacaa accttgcac cagagccctc     7440 cacatatcag tgtttgttca tactcacttc aacagcaaat gtgactgctg agattaagat    7500
tttacacaag atggtctgta atttcacagt tagtttatc ccattaggta tgaaagaatt      7560
agcataattc cccttaaaca tgaatgaatc ttagattttt taataaatag ttttggaagt    7620
aaagacagag acatcaggag cacaaggaat agcctgagag gacaaacaga acaagaaaga    7680
gtctggaaat acacaggatg ttcttggcct cctcaaagca agtgcaagca gatagtacca    7740
gcagccccag gctatcagag cccagtgaag agaagtacca tgaaagccac agctctaacc    7800
accctgttcc agagtgacag acagtcccca agacaagcca gcctgagcca gagagagaac    7860
tgcaagagaa agtttctaat ttaggttctg ttagattcag acaagtgcag gtcatcctct    7920
ctccacagct actcacctct ccagcctaac aaagcctgca gtccacactc caaccctggt    7980
gtctcacctc ctagcctctc ccaacatcct gctctctgac catcttctgc atctctcatc    8040
tcaccatctc ccactgtcta cagcctactc ttgcaactac catctcattt tctgacatcc    8100
tgtctacatc ttctgccata ctctgccatc taccatacca cctcttacca tctaccacac    8160
catcttttat ctccatccct ctcagaagcc tccaagctga atcctgcttt atgtgttcat    8220
ctcagcccct gcatggaaag ctgaccccag aggcagaact attcccagag agcttggcca    8280
agaaaaacaa aactaccagc ctggccaggc tcaggagtag taagctgcag tgtctgttgt    8340
gttctagctt caacagctgc aggagttcca ctctcaaatg ctccacattt ctcacatcct    8400
```

```
cctgattctg gtcactaccc atcttcaaag aacagaatat ctcacatcag catactgtga   8460
aggactagtc atgggtgcag ctgctcagag ctgcaaagtc attctggatg gtggagagct   8520
tacaaacatt tcatgatgct ccccccgctc tgatggctgg agcccaatcc ctacacagac   8580
tcctgctgta tgtgttttcc tttcactctg agccacagcc agagggcagg cattcagtct   8640
cctcttcagg ctggggctgg ggcactgaga actcacccaa caccttgctc tcactccttc   8700
tgcaaaacaa gaaagagctt tgtgctgcag tagccatgaa gaatgaaagg aaggctttaa   8760
ctaaaaaatg tcagagatta ttttcaaccc cttactgtgg atcaccagca aggaggaaac   8820
acaacacaga gacatttttt cccctcaaat tatcaaaaga atcactgcat ttgttaaaga   8880
gagcaactga atcaggaagc agagttttga acatatcaga agttaggaat ctgcatcaga   8940
gacaaatgca gtcatggttg tttgctgcat accagcccta atcattagaa gcctcatgga   9000
cttcaaacat cattccctct gacaagatgc tctagcctaa ctccatgaga taaaataaat   9060 ctgccttca gagccaaaga agagtccacc agcttcttct cagtgtgaac aagagctcca    9120
gtcaggttag tcagtccagt gcagtagagg agaccagtct gcatcctcta attttcaaag   9180
gcaagaagat ttgtttaccc tggacaccag gcacaagtga ggtcacagag ctcttagata   9240
tgcagtcctc atgagtgagg agactaaagc gcatgccatc aagacttcag tgtagagaaa   9300
acctccaaaa aagcctcctc actacttctg gaatagctca gaggccgagg cggcctcggc   9360
ctctgcataa ataaaaaaaa ttagtcagcc atggggcgga gaatgggcgg aactgggcgg   9420
agttaggggc gggatgggcg gagttagggg cgggactatg gttgctgact aattgagatg   9480
catgctttgc atacttctgc ctgctgggga gcctggggac tttccacacc tggttgctga   9540
ctaattgaga tgcatgcttt gcatacttct gcctgctggg gagcctgggg actttccaca   9600
ccctaactga cacacattcc acagctgcat taatgaatcg gccaacgcgc ggggagaggc   9660
ggtttgcgta ttgggcgctc ttccgcttcc tcgctcactg actcgctgcg ctcggtcgtt   9720
cggctgcggc gagcggtatc agctcactca aaggcggtaa tacggttatc cacagaatca   9780
ggggataacg caggaaagaa catgtgagca aaaggccagc aaaaggccag gaaccgtaaa   9840
aaggccgcgt tgctggcgtt tttccatagg ctccgccccc ctgacgagca tcacaaaaat   9900
cgacgctcaa gtcagaggtg gcgaaacccg acaggactat aaagatacca ggcgtttccc   9960
cctggaagct ccctcgtgcg ctctcctgtt ccgaccctgc cgcttaccgg atacctgtcc  10020
gcctttctcc cttcgggaag cgtggcgctt tctcatagct cacgctgtag gtatctcagt  10080
tcggtgtagg tcgttcgctc caagctgggc tgtgtgcacg aaccccccgt tcagcccgac  10140
cgctgcgcct tatccggtaa ctatcgtctt gagtccaacc cggtaagaca cgacttatcg  10200
ccactggcag cagccactgg taacaggatt agcagagcga ggtatgtagg cggtgctaca  10260
gagttcttga agtggtggcc taactacggc tacactagaa gaacagtatt tggtatctgc  10320
gctctgctga agccagttac cttcggaaaa agagttggta gctcttgatc cggcaaacaa  10380
accaccgctg gtagcggtgg ttttttttgtt tgcaagcagc agattacgcg cagaaaaaaa  10440
ggatctcaag aagatccttt gatcttttct acgggtctg acgctcagtg gaacgaaaac    10500
tcacgttaag ggattttggt catgagatta tcaaaaagga tcttcaccta gatcctttta  10560
aattaaaaat gaagttttaa atcaatctaa agtatatatg agtaaacttg gtctgacagt  10620
taccaatgct taatcagtga ggcacctatc tcagcgatct gtctatttcg ttcatccata  10680
gttgcctgac tccctgcaaac cacgttgtgt ctcaaaatct ctgatgttac attgcacaag  10740
```

| | | | | | |
|---|---|---|---|---|---|
| ataaaaatat | atcatcatga | acaataaaac | tgtctgctta | cataaacagt | aatacaaggg | 10800 |
| gtgttatgag | ccatattcaa | cgggaaacgt | cttgctcgag | gccgcgatta | aattccaaca | 10860 |
| tggatgctga | tttatatggg | tataaatggg | ctcgcgataa | tgtcgggcaa | tcaggtgcga | 10920 |
| caatctatcg | attgtatggg | aagcccgatg | cgccagagtt | gtttctgaaa | catggcaaag | 10980 |
| gtagcgttgc | caatgatgtt | acagatgaga | tggtcagact | aaactggctg | acggaattta | 11040 |
| tgcctcttcc | gaccatcaag | cattttatcc | gtactcctga | tgatgcatgg | ttactcacca | 11100 |
| ctgcgatccc | cgggaaaaca | gcattccagg | tattagaaga | atatcctgat | tcaggtgaaa | 11160 |
| atattgttga | tgcgctggca | gtgttcctgc | gccggttgca | ttcgattcct | gtttgtaatt | 11220 |
| gtccttttaa | cagcgatcgc | gtatttcgtc | tcgctcaggc | gcaatcacga | atgaataacg | 11280 |
| gtttggttga | tgcgagtgat | tttgatgacg | agcgtaatgg | ctggcctgtt | gaacaagtct | 11340 |
| ggaaagaaat | gcataagctt | ttgccattct | caccggattc | agtcgtcact | catggtgatt | 11400 |
| tctcacttga | taaccttatt | tttgacgagg | ggaaattaat | aggttgtatt | gatgttggac | 11460 |
| gagtcggaat | cgcagaccga | taccaggatc | ttgccatcct | atggaactgc | ctcggtgagt | 11520 |
| tttctccttc | attacagaaa | cggctttttc | aaaaatatgg | tattgataat | cctgatatga | 11580 |
| ataaattgca | gtttcatttg | atgctcgatg | agttttcta | agggcggcct | gccaccatac | 11640 |
| ccacgccgaa | acaagcgctc | atgagcccga | agtggcgagc | ccgatcttcc | ccatcggtga | 11700 |
| tgtcggcgat | ataggcgcca | gcaaccgcac | ctgtggcgcc | ggtgatgagg | gcgcgccaag | 11760 |
| tcgacgtccg | gcagtc | | | | | 11776 |

<210> SEQ ID NO 41
<211> LENGTH: 11348
<212> TYPE: DNA
<213> ORGANISM: Artificial sequence
<220> FEATURE:
<223> OTHER INFORMATION: Synthetic polynucleotide

<400> SEQUENCE: 41

| | | | | | |
|---|---|---|---|---|---|
| ttggccactc | cctctctgcg | cgctcgctcg | ctcactgagg | ccgggcgacc | aaaggtcgcc | 60 |
| cgacgcccgg | gctttgcccg | gcggccctca | gtgagcgagc | gagcgcgcag | agagggagtg | 120 |
| gccaactcca | tcactagggg | ttcctgctag | ctctgggtat | ttaagcccga | gtgagcacgc | 180 |
| agggtctcca | ttttgaagcg | ggaggttacg | cgttcgtcga | ctactagtgg | gtaccagagc | 240 |
| tccctaggtt | ctagaaccgg | tgacgtctcc | catggtgaag | cttggatctg | agggcggagt | 300 |
| tagggcggag | ccaatcagcg | tgcgccgttc | cgaaagttgc | cttttatggc | tgggcggaga | 360 |
| atgggcggtg | aacgccgatg | attatataag | gacgcgccgg | gtgtggcaca | gctagttccg | 420 |
| tcgcagccgg | gatttgggtc | gcggttcttg | tttgtggatc | cctgtgatcg | tcacttggta | 480 |
| agtcactgac | tgtctatgcc | tgggaaaggg | tgggcaggag | atgggcagt | gcaggaaaag | 540 |
| tggcactatg | aaccctcctg | gtggcgaggg | aggggggtg | gtcctcgaac | gccttgcaga | 600 |
| actggcctgg | atacagagtg | gaccggctgg | ccccatctgg | aagacttcga | gatacactgt | 660 |
| tgtcttactg | cgctcaacag | tgtatctcga | agtcttccaa | atggtgccag | ccatcgcagc | 720 |
| ggggtgcagg | aaatggggc | agccccccctt | tttggctatc | cttccacgtg | ttctttttg | 780 |
| tatcttttgt | gtttcctaga | aaacatctca | gtcaccaccg | cagccctagg | aatgcatcta | 840 |
| gacaattgta | ctaaccttct | tctctttcct | ctcctgacag | tccggaaagc | caccatgtgg | 900 |
| cagtgtgggg | ccagcctgtg | ctgcctgctg | gtgctggcca | cgcccgcag | ccgccccagc | 960 |
| ttccaccccc | tgagcgacga | gctggtgaac | tacgtgaaca | agcgcaacac | cacctggcag | 1020 |

```
gccggccaca acttctacaa cgtggacatg agctacctga agcgcctgtg cggcaccttc    1080
ctgggcggcc ccaagccccc ccagcgcgtg atgttcaccg aggacctgaa gctgcccgcc    1140
agcttcgacg cccgcgagca gtggcccagt gcccccacca tcaaggagat ccgcgaccag    1200
ggcagctgcg gcagctgctg ggccttcggc gccgtggagg ccatcagcga ccgcatctgc    1260
atccacacca acgcccacgt gagcgtggag gtgagcgccg aggacctgct gacctgctgc    1320
ggcagcatgt gcggcgacgg ctgcaacggc ggctaccccg ccgaggcctg gaacttctgg    1380
acccgcaagg gcctggtgag cggcggcctg tacgagagcc acgtgggctg ccgcccctac    1440
agcatccccc cctgcgagca ccacgtgaac ggcagccgcc cccctgcac cggcgagggc    1500 gacaccccca gtgcagcaa gatctgcgag cccggctaca gccccaccta caagcaggac    1560
aagcactacg gctacaacag ctacagcgtg agcaacagcg agaaggacat catggccgag    1620
atctacaaga cggccccgt ggagggcgcc ttcagcgtgt acagcgactt cctgctgtac    1680
aagagcggcg tgtaccagca cgtgaccggc gagatgatgg cggccacgc catccgcatc    1740 ctgggctggg gcgtggagaa cggcaccccc tactggctgg tggccaacag ctggaacacc    1800
gactggggcg acaacggctt cttcaagatc ctgcgcggcc aggaccactg cggcatcgag    1860
agcgaggtgg tggccggcat cccccgcacc gaccagtact gggagaagat cgagggcaga    1920
ggaagtcttc tgacatgcgg agacgtggaa gagaatcccg ccctatgga attcagcagc    1980 cccagcagag aggaatgccc caagcctctg agccgggtgt caatcatggc cggatctctg    2040
acaggactgc tgctgcttca ggccgtgtct gggcttctg cgctagacc ttgcatcccc    2100 aagagcttcg gctacagcag cgtcgtgtgc gtgtgcaatg ccacctactg cgacagcttc    2160
gaccctccta cctttcctgc tctgggcacc ttcagcagat acgagagcac cagatccggc    2220
agacggatgg aactgagcat gggacccatc caggccaatc acacaggcac tggcctgctg    2280
ctgacactgc agcctgagca gaaattccag aaagtgaaag gcttcggcgg agccatgaca    2340
gatgccgccg ctctgaatat cctggctctg tctccaccag ctcagaacct gctgctcaag    2400
agctacttca gcgaggaagg catcggctac aacatcatca gagtgcccat ggccagctgc    2460
gacttcagca tcaggaccta cacctacgcc gacacacccg acgatttcca gctgcacaac    2520
ttcagcctgc ctgaagagga caccaagctg aagatccctc tgatccacag agccctgcag    2580
ctggcacaaa gacccgtgtc actgctggcc tctccatgga catctcccac ctggctgaaa    2640
acaaatggcg ccgtgaatgg caagggcagc ctgaaaggcc aacctggcga catctaccac    2700
cagacctggg ccagatactt cgtgaagttc ctggacgcct atgccgagca aagctgcag    2760 ttttgggccg tgacagccga gaacgaacct tctgctggac tgctgagcgg ctaccccttt    2820
cagtgcctgg gctttacacc cgagcaccag cgggacttta tcgcccgtga tctgggaccc    2880
acactggcca atagcaccca ccataatgtg cggctgctga tgctggacga ccagagactg    2940
cttctgcccc actgggctaa agtggtgctg acagatcctg aggccgccaa atacgtgcac    3000
ggaatcgccg tgcactggta tctggacttt ctggcccctg ccaaggccac actgggagag    3060
acacacagac tgttccccaa caccatgctg ttcgccagcg aagcctgtgt gggcagcaag    3120
ttttgggaac agagcgtgcg gctcggcagc tgggatagag catgcagta cagccacagc    3180 atcatcacca acctgctgta ccacgtcgtc ggctggaccg actggaatct ggccctgaat    3240
cctgaaggcg ccctaactg ggtccgaaac ttcgtggaca gccccatcat cgtggacatc    3300
accaaggaca ccttctacaa gcagcccatg ttctaccacc tgggacactt cagcaagttc    3360
```

```
atccccgagg gctctcagcg cgttggactg gtggcttccc agaagaacga tctggacgcc      3420
gtggctctga tgcaccctga tggatctgct gtggtggtgg tcctgaaccg cagcagcaaa      3480
gatgtgcccc tgaccatcaa ggatcccgcc gtgggattcc tggaaacaat cagccctggc      3540
tactccatcc acacctacct gtggcgtaga cagtgacaat tgttaattaa gtttaaaccc      3600
tcgaggccgc aagcttatcg ataatcaacc tctggattac aaaatttgtg aaagattgac      3660
tggtattctt aactatgttg ctccttttac gctatgtgga tacgctgctt taatgccttt      3720
gtatcatgct attgcttccc gtatggcttt cattttctcc tccttgtata atcctggtt      3780 gctgtctctt tatgaggagt tgtggcccgt tgtcaggcaa cgtggcgtgg tgtgcactgt      3840
gtttgctgac gcaacccca ctggttgggg cattgccacc acctgtcagc tcctttccgg      3900
gactttcgct ttcccccctcc ctattgccac ggcggaactc atcgccgcct gccttgcccg      3960
ctgctggaca ggggctcggc tgttgggcac tgacaattcc gtggtgttgt cggggaaatc      4020
atcgtccttt ccttggctgc tcgcctgtgt tgccacctgg attctgcgcg gacgtccttt      4080
ctgctacgtc ccttcggccc tcaatccagc ggaccttcct tcccgcggcc tgctgccggc      4140
tctgcggcct cttccgcgtc ttcgccttcg ccctcagacg agtcggatct cccttgggc      4200 cgcctccccg catcgatacc gtcgactaga gctcgctgat cagcctcgac tgtgccttct      4260
agttgccagc catctgttgt ttgcccctcc cccgtgcctt ccttgaccct ggaaggtgcc      4320
actcccactg tcctttccta ataaaatgag gaaattgcat cgcattgtct gagtaggtgt      4380
cattctattc tggggggtgg ggtggggcag gacagcaagg gggaggattg ggaagacaat      4440
agcaggcatg ctggggagag atccacgata acaaacagct ttttgggggt gaacatattg      4500
actgaattcc ctgcaggttg gccactccct ctctgcgcgc tcgctcgctc actgaggccg      4560
cccgggcaaa gcccgggcgt cgggcgacct ttggtcgccc ggcctcagtg agcgagcgag      4620
cgcgcagaga gggagtggcc aactccatca ctaggggttc ctgcggccgc tcgtacggtc      4680
tcgaggaatt cctgcaggat aacttgccaa cctcattcta aatgtatat agaagcccaa      4740 aagacaataa caaaaatatt cttgtagaac aaaatgggaa agaatgttcc actaaatatc      4800
aagatttaga gcaaagcatg agatgtgtgg ggatagacag tgaggctgat aaaatagagt      4860
agagctcaga aacagaccca ttgatatatg taagtgacct atgaaaaaaa tatggcattt      4920
tacaatggga aaatgatggt cttttctctt tttagaaaaa cagggaaata tatttatatg      4980 taaaaataa aagggaaccc atatgtcata ccatacacac aaaaaaattc cagtgaatta      5040
taagtctaaa tggagaaggc aaaactttaa atcttttaga aaataatata gaagcatgca      5100
gaccagcctg gccaacatga tgaaaccctc tctactaata ataaaatcag tagaactact      5160
caggactact ttgagtggga agtccttttc tatgaagact tctttggcca aaattaggct      5220
ctaaatgcaa ggagatagtg catcatgcct ggctgcactt actgataaat gatgttatca      5280
ccatctttaa ccaaatgcac aggaacaagt tatggtactg atgtgctgga ttgagaagga      5340
gctctacttc cttgacagga cacatttgta tcaacttaaa aaagcagatt tttgccagca      5400
gaactattca ttcagaggta ggaaacttag aatagatgat gtcactgatt agcatggctt      5460
ccccatctcc acagctgctt cccacccagg ttgcccacag ttgagtttgt ccagtgctca      5520
gggctgccca ctctcagtaa gaagccccac accagcccct ctccaaatat gttggctgtt      5580
ccttccatta aagtgacccc acttagagc agcaagtgga tttctgtttc ttacagttca      5640
ggaaggagga gtcagctgtg agaacctgga gcctgagatg cttctaagtc ccactgctac      5700
tggggtcagg gaagccagac tccagcatca gcagtcagga gcactaagcc cttgccaaca      5760
```

```
tcctgtttct cagagaaact gcttccatta taatggttgt cctttttta agctatcaagc    5820
caaacaacca gtgtctacca ttattctcat cacctgaagc caagggttct agcaaaagtc    5880
aagctgtctt gtaatggttg atgtgcctcc agcttctgtc ttcagtcact ccactcttag    5940
cctgctctga atcaactctg accacagttc cctggagccc ctgccacctg ctgcccctgc    6000
caccttctcc atctgcagtg ctgtgcagcc ttctgcactc ttgcagagct aataggtgga    6060
gacttgaagg aagaggagga aagtttctca taatagcctt gctgcaagct caaatgggag    6120
gtgggcactg tgcccaggag ccttggagca aaggctgtgc ccaacctctg actgcatcca    6180
ggtttggtct tgacagagat aagaagccct ggcttttgga gccaaaatct aggtcagact    6240
taggcaggat tctcaaagtt tatcagcaga acatgaggca gaagaccctt tctgctccag    6300
cttcttcagg ctcaaccttc atcagaatag atagaaagag aggctgtgag ggttcttaaa    6360
acagaagcaa atctgactca gagaataaac aacctcctag taaactacag cttagacaga    6420
gcatctggtg gtgagtgtgc tcagtgtcct actcaactgt ctggtatcag ccctcatgag    6480
gacttctctt cttcccctca tagacctcca tctctgtttt ccttagcctg cagaaatctg    6540
gatggctatt cacagaatgc ctgtgctttc agagttgcat ttttctctg gtattctggt    6600
tcaagcattt gaaggtagga aaggttctcc aagtgcaaga aagccagccc tgagcctcaa    6660
ctgcctggct agtgtggtca gtaggatgca aaggctgttg aatgccacaa ggccaaactt    6720
taacctgtgt accacaagcc tagcagcaga ggcagctctg ctcactggaa ctctctgtct    6780
tctttctcct gagccttttc ttttcctgag ttttctagct ctcctcaacc ttacctctgc    6840
cctacccagg acaaacccaa gagccactgt ttctgtgatg tcctctccag ccctaattag    6900
gcatcatgac ttcagcctga ccttccatgc tcagaagcag tgctaatcca cttcagatga    6960
gctgctctat gcaacacagg cagagcctac aaacctttgc accagagccc tccacatatc    7020
agtgtttgtt catactcact tcaacagcaa atgtgactgc tgagattaag attttacaca    7080
agatggtctg taatttcaca gttagtttta tcccattagg tatgaaagaa ttagcataat    7140
tccccttaaa catgaatgaa tcttagattt tttaataaat agttttggaa gtaaagacag    7200
agacatcagg agcacaagga atagcctgag aggacaaaca gaacaagaaa gagtctggaa    7260
atacacagga tgttcttggc ctcctcaaag caagtgcaag cagatagtac cagcagcccc    7320
aggctatcag agcccagtga agagaagtac catgaaagcc acagtctaa ccaccctgtt    7380
ccagagtgac agacagtccc caagacaagc cagcctgagc cagagagaga actgcaagag    7440
aaagtttcta atttaggttc tgttagattc agacaagtgc aggtcatcct ctctccacag    7500
ctactcacct ctccagccta acaaagcctg cagtccacac tccaaccctg tgtctcacc    7560
tcctagcctc tcccaacatc ctgctctctg accatcttct gcatctctca tctccacatc    7620
tcccactgtc tacagcctac tcttgcaact accatctcat tttctgacat cctgtctaca    7680
tcttctgcca tactctgcca tctaccatac cacctcttac catctaccac accatctttt    7740
atctccatcc ctctcagaag cctccaagct gaatcctgct ttatgtgttc atctcagccc    7800
ctgcatggaa agctgacccc agaggcagaa ctattcccag agagcttggc caagaaaaac    7860
aaaactacca gcctggccag gctcaggagt agtaagctgc agtgtctgtt gtgttctagc    7920
ttcaacagct gcaggagttc cactctcaaa tgctccacat ttctcacatc ctcctgattc    7980
tggtcactac ccatcttcaa agaacagaat atctcacatc agcatactgt gaaggactag    8040
tcatgggtgc agctgctcag agctgcaaag tcattctgga tggtggagag cttacaaaca    8100
```

```
tttcatgatg ctccccccgc tctgatggct ggagcccaat ccctacacag actcctgctg    8160
tatgtgtttt cctttcactc tgagccacag ccagagggca ggcattcagt ctcctcttca    8220
ggctggggct ggggcactga gaactcaccc aacaccttgc tctcactcct tctgcaaaac    8280
aagaaagagc tttgtgctgc agtagccatg aagaatgaaa ggaaggcttt aactaaaaaa    8340
tgtcagagat tattttcaac cccttactgt ggatcaccag caaggaggaa acacaacaca    8400
gagacatttt ttcccctcaa attatcaaaa gaatcactgc atttgttaaa gagagcaact    8460
gaatcaggaa gcagagtttt gaacatatca gaagttagga atctgcatca gagacaaatg    8520
cagtcatggt tgtttgctgc ataccagccc taatcattag aagcctcatg gacttcaaac    8580
atcattccct ctgacaagat gctctagcct aactccatga gataaaataa atctgccttt    8640
cagagccaaa gaagagtcca ccagcttctt ctcagtgtga acaagagctc cagtcaggtt    8700
agtcagtcca gtgcagtaga ggagaccagt ctgcatcctc taattttcaa aggcaagaag    8760
atttgtttac cctggacacc aggcacaagt gaggtcacag agctcttaga tatgcagtcc    8820
tcatgagtga ggagactaaa gcgcatgcca tcaagacttc agtgtagaga aaacctccaa    8880
aaaagcctcc tcactacttc tggaatagct cagaggccga ggcggcctcg gcctctgcat    8940
aaataaaaaa aattagtcag ccatggggcg gagaatgggc ggaactgggc ggagttaggg    9000
gcgggatggg cggagttagg ggcgggacta tggttgctga ctaattgaga tgcatgcttt    9060
gcatacttct gcctgctggg gagcctgggg actttccaca cctggttgct gactaattga    9120
gatgcatgct ttgcatactt ctgcctgctg gggagcctgg ggactttcca caccctaact    9180
gacacacatt ccacagctgc attaatgaat cggccaacgc gcggggagag gcggtttgcg    9240
tattgggcgc tcttccgctt cctcgctcac tgactcgctg cgctcggtcg ttcggctgcg    9300
gcgagcggta tcagctcact caaaggcggt aatacggtta tccacagaat caggggataa    9360
cgcaggaaag aacatgtgag caaaaggcca gcaaaggcca ggaaccgta aaaaggccgc    9420 gttgctggcg ttttccata ggctccgccc ccctgacgag catcacaaaa atcgacgctc    9480
aagtcagagg tggcgaaacc cgacaggact ataaagatac caggcgtttc ccctggaag    9540 ctccctcgtg cgctctcctg ttccgaccct gccgcttacc ggatacctgt ccgcctttct    9600
cccttcggga agcgtggcgc tttctcatag ctcacgctgt aggtatctca gttcggtgta    9660
ggtcgttcgc tccaagctgg gctgtgtgca cgaaccccc gttcagcccg accgctgcgc    9720
cttatccggt aactatcgtc ttgagtccaa cccggtaaga cacgacttat cgccactggc    9780
agcagccact ggtaacagga ttagcagagc gaggtatgta ggcggtgcta cagagttctt    9840
gaagtggtgg cctaactacg gctacactag aagaacagta tttggtatct gcgctctgct    9900
gaagccagtt accttcggaa aaagagttgg tagctcttga tccggcaaac aaaccaccgc    9960
tggtagcggt ggtttttttg tttgcaagca gcagattacg cgcagaaaaa aaggatctca    10020
agaagatcct ttgatctttt ctacggggtc tgacgctcag tggaacgaaa actcacgtta    10080
agggattttg gtcatgagat tatcaaaaag gatcttcacc tagatccttt taaattaaaa    10140
atgaagtttt aaatcaatct aaagtatata tgagtaaact tggtctgaca gttaccaatg    10200
cttaatcagt gaggcaccta tctcagcgat ctgtctattt cgttcatcca tagttgcctg    10260 actccctgcaa accacgttgt gtctcaaaat ctctgatgtt acattgcaca agataaaaat    10320
atatcatcat gaacaataaa actgtctgct tacataaaca gtaatacaag gggtgttatg    10380
agccatattc aacgggaaac gtcttgctcg aggccgcgat taaattccaa catggatgct    10440
gatttatatg ggtataaatg ggctcgcgat aatgtcgggc aatcaggtgc gacaatctat    10500
```

```
cgattgtatg ggaagcccga tgcgccagag ttgtttctga acatggcaa aggtagcgtt    10560 gccaatgatg ttacagatga gatggtcaga ctaaactggc tgacggaatt tatgcctctt    10620
ccgaccatca agcattttat ccgtactcct gatgatgcat ggttactcac cactgcgatc    10680
cccgggaaaa cagcattcca ggtattagaa gaatatcctg attcaggtga aaatattgtt    10740
gatgcgctgg cagtgttcct gcgccggttg cattcgattc ctgtttgtaa ttgtccttt    10800 aacagcgatc gcgtatttcg tctcgctcag gcgcaatcac gaatgaataa cggtttggtt    10860
gatgcgagtg attttgatga cgagcgtaat ggctggcctg ttgaacaagt ctggaaagaa    10920
atgcataagc ttttgccatt ctcaccggat tcagtcgtca ctcatggtga tttctcactt    10980
gataacctta tttttgacga ggggaaatta ataggttgta ttgatgttgg acgagtcgga    11040
atcgcagacc gataccagga tcttgccatc ctatggaact gcctcggtga gttttctcct    11100
tcattacaga aacggctttt tcaaaaatat ggtattgata atcctgatat gaataaattg    11160
cagtttcatt tgatgctcga tgagttttc taagggcggc ctgccaccat acccacgccg    11220
aaacaagcgc tcatgagccc gaagtggcga gcccgatctt ccccatcggt gatgtcggcg    11280 ataggcgc cagcaaccgc acctgtggcg ccggtgatga gggcgcgcca agtcgacgtc    11340
cggcagtc                                                             11348

<210> SEQ ID NO 42
<211> LENGTH: 11433
<212> TYPE: DNA
<213> ORGANISM: Artificial sequence
<220> FEATURE:
<223> OTHER INFORMATION: Synthetic polynucleotide

<400> SEQUENCE: 42
ttggccactc cctctctgcg cgctcgctcg ctcactgagg ccgggcgacc aaaggtcgcc       60
cgacgcccgg gctttgcccg gcggcctca gtgagcgagc gagcgcgcag agagggagtg      120
gccaactcca tcactagggg ttcctgctag ctctgggtat ttaagcccga gtgagcacgc      180
agggtctcca ttttgaagcg ggaggttacg cgttcgtcga ctactagtgg gtaccagagc      240
tccctaggtt ctagaaccgg tgacgtctcc catggtgaag cttggatctg agggcggagt      300
tagggcggag ccaatcagcg tgcgccgttc cgaaagttgc cttttatggc tgggcggaga      360
atgggcggtg aacgccgatg attatataag gacgcgccgg gtgtggcaca gctagttccg      420
tcgcagccgg gatttgggtc gcggttcttg tttgtggatc cctgtgatcg tcacttggta      480
agtcactgac tgtctatgcc tgggaaaggg tgggcaggag atggggcagt gcaggaaaag      540
tggcactatg aaccctcctg gtggcgaggg gaggggggtg gtcctcgaac gccttgcaga      600
actggcctgg atacagagtg gaccggctgg ccccatctgg aagacttcga gatacactgt      660
tgtcttactg cgctcaacag tgtatctcga agtcttccaa atggtgccag ccatcgcagc      720
ggggtgcagg aaatggggc agccccctt tttggctatc cttccacgtg ttcttttttg      780
tatcttttgt gtttcctaga aaacatctca gtcaccaccg cagccctagg aatgcatcta      840
gacaattgta ctaaccttct tctctttcct ctcctgacag tccggaaagc caccatggaa      900
ttcagcagcc ccagcagaga ggaatgcccc aagcctctga gccgggtgtc aatcatggcc      960
ggatctctga caggactgct gctgcttcag gccgtgtctt gggcttctgg cgctagacct     1020
tgcatcccca agagcttcgg ctacagcagc gtcgtgtgcg tgtgcaatgc cacctactgc     1080
gacagcttcg accctcctac ctttcctgct ctgggcacct tcagcagata cgagagcacc     1140
```

-continued

| | |
|---|---|
| agatccggca gacggatgga actgagcatg ggacccatcc aggccaatca cacaggcact | 1200 |
| ggcctgctgc tgacactgca gcctgagcag aaattccaga aagtgaaagg cttcggcgga | 1260 |
| gccatgacag atgccgccgc tctgaatatc ctggctctgt ctccaccagc tcagaacctg | 1320 |
| ctgctcaaga gctacttcag cgaggaaggc atcggctaca acatcatcag agtgcccatg | 1380 |
| gccagctgcg acttcagcat caggacctac acctacgccg acacaccega cgatttccag | 1440 |
| ctgcacaact tcagcctgcc tgaagaggac accaagctga agatccctct gatccacaga | 1500 |
| gccctgcagc tggcacaaag acccgtgtca ctgctggcct ctccatggac atctcccacc | 1560 |
| tggctgaaaa caaatggcgc cgtgaatggc aagggcagcc tgaaaggcca acctggcgac | 1620 |
| atctaccacc agacctgggc cagatacttc gtgaagttcc tggacgccta tgccgagcac | 1680 |
| aagctgcagt tttgggccgt gacagccgag aacgaaccett ctgctggact gctgagcggc | 1740 |
| taccccttte agtgcctggg ctttacaccc gagcaccagc gggactttat cgcccgtgat | 1800 |
| ctgggaccca cactggccaa tagcacccac cataatgtgc ggctgctgat gctggacgac | 1860 |
| cagagactgc ttctgcccca ctgggctaaa gtggtgctga cagatcctga ggccgccaaa | 1920 |
| tacgtgcacg gaatcgccgt gcactggtat ctggactttc tggcccctgc caaggccaca | 1980 |
| ctgggagaga cacacagact gttccccaac accatgctgt tcgccagcga agcctgtgtg | 2040 |
| ggcagcaagt tttgggaaca gagcgtgcgg ctcggcagct gggatagagg catgcagtac | 2100 |
| agccacagca tcatcaccaa cctgctgtac cacgtcgtcg gctggaccga ctggaatctg | 2160 |
| gccctgaatc ctgaaggcgg ccctaactgg gtccgaaact tcgtggacag ccccatcatc | 2220 |
| gtggacatca ccaaggacac cttctacaag cagcccatgt tctaccacct gggcacttc | 2280 |
| agcaagttca tccccgaggg ctctcagcgc gttggactgg tggcttccca gaagaacgat | 2340 |
| ctggacgccg tggctctgat gcaccctgat ggatctgctg tggtggtggt cctgaaccgc | 2400 |
| agcagcaaag atgtgcccct gaccatcaag gatcccgccg tgggattcct ggaaacaatc | 2460 |
| agccctggct actccatcca cacctacctg tggcgtagac aggagggcag aggaagtctt | 2520 |
| ctgacatgcg agacgtgga agagaatccc ggccctatgc ccgctacgg cgccagcctg | 2580 |
| cgccagagct gccccgcag cggccgcgag cagggccagg acggcaccgc cggcgccccc | 2640 |
| ggcctgctgt ggatgggcct ggtgctggcc ctggccctgg ccctggccct ggccctggcc | 2700 |
| ctgagcgaca gccgcgtgct gtgggccccc gccgaggccc accccctgag ccccagggc | 2760 |
| caccccgccc gcctgcaccg catcgtgccc cgcctgcgcg acgtgttcgg ctggggcaac | 2820 |
| ctgacctgcc ccatctgcaa gggcctgttc accgccatca acctgggcct gaagaaggag | 2880 |
| cccaacgtgg ccgcgtggg cagcgtggcc atcaagctgt gcaacctgct gaagatcgcc | 2940 |
| cccccgccg tgtgccagag catcgtgcac ctgttcgagg acgacatggt ggaggtgtgg | 3000 |
| cgccgcagcg tgctgagccc cagcgaggcc tgcggcctgc tgctgggcag cacctgcggc | 3060 |
| cactgggaca tcttcagcag ctggaacatc agcctgccca ccgtgcccaa gccccccccc | 3120 |
| aagcccccca gccccccgc ccccggcgcc ccgtgagcc gcatcctgtt cctgaccgac | 3180 |
| ctgcactggg accacgacta cctggagggc accgaccccg actgcgccga ccccctgtgc | 3240 |
| tgccgccgcg gcagcggcct gcccccccgcc agccgccccg cgccggcta ctggggcgag | 3300 |
| tacagcaagt gcgacctgcc cctgcgcacc ctggagagct gctgagcgg cctgggcccc | 3360 |
| gccggcccct tcgacatggt gtactggacc ggcgacatcc ccgcccacga cgtgtggcac | 3420 |
| cagacccgcc aggaccagct gcgcgccctg accaccgtga ccgccctggt gcgcaagttc | 3480 |
| ctgggcccg tgccgtgta cccgccgtg ggcaaccacg agagcacccc cgtgaacagc | 3540 |

```
ttccccccc  ccttcatcga  gggcaaccac  agcagccgct  ggctgtacga  ggccatggcc   3600
aaggcctggg  agccctggct  gcccgccgag  gccctgcgca  ccctgcgcat  cggcggcttc   3660
tacgccctga  gcccctaccc  cggcctgcgc  ctgatcagcc  tgaacatgaa  cttctgcagc   3720
cgcgagaact  tctggctgct  gatcaacagc  accgaccccg  ccggccagct  gcagtggctg   3780
gtgggcgagc  tgcaggccgc  cgaggaccgc  ggcgacaagg  tgcacatcat  cggccacatc   3840
ccccccggcc  actgcctgaa  gagctggagc  tggaactact  accgcatcgt  ggcccgctac   3900
gagaacaccc  tggccgccca  gttcttcggc  cacacccacg  tggacgagtt  cgaggtgttc   3960
tacgacgagg  agaccctgag  ccgcccctg   gccgtggcct  tcctggcccc  cagcgccacc   4020
acctacatcg  gcctgaaccc  cggctaccgc  gtgtaccaga  tcgacggcaa  ctacagcggc   4080
agcagccacg  tggtgctgga  ccacgagacc  tacatcctga  acctgaccca  ggccaacatc   4140
cccggcgcca  tcccccactg  gcagctgctg  taccgcgccc  gcgagaccta  cggcctgccc   4200
aacaccctgc  ccaccgcctg  gcacaacctg  gtgtaccgca  tgcgcggcga  catgcagctg   4260
ttccagacct  tctggttcct  gtaccacaag  ggccaccccc  ccagcgagcc  ctgcggcacc   4320
ccctgccgcc  tggccaccct  gtgcgccag   ctgagcgccc  gcgccgacag  ccccgccctg   4380
tgccgccacc  tgatgcccga  cggcagcctg  cccgaggccc  agagcctgtg  gccccgcccc   4440
ctgttctgct  aatgacaatt  gttaattaag  tttaaaccct  cgaggccgca  agcaataaaa   4500
tatctttatt  ttcattacat  ctgtgtgttg  gttttttgtg  tggagatcca  cgataacaaa   4560 cagcttttt   ggggtgaaca  tattgactga  attccctgca  ggttggccac  tccctctctg   4620
cgcgctcgct  cgctcactga  ggccgcccgg  gcaaagcccg  ggcgtcgggc  gacctttggt   4680 cgccggcct   cagtgagcga  gcgagcgcgc  agagagggag  tggccaactc  catcactagg   4740
ggttcctgcg  gccgctcgta  cggtctcgag  gaattcctgc  aggataactt  gccaacctca   4800
ttctaaaatg  tatatagaag  cccaaaagac  aataacaaaa  atattcttgt  agaacaaaat   4860
gggaaagaat  gttccactaa  atatcaagat  ttagagcaaa  gcatgagatg  tgtggggata   4920
gacagtgagg  ctgataaaat  agagtagagc  tcagaaacag  acccattgat  atatgtaagt   4980
gacctatgaa  aaaaatatgg  cattttacaa  tgggaaaatg  atggtctttt  tcttttttag   5040
aaaaacaggg  aaatatattt  atatgtaaaa  aataaagggg  aacccatatg  tcataccata   5100
cacacaaaaa  aattccagtg  aattataagt  ctaaatggag  aaggcaaaac  tttaaatctt   5160
ttagaaaata  atatagaagc  atgcagacca  gcctggccaa  catgatgaaa  ccctctctac   5220
taataataaa  atcagtagaa  ctactcagga  ctactttgag  tgggaagtcc  ttttctatga   5280
agacttcttt  ggccaaaatt  aggctctaaa  tgcaaggaga  tagtgcatca  tgcctggctg   5340
cacttactga  taaatgatgt  tatcaccatc  tttaaccaaa  tgcacaggaa  caagttatgg   5400
tactgatgtg  ctggattgag  aaggagctct  acttccttga  caggacacat  ttgtatcaac   5460
ttaaaaaagc  agattttgc   cagcagaact  attcattcag  aggtaggaaa  cttagaatag   5520
atgatgtcac  tgattagcat  ggcttcccca  tctccacagc  tgcttcccac  ccaggttgcc   5580
cacagttgag  tttgtccagt  gctcagggct  gcccactctc  agtaagaagc  cccacaccag   5640
cccctctcca  aatatgttgg  ctgttccttc  cattaaagtg  accccacttt  agagcagcaa   5700
gtggatttct  gtttcttaca  gttcaggaag  gaggagtcag  ctgtgagaac  ctggagcctg   5760
agatgcttct  aagtcccact  gctactgggg  tcagggaagc  cagactccag  catcagcagt   5820
caggagcact  aagcccttgc  caacatcctg  tttctcagag  aaactgcttc  cattataatg   5880
```

-continued

| | |
|---|---|
| gttgtcctttt tttaagctat caagccaaac aaccagtgtc taccattatt ctcatcacct | 5940 |
| gaagccaagg gttctagcaa aagtcaagct gtcttgtaat ggttgatgtg cctccagctt | 6000 |
| ctgtcttcag tcactccact cttagcctgc tctgaatcaa ctctgaccac agttccctgg | 6060 |
| agccctgcc acctgctgcc cctgccacct tctccatctg cagtgctgtg cagccttctg | 6120 |
| cactcttgca gagctaatag gtggagactt gaaggaagag gaggaaagtt tctcataata | 6180 |
| gccttgctgc aagctcaaat gggaggtggg cactgtgccc aggagccttg gagcaaaggc | 6240 |
| tgtgcccaac ctctgactgc atccaggttt ggtcttgaca gagataagaa gccctggctt | 6300 |
| ttggagccaa aatctaggtc agacttaggc aggattctca aagtttatca gcagaacatg | 6360 |
| aggcagaaga ccctttctgc tccagcttct tcaggctcaa ccttcatcag aatagataga | 6420 |
| aagagaggct gtgagggttc ttaaaacaga agcaaatctg actcagagaa taaacaacct | 6480 |
| cctagtaaac tacagcttag acagagcatc tggtggtgag tgtgctcagt gtcctactca | 6540 |
| actgtctggt atcagccctc atgaggactt ctcttctttc cctcatagac ctccatctct | 6600 |
| gttttcctta gcctgcagaa atctggatgg ctattcacag aatgcctgtg ctttcagagt | 6660 |
| tgcatttttt ctctggtatt ctggttcaag catttgaagg taggaaaggt tctccaagtg | 6720 |
| caagaaagcc agccctgagc ctcaactgcc tggctagtgt ggtcagtagg atgcaaaggc | 6780 |
| tgttgaatgc cacaaggcca aactttaacc tgtgtaccac aagcctagca gcagaggcag | 6840 |
| ctctgctcac tggaactctc tgtcttcttt ctcctgagcc ttttcttttc ctgagttttc | 6900 |
| tagctctcct caaccttacc tctgccctac ccaggacaaa cccaagagcc actgtttctg | 6960 |
| tgatgtcctc tccagcccta attaggcatc atgacttcag cctgaccttc catgctcaga | 7020 |
| agcagtgcta atccacttca gatgagctgc tctatgcaac acaggcagag cctacaaacc | 7080 |
| tttgcaccag agccctccac atatcagtgt ttgttcatac tcacttcaac agcaaatgtg | 7140 |
| actgctgaga ttaagatttt acacaagatg gtctgtaatt tcacagttag ttttatccca | 7200 |
| ttaggtatga aagaattagc ataattcccc ttaaacatga atgaatctta gattttttaa | 7260 |
| taaatagttt tggaagtaaa gacagagaca tcaggagcac aaggaatagc ctgagaggac | 7320 |
| aaacagaaca agaaagagtc tggaaataca caggatgttc ttggcctcct caaagcaagt | 7380 |
| gcaagcagat agtaccagca gccccaggct atcagagccc agtgaagaga agtaccatga | 7440 |
| aagccacagc tctaaccacc ctgttccaga gtgacagaca gtccccaaga caagccagcc | 7500 |
| tgagccagag agagaactgc aagagaaagt ttctaattta ggttctgtta gattcagaca | 7560 |
| agtgcaggtc atcctctctc cacagctact cacctctcca gcctaacaaa gcctgcagtc | 7620 |
| cacactccaa ccctggtgtc tcacctccta gcctctccca acatcctgct ctctgaccat | 7680 |
| cttctgcatc tctcatctca ccatctccca ctgtctacag cctactcttg caactaccat | 7740 |
| ctcattttct gacatcctgt ctacatcttc tgccatactc tgccatctac cataccacct | 7800 |
| cttaccatct accacaccat cttttatctc catccctctc agaagcctcc aagctgaatc | 7860 |
| ctgctttatg tgttcatctc agcccctgca tggaaagctg accccagagg cagaactatt | 7920 |
| cccagagagc ttggccaaga aaaacaaaac taccagcctg gccaggctca ggagtagtaa | 7980 |
| gctgcagtgt ctgttgtgtt ctagcttcaa cagctgcagg agttccactc tcaaatgctc | 8040 |
| cacatttctc acatcctcct gattctggtc actacccatc ttcaaagaac agaatatctc | 8100 |
| acatcagcat actgtgaagg actagtcatg ggtgcagctg ctcagagctg caaagtcatt | 8160 |
| ctggatggtg gagagcttac aaacatttca tgatgctccc ccgctctga tggctggagc | 8220 |
| ccaatcccta cacagactcc tgctgtatgt gttttccttt cactctgagc cacagccaga | 8280 |

-continued

```
gggcaggcat tcagtctcct cttcaggctg gggctggggc actgagaact cacccaacac    8340
cttgctctca ctccttctgc aaaacaagaa agagctttgt gctgcagtag ccatgaagaa    8400
tgaaaggaag ctttaactaa aaaatgtcag agattatttt tcaaccccctt actgtggatc   8460
accagcaagg aggaaacaca acacagagac attttttccc ctcaaattat caaaagaatc    8520
actgcatttg ttaaagagag caactgaatc aggaagcaga gttttgaaca tatcagaagt    8580
taggaatctg catcagagac aaatgcagtc atggttgttt gctgcatacc agccctaatc    8640
attagaagcc tcatggactt caaacatcat tccctctgac aagatgctct agcctaactc    8700
catgagataa aataaatctg cctttcagag ccaaagaaga gtccaccagc ttcttctcag    8760
tgtgaacaag agctccagtc aggttagtca gtccagtgca gtagaggaga ccagtctgca    8820
tcctctaatt ttcaaaggca agaagatttg tttaccctgg acaccaggca caagtgaggt    8880
cacagagctc ttagatatgc agtcctcatg agtgaggaga ctaaagcgca tgccatcaag    8940
acttcagtgt agagaaaacc tccaaaaaag cctcctcact acttctggaa tagctcagag    9000
gccgaggcgg cctcggcctc tgcataaata aaaaaaatta gtcagccatg ggcggagaa     9060
tgggcggaac tgggcggagt taggggcggg atgggcggag ttaggggcgg gactatggtt    9120
gctgactaat tgagatgcat gctttgcata cttctgcctg ctggggagcc tggggacttt    9180
ccacacctgg ttgctgacta attgagatgc atgctttgca tacttctgcc tgctggggag    9240
cctggggact ttccacaccc taactgacac acattccaca gctgcattaa tgaatcggcc    9300
aacgcgcggg gagaggcggt ttgcgtattg ggcgctcttc cgcttcctcg ctcactgact    9360
cgctgcgctc ggtcgttcgg ctgcggcgag cggtatcagc tcactcaaag gcggtaatac    9420
ggttatccac agaatcaggg gataacgcag gaaagaacat gtgagcaaaa ggccagcaaa    9480
aggccaggaa ccgtaaaaag gccgcgttgc tggcgttttt ccataggctc cgcccccctg    9540
acgagcatca caaaaatcga cgctcaagtc agaggtggcg aaacccgaca ggactataaa    9600
gataccaggc gtttccccct ggaagctccc tcgtgcgctc tcctgttccg accctgccgc    9660
ttaccggata cctgtccgcc tttctccctt cgggaagcgt ggcgctttct catagctcac    9720
gctgtaggta tctcagttcg gtgtaggtcg ttcgctccaa gctgggctgt gtgcacgaac    9780
cccccgttca gcccgaccgc tgcgccttat ccggtaacta tcgtcttgag tccaacccgg    9840
taagacacga cttatcgcca ctggcagcag ccactggtaa caggattagc agagcgaggt    9900
atgtaggcgg tgctacagag ttcttgaagt ggtggcctaa ctacggctac actagaagaa    9960
cagtatttgg tatctgcgct ctgctgaagc cagttacctt cggaaaaaga gttggtagct   10020
cttgatccgg caaacaaacc accgctggta gcggtggttt ttttgtttgc aagcagcaga   10080
ttacgcgcag aaaaaaagga tctcaagaag atcctttgat cttttctacg ggtctgacg    10140
ctcagtggaa cgaaaactca cgttaaggga ttttggtcat gagattatca aaaaggatct   10200
tcacctagat ccttttaaat taaaaatgaa gttttaaatc aatctaaagt atatatgagt   10260
aaacttggtc tgacagttac caatgcttaa tcagtgaggc acctatctca gcgatctgtc   10320
tatttcgttc atccatagtt gcctgactcc tgcaaaccac gttgtgtctc aaaatctctg   10380
atgttacatt gcacaagata aaaatatatc atcatgaaca ataaaactgt ctgcttacat   10440
aaacagtaat acaaggggtg ttatgagcca tattcaacgg gaaacgtctt gctcgaggcc   10500
gcgattaaat tccaacatgg atgctgattt atatgggtat aaatgggctc gcgataatgt   10560
cgggcaatca ggtgcgacaa tctatcgatt gtatgggaag cccgatgcgc cagagttgtt   10620
```

```
tctgaaacat ggcaaaggta gcgttgccaa tgatgttaca gatgagatgg tcagactaaa    10680
ctggctgacg gaatttatgc ctcttccgac catcaagcat tttatccgta ctcctgatga    10740
tgcatggtta ctcaccactg cgatccccgg gaaaacagca ttccaggtat tagaagaata    10800
tcctgattca ggtgaaaata ttgttgatgc gctggcagtg ttcctgcgcc ggttgcattc    10860
gattcctgtt tgtaattgtc cttttaacag cgatcgcgta tttcgtctcg ctcaggcgca    10920
atcacgaatg aataacggtt tggttgatgc gagtgatttt gatgacgagc gtaatggctg    10980
gcctgttgaa caagtctgga agaaatgca taagcttttg ccattctcac cggattcagt     11040
cgtcactcat ggtgatttct cacttgataa ccttattttt gacgagggga aattaatagg    11100
ttgtattgat gttggacgag tcggaatcgc agaccgatac caggatcttg ccatcctatg    11160
gaactgcctc ggtgagtttt ctccttcatt acagaaacgg cttttcaaa  aatatggtat    11220 tgataatcct gatatgaata aattgcagtt tcatttgatg ctcgatgagt ttttctaagg    11280
gcggcctgcc accataccca cgccgaaaca agcgctcatg agcccgaagt ggcgagcccg    11340
atcttcccca tcggtgatgt cggcgatata ggcgccagca accgcacctg tggcgccggt    11400
gatgagggcg cgccaagtcg acgtccggca gtc                                 11433

<210> SEQ ID NO 43
<211> LENGTH: 11776
<212> TYPE: DNA
<213> ORGANISM: Artificial sequence
<220> FEATURE:
<223> OTHER INFORMATION: Synthetic polynucleotide

<400> SEQUENCE: 43
ttggccactc cctctctgcg cgctcgctcg ctcactgagg ccgggcgacc aaaggtcgcc       60
cgacgcccgg gctttgcccg gcggcctca  gtgagcgagc gagcgcgcag agagggagtg      120
gccaactcca tcactagggg ttcctgctag ctctgggtat ttaagcccga gtgagcacgc      180
agggtctcca ttttgaagcg ggaggttacg cgttcgtcga ctactagtgg gtaccagagc      240
tccctaggtt ctagaaccgg tgacgtctcc catggtgaag cttggatctg agggcggagt      300
tagggcggag ccaatcagcg tgcgccgttc cgaaagttgc cttttatggc tgggcggaga      360
atgggcggtg aacgccgatg attatataag gacgcgccgg gtgtggcaca gctagttccg      420
tcgcagccgg gatttgggtc gcggttcttg tttgtggatc cctgtgatcg tcacttggta      480
agtcactgac tgtctatgcc tgggaaaggg tgggcaggag atgggcagt  gcaggaaaag     540 tggcactatg aaccctgcag ccctaggaat gcatctagac aattgtacta accttcttct      600 cttttcctctc ctgacagtcc ggaaagccac catggccgag tggctgctga gcgccagctg     660
gcagcgccgc gccaaggcca tgaccgccgc gccggcagc  gccggccgcg ccgccgtgcc     720
cctgctgctg tgcgccctgc tggcccccgg cggcgcctac gtgctggacg acagcgacgg      780
cctgggccgc gagttcgacg gcatcggcgc cgtgagcggc ggcggcgcca ccagccgcct      840
gctggtgaac taccccgagc cctaccgcag ccagatcctg gactacctgt tcaagcccaa      900
cttcggcgcc agcctgcaca tcctgaaggt ggagatcggc ggcgacggcc agaccaccga      960
cggcaccgag cccagccaca tgcactacgc cctggacgag aactacttcc gcggctacga     1020
gtggtggctg atgaaggagg ccaagaagcg caaccccaac atcaccctga tcggcctgcc     1080
ctggagcttc cccggctggc tgggcaaggg cttcgactgg ccctacgtga acctgcagct     1140
gaccgcctac tacgtggtga cctggatcgt gggcgccaag cgctaccacg acctggacat     1200
cgactacatc ggcatctgga acgagcgcag ctacaacgcc aactacatca gatcctgcg      1260
```

| | |
|---|---|
| caagatgctg aactaccagg gcctgcagcg cgtgaagatc atcgccagcg acaacctgtg | 1320 |
| ggagagcatc agcgccagca tgctgctgga cgccgagctg ttcaaggtgg tggacgtgat | 1380 |
| cggcgcccac tacccggca cccacagcgc caaggacgcc aagctgaccg gcaagaagct | 1440 |
| gtggagcagc gaggacttca gcaccctgaa cagcgacatg ggcgccggct gctggggccg | 1500 |
| catcctgaac cagaactaca tcaacggcta catgaccagc accatcgcct ggaacctggt | 1560 |
| ggccagctac tacgagcagc tgccctacgg ccgctgcggc ctgatgaccg cccaggagcc | 1620 |
| ctggagcggc cactacgtgg tggagagccc cgtgtgggtg agcgcccaca ccacccagtt | 1680 |
| cacccagccc ggctggtact acctgaagac cgtgggccac ctggagaagg gcggcagcta | 1740 |
| cgtggccctg accgacggcc tgggcaacct gaccatcatc atcgagacca tgagccacaa | 1800 |
| gcacagcaag tgcatccgcc ccttcctgcc ctacttcaac gtgagccagc agttcgccac | 1860 |
| cttcgtgctg aagggcagct tcagcgagat ccccgagctg caggtgtggt acaccaagct | 1920 |
| gggcaagacc agcgagcgct tcctgttcaa gcagctggac agcctgtggc tgctggacag | 1980 |
| cgacggcagc ttcaccctga gcctgcacga ggacgagctg ttcaccctga ccaccctgac | 2040 |
| caccggccga agggcagct accccctgcc ccccaagagc cagcccttcc ccagcaccta | 2100 |
| caaggacgac ttcaacgtgg actacccctt cttcagcgag gccccaact tcgccgacca | 2160 |
| gaccggcgtt tcgagtact tcaccaacat cgaggacccc ggcgagcacc acttcaccct | 2220 |
| gcgccaggtg ctgaaccagc gccccatcac ctgggccgcc gacgccagca acaccatcag | 2280 |
| catcatcggc gactacaact ggaccaacct gaccatcaag tgcgacgtgt acatcgagac | 2340 |
| ccccgacacc ggcggcgtgt tcatcgccgg ccgcgtgaac aagggcggca tcctgatccg | 2400 |
| cagcgcccgc ggcatcttct tctggatctt cgccaacggc agctaccgcg tgaccggcga | 2460 |
| cctggccggc tggatcatct acgccctggg ccgcgtggag gtgaccgcca agaagtggta | 2520 |
| caccctgacc ctgaccatca agggccactt caccagcggc atgctgaacg acaagagcct | 2580 |
| gtggaccgac atccccgtga acttccccaa gaacggctgg gccgccatcg gcacccacag | 2640 |
| cttcgagttc gcccagttcg acaacttcct ggtggaggcc acccgctgat tgtggccgaa | 2700 |
| ccgccgaact cagaggccgg ccccagaaaa cccgagcgag tagggggcgg cgcgcaggag | 2760 |
| ggaggagaac tgggggcgcg ggaggctggt gggtgtgggg ggtggagatg tagaagatgt | 2820 |
| gacgccgcgg cccggcgggt gccagattag cggacgcggt gcccgcggtt gcaacgggat | 2880 |
| cccgggcgct gcagcttggg aggcggctct ccccaggcgg cgtccgcgga gacacccatc | 2940 |
| cgtgaacccc aggtcccggg ccgccggctc gccgcgcacc aggggccggc ggacagaaga | 3000 |
| gcggccgagc ggctcgaggc tggggaccg cgggcgcggc cgcgcgctgc cgggcgggag | 3060 |
| gctgggggc cggggccggg gccgtgcccc ggagcgggtc ggaggccggg gccggggccg | 3120 |
| ggggacggcg gctccccgcg cggctccagc ggctcgggga tcccggccgg gccccgcagg | 3180 |
| gaccatgatg gaattcagca gccccagcag agaggaatgc cccaagcctc tgagccgggt | 3240 |
| gtcaatcatg gccggatctc tgacaggact gctgctgctt caggccgtgt cttgggcttc | 3300 |
| tggcgctaga ccttgcatcc ccaagagctt cggctacagc agcgtcgtgt gcgtgtgcaa | 3360 |
| tgccacctac tgcgacagct tcgacccctc taccttcct gctctgggca ccttcagcag | 3420 |
| atacgagagc accagatccg gcagacggat ggaactgagc atgggaccca tccaggccaa | 3480 |
| tcacacaggc actggcctgc tgctgacact gcagcctgag cagaaattcc agaaagtgaa | 3540 |
| aggcttcggc ggagccatga cagatgccgc cgctctgaat atcctggctc tgtctccacc | 3600 |

```
agctcagaac ctgctgctca agagctactt cagcgaggaa ggcatcggct acaacatcat   3660
cagagtgccc atggccagct gcgacttcag catcaggacc tacacctacg ccgacacacc   3720
cgacgatttc cagctgcaca acttcagcct gcctgaagag acaccaagc tgaagatccc    3780 tctgatccac agagccctgc agctggcaca aagacccgtg tcactgctgg cctctccatg   3840
gacatctccc acctggctga aaacaaatgg cgccgtgaat ggcaagggca gcctgaaagg   3900
ccaacctggc gacatctacc accagacctg ggccagatac ttcgtgaagt tcctggacgc   3960
ctatgccgag cacaagctgc agttttgggc cgtgacagcc gagaacgaac cttctgctgg   4020
actgctgagc ggctacccct ttcagtgcct gggctttaca cccgagcacc agcgggactt   4080
tatcgcccgt gatctgggac ccacactggc caatagcacc accataatg tgcggctgct    4140 gatgctggac gaccagagac tgcttctgcc ccactgggct aaagtggtgc tgacagatcc   4200
tgaggccgcc aaatacgtgc acggaatcgc cgtgcactgg tatctggact ttctggcccc   4260
tgccaaggcc acactgggag agacacacag actgttcccc aacaccatgc tgttcgccag   4320
cgaagcctgt gtgggcagca gttttggga acagagcgtg cggctcggca gctgggatag   4380
aggcatgcag tacagccaca gcatcatcac caacctgctg taccacgtcg tcggctggac   4440
cgactggaat ctggccctga tcctgaaggc cggccctaac tgggtccgaa acttcgtgga   4500
cagccccatc atcgtggaca tcaccaagga caccttctac aagcagccca tgttctacca   4560
cctgggacac ttcagcaagt tcatccccga gggctctcag cgcgttggac tggtggcttc   4620
ccagaagaac gatctggacg ccgtggctct gatgcaccct gatggatctg ctgtggtggt   4680
ggtcctgaac cgcagcagca agatgtgcc cctgaccatc aaggatcccg ccgtgggatt    4740
cctggaaaca atcagccctg ctactccat ccacacctac ctgtggcgta gacagtgaca    4800
attgttaatt aagtttaaac cctcgaggcc gcaagcaata aaatatcttt attttcatta   4860
catctgtgtg ttggtttttt gtgtggagat ccacgataac aaacagcttt ttggggtga   4920 acatattgac tgaattccct gcaggttggc cactccctct ctgcgcgctc gctcgctcac   4980
tgaggccgcc cgggcaaagc ccgggcgtcg ggcgaccttt ggtcgcccgg cctcagtgag   5040
cgagcgagcg cgcagagagg gagtggccaa ctccatcact aggggttcct gcggccgctc   5100
gtacggtctc gaggaattcc tgcaggataa cttgccaacc tcattctaaa atgtatatag   5160
aagcccaaaa gacaataaca aaatatattct tgtagaacaa atgggaaag aatgttccac    5220 taaatatcaa gatttagagc aaagcatgag atgtgtgggg atagacagtg aggctgataa   5280
aatagagtag agctcagaaa cagacccatt gatatatgta agtgacctat gaaaaaaata   5340
tggcatttta caatgggaaa atgatggtct ttttcttttt tagaaaaaca gggaaatata   5400
tttatatgta aaaataaaa gggaacccat atgtcatacc atacacacaa aaaaattcca   5460
gtgaattata agtctaaatg gagaaggcaa aactttaaat cttttagaaa ataatataga   5520
agcatgcaga ccagcctggc caacatgatg aaaccctctc tactaataat aaaatcagta   5580
gaactactca ggactacttt gagtgggaag tcctttcta tgaagacttc tttggccaaa   5640
attaggctct aaatgcaagg agatagtgca tcatgcctgg ctgcacttac tgataaatga   5700
tgttatcacc atctttaacc aaatgcacag gaacaagtta tggtactgat gtgctggatt   5760
gagaaggagc tctacttcct tgacaggaca catttgtatc aacttaaaaa agcagatttt   5820
tgccagcaga actattcatt cagaggtagg aaacttagaa tagatgatgt cactgattag   5880
catggcttcc ccatctccac agctgcttcc cacccaggtt gccacagttt gagtttgtcc   5940
agtgctcagg gctgcccact ctcagtaaga agccccacac cagcccctct ccaaatatgt   6000
```

-continued

```
tggctgttcc ttccattaaa gtgacccccac tttagagcag caagtggatt tctgtttctt    6060
acagttcagg aaggaggagt cagctgtgag aacctggagc ctgagatgct tctaagtccc    6120
actgctactg gggtcaggga agccagactc cagcatcagc agtcaggagc actaagccct    6180
tgccaacatc ctgtttctca gagaaactgc ttccattata atggttgtcc ttttttaagc    6240
tatcaagcca aacaaccagt gtctaccatt attctcatca cctgaagcca agggttctag    6300
caaaagtcaa gctgtcttgt aatggttgat gtgcctccag cttctgtctt cagtcactcc    6360
actcttagcc tgctctgaat caactctgac cacagttccc tggagcccct gccacctgct    6420
gcccctgcca ccttctccat ctgcagtgct gtgcagcctt ctgcactctt gcagagctaa    6480
taggtggaga cttgaaggaa gaggaggaaa gtttctcata atagccttgc tgcaagctca    6540
aatgggaggt gggcactgtg cccaggagcc ttggagcaaa ggctgtgccc aacctctgac    6600
tgcatccagg tttggtcttg acagagataa gaagccctgg cttttggagc caaaatctag    6660
gtcagactta ggcaggattc tcaaagttta tcagcagaac atgaggcaga agacccttc    6720 tgctccagct tcttcaggct caaccttcat cagaatagat agaaagagag gctgtgaggg    6780
ttcttaaaac agaagcaaat ctgactcaga gaataaacaa cctcctagta aactacagct    6840
tagacagagc atctggtggt gagtgtgctc agtgtcctac tcaactgtct ggtatcagcc    6900
ctcatgagga cttctcttct ttccctcata gacctccatc tctgttttcc ttagcctgca    6960
gaaatctgga tggctattca cagaatgcct gtgctttcag agttgcattt tttctctggt    7020
attctggttc aagcatttga aggtaggaaa ggttctccaa gtgcaagaaa gccagccctg    7080
agcctcaact gcctggctag tgtggtcagt aggatgcaaa ggctgttgaa tgccacaagg    7140
ccaaacttta acctgtgtac cacaagccta gcagcagagg cagctctgct cactggaact    7200
ctctgtcttc tttctcctga gccttttctt ttcctgagtt ttctagctct cctcaacctt    7260
acctctgccc tacccaggac aaacccaaga gccactgttt ctgtgatgtc ctctccagcc    7320
ctaattaggc atcatgactt cagcctgacc ttccatgctc agaagcagtg ctaatccact    7380
tcagatgagc tgctctatgc aacacaggca gagcctacaa accttgcac cagagccctc    7440 cacatatcag tgtttgttca tactcacttc aacagcaaat gtgactgctg agattaagat    7500
tttacacaag atggtctgta atttcacagt tagtttatc ccattaggta tgaaagaatt    7560
agcataattc cccttaaaca tgaatgaatc ttagattttt taataaatag ttttggaagt    7620
aaagacagag acatcaggag cacaaggaat agcctgagag gacaaacaga acaagaaaga    7680
gtctggaaat acacaggatg ttcttggcct cctcaaagca agtgcaagca gatagtacca    7740
gcagccccag gctatcagag cccagtgaag agaagtacca tgaaagccac agctctaacc    7800
accctgttcc agagtgacag acagtcccca agacaagcca gcctgagcca gagagagaac    7860
tgcaagagaa agtttctaat ttaggttctg ttagattcag acaagtgcag gtcatcctct    7920
ctccacagct actcacctct ccagcctaac aaagcctgca gtccacactc caaccctggt    7980
gtctcacctc ctagcctctc ccaacatcct gctctctgac catcttctgc atctctcatc    8040
tcaccatctc ccactgtcta cagcctactc ttgcaactac catctcattt tctgacatcc    8100
tgtctacatc ttctgccata ctctgccatc taccatacca cctcttacca tctaccacac    8160
catcttttat ctccatccct ctcagaagcc tccaagctga atcctgcttt atgtgttcat    8220
ctcagcccct gcatggaaag ctgaccccag aggcagaact attcccagag agcttggcca    8280
agaaaaacaa aactaccagc ctggccaggc tcaggagtag taagctgcag tgtctgttgt    8340
```

```
gttctagctt caacagctgc aggagttcca ctctcaaatg ctccacattt ctcacatcct   8400
cctgattctg gtcactaccc atcttcaaag aacagaatat ctcacatcag catactgtga   8460
aggactagtc atgggtgcag ctgctcagag ctgcaaagtc attctggatg gtggagagct   8520
tacaaacatt tcatgatgct cccccgctc tgatggctgg agcccaatcc ctacacagac    8580
tcctgctgta tgtgttttcc tttcactctg agccacagcc agagggcagg cattcagtct   8640
cctcttcagg ctggggctgg ggcactgaga actcacccaa caccttgctc tcactccttc   8700
tgcaaaacaa gaaagagctt tgtgctgcag tagccatgaa gaatgaaagg aaggctttaa   8760
ctaaaaaatg tcagagatta ttttcaaccc cttactgtgg atcaccagca aggaggaaac    8820
acaacacaga gacatttttt cccctcaaat tatcaaaaga atcactgcat ttgttaaaga   8880
gagcaactga atcaggaagc agagttttga acatatcaga agttaggaat ctgcatcaga   8940
gacaaatgca gtcatggttg tttgctgcat accagcccta atcattagaa gcctcatgga   9000
cttcaaacat cattccctct gacaagatgc tctagcctaa ctccatgaga taaaataaat   9060
ctgcctttca gagccaaaga agagtccacc agcttcttct cagtgtgaac aagagctcca   9120
gtcaggttag tcagtccagt gcagtagagg agaccagtct gcatcctcta attttcaaag   9180
gcaagaagat ttgtttaccc tggacaccag gcacaagtga ggtcacagag ctcttagata   9240
tgcagtcctc atgagtgagg agactaaagc gcatgccatc aagacttcag tgtagagaaa   9300
acctccaaaa aagcctcctc actacttctg gaatagctca gaggccgagg cggcctcggc   9360
ctctgcataa ataaaaaaaa ttagtcagcc atggggcgga gaatgggcgg aactgggcgg   9420
agttaggggc gggatgggcg gagttagggg cgggactatg gttgctgact aattgagatg   9480
catgctttgc atacttctgc ctgctgggga gcctggggac tttccacacc tggttgctga   9540
ctaattgaga tgcatgcttt gcatacttct gcctgctggg gagcctgggg actttccaca   9600
ccctaactga cacacattcc acagctgcat taatgaatcg gccaacgcgc ggggagaggc   9660
ggtttgcgta ttgggcgctc ttccgcttcc tcgctcactg actcgctgcg ctcggtcgtt   9720
cggctgcggc gagcggtatc agctcactca aaggcggtaa tacggttatc cacagaatca   9780
ggggataacg caggaaagaa catgtgagca aaaggccagc aaaaggccag gaaccgtaaa   9840
aaggccgcgt tgctggcgtt tttccatagg ctccgccccc ctgacgagca tcacaaaaat   9900
cgacgctcaa gtcagaggtg gcgaaacccg acaggactat aaagatacca ggcgtttccc   9960
cctggaagct ccctcgtgcg ctctcctgtt ccgaccctgc cgcttaccgg atacctgtcc  10020
gcctttctcc cttcgggaag cgtggcgctt tctcatagct cacgctgtag gtatctcagt  10080
tcggtgtagg tcgttcgctc caagctgggc tgtgtgcacg aaccccccgt tcagcccgac  10140
cgctgcgcct tatccggtaa ctatcgtctt gagtccaacc cggtaagaca cgacttatcg  10200
ccactggcag cagccactgg taacaggatt agcagagcga ggtatgtagg cggtgctaca  10260
gagttcttga agtggtggcc taactacggc tacactagaa gaacagtatt tggtatctgc  10320
gctctgctga agccagttac cttcggaaaa agagttggta gctcttgatc cggcaaacaa  10380
accaccgctg gtagcggtgg tttttttgtt tgcaagcagc agattacgcg cagaaaaaaa  10440
ggatctcaag aagatccttt gatcttttct acggggtctg acgctcagtg gaacgaaaac  10500
tcacgttaag ggattttggt catgagatta tcaaaaagga tcttcaccta gatccttta   10560 aattaaaaat gaagttttaa atcaatctaa agtatatatg agtaaacttg gtctgacagt  10620
taccaatgct taatcagtga ggcacctatc tcagcgatct gtctatttcg ttcatccata  10680
gttgcctgac tcctgcaaac cacgttgtgt ctcaaaatct ctgatgttac attgcacaag  10740
```

```
ataaaaatat atcatcatga acaataaaac tgtctgctta cataaacagt aatacaaggg    10800
gtgttatgag ccatattcaa cgggaaacgt cttgctcgag gccgcgatta aattccaaca    10860
tggatgctga tttatatggg tataaatggg ctcgcgataa tgtcgggcaa tcaggtgcga    10920
caatctatcg attgtatggg aagcccgatg cgccagagtt gtttctgaaa catggcaaag    10980
gtagcgttgc caatgatgtt acagatgaga tggtcagact aaactggctg acggaattta    11040
tgcctcttcc gaccatcaag cattttatcc gtactcctga tgatgcatgg ttactcacca    11100
ctgcgatccc cgggaaaaca gcattccagg tattagaaga atatcctgat tcaggtgaaa    11160
atattgttga tgcgctggca gtgttcctgc gccggttgca ttcgattcct gtttgtaatt    11220
gtccttttaa cagcgatcgc gtatttcgtc tcgctcaggc gcaatcacga atgaataacg    11280
gtttggttga tgcgagtgat tttgatgacg agcgtaatgg ctggcctgtt gaacaagtct    11340
ggaaagaaat gcataagctt ttgccattct caccggattc agtcgtcact catggtgatt    11400
tctcacttga taaccttatt tttgacgagg ggaaattaat aggttgtatt gatgttggac    11460
gagtcggaat cgcagaccga taccaggatc ttgccatcct atggaactgc ctcggtgagt    11520
tttctccttc attacagaaa cggctttttc aaaaatatgg tattgataat cctgatatga    11580
ataaattgca gtttcatttg atgctcgatg agttttccta agggcggcct gccaccatac    11640
ccacgccgaa acaagcgctc atgagcccga agtggcgagc ccgatcttcc ccatcggtga    11700
tgtcggcgat ataggcgcca gcaaccgcac ctgtggcgcc ggtgatgagg gcgcgccaag    11760
tcgacgtccg gcagtc                                                   11776

<210> SEQ ID NO 44
<211> LENGTH: 11064
<212> TYPE: DNA
<213> ORGANISM: Artificial sequence
<220> FEATURE:
<223> OTHER INFORMATION: Synthetic polynucleotide

<400> SEQUENCE: 44
ttggccactc cctctctgcg cgctcgctcg ctcactgagg ccgggcgacc aaaggtcgcc      60
cgacgcccgg gctttgcccg gcggcctca  gtgagcgagc gagcgcgcag agagggagtg     120
gccaactcca tcactagggg ttcctgctag ctctgggtat ttaagcccga gtgagcacgc     180
agggtctcca ttttgaagcg ggaggttacg cgttcgtcga ctactagtgg gtaccagagc     240
tccctaggtt ctagaaccgg tgacgtctcc catggtgaag cttggatctg agggcggagt     300
tagggcggag ccaatcagcg tgcgccgttc cgaaagttgc cttttatggc tgggcggaga     360
atgggcggtg aacgccgatg attatataag gacgcgccgg gtgtggcaca gctagttccg     420
tcgcagccgg gatttgggtc gcggttcttg tttgtggatc cctgtgatcg tcacttggta     480
agtcactgac tgtctatgcc tgggaaaggg tgggcaggag atgggcagt  gcaggaaaag     540 tggcactatg aaccctgcag ccctaggaat gcatctagac aattgtacta accttcttct     600
ctttcctctc ctgacagtcc ggaaagccac catggaattc agcagcccca gcagagagga     660 atgcccaag  cctctgagcc gggtgtcaat catggccgga tctctgacag gactgctgct     720
gcttcaggcc gtgtcttggg cttctggcgc tagaccttgc atcccaagag cttcggcta      780 cagcagcgtc gtgtgcgtgt gcaatgccac ctactgcgac agcttcgacc ctcctacctt     840
tcctgctctg ggcaccttca gcagatacga gagcaccaga tccggcagac ggatggaact     900
gagcatggga cccatccagg ccaatcacac aggcactggc ctgctgctga cactgcagcc     960
```

```
tgagcagaaa ttccagaaag tgaaaggctt cggcggagcc atgacagatg ccgccgctct   1020
gaatatcctg gctctgtctc caccagctca gaacctgctg ctcaagagct acttcagcga   1080
ggaaggcatc ggctacaaca tcatcagagt gcccatggcc agctgcgact tcagcatcag   1140
gacctacacc tacgccgaca cacccgacga tttccagctg cacaacttca gcctgcctga   1200
agaggacacc aagctgaaga tccctctgat ccacagagcc ctgcagctgg cacaaagacc   1260
cgtgtcactg ctggcctctc catggacatc tcccacctgg ctgaaaacaa atggcgccgt   1320
gaatggcaag ggcagcctga aggccaacct ggcgacatc taccaccaga cctgggccag   1380
atacttcgtg aagttcctgg acgcctatgc cgagcacaag ctgcagtttt ggccgtgac   1440 agccgagaac gaaccttctg ctggactgct gagcggctac ccctttcagt gcctgggctt   1500
tacacccgag caccagcggg actttatcgc ccgtgatctg ggaccacac tggccaatag   1560 cacccaccat aatgtgcggc tgctgatgct ggacgaccag agactgcttc tgccccactg   1620
ggctaaagtg gtgctgacag atcctgaggc cgccaaatac gtgcacggaa tcgccgtgca   1680
ctggtatctg gactttctgg cccctgccaa ggccacactg gagagacac acagactgtt   1740 ccccaacacc atgctgttcg ccagcgaagc ctgtgtgggc agcaagtttt gggaacagag   1800
cgtgcggctc ggcagctggg atagaggcat gcagtacagc cacagcatca tccaccaacct   1860 gctgtaccac gtcgtcggct ggaccgactg gaatctggcc ctgaatcctg aaggcggccc   1920
taactgggtc cgaaacttcg tggacagccc catcatcgtg gacatcacca aggacaccctt   1980 ctacaagcag cccatgttct accacctggg acacttcagc aagttcatcc ccgagggctc   2040
tcagcgcgtt ggactggtgg cttcccagaa gaacgatctg gacgccgtgg ctctgatgca   2100
ccctgatgga tctgctgtgg tggtggtcct gaaccgcagc agcaaagatg tgccccctgac   2160 catcaaggat cccgccgtgg gattcctgga aacaatcagc cctggctact ccatccacac   2220
ctacctgtgg cgtagacagt gacaattgtt aattaagttt aaaccctcga ggccgcaagc   2280
cgcatcgata ccgtcgacta gagctcgctg atcagcctcg actgtgcctt ctagttgcca   2340
gccatctgtt gtttgcccct ccccgtgcc ttccttgacc ctggaaggtg ccactcccac   2400
tgtcctttcc taataaaatg aggaaattgc atcgcattgt ctgagtaggt gtcattctat   2460 tctgggggt ggggtggggc aggacagcaa gggggaggat tgggaagaca atagcaggca   2520
tgctggggag agatccacga taacaaacag cttttttggg ggcggagt tagggcggag   2580 ccaatcagcg tgcgccgttc cgaaagttgc cttttatggc tgggcggaga tgggcggtg   2640 aacgccgatg attatataag gacgcgccgg gtgtggcaca gctagttccg tcgcagccgg   2700
gatttgggtc gcggttcttg tttgtggatc cctgtgatcg tcacttggta agtcactgac   2760
tgtctatgcc tgggaaaggg tgggcaggag atggggcagt gcaggaaaag tggcactatg   2820
aaccctgcag ccctaggaat gcatctagac aattgtacta accttcttct ctttcctctc   2880
ctgacagtcc ggaaagccac catgtggcag ctgtgggcca gctgtgctg cctgctggtg   2940 ctggccaacg cccgcagccg ccccagcttc cacccctga cgacgagct ggtgaactac   3000 gtgaacaagc gcaacaccac ctggcaggcc ggccacaact tctacaacgt ggacatgagc   3060
tacctgaagc gcctgtgcgg caccttcctg ggcggcccca gccccccca gcgcgtgatg   3120 ttcaccgagg acctgaagct gccgccagc ttcgacgccc gcagcagtg gccccagtgc   3180 cccaccatca aggagatccg cgaccagggc agctgcggca gctgctgggc cttcggcgcc   3240
gtggaggcca tcgcgaccg catctgcatc cacaccaacg cccacgtgag cgtggaggtg   3300
agcgccgagg acctgctgac ctgctgcggc agcatgtgcg gcgacggctg caacggcggc   3360
```

```
taccccgccg aggcctggaa cttctggacc cgcaagggcc tggtgagcgg cggcctgtac    3420
gagagccacg tgggctgccg cccctacagc atcccccct gcgagcacca cgtgaacggc     3480
agccgccccc cctgcaccgg cgagggcgac accccaagt gcagcaagat ctgcgagccc     3540
ggctacagcc ccacctacaa gcaggacaag cactacggct acaacagcta cagcgtgagc   3600
aacagcgaga aggacatcat ggccgagatc tacaagaacg ccccgtgga gggcgccttc    3660 agcgtgtaca cgcacttcct gctgtacaag agcggcgtgt accagcacgt gaccggcgag   3720
atgatgggcg ccacgccat ccgcatcctg gctggggcg tggagaacgg cacccctac      3780 tggctggtgg ccaacagctg gaacaccgac tggggcgaca acggcttctt caagatcctg   3840
cgcggccagg accactgcgg catcgagagc gaggtggtgg ccggcatccc ccgcaccgac   3900
cagtactggg agaagatctg acccagggga ctcagcggcc gctcgagtct agagggcccg   3960
tttaaacccg ctgatcagcc tcgaagacat gataagatac attgatgagt ttggacaaac   4020
cacaacaaga atgcagtgaa aaaaatgctt tatttgtgaa atttgtgatg ctattgcttt    4080
atttgtaacc attataagct gcaataaaca agttaacaac aacaattgca ttcattttat    4140
gtttcaggtt cagggggaga tgtgggaggt tttttaaagc aagtaaaacc tctacaaatg   4200
tggtatgaac atattgactg aattccctgc aggttggcca ctccctctct gcgcgctcgc   4260
tcgctcactg aggccgcccg ggcaaagccc gggcgtcggg cgacctttgg tcgcccggcc   4320
tcagtgagcg agcgagcgcg cagagaggga gtggccaact ccatcactag gggttcctgc   4380
ggccgctcgt acggtctcga ggaattcctg caggataact tgccaacctc attctaaaat   4440
gtatatagaa gcccaaaaga caataacaaa aatattcttg tagaacaaaa tgggaaagaa   4500
tgttccacta aatatcaaga tttagagcaa agcatgagat gtgtggggat agacagtgag   4560
gctgataaaa tagagtagag ctcagaaaca gacccattga tatatgtaag tgacctatga   4620
aaaaaatatg gcattttaca atgggaaaat gatggtcttt ttcttttta gaaaacagg     4680 gaaatatatt tatatgtaaa aaataaaagg gaacccatat gtcataccat acacacaaaa    4740
aaattccagt gaattataag tctaaatgga gaagcaaaa cttttaaatct tttagaaaat    4800 aatatagaag catgcagacc agcctggcca acatgatgaa accctctcta ctaataataa   4860
aatcagtaga actactcagg actactttga gtgggaagtc cttttctatg aagacttctt   4920
tggccaaaat taggctctaa atgcaaggag atagtgcatc atgcctggct gcacttactg   4980
ataaatgatg ttatcaccat cttaaccaa atgcacagga acaagttatg gtactgatgt    5040
gctggattga gaaggagctc tacttccttg acaggacaca tttgtatcaa cttaaaaaag   5100 cagattttg ccagcagaac tattcattca gaggtaggaa acttagaata gatgatgtca    5160
ctgattagca tggcttcccc atctccacag ctgcttccca cccaggttgc ccacagttga    5220
gtttgtccag tgctcagggc tgcccactct cagtaagaag ccccacacca gcccctctcc   5280
aaatatgttg gctgttcctt ccattaaagt gaccccactt tagagcagca agtggatttc   5340
tgtttcttac agttcaggaa ggaggagtca gctgtgagaa cctggagcct gagatgcttc   5400
taagtcccac tgctactggg gtcagggaag ccagactcca gcatcagcag tcaggagcac   5460
taagcccttg ccaacatcct gtttctcaga gaaactgctt ccattataat ggttgtcctt   5520
ttttaagcta tcaagccaaa caaccagtgt ctaccattat tctcatcacc tgaagccaag   5580
ggttctagca aaagtcaagc tgtcttgtaa tggttgatgt gcctccagct tctgtcttca   5640
gtcactccac tcttagcctg ctctgaatca actctgacca cagttccctg gagcccctgc   5700
```

```
cacctgctgc ccctgccacc ttctccatct gcagtgctgt gcagccttct gcactcttgc    5760
agagctaata ggtggagact tgaaggaaga ggaggaaagt ttctcataat agccttgctg    5820
caagctcaaa tgggaggtgg gcactgtgcc caggagcctt ggagcaaagg ctgtgcccaa    5880
cctctgactg catccaggtt tggtcttgac agagataaga agccctggct tttggagcca    5940
aaatctaggt cagacttagg caggattctc aaagtttatc agcagaacat gaggcagaag    6000 acccttctg ctccagcttc ttcaggctca accttcatca gaatagatag aaagagaggc     6060
tgtgagggtt cttaaaacag aagcaaatct gactcagaga ataaacaacc tcctagtaaa    6120
ctacagctta gacagagcat ctggtggtga gtgtgctcag tgtcctactc aactgtctgg    6180
tatcagccct catgaggact tctcttcttt ccctcataga cctccatctc tgttttcctt    6240
agcctgcaga aatctggatg gctattcaca gaatgcctgt gctttcagag ttgcatttt     6300 tctctggtat tctggttcaa gcatttgaag gtaggaaagg ttctccaagt gcaagaaagc    6360
cagccctgag cctcaactgc ctggctagtg tggtcagtag gatgcaaagg ctgttgaatg    6420
ccacaaggcc aaactttaac ctgtgtacca caagcctagc agcagaggca gctctgctca    6480
ctggaactct ctgtcttctt tctcctgagc cttttctttt cctgagtttt ctagctctcc    6540
tcaaccttac ctctgcccta cccaggacaa acccaagagc cactgttcct gtgatgtcct    6600
ctccagccct aattaggcat catgacttca gcctgacctt ccatgctcag aagcagtgct    6660
aatccacttc agatgagctg ctctatgcaa cacaggcaga gcctacaaac ctttgcacca    6720
gagccctcca catatcagtg tttgttcata ctcacttcaa cagcaaatgt gactgctgag    6780
attaagattt tacacaagat ggtctgtaat ttcacagtta gttttatccc attaggtatg    6840
aaagaattag cataattccc cttaaacatg aatgaatctt agattttta ataaatagtt     6900 ttggaagtaa agacagagac atcaggagca caaggaatag cctgagagga caaacagaac    6960
aagaaagagt ctggaaatac acaggatgtt cttggcctcc tcaaagcaag tgcaagcaga    7020
tagtaccagc agccccaggc tatcagagcc cagtgaagag aagtaccatg aaagccacag    7080
ctctaaccac cctgttccag agtgacagac agtccccaag acaagccagc ctgagccaga    7140
gagagaactg caagagaaag tttctaattt aggttctgtt agattcagac aagtgcaggt    7200
catcctctct ccacagctac tcacctctcc agcctaacaa agcctgcagt ccacactcca    7260
accctggtgt ctcacctcct agcctctccc aacatcctgc tctctgacca tcttctgcat    7320
ctctcatctc accatctccc actgtctaca gcctactctt gcaactacca tctcattttc    7380
tgacatcctg tctacatctt ctgccatact ctgccatcta ccataccacc tcttaccatc    7440
taccacacca tcttttatct ccatccctct cagaagcctc caagctgaat cctgctttat    7500
gtgttcatct cagcccctgc atggaaagct gaccccagag gcagaactat tcccagagag    7560
cttggccaag aaaaacaaaa ctaccagcct ggccaggctc aggagtagta agctgcagtg    7620
tctgttgtgt tctagcttca acagctgcag gagttccact ctcaaatgct ccacatttct    7680
cacatcctcc tgattctggt cactacccat cttcaaagaa cagaatatct cacatcagca    7740
tactgtgaag gactagtcat gggtgcagct gctcagagct gcaaagtcat tctggatggt    7800
ggagagctta caaacatttc atgatgctcc ccccgctctg atggctggag cccaatccct    7860
acacagactc ctgctgtatg tgttttcctt tcactctgag ccacagccag agggcaggca    7920
ttcagtctcc tcttcaggct ggggctgggg cactgagaac tcacccaaca ccttgctctc    7980
actccttctg caaaacaaga aagagctttg tgctgcagta gccatgaaga atgaaaggaa    8040
ggctttaact aaaaaatgtc agagattatt ttcaaccccct tactgtggat caccagcaag    8100
```

```
gaggaaacac aacacagaga catttttttcc cctcaaatta tcaaaagaat cactgcattt    8160
gttaaagaga gcaactgaat caggaagcag agttttgaac atatcagaag ttaggaatct    8220
gcatcagaga caaatgcagt catggttgtt tgctgcatac cagccctaat cattagaagc    8280
ctcatggact tcaaacatca ttccctctga caagatgctc tagcctaact ccatgagata    8340
aaataaatct gcctttcaga gccaaagaag agtccaccag cttcttctca gtgtgaacaa    8400
gagctccagt caggttagtc agtccagtgc agtagaggag accagtctgc atcctctaat    8460
tttcaaaggc aagaagattt gtttaccctg acaccaggc acaagtgagg tcacagagct     8520
cttagatatg cagtcctcat gagtgaggag actaaagcgc atgccatcaa gacttcagtg    8580
tagagaaaac ctccaaaaaa gcctcctcac tacttctgga atagctcaga ggccgaggcg    8640
gcctcggcct ctgcataaat aaaaaaaatt agtcagccat ggggcggaga atgggcggaa    8700
ctgggcggag ttaggggcgg gatgggcgga gttaggggcg ggactatggt tgctgactaa    8760
ttgagatgca tgcttttgcat acttctgcct gctggggagc ctggggactt tccacacctg   8820
gttgctgact aattgagatg catgctttgc atacttctgc ctgctgggga gcctggggac    8880
tttccacacc ctaactgaca cacattccac agctgcatta atgaatcggc caacgcgcgg    8940
ggagaggcgg tttgcgtatt gggcgctctt ccgcttcctc gctcactgac tcgctgcgct    9000
cggtcgttcg gctgcggcga gcggtatcag ctcactcaaa ggcggtaata cggttatcca    9060
cagaatcagg ggataacgca ggaaagaaca tgtgagcaaa aggccagcaa aaggccagga    9120
accgtaaaaa ggccgcgttg ctggcgtttt tccataggct ccgcccccct gacgagcatc    9180
acaaaaatcg acgctcaagt cagaggtggc gaaacccgac aggactataa agataccagg    9240
cgtttccccc tggaagctcc ctcgtgcgct ctcctgttcc gaccctgccg cttaccggat    9300
acctgtccgc ctttctccct tcgggaagcg tggcgctttc tcatagctca cgctgtaggt    9360
atctcagttc ggtgtaggtc gttcgctcca agctgggctg tgtgcacgaa ccccccgttc    9420
agcccgaccg ctgcgcctta tccggtaact atcgtcttga gtccaacccg gtaagacacg    9480
acttatcgcc actggcagca gccactggta acaggattag cagagcgagg tatgtaggcg    9540
gtgctacaga gttcttgaag tggtggccta actacggcta cactagaaga acagtatttg    9600
gtatctgcgc tctgctgaag ccagttacct tcggaaaaag agttggtagc tcttgatccg    9660
gcaaacaaac caccgctggt agcggtggtt ttttgtttg caagcagcag attacgcgca      9720
gaaaaaaagg atctcaagaa gatcctttga tcttttctac ggggtctgac gctcagtgga    9780
acgaaaactc acgttaaggg attttggtca tgagattatc aaaaaggatc ttcacctaga    9840
tccttttaaa ttaaaaatga agttttaaat caatctaaag tatatatgag taaacttggt    9900
ctgacagtta ccaatgctta atcagtgagg cacctatctc agcgatctgt ctatttcgtt    9960
catccatagt tgcctgactc ctgcaaacca cgttgtgtct caaaatctct gatgttacat   10020
tgcacaagat aaaaatatat catcatgaac aataaaactg tctgcttaca taaacagtaa   10080
tacaagggt gttatgagcc atattcaacg ggaaacgtct tgctcgaggc cgcgattaaa    10140
ttccaacatg gatgctgatt tatatgggta taaatgggct cgcgataatg tcggcaatc    10200
aggtgcgaca atctatcgat tgtatgggaa gcccgatgcg ccagagttgt ttctgaaaca   10260
tggcaaaggt agcgttgcca atgatgttac agatgagatg gtcagactaa actggctgac   10320
ggaatttatg cctcttccga ccatcaagca tttatccgt actcctgatg atgcatggtt    10380
actcaccact gcgatccccg ggaaaacagc attccaggta ttagaagaat atcctgattc   10440
```

-continued

```
aggtgaaaat attgttgatg cgctggcagt gttcctgcgc cggttgcatt cgattcctgt    10500
ttgtaattgt cctttaaca gcgatcgcgt atttcgtctc gctcaggcgc aatcacgaat     10560
gaataacggt ttggttgatg cgagtgattt tgatgacgag cgtaatggct ggcctgttga    10620
acaagtctgg aaagaaatgc ataagctttt gccattctca ccggattcag tcgtcactca    10680
tggtgatttc tcacttgata acctattttt tgacgagggg aaattaatag gttgtattga    10740
tgttggacga gtcggaatcg cagaccgata ccaggatctt gccatcctat ggaactgcct    10800
cggtgagttt tctccttcat tacagaaacg gcttttttcaa aaatatggta ttgataatcc    10860
tgatatgaat aaattgcagt ttcatttgat gctcgatgag tttttctaag ggcggcctgc    10920
caccataccc acgccgaaac aagcgctcat gagcccgaag tggcgagccc gatcttcccc    10980
atcggtgatg tcggcgatat aggcgccagc aaccgcacct gtggcgccgg tgatgagggc    11040
gcgccaagtc gacgtccggc agtc                                          11064
```

<210> SEQ ID NO 45
<211> LENGTH: 250
<212> TYPE: PRT
<213> ORGANISM: Artificial sequence
<220> FEATURE:
<223> OTHER INFORMATION: Synthetic polypeptide

<400> SEQUENCE: 45

```
Met Glu Lys Gly Pro Val Arg Ala Pro Ala Glu Lys Pro Arg Gly Ala
1               5                   10                  15

Arg Cys Ser Asn Gly Phe Pro Glu Arg Asp Pro Pro Arg Pro Gly Pro
            20                  25                  30

Ser Arg Pro Ala Glu Lys Pro Arg Pro Glu Ala Lys Ser Ala Gln
        35                  40                  45

Pro Ala Asp Gly Trp Lys Gly Glu Arg Pro Arg Ser Glu Glu Asp Asn
    50                  55                  60

Glu Leu Asn Leu Pro Asn Leu Ala Ala Ala Tyr Ser Ser Ile Leu Ser
65                  70                  75                  80

Ser Leu Gly Glu Asn Pro Gln Arg Gln Gly Leu Leu Lys Thr Pro Trp
                85                  90                  95

Arg Ala Ala Ser Ala Met Gln Phe Phe Thr Lys Gly Tyr Gln Glu Thr
            100                 105                 110

Ile Ser Asp Val Leu Asn Asp Ala Ile Phe Asp Glu Asp His Asp Glu
        115                 120                 125

Met Val Ile Val Lys Asp Ile Asp Met Phe Ser Met Cys Glu His His
    130                 135                 140

Leu Val Pro Phe Val Gly Lys Val His Ile Gly Tyr Leu Pro Asn Lys
145                 150                 155                 160

Gln Val Leu Gly Leu Ser Lys Leu Ala Arg Ile Val Glu Ile Tyr Ser
                165                 170                 175

Arg Arg Leu Gln Val Gln Glu Arg Leu Thr Lys Gln Ile Ala Val Ala
            180                 185                 190

Ile Thr Glu Ala Leu Arg Pro Ala Gly Val Gly Val Val Glu Ala
        195                 200                 205

Thr His Met Cys Met Val Met Arg Gly Val Gln Lys Met Asn Ser Lys
    210                 215                 220

Thr Val Thr Ser Thr Met Leu Gly Val Phe Arg Glu Asp Pro Lys Thr
225                 230                 235                 240

Arg Glu Glu Phe Leu Thr Leu Ile Arg Ser
                245                 250
```

<210> SEQ ID NO 46
<211> LENGTH: 750
<212> TYPE: DNA
<213> ORGANISM: Artificial sequence
<220> FEATURE:
<223> OTHER INFORMATION: Synthetic polynucleotide

<400> SEQUENCE: 46

```
atggagaagg cccccgtgcg cgcccccgcc gagaagcccc gcggcgcccg ctgcagcaac      60
ggcttccccg agcgcgaccc ccccgcccc ggccccagcc gccccgccga aagcccccc      120
cgccccgagg ccaagagcgc ccagcccgcc gacggctgga agggcgagcg cccccgcagc     180
gaggaggaca acgagctgaa cctgcccaac ctggccgccg cctacagcag catcctgagc     240
agcctgggcg agaacccca gcgccagggc ctgctgaaga ccccctggcg cgccgccagc     300
gccatgcagt tcttcaccaa gggctaccag agaccatca gcgacgtgct gaacgacgcc     360
atcttcgacg aggaccacga cgagatggtg atcgtgaagg acatcgacat gttcagcatg     420
tgcgagcacc acctggtgcc cttcgtgggc aaggtgcaca tcggctacct gcccaacaag     480
caggtgctgg gcctgagcaa gctggcccgc atcgtgaaga tctacagccg ccgcctgcag     540
gtgcaggagc gcctgaccaa gcagatcgcc gtggccatca ccgaggccct cgccccgcc     600
ggcgtgggcg tggtggtgga ggccacccac atgtgcatgg tgatgcgcgg cgtgcagaag     660
atgaacagca agaccgtgac cagcaccatg ctgggcgtgt ccgcgagga ccccaagacc     720
cgcgaggagt cctgacccct gatccgcagc                                    750
```

<210> SEQ ID NO 47
<211> LENGTH: 203
<212> TYPE: PRT
<213> ORGANISM: Artificial sequence
<220> FEATURE:
<223> OTHER INFORMATION: Synthetic polypeptide

<400> SEQUENCE: 47

```
Met Gly Ser Arg Asp His Leu Phe Lys Val Leu Val Val Gly Asp Ala
1               5                   10                  15

Ala Val Gly Lys Thr Ser Leu Val Gln Arg Tyr Ser Gln Asp Ser Phe
                20                  25                  30

Ser Lys His Tyr Lys Ser Thr Val Gly Val Asp Phe Ala Leu Lys Val
            35                  40                  45

Leu Gln Trp Ser Asp Tyr Glu Ile Val Arg Leu Gln Leu Trp Asp Ile
        50                  55                  60

Ala Gly Gln Glu Arg Phe Thr Ser Met Thr Arg Leu Tyr Tyr Arg Asp
65                  70                  75                  80

Ala Ser Ala Cys Val Ile Met Phe Asp Val Thr Asn Ala Thr Thr Phe
                85                  90                  95

Ser Asn Ser Gln Arg Trp Lys Gln Asp Leu Asp Ser Lys Leu Thr Leu
            100                 105                 110

Pro Asn Gly Glu Pro Val Pro Cys Leu Leu Leu Ala Asn Lys Cys Asp
        115                 120                 125

Leu Ser Pro Trp Ala Val Ser Arg Asp Gln Ile Asp Arg Phe Ser Lys
    130                 135                 140

Glu Asn Gly Phe Thr Gly Trp Thr Glu Thr Ser Val Lys Glu Asn Lys
145                 150                 155                 160

Asn Ile Asn Glu Ala Met Arg Val Leu Ile Glu Lys Met Met Arg Asn
                165                 170                 175
```

Ser Thr Glu Asp Ile Met Ser Leu Ser Thr Gln Gly Asp Tyr Ile Asn
            180                 185                 190

Leu Gln Thr Lys Ser Ser Ser Trp Ser Cys Cys
        195                 200

<210> SEQ ID NO 48
<211> LENGTH: 609
<212> TYPE: DNA
<213> ORGANISM: Artificial sequence
<220> FEATURE:
<223> OTHER INFORMATION: Synthetic polynucleotide

<400> SEQUENCE: 48
atgggcagcc gcgaccacct gttcaaggtg ctggtggtgg gcgacgccgc cgtgggcaag     60
accagcctgg tgcagcgcta cagccaggac agcttcagca agcactacaa gagcaccgtg    120
ggcgtggact tcgccctgaa ggtgctgcag tggagcgact acgagatcgt cgcctgcag    180 ctgtgggaca tcgccggcca ggagcgcttc accagcatga cccgcctgta ctaccgcgac    240
gccagcgcct gcgtgatcat gttcgacgtg accaacgcca ccaccttcag caacagccag    300
cgctggaagc aggacctgga cagcaagctg accctgccca acggcgagcc cgtgccctgc    360
ctgctgctgg ccaacaagtg cgacctgagc ccctgggccg tgagccgcga ccagatcgac    420
cgcttcagca aggagaacgg cttcaccggc tggaccgaga ccagcgtgaa ggagaacaag    480
aacatcaacg aggccatgcg cgtgctgatc gagaagatga tgcgcaacag caccgaggac    540
atcatgagcc tgagcaccca gggcgactac atcaacctgc agaccaagag cagcagctgg    600
agctgctgc                                                            609

<210> SEQ ID NO 49
<211> LENGTH: 796
<212> TYPE: PRT
<213> ORGANISM: Artificial sequence
<220> FEATURE:
<223> OTHER INFORMATION: Synthetic polypeptide

<400> SEQUENCE: 49

Met Pro Thr Thr Gln Gln Ser Pro Gln Asp Glu Gln Glu Lys Leu Leu
1               5                   10                  15

Asp Glu Ala Ile Gln Ala Val Lys Val Gln Ser Phe Gln Met Lys Arg
            20                  25                  30

Cys Leu Asp Lys Asn Lys Leu Met Asp Ala Leu Lys His Ala Ser Asn
        35                  40                  45

Met Leu Gly Glu Leu Arg Thr Ser Met Leu Ser Pro Lys Ser Tyr Tyr
    50                  55                  60

Glu Leu Tyr Met Ala Ile Ser Asp Glu Leu His Tyr Leu Glu Val Tyr
65                  70                  75                  80

Leu Thr Asp Glu Phe Ala Lys Gly Arg Lys Val Ala Asp Leu Tyr Glu
                85                  90                  95

Leu Val Gln Tyr Ala Gly Asn Ile Ile Pro Arg Leu Tyr Leu Leu Ile
            100                 105                 110

Thr Val Gly Val Val Tyr Val Lys Ser Phe Pro Gln Ser Arg Lys Asp
        115                 120                 125

Ile Leu Lys Asp Leu Val Glu Met Cys Arg Gly Val Gln His Pro Leu
    130                 135                 140

Arg Gly Leu Phe Leu Arg Asn Tyr Leu Leu Gln Cys Thr Arg Asn Ile
145                 150                 155                 160

-continued

Leu Pro Asp Glu Gly Glu Pro Thr Asp Glu Thr Thr Gly Asp Ile
            165                 170                 175

Ser Asp Ser Met Asp Phe Val Leu Leu Asn Phe Ala Glu Met Asn Lys
        180                 185                 190

Leu Trp Val Arg Met Gln His Gln Gly His Ser Arg Asp Arg Glu Lys
        195                 200                 205

Arg Glu Arg Glu Arg Gln Glu Leu Arg Ile Leu Val Gly Thr Asn Leu
    210                 215                 220

Val Arg Leu Ser Gln Leu Glu Gly Val Asn Val Glu Arg Tyr Lys Gln
225                 230                 235                 240

Ile Val Leu Thr Gly Ile Leu Glu Gln Val Val Asn Cys Arg Asp Ala
                245                 250                 255

Leu Ala Gln Glu Tyr Leu Met Glu Cys Ile Ile Gln Val Phe Pro Asp
            260                 265                 270

Glu Phe His Leu Gln Thr Leu Asn Pro Phe Leu Arg Ala Cys Ala Glu
        275                 280                 285

Leu His Gln Asn Val Asn Val Lys Asn Ile Ile Ala Leu Ile Asp
        290                 295                 300

Arg Leu Ala Leu Phe Ala His Arg Glu Asp Gly Pro Gly Ile Pro Ala
305                 310                 315                 320

Asp Ile Lys Leu Phe Asp Ile Phe Ser Gln Gln Val Ala Thr Val Ile
                325                 330                 335

Gln Ser Arg Gln Asp Met Pro Ser Glu Asp Val Val Ser Leu Gln Val
            340                 345                 350

Ser Leu Ile Asn Leu Ala Met Lys Cys Tyr Pro Asp Arg Val Asp Tyr
        355                 360                 365

Val Asp Lys Val Leu Glu Thr Thr Val Glu Ile Phe Asn Lys Leu Asn
    370                 375                 380

Leu Glu His Ile Ala Thr Ser Ser Ala Val Ser Lys Glu Leu Thr Arg
385                 390                 395                 400

Leu Leu Lys Ile Pro Val Asp Thr Tyr Asn Asn Ile Leu Thr Val Leu
                405                 410                 415

Lys Leu Lys His Phe His Pro Leu Phe Glu Tyr Phe Asp Tyr Glu Ser
            420                 425                 430

Arg Lys Ser Met Ser Cys Tyr Val Leu Ser Asn Val Leu Asp Tyr Asn
        435                 440                 445

Thr Glu Ile Val Ser Gln Asp Gln Val Asp Ser Ile Met Asn Leu Val
    450                 455                 460

Ser Thr Leu Ile Gln Asp Gln Pro Asp Gln Pro Val Glu Asp Pro Asp
465                 470                 475                 480

Pro Glu Asp Phe Ala Asp Glu Gln Ser Leu Val Gly Arg Phe Ile His
                485                 490                 495

Leu Leu Arg Ser Glu Asp Pro Asp Gln Gln Tyr Leu Ile Leu Asn Thr
            500                 505                 510

Ala Arg Lys His Phe Gly Ala Gly Gly Asn Gln Arg Ile Arg Phe Thr
        515                 520                 525

Leu Pro Pro Leu Val Phe Ala Ala Tyr Gln Leu Ala Phe Arg Tyr Lys
    530                 535                 540

Glu Asn Ser Lys Val Asp Asp Lys Trp Glu Lys Lys Cys Gln Lys Ile
545                 550                 555                 560

Phe Ser Phe Ala His Gln Thr Ile Ser Ala Leu Ile Lys Ala Glu Leu
                565                 570                 575

```
Ala Glu Leu Pro Leu Arg Leu Phe Leu Gln Gly Ala Leu Ala Ala Gly
            580                 585                 590

Glu Ile Gly Phe Glu Asn His Glu Thr Val Ala Tyr Glu Phe Met Ser
        595                 600                 605

Gln Ala Phe Ser Leu Tyr Glu Asp Glu Ile Ser Asp Ser Lys Ala Gln
    610                 615                 620

Leu Ala Ala Ile Thr Leu Ile Ile Gly Thr Phe Glu Arg Met Lys Cys
625                 630                 635                 640

Phe Ser Glu Glu Asn His Glu Pro Leu Arg Thr Gln Cys Ala Leu Ala
                645                 650                 655

Ala Ser Lys Leu Leu Lys Lys Pro Asp Gln Gly Arg Ala Val Ser Thr
            660                 665                 670

Cys Ala His Leu Phe Trp Ser Gly Arg Asn Thr Asp Lys Asn Gly Glu
        675                 680                 685

Glu Leu His Gly Gly Lys Arg Val Met Glu Cys Leu Lys Lys Ala Leu
    690                 695                 700

Lys Ile Ala Asn Gln Cys Met Asp Pro Ser Leu Gln Val Gln Leu Phe
705                 710                 715                 720

Ile Glu Ile Leu Asn Arg Tyr Ile Tyr Phe Tyr Glu Lys Glu Asn Asp
                725                 730                 735

Ala Val Thr Ile Gln Val Leu Asn Gln Leu Ile Gln Lys Ile Arg Glu
            740                 745                 750

Asp Leu Pro Asn Leu Glu Ser Ser Glu Glu Thr Glu Gln Ile Asn Lys
        755                 760                 765

His Phe His Asn Thr Leu Glu His Leu Arg Leu Arg Arg Glu Ser Pro
    770                 775                 780

Glu Ser Glu Gly Pro Ile Tyr Glu Gly Leu Ile Leu
785                 790                 795

<210> SEQ ID NO 50
<211> LENGTH: 2388
<212> TYPE: DNA
<213> ORGANISM: Artificial sequence
<220> FEATURE:
<223> OTHER INFORMATION: Synthetic polynucleotide

<400> SEQUENCE: 50
atgcccacca cccagcagag cccccaggac gagcaggaga agctgctgga cgaggccatc      60
caggccgtga aggtgcagag cttccagatg aagcgctgcc tggacaagaa caagctgatg     120
gacgccctga agcacgccag caacatgctg ggcgagctgc gcaccagcat gctgagcccc     180
aagagctact acgagctgta catggccatc agcgacgagc tgcactacct ggaggtgtac     240
ctgaccgacg agttcgccaa gggccgcaag gtggccgacc tgtacgagct ggtgcagtac     300
gccggcaaca tcatcccccg cctgtacctg ctgatcaccg tgggcgtggt gtacgtgaag     360
agcttccccc agagccgcaa ggacatcctg aaggacctgg tggagatgtg ccgcggcgtg     420
cagcaccccc tgcgcggcct gttcctgcgc aactacctgc tgcagtgcac ccgcaacatc     480
ctgcccgacg agggcgagcc caccgacgag gagaccaccg cgacatcag cgacagcatg     540 gacttcgtgc tgctgaactt cgccgagatg aacaagctgt gggtgcgcat gcagcaccag     600
ggccacagcc gcgaccgcga agcgcgag cgcgagcgcc aggagctgcg catcctggtg     660
ggcaccaacc tggtgcgcct gagccagctg agggcgtga acgtggagcg ctacaagcag     720
atcgtgctga ccggcatcct ggagcaggtg gtgaactgcc gcgacgccct ggcccaggag     780
```

| | |
|---|---|
| tacctgatgg agtgcatcat ccaggtgttc cccgacgagt tccacctgca gaccctgaac | 840 |
| cccttcctgc gcgcctgcgc cgagctgcac cagaacgtga acgtgaagaa catcatcatc | 900 |
| gccctgatcg accgcctggc cctgttcgcc caccgcgagg acggccccgg catccccgcc | 960 |
| gacatcaagc tgttcgacat cttcagccag caggtggcca ccgtgatcca gagccgccag | 1020 |
| gacatgccca gcgaggacgt ggtgagcctg caggtgagcc tgatcaacct ggccatgaag | 1080 |
| tgctaccccg accgcgtgga ctacgtggac aaggtgctgg agaccaccgt ggagatcttc | 1140 |
| aacaagctga acctggagca catcgccacc agcagcgccg tgagcaagga gctgacccgc | 1200 |
| ctgctgaaga tccccgtgga cacctacaac aacatcctga ccgtgctgaa gctgaagcac | 1260 |
| ttccaccccc tgttcgagta cttcgactac gagagccgca gagcatgag ctgctacgtg | 1320 |
| ctgagcaacg tgctggacta caacaccgag atcgtgagcc aggaccaggt ggacagcatc | 1380 |
| atgaacctgg tgagcaccct gatccaggac cagcccgacc agcccgtgga ggaccccgac | 1440 |
| cccgaggact cgccgacga gcagagcctg gtgggccgct tcatccacct gctgcgcagc | 1500 |
| gaggaccccg accagcagta cctgatcctg aacaccgccc gcaagcactt cggcgccggc | 1560 |
| ggcaaccagc gcatccgctt caccctgccc ccctggtgt cgccgccta ccagctggcc | 1620 |
| ttccgctaca aggagaacag caaggtggac gacaagtggg agaagaagtg ccagaagatc | 1680 |
| ttcagcttcg cccaccagac catcagcgcc ctgatcaagg ccgagctggc cgagctgccc | 1740 |
| ctgcgcctgt cctgcaggg cgccctggcc gccggcgaga tcggcttcga gaaccacgag | 1800 |
| accgtggcct acgagttcat gagccaggcc ttcagcctgt acgaggacga gatcagcgac | 1860 |
| agcaaggccc agctggccgc catcaccctg atcatcggca ccttcgagcg catgaagtgc | 1920 |
| ttcagcgagg agaaccacga gccctgcgc acccagtgcg ccctggccgc cagcaagctg | 1980 |
| ctgaagaagc ccgaccaggg ccgcgccgtg agcacctgcg cccacctgtt ctggagcggc | 2040 |
| cgcaacaccg acaagaacgg cgaggagctg cacggcggca gcgcgtgat ggagtgcctg | 2100 |
| aagaaggccc tgaagatcgc caaccagtgc atggacccca gcctgcaggt gcagctgttc | 2160 |
| atcgagatcc tgaaccgcta catctacttc tacgagaagg agaacgacgc cgtgaccatc | 2220 |
| caggtgctga accagctgat ccagaagatc cgcgaggacc tgcccaacct ggagagcagc | 2280 |
| gaggagaccg agcagatcaa caagcacttc cacaacaccc tggagcacct gcgcctgcgc | 2340 |
| cgcgagagcc ccgagagcga gggcccccatc tacgagggcc tgatcctg | 2388 |

<210> SEQ ID NO 51
<211> LENGTH: 11081
<212> TYPE: DNA
<213> ORGANISM: Artificial sequence
<220> FEATURE:
<223> OTHER INFORMATION: Synthetic polynucleotide

<400> SEQUENCE: 51

| | |
|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctgctag ctctgggtat ttaagcccga gtgagcacgc | 180 |
| agggtctcca ttttgaagcg ggaggttacg cgttcgtcga ctactagtgg gtaccagagc | 240 |
| tccctaggtt ctagaaccgg tgacgtctcc catggtgaag cttggatctg agggcggagt | 300 |
| tagggcggag ccaatcagcg tgcgccgttc cgaaagttgc cttttatggc tgggcggaga | 360 |
| atgggcggtg aacgccgatg attatataag gacgcgccgg gtgtggcaca gctagttccg | 420 |
| tcgcagccgg gatttgggtc gcggttcttg tttgtggatc cctgtgatcg tcacttggta | 480 |

```
agtcactgac tgtctatgcc tgggaaaggg tgggcaggag atggggcagt gcaggaaaag    540
tggcactatg aaccctcctg gtggcgaggg gagggggtg gtcctcgaac gccttgcaga    600
actggcctgg atacagagtg gaccggctgg ccccatctgg aagacttcga gatacactgt    660
tgtcttactg cgctcaacag tgtatctcga agtcttccaa atggtgccag ccatcgcagc    720
ggggtgcagg aaatggggc agccccctt tttggctatc cttccacgtg ttctttttg    780 tatcttttgt gtttcctaga aaacatctca gtcaccaccg cagccctagg aatgcatcta    840
gacaattgta ctaaccttct tctctttcct ctcctgacag tccggaaagc caccatggaa    900
ttcagcagcc ccagcagaga ggaatgcccc aagcctctga gccgggtgtc aatcatggcc    960
ggatctctga caggactgct gctgcttcag gccgtgtctt gggcttctgg cgctagacct   1020
tgcatcccca agagcttcgg ctacagcagc gtcgtgtgcg tgtgcaatgc cacctactgc   1080
gacagcttcg accctcctac ctttcctgct ctgggcacct cagcagata cgagagcacc   1140 agatccggca gacggatgga actgagcatg ggacccatcc aggccaatca cacaggcact   1200
ggcctgctgc tgacactgca gcctgagcag aaattccaga agtgaaagg cttcggcgga   1260 gccatgacag atgccgccgc tctgaatatc ctggctctgt ctccaccagc tcagaacctg   1320
ctgctcaaga gctacttcag cgaggaaggc atcggctaca acatcatcag agtgcccatg   1380
gccagctgcg acttcagcat caggacctac acctacgccg acacacccga cgatttccag   1440
ctgcacaact tcagcctgcc tgaagaggac accaagctga agatccctct gatccacaga   1500
gccctgcagc tggcacaaag acccgtgtca ctgctggcct ctccatggac atctcccacc   1560
tggctgaaaa caaatggcgc cgtgaatggc aagggcagcc tgaaaggcca acctggcgac   1620
atctaccacc agacctgggc cagatacttc gtgaagttcc tggacgccta tgccgagcac   1680
aagctgcagt ttgggccgt gacagccgag aacgaaacct tctgctggact gctgagcggc   1740 taccccttc agtgcctggg cttacaccc gagcaccagc gggactttat cgcccgtgat   1800
ctgggaccca cactggccaa tagcacccac cataatgtgc ggctgctgat gctggacgac   1860
cagagactgc ttctgcccca ctgggctaaa gtggtgctga cagatcctga ggccgccaaa   1920
tacgtgcacg aatcgccgt gcactggtat ctggactttc tggcccctgc caaggccaca   1980 ctggagaga cacacagact gttccccaac accatgctgt cgccagcga agcctgtgtg   2040 ggcagcaagt tttgggaaca gagcgtgcg ctcggcagct gggatagagg catgcagtac   2100
agccacagca tcatcaccaa cctgctgtac cacgtcgtcg gctggaccga ctggaatctg   2160
gccctgaatc ctgaaggcgg ccctaactgg gtccgaaact tcgtggacag ccccatcatc   2220
gtggacatca ccaaggacac cttctacaag cagcccatgt ctaccacct gggacacttc   2280 agcaagttca tccccgaggg ctctcagcgc gttggactgg tggcttccca aagaacgat   2340 ctggacgccg tggctctgat gcaccctgat ggatctgctg tggtggtggt cctgaaccgc   2400
agcagcaaag atgtgcccct gaccatcaag gatcccgccg tgggattcct ggaaacaatc   2460
agccctggct actccatcca cacctacctg tggcgtagac aggagggcag aggaagtctt   2520
ctgacatgcg gagacgtgga agagaatccc ggccctatgg agaagggccc cgtgcgcgcc   2580
cccgccgaga gccccgcgg cgcccgctgc agcaacggct tccccgagcg cgacccccccc   2640 cgccccggcc ccagccgccc cgccgagaag ccccccgcc ccgaggccaa gagcgcccag   2700
cccgccgacg gctggaaggg cgagcgcccc gcagcgagg aggacaacga gctgaacctg   2760
cccaacctgg ccgccgccta cagcagcatc ctgagcagcc tgggcgagaa ccccccagcgc   2820
```

```
cagggcctgc tgaagacccc ctggcgcgcc gccagcgcca tgcagttctt caccaagggc    2880
taccaggaga ccatcagcga cgtgctgaac gacgccatct tcgacgagga ccacgacgag    2940
atggtgatcg tgaaggacat cgacatgttc agcatgtgcg agcaccacct ggtgcccttc    3000
gtgggcaagg tgcacatcgg ctacctgccc aacaagcagg tgctgggcct gagcaagctg    3060
gcccgcatcg tggagatcta cagccgccgc ctgcaggtgc aggagcgcct gaccaagcag    3120
atcgccgtgg ccatcaccga ggccctgcgc cccgccggcg tgggcgtggt ggtgaaggcc    3180
acccacatgt gcatggtgat gcgcggcgtg cagaagatga acagcaagac cgtgaccagc    3240
accatgctgg gcgtgttccg cgaggacccc aagacccgcg aggagttcct gaccctgatc    3300
cgcagctgac aattgttaat taagtttaaa ccctcgaggc cgcaagctta tcgataatca    3360
acctctggat tacaaaattt gtgaaagatt gactggtatt cttaactatg ttgctccttt    3420
tacgctatgt ggatacgctg ctttaatgcc tttgtatcat gctattgctt cccgtatggc    3480
tttcattttc tcctccttgt ataaatcctg gttgctgtct ctttatgagg agttgtggcc    3540
cgttgtcagg caacgtggcg tggtgtgcac tgtgtttgct gacgcaaccc ccactggttg    3600
gggcattgcc accacctgtc agctcctttc cgggactttc gctttccccc tccctattgc    3660
cacggcggaa ctcatcgccg cctgccttgc ccgctgctgg acaggggctc ggctgttggg    3720
cactgacaat tccgtggtgt tgtcggggaa atcatcgtcc tttccttggc tgctcgcctg    3780
tgttgccacc tggattctgc gcgggacgtc ttctgctac gtcccttcgg ccctcaatcc    3840
agcggacctt ccttcccgcg gcctgctgcc ggctctgcgg cctcttccgc gtcttcgcct    3900
tcgccctcag acgagtcgga tctccctttg ggccgcctcc ccgcatcgat accgtcgact    3960
agagctcgct gatcagcctc gactgtgcct tctagttgcc agccatctgt tgtttgcccc    4020
tcccccgtgc cttccttgac cctggaaggt gccactccca ctgtcctttc ctaataaaat    4080
gaggaaattg catcgcattg tctgagtagg tgtcattcta ttctgggggg tggggtgggg    4140
caggacagca agggggagga ttgggaagac aatagcaggc atgctgggga gagatccacg    4200
ataacaaaca gctttttggg ggtgaacata ttgactgaat tccctgcagg ttggccactc    4260
cctctctgcg cgctcgctcg ctcactgagg ccgcccgggc aaagcccggg cgtcgggcga    4320
cctttggtcg cccggcctca gtgagcgagc gagcgcgcag agagggagtg gccaactcca    4380
tcactagggg ttcctgcggc cgctcgtacg gtctcgagga attcctgcag gataacttgc    4440
caacctcatt ctaaaatgta tatagaagcc caaaagacaa taacaaaaat attcttgtag    4500
aacaaaatgg gaaagaatgt tccactaaat atcaagattt agagcaaagc atgagatgtg    4560
tggggataga cagtgaggct gataaaatag agtagagctc agaaacagac ccattgatat    4620
atgtaagtga cctatgaaaa aaatatggca ttttacaatg ggaaaatgat ggtcttttc    4680 ttttttagaa aaacagggaa atatatttat atgtaaaaaa taaagggaa cccatatgtc    4740 ataccataca cacaaaaaaa ttccagtgaa ttataagtct aaatggagaa ggcaaaactt    4800
taaatctttt agaaaataat atagaagcat gcagaccagc ctggccaaca tgatgaaacc    4860
ctctctacta ataataaaat cagtagaact actcaggact actttgagtg ggaagtcctt    4920
ttctatgaag acttctttgg ccaaaattag gctctaaatg caaggagata gtgcatcatg    4980
cctggctgca cttactgata aatgatgtta tcaccatctt taaccaaatg cacaggaaca    5040
agttatggta ctgatgtgct ggattgagaa ggagctctac ttccttgaca ggacacattt    5100
gtatcaactt aaaaaagcag attttttgcca gcagaactat tcattcagag gtaggaaact    5160
tagaatagat gatgtcactg attagcatgg cttccccatc tccacagctg cttcccaccc    5220
```

```
aggttgccca cagttgagtt tgtccagtgc tcagggctgc ccactctcag taagaagccc    5280
cacaccagcc cctctccaaa tatgttggct gttccttcca ttaaagtgac cccactttag    5340
agcagcaagt ggatttctgt ttcttacagt tcaggaagga ggagtcagct gtgagaacct    5400
ggagcctgag atgcttctaa gtcccactgc tactggggtc agggaagcca gactccagca    5460
tcagcagtca ggagcactaa gcccttgcca acatcctgtt tctcagagaa actgcttcca    5520
ttataatggt tgtcctttt taagctatca agccaaacaa ccagtgtcta ccattattct      5580
catcacctga agccaagggt tctagcaaaa gtcaagctgt cttgtaatgg ttgatgtgcc    5640
tccagcttct gtcttcagtc actccactct tagcctgctc tgaatcaact ctgaccacag    5700
ttccctggag ccctgccac ctgctgcccc tgccaccttc tccatctgca gtgctgtgca      5760
gccttctgca ctcttgcaga gctaataggt ggagacttga aggaagagga ggaaagtttc    5820
tcataatagc cttgctgcaa gctcaaatgg gaggtgggca ctgtgcccag gagccttgga    5880
gcaaaggctg tgcccaacct ctgactgcat ccaggtttgg tcttgacaga gataagaagc    5940
cctggctttt ggagccaaaa tctaggtcag acttaggcag gattctcaaa gtttatcagc    6000
agaacatgag gcagaagacc ctttctgctc cagcttcttc aggctcaacc ttcatcagaa    6060
tagatagaaa gagaggctgt gagggttctt aaaacagaag caaatctgac tcagagaata    6120
aacaacctcc tagtaaacta cagcttagac agagcatctg gtggtgagtg tgctcagtgt    6180
cctactcaac tgtctggtat cagccctcat gaggacttct cttctttccc tcatagacct    6240
ccatctctgt tttccttagc ctgcagaaat ctggatggct attcacagaa tgcctgtgct    6300
ttcagagttg cattttttct ctggtattct ggttcaagca tttgaaggta ggaaaggttc    6360
tccaagtgca agaaagccag ccctgagcct caactgcctg gctagtgtgg tcagtaggat    6420
gcaaaggctg ttgaatgcca caaggccaaa ctttaacctg tgtaccacaa gcctagcagc    6480
agaggcagct ctgctcactg gaactctctg tcttctttct cctgagcctt ttcttttcct      6540
gagttttcta gctctcctca accttacctc tgccctaccc aggacaaacc caagagccac    6600
tgtttctgtg atgtcctctc cagccctaat taggcatcat gacttcagcc tgaccttcca    6660
tgctcagaag cagtgctaat ccacttcaga tgagctgctc tatgcaacac aggcagagcc    6720
tacaaacctt tgcaccagag ccctccacat atcagtgttt gttcatactc acttcaacag    6780
caaatgtgac tgctgagatt aagatttac acaagatggt ctgtaatttc acagttagtt      6840
ttatcccatt aggtatgaaa gaattagcat aattcccctt aaacatgaat gaatcttaga    6900 tttttaata aatagttttg gaagtaaaga cagagacatc aggagcacaa ggaatagcct      6960
gagaggacaa acagaacaag aaagagtctg gaaatacaca ggatgttctt ggcctcctca    7020
aagcaagtgc aagcagatag taccagcagc cccaggctat cagagcccag tgaagagaag    7080
taccatgaaa gccacagctc taaccaccct gttccagagt gacagacagt ccccaagaca    7140
agccagcctg agcagagag agaactgcaa gagaaagttt ctaatttagg ttctgttaga     7200
ttcagacaag tgcaggtcat cctctctcca cagctactca cctctccagc ctaacaaagc    7260
ctgcagtcca cactccaacc ctggtgtctc acctcctagc ctctcccaac atcctgctct    7320
ctgaccatct tctgcatctc tcatctcacc atctcccact gtctacagcc tactcttgca    7380
actaccatct cattttctga catcctgtct acatcttctg ccatactctg ccatctacca    7440
taccacctct taccatctac cacaccatct tttatctcca tccctctcag aagcctccaa    7500
gctgaatcct gctttatgtg ttcatctcag cccctgcatg gaaagctgac cccagaggca    7560
```

```
gaactattcc cagagagctt ggccaagaaa acaaaactaa ccagcctggc caggctcagg    7620
agtagtaagc tgcagtgtct gttgtgttct agcttcaaca gctgcaggag ttccactctc    7680
aaatgctcca catttctcac atcctcctga ttctggtcac tacccatctt caaagaacag    7740
aatatctcac atcagcatac tgtgaaggac tagtcatggg tgcagctgct cagagctgca    7800
aagtcattct ggatggtgga gagcttacaa acatttcatg atgctccccc cgctctgatg    7860
gctggagccc aatccctaca cagactcctg ctgtatgtgt tttcctttca ctctgagcca    7920
cagccagagg gcaggcattc agtctcctct tcaggctggg gctggggcac tgagaactca    7980
cccaacacct tgctctcact ccttctgcaa acaagaaag agctttgtgc tgcagtagcc    8040
atgaagaatg aaaggaaggc tttaactaaa aaatgtcaga gattattttc aaccccttac    8100
tgtggatcac cagcaaggag gaaacacaac acagagacat ttttcccct caaattatca     8160 aaagaatcac tgcatttgtt aaagagagca actgaatcag gaagcagagt tttgaacata    8220
tcagaagtta ggaatctgca tcagagacaa atgcagtcat ggttgtttgc tgcataccag    8280
ccctaatcat tagaagcctc atggacttca aacatcattc cctctgacaa gatgctctag    8340
cctaactcca tgagataaaa taaatctgcc tttcagagcc aaagaagagt ccaccagctt    8400
cttctcagtg tgaacaagag ctccagtcag gttagtcagt ccagtgcagt agaggagacc    8460
agtctgcatc ctctaatttt caaaggcaag aagatttgtt taccctggac accaggcaca    8520
agtgaggtca cagagctctt agatatgcag tcctcatgag tgaggagact aaagcgcatg    8580
ccatcaagac ttcagtgtag agaaaacctc caaaaaagcc tcctcactac ttctggaata    8640
gctcagaggc cgaggcggcc tcggcctctg cataaataaa aaaaattagt cagccatggg    8700
gcggagaatg ggcggaactg ggcggagtta ggggcgggat gggcggagtt aggggcggga    8760
ctatggttgc tgactaattg agatgcatgc tttgcatact tctgcctgct ggggagcctg    8820
gggactttcc acacctggtt gctgactaat tgagatgcat gctttgcata cttctgcctg    8880
ctggggagcc tggggacttt ccacacccta actgacacac attccacagc tgcattaatg    8940
aatcggccaa cgcgcgggga gaggcggttt gcgtattggg cgctcttccg cttcctcgct    9000
cactgactcg ctgcgctcgg tcgttcggct gcggcgagcg gtatcagctc actcaaaggc    9060
ggtaatacgg ttatccacag aatcagggga taacgcagga agaacatgt gagcaaaagg     9120 ccagcaaaag gccaggaacc gtaaaaaggc cgcgttgctg gcgttttcc ataggctccg      9180 ccccctgac gagcatcaca aaaatcgacg ctcaagtcag aggtggcgaa acccgacagg      9240
actataaaga taccaggcgt ttccccctgg aagctccctc gtgcgctctc ctgttccgac     9300
cctgccgctt accggatacc tgtccgcctt tctcccttcg ggaagcgtgg cgctttctca    9360
tagctcacgc tgtaggtatc tcagttcggt gtaggtcgtt cgctccaagc tgggctgtgt    9420
gcacgaaccc cccgttcagc ccgaccgctg cgccttatcc ggtaactatc gtcttgagtc    9480
caacccggta agacacgact tatcgccact ggcagcagcc actggtaaca ggattagcag    9540
agcgaggtat gtaggcggtg ctacagagtt cttgaagtgg tggcctaact acggctacac    9600
tagaagaaca gtatttggta tctgcgctct gctgaagcca gttaccttcg gaaaaagagt    9660
tggtagctct tgatccggca acaaaccac cgctggtagc ggtggttttt ttgtttgcaa     9720
gcagcagatt acgcgcagaa aaaaggatc tcaagaagat cctttgatct tttctacggg    9780
gtctgacgct cagtggaacg aaaactcacg ttaagggatt ttggtcatga gattatcaaa    9840
aaggatcttc acctagatcc ttttaaatta aaaatgaagt tttaaatcaa tctaaagtat    9900
atatgagtaa acttggtctg acagttacca atgcttaatc agtgaggcac ctatctcagc    9960
```

| | | |
|---|---|---|
| gatctgtcta tttcgttcat ccatagttgc ctgactcctg caaaccacgt tgtgtctcaa | 10020 |
| aatctctgat gttacattgc acaagataaa aatatatcat catgaacaat aaaactgtct | 10080 |
| gcttacataa acagtaatac aagggqtgtt atgagccata ttcaacggga aacgtcttgc | 10140 |
| tcgaggccgc gattaaattc caacatggat gctgatttat atgggtataa atgggctcgc | 10200 |
| gataatgtcg ggcaatcagg tgcgacaatc tatcgattgt atgggaagcc cgatgcgcca | 10260 |
| gagttgtttc tgaaacatgg caaaggtagc gttgccaatg atgttacaga tgagatggtc | 10320 |
| agactaaact ggctgacgga atttatgcct cttccgacca tcaagcattt tatccgtact | 10380 |
| cctgatgatg catggttact caccactgcg atccccggga aaacagcatt ccaggtatta | 10440 |
| gaagaatatc ctgattcagg tgaaaatatt gttgatgcgc tggcagtgtt cctgcgccgg | 10500 |
| ttgcattcga ttcctgtttg taattgtcct tttaacagcg atcgcgtatt tcgtctcgct | 10560 |
| caggcgcaat cacgaatgaa taacggtttg gttgatgcga gtgattttga tgacgagcgt | 10620 |
| aatggctggc ctgttgaaca agtctggaaa gaaatgcata gcttttgcc attctcaccg | 10680 |
| gattcagtcg tcactcatgg tgatttctca cttgataacc ttatttttga cgaggggaaa | 10740 |
| ttaataggtt gtattgatgt tggacgagtc ggaatcgcag accgatacca ggatcttgcc | 10800 |
| atcctatgga actgcctcgg tgagttttct ccttcattac agaaacggct ttttcaaaaa | 10860 |
| tatggtattg ataatcctga tatgaataaa ttgcagtttc atttgatgct cgatgagttt | 10920 |
| ttctaagggc ggcctgccac catacccacg ccgaaacaag cgctcatgag cccgaagtgg | 10980 |
| cgagcccgat cttccccatc ggtgatgtcg gcgatatagg cgccagcaac cgcacctgtg | 11040 |
| gcgccggtga tgagggcgcg ccaagtcgac gtccggcagt c | 11081 |

<210> SEQ ID NO 52
<211> LENGTH: 10940
<212> TYPE: DNA
<213> ORGANISM: Artificial sequence
<220> FEATURE:
<223> OTHER INFORMATION: Synthetic polynucleotide

<400> SEQUENCE: 52

| | | |
|---|---|---|
| ttggccactc cctctctgcg cgctcgctcg ctcactgagg ccgggcgacc aaaggtcgcc | 60 |
| cgacgcccgg gctttgcccg ggcggcctca gtgagcgagc gagcgcgcag agagggagtg | 120 |
| gccaactcca tcactagggg ttcctgctag ctctgggtat ttaagcccga gtgagcacgc | 180 |
| agggtctcca ttttgaagcg ggaggttacg cgttcgtcga ctactagtgg gtaccagagc | 240 |
| tccctaggtt ctagaaccgg tgacgtctcc catggtgaag cttggatctg agggcggagt | 300 |
| tagggcggag ccaatcagcg tgcgccgttc cgaaagttgc cttttatggc tgggcggaga | 360 |
| atgggcggtg aacgccgatg attatataag gacgcgccgg gtgtggcaca gctagttccg | 420 |
| tcgcagccgg gatttgggtc gcggttcttg tttgtggatc cctgtgatcg tcacttggta | 480 |
| agtcactgac tgtctatgcc tgggaaaggg tgggcaggag atggggcagt gcaggaaaag | 540 |
| tggcactatg aaccctcctg gtggcgaggg gaggggggtg gtcctcgaac gccttgcaga | 600 |
| actggcctgg atacagagtg gaccggctgg ccccatctgg aagacttcga gatacactgt | 660 |
| tgtcttactg cgctcaacag tgtatctcga agtcttccaa atggtgccag ccatcgcagc | 720 |
| ggggtgcagg aaatggggc agcccccctt tttggctatc cttccacgtg ttctttttg | 780 |
| tatcttttgt gtttcctaga aaacatctca gtcaccaccg cagccctagg aatgcatcta | 840 |
| gacaattgta ctaaccttct ctctctttcct ctcctgacag tccggaaagc caccatgggc | 900 |

| | |
|---|---|
| agccgcgacc acctgttcaa ggtgctggtg gtgggcgacg ccgccgtggg caagaccagc | 960 |
| ctggtgcagc gctacagcca ggacagcttc agcaagcact acaagagcac cgtgggcgtg | 1020 |
| gacttcgccc tgaaggtgct gcagtggagc gactacgaga tcgtgcgcct gcagctgtgg | 1080 |
| gacatcgccg gccaggagcg cttcaccagc atgacccgcc tgtactaccg cgacgccagc | 1140 |
| gcctgcgtga tcatgttcga cgtgaccaac gccaccacct tcagcaacag ccagcgctgg | 1200 |
| aagcaggacc tggacagcaa gctgaccctg cccaacggcg agcccgtgcc ctgcctgctg | 1260 |
| ctggccaaca agtgcgacct gagcccctgg gccgtgagcc gcgaccagat cgaccgcttc | 1320 |
| agcaaggaga acggcttcac cggctggacc gagaccagcg tgaaggagaa caagaacatc | 1380 |
| aacgaggcca tgcgcgtgct gatcgagaag atgatgcgca acagcaccga ggacatcatg | 1440 |
| agcctgagca cccagggcga ctacatcaac ctgcagacca gagcagcag ctggagctgc | 1500 |
| tgcgagggca gaggaagtct tctgacatgc ggagacgtgg aagagaatcc cggccctatg | 1560 |
| gaattcagca gccccagcag agaggaatgc cccaagcctc tgagccgggt gtcaatcatg | 1620 |
| gccggatctc tgacaggact gctgctgctt caggccgtgt cttgggcttc tggcgctaga | 1680 |
| ccttgcatcc ccaagagctt cggctacagc agcgtcgtgt cgtgtgcaa tgccacctac | 1740 |
| tgcgacagct tcgaccctcc tacctttcct gctctgggca ccttcagcag atacgagagc | 1800 |
| accagatccg gcagacggat ggaactgagc atgggaccca tccaggccaa tcacacaggc | 1860 |
| actggcctgc tgctgacact gcagcctgag cagaaattcc agaaagtgaa aggcttcggc | 1920 |
| ggagccatga cagatgccgc cgctctgaat atcctggctc tgtctccacc agctcagaac | 1980 |
| ctgctgctca gagctacttt cagcgaggaa ggcatcggct acaacatcat cagagtgccc | 2040 |
| atggccagct gcgacttcag catcaggacc tacacctacg ccgacacacc cgacgatttc | 2100 |
| cagctgcaca acttcagcct gcctgaagag gacaccaagc tgaagatccc tctgatccac | 2160 |
| agagccctgc agctggcaca aagacccgtg tcactgctgg cctctccatg gacatctccc | 2220 |
| acctggctga aaacaaatgg cgccgtgaat ggcaagggca gcctgaaagg ccaacctggc | 2280 |
| gacatctacc accagacctg ggccagatac ttcgtgaagt tcctggacgc ctatgccgag | 2340 |
| cacaagctgc agttttgggc cgtgacagcc gagaacgaac cttctgctgg actgctgagc | 2400 |
| ggctacccct ttcagtgcct gggctttaca cccgagcacc agcgggactt tatcgcccgt | 2460 |
| gatctgggac ccacactggc caatagcacc accataatg tgcggctgct gatgctggac | 2520 |
| gaccagagac tgcttctgcc ccactgggct aaagtggtgc tgacagatcc tgaggccgcc | 2580 |
| aaatacgtgc acggaatcgc cgtgcactgg tatctggact ttctggcccc tgccaaggcc | 2640 |
| acactgggag agacacacag actgttcccc aacaccatgc tgttcgccag cgaagcctgt | 2700 |
| gtgggcagca gttttgggga acagagcgtg cggctcggca gctgggatag aggcatgcag | 2760 |
| tacagccaca gcatcatcac caacctgctg taccacgtcg tcggctggac cgactggaat | 2820 |
| ctggccctga atcctgaagg cggccctaac tgggtccgaa acttcgtgga cagccccatc | 2880 |
| atcgtggaca tcaccaagga caccttctac aagcagccca tgttctacca cctgggacac | 2940 |
| ttcagcaagt tcatccccga gggctctcag cgcgttggac tggtggcttc ccagaagaac | 3000 |
| gatctggacg ccgtggctct gatgcaccct gatggatctg ctgtggtggt ggtcctgaac | 3060 |
| cgcagcagca agatgtgcc cctgaccatc aaggatcccg ccgtgggatt cctggaaaca | 3120 |
| atcagccctg ctactccat ccacacctac ctgtggcgta cagtgaca attgttaatt | 3180 |
| aagtttaaac cctcgaggcc gcaagcttat cgataatcaa cctctggatt acaaaatttg | 3240 |
| tgaaagattg actggtattc ttaactatgt tgctcctttt acgctatgtg gatacgctgc | 3300 |

| | |
|---|---|
| tttaatgcct tgtatcatg ctattgcttc ccgtatggct ttcattttct cctccttgta | 3360 |
| taaatcctgg ttgctgtctc tttatgagga gttgtggccc gttgtcaggc aacgtggcgt | 3420 |
| ggtgtgcact gtgtttgctg acgcaacccc cactggttgg ggcattgcca ccacctgtca | 3480 |
| gctccttttcc gggactttcg ctttccccct ccctattgcc acggcggaac tcatcgccgc | 3540 |
| ctgccttgcc cgctgctgga caggggctcg gctgttgggc actgacaatt ccgtggtgtt | 3600 |
| gtcggggaaa tcatcgtcct ttccttggct gctcgcctgt gttgccacct ggattctgcg | 3660 |
| cgggacgtcc ttctgctacg tcccttcggc cctcaatcca gcggaccttc cttcccgcgg | 3720 |
| cctgctgccg gctctgcggc ctcttccgcg tcttcgcctt cgccctcaga cgagtcggat | 3780 |
| ctcccttttgg gccgcctccc cgcatcgata ccgtcgacta gagctcgctg atcagcctcg | 3840 |
| actgtgcctt ctagttgcca gccatctgtt gtttgcccct cccccgtgcc ttccttgacc | 3900 |
| ctggaaggtg ccactcccac tgtccttttcc taataaaatg aggaaattgc atcgcattgt | 3960 |
| ctgagtaggt gtcattctat ctgggggt ggggtgggc aggacagcaa ggggaggat | 4020 |
| tgggaagaca atagcaggca tgctggggag agatccacga taacaaacag cttttttggg | 4080 |
| gtgaacatat tgactgaatt ccctgcaggt tggccactcc ctctctgcgc gctcgctcgc | 4140 |
| tcactgaggc cgcccgggca agcccgggc gtcgggcgac ctttggtcgc ccggcctcag | 4200 |
| tgagcgagcg agcgcgcaga gagggagtgg ccaactccat cactagggt tcctgcggcc | 4260 |
| gctcgtacgg tctcgaggaa ttcctgcagg ataacttgcc aacctcattc taaaatgtat | 4320 |
| atagaagccc aaaagacaat aacaaaaata ttcttgtaga acaaatggg aagaatgtt | 4380 |
| ccactaaata tcaagattta gagcaaagca tgagatgtgt ggggatagac agtgaggctg | 4440 |
| ataaaataga gtagagctca gaaacagacc cattgatata tgtaagtgac ctatgaaaaa | 4500 |
| aatatggcat tttacaatgg gaaaatgatg gtcttttttct tttttagaaa acagggaaa | 4560 |
| tatatttata tgtaaaaaat aaagggaac ccatatgtca taccatacac acaaaaaaat | 4620 |
| tccagtgaat tataagtcta aatggagaag gcaaaacttt aaatctttta gaaaataata | 4680 |
| tagaagcatg cagaccagcc tggccaacat gatgaaaccc tctctactaa taataaaatc | 4740 |
| agtagaacta ctcaggacta cttttgagtgg gaagtccttt tctatgaaga cttcttggc | 4800 |
| caaaattagg ctctaaatgc aaggagatag tgcatcatgc ctggctgcac ttactgataa | 4860 |
| atgatgttat caccatcttt aaccaaatgc acaggaacaa gttatggtac tgatgtgctg | 4920 |
| gattgagaag gagctctact tccttgacag gacacatttg tatcaactta aaaaagcaga | 4980 |
| tttttgccag cagaactatt cattcagagg taggaaactt agaatagatg atgtcactga | 5040 |
| ttagcatggc ttccccatct ccacagctgc ttcccaccca ggttgcccac agttgagttt | 5100 |
| gtccagtgct cagggctgcc cactctcagt aagaagcccc acaccagccc ctctccaaat | 5160 |
| atgttggctg ttccttccat taaagtgacc ccactttaga gcagcaagtg gatttctgtt | 5220 |
| tcttacagtt caggaaggag gagtcagctg tgagaacctg gagcctgaga tgcttctaag | 5280 |
| tcccactgct actggggtca gggaagccag actccagcat cagcagtcag gagcactaag | 5340 |
| cccttgccaa catcctgttt ctcagagaaa ctgcttccat tataatggtt gtccttttt | 5400 |
| aagctatcaa gccaaacaac cagtgtctac cattattctc atcacctgaa gccagggtt | 5460 |
| ctagcaaaag tcaagctgtc ttgtaatggt tgatgtgcct ccagcttctg tcttcagtca | 5520 |
| ctccactctt agcctgctct gaatcaactc tgaccacagt tccctggagc ccctgccacc | 5580 |
| tgctgcccct gccaccttct ccatctgcag tgctgtgcag ccttctgcac tcttgcagag | 5640 |

```
ctaataggtg gagacttgaa ggaagaggag gaaagtttct cataatagcc ttgctgcaag    5700
ctcaaatggg aggtgggcac tgtgcccagg agccttggag caaaggctgt gcccaacctc    5760
tgactgcatc caggtttggt cttgacagag ataagaagcc ctggcttttg gagccaaaat    5820
ctaggtcaga cttaggcagg attctcaaag tttatcagca gaacatgagg cagaagaccc    5880
tttctgctcc agcttcttca ggctcaacct tcatcagaat agatagaaag agaggctgtg    5940
agggttctta aaacagaagc aaatctgact cagagaataa acaacctcct agtaaactac    6000
agcttagaca gagcatctgg tggtgagtgt gctcagtgtc ctactcaact gtctggtatc    6060
agccctcatg aggacttctc ttcttttccct catagacctc catctctgtt ttccttagcc    6120
tgcagaaatc tggatggcta ttcacagaat gcctgtgctt tcagagttgc attttttctc    6180
tggtattctg gttcaagcat ttgaaggtag gaaaggttct ccaagtgcaa gaaagccagc    6240
cctgagcctc aactgcctgg ctagtgtggt cagtaggatg caaaggctgt tgaatgccac    6300
aaggccaaac tttaacctgt gtaccacaag cctagcagca gaggcagctc tgctcactgg    6360
aactctctgt cttctttctc ctgagccttt tcttttcctg agttttctag ctctcctcaa    6420
ccttacctct gccctaccca ggacaaaccc aagagccact gtttctgtga tgtcctctcc    6480
agccctaatt aggcatcatg acttcagcct gaccttccat gctcagaagc agtgctaatc    6540
cacttcagat gagctgctct atgcaacaca ggcagagcct acaaaccttt gcaccagagc    6600
cctccacata tcagtgtttg ttcatactca cttcaacagc aaatgtgact gctgagatta    6660
agattttaca caagatggtc tgtaatttca cagttagttt tatcccatta ggtatgaaag    6720
aattagcata attccccctta aacatgaatg aatcttagat tttttaataa atagttttgg    6780
aagtaaagac agagacatca ggagcacaag gaatagcctg agaggacaaa cagaacaaga    6840
aagagtctgg aaatacacag gatgttcttg gcctcctcaa agcaagtgca agcagatagt    6900
accagcagcc ccaggctatc agagcccagt gaagagaagt accatgaaag ccacagctct    6960
aaccaccctg ttccagagtg acagacagtc cccaagacaa gccagcctga gccagagaga    7020
gaactgcaag agaaagtttc taatttaggt tctgttagat tcagacaagt gcaggtcatc    7080
ctctctccac agctactcac ctctccagcc taacaaagcc tgcagtccac actccaaccc    7140
tggtgtctca cctcctagcc tctcccaaca tcctgctctc tgaccatctt ctgcatctct    7200
catctcacca tctcccactg tctacagcct actcttgcaa ctaccatctc attttctgac    7260
atcctgtcta tcatcttctgc atactctgc catctaccat accacctctt accatctacc    7320
acaccatctt ttatctccat ccctctcaga agctccaag ctgaatcctg ctttatgtgt    7380
tcatctcagc ccctgcatgg aaagctgacc ccagaggcag aactattccc agagagcttg    7440
gccaagaaaa acaaaactac cagcctggcc aggctcagga gtagtaagct gcagtgtctg    7500
ttgtgttcta gcttcaacag ctgcaggagt tccactctca aatgctccac atttctcaca    7560
tcctcctgat tctggtcact acccatcttc aaagaacaga atatctcaca tcagcatact    7620
gtgaaggact agtcatgggt gcagctgctc agagctgcaa agtcattctg gatggtggag    7680
agcttacaaa catttcatga tgctcccccc gctctgatgg ctggagccca atccctacac    7740
agactcctgc tgtatgtgtt ttccttttcac tctgagccac agccagaggg caggcattca    7800
gtctcctctt caggctgggg ctgggcact gagaactcac ccaacacctt gctctcactc    7860
cttctgcaaa acaagaaaga gctttgtgct gcagtagcca tgaagaatga aaggaaggct    7920
ttaactaaaa aatgtcagag attatttca accccttact gtggatcacc agcaaggagg    7980
aaacacaaca cagagacatt ttttcccctc aaattatcaa aagaatcact gcatttgtta    8040
```

```
aagagagcaa ctgaatcagg aagcagagtt ttgaacatat cagaagttag gaatctgcat    8100
cagagacaaa tgcagtcatg gttgtttgct gcataccagc cctaatcatt agaagcctca    8160
tggacttcaa acatcattcc ctctgacaag atgctctagc ctaactccat gagataaaat    8220
aaatctgcct ttcagagcca aagaagagtc caccagcttc ttctcagtgt gaacaagagc    8280
tccagtcagg ttagtcagtc cagtgcagta gaggagacca gtctgcatcc tctaattttc    8340
aaaggcaaga agatttgttt accctggaca ccaggcacaa gtgaggtcac agagctctta    8400
gatatgcagt cctcatgagt gaggagacta aagcgcatgc catcaagact tcagtgtaga    8460
gaaaacctcc aaaaaagcct cctcactact tctggaatag ctcagaggcc gaggcggcct    8520
cggcctctgc ataaataaaa aaaattagtc agccatgggg cggagaatgg gcggaactgg    8580
gcggagttag gggcgggatg ggcggagtta ggggcgggac tatggttgct gactaattga    8640
gatgcatgct ttgcatactt ctgcctgctg gggagcctgg ggactttcca cacctggttg    8700
ctgactaatt gagatgcatg ctttgcatac ttctgcctgc tggggagcct ggggactttc    8760
cacaccctaa ctgacacaca ttccacagct gcattaatga atcggccaac gcgcggggag    8820
aggcggtttg cgtattgggc gctcttccgc ttcctcgctc actgactcgc tgcgctcggt    8880
cgttcggctg cggcgagcgg tatcagctca ctcaaaggcg gtaatacggt tatccacaga    8940
atcaggggat aacgcaggaa agaacatgtg agcaaaaggc cagcaaaagg ccaggaaccg    9000
taaaaaggcc gcgttgctgg cgttttttcca taggctccgc cccctgacg agcatcacaa    9060 aaatcgacgc tcaagtcaga ggtggcgaaa cccgacagga ctataaagat accaggcgtt    9120 tcccctgga agctccctcg tgcgctctcc tgttccgacc ctgccgctta ccggatacct    9180
gtccgccttt ctcccttcgg gaagcgtggc gctttctcat agctcacgct gtaggtatct    9240
cagttcggtg taggtcgttc gctccaagct gggctgtgtg cacgaacccc ccgttcagcc    9300
cgaccgctgc gccttatccg gtaactatcg tcttgagtcc aacccggtaa gacacgactt    9360
atcgccactg gcagcagcca ctggtaacag gattagcaga gcgaggtatg taggcggtgc    9420
tacagagttc ttgaagtggt ggcctaacta cggctacact agaagaacag tatttggtat    9480
ctgcgctctg ctgaagccag ttaccttcgg aaaaagagtt ggtagctctt gatccggcaa    9540
acaaaccacc gctggtagcg gtggtttttt tgtttgcaag cagcagatta cgcgcagaaa    9600
aaaaggatct caagaagatc ctttgatctt ttctacgggg tctgacgctc agtggaacga    9660
aaactcacgt taagggattt tggtcatgag attatcaaaa aggatcttca cctagatcct    9720
tttaaattaa aaatgaagtt ttaaatcaat ctaaagtata tatgagtaaa cttggtctga    9780
cagttaccaa tgcttaatca gtgaggcacc tatctcagcg atctgtctat ttcgttcatc    9840
catagttgcc tgactcctgc aaaccacgtt gtgtctcaaa atctctgatg ttacattgca    9900
caagataaaa atatatcatc atgaacaata aaactgtctg cttacataaa cagtaataca    9960 agggggtgtta tgagccatat tcaacgggaa acgtcttgct cgaggccgcg attaaattcc    10020
aacatggatg ctgatttata tgggtataaa tgggctcgcg ataatgtcgg gcaatcaggt    10080
gcgacaatct atcgattgta tgggaagccc gatgcgccag agttgtttct gaaacatggc    10140
aaaggtagcg ttgccaatga tgttacagat gagatggtca gactaaactg gctgacggaa    10200
tttatgcctc ttccgaccat caagcatttt atccgtactc ctgatgatgc atggttactc    10260
accactgcga tccccgggaa aacagcattc caggtattag aagaatatcc tgattcaggt    10320
gaaaatattg ttgatgcgct ggcagtgttc ctgcgccggt tgcattcgat tcctgtttgt    10380
```

| | |
|---|---:|
| aattgtcctt ttaacagcga tcgcgtattt cgtctcgctc aggcgcaatc acgaatgaat | 10440 |
| aacggtttgg ttgatgcgag tgattttgat gacgagcgta atggctggcc tgttgaacaa | 10500 |
| gtctggaaag aaatgcataa gcttttgcca ttctcaccgg attcagtcgt cactcatggt | 10560 |
| gatttctcac ttgataacct tatttttgac gaggggaaat taataggttg tattgatgtt | 10620 |
| ggacgagtcg gaatcgcaga ccgataccag gatcttgcca tcctatggaa ctgcctcggt | 10680 |
| gagttttctc cttcattaca gaaacggctt tttcaaaaat atggtattga taatcctgat | 10740 |
| atgaataaat tgcagtttca tttgatgctc gatgagtttt tctaagggcg gcctgccacc | 10800 |
| atacccacgc cgaaacaagc gctcatgagc ccgaagtggc gagcccgatc ttccccatcg | 10860 |
| gtgatgtcgg cgatataggc gccagcaacc gcacctgtgg cgccggtgat gagggcgcgc | 10920 |
| caagtcgacg tccggcagtc | 10940 |

<210> SEQ ID NO 53
<211> LENGTH: 10934
<212> TYPE: DNA
<213> ORGANISM: Artificial sequence
<220> FEATURE:
<223> OTHER INFORMATION: Synthetic polynucleotide

<400> SEQUENCE: 53

| | |
|---|---:|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctgctag ctctgggtat ttaagcccga gtgagcacgc | 180 |
| agggtctcca ttttgaagcg ggaggttacg cgttcgtcga ctactagtgg gtaccagagc | 240 |
| tccctaggtt ctagaaccgg tgacgtctcc catggtgaag cttggatctg agggcggagt | 300 |
| tagggcggag ccaatcagcg tgcgccgttc cgaaagttgc cttttatggc tgggcggaga | 360 |
| atgggcggtg aacgccgatg attatataag gacgcgccgg gtgtggcaca gctagttccg | 420 |
| tcgcagccgg gatttgggtc gcggttcttg tttgtggatc cctgtgatcg tcacttggta | 480 |
| agtcactgac tgtctatgcc tgggaaaggg tgggcaggag atggggcagt gcaggaaaag | 540 |
| tggcactatg aaccctcctg gtggcgaggg gagggggtg gtcctcgaac gccttgcaga | 600 |
| actggcctgg atacagagtg gaccggctgg ccccatctgg aagacttcga gatacactgt | 660 |
| tgtcttactg cgctcaacag tgtatctcga agtcttccaa atggtgccag ccatcgcagc | 720 |
| ggggtgcagg aaatggggc agccccctt tttggctatc cttccacgtg ttcttttttg | 780 |
| tatcttttgt gtttcctaga aaacatctca gtcaccaccg cagccctagg aatgcatcta | 840 |
| gacaattgta ctaaccttct tctctttcct ctcctgacag tccggaaagc caccatggaa | 900 |
| ttcagcagcc ccagcagaga ggaatgcccc aagcctctga gccgggtgtc aatcatggcc | 960 |
| ggatctctga caggactgct gctgcttcag gccgtgtctt gggcttctgg cgctagacct | 1020 |
| tgcatcccca gagcttcgg ctacagcagc gtcgtgtgcg tgtgcaatgc cacctactgc | 1080 |
| gacagcttcg accctcctac ctttcctgct ctgggcacct tcagcagata cgagagcacc | 1140 |
| agatccggca gacggatgga actgagcatg ggacccatcc aggccaatca cacaggcact | 1200 |
| ggcctgctgc tgacactgca gcctgagcag aaattccaga agtgaaagg cttcggcgga | 1260 |
| gccatgacag atgccgccgc tctgaatatc ctggctctgt ctccaccagc tcagaacctg | 1320 |
| ctgctcaaga gctacttcag cgaggaaggc atcggctaca acatcatcag agtgccatg | 1380 |
| gccagctgcg acttcagcat caggacctac acctacgccg acacacccga cgatttccag | 1440 |
| ctgcacaact tcagcctgcc tgaagaggac accaagctga agatccctct gatccacaga | 1500 |

```
gccctgcagc tggcacaaag acccgtgtca ctgctggcct ctccatggac atctcccacc    1560
tggctgaaaa caaatggcgc cgtgaatggc aagggcagcc tgaaaggcca acctggcgac    1620
atctaccacc agacctgggc cagatacttc gtgaagttcc tggacgccta tgccgagcac    1680
aagctgcagt tttgggccgt gacagccgag aacgaacctt ctgctggact gctgagcggc    1740
tacccctttc agtgcctggg ctttacaccc gagcaccagc gggactttat cgcccgtgat    1800
ctgggaccca cactggccaa tagcacccac cataatgtgc ggctgctgat gctggacgac    1860
cagagactgc ttctgcccca ctgggctaaa gtggtgctga cagatcctga ggccgccaaa    1920
tacgtgcacg gaatcgccgt gcactggtat ctggactttc tggcccctgc caaggccaca    1980
ctgggagaga cacacagact gttccccaac accatgctgt tcgccagcga agcctgtgtg    2040
ggcagcaagt tttgggaaca gagcgtgcgg ctcggcagct gggatagagg catgcagtac    2100
agccacagca tcatcaccaa cctgctgtac cacgtcgtcg gctggaccga ctggaatctg    2160
gccctgaatc ctgaaggcgg ccctaactgg gtccgaaact tcgtggacag ccccatcatc    2220
gtggacatca ccaaggacac cttctacaag cagcccatgt tctaccacct gggacacttc    2280
agcaagttca tccccgaggg ctctcagcgc gttggactgg tggcttccca gaagaacgat    2340
ctggacgccg tggctctgat gcaccctgat ggatctgctg tggtggtggt cctgaaccgc    2400
agcagcaaag atgtgcccct gaccatcaag gatcccgccg tgggattcct ggaaacaatc    2460
agccctggct actccatcca cacctacctg tggcgtagac agtgattgtg gccgaaccgc    2520
cgaactcaga ggccggcccc agaaaacccg agcgagtagg gggcggcgcg caggagggag    2580
gagaactggg ggcgcgggag gctggtgggt gtgggggtg gagatgtaga agatgtgacg    2640
ccgcggcccg gcgggtgcca gattagcgga cgcggtgccc gcggttgcaa cgggatcccg    2700
ggcgctgcag cttgggaggc ggctctcccc aggcggcgtc cgcggagaca cccatccgtg    2760
aaccccaggt cccgggccgc cggctcgccg cgcaccaggg gccggcggac agaagagcgg    2820
ccgagcggct cgaggctggg ggaccgcggg cgcggccgcg cgctgccggg cgggaggctg    2880
gggggccggg gccggggccg tgccccggag cgggtcggag gccggggccg gggccgggg    2940
acggcggctc cccgcgcggc tccagcggct cggggatccc ggccgggccc cgcagggacc    3000
atgatggaga agggcccgt gcgcgccccc gccgagaagc cccgcggcgc ccgctgcagc    3060
aacggcttcc ccgagcgcga cccccccgc cccggcccca gccgccccgc cgagaagccc    3120
ccccgcccg aggccaagag cgcccagccc gccgacggct ggaagggcga gcgccccgc    3180
agcgaggagg acaacgagct gaacctgccc aacctggccg ccgcctacag cagcatcctg    3240
agcagcctgg gcgagaaccc ccagcgccag ggcctgctga agacccctg gcgcgccgcc    3300
agcgccatgc agttcttcac caagggctac caggagacca tcagcgacgt gctgaacgac    3360
gccatcttcg acgaggacca cgacgagatg gtgatcgtga aggacatcga catgttcagc    3420
atgtgcgagc accacctggt gcccttcgtg ggcaaggtgc acatcggcta cctgcccaac    3480
aagcaggtgc tgggcctgag caagctggcc cgcatcgtgg agatctacag ccgccgcctg    3540
caggtgcagg agcgcctgac caagcagatc gccgtggcca tcaccgaggc cctgcgcccc    3600
gccgcgtgg gcgtggtggt ggaggccacc cacatgtgca tggtgatgcg cggcgtgcag    3660
aagatgaaca gcaagaccgt gaccagcacc atgctgggcg tgttccgcga ggaccccaag    3720
acccgcgagg agttcctgac cctgatccgc agctgacaat tgttaattaa gtttaaaccc    3780
tcgaggccgc aagccgcatc gataccgtcg actagagctc gctgatcagc ctcgactgtg    3840
```

-continued

```
ccttctagtt gccagccatc tgttgtttgc ccctcccccg tgccttcctt gaccctggaa    3900
ggtgccactc ccactgtcct ttcctaataa aatgaggaaa ttgcatcgca ttgtctgagt    3960
aggtgtcatt ctattctggg gggtggggtg gggcaggaca gcaaggggga ggattgggaa    4020
gacaatagca ggcatgctgg ggagagatcc acgataacaa acagctttt tggggtgaac     4080
atattgactg aattccctgc aggttggcca ctccctctct gcgcgctcgc tcgctcactg    4140
aggccgcccg ggcaaagccc gggcgtcggg cgaccttttgg tcgcccggcc tcagtgagcg   4200
agcgagcgcg cagagaggga gtggccaact ccatcactag gggttcctgc ggccgctcgt    4260
acggtctcga ggaattcctg caggataact tgccaacctc attctaaaat gtatatagaa    4320
gcccaaaaga caataacaaa aatattcttg tagaacaaaa tgggaaagaa tgttccacta    4380
aatatcaaga tttagagcaa agcatgagat gtgtggggat agacagtgag gctgataaaa    4440
tagagtagag ctcagaaaca gacccattga tatatgtaag tgacctatga aaaaaatatg    4500
gcattttaca atgggaaaat gatggtcttt ttcttttta gaaaaacagg gaaatatatt     4560
tatatgtaaa aaataaaagg gaacccatat gtcataccat acacacaaaa aaattccagt    4620
gaattataag tctaaatgga gaaggcaaaa ctttaaatct tttagaaaat aatatagaag    4680
catgcagacc agcctggcca acatgatgaa accctctcta ctaataataa aatcagtaga    4740
actactcagg actactttga gtgggaagtc cttttctatg aagacttctt tggccaaaat    4800
taggctctaa atgcaaggag atagtgcatc atgcctggct gcacttactg ataaatgatg    4860
ttatcaccat cttaaccaa atgcacagga acaagttatg gtactgatgt gctggattga     4920
gaaggagctc tacttccttg acaggacaca tttgtatcaa cttaaaaaag cagattttg     4980
ccagcagaac tattcattca gaggtaggaa acttagaata gatgatgtca ctgattagca    5040
tggcttcccc atctccacag ctgcttccca cccaggttgc ccacagttga gtttgtccag    5100
tgctcagggc tgcccactct cagtaagaag ccccacacca gcccctctcc aaatatgttg    5160
gctgttcctt ccattaaagt gaccccactt tagagcagca agtggatttc tgtttcttac    5220
agttcaggaa ggaggagtca gctgtgagaa cctggagcct gagatgcttc taagtcccac    5280
tgctactggg gtcagggaag ccagactcca gcatcagcag tcaggagcac taagcccttg    5340
ccaacatcct gtttctcaga gaaactgctt ccattataat ggttgtcctt ttttaagcta    5400
tcaagccaaa caaccagtgt ctaccattat tctcatcacc tgaagccaag ggttctagca    5460
aaagtcaagc tgtcttgtaa tggttgatgt gcctccagct tctgtcttca gtcactccac    5520
tcttagcctg ctctgaatca actctgacca cagttccctg gagcccctgc cacctgctgc    5580
ccctgccacc ttctccatct gcagtgctgt gcagccttct gcactcttgc agagctaata    5640
ggtggagact tgaaggaaga ggaggaaagt ttctcataat agccttgctg caagctcaaa    5700
tgggaggtgg gcactgtgcc caggagcctt ggagcaaagg ctgtgcccaa cctctgactg    5760
catccaggtt tggtcttgac agagataaga agccctggct tttggagcca aaatctaggt    5820
cagacttagg caggattctc aaagtttatc agcagaacat gaggcagaag acccttctg     5880
ctccagcttc ttcaggctca accttcatca gaatagatag aaagagaggc tgtgagggtt    5940
cttaaaacag aagcaaatct gactcagaga ataaacaacc tcctagtaaa ctacagctta    6000
gacagagcat ctggtggtga gtgtgctcag tgtcctactc aactgtctgg tatcagccct    6060
catgaggact tctcttcttt ccctcataga cctccatctc tgttttcctt agcctgcaga    6120
aatctggatg gctattcaca gaatgcctgt gctttcagag ttgcattttt tctctggtat    6180
tctggttcaa gcatttgaag gtaggaaagg ttctccaagt gcaagaaagc cagccctgag    6240
```

```
cctcaactgc ctggctagtg tggtcagtag gatgcaaagg ctgttgaatg ccacaaggcc   6300
aaactttaac ctgtgtacca caagcctagc agcagaggca gctctgctca ctggaactct   6360
ctgtcttctt tctcctgagc cttttctttt cctgagtttt ctagctctcc tcaaccttac   6420 ctctgccta cccaggacaa acccaagagc cactgtttct gtgatgtcct ctccagccct   6480
aattaggcat catgacttca gcctgacctt ccatgctcag aagcagtgct aatccacttc   6540
agatgagctg ctctatgcaa cacaggcaga gcctacaaac ctttgcacca gagccctcca   6600
catatcagtg tttgttcata ctcacttcaa cagcaaatgt gactgctgag attaagattt   6660
tacacaagat ggtctgtaat ttcacagtta gttttatccc attaggtatg aaagaattag   6720
cataattccc cttaaacatg aatgaatctt agattttta ataaatagtt ttggaagtaa    6780
agacagagac atcaggagca caaggaatag cctgagagga caaacagaac aagaaagagt   6840
ctggaaatac acaggatgtt cttggcctcc tcaaagcaag tgcaagcaga tagtaccagc   6900
agccccaggc tatcagagcc cagtgaagag aagtaccatg aaagccacag ctctaaccac   6960
cctgttccag agtgacagac agtccccaag acaagccagc ctgagccaga gagagaactg   7020
caagagaaag tttctaattt aggttctgtt agattcagac aagtgcaggt catcctctct   7080
ccacagctac tcacctctcc agcctaacaa agcctgcagt ccacactcca accctggtgt   7140
ctcacctcct agcctctccc aacatcctgc tctctgacca tcttctgcat ctctcatctc   7200
accatctccc actgtctaca gcctactctt gcaactacca tctcattttc tgacatcctg   7260
tctacatctt ctgccatact ctgccatcta ccataccacc tcttaccatc taccacacca   7320
tcttttatct ccatccctct cagaagcctc caagctgaat cctgctttat gtgttcatct   7380
cagcccctgc atggaaagct gaccccagag gcagaactat tcccagagag cttggccaag   7440
aaaaacaaaa ctaccagcct ggccaggctc aggagtagta agctgcagtg tctgttgtgt   7500
tctagcttca acagctgcag gagttccact ctcaaatgct ccacatttct cacatcctcc   7560
tgattctggt cactacccat cttcaaagaa cagaatatct cacatcagca tactgtgaag   7620
gactagtcat gggtgcagct gctcagagct gcaaagtcat tctggatggt ggagagctta   7680
caaacatttc atgatgctcc ccccgctctg atggctggag cccaatccct acacagactc   7740
ctgctgtatg tgttttcctt tcactctgag ccacagccag agggcaggca ttcagtctcc   7800
tcttcaggct ggggctgggg cactgagaac tcacccaaca ccttgctctc actccttctg   7860
caaaacaaga aagagctttg tgctgcagta gccatgaaga atgaaaggaa ggctttaact   7920
aaaaaatgtc agagattatt ttcaacccct tactgtggat caccagcaag gaggaaacac   7980
aacacagaga cattttttcc cctcaaatta tcaaaagaat cactgcattt gttaaagaga   8040
gcaactgaat caggaagcag agttttgaac atatcagaag ttaggaatct gcatcagaga   8100
caaatgcagt catggttgtt tgctgcatac cagccctaat cattagaagc ctcatggact   8160
tcaaacatca ttccctctga caagatgctc tagcctaact ccatgagata aaataaatct   8220
gcctttcaga gccaaagaag agtccaccag cttcttctca gtgtgaacaa gagctccagt   8280
caggttagtc agtccagtgc agtagaggag accagtctgc atcctctaat tttcaaaggc   8340
aagaagattt gtttaccctg gacaccaggc acaagtgagg tcacagagct cttagatatg   8400
cagtcctcat gagtgaggag actaaagcgc atgccatcaa gacttcagtg tagagaaaac   8460
ctccaaaaaa gcctcctcac tacttctgga atagctcaga ggccgaggcg gcctcggcct   8520
ctgcataaat aaaaaaaatt agtcagccat ggggcggaga atgggcggaa ctgggcggag   8580
```

-continued

```
ttaggggcgg gatgggcgga gttaggggcg ggactatggt tgctgactaa ttgagatgca      8640
tgctttgcat acttctgcct gctggggagc ctggggactt tccacacctg gttgctgact      8700
aattgagatg catgctttgc atacttctgc ctgctgggga gcctggggac tttccacacc      8760
ctaactgaca cacattccac agctgcatta atgaatcggc caacgcgcgg ggagaggcgg      8820
tttgcgtatt gggcgctctt ccgcttcctc gctcactgac tcgctgcgct cggtcgttcg      8880
gctgcggcga gcggtatcag ctcactcaaa ggcggtaata cggttatcca cagaatcagg      8940
ggataacgca ggaaagaaca tgtgagcaaa aggccagcaa aaggccagga accgtaaaaa      9000
ggccgcgttg ctggcgtttt tccataggct ccgcccccct gacgagcatc acaaaaatcg      9060
acgctcaagt cagaggtggc gaaacccgac aggactataa agataccagg cgtttccccc      9120
tggaagctcc ctcgtgcgct ctcctgttcc gaccctgccg cttaccggat acctgtccgc      9180
ctttctccct tcgggaagcg tggcgctttc tcatagctca cgctgtaggt atctcagttc      9240
ggtgtaggtc gttcgctcca agctgggctg tgtgcacgaa ccccccgttc agcccgaccg      9300
ctgcgcctta tccggtaact atcgtcttga gtccaacccg gtaagacacg acttatcgcc      9360
actggcagca gccactggta acaggattag cagagcgagg tatgtaggcg gtgctacaga      9420
gttcttgaag tggtggccta actacggcta cactagaaga acagtatttg gtatctgcgc      9480
tctgctgaag ccagttacct tcggaaaaag agttggtagc tcttgatccg gcaaacaaac      9540
caccgctggt agcggtggtt ttttgtttg caagcagcag attacgcgca gaaaaaaagg      9600
atctcaagaa gatcctttga tcttttctac ggggtctgac gctcagtgga acgaaaactc      9660
acgttaaggg attttggtca tgagattatc aaaaaggatc ttcacctaga tccttttaaa      9720
ttaaaaatga agttttaaat caatctaaag tatatatgag taaacttggt ctgacagtta      9780
ccaatgctta atcagtgagg cacctatctc agcgatctgt ctatttcgtt catccatagt      9840
tgcctgactc ctgcaaacca cgttgtgtct caaaatctct gatgttacat tgcacaagat      9900
aaaaatatat catcatgaac aataaaactg tctgcttaca taaacagtaa tacaaggggg      9960
gttatgagcc atattcaacg ggaaacgtct tgctcgaggc cgcgattaaa ttccaacatg     10020
gatgctgatt tatatgggta taatgggct cgcgataatg tcgggcaatc aggtgcgaca     10080
atctatcgat tgtatgggaa gcccgatgcg ccagagttgt ttctgaaaca tggcaaaggt     10140
agcgttgcca atgatgttac agatgagatg gtcagactaa actggctgac ggaatttatg     10200
cctcttccga ccatcaagca tttatccgt actcctgatg atgcatggtt actcaccact     10260
gcgatcccg ggaaaacagc attccaggta ttagaagaat atcctgattc aggtgaaaat     10320
attgttgatg cgctggcagt gttcctgcgc cggttgcatt cgattcctgt ttgtaattgt     10380
ccttttaaca gcgatcgcgt atttcgtctc gctcaggcgc aatcacgaat gaataacggt     10440
ttggttgatg cgagtgattt tgatgacgag cgtaatggct ggcctgttga acaagtctgg     10500
aaagaaatgc ataagctttt gccattctca ccggattcag tcgtcactca tggtgatttc     10560
tcacttgata accttatttt tgacgagggg aaattaatag gttgtattga tgttggacga     10620
gtcggaatcg cagaccgata ccaggatctt gccatcctat ggaactgcct cggtgagttt     10680
tctccttcat tacagaaacg gcttttcaa aaatatggta ttgataatcc tgatatgaat     10740
aaattgcagt ttcatttgat gctcgatgag ttttctaag gcggcctgc caccataccc     10800
acgccgaaac aagcgctcat gagcccgaag tggcgagccc gatcttcccc atcggtgatg     10860
tcggcgatat aggcgccagc aaccgcacct gtggcgccgg tgatgagggc gcgccaagtc     10920
gacgtccggc agtc                                                      10934
```

<210> SEQ ID NO 54
<211> LENGTH: 11138
<212> TYPE: DNA
<213> ORGANISM: Artificial sequence
<220> FEATURE:
<223> OTHER INFORMATION: Synthetic polynucleotide

<400> SEQUENCE: 54

| | | | | | |
|---|---|---|---|---|---|
| ttggccactc | cctctctgcg | cgctcgctcg | ctcactgagg | ccgggcgacc | aaaggtcgcc | 60 |
| cgacgcccgg | gctttgcccg | ggcggcctca | gtgagcgagc | gagcgcgcag | agagggagtg | 120 |
| gccaactcca | tcactagggg | ttcctgctag | ctctgggtat | ttaagcccga | gtgagcacgc | 180 |
| agggtctcca | ttttgaagcg | ggaggttacg | cgttcgtcga | ctactagtgg | gtaccagagc | 240 |
| tccctaggtt | ctagaaccgg | tgacgtctcc | catggtgaag | cttggatctg | agtaagtcac | 300 |
| tgactgtcta | tgcctgggaa | agggtgggca | ggagatgggg | cagtgcagga | aaagtggcac | 360 |
| tatgaaccct | cctggtggcg | aggggagggg | ggtggtcctc | gaacgccttg | cagaactggc | 420 |
| ctggatacag | agtggaccgg | ctggccccat | ctggaagact | tcgagataca | ctgttgtctt | 480 |
| actgcgctca | acagtgtatc | tcgaagtctt | ccaaatggtg | ccagccatcg | cagcggggtg | 540 |
| caggaaatgg | gggcagcccc | ccttttggc | tatccttcca | cgtgttcttt | tttgtatctt | 600 |
| ttgtgtttcc | tagaaaacat | ctcagtcacc | accgtgatat | cacaaggtcc | cagggctggg | 660 |
| gtcagaaatt | ctctcccgag | ggaatgaagc | cacaggagcc | aagagcagga | ggaccaaggc | 720 |
| cctggcgaag | gccgtggcct | cgttcaagta | aaagatccta | gtacagtgca | ggtcccaatg | 780 |
| tgtactagga | tcttttactt | gaacggggac | gccggcatcc | gggctcagga | cccccctctc | 840 |
| tgccagaggc | accaacacca | gagttcacaa | atcagtctcc | tgcccttgc | atgtagcaaa | 900 |
| gcagccctag | gaatgcatct | agacaattgt | actaaccttc | ttctctttcc | tctcctgaca | 960 |
| gtccggaaag | ccaccatgcc | caccacccag | cagagccccc | aggacgagca | ggagaagctg | 1020 |
| ctggacgagg | ccatccaggc | cgtgaaggtg | cagagcttcc | agatgaagcg | ctgcctggac | 1080 |
| aagaacaagc | tgatggacgc | cctgaagcac | gccagcaaca | tgctgggcga | gctgcgcacc | 1140 |
| agcatgctga | gccccaagag | ctactacgag | ctgtacatgg | ccatcagcga | cgagctgcac | 1200 |
| tacctggagg | tgtacctgac | cgacgagttc | gccaagggcc | gcaaggtggc | cgacctgtac | 1260 |
| gagctggtgc | agtacgccgg | caacatcatc | ccccgcctgt | acctgctgat | caccgtgggc | 1320 |
| gtggtgtacg | tgaagagctt | ccccagagc | cgcaaggaca | tcctgaagga | cctggtggag | 1380 |
| atgtgccgcg | gcgtgcagca | cccctgcgc | ggcctgttcc | tgcgcaacta | cctgctgcag | 1440 |
| tgcacccgca | acatcctgcc | cgacgagggc | gagcccaccg | acgaggagac | caccggcgac | 1500 |
| atcagcgaca | gcatggactt | cgtgctgctg | aacttcgccg | agatgaacaa | gctgtgggtg | 1560 |
| cgcatgcagc | accagggcca | cagccgcgac | cgcgagaagc | gcgagcgcga | cgccaggag | 1620 |
| ctgcgcatcc | tggtgggcac | caacctggtg | cgcctgagcc | agctggaggg | cgtgaacgtg | 1680 |
| gagcgctaca | agcagatcgt | gctgaccggc | atcctggagc | aggtggtgaa | ctgccgcgac | 1740 |
| gccctggccc | aggagtacct | gatggagtgc | atcatccagg | tgttcccga | cgagttccac | 1800 |
| ctgcagaccc | tgaacccctt | cctgcgcgcc | tgcgccgagc | tgcaccagaa | cgtgaacgtg | 1860 |
| aagaacatca | tcatcgccct | gatcgaccgc | ctggccctgt | cgcccaccg | cgaggacggc | 1920 |
| cccgggcatcc | ccgccgacat | caagctgttc | gacatcttca | gccagcaggt | ggccaccgtg | 1980 |
| atccagagcc | gccaggacat | gcccagcgag | gacgtggtga | gcctgcaggt | gagcctgatc | 2040 |

```
aacctggcca tgaagtgcta ccccgaccgc gtggactacg tggacaaggt gctggagacc    2100
accgtggaga tcttcaacaa gctgaacctg gagcacatcg ccaccagcag cgccgtgagc    2160
aaggagctga cccgcctgct gaagatcccc gtggacacct acaacaacat cctgaccgtg    2220
ctgaagctga agcacttcca ccccctgttc gagtacttcg actacgagag ccgcaagagc    2280
atgagctgct acgtgctgag caacgtgctg gactacaaca ccgagatcgt gagccaggac    2340
caggtggaca gcatcatgaa cctggtgagc accctgatcc aggaccagcc cgaccagccc    2400
gtggaggacc ccgaccccga ggacttcgcc gacgagcaga gcctggtggg ccgcttcatc    2460
cacctgctgc gcagcgagga ccccgaccag cagtacctga tcctgaacac cgcccgcaag    2520
cacttcggcg ccggcggcaa ccagcgcatc cgcttcaccc tgccccccct ggtgttcgcc    2580
gcctaccagc tggccttccg ctacaaggag aacagcaagg tggacgacaa gtgggagaag    2640
aagtgccaga agatcttcag cttcgcccac cagaccatca gcgccctgat caaggccgag    2700
ctggccgagc tgcccctgcg cctgttcctg cagggcgccc tggccgccgg cgagatcggc    2760
ttcgagaacc acgagaccgt ggcctacgag ttcatgagcc aggccttcag cctgtacgag    2820
gacgagatca gcgacagcaa ggcccagctg gccgccatca ccctgatcat cggcaccttc    2880
gagcgcatga agtgcttcag cgaggagaac cacgagcccc tgcgcaccca gtgcgccctg    2940
gccgccagca agctgctgaa gaagcccgac cagggccgcg ccgtgagcac ctgcgcccac    3000
ctgttctgga gcgccgcaa caccgacaag aacggcgagg agctgcacgg cggcaagcgc    3060
gtgatggagt gcctgaagaa ggccctgaag atcgccaacc agtgcatgga ccccagcctg    3120
caggtgcagc tgttcatcga gatcctgaac cgctacatct acttctacga gaaggagaac    3180
gacgccgtga ccatccaggt gctgaaccag ctgatccaga agatccgcga ggacctgccc    3240
aacctggaga gcagcgagga gaccgagcag atcaacaagc acttccacaa caccctggag    3300
cacctgcgcc tgcgccgcga gagccccgag agcgagggcc ccatctacga gggcctgatc    3360
ctgtgacaat tgttaattaa gtttaaaccc tcgaggccgc aagcttatcg ataatcaacc    3420
tctggattac aaaatttgtg aaagattgac tggtattctt aactatgttg ctccttttac    3480
gctatgtgga tacgctgctt taatgccttt gtatcatgct attgcttccc gtatggcttt    3540
cattttctcc tccttgtata atcctggtt gctgtctctt tatgaggagt tgtggcccgt    3600
tgtcaggcaa cgtggcgtgg tgtgcactgt gtttgctgac gcaacccca ctggttgggg    3660 cattgccacc acctgtcagc tcctttccgg gactttcgct ttccccctcc ctattgccac    3720
ggcggaactc atcgccgcct gccttgcccg ctgctggaca ggggctcggc tgttgggcac    3780
tgacaattcc gtggtgttgt cggggaaatc atcgtccttt ccttggctgc tcgcctgtgt    3840
tgccacctgg attctgcgcg ggacgtcctt ctgctacgtc ccttcggccc tcaatccagc    3900
ggaccttcct tcccgcggcc tgctgccggc tctgcggcct cttccgcgtc ttcgccttcg    3960
ccctcagacg agtcggatct ccctttgggc cgcctcccg catcgatacc gtcgactaga    4020
gctcgctgat cagcctcgac tgtgccttct agttgccagc catctgttgt ttgcccctcc    4080
cccgtgcctt ccttgaccct ggaaggtgcc actcccactg tcctttccta ataaaatgag    4140
gaaattgcat cgcattgtct gagtaggtgt cattctattc tggggggtgg ggtggggcag    4200
gacagcaagg gggaggattg ggaagacaat agcaggcatg ctggggagag atccacgata    4260
acaaacagct ttttggggt gaacatattg actgaattcc ctgcaggttg gccactccct    4320
ctctgcgcgc tcgctcgctc actgaggccg cccgggcaaa gcccgggcgt cgggcgacct    4380
ttggtcgccc ggcctcagtg agcgagcgag cgcgcagaga gggagtggcc aactccatca    4440
```

```
ctaggggttc ctgcggccgc tcgtacggtc tcgaggaatt cctgcaggat aacttgccaa    4500
cctcattcta aaatgtatat agaagcccaa aagacaataa caaaaatatt cttgtagaac    4560
aaaatgggaa agaatgttcc actaaatatc aagatttaga gcaaagcatg agatgtgtgg    4620
ggatagacag tgaggctgat aaaatagagt agagctcaga acagaccca ttgatatatg     4680 taagtgacct atgaaaaaaa tatggcattt tacaatggga aaatgatggt cttttctttt    4740
tttagaaaaa cagggaaata tatttatatg taaaaaataa aagggaaccc atatgtcata    4800
ccatacacac aaaaaaattc cagtgaatta taagtctaaa tggagaaggc aaaactttaa    4860
atcttttaga aaataatata gaagcatgca gaccagcctg gccaacatga tgaaaccctc    4920
tctactaata ataaaatcag tagaactact caggactact ttgagtggga agtccttttc    4980
tatgaagact tctttggcca aaattaggct ctaaatgcaa ggagatagtg catcatgcct    5040
ggctgcactt actgataaat gatgttatca ccatctttaa ccaaatgcac aggaacaagt    5100
tatggtactg atgtgctgga ttgagaagga gctctacttc cttgacagga cacatttgta    5160
tcaacttaaa aaagcagatt tttgccagca gaactattca ttcagaggta ggaaacttag    5220
aatagatgat gtcactgatt agcatggctt ccccatctcc acagctgctt cccacccagg    5280
ttgcccacag ttgagtttgt ccagtgctca gggctgccca ctctcagtaa gaagcccac     5340 accagcccct ctccaaatat gttggctgtt ccttccatta aagtgacccc actttagagc    5400
agcaagtgga tttctgtttc ttacagttca ggaaggagga gtcagctgtg agaacctgga    5460
gcctgagatg cttctaagtc ccactgctac tggggtcagg gaagccagac tccagcatca    5520
gcagtcagga gcactaagcc cttgccaaca tcctgtttct cagagaaact gcttccatta    5580
taatggttgt ccttttttaa gctatcaagc caaacaacca gtgtctacca ttattctcat    5640
cacctgaagc caagggttct agcaaaagtc aagctgtctt gtaatggttg atgtgcctcc    5700
agcttctgtc ttcagtcact ccactcttag cctgctctga atcaactctg accacagttc    5760
cctggagccc ctgccacctg ctgccctgc caccttctcc atctgcagtg ctgtgcagcc     5820
ttctgcactc ttgcagagct aataggtgga gacttgaagg aagaggagga aagtttctca    5880
taatagcctt gctgcaagct caaatgggag gtgggcactg tgcccaggag ccttggagca    5940
aaggctgtgc ccaacctctg actgcatcca ggtttggtct tgacagagat aagaagccct    6000
ggcttttgga gccaaaatct aggtcagact taggcaggat tctcaaagtt tatcagcaga    6060
acatgaggca gaagacccct tctgctccag cttcttcagg ctcaaccttc atcagaatag    6120
atagaaagag aggctgtgag ggttcttaaa acagaagcaa atctgactca gagaataaac    6180
aacctcctag taaactacag cttagacaga gcatctggtg gtgagtgtgc tcagtgtcct    6240
actcaactgt ctggtatcag ccctcatgag gacttctctt ctttccctca tagacctcca    6300
tctctgtttt ccttagcctg cagaaatctg gatggctatt cacagaatgc ctgtgctttc    6360
agagttgcat ttttctctg gtattctggt tcaagcattt gaaggtagga aaggttctcc     6420
aagtgcaaga aagccagccc tgagcctcaa ctgcctggct agtgtggtca gtaggatgca    6480
aaggctgttg aatgccacaa ggccaaactt taacctgtgt accacaagcc tagcagcaga    6540
ggcagctctg ctcactggaa ctctctgtct tctttctcct gagccttttc ttttcctgag    6600
ttttctagct ctcctcaacc ttacctctgc cctacccagg acaaacccaa gagccactgt    6660
ttctgtgatg tcctctccag ccctaattag gcatcatgac ttcagcctga ccttccatgc    6720
tcagaagcag tgctaatcca cttcagatga gctgctctat gcaacacagg cagagcctac    6780
```

```
aaacctttgc accagagccc tccacatatc agtgtttgtt catactcact tcaacagcaa    6840
atgtgactgc tgagattaag attttacaca agatggtctg taatttcaca gttagtttta    6900
tcccattagg tatgaaagaa ttagcataat tccccttaaa catgaatgaa tcttagattt    6960
tttaataaat agttttggaa gtaaagacag agacatcagg agcacaagga atagcctgag    7020
aggacaaaca gaacaagaaa gagtctggaa atacacagga tgttcttggc ctcctcaaag    7080
caagtgcaag cagatagtac cagcagcccc aggctatcag agcccagtga agagaagtac    7140
catgaaagcc acagctctaa ccaccctgtt ccagagtgac agacagtccc caagacaagc    7200
cagcctgagc cagagagaga actgcaagag aaagtttcta atttaggttc tgttagattc    7260
agacaagtgc aggtcatcct ctctccacag ctactcacct ctccagccta caaagcctg    7320
cagtccacac tccaacctg tgtctcacc tcctagcctc tcccaacatc ctgctctctg    7380
accatcttct gcatctctca tctcaccatc tcccactgtc tacagcctac tcttgcaact    7440
accatctcat tttctgacat cctgtctaca tcttctgcca tactctgcca tctaccatac    7500
cacctcttac catctaccac accatctttt atctccatcc ctctcagaag cctccaagct    7560
gaatcctgct ttatgtgttc atctcagccc ctgcatggaa agctgacccc agaggcagaa    7620
ctattcccag agagcttggc caagaaaaac aaaactacca gcctggccag gctcaggagt    7680
agtaagctgc agtgtctgtt gtgttctagc ttcaacagct gcaggagttc cactctcaaa    7740
tgctccacat ttctcacatc ctcctgattc tggtcactac ccatcttcaa agaacagaat    7800
atctcacatc agcatactgt gaaggactag tcatgggtgc agctgctcag agctgcaaag    7860
tcattctgga tggtggagag cttacaaaca tttcatgatg ctccccccgc tctgatggct    7920
ggagcccaat ccctacacag actcctgctg tatgtgtttt cctttcactc tgagccacag    7980
ccagagggca ggcattcagt ctcctcttca ggctgggct ggggcactga gaactcaccc    8040
aacaccttgc tctcactcct tctgcaaaac aagaaagagc tttgtgctgc agtagccatg    8100
aagaatgaaa ggaaggcttt aactaaaaaa tgtcagagat tattttcaac cccttactgt    8160
ggatcaccag caaggaggaa acacaacaca gagacatttt ttcccctcaa attatcaaaa    8220
gaatcactgc atttgttaaa gagagcaact gaatcaggaa gcagagtttt gaacatatca    8280
gaagttagga atctgcatca gagacaaatg cagtcatggt tgtttgctgc ataccagccc    8340
taatcattag aagcctcatg gacttcaaac atcattccct ctgacaagat gctctagcct    8400
aactccatga gataaaataa atctgccttt cagagccaaa gaagagtcca ccagcttctt    8460
ctcagtgtga acaagagctc cagtcaggtt agtcagtcca gtgcagtaga ggagaccagt    8520
ctgcatcctc taattttcaa aggcaagaag atttgtttac cctggacacc aggcacaagt    8580
gaggtcacag agctcttaga tatgcagtcc tcatgagtga ggagactaaa gcgcatgcca    8640
tcaagacttc agtgtagaga aaacctccaa aaaagcctcc tcactacttc tggaatagct    8700
cagaggccga ggcggcctcg gcctctgcat aaataaaaaa aattagtcag ccatggggcg    8760
gagaatgggc ggaactgggc ggagttaggg gcgggatggg cggagttagg ggcgggacta    8820
tggttgctga ctaattgaga tgcatgcttt gcatacttct gcctgctggg gagcctgggg    8880
actttccaca cctggttgct gactaattga gatgcatgct ttgcatactt ctgcctgctg    8940
gggagcctgg ggactttcca caccctaact gacacacatt ccacagctgc attaatgaat    9000
cggccaacgc gcggggagag gcggtttgcg tattgggcgc tcttccgctt cctcgctcac    9060
tgactcgctg cgctcggtcg ttcggctgcg gcgagcggta tcagctcact caaaggcggt    9120
aatacggtta tccacagaat caggggataa cgcaggaaag aacatgtgag caaaaggcca    9180
```

```
gcaaaaggcc aggaaccgta aaaaggccgc gttgctggcg ttttttccata ggctccgccc    9240
ccctgacgag catcacaaaa atcgacgctc aagtcagagg tggcgaaacc cgacaggact    9300
ataaagatac caggcgtttc ccctggaag ctccctcgtg cgctctcctg ttccgaccct     9360
gccgcttacc ggatacctgt ccgcctttct cccttcggga agcgtggcgc tttctcatag    9420
ctcacgctgt aggtatctca gttcggtgta ggtcgttcgc tccaagctgg gctgtgtgca    9480
cgaacccccc gttcagcccg accgctgcgc cttatccggt aactatcgtc ttgagtccaa    9540
cccggtaaga cacgacttat cgccactggc agcagccact ggtaacagga ttagcagagc    9600
gaggtatgta ggcggtgcta cagagttctt gaagtggtgg cctaactacg gctacactag    9660
aagaacagta tttggtatct gcgctctgct gaagccagtt accttcggaa aaagagttgg    9720
tagctcttga tccggcaaac aaaccaccgc tggtagcggt ggtttttttg tttgcaagca    9780
gcagattacg cgcagaaaaa aaggatctca agaagatcct ttgatctttt ctacggggtc    9840
tgacgctcag tggaacgaaa actcacgtta agggattttg gtcatgagat tatcaaaaag    9900
gatcttcacc tagatccttt taaattaaaa atgaagtttt aaatcaatct aaagtatata    9960
tgagtaaact tggtctgaca gttaccaatg cttaatcagt gaggcaccta tctcagcgat    10020
ctgtctattt cgttcatcca tagttgcctg actcctgcaa accacgttgt gtctcaaaat    10080
ctctgatgtt acattgcaca agataaaaat atatcatcat gaacaataaa actgtctgct    10140
tacataaaca gtaatacaag gggtgttatg agccatattc aacgggaaac gtcttgctcg    10200
aggccgcgat taaattccaa catggatgct gatttatatg ggtataaatg gctcgcgat    10260
aatgtcgggc aatcaggtgc gacaatctat cgattgtatg ggaagcccga tgcgccagag    10320
ttgtttctga acatggcaa aggtagcgtt gccaatgatg ttacagatga gatggtcaga    10380
ctaaactggc tgacggaatt tatgcctctt ccgaccatca agcattttat ccgtactcct    10440
gatgatgcat ggttactcac cactgcgatc cccgggaaaa cagcattcca ggtattagaa    10500
gaatatcctg attcaggtga aaatattgtt gatgcgctgg cagtgttcct gcgccggttg    10560
cattcgattc ctgtttgtaa ttgtcctttt aacagcgatc gcgtatttcg tctcgctcag    10620
gcgcaatcac gaatgaataa cggtttggtt gatgcgagtg attttgatga cgagcgtaat    10680
ggctggcctg ttgaacaagt ctggaaagaa atgcataagc ttttgccatt ctcaccggat    10740
tcagtcgtca ctcatggtga tttctcactt gataacctta ttttttgacga ggggaaatta    10800
ataggttgta ttgatgttgg acgagtcgga atcgcagacc gataccagga tcttgccatc    10860
ctatggaact gcctcggtga gttttctcct tcattacaga aacggctttt tcaaaaatat    10920
ggtattgata atcctgatat gaataaattg cagtttcatt tgatgctcga tgagttttc    10980
taagggcggc ctgccaccat acccacgccg aaacaagcgc tcatgagccc gaagtggcga    11040
gcccgatctt ccccatcggt gatgtcggcg atataggcgc cagcaaccgc acctgtggcg    11100
ccggtgatga gggcgcgcca agtcgacgtc cggcagtc                            11138
```

<210> SEQ ID NO 55
<211> LENGTH: 242
<212> TYPE: PRT
<213> ORGANISM: Artificial sequence
<220> FEATURE:
<223> OTHER INFORMATION: Synthetic polypeptide

<400> SEQUENCE: 55

```
Met Pro Arg Gly Phe Thr Trp Leu Arg Tyr Leu Gly Ile Phe Leu Gly
1               5                   10                  15
```

Val Ala Leu Gly Asn Glu Pro Leu Glu Met Trp Pro Leu Thr Gln Asn
        20                  25                  30

Glu Glu Cys Thr Val Thr Gly Phe Leu Arg Asp Lys Leu Gln Tyr Arg
            35                  40                  45

Ser Arg Leu Gln Tyr Met Lys His Tyr Phe Pro Ile Asn Tyr Lys Ile
50                  55                  60

Ser Val Pro Tyr Glu Gly Val Phe Arg Ile Ala Asn Val Thr Arg Leu
65                  70                  75                  80

Gln Arg Ala Gln Val Ser Glu Arg Glu Leu Arg Tyr Leu Trp Val Leu
                85                  90                  95

Val Ser Leu Ser Ala Thr Glu Ser Val Gln Asp Val Leu Leu Glu Gly
            100                 105                 110

His Pro Ser Trp Lys Tyr Leu Gln Glu Val Glu Thr Leu Leu Leu Asn
        115                 120                 125

Val Gln Gln Gly Leu Thr Asp Val Glu Val Ser Pro Lys Val Glu Ser
130                 135                 140

Val Leu Ser Leu Leu Asn Ala Pro Gly Pro Asn Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Ser Val Leu Asn Trp Gln Asp Cys Glu
            180                 185                 190

Val Pro Ser Pro Gln Ser Cys Ser Pro Glu Pro Ser Leu Gln Tyr Ala
        195                 200                 205

Ala Thr Gln Leu Tyr Pro Pro Pro Trp Ser Pro Ser Ser Pro Pro
210                 215                 220

His Ser Thr Gly Ser Val Arg Pro Val Arg Ala Gln Gly Glu Gly Leu
225                 230                 235                 240

Leu Pro

<210> SEQ ID NO 56
<211> LENGTH: 729
<212> TYPE: DNA
<213> ORGANISM: Artificial sequence
<220> FEATURE:
<223> OTHER INFORMATION: Synthetic polynucleotide

<400> SEQUENCE: 56
atgccccgcg gcttcacctg gctgcgctac ctgggcatct tcctgggcgt ggccctgggc      60
aacgagcccc tggagatgtg gcccctgacc cagaacgagg agtgcaccgt gaccggcttc     120
ctgcgcgaca agctgcagta ccgcagccgc ctgcagtaca tgaagcacta cttccccatc     180
aactacaaga tcagcgtgcc ctacgagggc gtgttccgca tcgccaacgt gacccgcctg     240
cagcgcgccc aggtgagcga gcgcgagctg cgctacctgt gggtgctggt gagcctgagc     300
gccaccgaga gcgtgcagga cgtgctgctg gagggccacc ccagctggaa gtacctgcag     360
gaggtggaga ccctgctgct gaacgtgcag cagggcctga ccgacgtgga ggtgagcccc     420
aaggtggaga gcgtgctgag cctgctgaac gccccggcc  caacctgaa gctggtgcgc     480 cccaaggccc tgctggacaa ctgcttccgc gtgatggagc tgctgtactg cagctgctgc     540
aagcagagca gcgtgctgaa ctggcaggac tgcgaggtgc ccagccccca gagctgcagc     600

```
cccgagccca gcctgcagta cgccgccacc cagctgtacc ccccccccc ctggagcccc    660 agcagccccc cccacagcac cggcagcgtg cgccccgtgc gcgcccaggg cgagggcctg    720
ctgccctaa                                                           729
```

<210> SEQ ID NO 57
<211> LENGTH: 230
<212> TYPE: PRT
<213> ORGANISM: Artificial sequence
<220> FEATURE:
<223> OTHER INFORMATION: Synthetic polypeptide

<400> SEQUENCE: 57

```
Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
    50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
        115                 120                 125

Leu Ala Asp Pro Leu Asp His Arg Asp Ala Gly Asp Leu Trp Phe Pro
    130                 135                 140

Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser Ile Leu
                165                 170                 175

Leu Leu Leu Ala Cys Ile Phe Leu Ile Lys Ile Leu Ala Ala Ser Ala
            180                 185                 190

Leu Trp Ala Ala Ala Trp His Gly Gln Lys Pro Gly Thr His Pro Pro
        195                 200                 205

Ser Glu Leu Asp Cys Gly His Asp Pro Gly Tyr Gln Leu Gln Thr Leu
    210                 215                 220

Pro Gly Leu Arg Asp Thr
225                 230
```

<210> SEQ ID NO 58
<211> LENGTH: 690
<212> TYPE: DNA
<213> ORGANISM: Artificial sequence
<220> FEATURE:
<223> OTHER INFORMATION: Synthetic polynucleotide

<400> SEQUENCE: 58

```
atggagcccc tgcgcctgct gatcctgctg ttcgtgaccg agctgagcgg cgcccacaac    60
accaccgtgt tccagggcgt ggccggccag agcctgcagg tgagctgccc ctacgacagc    120
atgaagcact ggggccgccg caaggcctgg tgccgccagc tgggcgagaa gggcccctgc    180
cagcgcgtgg tgagcaccca caacctgtgg ctgctgagct tcctgcgccg ctggaacggc    240
```

```
agcaccgcca tcaccgacga caccctgggc ggcaccctga ccatcaccct gcgcaacctg      300
cagccccacg acgccggcct gtaccagtgc cagagcctgc acggcagcga ggccgacacc      360
ctgcgcaagg tgctggtgga ggtgctggcc gaccccctgg accaccgcga cgccggcgac      420
ctgtggttcc ccggcgagag cgagagcttc gaggacgccc acgtggagca cagcatcagc      480
cgcagcctgc tggagggcga gatccccttc ccccccacca gcatcctgct gctgctggcc      540
tgcatcttcc tgatcaagat cctggccgcc agcgccctgt gggccgccgc ctggcacggc      600
cagaagcccg gcacccaccc ccccagcgag ctggactgcg ccacgaccc cggctaccag      660 ctgcagaccc tgcccggcct gcgcgacacc                                      690

<210> SEQ ID NO 59
<211> LENGTH: 11060
<212> TYPE: DNA
<213> ORGANISM: Artificial sequence
<220> FEATURE:
<223> OTHER INFORMATION: Synthetic polynucleotide

<400> SEQUENCE: 59
ttggccactc cctctctgcg cgctcgctcg ctcactgagg ccgggcgacc aaaggtcgcc       60
cgacgcccgg gctttgcccg ggcggcctca gtgagcgagc gagcgcgcag agagggagtg      120
gccaactcca tcactagggg ttcctgctag ctctgggtat ttaagcccga gtgagcacgc      180
agggtctcca ttttgaagcg ggaggttacg cgttcgtcga ctactagtgg gtaccagagc      240
tccctaggtt ctagaaccgg tgacgtctcc catggtgaag cttggatctg agggcggagt      300
tagggcggag ccaatcagcg tgcgccgttc cgaaagttgc cttttatggc tgggcggaga      360
atgggcggtg aacgccgatg attatataag gacgcgccgg gtgtggcaca gctagttccg      420
tcgcagccgg gatttgggtc gcggttcttg tttgtggatc cctgtgatcg tcacttggta      480
agtcactgac tgtctatgcc tgggaaaggg tgggcaggag atgggcagt gcaggaaaag      540 tggcactatg aaccctcctg gtggcgaggg gaggggggtg gtcctcgaac gccttgcaga      600
actggcctgg atacagagtg gaccggctgg ccccatctgg aagacttcga gatacactgt      660
tgtcttactg cgctcaacag tgtatctcga agtcttccaa atggtgccag ccatcgcagc      720
ggggtgcagg aaatggggc agcccccctt tttggctatc cttccacgtg ttcttttttg      780
tatcttttgt gtttcctaga aaacatctca gtcaccaccg cagccctagg aatgcatcta      840
gacaattgta ctaaccttct tctctttcct ctcctgacag tccggaaagc caccatggaa      900
ttcagcagcc ccagcagaga ggaatgcccc aagcctctga gccgggtgtc aatcatggcc      960
ggatctctga caggactgct gctgcttcag gccgtgtctt gggcttctgg cgctagacct     1020
tgcatcccca gagcttcgg ctacagcagc gtcgtgtgcg tgtgcaatgc cacctactgc     1080
gacagcttcg accctcctac ctttcctgct ctgggcacct tcagcagata cgagagcacc     1140
agatccggca cggatgga actgagcatg gacccatcc aggccaatca cacaggcact     1200
ggcctgctgc tgacactgca gcctgagcag aaattccaga agtgaaagg cttcggcgga     1260 gccatgacag atgccgccgc tctgaatatc ctggctctgt ctccaccagc tcagaacctg     1320
ctgctcaaga gctacttcag cgaggaaggc atcggctaca acatcatcag agtgccatg     1380 gccagctgcg acttcagcat caggacctac acctacgccg acacacccga cgatttccag     1440
ctgcacaact tcagcctgcc tgaagaggac accaagctga gatccctct gatccacaga     1500 gccctgcagc tggcacaaag acccgtgtca ctgctggcct ctccatggac atctcccacc     1560
```

```
tggctgaaaa caaatggcgc cgtgaatggc aagggcagcc tgaaaggcca acctggcgac   1620
atctaccacc agacctgggc cagatacttc gtgaagttcc tggacgccta tgccgagcac   1680
aagctgcagt tttgggccgt gacagccgag aacgaacctt ctgctggact gctgagcggc   1740 taccccttc agtgcctggg cttacacccc gagcaccagc gggactttat cgcccgtgat   1800
ctgggaccca cactggccaa tagcacccac cataatgtgc ggctgctgat gctggacgac   1860
cagagactgc ttctgcccca ctgggctaaa gtggtgctga cagatcctga ggccgccaaa   1920
tacgtgcacg aatcgccgt gcactggtat ctggactttc tggccctgc caaggccaca    1980 ctgggagaga cacacagact gttccccaac accatgctgt tcgccagcga agcctgtgtg   2040
ggcagcaagt tttgggaaca gagcgtgcgg ctcggcagct gggatagagg catgcagtac   2100
agccacagca tcatcaccaa cctgctgtac cacgtcgtcg gctggaccga ctggaatctg   2160
gccctgaatc ctgaaggcgg ccctaactgg gtccgaaact tcgtggacag ccccatcatc   2220
gtggacatca ccaaggacac cttctacaag cagcccatgt tctaccacct gggacacttc   2280
agcaagttca tccccgaggg ctctcagcgc gttggactgg tggcttccca gaagaacgat   2340
ctggacgccg tggctctgat gcaccctgat ggatctgctg tggtggtggt cctgaaccgc   2400
agcagcaaag atgtgcccct gaccatcaag gatcccgccg tgggattcct ggaaacaatc   2460
agccctggct actccatcca cacctacctg tggcgtagac aggagggcag aggaagtctt   2520
ctgacatgcg gagacgtgga agagaatccc ggccctatgc cccgcggctt cacctggctg   2580
cgctacctgg gcatcttcct gggcgtggcc ctgggcaacg agcccctgga gatgtggccc   2640
ctgacccaga acgaggagtg caccgtgacc ggcttcctgc gcgacaagct gcagtaccgc   2700
agccgcctgc agtacatgaa gcactacttc cccatcaact acaagatcag cgtgccctac   2760
gagggcgtgt ccgcatcgc caacgtgacc cgcctgcagc gcgcccaggt gagcgagcgc   2820
gagctgcgct acctgtgggt gctggtgagc ctgagcgcca ccgagagcgt gcaggacgtg   2880
ctgctggagg gccaccccag ctggaagtac ctgcaggagg tggagaccct gctgctgaac   2940
gtgcagcagg gcctgaccga cgtggaggtg agccccaagg tggagagcgt gctgagcctg   3000
ctgaacgccc ccggccccaa cctgaagctg gtgcgcccca aggccctgct ggacaactgc   3060
ttccgcgtga tggagctgct gtactgcagc tgctgcaagc agagcagcgt gctgaactgg   3120
caggactgcg aggtgcccag cccccagagc tgcagcccg agcccagcct gcagtacgcc   3180
gccacccagc tgtaccccc cccccctgg agcccagca gcccccccca cagcaccggc   3240
agcgtgcgcc ccgtgcgcgc ccagggcgag ggcctgctgc ctaatgaca attgttaatt   3300 aagtttaaac cctcgaggcc gcaagcttat cgataatcaa cctctggatt acaaaatttg   3360
tgaaagattg actggtattc ttaactatgt tgctcctttt acgctatgtg gatacgctgc   3420
tttaatgcct ttgtatcatg ctattgcttc ccgtatggct ttcattttct cctccttgta   3480
taaatcctgg ttgctgtctc tttatgagga gttgtggccc gttgtcaggc aacgtggcgt   3540
ggtgtgcact gtgtttgctg acgcaacccc cactggttgg gcattgcca ccacctgtca    3600 gctcctttcc gggactttcg ctttccccct cctattgcc acggcggaac tcatcgccgc    3660
ctgccttgcc cgctgctgga caggggctcg gctgttgggc actgacaatt ccgtggtgtt   3720
gtcggggaaa tcatcgtcct tccttggct gctcgcctgt gttgccacct ggattctgcg   3780
cgggacgtcc ttctgctacg tcccttcggc cctcaatcca gcggaccttc cttcccgcgg   3840
cctgctgccg gctctgcggc ctcttccgcg tcttcgcctt cgccctcaga cgagtcggat   3900
ctccctttgg gccgcctccc cgcatcgata ccgtcgacta gagctcgctg atcagcctcg   3960
```

```
actgtgcctt ctagttgcca gccatctgtt gtttgccct cccccgtgcc ttccttgacc      4020
ctggaaggtg ccactcccac tgtcctttcc taataaaatg aggaaattgc atcgcattgt      4080
ctgagtaggt gtcattctat tctgggggt ggggtggggc aggacagcaa gggggaggat       4140
tgggaagaca atagcaggca tgctggggag agatccacga taacaaacag cttttttggg      4200
gtgaacatat tgactgaatt ccctgcaggt tggccactcc ctctctgcgc gctcgctcgc      4260
tcactgaggc cgcccgggca aagcccgggc gtcgggcgac ctttggtcgc ccggcctcag      4320
tgagcgagcg agcgcgcaga gagggagtgg ccaactccat cactagggt tcctgcggcc       4380 gctcgtacgg tctcgaggaa ttcctgcagg ataacttgcc aacctcattc taaaatgtat      4440
atagaagccc aaaagacaat aacaaaaata ttcttgtaga acaaatggg aagaatgtt        4500 ccactaaata tcaagattta gagcaaagca tgagatgtgt ggggatagac agtgaggctg      4560
ataaaataga gtagagctca gaaacagacc cattgatata tgtaagtgac ctatgaaaaa     4620 aatatgcat tttacaatgg gaaaatgatg gtcttttttct tttttagaaa acagggaaa       4680 tatatttata tgtaaaaaat aaaagggaac ccatatgtca taccatacac acaaaaaaat     4740
tccagtgaat tataagtcta aatggagaag gcaaaacttt aaatctttta gaaaataata     4800
tagaagcatg cagaccagcc tggccaacat gatgaaaccc tctctactaa taataaaatc     4860
agtagaacta ctcaggacta cttttgagtgg gaagtccttt tctatgaaga cttcttggc      4920 caaaattagg ctctaaatgc aaggagatag tgcatcatgc ctggctgcac ttactgataa     4980
atgatgttat caccatctt aaccaaatgc acaggaacaa gttatggtac tgatgtgctg       5040
gattgagaag gagctctact tccttgacag gacacatttg tatcaactta aaaaagcaga     5100
tttttgccag cagaactatt cattcagagg taggaaactt agaatagatg atgtcactga     5160
ttagcatggc ttccccatct ccacagctgc ttcccaccca ggttgcccac agttgagttt     5220
gtccagtgct cagggctgcc cactctcagt aagaagcccc acaccagccc ctctccaaat     5280
atgttggctg ttccttccat taaagtgacc ccactttaga gcagcaagtg gatttctgtt     5340
tcttacagtt caggaaggag gagtcagctg tgagaacctg gagcctgaga tgcttctaag     5400
tcccactgct actggggtca gggaagccag actccagcat cagcagtcag gagcactaag     5460
cccttgccaa catcctgttt ctcagagaaa ctgcttccat tataatggtt gtccttttt     5520 aagctatcaa gccaaacaac cagtgtctac cattattctc atcacctgaa gccaaggtt     5580 ctagcaaaag tcaagctgtc ttgtaatggt tgatgtgcct ccagcttctg tcttcagtca     5640
ctccactctt agcctgctct gaatcaactc tgaccacagt tccctggagc ccctgccacc     5700
tgctgcccct gccaccttct ccatctgcag tgctgtgcag ccttctgcac tcttgcagag     5760
ctaataggtg gagacttgaa ggaagaggag gaaagtttct cataatagcc ttgctgcaag     5820
ctcaaatggg aggtgggcac tgtgcccagg agccttggag caaaggctgt gcccaacctc     5880
tgactgcatc caggtttggt cttgacagag ataagaagcc ctggcttttg gagccaaaat     5940
ctaggtcaga cttaggcagg attctcaaag tttatcagca gaacatgagg cagaagaccc     6000
tttctgctcc agcttcttca ggctcaacct tcatcagaat agatagaaag agaggctgtg     6060
agggttctta aaacagaagc aaatctgact cagagaataa acaacctcct agtaaactac     6120
agcttagaca gagcatctgg tggtgagtgt gctcagtgtc ctactcaact gtctggtatc     6180
agccctcatg aggacttctc ttcttttccct catagacctc catctctgtt ttccttagcc     6240
tgcagaaatc tggatggcta ttcacagaat gcctgtgctt tcagagttgc attttttctc     6300
```

```
tggtattctg gttcaagcat ttgaaggtag gaaaggttct ccaagtgcaa gaaagccagc    6360
cctgagcctc aactgcctgg ctagtgtggt cagtaggatg caaaggctgt tgaatgccac    6420
aaggccaaac tttaacctgt gtaccacaag cctagcagca gaggcagctc tgctcactgg    6480
aactctctgt cttctttctc ctgagccttt tcttttcctg agttttctag ctctcctcaa    6540
ccttacctct gccctaccca ggacaaaccc aagagccact gtttctgtga tgtcctctcc    6600
agccctaatt aggcatcatg acttcagcct gaccttccat gctcagaagc agtgctaatc    6660
cacttcagat gagctgctct atgcaacaca ggcagagcct acaaaccttt gcaccagagc    6720
cctccacata tcagtgtttg ttcatactca cttcaacagc aaatgtgact gctgagatta    6780
agattttaca caagatggtc tgtaatttca cagttagttt tatcccatta ggtatgaaag    6840
aattagcata attcccctta aacatgaatg aatcttagat tttttaataa atagttttgg    6900
aagtaaagac agagacatca ggagcacaag gaatagcctg agaggacaaa cagaacaaga    6960
aagagtctgg aaatacacag gatgttcttg gcctcctcaa agcaagtgca agcagatagt    7020
accagcagcc ccaggctatc agagcccagt gaagagaagt accatgaaag ccacagctct    7080
aaccaccctg ttccagagtg acagacagtc cccaagacaa gccagcctga gccagagaga    7140
gaactgcaag agaaagtttc taatttaggt tctgttagat tcagacaagt gcaggtcatc    7200
ctctctccac agctactcac ctctccagcc taacaaagcc tgcagtccac actccaaccc    7260
tggtgtctca cctcctagcc tctcccaaca tcctgctctc tgaccatctt ctgcatctct    7320
catctcacca tctcccactg tctacagcct actcttgcaa ctaccatctc attttctgac    7380
atcctgtcta catcttctgc catactctgc catctaccat accacctctt accatctacc    7440
acaccatctt ttatctccat ccctctcaga agcctccaag ctgaatcctg ctttatgtgt    7500
tcatctcagc ccctgcatgg aaagctgacc ccagaggcag aactattccc agagagcttg    7560
gccaagaaaa acaaaactac cagcctggcc aggctcagga gtagtaagct gcagtgtctg    7620
ttgtgttcta gcttcaacag ctgcaggagt tccactctca aatgctccac atttctcaca    7680
tcctcctgat tctggtcact acccatcttc aaagaacaga atatctcaca tcagcatact    7740
gtgaaggact agtcatgggt gcagctgctc agagctgcaa agtcattctg gatggtggag    7800
agcttacaaa catttcatga tgctcccccc gctctgatgg ctggagccca atccctacac    7860
agactcctgc tgtatgtgtt ttcctttcac tctgagccac agccagaggg caggcattca    7920
gtctcctctt caggctgggg ctggggcact gagaactcac ccaacacctt gctctcactc    7980
cttctgcaaa acaagaaaga gctttgtgct gcagtagcca tgaagaatga aaggaaggct    8040
ttaactaaaa aatgtcagag attatttttca accccttact gtggatcacc agcaaggagg    8100
aaacacaaca cagagacatt ttttcccctc aaattatcaa aagaatcact gcatttgtta    8160
aagagagcaa ctgaatcagg aagcagagtt ttgaacatat cagaagttag gaatctgcat    8220
cagagacaaa tgcagtcatg gttgtttgct gcataccagc cctaatcatt agaagcctca    8280
tggacttcaa acatcattcc ctctgacaag atgctctagc ctaactccat gagataaaat    8340
aaatctgcct ttcagagcca agaagagtc caccagcttc ttctcagtgt gaacaagagc    8400
tccagtcagg ttagtcagtc cagtgcagta gaggagacca gtctgcatcc tctaattttc    8460
aaaggcaaga agatttgttt accctggaca ccaggcacaa gtgaggtcac agagctctta    8520
gatatgcagt cctcatgagt gaggagacta aagcgcatgc catcaagact tcagtgtaga    8580 gaaacctcc aaaaaagcct cctcactact tctggaatag ctcagaggcc gaggcggcct    8640
cggcctctgc ataaataaaa aaaattagtc agccatgggg cggagaatgg gcggaactgg    8700
```

```
gcggagttag gggcgggatg ggcggagtta ggggcgggac tatggttgct gactaattga    8760
gatgcatgct ttgcatactt ctgcctgctg gggagcctgg ggactttcca cacctggttg    8820
ctgactaatt gagatgcatg ctttgcatac ttctgcctgc tggggagcct ggggactttc    8880
cacaccctaa ctgacacaca ttccacagct gcattaatga atcggccaac gcgcggggag    8940
aggcggtttg cgtattgggc gctcttccgc ttcctcgctc actgactcgc tgcgctcggt    9000
cgttcggctg cggcgagcgg tatcagctca ctcaaaggcg gtaatacggt tatccacaga    9060
atcaggggat aacgcaggaa agaacatgtg agcaaaaggc cagcaaaagg ccaggaaccg    9120
taaaaaggcc gcgttgctgg cgttttccca taggctccgc cccctgacg agcatcacaa      9180 aaatcgacgc tcaagtcaga ggtggcgaaa cccgacagga ctataaagat accaggcgtt    9240
tccccctgga agctccctcg tgcgctctcc tgttccgacc ctgccgctta ccggatacct    9300
gtccgccttt ctcccttcgg gaagcgtggc gctttctcat agctcacgct gtaggtatct    9360
cagttcggtg taggtcgttc gctccaagct gggctgtgtg cacgaacccc ccgttcagcc    9420
cgaccgctgc gccttatccg gtaactatcg tcttgagtcc aacccggtaa gacacgactt    9480
atcgccactg gcagcagcca ctggtaacag gattagcaga gcgaggtatg taggcggtgc    9540
tacagagttc ttgaagtggt ggcctaacta cggctacact agaagaacag tatttggtat    9600
ctgcgctctg ctgaagccag ttaccttcgg aaaaagagtt ggtagctctt gatccggcaa    9660
acaaaccacc gctggtagcg gtggtttttt tgtttgcaag cagcagatta cgcgcagaaa    9720
aaaaggatct caagaagatc ctttgatctt ttctacgggg tctgacgctc agtggaacga    9780
aaactcacgt taagggattt tggtcatgag attatcaaaa aggatcttca cctagatcct    9840
tttaaattaa aaatgaagtt ttaaatcaat ctaaagtata tatgagtaaa cttggtctga    9900
cagttaccaa tgcttaatca gtgaggcacc tatctcagcg atctgtctat ttcgttcatc    9960
catagttgcc tgactcctgc aaaccacgtt gtgtctcaaa atctctgatg ttacattgca    10020
caagataaaa atatatcatc atgaacaata aaactgtctg cttacataaa cagtaataca    10080
aggggtgtta tgagccatat tcaacgggaa acgtcttgct cgaggccgcg attaaattcc    10140
aacatggatg ctgatttata tgggtataaa tgggctcgcg ataatgtcgg gcaatcaggt    10200
gcgacaatct atcgattgta tgggaagccc gatgcgccag agttgtttct gaaacatggc    10260
aaaggtagcg ttgccaatga tgttacagat gagatggtca gactaaactg gctgacggaa    10320
tttatgcctc ttccgaccat caagcatttt atccgtactc ctgatgatgc atggttactc    10380
accactgcga tccccgggaa aacagcattc caggtattag aagaatatcc tgattcaggt    10440
gaaaatattg ttgatgcgct ggcagtgttc ctgcgccggt tgcattcgat tcctgtttgt    10500
aattgtcctt ttaacagcga tcgcgtattt cgtctcgctc aggcgcaatc acgaatgaat    10560
aacggtttgg ttgatgcgag tgattttgat gacgagcgta atggctggcc tgttgaacaa    10620
gtctggaaag aaatgcataa gcttttgcca ttctcaccgg attcagtcgt cactcatggt    10680
gatttctcac ttgataacct tatttttgac gaggggaaat taataggttg tattgatgtt    10740
ggacgagtcg gaatcgcaga ccgataccag gatcttgcca tcctatggaa ctgcctcggt    10800
gagttttctc cttcattaca gaaacggctt tttcaaaaat atggtattga taatcctgat    10860
atgaataaat tgcagtttca tttgatgctc gatgagtttt tctaagggcg gcctgccacc    10920
atacccacgc cgaaacaagc gctcatgagc ccgaagtggc gagcccgatc ttccccatcg    10980
```

```
gtgatgtcgg cgatataggc gccagcaacc gcacctgtgg cgccggtgat gagggcgcgc   11040
caagtcgacg tccggcagtc                                                11060

<210> SEQ ID NO 60
<211> LENGTH: 10913
<212> TYPE: DNA
<213> ORGANISM: Artificial sequence
<220> FEATURE:
<223> OTHER INFORMATION: Synthetic polynucleotide

<400> SEQUENCE: 60
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg agggcggagt    300
tagggcggag ccaatcagcg tgcgccgttc cgaaagttgc cttttatggc tgggcggaga    360
atgggcggtg aacgccgatg attatataag gacgcgccgg gtgtggcaca gctagttccg    420
tcgcagccgg gatttgggtc gcggttcttg tttgtggatc cctgtgatcg tcacttggta    480
agtcactgac tgtctatgcc tgggaaaggg tgggcaggag atgggcagt gcaggaaaag    540 tggcactatg aaccctcctg gtggcgaggg gagggggggtg gtcctcgaac gccttgcaga    600
actggcctgg atacagagtg gaccggctgg ccccatctgg aagacttcga gatacactgt    660
tgtcttactg cgctcaacag tgtatctcga agtcttccaa atggtgccag ccatcgcagc    720
ggggtgcagg aaatggggc agcccccctt tttggctatc cttccacgtg ttctttttg    780 tatcttttgt gtttcctaga aaacatctca gtcaccaccg cagccctagg aatgcatcta    840
gacaattgta ctaaccttct tctctttcct ctcctgacag tccggaaagc caccatggaa    900
ttcagcagcc ccagcagaga ggaatgcccc aagcctctga gccgggtgtc aatcatggcc    960
ggatctctga caggactgct gctgcttcag gccgtgtctt gggcttctgg cgctagacct   1020
tgcatcccca agagcttcgg ctacagcagc gtcgtgtgcg tgtgcaatgc cacctactgc   1080
gacagcttcg accctcctac ctttcctgct ctgggcacct tcagcagata cgagagcacc   1140
agatccggca gacggatgga actgagcatg ggacccatcc aggccaatca cacaggcact   1200
ggcctgctgc tgacactgca gcctgagcag aaattccaga agtgaaaagg cttcggcgga   1260
gccatgacga atgccgccgc tctgaatatc ctggctctgt ctccaccagc tcagaacctg   1320
ctgctcaaga gctacttcag cgaggaaggc atcggctaca acatcatcag agtgcccatg   1380
gccagctgcg acttcagcat caggacctac acctacgccg acacacccga cgatttccag   1440
ctgcacaact tcagcctgcc tgaagaggac accaagctga gatccctct gatccacaga   1500 gccctgcagc tggcacaaag acccgtgtca ctgctggcct ctccatggac atctcccacc   1560
tggctgaaaa caaatggcgc cgtgaatggc aagggcagcc tgaaaggcca acctggcgac   1620
atctaccacc agacctgggc cagatacttc gtgaagttcc tggacgccta tgccgagcac   1680
aagctgcagt tttgggccgt gacagccgag aacgaacctt ctgctggact gctgagcggc   1740
tacccctttc agtgcctggg ctttacaccc gagcaccagc gggactttat cgcccgtgat   1800
ctggacccca cactgccaa tagcacccac cataatgtgc ggctgctgat gctgacgac   1860 cagagactgc ttctgcccca ctgggctaaa gtggtgctga cagatcctga ggccgccaaa   1920
```

```
tacgtgcacg gaatcgccgt gcactggtat ctggactttc tggcccctgc caaggccaca    1980
ctgggagaga cacacagact gttccccaac accatgctgt tcgccagcga agcctgtgtg    2040
ggcagcaagt tttgggaaca gagcgtgcgg ctcggcagct gggatagagg catgcagtac    2100
agccacagca tcatcaccaa cctgctgtac cacgtcgtcg gctggaccga ctggaatctg    2160
gccctgaatc ctgaaggcgg ccctaactgg gtccgaaact tcgtggacag ccccatcatc    2220
gtggacatca ccaaggacac cttctacaag cagcccatgt tctaccacct gggacacttc    2280
agcaagttca tccccgaggg ctctcagcgc gttggactgg tggcttccca gaagaacgat    2340
ctggacgccg tggctctgat gcaccctgat ggatctgctg tggtggtggt cctgaaccgc    2400
agcagcaaag atgtgcccct gaccatcaag gatcccgccg tgggattcct ggaaacaatc    2460
agccctggct actccatcca cacctacctg tggcgtagac agtgattgtg ccgaaccgc    2520 cgaactcaga ggccggcccc agaaaacccg agcgagtagg gggcggcgcg caggagggag    2580
gagaactggg ggcgcgggag gctggtgggt gtgggggtg gagatgtaga agatgtgacg    2640
ccgcggcccg gcgggtgcca gattagcgga cgcggtgccc gcggttgcaa cgggatcccg    2700
ggcgctgcag cttgggaggc ggctctcccc aggcggcgtc cgcggagaca cccatccgtg    2760
aaccccaggt cccgggccgc cggctcgccg cgcaccaggg gccggcggac agaagagcgg    2820
ccgagcggct cgaggctggg ggaccgcggg cgcggccgcg cgctgccggg cgggaggctg    2880
gggggccggg gccggggccg tgccccggag cgggtcggag gccggggccg gggccggggg    2940
acggcggctc cccgcgcggc tccagcggct cggggatccc ggccgggccc gcagggacc    3000 atgatgcccc gcggcttcac ctggctgcgc tacctgggca tcttcctggg cgtggccctg    3060
ggcaacgagc ccctggagat gtggcccctg acccagaacg aggagtgcac cgtgaccggc    3120
ttcctgcgcg acaagctgca gtaccgcagc cgcctgcagt acatgaagca ctacttcccc    3180
atcaactaca gatcagcgt gccctacgag ggcgtgttcc gcatcgccaa cgtgacccgc    3240
ctgcagcgcg cccaggtgag cgagcgcgag ctgcgctacc tgtgggtgct ggtgagcctg    3300
agcgccaccg agagcgtgca ggacgtgctg ctggagggcc accccagctg gaagtacctg    3360
caggaggtgg agaccctgct gctgaacgtg cagcagggcc tgaccgacgt ggaggtgagc    3420
cccaaggtgg agagcgtgct gagcctgctg aacgcccccg gccccaacct gaagctggtg    3480
cgccccaagg ccctgctgga caactgcttc cgcgtgatgg agctgctgta ctgcagctgc    3540
tgcaagcaga gcagcgtgct gaactggcag gactgcgagg tgcccagccc ccagagctgc    3600
agccccgagc ccagcctgca gtacgccgcc acccagctgt accccccccc ccctggagc    3660 cccagcagcc cccccacag caccggcagc gtgcgccccg tgcgcgccca gggcgagggc    3720
ctgctgccct aatgacaatt gttaattaag tttaaaccct cgaggccgca agccgcatcg    3780
ataccgtcga ctagagctcg ctgatcagcc tcgactgtgc cttctagttg ccagccatct    3840
gttgtttgcc cctcccccgt gccttccttg accctggaag gtgccactcc cactgtcctt    3900
tcctaataaa atgaggaaat tgcatcgcat tgtctgagta ggtgtcattc tattctgggg    3960
ggtggggtgg ggcaggacag caaggggag gattgggaag acaatagcag gcatgctggg    4020
gagagatcca cgataacaaa cagctttttt ggggtgaaca tattgactga attccctgca    4080
ggttggccac tccctctctg cgcgctcgct cgctcactga ggccgcccgg gcaaagcccg    4140
ggcgtcgggc gacctttggt cgcccggcct cagtgagcga gcgagcgcgc agagagggag    4200
tggccaactc catcactagg ggttcctgcg gccgctcgta cggtctcgag gaattcctgc    4260
aggataactt gccaacctca ttctaaaatg tatatagaag cccaaaagac aataacaaaa    4320
```

```
atattcttgt agaacaaaat gggaaagaat gttccactaa atatcaagat ttagagcaaa    4380
gcatgagatg tgtggggata gacagtgagg ctgataaaat agagtagagc tcagaaacag    4440
acccattgat atatgtaagt gacctatgaa aaaatatgg cattttacaa tgggaaaatg     4500
atggtctttt tcttttttag aaaaacaggg aaatatattt atatgtaaaa aataaaaggg    4560
aacccatatg tcataccata cacacaaaaa aattccagtg aattataagt ctaaatggag    4620
aaggcaaaac tttaaatctt ttagaaaata atatagaagc atgcagacca gcctggccaa    4680
catgatgaaa ccctctctac taataataaa atcagtagaa ctactcagga ctactttgag    4740
tgggaagtcc ttttctatga agacttcttt ggccaaaatt aggctctaaa tgcaaggaga    4800
tagtgcatca tgcctggctg cacttactga taaatgatgt tatcaccatc tttaaccaaa    4860
tgcacaggaa caagttatgg tactgatgtg ctggattgag aaggagctct acttccttga    4920
caggacacat ttgtatcaac ttaaaaaagc agattttgc  cagcagaact attcattcag    4980
aggtaggaaa cttagaatag atgatgtcac tgattagcat ggcttcccca tctccacagc    5040
tgcttcccac ccaggttgcc cacagttgag tttgtccagt gctcagggct gcccactctc    5100
agtaagaagc cccacaccag cccctctcca aatatgttgg ctgttccttc cattaaagtg    5160
accccacttt agagcagcaa gtggatttct gtttcttaca gttcaggaag gaggagtcag    5220
ctgtgagaac ctggagcctg agatgcttct aagtcccact gctactgggg tcagggaagc    5280
cagactccag catcagcagt caggagcact aagcccttgc caacatcctg tttctcagag    5340
aaactgcttc cattataatg gttgtccttt tttaagctat caagccaaac aaccagtgtc    5400
taccattatt ctcatcacct gaagccaagg gttctagcaa aagtcaagct gtcttgtaat    5460
ggttgatgtg cctccagctt ctgtcttcag tcactccact cttagcctgc tctgaatcaa    5520
ctctgaccac agttccctgg agcccctgcc acctgctgcc cctgccacct tctccatctg    5580
cagtgctgtg cagccttctg cactcttgca gagctaatag gtggagactt gaaggaagag    5640
gaggaaagtt tctcataata gccttgctgc aagctcaaat gggaggtggg cactgtgccc    5700
aggagccttg gagcaaaggc tgtgcccaac ctctgactgc atccaggttt ggtcttgaca    5760
gagataagaa gccctggctt ttggagccaa aatctaggtc agacttaggc aggattctca    5820
aagtttatca gcagaacatg aggcagaaga ccctttctgc tccagcttct tcaggctcaa    5880
ccttcatcag aatagataga aagagaggct gtgagggttc ttaaaacaga agcaaatctg    5940
actcagagaa taaacaacct cctagtaaac tacagcttag acagagcatc tggtggtgag    6000
tgtgctcagt gtcctactca actgtctggt atcagccctc atgaggactt ctcttctttc    6060
cctcatagac ctccatctct gttttcctta gcctgcagaa atctggatgg ctattcacag    6120
aatgcctgtg ctttcagagt tgcatttttt ctctggtatt ctggttcaag catttgaagg    6180
taggaaaggt tctccaagtg caagaaagcc agccctgagc ctcaactgcc tggctagtgt    6240
ggtcagtagg atgcaaaggc tgttaatgc  acaaggcca acttaacc   tgtgtaccac     6300 aagcctagca gcagaggcag ctctgctcac tggaactctc tgtcttcttt ctcctgagcc    6360 ttttctttc  ctgagttttc tagctctcct caaccttacc tctgccctac ccaggacaaa    6420
cccaagagcc actgtttctg tgatgtcctc tccagcccta attaggcatc atgacttcag    6480
cctgaccttc catgctcaga agcagtgcta atccacttca gatgagctgc tctatgcaac    6540
acaggcagag cctacaaacc tttgcaccag agccctccac atatcagtgt ttgttcatac    6600
tcacttcaac agcaaatgtg actgctgaga ttaagatttt acacaagatg gtctgtaatt    6660
```

-continued

```
tcacagttag ttttatccca ttaggtatga aagaattagc ataattcccc ttaaacatga    6720
atgaatctta gatttttta taaatagttt tggaagtaaa gacagagaca tcaggagcac    6780
aaggaatagc ctgagaggac aaacagaaca agaaagagtc tggaaataca caggatgttc    6840
ttggcctcct caaagcaagt gcaagcagat agtaccagca gccccaggct atcagagccc    6900
agtgaagaga agtaccatga aagccacagc tctaaccacc ctgttccaga gtgacagaca    6960
gtccccaaga caagccagcc tgagccgag agagaactgc aagagaaagt ttctaattta    7020
ggttctgtta gattcagaca agtgcaggtc atcctctctc cacagctact cacctctcca    7080
gcctaacaaa gcctgcagtc cacactccaa ccctggtgtc tcacctccta gcctctccca    7140
acatcctgct ctctgaccat cttctgcatc tctcatctca ccatctccca ctgtctacag    7200
cctactcttg caactaccat ctcattttct gacatcctgt ctacatcttc tgccatactc    7260
tgccatctac cataccacct cttaccatct accacaccat cttttatctc catccctctc    7320
agaagcctcc aagctgaatc ctgctttatg tgttcatctc agccctgca tggaaagctg    7380 accccagagg cagaactatt cccagagagc ttggccaaga aaaacaaaac taccagcctg    7440
gccaggctca ggagtagtaa gctgcagtgt ctgttgtgtt ctagcttcaa cagctgcagg    7500
agttccactc tcaaatgctc cacatttctc acatcctcct gattctggtc actacccatc    7560
ttcaaagaac agaatatctc acatcagcat actgtgaagg actagtcatg ggtgcagctg    7620
ctcagagctg caaagtcatt ctggatggtg gagagcttac aaacatttca tgatgctccc    7680
cccgctctga tggctggagc ccaatcccta cacagactcc tgctgtatgt gttttccttt    7740
cactctgagc cacagccaga gggcaggcat tcagtctcct cttcaggctg gggctggggc    7800
actgagaact cacccaacac cttgctctca ctccttctgc aaaacaagaa agagctttgt    7860
gctgcagtag ccatgaagaa tgaaaggaag gctttaacta aaaaatgtca gagattattt    7920 tcaaccccctt actgtggatc accagcaagg aggaaacaca acacagagac atttttttccc    7980 ctcaaattat caaagaatc actgcatttg ttaaagagag caactgaatc aggaagcaga    8040
gttttgaaca tatcagaagt taggaatctg catcagagac aaatgcagtc atggttgttt    8100
gctgcatacc agccctaatc attagaagcc tcatggactt caaacatcat tccctctgac    8160
aagatgctct agcctaactc catgagataa aataaatctg cctttcagag ccaaagaaga    8220
gtccaccagc ttcttctcag tgtgaacaag agctccagtc aggttagtca gtccagtgca    8280
gtagaggaga ccagtctgca tcctctaatt ttcaaaggca agaagatttg tttaccctgg    8340
acaccaggca caagtgaggt cacagagctc ttagatatgc agtcctcatg agtgaggaga    8400
ctaaagcgca tgccatcaag acttcagtgt agagaaaacc tccaaaaaag cctcctcact    8460
acttctggaa tagctcagag gccgaggcgg cctcggcctc tgcataaata aaaaaaatta    8520
gtcagccatg gggcggagaa tgggcggaac tgggcggagt taggggcggg atgggcggag    8580
ttaggggcgg gactatggtt gctgactaat tgagatgcat gctttgcata cttctgcctg    8640
ctggggagcc tggggacttt ccacacctgg ttgctgacta attgagatgc atgctttgca    8700
tacttctgcc tgctggggag cctggggact ttccacaccc taactgacac acattccaca    8760
gctgcattaa tgaatcggcc aacgcgcggg gagaggcggt ttgcgtattg ggcgctcttc    8820
cgcttcctcg ctcactgact cgctgcgctc ggtcgttcgg ctgcggcgag cggtatcagc    8880
tcactcaaag gcggtaatac ggttatccac agaatcaggg gataacgcag gaaagaacat    8940
gtgagcaaaa ggccagcaaa aggccaggaa ccgtaaaaag gccgcgttgc tggcgttttt    9000
ccataggctc cgcccccctg acgagcatca caaaaatcga cgctcaagtc agaggtggcg    9060
```

```
aaacccgaca ggactataaa gataccaggc gtttccccct ggaagctccc tcgtgcgctc    9120
tcctgttccg accctgccgc ttaccggata cctgtccgcc tttctccctt cgggaagcgt    9180
ggcgctttct catagctcac gctgtaggta tctcagttcg gtgtaggtcg ttcgctccaa    9240
gctgggctgt gtgcacgaac ccccgttca gcccgaccgc tgcgccttat ccggtaacta    9300
tcgtcttgag tccaacccgg taagacacga cttatcgcca ctggcagcag ccactggtaa    9360
caggattagc agagcgaggt atgtaggcgg tgctacagag ttcttgaagt ggtggcctaa    9420
ctacggctac actagaagaa cagtatttgg tatctgcgct ctgctgaagc cagttacctt    9480
cggaaaaaga gttggtagct cttgatccgg caaacaaacc accgctggta gcggtggttt    9540
ttttgtttgc aagcagcaga ttacgcgcag aaaaaaagga tctcaagaag atcctttgat    9600
cttttctacg gggtctgacg ctcagtggaa cgaaaactca cgttaaggga ttttggtcat    9660
gagattatca aaaggatctc tcacctagat ccttttaaat taaaaatgaa gttttaaatc    9720
aatctaaagt atatatgagt aaacttggtc tgacagttac caatgcttaa tcagtgaggc    9780
acctatctca gcgatctgtc tatttcgttc atccatagtt gcctgactcc tgcaaaccac    9840
gttgtgtctc aaaatctctg atgttacatt gcacaagata aaaatatatc atcatgaaca    9900
ataaaactgt ctgcttacat aaacagtaat acaagggggtg ttatgagcca tattcaacgg    9960
gaaacgtctt gctcgaggcc gcgattaaat tccaacatgg atgctgattt atatgggtat   10020
aaatgggctc gcgataatgt cggcaatca ggtgcgacaa tctatcgatt gtatgggaag   10080
cccgatgcgc cagagttgtt tctgaaacat ggcaaaggta gcgttgccaa tgatgttaca   10140
gatgagatgg tcagactaaa ctggctgacg gaatttatgc ctcttccgac catcaagcat   10200
tttatccgta ctcctgatga tgcatggtta ctcaccactg cgatccccgg aaaacagca   10260 ttccaggtat tagaagaata tcctgattca ggtgaaaata ttgttgatgc gctggcagtg   10320
ttcctgcgcc ggttgcattc gattcctgtt tgtaattgtc cttttaacag cgatcgcgta   10380
tttcgtctcg ctcaggcgca atcacgaatg aataacggtt tggttgatgc gagtgatttt   10440
gatgacgagc gtaatggctg gcctgttgaa caagtctgga agaaaatgca taagcttttg   10500
ccattctcac cggattcagt cgtcactcat ggtgatttct cacttgataa ccttattttt   10560
gacgagggga attaatagg ttgtattgat gttggacgag tcggaatcgc agaccgatac   10620
caggatcttg ccatcctatg gaactgcctc ggtgagtttt ctccttcatt acagaaacgg   10680 cttttttcaaa aatatggtat tgataatcct gatatgaata aattgcagtt tcatttgatg   10740
ctcgatgagt ttttctaagg gcggcctgcc accatacccca gccgaaaca gcgctcatg   10800 agcccgaagt ggcgagcccg atcttcccca tcggtgatgt cggcgatata ggcgccagca   10860
accgcacctg tggcgccggt gatgagggcg cgccaagtcg acgtccggca gtc           10913
```

<210> SEQ ID NO 61
<211> LENGTH: 11209
<212> TYPE: DNA
<213> ORGANISM: Artificial sequence
<220> FEATURE:
<223> OTHER INFORMATION: Synthetic polynucleotide

<400> SEQUENCE: 61

```
ttggccactc cctctctgcg cgctcgctcg ctcactgagg ccgggcgacc aaaggtcgcc     60
cgacgcccgg gctttgcccg gcggcctca gtgagcgagc gagcgcgcag agagggagtg    120
gccaactcca tcactagggg ttcctgctag ctctgggtat ttaagcccga gtgagcacgc    180
```

```
agggtctcca tttttgaagcg ggaggttacg cgttcgtcga ctactagtgg gtaccagagc    240
tccctaggtt ctagaaccgg tgacgtctcc catggtgaag cttggatctg agggcggagt    300
tagggcggag ccaatcagcg tgcgccgttc cgaaagttgc cttttatggc tgggcggaga    360
atgggcggtg aacgccgatg attatataag gacgcgccgg gtgtggcaca gctagttccg    420
tcgcagccgg gatttgggtc gcggttcttg tttgtggatc cctgtgatcg tcacttggta    480
agtcactgac tgtctatgcc tgggaaaggg tgggcaggag atggggcagt gcaggaaaag    540
tggcactatg aaccctgcag ccctaggaat gcatctagac aattgtacta accttcttct    600
ctttcctctc ctgacagtcc ggaaagccac catggaattc agcagcccca gcagagagga    660
atgccccaag cctctgagcc gggtgtcaat catggccgga tctctgacag gactgctgct    720
gcttcaggcc gtgtcttggg cttctggcgc tagaccttgc atccccaaga gcttcggcta    780
cagcagcgtc gtgtgcgtgt gcaatgccac ctactgcgac agcttcgacc ctcctacctt    840
tcctgctctg gcaccttca gcagatacga gagcaccaga tccggcagac ggatggaact    900
gagcatggga cccatccagg ccaatcacac aggcactggc ctgctgctga cactgcagcc    960
tgagcagaaa ttccagaaag tgaaaggctt cggcggagcc atgacagatg ccgccgctct   1020
gaatatcctg gctctgtctc caccagctca gaacctgctg ctcaagagct acttcagcga   1080
ggaaggcatc ggctacaaca tcatcagagt gcccatggcc agctgcgact tcagcatcag   1140
gacctacacc tacgccgaca cacccgacga tttccagctg cacaacttca gcctgcctga   1200
agaggacacc aagctgaaga tccctctgat ccacagagcc ctgcagctgg cacaaagacc   1260
cgtgtcactg ctggcctctc catggacatc tcccacctgg ctgaaaacaa atggcgccgt   1320
gaatggcaag ggcagcctga aaggccaacc tggcgacatc taccaccaga cctgggccag   1380
atacttcgtg aagttcctgg acgcctatgc cgagcacaag ctgcagtttt gggccgtgac   1440
agccgagaac gaaccttctg ctggactgct gagcggctac ccctttcagt gcctgggctt   1500
tacacccgag caccagcggg actttatcgc ccgtgatctg ggaccacaca tggccaatag   1560
cacccaccat aatgtgcggc tgctgatgct ggacgaccag agactgcttc tgccccactg   1620
ggctaaagtg gtgctgacag atcctgaggc cgccaaatac gtgcacggaa tcgccgtgca   1680
ctggtatctg gactttctgg cccctgccaa ggccacactg ggagagacac acagactgtt   1740
ccccaacacc atgctgttcg ccagcgaagc tgtgtgggc agcaagttt gggaacagag   1800
cgtgcggctc ggcagctggg atagaggcat gcagtacagc cacagcatca tcaccaacct   1860
gctgtaccac gtcgtcggct ggaccgactg gaatctggcc ctgaatcctg aaggcggccc   1920
taactgggtc cgaaacttcg tggacagccc catcatcgtg gacatcacca aggacacctt   1980
ctacaagcag cccatgttct accacctggg acacttcagc aagttcatcc ccagagggctc   2040
tcagcgcgtt ggactggtgg cttcccagaa gaacgatctg gacgccgtgg ctctgatgca   2100
ccctgatgga tctgctgtgg tggtggtcct gaaccgcagc agcaaagatg tgcccctgac   2160
catcaaggat cccgccgtgg gattcctgga acaatcagc cctggctact ccatccacac   2220
ctacctgtgg cgtagacagt gacaattgtt aattaagttt aaaccctcga ggccgcaagc   2280
cgcatcgata ccgtcgacta gagctcgctg atcagcctcg actgtgcctt ctagttgcca   2340
gccatctgtt gtttgcccct cccccgtgcc ttccttgacc ctggaaggtg ccactcccac   2400
tgtcctttcc taataaaatg aggaaattgc atcgcattgt ctgagtaggt gtcattctat   2460
tctgggggt ggggtgggggc aggacagcaa ggggaggat tggaagaca atagcaggca   2520
tgctggggag agatccacga taacaaacag cttttttggg ggatatcaaa ctgcctgttt   2580
```

```
gggcttctca tttcttacct cccct tccct ctcccacctg ctactgggtg catctctgct    2640
ccccccttcc ccagcagatg gttacctttg ggctgttgct ttcttgtcac catctgagtt    2700
ctcagacgct ggaaagccat gttctcggct ctgtgaatga caatgctgac tggagtgctg    2760
cccctctgta aagggctggg tgtggatggt cacaagcccc tcacatgcct cagccaagag    2820
gaagtagtac aggggtcagc ccagaggtcc aggggaaagg agtggaaacc gatttcccca    2880
ccaagggagg ggcctgtacc tcagctgttc ccatagctta cttgccacaa ctgccaagca    2940
agtttcgctg agtttgacac atggatccct gtggatcaac tgccctagga ctccgtttgc    3000
acccatgtga cactgttgac tttgccctga cgaagcaggg ccaacagtcc cctaacttaa    3060
ttacaaaaac taatgactaa gagagaggtg gctagagctg aggcccctga gtcaggctgt    3120
gggtgggatc atctccagta caggaagtga gactttcatt tcctcctttc caagagaggg    3180
ctgagggagc agggttgagc aactggtgca gacagcctag ctggactttg ggtgaggcgg    3240
ttcagccata tcgaattctg ctggggctac tggcaggtaa ggaggaagga ggctgagggg    3300
aggggggccc tgggagggag cctgccctgg gttgctaacc atctcctctc tgccaaaagt    3360
ccggaaagcc accatggagc ccctgcgcct gctgatcctg ctgttcgtga ccagctgag    3420
cggcgcccac aacaccaccg tgttccaggg cgtggccggc cagagcctgc aggtgagctg    3480
cccctacgac agcatgaagc actggggcg ccgcaaggcc tggtgccgcc agctgggcga    3540
gaagggcccc tgccagcgcg tggtgagcac ccacaacctg tggctgctga gcttcctgcg    3600
ccgctggaac ggcagcaccg ccatcaccga cgacacc ctg ggcggcaccc tgaccatcac    3660
cctgcgcaac ctgcagcccc acgacgccgg cctgtaccag tgccagagcc tgcacggcag    3720
cgaggccgac accctgcgca aggtgctggt ggaggtgctg gccgaccccc tggaccaccg    3780
cgacgccggc gacctgtggt tccccggcga gagcgagagc ttcgaggacg cccacgtgga    3840
gcacagcatc agccgcagcc tgctggaggg cgagatcccc ttccccccca ccagcatcct    3900
gctgctgctg gcctgcatct tcctgatcaa gatcctggcc gccagcgccc tgtgggccgc    3960
cgcctggcac ggccagaagc ccggcaccca cccccccagc gagctggact gcggccacga    4020
ccccggctac cagctgcaga ccctgcccgg cctgcgcgac acctgaccca ggggactcag    4080
cggccgctcg agtctagagg gcccgtttaa acccgctgat cagcctcgaa gacatgataa    4140
gatacattga tgagtttgga caaccacaa caagaatgca gtgaaaaaaa tgctttattt    4200
gtgaaatttg tgatgctatt gctttatttg taaccattat aagctgcaat aaacaagtta    4260
acaacaacaa ttgcattcat tttatgtttc aggttcaggg ggagatgtgg gaggtttttt    4320
aaagcaagta aacctctac aaatgtggta tgaacatatt gactgaattc cctgcaggtt    4380
ggccactccc tctctgcgcg ctcgctcgct cactgaggcc gcccgggcaa agcccgggcg    4440
tcgggcgacc tttggtcgcc cggcctcagt gagcgagcga gcgcgcagag agggagtggc    4500
caactccatc actaggggtt cctgcggccg ctcgtacggt ctcgaggaat tcctgcagga    4560
taacttgcca acctcattct aaaatgtata tagaagccca aaagacaata acaaaaatat    4620
tcttgtagaa caaatggga aagaatgttc cactaaatat caagatttag agcaaagcat    4680
gagatgtgtg gggatagaca gtgaggctga taaaatagag tagagctcag aaacagaccc    4740
attgatatat gtaagtgacc tatgaaaaaa atatggcatt ttacaatggg aaaatgatgg    4800
tctttttctt tttagaaaaa acagggaaat atatttatat gtaaaaaata aagggaacc    4860
catatgtcat accatacaca caaaaaaatt ccagtgaatt ataagtctaa atggagaagg    4920
```

```
caaaacttta aatcttttag aaaataatat agaagcatgc agaccagcct ggccaacatg    4980
atgaaaccct ctctactaat aataaaatca gtagaactac tcaggactac tttgagtggg    5040
aagtcctttt ctatgaagac ttctttggcc aaaattaggc tctaaatgca aggagatagt    5100
gcatcatgcc tggctgcact tactgataaa tgatgttatc accatcttta accaaatgca    5160
caggaacaag ttatggtact gatgtgctgg attgagaagg agctctactt ccttgacagg    5220
acacatttgt atcaacttaa aaaagcagat ttttgccagc agaactattc attcagaggt    5280
aggaaactta gaatagatga tgtcactgat tagcatggct tccccatctc cacagctgct    5340
tcccacccag gttgcccaca gttgagtttg tccagtgctc agggctgccc actctcagta    5400
agaagcccca ccagccccc tctccaaata tgttggctgt tccttccatt aaagtgaccc     5460
cactttagag cagcaagtgg atttctgttt cttacagttc aggaaggagg agtcagctgt    5520
gagaacctgg agcctgagat gcttctaagt cccactgcta ctggggtcag ggaagccaga    5580
ctccagcatc agcagtcagg agcactaagc ccttgccaac atcctgtttc tcagagaaac    5640
tgcttccatt ataatggttg tccttttta agctatcaag ccaaacaacc agtgtctacc     5700
attattctca tcacctgaag ccaagggttc tagcaaaagt caagctgtct tgtaatggtt    5760
gatgtgcctc cagcttctgt cttcagtcac tccactctta gcctgctctg aatcaactct    5820
gaccacagtt ccctggagcc cctgccacct gctgcccctg ccaccttctc catctgcagt    5880
gctgtgcagc cttctgcact cttgcagagc taataggtgg agacttgaag gaagaggagg    5940
aaagtttctc ataatagcct tgctgcaagc tcaaatggga ggtgggcact gtgcccagga    6000
gccttggagc aaaggctgtg cccaacctct gactgcatcc aggtttggtc ttgacagaga    6060
taagaagccc tggcttttgg agccaaaatc taggtcagac ttaggcagga ttctcaaagt    6120
ttatcagcag aacatgaggc agaagaccct ttctgctcca gcttcttcag gctcaacctt    6180
catcagaata gatagaaaga gaggctgtga gggttcttaa aacagaagca aatctgactc    6240
agagaataaa caacctccta gtaaactaca gcttagacag agcatctggt ggtgagtgtg    6300
ctcagtgtcc tactcaactg tctggtatca gccctcatga ggacttctct tctttccctc    6360
atagacctcc atctctgttt tccttagcct gcagaaatct ggatggctat tcacagaatg    6420
cctgtgcttt cagagttgca ttttttctct ggtattctgg ttcaagcatt tgaaggtagg    6480
aaaggttctc caagtgcaag aaagccagcc ctgagcctca actgcctggc tagtgtggtc    6540
agtaggatgc aaaggctgtt gaatgccaca aggccaaact ttaacctgtg taccacaagc    6600
ctagcagcag aggcagctct gctcactgga actctctgtc ttctttctcc tgagcctttt    6660
cttttcctga gttttctagc tctcctcaac cttacctctg ccctacccag gacaaaccca    6720
agagccactg tttctgtgat gtcctctcca gccctaatta ggcatcatga cttcagcctg    6780
accttccatg ctcagaagca gtgctaatcc acttcagatg agctgctcta tgcaacacag    6840
gcagagccta caaacctttg caccagagcc ctccacatat cagtgtttgt tcatactcac    6900
ttcaacagca aatgtgactg ctgagattaa gattttacac aagatggtct gtaatttcac    6960
agttagtttt atcccattag gtatgaaaga attagcataa ttccccttaa acatgaatga    7020
atcttagatt ttttaataaa tagttttgga agtaaagaca gagacatcag gagcacaagg    7080
aatagcctga gaggacaaac agaacaagaa agagtctgga aatacacagg atgttcttgg    7140
cctcctcaaa gcaagtgcaa gcagatagta ccagcagccc caggctatca gagcccagtg    7200
aagagaagta ccatgaaagc cacagctcta accaccctgt tccagagtga cagacagtcc    7260
ccaagacaag ccagcctgag ccagagagag aactgcaaga gaaagtttct aatttaggtt    7320
```

-continued

| | |
|---|---|
| ctgttagatt cagacaagtg caggtcatcc tctctccaca gctactcacc tctccagcct | 7380 |
| aacaaagcct gcagtccaca ctccaaccct ggtgtctcac ctcctagcct ctcccaacat | 7440 |
| cctgctctct gaccatcttc tgcatctctc atctcaccat ctcccactgt ctacagccta | 7500 |
| ctcttgcaac taccatctca ttttctgaca tcctgtctac atcttctgcc atactctgcc | 7560 |
| atctaccata ccacctctta ccatctacca caccatcttt tatctccatc cctctcagaa | 7620 |
| gcctccaagc tgaatcctgc tttatgtgtt catctcagcc cctgcatgga aagctgaccc | 7680 |
| cagaggcaga actattccca gagagcttgg ccaagaaaaa caaaactacc agcctggcca | 7740 |
| ggctcaggag tagtaagctg cagtgtctgt tgtgttctag cttcaacagc tgcaggagtt | 7800 |
| ccactctcaa atgctccaca tttctcacat cctcctgatt ctggtcacta cccatcttca | 7860 |
| aagaacagaa tatctcacat cagcatactg tgaaggacta gtcatgggtg cagctgctca | 7920 |
| gagctgcaaa gtcattctgg atggtggaga gcttacaaac atttcatgat gctccccccg | 7980 |
| ctctgatggc tggagcccaa tccctacaca gactcctgct gtatgtgttt tcctttcact | 8040 |
| ctgagccaca gccagagggc aggcattcag tctcctcttc aggctggggc tggggcactg | 8100 |
| agaactcacc caacaccttg ctctcactcc ttctgcaaaa caagaaagag ctttgtgctg | 8160 |
| cagtagccat gaagaatgaa aggaaggctt taactaaaaa atgtcagaga ttattttcaa | 8220 |
| ccccttactg tggatcacca gcaaggagga aacacaacac agagacattt tttcccctca | 8280 |
| aattatcaaa gaatcactg catttgttaa agagagcaac tgaatcagga agcagagttt | 8340 |
| tgaacatatc agaagttagg aatctgcatc agagacaaat gcagtcatgg ttgtttgctg | 8400 |
| cataccagcc ctaatcatta gaagcctcat ggacttcaaa catcattccc tctgacaaga | 8460 |
| tgctctagcc taactccatg agataaaata aatctgcctt tcagagccaa agaagagtcc | 8520 |
| accagcttct tctcagtgtg aacaagagct ccagtcaggt tagtcagtcc agtgcagtag | 8580 |
| aggagaccag tctgcatcct ctaattttca aaggcaagaa gatttgttta ccctggacac | 8640 |
| caggcacaag tgaggtcaca gagctcttag atatgcagtc ctcatgagtg aggagactaa | 8700 |
| agcgcatgcc atcaagactt cagtgtagag aaaacctcca aaaaagcctc ctcactactt | 8760 |
| ctggaatagc tcagaggccg aggcggcctc ggcctctgca taaataaaaa aaattagtca | 8820 |
| gccatggggc ggagaatggg cggaactggg cggagttagg ggcgggatgg gcggagttag | 8880 |
| gggcgggact atggttgctg actaattgag atgcatgctt tgcatacttc tgcctgctgg | 8940 |
| ggagcctggg gactttccac acctggttgc tgactaattg agatgcatgc tttgcatact | 9000 |
| tctgcctgct ggggagcctg gggactttcc acacctaac tgcacacat tccacagctg | 9060 |
| cattaatgaa tcggccaacg cgcggggaga ggcggtttgc gtattgggcg ctcttccgct | 9120 |
| tcctcgctca ctgactcgct gcgctcggtc gttcggctgc ggcgagcggt atcagctcac | 9180 |
| tcaaaggcgg taatacggtt atccacagaa tcagggata acgcaggaaa gaacatgtga | 9240 |
| gcaaaaggcc agcaaaaggc caggaaccgt aaaaaggccg cgttgctggc gtttttccat | 9300 |
| aggctccgcc ccctgacga gcatcacaaa aatcgacgct caagtcagag gtggcgaaac | 9360 |
| ccgacaggac tataaagata ccaggcgttt ccccctggaa gctccctcgt gcgctctcct | 9420 |
| gttccgaccc tgccgcttac cggatacctg tccgcctttc tcccttcggg aagcgtggcg | 9480 |
| ctttctcata gctcacgctg taggtatctc agttcggtgt aggtcgttcg ctccaagctg | 9540 |
| ggctgtgtgc acgaaccccc cgttcagccc gaccgctgcg ccttatccgg taactatcgt | 9600 |
| cttgagtcca acccggtaag acacgactta tcgccactgg cagcagccac tggtaacagg | 9660 |

```
attagcagag cgaggtatgt aggcggtgct acagagttct tgaagtggtg gcctaactac    9720
ggctacacta gaagaacagt atttggtatc tgcgctctgc tgaagccagt taccttcgga    9780
aaaagagttg gtagctcttg atccggcaaa caaaccaccg ctggtagcgg tggttttttt    9840
gtttgcaagc agcagattac gcgcagaaaa aaaggatctc aagaagatcc tttgatcttt    9900
tctacggggt ctgacgctca gtggaacgaa aactcacgtt aagggatttt ggtcatgaga    9960
ttatcaaaaa ggatcttcac ctagatcctt taaattaaa aatgaagttt taaatcaatc    10020
taaagtatat atgagtaaac ttggtctgac agttaccaat gcttaatcag tgaggcacct    10080
atctcagcga tctgtctatt tcgttcatcc atagttgcct gactcctgca aaccacgttg    10140
tgtctcaaaa tctctgatgt tacattgcac aagataaaaa tatatcatca tgaacaataa    10200
aactgtctgc ttacataaac agtaataaca ggggtgttat gagccatatt caacgggaaa    10260
cgtcttgctc gaggccgcga ttaaattcca acatggatgc tgatttatat gggtataaat    10320
gggctcgcga taatgtcggg caatcaggtg cgacaatcta tcgattgtat gggaagcccg    10380
atgcgccaga gttgtttctg aaacatggca aaggtagcgt tgccaatgat gttacagatg    10440
agatggtcag actaaactgg ctgacggaat ttatgcctct tccgaccatc aagcatttta    10500
tccgtactcc tgatgatgca tggttactca ccactgcgat ccccgggaaa acagcattcc    10560
aggtattaga agaatatcct gattcaggtg aaaatattgt tgatgcgctg gcagtgttcc    10620
tgcgccggtt gcattcgatt cctgtttgta attgtccttt taacagcgat cgcgtatttc    10680
gtctcgctca ggcgcaatca cgaatgaata acggtttggt tgatgcgagt gattttgatg    10740
acgagcgtaa tggctggcct gttgaacaag tctggaaaga atgcataag cttttgccat    10800 tctcaccgga ttcagtcgtc actcatggtg attctcact tgataaccctt attttttgacg    10860 agggggaaatt aataggttgt attgatgttg gacgagtcgg aatcgcagac cgataccagg    10920
atcttgccat cctatggaac tgcctcggtg agttttctcc ttcattacag aaacggcttt    10980
ttcaaaaata tggtattgat aatcctgata tgaataaatt gcagtttcat ttgatgctcg    11040
atgagttttt ctaagggcgg cctgccacca tacccacgcc gaaacaagcg ctcatgagcc    11100
cgaagtggcg agcccgatct tccccatcgg tgatgtcggc gatataggcg ccagcaaccg    11160
cacctgtggc gccggtgatg agggcgcgcc aagtcgacgt ccggcagtc                11209
```

<210> SEQ ID NO 62
<211> LENGTH: 11459
<212> TYPE: DNA
<213> ORGANISM: Artificial sequence
<220> FEATURE:
<223> OTHER INFORMATION: Synthetic polynucleotide

<400> SEQUENCE: 62

```
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg      120
gccaactcca tcactagggg ttcctgctag ctctgggtat ttaagcccga gtgagcacgc      180
agggtctcca ttttgaagcg ggaggttacg cgttcgtcga ctactagtgg gtaccagagc      240
tccctaggtt ctagaaccgg tgacgtctcc catggtgaag cttggatctg aattcggtac     300
cctagttatt aatagtaatc aattacgggg tcattagttc atagcccata tatggagttc     360
cgcgttacat aacttacggt aaatggcccg cctggctgac cgcccaacga cccccgccca     420
ttgacgtcaa taatgacgta tgttcccata gtaacgccaa tagggacttt ccattgacgt     480
caatgggtgg actatttacg gtaaactgcc cacttggcag tacatcaagt gtatcatatg     540
```

```
ccaagtacgc cccctattga cgtcaatgac ggtaaatggc ccgcctggca ttatgcccag    600
tacatgacct tatgggactt tcctacttgg cagtacatct acgtattagt catcgctatt    660
accatggtcg aggtgagccc cacgttctgc ttcactctcc ccatctcccc cccctcccca    720
cccccaattt tgtatttatt tatttttaa ttattttgtg cagcgatggg ggcgggggg      780 ggggggggc gcgcgccagg cggggcgggg cggggcgagg ggcggggcgg ggcgaggcgg    840
agaggtgcgg cggcagccaa tcagagcggc gcgctccgaa agtttccttt tatggcgagg    900
cggcggcggc ggcggcccta taaaaagcga agcgcgcggc gggcgggagt cgctgcgacg    960
ctgccttcgc cccgtgcccc gctccgccgc cgcctcgcgc cgcccgcccc ggctctgact   1020
gaccgcgtta ctcccacagg tgagcgggcg ggacggccct tctcctccgg gctgtaatta   1080
gcgcttggtt taatgacggc ttgttttctg tggctgcgtg aaagccttga ggggctccgg   1140
gagctagagc ctctgctaac catgttcatg ccttcttctt tttcctacag ctcctgggca   1200
acgtgctggt tattgtgctg tctcatcatt ttggcaaaga attcctcgaa gatccgaagg   1260
gaaagtcttc cacgactgtg ggatccgttc gaagatatca ccggttgagc caccatggaa   1320
ttcagcagcc ccagcagaga ggaatgcccc aagcctctga gccgggtgtc aatcatggcc   1380
ggatctctga caggactgct gctgcttcag gccgtgtctt gggcttctgg cgctagacct   1440
tgcatcccca agagcttcgg ctacagcagc gtcgtgtgcg tgtgcaatgc cacctactgc   1500
gacagcttcg accctcctac ctttcctgct ctgggcacct tcagcagata cgagagcacc   1560
agatccggca gacggatgga actgagcatg ggacccatcc aggccaatca cacaggcact   1620
ggcctgctgc tgacactgca gcctgagcag aaattccaga aagtgaaagg cttcggcgga   1680
gccatgacag atgccgccgc tctgaatatc ctggctctgt ctccaccagc tcagaacctg   1740
ctgctcaaga gctacttcag cgaggaaggc atcggctaca acatcatcag agtgcccatg   1800
gccagctgcg acttcagcat caggacctac acctacgccg acacacccga cgatttccag   1860
ctgcacaact tcagcctgcc tgaagaggac accaagctga gatccctct gatccacaga   1920 gccctgcagc tggcacaaag acccgtgtca ctgctggcct ctccatggac atctcccacc   1980
tggctgaaaa caaatggcgc cgtgaatggc aagggcagct gaaaggcca acctggcgac   2040 atctaccacc agacctgggc cagatacttc gtgaagttcc tggacgccta tgccgagcac   2100
aagctgcagt tttgggccgt gacagccgag aacgaacctt ctgctggact gctgagcggc   2160
tacccctttc agtgcctggg ctttacaccc gagcaccagc gggactttat cgcccgtgat   2220
ctgggaccca cactggccaa tagcacccac cataatgtgc ggctgctgat gctggacgac   2280
cagagactgc ttctgcccca ctgggctaaa gtggtgctga cagatcctga ggccgccaaa   2340
tacgtgcacg gaatcgccgt gcactggtat ctggactttc tggcccctgc caaggccaca   2400
ctgggagaga cacacagact gttccccaac accatgctgt cgccagcga agcctgtgtg   2460 ggcagcaagt tttgggaaca gagcgtgcgg ctcggcagct gggatagagg catgcagtac   2520
agccacagca tcatcaccaa cctgctgtac cacgtcgtcg gctggaccga ctggaatctg   2580
gccctgaatc ctgaaggcgg ccctaactgg gtccgaaact tcgtggacag ccccatcatc   2640
gtggacatca ccaaggacac cttctacaag cagcccatgt tctaccacct gggacacttc   2700
agcaagttca tccccgaggg ctctcagcgc gttggactgg tggcttccca gaagaacgat   2760
ctggacgccg tggctctgat gcaccctgat ggatctgctg tggtggtggt cctgaaccgc   2820
agcagcaaag atgtgcccct gaccatcaag gatcccgccg tgggattcct ggaaacaatc   2880
```

```
agccctggct actccatcca cacctacctg tggcgtagac agtgacaatt gttaattaag    2940
tttaaaccct cgaggccgca agccgcatcg ataccgtcga ctagagctcg ctgatcagcc    3000
tcgactgtgc cttctagttg ccagccatct gttgtttgcc cctcccccgt gccttccttg    3060
accctggaag gtgccactcc cactgtcctt tcctaataaa atgaggaaat tgcatcgcat    3120
tgtctgagta ggtgtcattc tattctgggg gtggggtgg ggcaggacag caaggggag    3180
gattgggaag acaatagcag gcatgctggg gagagatcca cgataacaaa cagcttttt    3240
ggggggcgg agttagggcg gagccaatca gcgtgcgccg ttccgaaagt tgcctttat    3300
ggctgggcgg agaatgggcg gtgaacgccg atgattatat aaggacgcgc cgggtgtggc    3360
acagctagtt ccgtcgcagc cgggatttgg gtcgcggttc ttgtttgtgg atccctgtga    3420
tcgtcacttg gtaagtcact gactgtctat gcctgggaaa gggtgggcag gagatggggc    3480
agtgcaggaa aagtggcact atgaaccctg cagccctagg aatgcatcta gacaattgta    3540
ctaaccttct tctctttcct ctcctgacag tccggaaagc caccatgccc cgcggcttca    3600
cctggctgcg ctacctgggc atcttcctgg gcgtggccct gggcaacgag cccctggaga    3660
tgtggcccct gacccagaac gaggagtgca ccgtgaccgg cttcctgcgc gacaagctgc    3720
agtaccgcag ccgcctgcag tacatgaagc actacttccc catcaactac aagatcagcg    3780
tgccctacga gggcgtgttc cgcatcgcca acgtgacccg cctgcagcgc gcccaggtga    3840
gcgagcgca gctgcgctac ctgtgggtgc tggtgagcct gagcgccacc gagagcgtgc    3900
aggacgtgct gctggagggc caccccagct ggaagtacct gcaggaggtg agaccctgc    3960
tgctgaacgt gcagcagggc ctgaccgacg tggaggtgag ccccaaggtg gagagcgtgc    4020
tgagcctgct gaacgccccc ggccccaacc tgaagctggt gcgccccaag gccctgctgg    4080
acaactgctt ccgcgtgatg gagctgctgt actgcagctg ctgcaagcag agcagcgtgc    4140
tgaactggca ggactgcgag gtgcccagcc cccagagctg cagccccgag cccagcctgc    4200
agtacgccgc cacccagctg taccccccccc ccccctggag cccagcagc ccccccccaca    4260
gcaccggcag cgtgcgcccc gtgcgcgccc agggcgaggg cctgctgccc taatgaccca    4320
ggggactcag cggccgctcg agtctagagg gcccgtttaa acccgctgat cagcctcgaa    4380
gacatgataa gatacattga tgagtttgga caaaccacaa caagaatgca gtgaaaaaa    4440
tgctttattt gtgaaatttg tgatgctatt gctttatttg taaccattat aagctgcaat    4500
aaacaagtta acaacaacaa ttgcattcat tttatgtttc aggttcaggg ggagatgtgg    4560
gaggtttttt aaagcaagta aaacctctac aaatgtggta tgaacatatt gactgaattc    4620
cctgcaggtt ggccactccc tctctgcgcg ctcgctcgct cactgaggcc gcccgggcaa    4680
agcccgggcg tcgggcgacc tttggtcgcc cggcctcagt gagcgagcga gcgcgcagag    4740
agggagtggc caactccatc actagggtt cctgcggccg ctcgtacggt ctcgaggaat    4800
tcctgcagga taacttgcca acctcattct aaaatgtata tagaagccca aaagacaata    4860
acaaaaatat tcttgtagaa caaaatggga agaatgttc cactaaatat caagatttag    4920
agcaaagcat gagatgtgtg gggatagaca gtgaggctga taaaatagag tagagctcag    4980
aaacagaccc attgatatat gtaagtgacc tatgaaaaaa atatggcatt ttacaatggg    5040
aaaatgatgg tctttttctt ttttagaaaa acagggaaat atatttatat gtaaaaaata    5100
aaagggaacc catatgtcat accatacaca caaaaaaatt ccagtgaatt ataagtctaa    5160
atggagaagg caaaacttta aatctttag aaaataat agaagcatgc agaccagcct    5220
ggccaacatg atgaaaccct ctctactaat aataaaatca gtagaactac tcaggactac    5280
```

```
tttgagtggg aagtcctttt ctatgaagac ttctttggcc aaaattaggc tctaaatgca      5340
aggagatagt gcatcatgcc tggctgcact tactgataaa tgatgttatc accatcttta      5400
accaaatgca caggaacaag ttatggtact gatgtgctgg attgagaagg agctctactt      5460
ccttgacagg acacatttgt atcaacttaa aaaagcagat ttttgccagc agaactattc      5520
attcagaggt aggaaactta gaatagatga tgtcactgat tagcatggct tccccatctc      5580
cacagctgct tcccacccag gttgcccaca gttgagtttg tccagtgctc agggctgccc      5640
actctcagta agaagcccca caccagcccc tctccaaata tgttggctgt tccttccatt      5700
aaagtgaccc cactttagag cagcaagtgg atttctgttt cttacagttc aggaaggagg      5760
agtcagctgt gagaacctgg agcctgagat gcttctaagt cccactgcta ctggggtcag      5820
ggaagccaga ctccagcatc agcagtcagg agcactaagc ccttgccaac atcctgtttc      5880
tcagagaaac tgcttccatt ataatggttg tccttttta agctatcaag ccaaacaacc      5940
agtgtctacc attattctca tcacctgaag ccaagggttc tagcaaaagt caagctgtct      6000
tgtaatggtt gatgtgcctc cagcttctgt cttcagtcac tccactctta gcctgctctg      6060
aatcaactct gaccacagtt ccctggagcc cctgccacct gctgcccctg ccaccttctc      6120
catctgcagt gctgtgcagc cttctgcact cttgcagagc taataggtgg agacttgaag      6180
gaagaggagg aaagtttctc ataatagcct tgctgcaagc tcaaatggga ggtgggcact      6240
gtgcccagga gccttggagc aaaggctgtg cccaacctct gactgcatcc aggtttggtc      6300
ttgacagaga taagaagccc tggcttttgg agccaaaatc taggtcagac ttaggcagga      6360
ttctcaaagt ttatcagcag aacatgaggc agaagaccct ttctgctcca gcttcttcag      6420
gctcaacctt catcagaata gatagaaaga gaggctgtga gggttcttaa aacagaagca      6480
aatctgactc agagaataaa caacctccta gtaaactaca gcttagacag agcatctggt      6540
ggtgagtgtg ctcagtgtcc tactcaactg tctggtatca gccctcatga ggacttctct      6600 tcttccctc atagacctcc atctctgttt tccttagcct gcagaaatct ggatggctat      6660
tcacagaatg cctgtgcttt cagagttgca ttttttctct ggtattctgg ttcaagcatt      6720
tgaaggtagg aaaggttctc caagtgcaag aaagccagcc ctgagcctca actgcctggc      6780
tagtgtggtc agtaggatgc aaaggctgtt gaatgccaca aggccaaact ttaacctgtg      6840
taccacaagc ctagcagcag aggcagctct gctcactgga actctctgtc ttctttctcc      6900
tgagcctttt cttttcctga gttttctagc tctcctcaac cttacctctg ccctacccag      6960
gacaaaccca agagccactg tttctgtgat gtcctctcca gccctaatta ggcatcatga      7020
cttcagcctg accttccatg ctcagaagca gtgctaatcc acttcagatg agctgctcta      7080
tgcaacacag gcagagccta caaacctttg caccagagcc ctccacatat cagtgtttgt      7140
tcatactcac ttcaacagca aatgtgactg ctgagattaa gattttacac aagatggtct      7200
gtaatttcac agttagtttt atcccattag gtatgaaaga attagcataa ttccccttaa      7260
acatgaatga atcttagatt ttttaataaa tagttttgga agtaaagaca gagacatcag      7320
gagcacaagg aatagcctga gaggacaaac agaacaagaa agagtctgga aatacacagg      7380
atgttcttgg cctcctcaaa gcaagtgcaa gcagatagta ccagcagccc caggctatca      7440
gagcccagtg aagagaagta ccatgaaagc cacagctcta accaccctgt tccagagtga      7500
cagacagtcc ccaagacaag ccagcctgag ccagagagag aactgcaaga gaaagtttct      7560
aatttaggtt ctgttagatt cagacaagtg caggtcatcc tctctccaca gctactcacc      7620
```

```
tctccagcct aacaaagcct gcagtccaca ctccaaccct ggtgtctcac ctcctagcct    7680
ctcccaacat cctgctctct gaccatcttc tgcatctctc atctcaccat ctcccactgt    7740
ctacagccta ctcttgcaac taccatctca tttttctgaca tcctgtctac atcttctgcc   7800
atactctgcc atctaccata ccacctctta ccatctacca caccatcttt tatctccatc    7860
cctctcagaa gcctccaagc tgaatcctgc tttatgtgtt catctcagcc cctgcatgga    7920
aagctgaccc cagaggcaga actattccca gagagcttgg ccaagaaaaa caaaactacc    7980
agcctggcca ggctcaggag tagtaagctg cagtgtctgt tgtgttctag cttcaacagc    8040
tgcaggagtt ccactctcaa atgctccaca tttctcacat cctcctgatt ctggtcacta    8100
cccatcttca aagaacagaa tatctcacat cagcatactg tgaaggacta gtcatgggtg    8160
cagctgctca gagctgcaaa gtcattctgg atggtggaga gcttacaaac atttcatgat    8220 gctcccccg ctctgatggc tggagcccaa tccctacaca gactcctgct gtatgtgttt     8280
tcctttcact ctgagccaca gccagagggc aggcattcag tctcctcttc aggctggggc    8340
tggggcactg agaactcacc caacaccttg ctctcactcc ttctgcaaaa caagaaagag    8400
ctttgtgctg cagtagccat gaagaatgaa aggaaggctt taactaaaaa atgtcagaga    8460
ttattttcaa cccttactg tggatcacca gcaaggagga aacacaacac agagacattt      8520
tttcccctca aattatcaaa agaatcactg catttgttaa agagagcaac tgaatcagga    8580
agcagagttt tgaacatatc agaagttagg aatctgcatc agagacaaat gcagtcatgg    8640
ttgtttgctg cataccagcc ctaatcatta gaagcctcat ggacttcaaa catcattccc    8700
tctgacaaga tgctctagcc taactccatg agataaaata aatctgcctt tcagagccaa    8760
agaagagtcc accagcttct tctcagtgtg aacaagagct ccagtcaggt tagtcagtcc    8820
agtgcagtag aggagaccag tctgcatcct ctaattttca aaggcaagaa gatttgttta    8880
ccctggacac caggcacaag tgaggtcaca gagctcttag atatgcagtc ctcatgagtg    8940
aggagactaa agcgcatgcc atcaagactt cagtgtagag aaaacctcca aaaaagcctc    9000
ctcactactt ctggaatagc tcagaggccg aggcggcctc ggcctctgca taaataaaaa    9060
aaattagtca gccatggggc ggagaatggg cggaactggg cggagttagg ggcgggatgg    9120
gcggagttag gggcgggact atggttgctg actaattgag atgcatgctt tgcatacttc    9180
tgcctgctgg ggagcctggg gactttccac acctggttgc tgactaattg agatgcatgc    9240
tttgcatact tctgcctgct ggggagcctg gggactttcc acaccctaac tgacacacat    9300
tccacagctg cattaatgaa tcggccaacg cgcggggaga ggcggtttgc gtattgggcg    9360
ctcttccgct tcctcgctca ctgactcgct gcgctcggtc gttcggctgc ggcgagcggt    9420
atcagctcac tcaaaggcgg taatacggtt atccacagaa tcaggggata acgcaggaaa    9480
gaacatgtga gcaaaaggcc agcaaaaggc caggaaccgt aaaaaggccg cgttgctggc    9540
gtttttccat aggctccgcc cccctgacga gcatcacaaa aatcgacgct caagtcagag    9600
gtggcgaaac ccgacaggac tataaagata ccaggcgttt ccccctggaa gctccctcgt    9660
gcgctctcct gttccgaccc tgccgcttac cggatacctg tccgcctttc tcccttcggg    9720
aagcgtggcg ctttctcata gctcacgctg taggtatctc agttcggtgt aggtcgttcg    9780
ctccaagctg ggctgtgtgc acgaaccccc cgttcagccc gaccgctgcg ccttatccgg    9840
taactatcgt cttgagtcca acccggtaag acacgactta tcgccactgg cagcagccac    9900
tggtaacagg attagcagag cgaggtatgt aggcggtgct acagagttct tgaagtggtg    9960
gcctaactac ggctacacta gaagaacagt atttggtatc tgcgctctgc tgaagccagt   10020
```

```
taccttcgga aaaagagttg gtagctcttg atccggcaaa caaaccaccg ctggtagcgg   10080
tggttttttt gtttgcaagc agcagattac gcgcagaaaa aaaggatctc aagaagatcc   10140
tttgatcttt tctacggggt ctgacgctca gtggaacgaa aactcacgtt aagggatttt   10200
ggtcatgaga ttatcaaaaa ggatcttcac ctagatcctt taaattaaa aatgaagttt    10260 taaatcaatc taaagtatat atgagtaaac ttggtctgac agttaccaat gcttaatcag   10320
tgaggcacct atctcagcga tctgtctatt tcgttcatcc atagttgcct gactcctgca   10380
aaccacgttg tgtctcaaaa tctctgatgt tacattgcac aagataaaaa tatatcatca   10440
tgaacaataa aactgtctgc ttacataaac agtaatacaa ggggtgttat gagccatatt   10500
caacgggaaa cgtcttgctc gaggccgcga ttaaattcca acatggatgc tgatttatat   10560
gggtataaat gggctcgcga taatgtcggg caatcaggtg cgacaatcta tcgattgtat   10620
gggaagcccg atgcgccaga gttgtttctg aaacatggca aaggtagcgt tgccaatgat   10680
gttacagatg agatggtcag actaaactgg ctgacggaat ttatgcctct tccgaccatc   10740
aagcatttta tccgtactcc tgatgatgca tggttactca ccactgcgat ccccgggaaa   10800
acagcattcc aggtattaga agaatatcct gattcaggtg aaaatattgt tgatgcgctg   10860
gcagtgttcc tgcgccggtt gcattcgatt cctgtttgta attgtccttt taacagcgat   10920
cgcgtatttc gtctcgctca ggcgcaatca cgaatgaata cggtttggt tgatgcgagt    10980 gattttgatg acgagcgtaa tggctggcct gttgaacaag tctggaaaga atgcataag    11040 cttttgccat tctcaccgga ttcagtcgtc actcatggtg attctcact gataaacctt    11100 atttttgacg aggggaaatt aataggttgt attgatgttg gacgagtcgg aatcgcagac   11160
cgataccagg atcttgccat cctatggaac tgcctcggtg agttttctcc ttcattacag   11220
aaacggcttt ttcaaaaata tggtattgat aatcctgata tgaataaatt gcagtttcat   11280
ttgatgctcg atgagttttt ctaagggcgg cctgccacca tacccacgcc gaaacaagcg   11340
ctcatgagcc cgaagtggcg agcccgatct tccccatcgg tgatgtcggc gatataggcg   11400
ccagcaaccg cacctgtggc gccggtgatg agggcgcgcc aagtcgacgt ccggcagtc    11459
```

<210> SEQ ID NO 63
<211> LENGTH: 274
<212> TYPE: PRT
<213> ORGANISM: Artificial sequence
<220> FEATURE:
<223> OTHER INFORMATION: Synthetic polypeptide

<400> SEQUENCE: 63

```
Met Gly Lys Ser Leu Ser His Leu Pro Leu His Ser Ser Lys Glu Asp
1               5                   10                  15

Ala Tyr Asp Gly Val Thr Ser Glu Asn Met Arg Asn Gly Leu Val Asn
            20                  25                  30

Ser Glu Val His Asn Glu Asp Gly Arg Asn Gly Asp Val Ser Gln Phe
        35                  40                  45

Pro Tyr Val Glu Phe Thr Gly Arg Asp Ser Val Thr Cys Pro Thr Cys
    50                  55                  60

Gln Gly Thr Gly Arg Ile Pro Arg Gly Gln Glu Asn Gln Leu Val Ala
65                  70                  75                  80

Leu Ile Pro Tyr Ser Asp Gln Arg Leu Arg Pro Arg Thr Lys Leu
            85                  90                  95

Tyr Val Met Ala Ser Val Phe Val Cys Leu Leu Leu Ser Gly Leu Ala
            100                 105                 110
```

Val Phe Phe Leu Phe Pro Arg Ser Ile Asp Val Lys Tyr Ile Gly Val
            115                 120                 125

Lys Ser Ala Tyr Val Ser Tyr Asp Val Gln Lys Arg Thr Ile Tyr Leu
130                 135                 140

Asn Ile Thr Asn Thr Leu Asn Ile Thr Asn Asn Tyr Tyr Ser Val
145                 150                 155                 160

Glu Val Glu Asn Ile Thr Ala Gln Val Gln Phe Ser Lys Thr Val Ile
                165                 170                 175

Gly Lys Ala Arg Leu Asn Asn Ile Thr Ile Gly Pro Leu Asp Met
            180                 185                 190

Lys Gln Ile Asp Tyr Thr Val Pro Thr Val Ile Ala Glu Glu Met Ser
            195                 200                 205

Tyr Met Tyr Asp Phe Cys Thr Leu Ile Ser Ile Lys Val His Asn Ile
    210                 215                 220

Val Leu Met Met Gln Val Thr Val Thr Thr Tyr Phe Gly His Ser
225                 230                 235                 240

Glu Gln Ile Ser Gln Glu Arg Tyr Gln Tyr Val Asp Cys Gly Arg Asn
                245                 250                 255

Thr Thr Tyr Gln Leu Gly Gln Ser Glu Tyr Leu Asn Val Leu Gln Pro
            260                 265                 270

Gln Gln

<210> SEQ ID NO 64
<211> LENGTH: 825
<212> TYPE: DNA
<213> ORGANISM: Artificial sequence
<220> FEATURE:
<223> OTHER INFORMATION: Synthetic polynucleotide

<400> SEQUENCE: 64

```
atgggcaaga gcctgagcca cctgcccctg cacagcagca aggaggacgc ctacgacggc    60
gtgaccagcg agaacatgcg caacggcctg gtgaacagcg aggtgcacaa cgaggacggc   120
cgcaacggcg acgtgagcca gttcccctac gtggagttca ccggccgcga cagcgtgacc   180
tgccccacct gccagggcac cggccgcatc ccccgcggcc aggagaacca gctggtggcc   240
ctgatcccct acagcgacca gcgcctgcgc cccgccgca ccaagctgta cgtgatggcc   300
agcgtgttcg tgtgcctgct gctgagcggc ctggccgtgt tcttcctgtt ccccgcagc   360
atcgacgtga agtacatcgg cgtgaagagc gcctacgtga gctacgacgt gcagaagcgc   420
accatctacc tgaacatcac caacaccctg aacatcacca acaacaacta ctacagcgtg   480
gaggtggaga acatcaccgc ccaggtgcag ttcagcaaga ccgtgatcgg caaggcccgc   540
ctgaacaaca tcaccatcat cggccccctg gacatgaagc agatcgacta caccgtgccc   600
accgtgatcg ccgaggagat gagctacatg tacgacttct gcaccctgat cagcatcaag   660
gtgcacaaca tcgtgctgat gatgcaggtg accgtgacca ccacctactt cggccacagc   720
gagcagatca gccaggagcg ctaccagtac gtggactgcg ccgcaacac cacctaccag   780
ctgggccaga gcgagtacct gaacgtgctg cagccccagc agtaa                    825
```

<210> SEQ ID NO 65
<211> LENGTH: 267
<212> TYPE: DNA
<213> ORGANISM: Artificial sequence
<220> FEATURE:
<223> OTHER INFORMATION: Synthetic polynucleotide

<400> SEQUENCE: 65

```
gtgatatcac aaggtcccag ggctggggtc agaaattctc tcccgaggga atgaagccac    60
aggagccaag agcaggagga ccaaggccct ggcgaaggcc gtggcctcgt tcaagtaaaa   120
gatcctagta cagtgcaggt cccaatgtgt actaggatct tttacttgaa cggggacgcc   180
ggcatccggg ctcaggaccc cctctctgc cagaggcacc aacaccagag ttcacaaatc    240
agtctcctgc cctttgcatg tagcaaa                                       267
```

<210> SEQ ID NO 66
<211> LENGTH: 267
<212> TYPE: DNA
<213> ORGANISM: Artificial sequence
<220> FEATURE:
<223> OTHER INFORMATION: Synthetic polynucleotide

<400> SEQUENCE: 66

```
tttgctacat gcaaagggca ggagactgat ttgtgaactc tggtgttggt gcctctggca    60
gagaggggg tcctgagccc ggatgccggc gtccccgttc aagtaaaaga tcctagtaca   120
cattgggacc tgcactgtac taggatcttt tacttgaacg aggccacggc cttcgccagg   180
gccttggtcc tcctgctctt ggctcctgtg gcttcattcc ctcgggagag aatttctgac   240
cccagccctg ggaccttgtg atatcac                                       267
```

<210> SEQ ID NO 67
<211> LENGTH: 593
<212> TYPE: PRT
<213> ORGANISM: Artificial sequence
<220> FEATURE:
<223> OTHER INFORMATION: Synthetic polypeptide

<400> SEQUENCE: 67

```
Met Trp Thr Leu Val Ser Trp Val Ala Leu Thr Ala Gly Leu Val Ala
1               5                   10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Gly Pro Cys Gln Val Asp
    50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
        115                 120                 125

Ser Gln Phe Glu Cys Pro Asp Phe Ser Thr Cys Cys Val Met Val Asp
    130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190
```

```
Ala Gln Arg Thr Asn Arg Ala Val Ala Leu Ser Ser Val Met Cys
        195                 200                 205

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
        260                 265                 270

Lys Leu Pro Ala His Thr Val Gly Asp Val Lys Cys Asp Met Glu Val
            275                 280                 285

Ser Cys Pro Asp Gly Tyr Thr Cys Cys Arg Leu Gln Ser Gly Ala Trp
    290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
        340                 345                 350

Ser Leu Pro Asp Pro Gln Ala Leu Lys Arg Asp Val Pro Cys Asp Asn
            355                 360                 365

Val Ser Ser Cys Pro Ser Ser Asp Thr Cys Cys Gln Leu Thr Ser Gly
    370                 375                 380

Glu Trp Gly Cys Cys Pro Ile Pro Glu Ala Val Cys Cys Ser Asp His
385                 390                 395                 400

Gln His Cys Cys Pro Gln Gly Tyr Thr Cys Val Ala Glu Gly Gln Cys
                405                 410                 415

Gln Arg Gly Ser Glu Ile Val Ala Gly Leu Glu Lys Met Pro Ala Arg
        420                 425                 430

Arg Ala Ser Leu Ser His Pro Arg Asp Ile Gly Cys Asp Gln His Thr
            435                 440                 445

Ser Cys Pro Val Gly Gln Thr Cys Cys Pro Ser Leu Gly Gly Ser Trp
    450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
        500                 505                 510

His Val Gly Val Lys Asp Val Glu Cys Gly Glu Gly His Phe Cys His
            515                 520                 525

Asp Asn Gln Thr Cys Cys Arg Asp Asn Arg Gln Gly Trp Ala Cys Cys
    530                 535                 540

Pro Tyr Arg Gln Gly Val Cys Cys Ala Asp Arg His Cys Cys Pro
545                 550                 555                 560

Ala Gly Phe Arg Cys Ala Ala Arg Gly Thr Lys Cys Leu Arg Arg Glu
                565                 570                 575

Ala Pro Arg Trp Asp Ala Pro Leu Arg Asp Pro Ala Leu Arg Gln Leu
        580                 585                 590

Leu
```

<210> SEQ ID NO 68
<211> LENGTH: 1779
<212> TYPE: DNA
<213> ORGANISM: Artificial sequence
<220> FEATURE:
<223> OTHER INFORMATION: Synthetic polynucleotide

<400> SEQUENCE: 68

```
atgtggaccc tggtgagctg ggtggccctg accgccggcc tggtggccgg cacccgctgc      60
cccgacggcc agttctgccc cgtggcctgc tgcctggacc ccggcggcgc cagctacagc     120
tgctgccgcc ccctgctgga caagtggccc accaccctga ccgccacct gggcggcccc      180
tgccaggtgg acgccactg cagcgccggc cacagctgca tcttcaccgt gagcggcacc      240
agcagctgct gccccttccc cgaggccgtg gcctgcggcg acgccacca ctgctgcccc      300
cgcggcttcc actgcagcgc cgacggccgc agctgcttcc agcgcagcgg caacaacagc     360
gtgggcgcca tccagtgccc cgacagccag ttcgagtgcc ccgacttcag cacctgctgc     420
gtgatggtgg acggcagctg ggctgctgc cccatgcccc aggccagctg ctgcgaggac      480
cgcgtgcact gctgccccca cggcgccttc tgcgacctgg tgcacacccg ctgcatcacc     540
cccaccggca cccacccct ggccaagaag ctgcccgccc agcgcaccaa ccgcgccgtg       600
gccctgagca gcagcgtgat gtgccccgac gcccgcagcc gctgccccga cggcagcacc     660
tgctgcgagc tgcccagcgg caagtacggc tgctgcccca tgcccaacgc cacctgctgc     720
agcgaccacc tgcactgctg cccccaggac accgtgtgcg acctgatcca gagcaagtgc     780
ctgagcaagg agaacgccac caccgacctg ctgaccaagc tgcccgccca ccgtgggc      840
gacgtgaagt gcgacatgga ggtgagctgc cccgacggct acacctgctg ccgcctgcag     900
agcggcgcct ggggctgctg cccttcacc caggccgtgt gctgcgagga ccacatccac      960
tgctgccccg ccggcttcac ctgcgacacc cagaagggca cctgcgagca gggccccac     1020
caggtgccct ggatggagaa ggccccgcc cacctgagcc tgcccgaccc ccaggccctg     1080
aagcgcgacg tgccctgcga caacgtgagc agctgcccca gcagcgacac ctgctgccag     1140
ctgaccagcg gcgagtgggg ctgctgcccc atccccgagg ccgtgtgctg cagcgaccac     1200
cagcactgct gccccagggg ctacacctgc gtggccgagg ccagtgcca gcgcggcagc     1260
gagatcgtgg ccggcctgga aagatgccc gcccgccgcg ccagcctgag ccaccccgc     1320
gacatcggct gcgaccagca caccagctgc cccgtgggcc agacctgctg ccccagcctg     1380
ggcggcagct gggcctgctg ccagctgccc cacgccgtgt gctgcgagga ccgccagcac     1440
tgctgccccg ccggctacac ctgcaacgtg aaggcccgca gctgcgagaa ggaggtggtg     1500
agcgcccagc ccgccaccTt cctggcccgc agccccacg tgggcgtgaa ggacgtggag     1560
tgcggcgagg ccacttctg ccacgacaac cagacctgct gccgcgacaa ccgccagggc     1620
tgggcctgct gccccctaccg ccaggccgtg tgctgcgccg accgccgcca ctgctgcccc    1680
gccggcttcc gctgcgccgc ccgcggcacc aagtgcctgc gccgcgaggc ccccgctgg     1740
gacgcccccc tgcgcgaccc cgccctgcgc cagctgctg                         1779
```

<210> SEQ ID NO 69
<211> LENGTH: 10871
<212> TYPE: DNA
<213> ORGANISM: Artificial sequence
<220> FEATURE:
<223> OTHER INFORMATION: Synthetic polynucleotide

<400> SEQUENCE: 69

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctgctag ctctgggtat ttaagcccga gtgagcacgc     180
agggtctcca ttttgaagcg ggaggttacg cgttcgtcga ctactagtgg gtaccagagc     240
tccctaggtt ctagaaccgg tgacgtctcc catggtgaag cttggatctg aattcggtac     300
ctagttatta atagtaatca attacgggt cattagttca tagcccatat atggagttcc     360
gcgttacata acttacggta aatggcccgc ctggctgacc gcccaacgac ccccgcccat     420
tgacgtcaat aatgacgtat gttcccatag taacgccaat agggactttc cattgacgtc     480
aatgggtgga gtatttacgg taaactgccc acttggcagt acatcaagtg tatcatatgc     540
caagtacgcc ccctattgac gtcaatgacg gtaaatggcc cgcctggcat tatgcccagt     600
acatgacctt atgggacttt cctacttggc agtacatcta cgtattagtc atcgctatta     660
ccatggtcga ggtgagcccc acgttctgct tcactctccc catctccccc cctccccac     720
ccccaatttt gtatttattt attttttaat tattttgtgc agcgatgggg gcggggggg     780
ggggggggcg cgcgccaggc ggggcggggc ggggcgaggg gcggggcggg gcgaggcgga     840
gaggtgcggc ggcagccaat cagagcggcg cgctccgaaa gtttccttt atggcgaggc     900
ggcggcggcg gcggccctat aaaaagcgaa gcgcgcggcg ggcgggagtc gctgcgacgc     960
tgccttcgcc ccgtgccccg ctccgccgcc gcctcgcgcc gcccgccccg gctctgactg    1020
accgcgttac tcccacaggt gagcgggcgg gacggccctt ctcctccggg ctgtaattag    1080
cgcttggttt aatgacggct tgtttctttt ctgtggctgc gtgaaagcct tgaggggctc    1140
cgggagctag agcctctgct aaccatgttc atgccttctt cttttccta cagctcctgg    1200
gcaacgtgct ggttattgtg ctgtctcatc attttggcaa agaattcctc gaagatccga    1260
agggaaagtc ttccacgact gtgggatccg ttcgaagata tcaccggttg agccaccatg    1320
tggaccctgg tgagctgggt ggccctgacc gccggcctgg tggccggcac ccgctgcccc    1380
gacgccagt tctgccccgt ggcctgctgc ctggaccccg gcggccagc ctacagctgc    1440
tgccgccccc tgctggacaa gtggcccacc accctgagcc gccacctggg cggcccctgc    1500
caggtggacg cccactgcag cgccggccac agctgcatct tcaccgtgag cggcaccagc    1560
agctgctgcc ccttccccga ggccgtggcc tgcggcgacg gccaccactg ctgccccgc    1620
ggcttccact gcagcgccga cggccgcagc tgcttccagc gcagcggcaa caacagcgtg    1680
ggcgccatcc agtgccccga cagccagttc gagtgccccg acttcagcac ctgctgcgtg    1740
atggtggacg gcagctgggg ctgctgcccc atgccccagg ccagctgctg cgaggaccgc    1800
gtgcactgct gccccacgg cgccttctgc gacctggtgc acacccgctg catcaccccc    1860
accggcaccc ccccctggc caagaagctg cccgcccagc gcaccaaccg cgccgtggcc    1920
ctgagcagca gcgtgatgtg cccgacgcc cgcagccgct gccccgacgg cagcacctgc    1980
tgcgagctgc ccagcggcaa gtacggctgc tgcccatgc caacgccac ctgctgcagc    2040
gaccacctgc actgctgccc ccaggacacc gtgtgcgacc tgatccagag caagtgcctg    2100
agcaaggaga acgccaccac cgacctgctg accaagctgc ccgcccacac cgtgggcgac    2160
gtgaagtgcg acatggaggt gagctgcccc gacggctaca cctgctgccg cctgcagagc    2220
ggcgcctggg gctgctgccc cttcacccag gccgtgtgct gcgaggacca catccactgc    2280
```

-continued

```
tgccccgccg gcttcacctg cgacacccag aagggcacct gcgagcaggg cccccaccag    2340
gtgccctgga tggagaaggc ccccgcccac ctgagcctgc ccgaccccca ggccctgaag    2400
cgcgacgtgc cctgcgacaa cgtgagcagc tgccccagca gcgacacctg ctgccagctg    2460
accagcggcg agtggggctg ctgccccatc cccgaggccg tgtgctgcag cgaccaccag    2520
cactgctgcc cccagggcta cacctgcgtg gccgagggcc agtgccagcg cggcagcgag    2580
atcgtggccg gcctggagaa gatgcccgcc cgccgcgcca gcctgagcca ccccgcgac     2640 atcggctgcg accagcacac cagctgcccc gtgggccaga cctgctgccc cagcctgggc    2700
ggcagctggg cctgctgcca gctgcccac gccgtgtgct gcgaggaccg ccagcactgc     2760
tgccccgccg gctacacctg caacgtgaag gcccgcagct gcgagaagga ggtggtgagc    2820
gcccagcccg ccaccttcct ggccgcagc ccccacgtgg gcgtgaagga cgtggagtgc     2880
ggcgagggcc acttctgcca cgacaaccag acctgctgcc gcgacaaccg ccagggctgg    2940
gcctgctgcc cctaccgcca gggcgtgtgc tgcgccgacc gccgccactg ctgccccgcc    3000
ggcttccgct gcgccgcccg cggcaccaag tgcctgcgcc gcgaggcccc ccgctgggac    3060
gcccccctgc gcgaccccgc cctgcgccag ctgctgtgac aattgttaat taagttttaaa   3120 ccctcgaggc cgcaagctta tcgataatca acctctggat tacaaaattt gtgaaagatt    3180
gactggtatt cttaactatg ttgctccttt tacgctatgt ggatacgctg ctttaatgcc    3240
tttgtatcat gctattgctt cccgtatggc tttcattttc tcctccttgt ataaatcctg    3300
gttgctgtct ctttatgagg agttgtggcc cgttgtcagg caacgtggcg tggtgtgcac    3360
tgtgtttgct gacgcaaccc ccactggttg gggcattgcc accacctgtc agctccttt    3420 cgggactttc gctttccccc tccctattgc cacggcggaa ctcatcgccg cctgccttgc    3480
ccgctgctgg acaggggctc ggctgttggg cactgacaat tccgtggtgt tgtcggggaa    3540
atcatcgtcc tttccttggc tgctcgcctg tgttgccacc tggattctgc gcgggacgtc    3600
cttctgctac gtcccttcgg ccctcaatcc agcggacctt ccttcccgcg gcctgctgcc    3660
ggctctgcgg cctcttccgc gtcttcgcct tcgccctcag acgagtcgga tctccctttg    3720
ggccgcctcc ccgcatcgat accgtcgact agagctcgct gatcagcctc gactgtgcct    3780
tctagttgcc agccatctgt tgtttgcccc tcccccgtgc cttccttgac cctggaaggt    3840
gccactccca ctgtcctttc ctaataaaat gaggaaattg catcgcattg tctgagtagg    3900
tgtcattcta ttctgggggg tggggtgggg caggacagca agggggagga ttgggaagac    3960
aatagcaggc atgctgggga gagatccacg ataacaaaca gcttttttgg ggtgaacata    4020
ttgactgaat tccctgcagg ttggccactc cctctctgcg cgctcgctcg ctcactgagg    4080
ccgcccgggc aaagcccggg cgtcgggcga ccttggtcg cccggcctca gtgagcgagc     4140
gagcgcgcag agagggagtg gccaactcca tcactagggg ttcctgcggc cgctcgtacg    4200
gtctcgagga attcctgcag gataacttgc caacctcatt ctaaaatgta tatagaagcc    4260
caaaagacaa taacaaaaat attcttgtag aacaaaatgg gaaagaatgt tccactaaat    4320
atcaagattt agagcaaagc atgagatgtg tggggataga cagtgaggct gataaaatag    4380
agtagagctc agaaacagac ccattgatat atgtaagtga cctatgaaaa aaatatggca    4440
ttttacaatg ggaaatgat ggtcttttc ttttttagaa aaacagggaa atatatttat      4500
atgtaaaaaa taaagggaa cccatatgtc ataccataca cacaaaaaaa ttccagtgaa     4560
ttataagtct aaatggagaa ggcaaaactt taaatctttt agaaaataat atagaagcat    4620
gcagaccagc ctggccaaca tgatgaaacc ctctctacta ataataaaat cagtagaact    4680
```

```
actcaggact actttgagtg ggaagtcctt ttctatgaag acttctttgg ccaaaattag    4740
gctctaaatg caaggagata gtgcatcatg cctggctgca cttactgata aatgatgtta    4800
tcaccatctt taaccaaatg cacaggaaca agttatggta ctgatgtgct ggattgagaa    4860
ggagctctac ttccttgaca ggacacattt gtatcaactt aaaaaagcag atttttgcca    4920
gcagaactat tcattcagag gtaggaaact tagaatagat gatgtcactg attagcatgg    4980
cttccccatc tccacagctg cttcccaccc aggttgccca cagttgagtt tgtccagtgc    5040
tcagggctgc ccactctcag taagaagccc acaccagcc cctctccaaa tatgttggct     5100
gttccttcca ttaaagtgac cccactttag agcagcaagt ggatttctgt ttcttacagt    5160
tcaggaagga ggagtcagct gtgagaacct ggagcctgag atgcttctaa gtcccactgc    5220
tactggggtc agggaagcca gactccagca tcagcagtca ggagcactaa gcccttgcca    5280
acatcctgtt tctcagagaa actgcttcca ttataatggt tgtccttttt taagctatca    5340
agccaaacaa ccagtgtcta ccattattct catcacctga agccaagggt tctagcaaaa    5400
gtcaagctgt cttgtaatgg ttgatgtgcc tccagcttct gtcttcagtc actccactct    5460
tagcctgctc tgaatcaact ctgaccacag ttccctggag cccctgccac ctgctgcccc    5520
tgccaccttc tccatctgca gtgctgtgca gccttctgca ctcttgcaga gctaataggt    5580
ggagacttga aggaagagga ggaaagtttc tcataatagc cttgctgcaa gctcaaatgg    5640
gaggtgggca ctgtgcccag gagccttgga gcaaaggctg tgcccaacct ctgactgcat    5700
ccaggtttgg tcttgacaga gataagaagc cctggctttt ggagccaaaa tctaggtcag    5760
acttaggcag gattctcaaa gtttatcagc agaacatgag gcagaagacc ctttctgctc    5820
cagcttcttc aggctcaacc ttcatcagaa tagatagaaa gagaggctgt gagggttctt    5880
aaaacagaag caaatctgac tcagagaata aacaacctcc tagtaaacta cagcttagac    5940
agagcatctg gtggtgagtg tgctcagtgt cctactcaac tgtctggtat cagccctcat    6000
gaggacttct cttctttccc tcatagacct ccatctctgt tttccttagc ctgcagaaat    6060
ctggatggct attcacagaa tgcctgtgct ttcagagttg catttttttct ctggtattct    6120 ggttcaagca tttgaaggta ggaaaggttc tccaagtgca agaaagccag ccctgagcct    6180
caactgcctg gctagtgtgg tcagtaggat gcaaaggctg ttgaatgcca caaggccaaa    6240 cttaacctg tgtaccacaa gcctagcagc agaggcagct ctgctcactg gaactctctg      6300
tcttctttct cctgagcctt ttcttttcct gagttttcta gctctcctca accttacctc    6360
tgccctaccc aggacaaacc caagagccac tgtttctgtg atgtcctctc cagcccctaat   6420 taggcatcat gacttcagcc tgaccttcca tgctcagaag cagtgctaat ccacttcaga    6480
tgagctgctc tatgcaacac aggcagagcc tacaaacctt gcaccagag ccctccacat     6540 atcagtgttt gttcatactc acttcaacag caaatgtgac tgctgagatt aagattttac    6600
acaagatggt ctgtaatttc acagttagtt ttatcccatt aggtatgaaa gaattagcat    6660
aattcccctt aaacatgaat gaatcttaga ttttttaata aatagttttg gaagtaaaga    6720
cagagacatc aggagcacaa ggaatagcct gagaggacaa acagaacaag aaagagtctg    6780
gaaatacaca ggatgttctt ggcctcctca aagcaagtgc aagcagatag taccagcagc    6840
cccaggctat cagagcccag tgaagagaag taccatgaaa gccacagctc taaccaccct    6900
gttccagagt gacagacagt ccccaagaca agccagcctg agccagagag agaactgcaa    6960
gagaaagttt ctaatttagg ttctgttaga ttcagacaag tgcaggtcat cctctctcca    7020
```

```
cagctactca cctctccagc ctaacaaagc ctgcagtcca cactccaacc ctggtgtctc      7080
acctcctagc ctctcccaac atcctgctct ctgaccatct tctgcatctc tcatctcacc      7140
atctcccact gtctacagcc tactcttgca actaccatct cattttctga catcctgtct      7200
acatcttctg ccatactctg ccatctacca taccacctct taccatctac cacaccatct      7260
tttatctcca tccctctcag aagcctccaa gctgaatcct gctttatgtg ttcatctcag      7320
cccctgcatg gaaagctgac cccagaggca gaactattcc cagagagctt ggccaagaaa      7380
aacaaaacta ccagcctggc caggctcagg agtagtaagc tgcagtgtct gttgtgttct      7440
agcttcaaca gctgcaggag ttccactctc aaatgctcca catttctcac atcctcctga      7500
ttctggtcac tacccatctt caaagaacag aatatctcac atcagcatac tgtgaaggac      7560
tagtcatggg tgcagctgct cagagctgca aagtcattct ggatggtgga gagcttacaa      7620
acatttcatg atgctccccc cgctctgatg gctggagccc aatccctaca cagactcctg      7680
ctgtatgtgt tttcctttca ctctgagcca cagccagagg gcaggcattc agtctcctct      7740
tcaggctggg gctggggcac tgagaactca cccaacacct tgctctcact ccttctgcaa      7800
aacaagaaag agctttgtgc tgcagtagcc atgaagaatg aaaggaaggc tttaactaaa      7860
aaatgtcaga gattattttc aaccccttac tgtggatcac cagcaaggag gaaacacaac      7920
acagagacat ttttttcccct caaattatca aaagaatcac tgcatttgtt aaagagagca      7980
actgaatcag gaagcagagt tttgaacata tcagaagtta ggaatctgca tcagagacaa      8040
atgcagtcat ggttgtttgc tgcataccag ccctaatcat tagaagcctc atggacttca      8100
aacatcattc cctctgacaa gatgctctag cctaactcca tgagataaaa taaatctgcc      8160
tttcagagcc aaagaagagt ccaccagctt cttctcagtg tgaacaagag ctccagtcag      8220
gttagtcagt ccagtgcagt agaggagacc agtctgcatc ctctaatttt caaaggcaag      8280
aagatttgtt taccctggac accaggcaca agtgaggtca cagagctctt agatatgcag      8340
tcctcatgag tgaggagact aaagcgcatg ccatcaagac ttcagtgtag agaaaacctc      8400
caaaaaagcc tcctcactac ttctggaata gctcagaggc cgaggcggcc tcggcctctg      8460
cataaataaa aaaaattagt cagccatggg gcggagaatg ggcggaactg ggcggagtta      8520
ggggcgggat gggcggagtt aggggcggga ctatggttgc tgactaattg agatgcatgc      8580
tttgcatact tctgcctgct ggggagcctg gggactttcc acacctggtt gctgactaat      8640
tgagatgcat gctttgcata cttctgcctg ctggggagcc tggggacttt ccacacccta      8700
actgacacac attccacagc tgcattaatg aatcggccaa cgcgcgggga gaggcggttt      8760
gcgtattggg cgctcttccg cttcctcgct cactgactcg ctgcgctcgg tcgttcggct      8820
gcggcgagcg gtatcagctc actcaaaggc ggtaatacgg ttatccacag aatcagggga      8880
taacgcagga agaacatgt gagcaaaagg ccagcaaaag gccaggaacc gtaaaaaggc      8940
cgcgttgctg gcgttttttcc ataggctccg ccccctgac gagcatcaca aaatcgacg      9000 ctcaagtcag aggtggcgaa acccgacagg actataaaga taccaggcgt ttccccctgg      9060
aagctccctc gtgcgctctc ctgttccgac cctgccgctt accggatacc tgtccgcctt      9120
tctcccttcg ggaagcgtgg cgctttctca tagctcacgc tgtaggtatc tcagttcggt      9180
gtaggtcgtt cgctccaagc tgggctgtgt gcacgaaccc cccgttcagc ccgaccgctg      9240
cgccttatcc ggtaactatc gtcttgagtc caacccggta agacacgact tatcgccact      9300
ggcagcagcc actggtaaca ggattagcag agcgaggtat gtaggcggtg ctacagagtt      9360
cttgaagtgg tggcctaact acggctacac tagaagaaca gtatttggta tctgcgctct      9420
```

-continued

```
gctgaagcca gttaccttcg gaaaaagagt tggtagctct tgatccggca aacaaaccac      9480
cgctggtagc ggtggttttt ttgtttgcaa gcagcagatt acgcgcagaa aaaaggatc       9540 tcaagaagat cctttgatct tttctacggg gtctgacgct cagtggaacg aaaactcacg     9600
ttaagggatt ttggtcatga gattatcaaa aaggatcttc acctagatcc ttttaaatta    9660
aaaatgaagt tttaaatcaa tctaaagtat atatgagtaa acttggtctg acagttacca   9720
atgcttaatc agtgaggcac ctatctcagc gatctgtcta tttcgttcat ccatagttgc   9780
ctgactcctg caaccacgt tgtgtctcaa atctctgat gttacattgc acaagataaa      9840
aatatatcat catgaacaat aaaactgtct gcttacataa acagtaatac aagggggtgtt   9900 atgagccata ttcaacggga aacgtcttgc tcgaggccgc gattaaattc caacatggat   9960
gctgatttat atgggtataa atgggctcgc gataatgtcg ggcaatcagg tgcgacaatc  10020
tatcgattgt atgggaagcc cgatgcgcca gagttgtttc tgaaacatgg caaaggtagc   10080
gttgccaatg atgttacaga tgagatggtc agactaaact ggctgacgga atttatgcct   10140
cttccgacca tcaagcattt tatccgtact cctgatgatg catggttact caccactgcg   10200
atccccggga aaacagcatt ccaggtatta gaagaatatc ctgattcagg tgaaaatatt  10260
gttgatgcgc tggcagtgtt cctgcgccgg ttgcattcga ttcctgtttg taattgtcct   10320
tttaacagcg atcgcgtatt tcgtctcgct caggcgcaat cacgaatgaa taacggtttg   10380
gttgatgcga gtgattttga tgacgagcgt aatggctggc ctgttgaaca gtctggaaaa  10440
gaaatgcata gcttttgcc attctcaccg gattcagtcg tcactcatgg tgatttctca    10500
cttgataacc ttattttga cgaggggaaa ttaataggtt gtattgatgt tggacgagtc    10560
ggaatcgcag accgatacca ggatcttgcc atcctatgga actgcctcgg tgagttttct    10620
ccttcattac agaaacggct ttttcaaaaa tatggtattg ataatcctga tatgaataaa  10680
ttgcagtttc atttgatgct cgatgagttt ttctaagggc ggcctgccac catacccacg   10740
ccgaaacaag cgctcatgag cccgaagtgg cgagcccgat cttccccatc ggtgatgtcg   10800
gcgatatagg cgccagcaac cgcacctgtg gcgccggtga tgagggcgcg ccaagtcgac  10860
gtccggcagt c                                                          10871
```

<210> SEQ ID NO 70  
<211> LENGTH: 4151  
<212> TYPE: DNA  
<213> ORGANISM: Artificial sequence  
<220> FEATURE:  
<223> OTHER INFORMATION: Synthetic polynucleotide

<400> SEQUENCE: 70

```
gggaggttac gcgttcgtcg actactagtg ggtaccagag cgggcggagt tagggcggag       60
ccaatcagcg tgcgccgttc cgaaagttgc cttttatggc tgggcggaga atgggcggtg      120
aacgccgatg attatataag gacgcgccgg ggtgtggcaca gctagttccg tcgcagccgg     180
gatttgggtc gcggttcttg tttgtggatc cctgtgatcg tcacttggta agtcactgac     240
tgtctatgcc tgggaaaggg tgggcaggag atggggcagt gcaggaaaag tggcactatg    300
aaccctgcag ccctaggaat gcatctagac aattgtacta accttcttct ctttcctctc    360
ctgacagtcc ggaaagccac catgtacgcc ctgttcctgc tggccagcct gctgggcgcc     420
gccctggccg ccccgtgct gggcctgaag gagtgcaccc gcggcagcgc cgtgtggtgc      480
cagaacgtga agaccgccag cgactgcggc gccgtgaagc actgcctgca gaccgtgtgg     540
```

| | | |
|---|---|---|
| aacaagccca ccgtgaagag cctgccctgc gacatctgca aggacgtggt gaccgccgcc | 600 | |
| ggcgacatgc tgaaggacaa cgccaccgag gaggagatcc tggtgtacct ggagaagacc | 660 | |
| tgcgactggc tgcccaagcc caacatgagc gccagctgca aggagatcgt ggacagctac | 720 | |
| ctgcccgtga tcctggacat catcaagggc gagatgagcc gccccggcga ggtgtgcagc | 780 | |
| gccctgaacc tgtgcgagag cctgcagaag cacctggccg agctgaacca ccagaagcag | 840 | |
| ctggagagca caagatccc cgagctggac atgaccgagg tggtggcccc cttcatggcc | 900 | |
| aacatccccc tgctgctgta ccccaggac ggcccccgca gcaagcccca gcccaaggac | 960 | |
| aacggcgacg tgtgccagga ctgcatccag atggtgaccg acatccagac cgccgtgcgc | 1020 | |
| accaacagca ccttcgtgca ggccctggtg gagcacgtga aggaggagtg cgaccgcctg | 1080 | |
| ggccccggca tggccgacat ctgcaagaac tacatcagcc agtacagcga gatcgccatc | 1140 | |
| cagatgatga tgcacatgca gcccaaggag atctgcgccc tggtgggctt ctgcgacgag | 1200 | |
| gtgaaggaga tgcccatgca gaccctggtg cccgccaagg tggccagcaa gaacgtgatc | 1260 | |
| cccgccctgg agctggtgga gccatcaag aagcacgagg tgcccgccaa gagcgacgtg | 1320 | |
| tactgcgagg tgtgcgagtt cctggtgaag gaggtgacca agctgatcga caacaacaag | 1380 | |
| accgagaagg agatcctgga cgccttcgac aagatgtgca gcaagctgcc caagagcctg | 1440 | |
| agcgaggagt gccaggaggt ggtggacacc tacggcagca gcatcctgag catcctgctg | 1500 | |
| gaggaggtga gccccgagct ggtgtgcagc atgctgcacc tgtgcagcgg cacccgcctg | 1560 | |
| cccgccctga ccgtgcacgt gacccagccc aaggacggcg gcttctgcga ggtgtgcaag | 1620 | |
| aagctggtgg gctacctgga ccgcaacctg gagaagaaca gcaccaagca ggagatcctg | 1680 | |
| gccgccctgg agaagggctg cagcttcctg cccgaccct accagaagca gtgcgaccag | 1740 | |
| ttcgtggccg agtacgagcc cgtgctgatc gagatcctgg tggaggtgat ggaccccagc | 1800 | |
| ttcgtgtgcc tgaagatcgg cgcctgcccc agcgcccaca gcccctgct gggcaccgag | 1860 | |
| aagtgcatct gggcccccag ctactggtgc agaacaccg agaccgccgc ccagtgcaac | 1920 | |
| gccgtggagc actgcaagcg ccacgtgtgg aacagaagaa agagaggaag tggagagggc | 1980 | |
| agaggaagtc ttctgacatg cggagacgtg aagagaatc ccggccctat gtggaccctg | 2040 | |
| gtgagctggg tggccctgac cgccggcctg gtggccggca cccgctgccc cgacggccag | 2100 | |
| ttctgccccg tggcctgctg cctggacccc ggcggcgcca gctacagctg ctgccgcccc | 2160 | |
| ctgctggaca agtggcccac caccctgagc cgccacctgg gcggcccctg ccaggtggac | 2220 | |
| gcccactgca gcgccggcca cagctgcatc ttcaccgtga gcggcaccag cagctgctgc | 2280 | |
| cccttccccg aggccgtggc ctgcggcgac ggccaccact gctgccccg gcttccac | 2340 | |
| tgcagcgccg acgccgcag ctgcttccag cgcagcggca caacagcgt gggcgccatc | 2400 | |
| cagtgccccg acagccagtt cgagtgcccc gacttcagca cctgctgcgt gatggtggac | 2460 | |
| ggcagctggg gctgctgccc catgcccag gccagctgct gcgaggaccg cgtgcactgc | 2520 | |
| tgcccccacg gcgccttctg cgacctggtg cacacccgct gcatcacccc caccggcacc | 2580 | |
| cacccctgg ccaagaagct gccgcccag cgcaccaacc gcgccgtggc cctgagcagc | 2640 | |
| agcgtgatgt gcccccgacgc ccgcagccgc tgccccgacg gcagcacctg ctgcgagctg | 2700 | |
| cccagcggca agtacggctg ctgcccatg cccaacgcca cctgctgcag cgaccacctg | 2760 | |
| cactgctgcc cccaggacac cgtgtgcgac ctgatccaga gcaagtgcct gagcaaggag | 2820 | |
| aacgccacca ccgacctgct gaccaagctg cccgcccaca ccgtgggcga cgtgaagtgc | 2880 | |
| gacatggagg tgagctgccc cgacggctac acctgctgcc gcctgcagag cggcgcctgg | 2940 | |

```
ggctgctgcc ccttcaccca ggccgtgtgc tgcgaggacc acatccactg ctgccccgcc    3000
ggcttcacct gcgacaccca gaagggcacc tgcgagcagg gccccacca ggtgccctgg    3060 atggagaagg cccccgccca cctgagcctg cccgaccccc aggccctgaa gcgcgacgtg    3120
ccctgcgaca acgtgagcag ctgccccagc agcgacacct gctgccagct gaccagcggc    3180
gagtggggct gctgccccat ccccgaggcc gtgtgctgca gcgaccacca gcactgctgc    3240
ccccagggct acacctgcgt ggccgagggc cagtgccagc gcggcagcga gatcgtggcc    3300
ggcctggaga agatgcccgc ccgccgcgcc agcctgagcc accccgcga catcggctgc    3360 gaccagcaca ccagctgccc cgtgggccag acctgctgcc ccagcctggg cggcagctgg    3420
gcctgctgcc agctgcccca cgccgtgtgc tgcgaggacc gccagcactg ctgccccgcc    3480
ggctacacct gcaacgtgaa ggcccgcagc tgcgagaagg aggtggtgag cgcccagccc    3540
gccaccttcc tggcccgcag ccccccacgtg ggcgtgaagg acgtggagtg cggcgagggc    3600
cacttctgcc acgacaacca gacctgctgc gcgacaacc gccagggctg ggcctgctgc    3660
ccctaccgcc agggcgtgtg ctgcgccgac cgccgccact gctgccccgc cggcttccgc    3720
tgcgccgccc gcggcaccaa gtgcctgcgc gcgcaggccc ccgctggga cgcccccctg    3780 cgcgaccccg ccctgcgcca gctgctgtga caattgttaa ttaagtttaa accctcgagg    3840
ccgcaagcaa taaatatct ttattttcat tacatctgtg tgttggtttt ttgtgtgaca    3900
attgttaatt aagtttaaac gttcgaggcc gcaagcgaga tccacgataa caaacagctt    3960 tttggggtg aacatattga ctgaattccc tgcaggttgg ccactccctc tctgcgcgct    4020
cgctcgctca ctgaggccgc ccgggcaaag cccggcgtc gggcgaccttc tggtcgcccg    4080 gcctcagtga gcgagcgagc gcgcagagag ggagtggcca actccatcac tagggggttcc    4140 tgcggccgct c                                                         4151

<210> SEQ ID NO 71
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 71
aagagggtgt tctctatgta ggc                                             23

<210> SEQ ID NO 72
<211> LENGTH: 22
<212> TYPE: DNA
<213> ORGANISM: Artificial sequence
<220> FEATURE:
<223> OTHER INFORMATION: Synthetic polynucleotide

<400> SEQUENCE: 72
gctcctccaa catttgtcac tt                                              22

<210> SEQ ID NO 73
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 73
acacagtacc taccgttata gca                                             23
```

```
<210> SEQ ID NO 74
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 74
tgttgtcaca gtaacttgca tca                                          23

<210> SEQ ID NO 75
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 75
ctgggctaca ctgagcacc                                               19

<210> SEQ ID NO 76
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 76
aagtggtcgt tgagggcaat g                                            21

<210> SEQ ID NO 77
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 77
tattagatct gatggccgcg                                              20

<210> SEQ ID NO 78
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 78
tccatcacta ggggttcctg                                              20
```